(12) United States Patent
Rooney et al.

(10) Patent No.: US 11,183,272 B2
(45) Date of Patent: Nov. 23, 2021

(54) METHOD AND SYSTEMS FOR PREDICTION OF HLA CLASS II-SPECIFIC EPITOPES AND CHARACTERIZATION OF CD4+ T CELLS

(71) Applicant: BioNTech US Inc., Cambridge, MA (US)

(72) Inventors: Michael Steven Rooney, Boston, MA (US); Jennifer Grace Abelin, Boston, MA (US); Dominik Barthelme, Belmont, MA (US); Robert Kamen, Sudbury, MA (US)

(73) Assignee: BIONTECH US INC., Cambridge, MA (US)

( * ) Notice: Subject to any disclaimer, the term of this patent is extended or adjusted under 35 U.S.C. 154(b) by 0 days.

(21) Appl. No.: 16/824,331

(22) Filed: Mar. 19, 2020

(65) Prior Publication Data

US 2020/0279616 A1     Sep. 3, 2020

Related U.S. Application Data

(63) Continuation of application No. PCT/US2019/068084, filed on Dec. 20, 2019.

(60) Provisional application No. 62/891,101, filed on Aug. 23, 2019, provisional application No. 62/855,379, filed on May 31, 2019, provisional application No. 62/826,827, filed on Mar. 29, 2019, provisional application No. 62/783,914, filed on Dec. 21, 2018.

(51) Int. Cl.
| | | |
|---|---|---|
| *G16B 30/00* | (2019.01) | |
| *G16B 40/00* | (2019.01) | |
| *A61K 39/39* | (2006.01) | |
| *G16B 40/20* | (2019.01) | |
| *C07K 16/28* | (2006.01) | |

(52) U.S. Cl.
CPC ............ *G16B 30/00* (2019.02); *A61K 39/39* (2013.01); *C07K 16/2833* (2013.01); *G16B 40/00* (2019.02); *G16B 40/20* (2019.02)

(58) Field of Classification Search
None
See application file for complete search history.

(56) References Cited

U.S. PATENT DOCUMENTS

| | | |
|---|---|---|
| 4,588,585 A | 5/1986 | Mark et al. |
| 4,703,004 A | 10/1987 | Hopp et al. |
| 4,751,180 A | 6/1988 | Cousens et al. |
| 4,851,341 A | 7/1989 | Hopp et al. |
| 4,935,233 A | 6/1990 | Bell et al. |
| 5,126,132 A | 6/1992 | Rosenberg |
| 5,185,146 A | 2/1993 | Altenburger |
| 5,443,983 A | 8/1995 | Ochoa et al. |
| 5,506,121 A | 4/1996 | Skerra et al. |
| 5,623,584 A | 4/1997 | Kurumida |
| 5,635,363 A | 6/1997 | Altman et al. |
| 5,658,785 A | 8/1997 | Johnson |
| 5,686,281 A | 11/1997 | Roberts |
| 5,723,584 A | 3/1998 | Schatz |
| 5,766,920 A | 6/1998 | Babbitt et al. |
| 5,833,975 A | 11/1998 | Paoletti et al. |
| 5,841,828 A | 11/1998 | Gordon et al. |
| 5,843,728 A | 12/1998 | Seed et al. |
| 5,846,827 A | 12/1998 | Celis et al. |
| 5,874,239 A | 2/1999 | Schatz |
| 5,906,936 A | 5/1999 | Eshhar et al. |
| 5,912,170 A | 6/1999 | Seed et al. |
| 5,912,172 A | 6/1999 | Eshhar et al. |
| 5,932,433 A | 8/1999 | Schatz |
| 5,942,235 A | 8/1999 | Paoletti |
| 5,994,136 A | 11/1999 | Naldini et al. |
| 6,004,811 A | 12/1999 | Seed et al. |
| 6,013,516 A | 1/2000 | Verma et al. |
| 6,090,393 A | 7/2000 | Fischer |
| 6,156,567 A | 12/2000 | Fischer |
| 6,165,782 A | 12/2000 | Naldini et al. |
| 6,194,207 B1 | 2/2001 | Bell et al. |
| 6,251,385 B1 | 6/2001 | Terman |
| 6,255,073 B1 | 7/2001 | Cai et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,392,013 B1 | 5/2002 | Seed et al. |
| 6,410,014 B1 | 6/2002 | Seed et al. |
| 6,428,953 B1 | 8/2002 | Naldini et al. |

(Continued)

FOREIGN PATENT DOCUMENTS

| | | |
|---|---|---|
| GB | 2370039 B | 10/2002 |
| WO | WO-03020763 A2 | 3/2003 |

(Continued)

OTHER PUBLICATIONS

Castelli et al. HLA-CP4, the Most Frequent HLA II Molecule, Defines a New Supertype of Peptide-Binding Specificity. J Immunol 2002, vol. 169, pp. 6928-6934 (Year: 2002).*
Abelin, J.G., Keskin, D.B., Sarkizova, S., Hartigan, C.R., Zhang, W., Sidney, J., Stevens, J., Lane, W., Zhang, G.L., Eisenhaure, T.M., et al. (2017). Mass Spectrometry Profiling of HLA-Associated Peptidomes in Mono-allelic Cells Enables More Accurate Epitope Prediction. Immunity 46, 315-326.
Alvarez, B et al., (2018). Computational Tools for the Identification and Interpretation of Sequence Motifs in Immunopeptidomes. PROTEOMICS 18, 1700252.

(Continued)

*Primary Examiner* — Olivia M. Wise
(74) *Attorney, Agent, or Firm* — Wilson Sonsini Goodrich & Rosatti

(57) ABSTRACT

Methods for preparing a personalized cancer vaccine and a method to train a machine-learning HLA-peptide presentation prediction model.

19 Claims, 108 Drawing Sheets

Specification includes a Sequence Listing.

(56) References Cited

U.S. PATENT DOCUMENTS

| | | | |
|---|---|---|---|
| 6,475,769 | B1 | 11/2002 | Wilson et al. |
| 6,489,458 | B2 | 12/2002 | Hackett et al. |
| 6,537,540 | B1 | 3/2003 | Burstein et al. |
| 6,537,594 | B1 | 3/2003 | Paoletti et al. |
| 6,753,162 | B1 | 6/2004 | Seed et al. |
| 6,780,407 | B1 | 8/2004 | Paoletti et al. |
| 6,793,926 | B1 | 9/2004 | Rasty et al. |
| 6,869,794 | B2 | 3/2005 | Vogels et al. |
| 6,893,865 | B1 | 5/2005 | Lockert et al. |
| 6,913,922 | B1 | 7/2005 | Bout et al. |
| 6,924,128 | B2 | 8/2005 | Allen |
| 6,936,466 | B2 | 8/2005 | Feldhaus |
| 6,943,019 | B2 | 9/2005 | Wilson et al. |
| 6,953,690 | B1 | 10/2005 | Gao et al. |
| 6,955,808 | B2 | 10/2005 | Curiel |
| 6,974,695 | B2 | 12/2005 | Vogels et al. |
| 6,991,797 | B2 | 1/2006 | Andersen et al. |
| 7,115,391 | B1 | 10/2006 | Chen et al. |
| 7,148,203 | B2 | 12/2006 | Hackett et al. |
| 7,160,682 | B2 | 1/2007 | Hackett et al. |
| 7,172,893 | B2 | 2/2007 | Rabinowitz et al. |
| 7,198,784 | B2 | 4/2007 | Kingsman et al. |
| 7,255,862 | B1 | 8/2007 | Tartaglia et al. |
| 7,259,015 | B2 | 8/2007 | Kingsman et al. |
| 7,303,910 | B2 | 12/2007 | Bebbington et al. |
| 7,351,581 | B2 | 4/2008 | Aulakh |
| 7,399,838 | B2 | 7/2008 | Reiter |
| 7,741,465 | B1 | 6/2010 | Eshhar et al. |
| 7,985,739 | B2 | 7/2011 | Kay et al. |
| 8,088,379 | B2 | 1/2012 | Robbins et al. |
| 8,211,422 | B2 | 7/2012 | Eshhar et al. |
| 8,227,432 | B2 | 7/2012 | Hackett et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 8,999,937 | B2 | 4/2015 | Srinivasan |
| 9,101,584 | B2 | 8/2015 | June et al. |
| 9,102,760 | B2 | 8/2015 | June et al. |
| 9,102,761 | B2 | 8/2015 | June et al. |
| 9,862,927 | B2 | 1/2018 | Banchereau et al. |
| 10,055,540 | B2 | 8/2018 | Yelensky et al. |
| 2004/0013648 | A1 | 1/2004 | Kingsman et al. |
| 2006/0258607 | A1 | 11/2006 | Jarosch et al. |
| 2007/0025970 | A1 | 2/2007 | Kingsman et al. |
| 2007/0134197 | A1 | 6/2007 | Eichner et al. |
| 2008/0254008 | A1 | 10/2008 | Dropulic et al. |
| 2009/0111106 | A1 | 4/2009 | Mitrophanous et al. |
| 2009/0130134 | A1 | 5/2009 | Pancre et al. |
| 2011/0293571 | A1 | 12/2011 | Widdowson et al. |
| 2012/0295960 | A1 | 11/2012 | Palfi et al. |
| 2013/0071414 | A1 | 3/2013 | Dotti et al. |
| 2014/0178438 | A1 | 6/2014 | Sahin et al. |
| 2015/0031566 | A1 | 1/2015 | Napper et al. |
| 2017/0199961 | A1* | 7/2017 | Yelensky ............... A61P 35/00 |
| 2017/0212984 | A1 | 7/2017 | Yelensky et al. |

FOREIGN PATENT DOCUMENTS

| | | |
|---|---|---|
| WO | WO-2004033685 A1 | 4/2004 |
| WO | WO-2004044004 A3 | 9/2004 |
| WO | WO-2004074322 A1 | 9/2004 |
| WO | WO-2005085323 A2 | 9/2005 |
| WO | WO-2005114215 A3 | 3/2006 |
| WO | WO-2005113595 A3 | 6/2006 |
| WO | WO-2006000830 A3 | 7/2006 |
| WO | WO-2006125962 A3 | 2/2007 |
| WO | WO-2008039818 A3 | 6/2008 |
| WO | WO-2008038002 A3 | 7/2008 |
| WO | WO-2011051489 A3 | 6/2011 |
| WO | WO-2012156969 A1 | 11/2012 |
| WO | WO-2012159643 A1 | 11/2012 |
| WO | WO-2012159754 A2 | 11/2012 |
| WO | WO-2013039889 A1 | 3/2013 |
| WO | WO-2013166321 A1 | 11/2013 |
| WO | WO-2014018863 A1 | 1/2014 |
| WO | WO-2014083173 A1 | 6/2014 |
| WO | WO-2014134165 A1 | 9/2014 |
| WO | WO-2015085147 A1 | 6/2015 |
| WO | WO-2016128060 A1 | 8/2016 |
| WO | WO-2017184590 A1 | 10/2017 |
| WO | WO-2018005559 A1 | 1/2018 |
| WO | WO-2018148671 A1 | 8/2018 |
| WO | WO-2019178081 A1 | 9/2019 |

OTHER PUBLICATIONS

Andreatta, M., Alvarez, B., and Nielsen, M. (2017). GibbsCluster: unsupervised clustering and alignment of peptide sequences. Nucleic Acids Res. 45, W458-W463.

Andreatta, M.,(2015). Accurate pan-specific prediction of peptide-MHC class II binding affinity with improved binding core identification. Immunogenetics 67.

Archila, L.L.D., and Kwok, W.W. (2017). Tetramer-Guided Epitope Mapping: A Rapid Approach to Identify HLA-Restricted T-Cell Epitopes from Composite Allergens. In Food Allergens: Methods and Protocols, J. Lin, and M. Alcocer, eds. (New York, NY: Springer New York), pp. 199-209.

Ashwell JD, et al.,1990, "Genetic and Mutational Analysis of the T-Cell Antigen Receptor" Annual Review of Immunology; 8: 139-167.

Ausubel, et al., (1987) Current Protocols in Molecular Biology. Wiley.

Ayers, M., et al. (2017). IFN-γ-related mRNA profile predicts clinical response to PD-1 blockade. J. Clin. Invest. 127, 2930-2940.

Balagaan et al., "Stable and efficient intraocular gene transfer using pseudotyped EIAV lentiviral vectors," J Gene Med, 8:275-285 (2005).

Barany et al. Solid-phase peptide synthesis. In: the Peptides: Analysis, Synthesis, Biology vol. 2: Special Methods in Peptide Synthesis Part A. New York: Academic Press.pp. 3-284 (1979).

Barra, C. (2018). Footprints of antigen processing boost MHC class II natural ligand predictions. Genome Med. 10, 84.

Bassani-Sternberg et al., Mass Spectrometry of Human Leukocyte Antigen Class I Peptidomes Reveals Strong Effects of Protein Abundance and Turnover on Antigen Presentation, Mol Cell Proteomics, 14:658-673 (2015).

Benton et al., Screening lambdagt recombinant clones by hybridization to single plaques in situ, Science, 196(4286):180-182 (1977).

Boen et al., Identification of T Cell Ligands in a Library of Peptides Covalently Attached to HLA-DR4, J Immunol, 165:2040-2047 (2000).

Bohm et al., DNA vector constructs that prime hepatitis B surface antigen-specific cytotoxic T lymphocyte and antibody responses in mice after intramuscular injection. Journal of immunological methods 193(1): 29-40 (1996).

Bozzacco, L. et al., (2011). Mass spectrometry analysis and quantitation of peptides presented on the MHC II molecules of mouse spleen dendritic cells. J. Proteome Res. 10, 5016-5030.

Buchschacher et al., "Human immunodeficiency virus vectors for inducible expression of foreign genes." Journal of virology, 66(5):2731-2739 (1992).

Bulik-Sullivan, B., Busby, J., Palmer, C.D., Davis, M.J., Murphy, T., Clark, A., Busby, M., Duke, F., Yang, A., Young, L., et al. (2018). Deep learning using tumor HLA peptide mass spectrometry datasets improves neoantigen identification. Nat. Biotechnol.

Butler, A.,et al. (2018). Integrating single-cell transcriptomic data across different conditions, technologies, and species. Nat. Biotechnol. 36, 411.

Cancer Genome Atlas Network (2015). Genomic Classification of Cutaneous Melanoma. Cell 161, 1681-1696.

Carithers, L.J..,et al. (2015). A Novel Approach to High-Quality Postmortem Tissue Procurement: The GTEx Project. Biopreservation Biobanking 13, 311-319.

Carter et al., Absolute quantification of somatic DNA alterations in human cancer, Nat Biotechnol, 30:413-21 (2012).

Castello, A., et al. (2012). Insights into RNA Biology from an Atlas of Mammalian mRNA-Binding Proteins. Cell 149, 1393-1406.

(56) References Cited

OTHER PUBLICATIONS

Cheng, J., et al., (2005), SCRATCH: a protein structure and structural feature prediction server. Nucleic Acids Res. 33, W72-W76.
Chiang et al. A dendritic cell vaccine pulsed with autologous hypochlorous acid-oxidized ovarian cancer lysate primes effective broad antitumor immunity: from bench to bedside. Clin Cancer Res 19(17):4801-4815 (2013).
Chong, C.et al,. (2018). High-throughput and Sensitive Immunopeptidomics Platform Reveals Profound Interferony-Mediated Remodeling of the Human Leukocyte Antigen (HLA) Ligandome. Mol. Cell. Proteomics MCP 17, 533-548.
Chroboczek et al., "The Sequence of the Genome of Adenovirus Type 5 and Its Comparison with the Genome of Adenovirus Type 2," Virology, 186:280-285 (1992).
Clement, C.C., et al., (2016). The Dendritic Cell Major Histocompatibility Complex II (MHC II) Peptidome Derives from a Variety of Processing Pathways and Includes Peptides with a Broad Spectrum of HLA-DM Sensitivity. J. Biol. Chem. 291, 5576-5595.
Cobbold et al., MHC class I-associated phosphopeptides are the targets of memory-like immunity in leukemia, Sci Trans Med. Sep. 18, 2013;5(203).
Costantino C.M., et al. (2012). Class II MHC Self-Antigen Presentation in Human B and T Lymphocytes. PLoS ONE 7, e29805.
Deniger, D.C., et al., (2018) T-cell Responses TP53 Hotspot Mutations and Neoantigens Expressed by Human Ovarian Cancers, Clin Cancer Res., 24, 5562.
Dobin, et al., Star: Ultrafast Universal RNA-Seq Aligner, Bioinformatics, Oct. 25, 2012, 29:15-21.
DuPage et al., "Expression of tumour-specific antigens underlies cancer immunoediting," Nature, 482(7385):405-409 (2012).
Emens, L.A., and Middleton, G. (2015). The interplay of immunotherapy and chemotherapy: harnessing potential synergies. Cancer Immunol. Res. 3, 436-443.
ENCODE project consortium, et al. An integrated encyclopedia of DNA elements in the human genome. Nature. Sep. 6, 2012;489(7414):57-74. doi: 10.1038/nature11247.
Evans et al., (1985) Isolation of monoclonal antibodies specific for human c-myc proto-oncogene productMol. Cell. Biol., 5:3610.
Ferguson, J., Construction and characterization of three yeast-*Escherichia coli* vectors designed for rapid subcloning of yeast genes on small DNA fragments, Gene, 16:191-7.
Field et al., (1988) Purification of a RAS-Responsive Adenylyl Cyclase Complex from *Saccharomyces cerevisiae* by Use of an Epitope Addition Method Mol. Cell. Biol., 8:2159.
Gluzman, Yakov, SV40-transformed simian cells support the replication of early SV40 mutants, Cell, 23:175-182 (1981).
Govorukhina, N.L., et al., Analysis of human serum by liquid chromatography-mass spectrometry: improved sample preparation and data analysis, J. Chromatography, vol. 1120, Issues 1-2, Jul. 2006 pp. 142-150.
Grunstein et al., Colony hybridization: a method for the isolation of cloned DNAs that contain a specific gene, PNAS, 72(10):3961-3965 (1975).
Han, Huamin et al., An Efficient Vector system to Modify Cells Genetically, PLOS ONE, Nov. 2011, vol. 6, Issue 11, pp. 1-9.
Hawkins, et al. Genome sequence of the Bacteroides fragilis phage ATCC 51477-B1. Virol J. Aug. 18, 2008;5:97. doi: 10.1186/1743-422X-5-97.
He, K., Zhang, X., Ren, S., and Sun, J. (2015). Delving Deep into Rectifiers: Surpassing Human-Level Performance on ImageNet Classification. In the IEEE International Conference on Computer Vision (ICCV), p.
Henikoff et al. Amino acid substitution matrices from protein blocks. PNAS USA 89(22):10915-10919 (1992).
Hinton, G.E. (2010). Rectified linear units improve restricted boltzmann machines vinod nair.
Hoof, et al. NetMHCpan, a method for MHC class I binding prediction beyond humans. Immunogenetics. 61.1 (2009):1-13. doi: 10.1007/s00251-008-0341-z. Epub Nov. 12, 2008.

Hoof, I., van Baarle, D., Hildebrand, W.H., and KeØmir C. (2012). Proteome Sampling by the HLA Class I Antigen Processing Pathway. PLoS Comput Biol 8, e1002517.
Hopp et al., a Short Polypeptide Marker Sequence Useful for Recombinant Protein Identification and Purification, BioTechnology, 6:1204, 1988.
Horig, et al. 2000. Phase I clinical trial of a recombinant canarypoxvirus (ALVAC) vaccine expressing human carcinoembryonic antigen and the B7.1 co-stimulatory molecule. Cancer Immunol Immunother 49:504-514.
Hortin,G.L., et al. (2008). High-Abundance Polypeptides of the Human Plasma Proteome Comprising the Top 4 Logs of Polypeptide Abundance. Clin. Chem. 54, 1608.
International Search Report and Written Opinion dated May 17, 2018 for PCT/US18/017849.
Ioffe, S.et al. (2015). Batch Normalization: Accelerating Deep Network Training by Reducing Internal Covariate Shift. Eprint ArXiv150203167 arXiv:1502.03167.
Jardetzky TS. et al., 1996, "Crystallographic analysis of endogenous peptides associated with HLA-DR1 suggests a common, polyproline II-like conformation for bound peptides." Proc. Natl. Acad. Sci. UDS, vol. 93, pp. 734-738.
Jerby-Arnon, et al. (2018). A Cancer Cell Program Promotes T Cell Exclusion and Resistance to Checkpoint Blockade. Cell 175, 984-997.e24.
Jiang, W. et al., High-throughput engineering and analysis of peptide binding to class II MHC, PNAS, vol. 107, No. 30, Jul. 27, 2010, pp. 13258-13263.
Johnson, D.B. et al. (2016). Melanoma-specific MHC-II expression represents a tumour-autonomous phenotype and predicts response to anti-PD-1/PD-L1 therapy. Nat. Commun. 7, 10582-10582.
Justensen, S., et al., (2009). Functional recombinant MHC class II molecules and high-throughput peptide-binding assays. Immunome Res. 5, 2-2.
Karanikas et al, High frequency of cytolytic T lymphocytes directed against a tumor-specific mutated antigen detectable with HLA tetramers in the blood of a lung carcinoma patient with long survival. Cancer Res. 61:3718-3724 (2001).
Karosiene, E., et al. (2013). NetMHCIIpan-3.0, a common pan-specific MHC class II prediction method including all three human MHC class II isotypes, HLA-DD, HLA-DP and HLA-DQ. Immunogenetics 65.
Kent, et al. The Human Genome Browser at UCSC. Genome Res. 2002. 12: 996-1006.
Kenter et al., Vaccination against HPV-16 oncoproteins for vulvar intraepithelial neoplasia, New England Journal of Medicine, 361(19):1838-1847 (2009).
Kim, Y., et al.. (2009). Derivation of an amino acid similarity matrix for peptide:MHC binding and its application as a Bayesian prior. BMC Bioinformatics 10, 1-11.
The validity of presumptive clones, Methods in enzymology, 152:507-511 (1987).
Kotin; Rm., "Prospects for the use of adeno-associated virus as a vector for human gene therapy. Hum Gene Ther. Jul. 1994;5(7):793-801."
Kreiter, S., et al. (2015). Mutant MHC class II epitopes drive therapeutic immune responses to cancer. Nature 520, 692-696.
Kronke et al., Lenalidomide causes selective degradation of IKZF1 and IKZF3 in multiple myeloma cells. Science. 343(6168):301-5 (2014).
Kronke et al., Lenalidomide induces ubiquitination and degradation of CK1alpha in del(5q) MDS. Nature. 523(7559):183-188 (2015).
Krutzik, P.O., et al(2011). Fluorescent cell barcoding for multiplex flow cytometry. Curr. Protoc. Cytom. Chapter 6, Unit-6.31.
Larsen et al., Large-scale validation of methods for cytotoxic T-lymphocyte epitope prediction, BMC Bioinformatics, 8:424-424 (2007).
Lecun, Y., et al. (1989). Backpropagation Applied to Handwritten Zip Code Recognition. Neural Comput. 1, 541-551.
Leitner, W.W., et al, Immune responses induced by intramuscular or gene gun injection of protective deoxyribonucleic acid vaccines that express the circumsporozoite protein from Plasmodium berghei malaria parasites, J ImmunolDec. 15, 1997,159(12)6112-6119.

(56) References Cited

OTHER PUBLICATIONS

Lennerz et al. The response of autologous T cells to a human melanoma is dominated by mutated neoantigens. PNAS USA 102(44):16013-16018 (2005).
Lewis et al., (1999) Multicistronic vectors are sometimes constructed to express more than one immunogen, or to express an immunogen and an immunostimulatory protein. Advances in Virus Research (Academic Press) 54: 129-88).
Li et al., The Sequence Alignment/Map format and SAMtools, Bioinformatics, 25(16):2078-2079 (2009).
Li, H., Courtois, E.T., Sengupta, D., Tan, Y., Chen, K.H., Goh, J.J.L., Kong, S.L., Chua, C., Hon, L.K., Tan, W.S., et al. (2017). Reference component analysis of single-cell transcriptomes elucidates cellular heterogeneity in human colorectal tumors. Nat. Genet. 49, 708.
Loffler, M.W., et al. (2018). Mapping the HLA Ligandome of Colorectal Cancer Reveals an Imprint of Malignant Cell Transformation. Cancer Res. 78, 4627.
Luckow and Summers, Trends in the Development of Baculovirus Expression Vectors, Bio/Technology 6:47 (1988).
Lundegaard et al. NetMHC-3.0: accurate web accessible predictions of human, mouse and monkey MHC class I affinities for peptides of length 8-11. Nucleic Acids Res 36:W509-512 (2008).
Lutz-Freyemuth et al., (1990) Quantitative determination that one of two potential RNA-binding domains of the A protein component of the U1 small nuclear ribonucleoprotein complex binds with high affinity to stem-loop II of U1 RNA., Proc. Natl. Acad. Sci. USA, 87:6393.
Álvaro-Benito, M., et al., (2018). Quantification of HLA-DM-Dependent Major Histocompatibility Complex of Class II Immunopeptidomes by the Peptide Landscape Antigenic Epitope Alignment Utility. Front. Immunol. 9, 872.
Magnan, C.N. et al.. (2014). SSpro/ACCpro 5: almost perfect prediction of protein secondary structure and relative solvent accessibility using profiles, machine learning and structural similarity. Bioinforma. Oxf. Engl. 30, 2592-2597.
Mandl et al., Immunotherapy with MVA-BN®o-HER2 induces HER-2-specific Th1 immunity and alters the intratumoral balance of effector and regulatory T cells, Cancer Immunol Immunother. Jan. 2012; 61(1): 19-29.
Maratea et al., "Deletion and fusion analysis of the phage ØX174 lysis gene E," Gene, 40:39-46, 1985.
Marshall, et al. 2000. Phase I study in advanced cancer patients of a diversified prime-and-boost vaccination protocol using recombinant vaccinia virus and recombinant nonreplicating avipox virus to elicit anti-carcinoembryonic antigen immune responses. J Clin Oncol 18:3964-3973.
Martin, et al. GAP domains responsible for ras p21-dependent inhibition of muscarinic atrial K+ channel currents. Science. Jan. 10, 1992;255(5041):192-4.
Matsushita et al, Cancer exome analysis reveals a T-cell-dependent mechanism of cancer immunoediting, Nature 482:400 (2012).
Mcgranahan, N., et al. (2017). Allele-Specific HLA Loss and Immune Escape in Lung Cancer Evolution. Cell 171, 1259-1271. e11.
Medzihradszky KF and Chalkley RJ, Lessons in de novo Peptide Sequencing by Tandem Mass Spectrometry,Mass Spectrom Rev. Jan.-Feb. 2015;34(1):43-63.
Merrifield et al. Solid Phase Peptide Synthesis I. J Am Chem Soc 85:2149-2154 (1963).
Merrifield, Solid Phase Synthesis, Science 232:341-347 (1986).
Meyer, H. et al., (1991), Mapping of deletions in the genome of the highly attenuated vaccinia virus MVA and their influence on virulence, J. Gen. Virol. 72, 1031-1038.
Miller et al. Construction and properties of retrovirus packaging cells based on gibbon ape leukemia virus. J Virol. 65(5):2220-2224 (1991).
Mommen et al., "Expanding the detectable HLA peptide repertoire using electron-transfer/higher-energy collision dissociation (EThcD)," PNAS III, 4507-4512 (2014).

Moss, Reflections on the Early Development of Poxvirus Vectors, Vaccine. 2013; 31(39): 4220-4222.
Murphy, J. R. et al., "Genetic construction, expression, and melanoma-selective cytotoxicity of a diptheria toxin-related α-melanocyte-stimulating hormone fusion protein," PNAS US.A., 83(21):8258-8262 (1986).
Musey, L. et al. HIV-1 vaccination administered intramuscularly can induce both systemic and mucosal T cell immunity in HIV-1-uninfected individuals. J Immunol 2003;171:1094-101.
Nanaware, P.P., et al. (2019). HLA-DO Modulates the Diversity of the MHC-II Self-peptidome. Mol. Amp Cell. Proteomics 18, 490.
Bassani-Sternberg, M.,, et al. (2016). Direct identification of clinically relevant neoepitopes presented on native human melanoma tissue by mass spectrometry. Nat. Commun. 7, 13404.
Nesbeth et al. CD4+ T cells elicit host immune responses to MHC class II-negative ovarian cancer through CCL5 secretion and CD40-mediated licensing of dendritic cells. J Immunol 184(10):5654-5662 (2010).
Nielsen et al. NN-align. An artificial neural network-based alignment algorithm for MHC class II peptide binding prediction. BMC Bioinformatics.Sep. 18, 2009;10:296.
Oates et al., D(2)P(2): database of disordered protein predictions, Nucleic Acids Res, 41:D508-D516 (2013).
Ong et al. Stable isotope labeling by amino acids in cell culture, SILAC, as a simple and accurate approach to expression proteomics. Mol Cell Proteomics 1(5):376-386 (2002).
Ooi, J.D., et al. (2017). Dominant protection from HLA-linked autoimmunity by antigen-specific regulatory T cells. Nature 545, 243-247.
Ossendorp, F., et al. (1998). Specific T Helper Cell Requirement for Optimal Induction of Cytotoxic T Lymphocytes against Major Histocompatibility Complex Class II Negative Tumors. J. Exp. Med. 187, 693.
Ott, P.A., et al. (2017). An immunogenic personal neoantigen vaccine for melanoma patients. Nature 547, 217.
Paborsky, et al., Mammalian cell transient expression of tissue factor for the production of antigen,Protein Engineering, 3:547-53.
Pacis, A., et al. (2018). Gene activation precedes DNA demethylation in response to infection in human dendritic cells. BioRxiv 358531.
Paoletti, E. 1996. Applications of pox virus vectors to vaccination: an update. Proc Natl Acad Sci U S A 93:11349-11353.
Paul, S., et al. (2018). Determination of a Predictive Cleavage Motif for Eluted Major Histocompatibility Complex Class II Ligands. Front. Immunol. 9, 1795.
Puram, S.V., et al. (2017). Single-Cell Transcriptomic Analysis of Primary and Metastatic Tumor Ecosystems in Head and Neck Cancer. Cell 171, 1611-1624.e24.
Quezada, S.A., et al. (2010). Tumor-reactive CD4+ T cells develop cytotoxic activity and eradicate large established melanoma after transfer into lymphopenic hosts. J. Exp. Med. 207, 637.
Rammensee et al., "SYFPEITHI: database for MHC ligands and peptide motifs," Immunogenetics, Nov. 1999 vol. 50 p. 213-219.
Rammensee HG."Chemistry of peptides associated with MHC class I and class Ii molecules,"Curr Opin Immunol. Feb. 1995;7(1):85-96.
Rappsilber et al., Protocol for micro-purification, enrichment, prefractionation and storage of peptides for proteomics using StageTips, Nat Protoc, 2(8):1896-1906 (2007).
Rasmussen, Michael, Uncovering the Peptide-Binding Specificities of HLA-C: A General Strategy to Determine the Specificity of Any MHC Class I Molecule, The Journal of Immunology, 2014, pp. 4790-4802.
Riberdy, J.M., et al. (1992). HLA-DR molecules from an antigen-processing mutant cell line are associated with invariant chain peptides. Nature 360, 474.
Robinson et al., "Integrative clinical genomics of advanced prostate cancer," Cell 2015; 161(5):1215-1228.
Roche and Furuta, The ins and outs of MHC class II-mediated antigen processing and presentation, Nat Rev Immunol. Apr. 2015 ; 15(4): 203-216. doi:10.1038/nri3818.
Roche, P.A. et al.(1991). Formation of a nine-subunit complex by HLA class II glycoproteins and the invariant chain. Nature 354, 392.
Rock, K.L., et al. (2016). Present Yourself! By MHC Class I and MHC Class II Molecules. Trends Immunol. 37, 724-737.

(56) References Cited

OTHER PUBLICATIONS

Rolph et al., Recombinant viruses as vaccines and immunological tools. Curr Opin Immunol 9:517-524, 1997.
Rose, C.M., et al. (2016). Highly Multiplexed Quantitative Mass Spectrometry Analysis of Ubiquitylomes. Cell Syst. 3, 395-403.e4.
Rossjohn, J., 2015,Annu Rev Immunol. 2015;33:169-200. {doi: 10.1146/annurev-immunol-032414-112334. Epub Dec. 10, 2014}.
Sade-Feldman, M., et al. (2017). Resistance to checkpoint blockade therapy through inactivation of antigen presentation. Nat. Commun. 8, 1136.
Sahin et al., Personalized RNA mutanome vaccines mobilize polyspecific therapeutic immunity against cancer, Nature, 547(7662):222-226 (2017).
Sampson et al, Immunologic escape after prolonged progression-free survival with epidermal growth factor receptor variant III peptide vaccination in patients with newly diagnosed glioblastoma J Clin Oncol. 28:4722-4729 (2010).
Saxena, M., and Bhardwaj, N. (2018). Re-Emergence of Dendritic Cell Vaccines for Cancer Treatment. Trends Cancer 4, 119-137.
Schmidt et al., Molecular interaction between the Strep-tag affinity peptide and its cognate target, streptavidin, J. Mol. Biol., 255(5):753-766, 1996.
Sharei et al. A vector-free microfluidic platform for intracellular delivery. Proc Natl Acad Sci U S A. Feb. 5, 2013; 110(6): 2082-2087.
Skinner et al. Use of the Glu-Glu-Phe C-terminal epitope for rapid purification of the catalytic domain of normal and mutant ras GTPase-activating proteins. J. Biol. Chem. 266:15163-15166 (1991).
Skinner, W. S., et al., Isolation and Identificifation of Paralytic Peptides from Hemolymph of the Lepidopteran insects manduca sexta, Spodoptera exigua, and Heliothis virescens, J. Biological Chemistry, vol. 266, No. 20, Jul. 15, 1991, pp. 12873-12877.
Sommnerfelt et al., Receptor interference groups of 20 retroviruses plating on human cells.(1990) Virol.176:58-59.
Srivastava, et al. Dropout: a simple way to prevent neural networks from overfilling. Journal of Machine Learning Research 15.1 (2014): 1929-1958.
Stern, L. J. et al. Crystal structure of the human class II MHC protein HLA-DR1 complexed with an influenza virus peptide. Nature 368, 215-221, doi: 10.1038/368215a0 (1994).
Thorvaldsdóttir, H. et al. (2013). Integrative Genomics Viewer (IGV): high-performance genomics data visualization and exploration. Brief. Bioinform. 14, 178-192.
Tirosh, I. et al. (2016). Dissecting the multicellular ecosystem of metastatic melanoma by single-cell RNA-seq. Science 352, 189.
Touw, W.G. et al. (2015). A series of PDB-related databanks for everyday needs. Nucleic Acids Res. 43, D364-D368.
Tran, E., et al. (2014). Cancer Immunotherapy Based on Mutation-Specific CD4+ T Cells in a Patient with Epithelial Cancer. Science 344, 641.
Udeshi et al., Methods for quantification of in vivo changes in protein ubiquitination following proteasome and deubiquitinase inhibition, Mot Cell Proteomics, 11:148-159 (2012).
Unanue et al., (2016), Variations in MHC Class II Antigen Processing and Presentation in Health and Disease, Annual Review of Immunology, vol. 34, 265-297.
Van Lith, M. et al. (2010). HLA-DP, HLA-DQ, and HLA-DR have different requirements for invariant chain and HLA-DM. J. Biol. Chem. 285, 40800-40808.
Verardi et al., A vaccinia virus renaissance New vaccine and immunotherapeutic uses after smallpox eradication, Hum Vaccin Immunother. Jul. 2012;8(7):961-70.
Vita et al., The immune epitope database (IEDB) 3.0, Nucleic Acids Res, 43:D405-D412 (2015).
Vita, R. et al.(2018). The Immune Epitope Database (IEDB): 2018 update. Nucleic Acids Res. gky1006-gky1006.
Wahl et al., [43] Molecular hybridization of immobilized nucleic acids: Theoretical concepts and practical considerations, Methods in enzymology, Academic Press, 152:399-407 (1987).
Weiner et al., (1999), Genetic Vaccines, Scientific American 281 (1): 34-41.
Wilson et al Formation of infectious hybrid virions with gibbon ape leukemia virus and human T-cell leukemia virus retroviral envelope glycoproteins and the gag and pol proteins of Moloney murine leukemia virus. J Virol 63(5):2374-2378 (1989).
Yadav, N. et al (2014). Transformations of the macromolecular landscape at mitochondria during DNA-damage-induced apoptotic cell death. Cell Death Amp Dis. 5, e1453.
Yang, J. et al. (2006). Multiplex mapping of CD4 T cell epitopes using class II tetramers. Clin. Immunol. 120, 21-32.
Yang, J. et al., In vivo biotinylation of the major histocompatibility complex (MHC) class II/peptide complex by coexpression of BirA enzyme for the generation of MHC class II/tetramers, Hum Immunol., Jul. 2004;65(7):692-9.
Yates, B. et al. (2016). Genenames.org: the HGNC and VGNC resources in 2017. Nucleic Acids Res. 45, D619-D625.
Yin, L.. et al. (2015). Evaluating the Role of HLA-DM in Mhc Class II-Peptide Association Reactions. J. Immunol. 195, 706.
Yoshihara, K. et al., Inferring tumour purity and stromal and immune cell admixture from expression data,: Nature communications 4:2612 (2013).
Yost, K.E. et al. (2019). Clonal replacement of tumor-specific T cells following PD-1 blockade. Nat. Med.
Zacharakis, N. et al. (2018). Immune recognition of somatic mutations leading to complete durable regression in metastatic breast cancer. Nat. Med. 24, 724-730.
Zarling AL., 2006, Identification of class I MHC-associated phosphopeptides as targets for cancer immunotherapy, PNAS Oct. 3, 2006 103 (40) 14889-14894.
Zarling AL., et al.,2000,Phosphorylated Peptides Are Naturally Processed and Presented by Major Histocompatibility Complex Class I Molecules in Vivo, J. Exp Med., 192(12): 1755-1762.
Friedman, K.M., et al. (2012). Tumor-specific CD4+ melanoma tumor-infiltrating lymphocytes. J. Immunother. Hagerstown Md 1997 35, 400-408.
Burr, Marian L., et al., MHC class I molecules are preferentially ubiquitinated on endoplasmic reticular luminal residues during HRD1 ubiquitin E3 ligase-mediated dislocation, PNAS, vol. 110, No. 35, Aug. 27, 2013, pp. 14290-14295.
Cherryholmes et al., Current methods of epitope identification for cancer vaccine design, Vaccine 2015, vol. 33, pp. 7408-7414 (Year: 2015).
International Search Report and Written Opinion dated May 19, 2020, for PCT/US2019/068084.
Shao, XM, High-throughput prediction of MCH Class I and Class II neoantigens with MHCnuggests, Cancer Immun Research, Dec. 23, 2019, pp. 1-34.
Graham, Daniel B. et al. Antigen discovery and specification of immunodominance hierarchies for MHCII-restricted epitopes, Nature Medicine, vol. 24, Nov. 2018, pp. 1762-1772.
Alarcon et al., DNA vaccines: technology and application as anti-parasite and anti-microbial agents, Advances in Parasitology, 42:343-410 (1999).
Hunt et al., Characterization of peptides bound to the class I MJC molecule HLA-A2.1 by mass spectrometry, Science, 255:1261-1263 (1992).
International Search Report dated Apr. 30, 2018 for PCT/US18/017849.
Non-Final Office Action dated Jun. 10, 2020, for U.S. Appl. No. 16/692,544.
Netzel-Arnett et al., Sequence Specificities of Human fibroblast and Neutrophil Collagenases, Biol. Chem., vol. 266, No. 11, Issue Apr. 15, 1991, pp. 6747-6755.
Bassani-Sternberg, M. et al, Unsupervised HLA Peptidome Deconvolution Improves Ligand Prediction Accuracy and Prediction Cooperative Effects in Peptide-HLA Interactions, The Journal of Immunology, vol. 197, No. 8/10/1016, p. 2492-2499.
Bergseng, E., et al. (2015). Different binding motifs of the celiac disease-associated HLA molecules DQ2.5, DQ2.2, and DQ7.5 revealed by relative quantitative proteomics of endogenous peptide repertoires. Immunogenetics 67, 73-84.

(56) References Cited

OTHER PUBLICATIONS

Buckwalter et al., "'It is the antigen(s), stupid' and other lessons from over a decade of vaccitherapy of human cancer," Seminars in Immunology, 20(5):296-300 (2008).
Kimmel et al., [54] Identification and characterization of specific clones: Strategy for confirming the validity of presumptive clones, Methods in Enzymology, 152:507-511 (1987).
Lambrechts, D., et al. (2018). Phenotype molding of stromal cells in the lung tumor microenvironment. Nat. Med. 24, 1277-1289.
Mor, et al., (1995), Complexity of the cytokine and antibody response elicited by immunizing mice with Plasmodium yoelii circumsporozoite protein plasmid DNA, The Journal of Immunology 155 (4): 2039-2046 (1995).
Robinson et al., The IPD and FMGT/HLA database: allele variant databases, Nucleic Acids Res, 43:D423-D431 (2015).
Sidney, J. et al. (2013) Measurement of MHC/peptide interactions by Gel Filtration or Monoclonal Antibody Capture. Curr. Protoc. Immunol. Chapter 18, Unit-18.3.
Berger, et al., "MHC class II transport at a glance" Cell Science at a Glance, (2019) Journal of Cell Science, 122 p. 1-4.
Caron et al., Analysis of MHC immunopeptidomes using mass spectrometry, Mol Cell Proteomics (2015), doi: 10.1074/mcp.0115.052431.
Hawkins, Oriana E. et al., Identification of Breast Cancer Peptide Epitopes Presented by HLA-A-0201, Journal of Proteome Research, vol. 7, No. 4. Apr. 2008, pp. 1445-1457.
Hickman, et al., "Mining the plasma immunopeptidome for cancer peptides as biomarkers and beyond" PNAS (2010) vol. 107, No. 44, pp. 18747-18748.
Shraibman, et al., "Identification of Tumor Antigens Among the HLA Peptidomes of Glioblastoma Tumors and Plasma" Molecular & Cellular Proteomics 18.6, p. 1255-1268.
Jiang, W. et al., High-throughout engineering and analysis of peptide binding and analysis of peptide, PNAC, vol. 107, No. 30, Jul. 9, 2010, pp. 13258-13263.
Kim, et al., "Divergent paths for the selection of immunodominant epitopes from distinct antigenic sources" (2014) Nature Communications, p. 1-16.
Pathak, et al., "Endocytic Recycling is Required for the Presentation of an Exogenous Peptide via MHC Class II Molecules" Traffic (2000) 1: p. 561-569.
Prilliman, et al., "Large-scale production of class I bound peptides: assigning a signature to HLA-B*1501" Immunogenetics (1997) 45: p. 379-385.
Trolle et al., "The Length Distribution of Class 1-Restricted T Cell Epitopes Is Determined by Both Peptide Supply and MHC Allele-Specific Binding Preference," J Immunol (2016), doi: 10.4049/jimmunol.1501721.
Sercarz, et al., "MHC-Guided processing: Binding of Large Antigen Fragments" Nature-Immunology (2003) vol. 3, p. 621-629.

\* cited by examiner

FIG. 17A

| Data Set | Best Gibb's Solution | #Clusters |
|---|---|---|
| Schuster OvCa104 | DRB1*03:01 \| DRB3*02:02 | 2 |
| Ritz Maver1 DR | DRB1*01:01 \| DRB1*13:01 \| DRB3*02:02 | 2 |
| Schuster OvCa80 | DRB1*01:01 \| DRB1*12:01 \| DRB3*02:02 | 4 |
| Schuster OvCa111 | DRB1*01:01 \| DRB1*03:01 \| DRB3*01:01 | 2 |
| Schuster OvCa64 | DRB1*03:01 \| DRB3*03:01 | 2 |
| Chong meningioma BR | DRB1*11:04 \| DRB3*01:01 | 1 |
| Chong CD165 | DRB1*11:01 \| DRB3*01:01 | 2 |
| Schuster OvCa13 | DRB1*08:01 \| DRB1*13:01 \| DRB3*03:01 | 3 |
| Schuster OvCa72 | DRB1*01:01 \| DRB1*03:01 \| DRB3*01:01 | 7 |
| Ritz DOHH2 DR | DRB1*01:01 \| DRB1*15:01 \| DRB5*01:01 | 2 |
| Mommen MUTZ3 | DRB1*10:01 \| DRB1*11:01 \| DRB3*01:01 | 5 |
| Khodadoust MCL037 | DRB1*11:01 \| DRB3*01:01 | 2 |
| Schuster OvCa105 | DRB1*13:02 \| DRB1*15:01 \| DRB3*03:01 \| DRB5*01:01 | 2 |
| Schuster OvCa84 | DRB1*15:01 \| DRB5*01:01 | 8 |
| Schuster OvCa16 | DRB1*08:01 \| DRB1*13:01 \| DRB1*14:01 \| DRB3*03:01 | 7 |
| Heyder T2 | DRB1*03:01 \| DRB3*01:01 | 5 |
| Schuster OvCa109 | DRB1*01:01 \| DRB1*13:02 \| DRB3*01:01 | 1 |
| Schuster OvCa100 | DRB1*13:03 \| DRB1*15:01 \| DRB3*01:01 \| DRB5*01:01 | 4 |
| Chong TIL3 | DRB1*12:01 \| DRB1*15:01 \| DRB3*01:01 \| DRB5*01:01 | 5 |
| Chong PD42 | DRB1*01:02 \| DRB1*15:01 | 7 |
| Schuster OvCa103 | DRB1*01:01 \| DRB1*15:02 \| DRB5*01:01 | 6 |
| Heyder BAL Patient7 | DRB1*03:01 \| DRB3*01:01 | 7 |
| Neon THP1 | DRB1*01:01 \| DRB1*15:01 \| DRB5*01:01 | 10 |

Legend: Clust. 1, Clust. 2, Clust. 3, Clust. 4, Clust. 5, Clust. 6, Clust. 7, Clust. 8, Clust. 9, Clust. 10, Trash

*DRB1*01:01*

*DRB1*11:01*

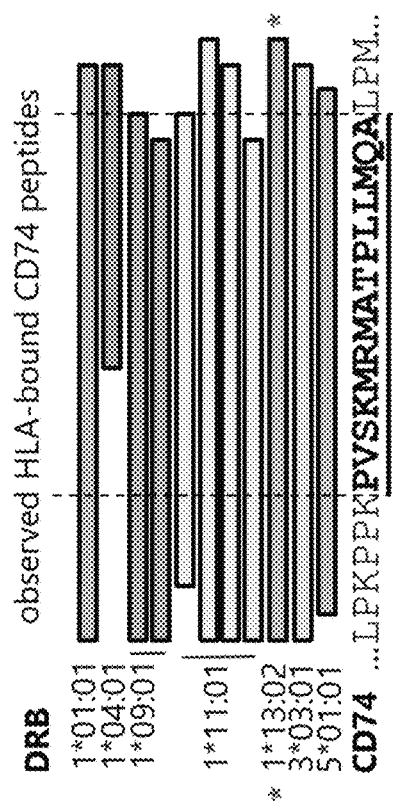
FIG. 25A
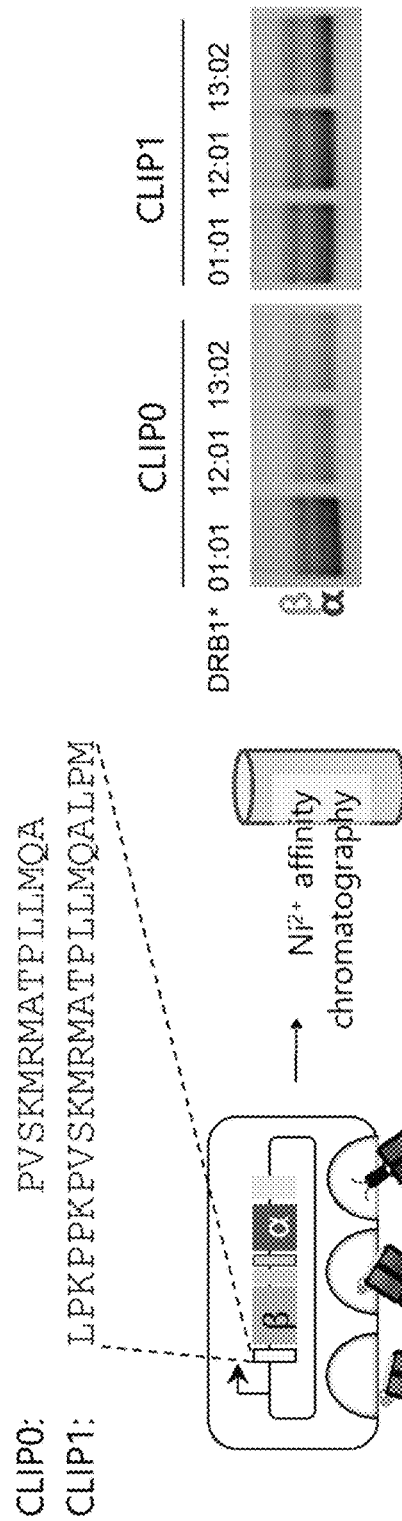
FIG. 25B
FIG. 25C

| Peptide | Average IC50 in nM (n=2) | | IC50 fold change |
|---|---|---|---|
| | L243 purified fDR1 | Ni purified fDR1 | L243 fDR1 to Ni fDR1 |
| Peptide 166 | 453 | 1128 | 2.5 |
| Peptide 165 | 70 | 163 | 2.3 |
| Peptide157 | 315 | 591 | 1.9 |
| Peptide163 | 941 | 1585 | 1.7 |
| Peptide158 | 357 | 542 | 1.5 |
| Peptide159 | 104 | 156 | 1.5 |
| Peptide190 | 992 | 1398 | 1.4 |
| Peptide162 | 3073 | 3384 | 1.1 |
| Peptide164 | 278 | 300 | 1.1 |
| Peptide161 | 946 | 875 | 0.9 |
| Peptide167 | 153 | 142 | 0.9 |
| Peptide189 | 7173 | 6132 | 0.9 |
| Peptide160 | 128 | 106 | 0.8 |
| Peptide191 | 1470 | 1124 | 0.8 |
| HA (Control) | 41 | 33 | 0.8 |

| Peptide | Average IC50 in nM (n=2) | | IC50 fold change |
| --- | --- | --- | --- |
| | Full length DR1 (fDR1) | Soluble DR1 (sDR1) | sDR1 to fDR1 |
| Peptide 161 | 875 | 6076 | 6.9 |
| Peptide 162 | 3384 | 20076 | 5.9 |
| Peptide 163 | 1585 | 8915 | 5.6 |
| Peptide 164 | 300 | 1517 | 5.1 |
| Peptide 190 | 1398 | 6695 | 4.8 |
| Peptide 160 | 106 | 457 | 4.3 |
| Peptide 167 | 142 | 614 | 4.3 |
| Peptide 165 | 163 | 529 | 3.2 |
| Peptide 157 | 591 | 1773 | 3 |
| HA (Control) | 33 | 72 | 2.2 |
| Peptide 158 | 542 | 1155 | 2.1 |
| Peptide 159 | 156 | 331 | 2.1 |
| Peptide 166 | 1128 | 1706 | 1.5 |
| Peptide 191 | 1124 | 1444 | 1.3 |
| Peptide 189 | 6132 | >50,000 | ND |

FIG. 28G

| Neoantigen peptide | NetMHCIIpan affinity (nM) | NetMHCIIpan %Rank | neonmhc2 %Rank | Status |
|---|---|---|---|---|
| GEGLFQPAHRYPDAG | 744 | 39.00% | 0.43% | hit |
| RNQWIKCLGKPVGAEM | 426 | 29.00% | 0.10% | assayed |
| VPAWTRAWRNSSPKG | 395 | 27.00% | 0.51% | hit |
| DGGSYFSLWKIWTQV | 354 | 26.00% | 0.11% | hit |
| LHPELLPLWRLLPDG | 367 | 26.00% | 0.23% | hit |
| PEASLYGALSKGSGG | 353 | 26.00% | 0.24% | hit |
| HEGGFPPILRRAAED | 325 | 24.00% | 0.63% | hit |
| LSPVWCLQWKLSGTD | 293 | 23.00% | 0.31% | hit |
| KNTIVYTTKQVQSCQ | 259 | 21.00% | 0.57% | assayed |
| PATYILILKEFCLVG | 246 | 20.00% | 0.32% | assayed |
| NNEQFQWKIRHVGPE | 222 | 19.00% | 0.50% | hit |
| YKGGYELVKKSQTEL | 200 | 17.00% | 0.37% | assayed |

FIG. 31D

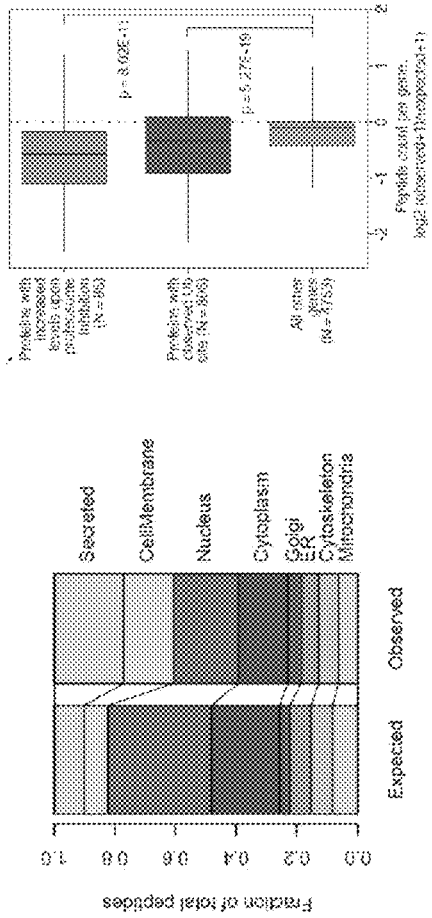
FIG. 32A
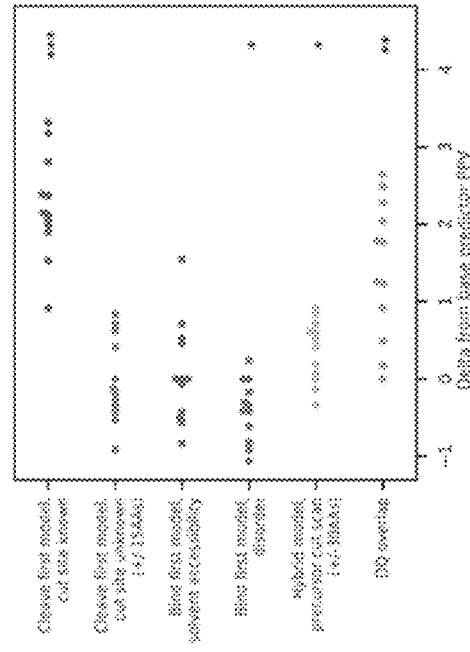
FIG. 32B
FIG. 32C
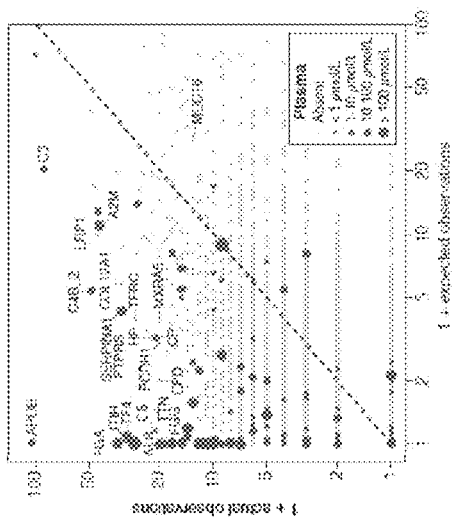
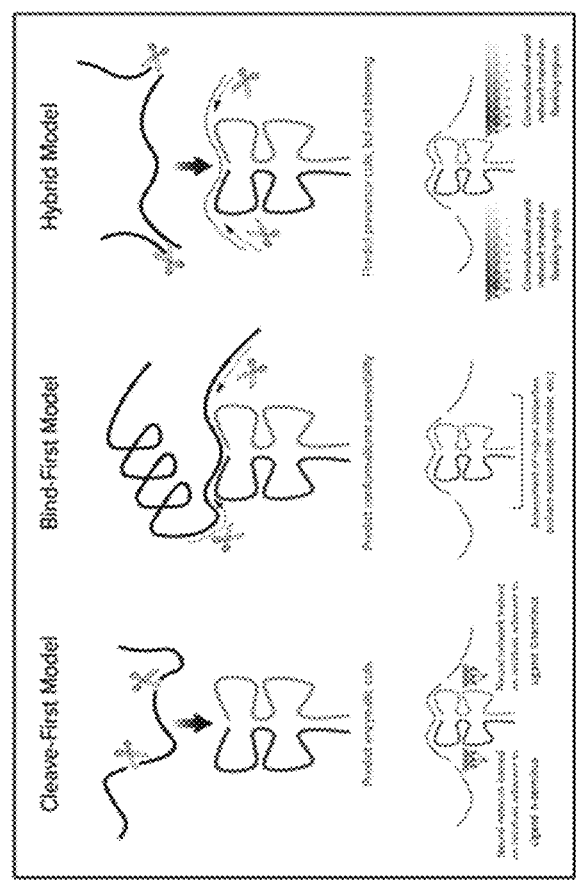
FIG. 32D
FIG. 32E

FIG. 35

| HLA-DRB1*01:01 | | | | | HLA-DRB1*09:01 | | | | | HLA-DRB1*11:01 | | | |
|---|---|---|---|---|---|---|---|---|---|---|---|---|---|
| Peptide and NetMHCIIpan-imputed binding core | NetMHCIIpan affinity | NetMHCIIpan percent rank | Measured affinity | | Peptide and NetMHCIIpan-imputed binding core | NetMHCIIpan affinity | NetMHCIIpan percent rank | Measured affinity | | Peptide and NetMHCIIpan-imputed binding core | NetMHCIIpan affinity | NetMHCIIpan percent rank | Measured affinity |
| ERYEMEDGKYIER | 218 | 31 | 54 | | SRLCPEGKMIISR | 990 | 32 | 5 | | SREYQGIPEAFGKG | 1103 | 43 | 159 |
| SGRNTTLSGETAYTS | 239 | 48 | 17 | | ERTVNDMSMQDVIN | 1132 | 43 | 39 | | SPEEFDEVSRIVNGSVE | 1704 | 65 | 59 |
| KTDGLIPESGKER | 193 | 34 | 12 | | VGGTMVRLGDPPA | 3415 | 80 | 40 | | LAGEKVLMHKAIT | 561 | 34 | 35 |
| LFRYEALRGEQPPG | 179 | 33 | 22 | | KEALEPSGENVIQ | 4850 | 85 | 23 | | SPAEFIDVRDAGYG | 1654 | 60 | 193 |
| EKKWILEGKEILVG | 353 | 60 | 27 | | RQBRILGSVQQLER | 850 | 41 | 22 | | DLEELEVLERKFLAG | 587 | 35 | 63 |
| KEAYHPEVAPDVR | 352 | 46 | 17 | | IDRALNEACESVIQ | 2919 | 75 | 262 | | GRNTVEANERFGSRNG | 853 | 45 | 79 |
| GAETEHDGGYEVAHQ | 332 | 55 | 78 | | NEUNLEEAKGLLODLR | 758 | 42 | 64 | | EFRKNWINKQQMEG | 611 | 36 | 12 |
| GRLDLQQPAEIFES | 212 | 46 | 189 | | DSKSLRTALQEITTR | 847 | 45 | 23 | | DFTEESVIDKFPG | 814 | 32 | 209 |
| LGRNEDEQKSERINSG | 131 | 36 | 18 | | TGGIMPAIERLL | 937 | 30 | 21 | | LMELEPIEKGGHGS | 977 | 40 | 67 |
| NPSFVRSDSBRQAB | 143 | 29 | 3 | | GLDMLKABVSQVEADL | 619 | 35 | 17 | | DVRHYAYVTREKSYR | 588 | 35 | 223 |
| GLRYKKLHDFKGKNIT | 189 | 40 | 30 | | DEERFYARDIRDDL | 1025 | 45 | 127 | | LAFTWEELSKKEFPG | 8213 | 95 | 174 |
| HIEKEHEAARNKNG | 234 | 44 | 38 | | EFAPALRAAKSAPER | 561 | 38 | 15 | | KRNEVIFMEHSAVD | 1199 | 44 | 36 |
| SVQRGLVGEIKR | 120 | 20 | 9 | | RRSYYRVEHTVD | 1759 | 60 | 76 | | EPYTARMEKIIDO | 421 | 18 | 128 |
| TWFNQPAKKLR | 155 | 7 | 8 | | NAVETVEAQNYADDN | 725 | 44 | 72 | | EEDMPKNMLAGGRLD | 297 | 18 | 254 |
| EFKKYEMMEMBER | 529 | 55 | 114 | | RDLAZYDAAHNEEF | 1227 | 50 | 297 | | NMGAYKVETRKVDFY | 308 | 19 | 12 |
| SPRAETEKTEGSETDL | 1100 | 75 | 333 | | | | | | | GGGTTYEQEKIVE | 685 | 20 | 145 |

| peptide | status | # Positive Wells | Well1 | Well2 | Well3 | Well4 | Well5 | Well6 | Well7 | Well8 |
|---|---|---|---|---|---|---|---|---|---|---|
| GEGLFQPAHRYPDAG | induction hit | 4 | 3.28 | 3.5 | 3.87 | 3.33 | 0.81 | | | |
| RNQWKCLGKPVGAEM | assayed | 0 | 1.88 | -1.44 | -1.27 | -15.43 | -10.18 | -0.09 | | |
| VPAWTRAWRNSSPKG | induction hit | 2 | 3.53 | 0.4 | -0.36 | 2.93 | 2.2 | 6.3 | | |
| LHPELLPLMRLLDDG | induction hit | 1 | -1.26 | 0.46 | -0.36 | -1.74 | 0.75 | 3.92 | | |
| DGGSYFSLMKIMWTQV | induction hit | 5 | 4.83 | 3.84 | 4.34 | 13.8 | 8.1 | | | |
| PEASLYGALSKGSGG | induction hit | 5 | 1.96 | 7.42 | 1.09 | 5.24 | 6.03 | 1.72 | 12.93 | 9.74 |
| HEGGFPPLLRRAAED | induction hit | 5 | -0.36 | 3.58 | 2.58 | -22.75 | 6.59 | 3.5 | 8.44 | 10.39 |
| LSPVWKCLQWKLSGTD | induction hit | 2 | -0.08 | 2.52 | 0.71 | 13.27 | 11.32 | | | |
| KNTIVYTKQVQSCQ | assayed | 0 | -1.19 | | | | | | | |
| PATYILIKEFCLVG | assayed | 0 | -0.02 | 0.69 | 1.47 | -0.17 | | | | |
| NNEGFCWKIHHVGPE | induction hit | 4 | 5.44 | 5.7 | 0.93 | 2.97 | 5.1 | 4.5 | | |
| YKGGYELVKKSQTEL | assayed | 0 | 2.28 | -2.01 | -2.31 | | | | | |

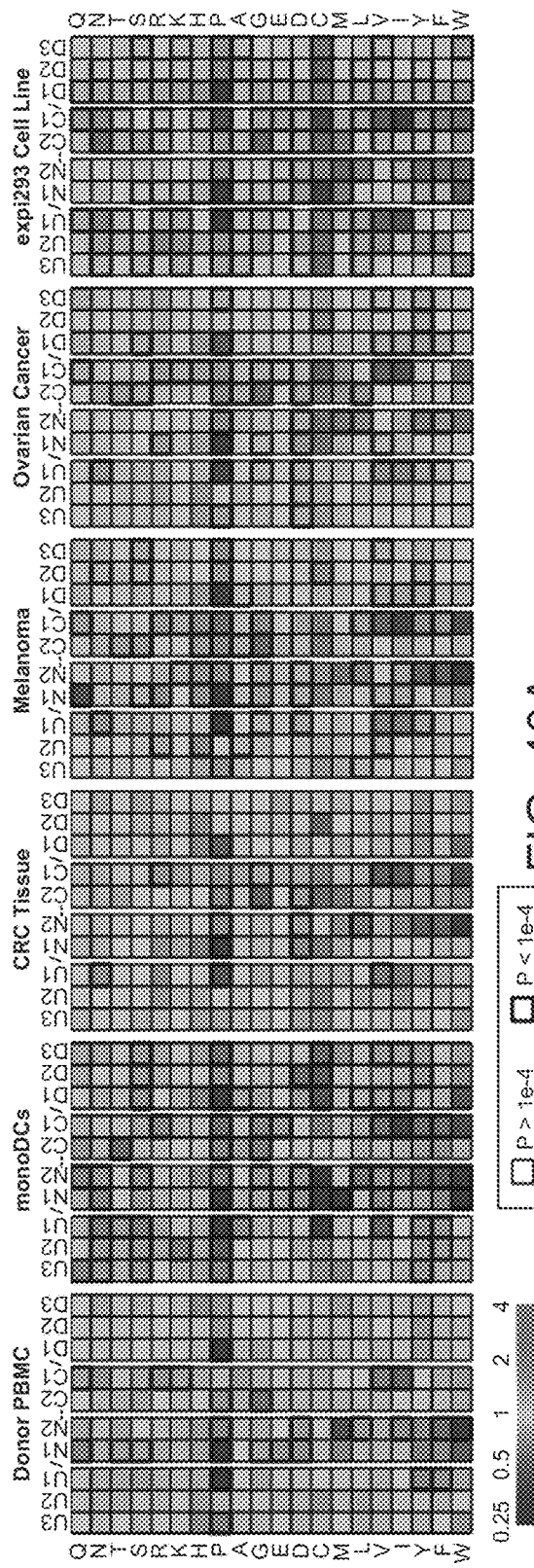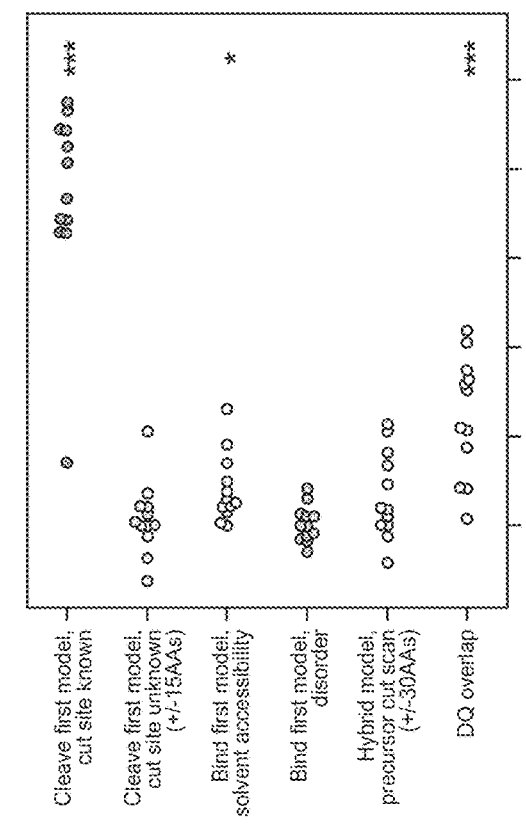
FIG. 40A
FIG. 40B

SEQUENCE LISTING

<160> NUMBER OF SEQ ID NOS: 96

<210> SEQ ID NO 1
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Pro Val Ser Lys Met Arg Met Ala Thr Pro Leu Leu Met Gln Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Glu Ala Ser Leu Tyr Gly Ala Leu Ser Lys Gly Ser Gly Gly
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Ala Thr Tyr Ile Leu Ile Leu Lys Glu Phe Cys Leu Val Gly
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 4-15 residues

<400> SEQUENCE: 4

His His His His His His His His His His His His His His His
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His His His His His His His His
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6
```

```
Glu Gly Arg Gly Ser Leu Thr Cys Gly Asp Val Glu Asn Pro Gly Pro
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Thr Asn Phe Ser Leu Lys Gln Ala Gly Asp Val Glu Asn Pro Gly
1               5                   10                  15

Pro

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Cys Thr Asn Tyr Ala Leu Lys Leu Ala Gly Asp Val Glu Ser Asn
1               5                   10                  15

Pro Gly Pro

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Lys Gln Thr Leu Asn Phe Asp Leu Lys Leu Ala Gly Asp Val Glu
1               5                   10                  15

Ser Asn Pro Gly Pro
            20

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ser Gly Gly Ser Gly Gly Ser Ala Gly Gly
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Leu Asn Asp Ile Phe Glu Ala Gln Lys Ile Glu Trp His Glu
```

```
1               5                   10                  15
```

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Ser Gly Gly Ser Gly Gly Ser Ala Gly Gly Leu Asn Asp Ile Phe
1               5                   10                  15

Glu Ala Gln Lys Ile Glu Trp His Glu
            20                  25
```

<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Gly Ser Tyr Pro Tyr Asp Val Pro Asp Tyr Ala
1               5                   10
```

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
His His His His His His
1               5
```

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gly Lys Ala Pro Ile Leu Ile Ala Thr Asp Val Ala Ser Arg Gly Leu
1               5                   10                  15

Asp Val
```

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Lys Ala Pro Ile Leu Ile Ala Thr Asp Val Ala Ser Arg Gly Leu
1               5                   10                  15

Asp

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ala Pro Ile Leu Ile Ala Thr Asp Val Ala Ser Arg Gly Leu Asp
1               5                   10                  15

Val

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Ala Pro Ile Leu Ile Ala Thr Asp Val Ala Ser Arg Gly Leu Asp
1               5                   10                  15

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His His His His His His His His His His
1               5                   10

<210> SEQ ID NO 21
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Pro Lys Pro Pro Lys Pro Val Ser Lys Met Arg Met Ala Thr Pro
1               5                   10                  15

Leu Leu Met Gln Ala Leu Pro Met
            20

```
<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Pro Leu Lys Met Leu Asn Ile Pro Ser Ile Asn Val His
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Lys Tyr Val Lys Gln Asn Thr Leu Lys Leu Ala Thr
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Pro Val Val His Phe Phe Lys Asn Ile Val Thr Pro Arg Thr Pro Pro
1               5                   10                  15

Tyr

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Tyr Ala Thr Phe Phe Ile Lys Ala Asn Ser Lys Phe Ile Gly Ile Thr
1               5                   10                  15

Glu

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Leu Ser Val Thr Phe Ile Gly Ala Ala Pro Leu Ile Leu Ser Tyr
1               5                   10                  15

<210> SEQ ID NO 27
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 27

Pro Val Val His Phe Phe Lys Asn Ile Val Thr Pro Arg Thr Pro Pro
1               5                   10                  15

Tyr

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Ala Arg Ile Arg Arg Asp Gly Cys Leu Leu Arg Leu Val Asp
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Leu Ser Val Thr Phe Ile Gly Ala Ala Pro Lys Ile Leu Ser Tyr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ala Arg Ile Lys Arg Asp Gly Cys Leu Leu Arg Leu Val Asp
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Pro Ile Asp Gly Tyr Pro Asn His Pro Cys Phe Glu Pro Glu
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Pro Gln Ile Leu Pro Tyr Pro Ala Pro Glu Glu Ala Gln Glu Asn
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Gln Leu Arg Gln Trp Trp Ala Gln Gly Ala Asp Pro Leu Ala
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Leu Arg Pro Gly Gln Ile Val Ala Phe Asp Ser Thr Ala Gln
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ser Leu Arg Ser Trp Pro Ser Thr Trp Ala Pro Trp Ala Ser
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Lys Ser Val Val Cys Glu Ala Leu
1               5

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Pro Asn Gly Gly Phe Ala Ser Ile Leu Leu Tyr Lys Ile Glu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Phe Cys Lys Gly Ser Phe Ala Ser Ile Leu Lys Leu Leu Gly Glu Phe
1               5                   10                  15

<210> SEQ ID NO 39
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(19)
<223> OTHER INFORMATION: Any amino acid

<400> SEQUENCE: 39

Gly Asp Thr Gly Leu Xaa Xaa Xaa Xaa Xaa Xaa Xaa Xaa Xaa Xaa
1               5                   10                  15

Xaa Xaa Xaa Gly Gly Gly Gly Ser Leu Val Pro Arg Gly Ser Gly Gly
            20                  25                  30

Gly Gly Ser Gly Asp Thr Arg Pro Arg Phe
        35                  40

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Tyr Glu Met Glu Asp Gly Lys Val Ile Glu Arg
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly His Met Thr Thr Leu Ser Gly Glu Glu Ile Ser Tyr Thr Gly
1               5                   10                  15

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Thr Phe Asp Gln Leu Thr Pro Glu Glu Ser Lys Glu Arg
1               5                   10

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 43

Leu Pro Arg Tyr Glu Ala Leu Arg Gly Glu Gln Pro Pro Asp
1               5                   10

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Lys Lys Asn Ile Ile Leu Glu Glu Gly Lys Glu Ile Leu Val Gly
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Glu Ala Ala Tyr His Pro Glu Val Ala Pro Asp Val Arg
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Ala Glu Phe Arg His Asp Ser Gly Tyr Glu Val His His Gln
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly His Pro Asp Leu Gln Gly Gln Pro Ala Glu Glu Ile Phe Glu Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Gly Lys Asn Phe Asp Phe Gln Lys Ser Asp Arg Ile Asn Ser Glu
1               5                   10                  15

<210> SEQ ID NO 49
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Pro Ser Phe Val Pro Ser Asp Gly Arg Gln Ala Ala Asp
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Leu Arg Tyr Lys Lys Leu His Asp Pro Lys Gly Trp Ile Thr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Ile Glu Lys Phe Glu Lys Glu Ala Ala Glu Met Gly Lys Gly
1               5                   10                  15

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Val Gln Arg Gly Leu Val Gly Glu Ile Ile Lys Arg
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Trp Phe Asn Gln Pro Ala Arg Lys Ile Arg
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

Glu Phe Lys Lys Tyr Glu Met Met Lys Glu His Glu Arg Arg
1               5                   10

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Pro His Ala Phe Lys Thr Glu Ser Gly Glu Glu Thr Asp Leu
1               5                   10                  15

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Asn Leu Cys Pro Ser Gly Ser Asn Ile Ile Ser Asn
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Glu Arg Pro Tyr Trp Asp Met Ser Asn Gln Asp Val Ile Asn
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Gly Gly Thr Met Val Arg Ser Gly Gln Asp Pro Tyr Ala
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Glu Ala Leu Glu Pro Ser Gly Glu Asn Val Ile Gln
1               5                   10

<210> SEQ ID NO 60
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 60

Arg Gln Arg Arg Leu Leu Gly Ser Val Gln Gln Asp Leu Glu Arg
1               5                   10                  15

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Asp Arg Ala Leu Asn Glu Ala Cys Glu Ser Val Ile Gln
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Glu Asn Asn Leu Glu Ser Ala Lys Gly Leu Leu Asp Asp Leu Arg
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Asp Ser Lys Ser Leu Arg Thr Ala Leu Gln Lys Glu Ile Thr Thr Arg
1               5                   10                  15

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Gly Gly Asp Ile Asn Ala Ala Ile Glu Arg Leu Leu
1               5                   10

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Leu Asp Asn Leu Lys Ala Ser Val Ser Gln Val Glu Ala Asp Leu
1               5                   10                  15

```
<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Glu Arg Arg Phe Lys Ala Ala Asp Leu Asn Gly Asp Leu
1               5                   10

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Pro Ala Pro Ala Leu Arg Ser Ala Arg Ser Ala Pro Glu Asn
1               5                   10                  15

<210> SEQ ID NO 68
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Thr Ser Tyr Val Thr Ser Val Glu Glu Asn Thr Val Asp
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Ala Val Glu Phe Gln Glu Ala Gln Ala Tyr Ala Asp Asp Asn
1               5                   10                  15

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Arg Asp Leu Ala Gln Tyr Asp Ala Ala His His Glu Glu Phe
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71
```

```
Gly Gln Gln Trp Thr Tyr Glu Gln Arg Lys Ile Val Glu
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Gly Glu Tyr Gln Gly Ile Pro Arg Ala Glu Ser Gly Gly
1               5                   10

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Pro Glu Glu Phe Asp Glu Val Ser Arg Ile Val Gly Ser Val Glu
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Ala Gly Glu Trp Gln Val Leu His Arg Glu Gly Ala Ile Thr
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Pro Ala Glu Phe Ile Ile Asp Thr Arg Asp Ala Gly Tyr Gly
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Leu Glu Glu Leu Glu Val Leu Glu Arg Lys Pro Ala Ala Gly
1               5                   10                  15

<210> SEQ ID NO 77
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 77

Gly Met Asn Ile Val Glu Ala Met Glu Arg Phe Gly Ser Arg Asn Gly
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Phe Asn Trp Asn Trp Ile Asn Lys Gln Gln Gly Lys Arg Gly
1               5                   10                  15

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Pro Phe Ser Phe Ser Val Ile Asp Lys Pro Pro Gly
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Asn Glu Leu Lys Pro Ile Ser Lys Gly Gly His Ser Ser
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Val Asn Glu Tyr Ala Pro Val Phe Lys Glu Lys Ser Tyr Lys
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Ala Pro Thr Trp Glu Glu Leu Ser Lys Lys Glu Phe Pro Gly
1               5                   10                  15
```

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Arg Asn Glu Val Ile Pro Met Ser His Pro Gly Ala Val Asp
1               5                   10                  15

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Asn Pro Tyr Phe Ala Pro Asn Pro Lys Ile Ile Arg Gln
1               5                   10

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Glu Asp Lys Phe Arg Asn Asn Leu Lys Gly Lys Arg Leu Asp
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Asn Gly Ala Tyr Lys Val Glu Thr Lys Lys Tyr Asp Phe Tyr
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Glu Gly Leu Phe Gln Pro Ala His Arg Tyr Pro Asp Ala Gly
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 88

Arg Asn Gln Trp Lys Cys Leu Gly Lys Pro Val Gly Ala Glu Met
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Val Pro Ala Trp Thr Arg Ala Trp Arg Asn Ser Ser Pro Lys Gly
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu His Pro Glu Leu Leu Pro Leu Trp Arg Leu Leu Pro Asp Gly
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Gly Gly Ser Tyr Phe Ser Leu Trp Lys Ile Trp Thr Gln Val
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Glu Gly Gly Phe Pro Pro Leu Leu Arg Arg Ala Ala Glu Asp
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Leu Ser Pro Val Trp Cys Leu Gln Trp Lys Leu Ser Gly Thr Asp
1               5                   10                  15

<210> SEQ ID NO 94
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 94

Lys Asn Thr Ile Val Tyr Thr Thr Lys Gln Val Gln Ser Cys Gln
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Asn Asn Glu Gln Phe Gln Trp Lys Ile Arg His Val Gly Pro Glu
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Tyr Lys Gly Gly Tyr Glu Leu Val Lys Lys Ser Gln Thr Glu Leu
1               5                   10                  15
```

METHOD AND SYSTEMS FOR PREDICTION OF HLA CLASS II-SPECIFIC EPITOPES AND CHARACTERIZATION OF CD4+ T CELLS

CROSS-REFERENCE

This application is a continuation of International Application No. PCT/US2019/068084 filed Dec. 20, 2019 which claims the benefit of U.S. Provisional Application No. 62/891,101, filed on Aug. 23, 2019; U.S. Provisional Application No. 62/855,379, filed on May 31, 2019; U.S. Provisional Application No. 62/826,827, filed on Mar. 29, 2019; and 62/783,914, filed on Dec. 21, 2018; each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jan. 31, 2020, is named 50401-735_301_SL.txt and is 27,415 bytes in size.

BACKGROUND

The major histocompatibility complex (MHC) is a gene complex encoding human leukocyte antigen (HLA) genes. HLA genes are expressed as protein heterodimers that are displayed on the surface of human cells to circulating T cells. HLA genes are highly polymorphic, allowing them to fine-tune the adaptive immune system. Adaptive immune responses rely, in part, on the ability of T cells to identify and eliminate cells that display disease-associated peptide antigens bound to human leukocyte antigen (HLA) heterodimers.

In humans, endogenous and exogenous proteins can be processed into peptides by the proteasome and by cytosolic and endosomal/lysosomal proteases and peptidases and presented by two classes of cell surface proteins encoded by MHC genes. These cell surface proteins are referred to as human leukocyte antigens (HLA class I and class II), and the group of peptides that bind them and elicit immune responses are termed HLA epitopes. HLA epitopes are a key component that enables the immune system to detect danger signals, such as pathogen infection and transformation of self. CD4+ T cells recognize class II MHC (HLA-DR, HLA-DQ, and HLA-DP) epitopes displayed on antigen presenting cells (APCs), such as dendritic cells and macrophages. The endogenous processing and presentation of HLA class II-ligands is a complex procedure and involves a variety of chaperones and a subset of enzymes that are not all well characterized. HLA class II-peptide presentation activates helper T cells, subsequently promoting B cell differentiation and antibody production as well as CTL responses. Activated helper T cells also secrete cytokines and chemokines that activate and induce differentiation of other T cells.

Understanding the peptide-binding preferences of every HLA class II heterodimer is the key to successfully predicting which cancer or tumor-specific antigens are likely to elicit the cancer or tumor-specific T cell responses. There is a need for methods of identifying and isolating specific HLA class II-associated peptides (e.g., neoantigen peptides). Such methodology and isolated molecules are useful, e.g., for the development of therapeutics, including but not limited to, immune based therapeutics.

SUMMARY

The methods and compositions described herein find uses in a wide range of applications. For example, the methods and compositions described herein can be used to identify immunogenic antigen peptides and can be used to develop drugs, such as personalized medicine drugs, and isolation and characterization of antigen-specific T cells.

CD4+ T cell responses may have anti-tumor activity. A high rate of CD4+ T cell responses may be shown without using Class II prediction (e.g., 60% of SLP epitopes in NeoVax study (49% in NT-001, see Ott et al., Nature, 2017 Jul. 13; 547(7662):217-221), and 48% of mRNA epitopes in Biontech study, see Sahin et al., Nature, 2017 Jul. 13; 547(7662):222-226). It may not be clear whether these epitopes are typically presented natively (by tumor or by phagocytic DCs). It may be desirable to translate high CD4+T response rates into therapeutic efficacy by improving identification of truly presented HLA class II binding epitopes.

The roles of gene expression, enzymatic cleavage, and pathway/localization bias may have not been robustly quantified. It may be unclear whether autophagy (HLA class II presentation by tumor cells) or phagocytosis (HLA class II presentation of tumor epitopes by APCs) is the more relevant pathway, although most existing MS data may be presumed to derive from autophagy. NetMHCIIpan may be the current prediction standard, but it may not be regarded as accurate. Of the three HLA class II loci (DR, DP, and DQ), data may only exist for certain common alleles of HLA-DR.

There may be different data generation approaches for learning the rules of HLA Class II presentation, including the field standard and the proposed approach. The field standard may comprise affinity measurements, which may be the basis for the NetMHCIIpan predictor, providing low throughput and requiring radioactive reagents, and it misses the role of processing. The proposed approach may comprise mass spectrometry, where data from cell lines/tissues/tumors may help determine processing rules for autophagy and mono-allelic MS may enable determination of allele-specific binding rules (multi-allelic MS data is presumed overly complex for efficient learning (Bassani-Sternberg. MCP. 2018)).

There may be different ways to validate the new HLA class II predictors: validation on held-out MS data, which may be default setting; retrospective of vaccine studies (e.g. NT-001), where immune monitoring data may assess vaccine peptide loading on APCs rather than tumor presentation and data may be thinly stretched across many different alleles; biochemical affinity measurements, which may be configured to get measurements for discordantly predicted peptides (only for 2-3 alleles); T cell inductions, which may be configured to test the rates at which Neon-preferred and NetMHCIIpan-preferred epitopes induce ex vivo T cell responses.

For validation through T cell inductions, the default approach may comprise assessing neoORFs from TCGA that are discordantly predicted, wherein induction materials may comprise healthy donor APCs and T cells and induction and readout may be via SLP (~15mer peptides). Random peptides may give a high rate of responses and SLP may insufficiently address processing. Possible solutions may comprise induction via mRNA.

The methods disclosed herein may comprise generating LC-MS/MS mono-allelic data for the training of allele-specific machine learning methods for epitope prediction.

Such methods may comprise increasing LC-MS/MS data quality utilizing a set of quality metrics to stringently remove false positives that increases the performance of a prediction model; identifying allele-specific HLA class II binding cores from HLA-ligandome LC-MS/MS datasets; utilizing machine learning algorithms to improve HLA class II-ligand and epitope prediction; and/or identifying biological variables that impact HLA class II-ligand presentation and improve HLA class II epitope prediction, such as gene expression, cleavability, gene bias, cellular localization, and secondary structure.

Provided herein is a method comprising: (a) processing amino acid information of a plurality of candidate peptide sequences using a machine learning HLA peptide presentation prediction model to generate a plurality of presentation predictions, wherein each candidate peptide sequence of the plurality of candidate peptide sequences is encoded by a genome or exome of a subject, wherein the plurality of presentation predictions comprises an HLA presentation prediction for each of the plurality of candidate peptide sequences, wherein each HLA presentation prediction is indicative of a likelihood that one or more proteins encoded by a class II HLA allele of a cell of the subject can present a given candidate peptide sequence of the plurality of candidate peptide sequences, wherein the machine learning HLA peptide presentation prediction model is trained using training data comprising sequence information of sequences of training peptides identified by mass spectrometry to be presented by an HLA protein expressed in training cells; and (b) identifying, based at least on the plurality of presentation predictions, a peptide sequence of the plurality of peptide sequences as being presented by at least one of the one or more proteins encoded by a class II HLA allele of a cell of the subject; wherein the machine learning HLA peptide presentation prediction model has a positive predictive value (PPV) of at least 0.07 according to a presentation PPV determination method.

Provided herein is a method comprising: (a) processing amino acid information of a plurality of peptide sequences of encoded by a genome or exome of a subject using a machine learning HLA peptide binding prediction model to generate a plurality of binding predictions, wherein the plurality of binding predictions comprises an HLA binding prediction for each of the plurality of candidate peptide sequences, each binding prediction indicative of a likelihood that one or more proteins encoded by a class II HLA allele of a cell of the subject binds to a given candidate peptide sequence of the plurality of candidate peptide sequences, wherein the machine learning HLA peptide binding prediction model is trained using training data comprising sequence information of sequences of peptides identified to bind to an HLA class II protein or an HLA class II protein analog; and (b) identifying, based at least on the plurality of binding predictions, a peptide sequence of the plurality of peptide sequences that has a probability greater than a threshold binding prediction probability value of binding to at least one of the one or more proteins encoded by a class II HLA allele of a cell of the subject; wherein the machine learning HLA peptide binding prediction model has a positive predictive value (PPV) of at least 0.1 according to a binding PPV determination method.

In some embodiments, the machine learning HLA peptide presentation prediction model is trained using training data comprising sequence information of sequences of training peptides identified by mass spectrometry to be presented by an HLA protein expressed in training cells.

In some embodiments, the method comprises ranking, based on the presentation predictions, at least two peptides identified as being presented by at least one of the one or more proteins encoded by a class II HLA allele of a cell of the subject.

In some embodiments, the method comprises selecting one or more peptides of the two or more ranked peptides.

In some embodiments, the method comprises selecting one or more peptides of the plurality that were identified as being presented by at least one of the one or more proteins encoded by a class II HLA allele of a cell of the subject.

In some embodiments, the method comprises selecting one or more peptides of two or more peptides ranked based on the presentation predictions.

In some embodiments, the machine learning HLA peptide presentation prediction model has a positive predictive value (PPV) of at least 0.07 when amino acid information of a plurality of test peptide sequences are processed to generate a plurality of test presentation predictions, each test presentation prediction indicative of a likelihood that the one or more proteins encoded by a class II HLA allele of a cell of the subject can present a given test peptide sequence of the plurality of test peptide sequences, wherein the plurality of test peptide sequences comprises at least 500 test peptide sequences comprising (i) at least one hit peptide sequence identified by mass spectrometry to be presented by an HLA protein expressed in cells and (ii) at least 499 decoy peptide sequences contained within a protein encoded by a genome of an organism, wherein the organism and the subject are the same species, wherein the plurality of test peptide sequences comprises a ratio of 1:499 of the at least one hit peptide sequence to the at least 499 decoy peptide sequences and a top percentage of the plurality of test peptide sequences are predicted to be presented by the HLA protein expressed in cells by the machine learning HLA peptide presentation prediction model.

In some embodiments, the machine learning HLA peptide presentation prediction model has a positive predictive value (PPV) of at least 0.1 when amino acid information of a plurality of test peptide sequences are processed to generate a plurality of test binding predictions, each test binding prediction indicative of a likelihood that the one or more proteins encoded by a class II HLA allele of a cell of the subject binds to a given test peptide sequence of the plurality of test peptide sequences, wherein the plurality of test peptide sequences comprises at least 20 test peptide sequences comprising (i) at least one hit peptide sequence identified by mass spectrometry to be presented by an HLA protein expressed in cells and (ii) at least 19 decoy peptide sequences contained within a protein comprising at least one peptide sequence identified by mass spectrometry to be presented by an HLA protein expressed in cells, such as a single HLA protein expressed in cells (e.g., mono-allelic cells), wherein the plurality of test peptide sequences comprises a ratio of 1:19 of the at least one hit peptide sequence to the at least 19 decoy peptide sequences and a top percentage of the plurality of test peptide sequences are predicted to bind to the HLA protein expressed in cells by the machine learning HLA peptide presentation prediction model.

In some embodiments, no amino acid sequence overlap exist among the at least one hit peptide sequence and the decoy peptide sequences.

In some embodiments, the machine learning HLA peptide presentation prediction model has a positive predictive value (PPV) of at least 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98 or 0.99.

In some embodiments, the at least one hit peptide sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 hit peptide sequences.

In some embodiments, the at least 499 decoy peptide sequences comprises at least 500 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 decoy peptide sequences. One of skill in the art is able to recognize that changing the ratio of hit: decoy changes the PPV.

In some embodiments, the at least 500 test peptide sequences comprises at least 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 test peptide sequences.

In some embodiments, the top percentage is a top 0.20%, 0.30%, 0.40%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90%, 5.00%, 5.10%, 5.20%, 5.30%, 5.40%, 5.50%, 5.60%, 5.70%, 5.80%, 5.90%, 6.00%, 6.10%, 6.20%, 6.30%, 6.40%, 6.50%, 6.60%, 6.70%, 6.80%, 6.90%, 7.00%, 7.10%, 7.20%, 7.30%, 7.40%, 7.50%, 7.60%, 7.70%, 7.80%, 7.90%, 8.00%, 8.10%, 8.20%, 8.30%, 8.40%, 8.50%, 8.60%, 8.70%, 8.80%, 8.90%, 9.00%, 9.10%, 9.20%, 9.30%, 9.40%, 9.50%, 9.60%, 9.70%, 9.80%, 9.90%, 10%, 11%, 12%, 13%, 14%, 15%, 16%, 17%, 18%, 19% or 20%.

In some embodiments, the at least one hit peptide sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 hit peptide sequences.

In some embodiments, the at least 19 decoy peptide sequences comprises at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 decoy peptide sequences.

In some embodiments, the at least 20 test peptide sequences comprises at least wherein the at least 500 test peptide sequences comprises at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 test peptide sequences test peptide sequences.

In some embodiments, the top percentage is a top 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%.

In some embodiments, the PPV is greater than the respective PPV of column 2 of Table 11 for the protein encoded by the corresponding HLA allele of Table 11. In some embodiments, the PPV is at least equal to the respective PPV of column 3 of Table 11 for the protein encoded by the corresponding HLA allele of Table 11.

In some embodiments, the PPV is equal to or greater than the respective PPV of column 2 of Table 12 for the protein encoded by an HLA class II allele.

In some embodiments, the PPV is greater than the respective PPV of column 2 of Table 16 for the protein encoded by an HLA class II allele.

In some embodiments, the subject is a single subject.
In some embodiments, the subject is a mammal.
In some embodiments, the subject is a human.
In some embodiments, the training cells are cells expressing a single protein encoded by a class II HLA allele of a cell of the subject.

In some embodiments, the training cells are monoallelic HLA cells, or cells expressing an HLA allele with an affinity tag.

In some embodiments, the cell of the subject comprises cancer cells.

In some embodiments, the method is for identifying peptide sequences.

In some embodiments, the method is for selecting peptide sequences.

In some embodiments, the method is for preparing a cancer therapy.

In some embodiments, the method is for preparing a subject-specific cancer therapy.

In some embodiments, the method is for preparing a cancer cell-specific cancer therapy.

In some embodiments, each peptide sequence of the plurality of peptide sequences is associated with a cancer.

In some embodiments, at least one peptide sequence of the plurality of peptide sequences is overexpressed by a cancer cell of the subject.

In some embodiments, each peptide sequence of the plurality of peptide sequences is overexpressed by a cancer cell of the subject.

In some embodiments, at least one peptide sequence of the plurality of peptide sequences is a cancer cell-specific peptide.

In some embodiments, each peptide sequence of the plurality of peptide sequences is a cancer cell-specific peptide.

In some embodiments, each peptide sequence of the plurality of peptide sequences is expressed by a cancer cell of the subject.

In some embodiments, at least one peptide sequence of the plurality of peptide sequences is not encoded by a non-cancer cell of the subject.

In some embodiments, each peptide sequence of the plurality of peptide sequences is not encoded by a non-cancer cell of the subject.

In some embodiments, at least one peptide sequence of the plurality of peptide sequences is not expressed by a non-cancer cell of the subject In some embodiments, each peptide sequence of the plurality of peptide sequences is not expressed by a non-cancer cell of the subject.

In some embodiments, the method comprises obtaining the plurality of peptide sequences of the subject.

In some embodiments, the method comprises obtaining a plurality of polynucleotide sequences of the subject.

In some embodiments, the method comprises obtaining a plurality of polynucleotide sequences of the subject that encodes the plurality of peptide sequences encoded by a genome or exome of a subject, or by a pathogen or virus in the subject.

In some embodiments, the method comprises obtaining a plurality of polynucleotide sequences of the subject that encodes the plurality of peptide sequences encoded by a genome or exome of a subject by a computer processor.

In some embodiments, the method comprises obtaining a plurality of polynucleotide sequences of the subject by genomic or exomic sequencing.

In some embodiments, the method comprises obtaining a plurality of polynucleotide sequences of the subject by whole genome sequencing or whole exome sequencing.

In some embodiments, processing comprises processing by a computer processor

In some embodiments, processing comprises generating a plurality of predictor variables based at least on the amino acid information of the plurality of peptide sequences In some embodiments, processing the plurality of predictor variables using the machine-learning HLA-peptide presentation prediction model.

In some embodiments, the that one or more proteins encoded by a class II HLA allele of a cell of the subject are one or more proteins encoded by a class II HLA allele that are expressed by the subject.

In some embodiments, the that one or more proteins encoded by a class II HLA allele of a cell of the subject are one or more proteins encoded by a class II HLA allele that are expressed by cancer cells of the subject.

In some embodiments, the that one or more proteins encoded by a class II HLA allele of a cell of the subject is a single protein encoded by a class II HLA allele of a cell of the subject.

In some embodiments, the that one or more proteins encoded by a class II HLA allele of a cell of the subject is two, three, four, five or six or more proteins encoded by a class II HLA allele of a cell of the subject.

In some embodiments, the that one or more proteins encoded by a class II HLA allele of a cell of the subject is each protein encoded by a class II HLA allele of a cell of the subject.

In some embodiments, the method further comprises administering to the subject a composition comprising one or more of the selected sub-set of peptide sequences.

In some embodiments, identifying the plurality of peptide sequences comprises comparing DNA, RNA, or protein sequences from cancer cells of the subject to DNA, RNA, or protein sequences from normal cells of the subject, wherein each of the plurality of the peptides comprise at least one mutation, which is present in the cancer cell of the subject, and not present in the normal cell of the subject.

In some embodiments, the machine-learning HLA-peptide presentation prediction model comprises a plurality of predictor variables identified at least based on the training data, wherein the training data comprises training peptide sequence information comprising amino acid position information, wherein the training peptide sequence information is associated with the HLA protein expressed in cells; and a function representing a relation between the amino acid position information and the presentation likelihood generated as output based on the amino acid position information and the plurality of predictor variables.

In some embodiments, identifying comprises identifying, based at least on the plurality of presentation predictions, a peptide sequence of the plurality of peptide sequences that has a probability greater than a threshold presentation prediction probability value of being presented by at least one of the one or more proteins encoded by a class II HLA allele of a cell of the subject.

In some embodiments, one or more of the 0.2% of the plurality of test peptide sequences predicted to be presented by the by the machine learning HLA peptide presentation prediction model has a probability greater than the threshold presentation prediction probability value of being presented by at least one of the one or more proteins encoded by a class II HLA allele of a cell of the subject.

In some embodiments, each of the 0.2% of the plurality of test peptide sequences predicted to be presented by the by the machine learning HLA peptide presentation prediction model has a probability greater than the threshold presentation prediction probability value of being presented by at least one of the one or more proteins encoded by a class II HLA allele of a cell of the subject.

In some embodiments, the number of positives is constrained to be equal to the number of hits.

In some embodiments, the mass spectrometry is mono-allelic mass spectrometry.

In some embodiments, the peptides are presented by a HLA protein expressed in cells through autophagy.

In some embodiments, the peptides are presented by a HLA protein expressed in cells through phagocytosis.

In some embodiments, the plurality of predictor variables comprises expression level predictor of the source protein comprising the peptide.

In some embodiments, the plurality of predictor variables comprises stability predictor of the source protein comprising the peptide.

In some embodiments, the plurality of predictor variables comprises degradation rate predictor of the source protein comprising the peptide.

In some embodiments, the plurality of predictor variables comprises protein cleavability predictor of the source protein comprising the peptide.

In some embodiments, the plurality of predictor variables comprises cellular or tissue localization predictor of the source protein comprising the peptide.

In some embodiments, the plurality of predictor variables comprises a predictor for the intracellular processing mode of the source protein comprising the peptide, wherein processing mode of the source protein comprises predictor for whether the source protein is subject to autophagy, phagocytosis, and intracellular transport, among others.

In some embodiments, quality of the training data is increased by using a plurality of quality metrics.

In some embodiments, the plurality of quality metrics comprises common contaminant peptide removal, high scored peak intensity, high score, and high mass accuracy.

In some embodiments, a scored peak intensity is at least 50%.

In some embodiments, the scored peak intensity is at least 60%.

In some embodiments, a score is at least 7.

In some embodiments, a mass accuracy is at most 5 ppm.

In some embodiments, the peptides presented by an HLA protein expressed in cells are peptides presented by a single immunoprecipitated HLA protein expressed in cells.

In some embodiments, the peptides presented by an HLA protein expressed in cells are peptides presented by a single exogenous HLA protein expressed in cells.

In some embodiments, the peptides presented by an HLA protein expressed in cells are peptides presented by a single recombinant HLA protein expressed in cells.

In some embodiments, the plurality of predictor variables comprises a peptide-HLA affinity predictor variable.

In some embodiments, the peptides presented by the HLA protein comprise peptides identified by searching a no-enzyme specificity without modification peptide database.

In some embodiments, the peptides presented by the HLA protein comprise peptides identified by searching a peptide database using a reversed-database search strategy.

In some embodiments, the HLA protein comprises an HLA-DR, HLA-DQ, or an HLA-DP protein.

In some embodiments, the HLA protein comprises an HLA class II protein selected from the group consisting of: HLA-DPB1*01:01/HLA-DPA1*01:03, HLA-DPB1*02:01/HLA-DPA1*01:03, HLA-DPB1*03:01/HLA-DPA1*01:03, HLA-DPB1*04:01/HLA-DPA1*01:03, HLA-DPB1*04:02/HLA-DPA1*01:03, HLA-DPB1*06:01/HLA-DPA1*01:03, HLA-DQB1*02:01/HLA-DQA1*05:01, HLA-DQB1*02:02/HLA-DQA1*02:01, HLA-DQB1*06:02/HLA-DQA1*01:02, HLA-DQB1*06:04/HLA-DQA1*01:02, HLA-DRB1*01:01, HLA-DRB1*01:02, HLA-DRB1*03:01, HLA-DRB1*03:02, HLA-DRB1*04:01, HLA-DRB1*04:02, HLA-DRB1*04:03, HLA-DRB1*04:04, HLA-DRB1*04:05, HLA-DRB1*04:07, HLA-DRB1*07:01, HLA-DRB1*08:01, HLA-DRB1*08:02, HLA-DRB1*08:03, HLA-DRB1*08:04, HLA-DRB1*09:01, HLA-DRB1*10:01, HLA-DRB1*11:01, HLA-DRB1*11:02, HLA-DRB1*11:04, HLA-DRB1*12:01, HLA-DRB1*12:02, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16:01, HLA-DRB3*01:01, HLA-DRB3*02:02, HLA-DRB3*03:01, HLA-DRB4*01:01, HLA-DRB5*01:01.

In some embodiments, the HLA-DR is paired with paired with DRA*01:01.

In some embodiments, the HLA protein is a HLA class II protein selected from the group consisting of: DPA*01:03/DPB*04:01, DRB1*01:01, DRB1*01:02, DRB1*03:01, DRB1*04:01, DRB1*04:02, DRB1*04:04, DRB1*04:05, DRB1*07:01, DRB1*08:01, DRB1*08:02, DRB1*08:03, DRB1*09:01, DRB1*11:01, DRB1*11:02, DRB1*11:04, DRB1*12:01, DRB1*13:01, DRB1*13:02, DRB1*13:03, DRB1*14:01, DRB1*15:01, DRB1*15:02, DRB1*15:03, DRB1*16:02, DRB3*01:01, DRB3*02:01, DRB3*02:02, DRB3*03:01, DRB4*01:01, DRB4*01:03 and DRB5*01:01.

In some embodiments, the HLA-DR protein comprises a DRA*01:01 in the dimer.

In some embodiments, the HLA protein comprises an HLA-DP protein selected from the group consisting of: DPB1*01:01, DPB1*02:01, DPB1*02:02, DPB1*03:01, DPB1*04:01, DPB1*04:02, DPB1*05:01, DPB1*06:01, DPB1*11:01, DPB1*13:01, DPB1*17:01.

In some embodiments, the HLA-DP protein is paired comprising DPA1*01:03.

In some embodiments, the HLA protein comprises an HLA-DQ protein complex selected from the group consisting of: A1*01:01+B1*05:01, A1*01:02+B1*06:02, A1*01:02+B1*06:04, A1*01:03+B1*06:03, A1*02:01+B1*02:02, A1*02:01+B1*03:03, A1*03:01+B1*03:02, A1*03:03+B1*03:01, A1*05:01+B1*02:01 and A1*05:05+B1*03:01.

In some embodiments, the peptides presented by the HLA protein comprise peptides identified by comparing a MS/MS spectra of the HLA-peptides with MS/MS spectra of one or more peptides or proteins in a peptide or protein database.

In some embodiments, the mutation is selected from the group consisting of a point mutation, a splice site mutation, a frameshift mutation, a read-through mutation, and a gene fusion mutation.

In some embodiments, the peptides presented by the HLA protein have a length of from 15-40 amino acids.

In some embodiments, the peptides presented by the HLA protein comprise peptides identified by identifying peptides presented by an HLA protein by comparing a MS/MS spectra of the HLA-peptides with MS/MS spectra of one or more peptides or proteins in a peptide or protein database.

In some embodiments, the personalized cancer therapy further comprises an adjuvant.

In some embodiments, the personalized cancer therapy further comprises an immune checkpoint inhibitor.

In some embodiments, the training data comprises structured data, time-series data, unstructured data, relational data, or any combination thereof.

In some embodiments, the unstructured data comprises image data.

In some embodiments, the relational data comprises data from a customer system, an enterprise system, an operational system, a website, web accessible application program interface (API), or any combination thereof.

In some embodiments, the training data is uploaded to a cloud-based database.

In some embodiments, the training is performed using convolutional neural networks.

In some embodiments, the convolutional neural networks comprise at least two convolutional layers.

In some embodiments, the convolutional neural networks comprise at least one batch normalization step.

In some embodiments, the convolutional neural networks comprise at least one spatial dropout step.

In some embodiments, the convolutional neural networks comprise at least one global max pooling step.

In some embodiments, the convolutional neural networks comprise at least one dense layer.

In some embodiments, identifying peptide sequences comprises identifying peptide sequences with a mutation expressed in cancer cells of a subject.

In some embodiments, identifying peptide sequences comprises identifying peptide sequences not expressed in normal cells of a subject.

In some embodiments, identifying peptide sequences comprises identifying viral peptide sequences.

In some embodiments, identifying peptide sequences comprises identifying overexpressed peptide sequences.

Provided herein is a method for identifying HLA class II specific peptides for immunotherapy for a subject, comprising: obtaining, by a computer processor, a candidate peptide comprising an epitope, and a plurality of peptide sequences, each comprising the epitope; processing, by a computer processor, amino acid information of the plurality of peptide sequences using a machine-learning HLA-peptide presentation prediction model to generate a presentation prediction for each of the plurality of peptide sequences to an immune cell, each presentation prediction indicative of a likelihood that one or more proteins encoded by an HLA class II allele can present a given peptide sequence of the plurality of peptide sequences, wherein the machine-learning HLA-peptide presentation prediction model is trained using training data comprising sequence information of sequences of peptides presented by an HLA protein expressed in cells and identified by mass spectrometry; selecting a protein from the one or more proteins encoded by the HLA class II allele of a cell of the subject, predicted to bind to the candidate peptide by the machine-learning HLA-peptide presentation prediction model, wherein the protein has a probability greater than a threshold presentation prediction probability value for presenting the candidate peptide to an immune cell; contacting the candidate peptide with the selected protein, such that the candidate peptide competes with a placeholder peptide associated with the selected protein; and identifying the candidate peptide as a peptide for immunotherapy specific for the selected protein based on whether the candidate peptide displaces the placeholder In some embodiments, obtaining comprises identifying the candidate peptide, wherein identifying the candidate peptide comprises comparing DNA, RNA, or protein sequences from cancer cells of the subject to DNA, RNA, or protein sequences from normal cells of the subject.

In some embodiments, processing comprises identifying a plurality of predictor variables based at least on the amino acid information of the plurality of peptide sequences, and processing the plurality of predictor variables using the machine-learning HLA-peptide presentation prediction model.

In some embodiments, the machine-learning HLA-peptide presentation prediction model comprises a plurality of predictor variables identified at least based on the training data, wherein the training data comprises: training peptide sequence information comprising amino acid position information, wherein the training peptide sequence information is associated with the HLA protein expressed in cells; and a function representing a relation between the amino acid position information and the presentation likelihood generated as output based on the amino acid position information and the plurality of predictor variables.

In some embodiments, the number of positives is constrained to be equal to the number of hits.

In some embodiments, the mass spectrometry is monoallelic mass spectrometry.

In some embodiments, the plurality of predictor variables comprises any one or more of: expression level predictor, stability predictor, degradation rate predictor, cleavability predictor, cellular or tissue localization predictor, and intracellular processing mode comprising autophagy, phagocytosis, and intracellular transport predictor, of the source protein comprising the peptide.

In some embodiments, quality of the training data is increased by using a plurality of quality metrics.

In some embodiments, the plurality of quality metrics comprises common contaminant peptide removal, high scored peak intensity, high score, and high mass accuracy.

In some embodiments, a scored peak intensity is at least 50%.

In some embodiments, the scored peak intensity is at least 60%.

In some embodiments, the placeholder peptide is a CLIP peptide.

In some embodiments, the placeholder peptide is a CMV peptide.

In some embodiments, the 3 method further comprises measuring the IC50 of displacement of the placeholder peptide by the target peptide.

In some embodiments, the IC50 of displacement of the placeholder peptide by the target peptide is less than 500 nM.

In some embodiments, the at least one protein from the one or more proteins encoded by the HLA class II allele of a cell of the subject is an HLA class II tetramer or multimer.

In some embodiments, the target peptide is further identified by mass spectrometry.

In some embodiments, the at least one protein encoded by the HLA class II allele of a cell of the subject is a recombinant protein.

In some embodiments, the at least one protein encoded by the HLA class II allele of a cell of the subject is expressed in a eukaryotic cell.

In some embodiments, the peptides are presented by a HLA protein expressed in cells through autophagy.

In some embodiments, the peptides are presented by a HLA protein expressed in cells through phagocytosis.

In some embodiments, the peptides presented by a HLA protein expressed in cells are peptides presented by a single immunoprecipitated HLA protein expressed in cells.

In some embodiments, the peptides presented by a HLA protein expressed in cells are peptides presented by a single exogenous HLA protein expressed in cells.

In some embodiments, the peptides presented by a HLA protein expressed in cells are peptides presented by a single recombinant HLA protein expressed in cells.

In some embodiments, the plurality of predictor variables comprises a peptide-HLA affinity predictor variable.

In some embodiments, the peptides presented by the HLA protein comprise peptides identified by searching a no-enzyme specificity without modification peptide database.

In some embodiments, the peptides presented by the HLA protein comprise peptides identified by searching a peptide database using a reversed-database search strategy.

In some embodiments, the HLA protein comprises an HLA-DR, HLA-DQ, or an HLA-DP protein.

In some embodiments, the immunotherapy is cancer immunotherapy.

In some embodiments, the epitope is a cancer specific epitope.

In some embodiments, the at least one protein encoded by the HLA class II allele comprises at least an alpha 1 subunit and a beta 1 subunit of the HLA protein, present in dimer form.

In some embodiments, the identity of the peptide is known.

In some embodiments, the identity of the peptide is not known.

In some embodiments, the identity of the peptide is determined by mass spectrometry.

In some embodiments, peptide exchange assay comprises detection of peptide fluorescent probes or tags.

In some embodiments, in the placeholder peptide is a CLIP peptide. In some embodiments, the placeholder peptide has an amino acid sequence of PVSKMRMATPLL-MQA (SEQ ID NO: 1).

In some embodiments, the polynucleic acid construct comprises an expression vector, further comprising one or more of: a promoter, a secretion signal, dimerization factors, ribosomal skipping sequence, one or more tags for purification and/or detection.

In some embodiments, the placeholder peptide sequence is encoded by a nucleic acid sequence within the vector.

In some embodiments, a sequence encoding a cleavable domain is placed in between the sequence encoding the placeholder peptide and the HLA beta1 peptide.

Provided herein is a method for assaying immunogenicity of a MHC class II binding peptide, comprising: selecting a protein encoded by an HLA class II allele predicted by a machine-learning HLA-peptide presentation prediction model to bind to the MHC class II binding peptide, wherein the machine-learning HLA-peptide presentation prediction model is configured to generate a presentation prediction for a given peptide sequence, the presentation prediction indicative of a likelihood that one or more proteins encoded by the HLA class II allele can present the given peptide sequence, and wherein the protein has a probability greater than a threshold presentation prediction probability value for presenting the MHC class II binding peptide; contacting the peptide with the selected protein such that the peptide competes with a placeholder peptide associated with the selected protein, and displaces the placeholder peptide, thereby forming a complex comprising the HLA class II protein and the MHC class II binding peptide; contacting the complex with a CD4+ T cell, and assaying for one or more of activation parameters of the CD4+ T cell, selected from the group consisting of: induction of a cytokine, induction of a chemokine, and expression of a cell surface marker.

In some embodiments, the HLA class II allele is a tetramer or multimer.

In some embodiments, the cytokine is IL-2.

Provided herein is a method for inducing a CD4+ T cells activation in a subject for cancer immunotherapy, the method comprising: identifying a peptide sequence associated with cancer and comprising a cancer mutation, wherein identifying the peptide sequence comprises comparing DNA, RNA, or protein sequences from cancer cells of the subject to DNA, RNA, or protein sequences from normal cells of the subject; selecting a protein encoded by an HLA class II allele that is normally expressed by a cell of the subject, and predicted by a machine-learning HLA-peptide presentation prediction model to bind to the peptide; wherein the prediction model has a positive predictive value of at least 0.1 at a recall rate of at least 0.1%, from 0.1%-50% or at most 50%. and wherein the protein has a probability greater than a threshold presentation prediction probability value for presenting the identified peptide sequence; contacting the identified peptide with the selected protein encoded by the HLA class II allele to verify whether the identified peptide competes with a placeholder peptide associated with the selected protein encoded by the HLA class II allele to displace the placeholder peptide with an IC50 value of less than 500 nM; optionally, purifying the identified peptide; and administering an effective amount of a polypeptide comprising a sequence of the identified peptide or a polynucleotide encoding the polypeptide to the subject.

Provided herein is a method of screening a drug comprising a polypeptide sequence for immunogenicity in a subject, comprising: obtaining, by a computer processor, a plurality of peptide sequences of the polypeptide sequence; processing, by a computer processor, amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class I or II MHC allele of a cell of the subject can present an epitope sequence of a given peptide sequence of the plurality of peptide sequences, wherein the machine-learning HLA-peptide presentation prediction model is trained using training data comprising sequence information associated with the HLA protein expressed in cells; determining or predicting that each of the plurality of peptide sequences of the polypeptide sequence would not be immunogenic to the subject based on the plurality of presentation predictions; and administering to the subject a composition comprising the drug.

Provided herein is a method for manufacturing HLA class II tetramers or multimers by conjugation of four individual HLA protein alpha1 and beta1 heterodimers, the method comprising: expressing in a eukaryotic cell, a vector comprising a nucleic acid sequence encoding an alpha chain and a beta chain of HLA protein, a secretion signal, a biotinylation motif and at least one tag for identification or for purification, such that each HLA protein alpha 1 and beta1 heterodimers is secreted in dimerized state, wherein the heterodimer is associated with a placeholder peptide, purifying the secreted heterodimer from cell medium, validating the peptide binding activity using peptide exchange assay, adding streptavidin thereby conjugating heterodimers into tetramers, purifying the tetramers and having a yield of greater than 1 mg/L. Multimers, for example pentamers, hexamers or octamers can also be likewise generated, which are equally contemplated herein.

In some embodiments, the vector comprises a CMV promoter.

In some embodiments, the vector comprises a sequence encoding a placeholder peptide linked via a cleavable site to the beta 1 chain.

In some embodiments, peptide exchange assay involves prior cleavage of the placeholder peptide from the beta chain.

In some embodiments, the cleavable site is a thrombin cleavage site.

In some embodiments, peptide exchange assay is a FRET assay.

In some embodiments, the purification is by any one of: column chromatography, ion exchange chromatography, size exclusion chromatography, affinity chromatography, or LC-MS.

Provided herein is an HLA class II tetramer or multimer comprising either HLA-DR, or HLA-DP, or HLA-DQ heterodimers, each heterodimer comprising an alpha and a beta chain, wherein the heterodimer is purified and present at a concentration of greater than 1 mg/L.

In some embodiments, the HLA class II tetramers are selected from Table 8A-8C.

In some embodiments, the HLA class II tetramer comprises heterodimer pairs selected from the group consisting of: an HLA-DR, an HLA-DP, and an HLA-DQ protein.

In some embodiments, the HLA protein is an HLA class II protein selected from the group consisting of: HLA-DPB1*01:01/HLA-DPA1*01:03, HLA-DPB1*02:01/HLA-DPA1*01:03, HLA-DPB1*03:01/HLA-DPA1*01:03, HLA-DPB1*04:01/HLA-DPA1*01:03, HLA-DPB1*04:02/HLA-DPA1*01:03, HLA-DPB1*06:01/HLA-DPA1*01:03, HLA-DQB1*02:01/HLA-DQA1*05:01, HLA-DQB1*02:02/HLA-DQA1*02:01, HLA-DQB1*06:02/HLA-DQA1*01:02, HLA-DQB1*06:04/HLA-DQA1*01:02, HLA-DRB1*01:01, HLA-DRB1*01:02, HLA-DRB1*03:01, HLA-DRB1*03:02, HLA-DRB1*04:01, HLA-DRB1*04:02, HLA-DRB1*04:03, HLA-DRB1*04:04, HLA-DRB1*04:05, HLA-DRB1*04:07, HLA-DRB1*07:01, HLA-DRB1*08:01, HLA-DRB1*08:02, HLA-DRB1*08:03, HLA-DRB1*08:04, HLA-DRB1*09:01, HLA-DRB1*10:01, HLA-DRB1*11:01, HLA-DRB1*11:02, HLA-DRB1*11:04, HLA-DRB1*12:01, HLA-DRB1*12:02, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16:01, HLA-DRB3*01:01, HLA-DRB3*02:02, HLA-DRB3*03:01, HLA-DRB4*01:01, and HLA-DRB5*01:01.

In some embodiments, the heterodimer pair is expressed in a eukaryotic cell.

In some embodiments, the heterodimer pairs are encoded by a vector.

Provided herein is a vector, wherein the vector comprises a nucleic acid sequence encoding an alpha chain and a beta chain of HLA protein described herein, a secretion signal, a biotinylation motif and at least one tag for identification or for purification, such that each HLA protein alpha 1 and beta1 heterodimers is secreted in dimerized state, wherein the secreted heterodimer is optionally associated with a placeholder peptide.

Provided herein is a cell, comprising a vector described herein.

In some embodiments, the HLA class II heterodimers are secreted from eukaryotic cells into cell culture medium, which is further purified by any one of: column chromatography, ion exchange chromatography, size exclusion chromatography, affinity chromatography or LC-MS.

Provided herein is a method of screening a drug comprising a polypeptide sequence for immunogenicity in a subject, comprising: obtaining, by a computer processor, a plurality of peptide sequences of the polypeptide sequence; processing, by a computer processor, amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class I or II MHC allele of a cell of the subject can present an epitope sequence of a given peptide sequence of the plurality of peptide sequences, wherein the machine-learning HLA-peptide presentation prediction model is trained using training data comprising sequence information of sequences of peptides presented by a HLA protein expressed in cells and identified by mass spectrometry; and determining or predicting that at least one of the plurality of peptide sequences of the polypeptide sequence would be immunogenic to the subject based on the plurality of presentation predictions.

Provided herein is a method of screening a drug comprising a polypeptide sequence for immunogenicity in a subject, the method comprising: inputting amino acid information of peptide sequences of the polypeptide sequence, using a computer processor, into a machine-learning HLA-peptide presentation prediction model to generate a set of presentation predictions for the peptide sequences, each presentation prediction representing a probability that one or more proteins encoded by a class I or II MHC allele of a cell of the subject will present an epitope sequence of a given peptide sequence; wherein the machine-learning HLA-peptide presentation prediction model comprises: a plurality of predictor variables identified at least based on training data, wherein the training data comprises: sequence information of sequences of peptides presented by a HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables; determining or predicting that each of the peptide sequences of the polypeptide sequence would not be immunogenic to the subject based on the set of presentation predictions; and administering to the subject a composition comprising the drug.

Provided herein is a method of screening a drug comprising a polypeptide sequence for immunogenicity in a subject, the method comprising: inputting amino acid information of peptide sequences of the polypeptide sequence, using a computer processor, into a machine-learning HLA-peptide presentation prediction model to generate a set of presentation predictions for the peptide sequences, each presentation prediction representing a probability that one or more proteins encoded by a class I or II MHC allele of a cell of the subject will present an epitope sequence of a given peptide sequence; wherein the machine-learning HLA-peptide presentation prediction model comprises: a plurality of predictor variables identified at least based on training data; wherein the training data comprises: sequence information of sequences of peptides presented by a HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables; determining or predicting that at least one of the peptide sequences of the polypeptide sequence would be immunogenic to the subject based on the set of presentation predictions.

Provided herein is a method of screening a drug comprising a polypeptide sequence for immunogenicity in a subject, comprising: obtaining, by a computer processor, a plurality of peptide sequences of the polypeptide sequence; processing, by a computer processor, amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class I or II MHC allele of a cell of the subject can present an epitope sequence of a given peptide sequence of the plurality of peptide sequences, wherein the machine-learning HLA-peptide presentation prediction model is trained using training data comprising sequence information associated with the HLA protein expressed in cells; determining or predicting that each of the plurality of peptide sequences of the polypeptide sequence would not be immunogenic to the subject based on the plurality of presentation predictions; and administering to the subject a composition comprising the drug.

In some embodiments, the method further comprises deciding not to administer the drug to the subject.

In some embodiments, the drug comprises an antibody or binding fragment thereof.

In some embodiments, the peptide sequences of the polypeptide sequence have a length of 8, 9, 10, 11, or 12 amino acids, and wherein the protein encoded by a class I or II MHC allele of a cell of the subject is a protein encoded by a class I MHC allele of a cell of the subject.

In some embodiments, the peptide sequences of the polypeptide sequence have a length of 15, 16, 17, 18, 19, 20, 21, 22, 23, 24, or 25 amino acids, and wherein the protein encoded by a class I or II MHC allele of a cell of the subject is a protein encoded by a class II MHC allele of a cell of the subject.

Provided herein is a method of treating a subject with an autoimmune disease or condition comprising: (a) identifying or predicting an epitope of an expressed protein presented by a class I or II MHC of a cell of the subject, wherein a complex comprising the identified or predicted epitope and the class I or II MHC is targeted by a CD8 or CD4 T cell of the subject; (b) identifying a T cell receptor (TCR) that binds to the complex; (c) expressing the TCR in a regulatory T cell from the subject or an allogeneic regulatory T cell; and (d) administering the regulatory T cell expressing the TCR to the subject.

In some embodiments, the autoimmune disease or condition is diabetes.

In some embodiments, the cell is an islet cell.

Provided herein is a method of treating a subject with an autoimmune disease or condition, comprising administering to the subject a regulatory T cell expressing a T cell receptor (TCR) that binds to a complex comprising: (i) an epitope of an expressed protein identified or predicted to be presented by a class I or II MHC of a cell of the subject, and (ii) the class I or II MHC, wherein the complex is targeted by a CD8 or CD4 T cell of the subject.

Provided herein is a computer system for identifying peptide sequences for a personalized cancer therapy of a subject, comprising: a database that is configured to store a plurality of peptide sequences of the subject; and one or more computer processors operatively coupled to said database, wherein said one or more computer processors are individually collectively programmed to: process amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class II MHC allele of a cell of the subject can present a given peptide sequence of the plurality of peptide sequences, wherein the machine-learning HLA-peptide presentation prediction model is trained using training data comprising sequence information of sequences of peptides presented by an HLA protein expressed in cells and identified by mass spectrometry; and select a subset of the plurality of peptide sequences for the personalized cancer therapy of the subject based at least on the plurality of presentation predictions.

Provided herein is a computer system for identifying HLA class II specific peptides for immunotherapy for a subject, comprising: a database that is configured to store a candidate peptide comprising an epitope, and a plurality of peptide sequences, each comprising the epitope; and one or more computer processors operatively coupled to said database, wherein said one or more computer processors are individually collectively programmed to: process amino acid information of the plurality of peptide sequences a machine-learning HLA-peptide presentation prediction model to generate a presentation prediction for each of the plurality of peptide sequences to an immune cell, each presentation prediction indicative of a likelihood that one or more proteins encoded by an HLA class II allele can present a given peptide sequence of the plurality of peptide sequences, wherein the machine-learning HLA-peptide presentation prediction model is trained using training data comprising sequence information of sequences of peptides presented by an HLA protein expressed in cells and identified by mass spectrometry; select a protein from the one or more proteins encoded by the HLA class II allele of a cell of the subject, predicted to bind to the candidate peptide by the machine-learning HLA-peptide presentation prediction model, wherein the protein has a probability greater than a threshold presentation prediction probability value for presenting the candidate peptide to an immune cell; and identify the candidate peptide as a peptide for immunotherapy specific for the selected protein based on whether the candidate peptide displaces the placeholder peptide, upon contacting the candidate peptide with the selected protein, such that the candidate peptide competes with a placeholder peptide associated with the selected protein.

Provided herein is a computer system for screening a drug comprising a polypeptide sequence for immunogenicity in a subject, comprising: a database that is configured to store a plurality of peptide sequences of the polypeptide sequence; and one or more computer processors operatively coupled to said database, wherein said one or more computer processors are individually collectively programmed to: process amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class I or II MHC allele of a cell of the subject can present an epitope sequence of a given peptide sequence of the plurality of peptide sequences, wherein the machine-learning HLA-peptide presentation prediction model is trained using training data comprising sequence information associated with the HLA protein expressed in cells; and determine or predict that each of the plurality of peptide sequences of the polypeptide sequence would not be immunogenic to the subject based on the plurality of presentation predictions, wherein a composition comprising the drug is administered to the subject.

Provided herein is a computer system for screening a drug comprising a polypeptide sequence for immunogenicity in a subject, comprising: a database that is configured to store a plurality of peptide sequences of the polypeptide sequence; and one or more computer processors operatively coupled to said database, wherein said one or more computer processors are individually collectively programmed to: process amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class I or II MHC allele of a cell of the subject can present an epitope sequence of a given peptide sequence of the plurality of peptide sequences, wherein the machine-learning HLA-peptide presentation prediction model is trained using training data comprising sequence information of sequences of peptides presented by a HLA protein expressed in cells and identified by mass spectrometry; and determine or predict that at least one of the plurality of peptide sequences of the polypeptide sequence would be immunogenic to the subject based on the plurality of presentation predictions.

Provided herein is a non-transitory computer readable medium comprising machine-executable code that, upon execution by one or more computer processors, implements a method for identifying peptide sequences for a personalized cancer therapy of a subject, said method comprising: obtaining a plurality of peptide sequences of the subject; processing amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class II MHC allele of a cell of the subject can present a given peptide sequence of the plurality of peptide sequences, wherein the machine-learning HLA-peptide presentation prediction model is trained using training data comprising sequence information of sequences of peptides presented by an HLA protein expressed in cells and identified by mass spectrometry; and selecting a subset of the plurality of peptide sequences for the personalized cancer therapy of the subject based at least on the plurality of presentation predictions.

Provided herein is a non-transitory computer readable medium comprising machine-executable code that, upon execution by one or more computer processors, implements a method for identifying HLA class II specific peptides for immunotherapy for a subject, comprising: obtaining a candidate peptide comprising an epitope, and a plurality of peptide sequences, each comprising the epitope; processing amino acid information of the plurality of peptide sequences a machine-learning HLA-peptide presentation prediction model to generate a presentation prediction for each of the plurality of peptide sequences to an immune cell, each presentation prediction indicative of a likelihood that one or more proteins encoded by an HLA class II allele can present a given peptide sequence of the plurality of peptide sequences, wherein the machine-learning HLA-peptide presentation prediction model is trained using training data comprising sequence information of sequences of peptides presented by an HLA protein expressed in cells and identified by mass spectrometry; selecting a protein from the one or more proteins encoded by the HLA class II allele of a cell of the subject, predicted to bind to the candidate peptide by the machine-learning HLA-peptide presentation prediction model, wherein the protein has a probability greater than a threshold presentation prediction probability value for presenting the candidate peptide to an immune cell; and identifying the candidate peptide as a peptide for immunotherapy specific for the selected protein based on whether the candidate peptide displaces the placeholder peptide, upon contacting the candidate peptide with the selected protein, such that the candidate peptide competes with a placeholder peptide Provided herein is a non-transitory computer readable medium comprising machine-executable code that, upon execution by one or more computer processors, implements a method of screening a drug comprising a polypeptide sequence for immunogenicity in a subject, comprising: obtaining a plurality of peptide sequences of the polypeptide sequence; processing amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class I or II MHC allele of a cell of the subject can present an epitope sequence of a given peptide sequence of the plurality of peptide sequences, wherein the machine-learning HLA-peptide presentation prediction model is trained using training data comprising sequence information associated with the HLA protein expressed in cells; and determining or predicting that each of the plurality of peptide sequences of the polypeptide sequence would not be immunogenic to the subject based on the plurality of presentation predictions, wherein a composition comprising the drug is administered to the subject.

Provided herein is a non-transitory computer readable medium comprising machine-executable code that, upon execution by one or more computer processors, implements a method of screening a drug comprising a polypeptide sequence for immunogenicity in a subject, comprising: obtaining a plurality of peptide sequences of the polypeptide sequence; processing amino acid information of the plurality of peptide sequences using a machine-learning HLA-peptide presentation prediction model to generate a presentation prediction for each of the plurality of peptide sequences, each presentation prediction indicative of a likelihood that one or more proteins encoded by a class I or II MHC allele of a cell of the subject can present an epitope sequence of a given peptide sequence of the plurality of peptide sequences, wherein the machine-learning HLA-peptide presentation prediction model is trained using training data comprising sequence information of sequences of peptides presented by a HLA protein expressed in cells and identified by mass spectrometry; and determining or predicting that at least one of the plurality of peptide sequences of the polypeptide sequence would be immunogenic to the subject based on the plurality of presentation predictions.

Provided herein is a method comprising: processing amino acid information of a plurality of candidate peptide sequences using a machine learning HLA peptide presentation prediction model to generate a plurality of presentation predictions, wherein each candidate peptide sequences of the plurality is encoded by a genome or exome of a subject, wherein the plurality of presentation predictions comprises an HLA presentation prediction for each of the plurality of candidate peptide sequences, wherein each presentation prediction indicative of a likelihood that one or more proteins encoded by a class II HLA allele of a cell of the subject can present a given candidate peptide sequence of the plurality, wherein the machine learning HLA peptide presentation prediction model is trained using training data comprising sequence information of sequences of training peptides identified by mass spectrometry to be presented by an HLA protein expressed in training cells; and identifying, based at least on the plurality of presentation predictions, a peptide sequence of the plurality of peptide sequences that has a probability greater than a threshold presentation prediction probability value of being presented by at least one of the one or more proteins encoded by a class II HLA allele of a cell of the subject; wherein the machine learning HLA peptide presentation prediction model has a positive predictive value (PPV) of at least 0.07 when amino acid information of a plurality of test peptide sequences are processed to generate a plurality of test presentation predictions, each test presentation prediction indicative of a likelihood that the one or more proteins encoded by a class II HLA allele of a cell of the subject can present a given test peptide sequence of the plurality of test peptide sequences, wherein the plurality of test peptide sequences comprises at least 500 test peptide sequences comprising (i) at least one hit peptide sequence identified by mass spectrometry to be presented by an HLA protein expressed in cells and (ii) at least 499 decoy peptide sequences contained within a protein encoded by a genome of an organism, wherein the organism and the subject are the same species, wherein the plurality of test peptide sequences comprises a ratio of 1:499 of the at least one hit peptide sequence to the at least 499 decoy peptide sequences and 0.2% of the plurality of test peptide sequences are predicted to be presented by the HLA protein expressed in cells by the machine learning HLA peptide presentation prediction model.

Provided herein is a method comprising: processing amino acid information of a plurality of peptide sequences of encoded by a genome or exome of a subject using a machine-learning HLA-peptide binding prediction model to generate a plurality of binding predictions, wherein the plurality of binding predictions comprises an HLA binding prediction for each of the plurality of candidate peptide sequences, each binding prediction indicative of a likelihood that one or more proteins encoded by a class II HLA allele of a cell of the subject binds to a given candidate peptide sequence of the plurality of candidate peptide sequences, wherein the machine learning HLA peptide binding prediction model is trained using training data comprising sequence information of sequences of peptides identified to bind to an HLA class II protein or an HLA class II protein analog; and identifying, based at least on the plurality of binding predictions, a peptide sequence of the plurality of peptide sequences that has a probability greater than a threshold binding prediction probability value of binding to at least one of the one or more proteins encoded by a class II HLA allele of a cell of the subject; wherein the machine learning HLA peptide binding prediction model has a positive predictive value (PPV) of at least 0.1 when amino acid information of a plurality of test peptide sequences are processed to generate a plurality of test binding predictions, each test binding prediction indicative of a likelihood that the one or more proteins encoded by a class II HLA allele of a cell of the subject binds to a given test peptide sequence of the plurality of test peptide sequences, wherein the plurality of test peptide sequences comprises at least 50 test peptide sequences comprising (i) at least one hit peptide sequence identified by mass spectrometry to be presented by an HLA protein expressed in cells and (ii) at least 19 decoy peptide sequences contained within a protein comprising a peptide sequence identified by mass spectrometry to be presented by an HLA protein expressed in cells, wherein the organism and the subject are the same species, wherein the plurality of test peptide sequences comprises a ratio of 1:19 of the at least one hit peptide sequence to the at least 19 decoy peptide sequences and 5% of the plurality of test peptide sequences are predicted to bind to the HLA protein expressed in cells by the machine learning HLA peptide presentation prediction model.

In some embodiments, the machine learning HLA peptide presentation prediction model is trained using training data comprising sequence information of sequences of training peptides identified by mass spectrometry to be presented by an HLA protein expressed in training cells In some embodiments, one or more of the 0.2% of the plurality of test peptide sequences predicted to be presented by the by the machine learning HLA peptide presentation prediction model has a probability greater than the threshold presentation prediction probability value of being presented by at least one of the one or more proteins encoded by a class II HLA allele of a cell of the subject.

In some embodiments, each of the 0.2% of the plurality of test peptide sequences predicted to be presented by the by the machine learning HLA peptide presentation prediction model has a probability greater than the threshold presentation prediction probability value of being presented by at least one of the one or more proteins encoded by a class II HLA allele of a cell of the subject.

In some embodiments, the PPV is greater than the respective PPV of column 2 of Table 11 for the protein encoded by the corresponding HLA allele of Table 13. In some embodiments, the PPV is at least equal to the respective PPV of column 3 of Table 11 for the protein encoded by the corresponding HLA allele of Table 11.

In some embodiments, the PPV is greater than the respective PPV of column 2 of Table 12 for the protein encoded by an HLA class II allele.

In some embodiments, the PPV is at least equal to the respective PPV of column 2 of Table 16 for the protein encoded by the corresponding HLA allele of Table 16.

Provided herein is a method for preparing a personalized cancer therapy, the method comprising: identifying peptide sequences, wherein the peptide sequences are associated with cancer, wherein identifying comprises comparing DNA, RNA or protein sequences from the cancer cells of the subject to DNA, RNA or protein sequences from the normal cells of the subject; inputting amino acid position information of the peptide sequences identified, using a computer processor, into a machine-learning HLA-peptide presentation prediction model to generate a set of presentation predictions for the peptide sequences identified, each presentation prediction representing a probability that one or more proteins encoded by an HLA class II allele of a cell of the subject will present a given sequence of a peptide sequence identified; wherein the machine-learning HLA-peptide presentation prediction model comprises: a plurality of predictor variables identified at least based on training data wherein the training data comprises: sequence information of sequences of peptides presented by an HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables; and selecting a subset of the peptide sequences identified based on the set of presentation predictions for preparing the personalized cancer therapy; wherein the prediction model has a positive predictive value of at least 0.1 at a recall rate of at least 0.1%, from 0.1%-50% or at the most 50%.

Provided herein is a method comprising training a machine-learning HLA-peptide presentation prediction model, wherein training comprises inputting amino acid position information sequences of HLA-peptides isolated from one or more HLA-peptide complexes from a cell expressing an HLA class II allele into the HLA-peptide presentation prediction model using a computer processor; the machine-learning HLA-peptide presentation prediction model comprising: a plurality of predictor variables identified at least based on training data that comprises: sequence information of sequences of peptides presented by an HLA protein expressed in cells and identified by mass spectrometry; training peptide sequence information comprising amino acid position information of training peptides, wherein the training peptide sequence information is associated with the HLA protein expressed in cells; and a function representing a relation between the amino acid position information received as input and a presentation likelihood generated as output based on the amino acid position information and the predictor variables.

In some embodiments, the presentation model has a positive predictive value of at least 0.25 at a recall rate at least 0.1%, from 0.1%-50% or at the most 50%.

In some embodiments, the presentation model has a positive predictive value of at least 0.4 at a recall rate of at least 0.1%, from 0.1%-50% or at the most 50%.

In some embodiments, the presentation model has a positive predictive value of at least 0.6 at a recall rate of at least 0.1%, from 0.1%-50% or at the most 50%.

In some embodiments, the mass spectrometry is mono-allelic mass spectrometry.

In some embodiments, the peptides are presented by an HLA protein expressed in cells through autophagy.

In some embodiments, the peptides are presented by an HLA protein expressed in cells through phagocytosis.

In some embodiments, quality of the training data is increased by using a plurality of quality metrics.

In some embodiments, the plurality of quality metrics comprises common contaminant peptide removal, high scored peak intensity, high score, and high mass accuracy.

In some embodiments, the scored peak intensity is at least 50%.

In some embodiments, the scored peak intensity is at least 60%.

In some embodiments, a score is at least 7.

In some embodiments, a mass accuracy is at most 5 ppm.

In some embodiments, a mass accuracy is at most 2 ppm.

In some embodiments, a backbone cleavage score is at least 5.

In some embodiments, a backbone cleavage score is at least 8.

In some embodiments, the peptides presented by an HLA protein expressed in cells are peptides presented by a single immunoprecipitated HLA protein expressed in cells.

In some embodiments, the peptides presented by an HLA protein expressed in cells are peptides presented by a single exogenous HLA protein expressed in cells.

In some embodiments, the peptides presented by an HLA protein expressed in cells are peptides presented by a single recombinant HLA protein expressed in cells.

In some embodiments, the plurality of predictor variables comprises a peptide-HLA affinity predictor variable.

In some embodiments, the plurality of predictor variables comprises a source protein expression level predictor variable.

In some embodiments, the plurality of predictor variables comprises a peptide cleavability predictor variable.

In some embodiments, the training peptide sequence information comprises sequences from the peptides presented by the HLA protein, which comprise peptides identified by searching a no-enzyme specificity without modification to a peptide database. In some embodiments, the peptides presented by the HLA protein comprise peptides identified by searching the de novo peptide sequencing tools.

In some embodiments, the peptides presented by the HLA protein comprise peptides identified by searching a peptide database using a reversed-database search strategy.

In some embodiments, the HLA protein comprises an HLA-DR, and HLA-DP or an HLA-DQ protein.

In some embodiments, the HLA protein comprises an HLA-DR protein selected from the group consisting of an HLA-DR, and HLA-DP or an HLA-DQ protein. In some embodiments, the HLA protein comprises an HLA-DR protein selected from the group consisting of: HLA-DPB1*01:01/HLA-DPA1*01:03, HLA-DPB1*02:01/HLA-DPA1*01:03, HLA-DPB1*03:01/HLA-DPA1*01:03, HLA-DPB1*04:01/HLA-DPA1*01:03, HLA-DPB1*04:02/HLA-DPA1*01:03, HLA-DPB1*06:01/HLA-DPA1*01:03, HLA-DQB1*02:01/HLA-DQA1*05:01, HLA-DQB1*02:02/

HLA-DQA1*02:01, HLA-DQB1*06:02/HLA-DQA1*01: 02, HLA-DQB1*06:04/HLA-DQA1*01:02, HLA-DRB1*01:01, HLA-DRB1*01:02, HLA-DRB1*03:01, HLA-DRB1*03:02, HLA-DRB1*04:01, HLA-DRB1*04: 02, HLA-DRB1*04:03, HLA-DRB1*04:04, HLA-DRB1*04:05, HLA-DRB1*04:07, HLA-DRB1*07:01, HLA-DRB1*08:01, HLA-DRB1*08:02, HLA-DRB1*08: 03, HLA-DRB1*08:04, HLA-DRB1*09:01, HLA-DRB1*10:01, HLA-DRB1*11:01, HLA-DRB1*11:02, HLA-DRB1*11:04, HLA-DRB1*12:01, HLA-DRB1*12: 02, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16: 01, HLA-DRB3*01:01, HLA-DRB3*02:02, HLA-DRB3*03:01, HLA-DRB4*01:01, and HLA-DRB5*01:01.

In some embodiments, the peptides presented by the HLA protein comprise peptides identified by comparing MS/MS spectra of the HLA-peptides with MS/MS spectra of one or more HLA-peptides in a peptide database.

In some embodiments, the mutation is selected from the group consisting of a point mutation, a splice site mutation, a frameshift mutation, a read-through mutation, and a gene fusion mutation.

In some embodiments, the peptides presented by the HLA protein have a length of 15-40 amino acids.

In some embodiments, the peptides presented by the HLA protein comprise peptides identified by (a) isolating one or more HLA complexes from a cell line expressing a single HLA class II allele; (b) isolating one or more HLA-peptides from the one or more isolated HLA complexes; (c) obtaining MS/MS spectra for the one or more isolated HLA-peptides; and (d) obtaining a peptide sequence that corresponds to the MS/MS spectra of the one or more isolated HLA-peptides from a peptide database; wherein one or more sequences obtained from step (d) identifies the sequence of the one or more isolated HLA-peptides.

In some embodiments, the personalized cancer therapy further comprises an adjuvant.

In some embodiments, the personalized cancer therapy further comprises an immune checkpoint inhibitor.

In some embodiments, the training data comprises structured data, time-series data, unstructured data, relational data, or any combination thereof.

In some embodiments, the unstructured data comprises image data.

In some embodiments, the relational data comprises data from a customer system, an enterprise system, an operational system, a website, web accessible application program interface (API), or any combination thereof.

In some embodiments, the training data is uploaded to a cloud-based database.

In some embodiments, the training is performed using convolutional neural networks.

In some embodiments, the convolutional neural networks comprise at least two convolutional layers.

In some embodiments, the convolutional neural networks (CNN) comprise at least one batch normalization step.

In some embodiments, the convolutional neural networks comprise at least one spatial dropout step.

In some embodiments, the convolutional neural networks comprise at least one global max pooling step.

In some embodiments, the convolutional neural networks comprise at least one dense layer.

In some embodiments, identifying peptide sequences comprises identifying peptide sequences with a mutation expressed in cancer cells of a subject.

In some embodiments, identifying peptide sequences comprises identifying peptide sequences not expressed in normal cells of a subject.

In some embodiments, identifying peptide sequences comprises identifying overexpressed peptide sequences.

In some embodiments, identifying peptide sequences comprises identifying viral peptide sequences. In one aspect, provided herein is a method for identifying HLA class II specific peptides for immunotherapy specific for a subject, the method comprising: identifying a candidate peptide comprising an epitope; inputting amino acid information of a plurality of peptide sequences, each comprising an epitope, using a computer processor, into a machine-learning HLA-peptide presentation prediction model to generate a set of HLA presentation predictions for the peptide sequence to an immune cell, each presentation prediction representing a probability that one or more proteins encoded by an HLA class II allele of a cell of the subject will present a given peptide sequence comprising the epitope; wherein the prediction model has a positive predictive value of at least 0.1 at a recall rate of at least 0.1%, from 0.1%-50% or at the most 50%, selecting a protein from the one or more proteins encoded by the HLA class II allele of a cell of the subject, predicted to bind to the candidate peptide by the prediction model, wherein the protein has a probability greater than a threshold presentation prediction probability value for presenting the candidate peptide to an immune cell; contacting the candidate peptide with the protein encoded by the HLA class II allele, such that the candidate peptide competes with a placeholder peptide associated with the protein encoded by the HLA class II allele; and, identifying the candidate peptide as a peptide for immunotherapy specific for the protein encoded by an HLA class II allele based on whether the candidate peptide displaces the placeholder peptide.

In some embodiments, the immunotherapy is cancer immunotherapy.

In some embodiments, identifying comprises comparing DNA, RNA or protein sequences from the cancer cells of the subject to DNA, RNA or protein sequences from the normal cells of the subject. In some embodiments, the epitope is a cancer specific epitope.

In some embodiments, the at least one protein encoded by the HLA class II allele comprises at least an alpha 1 subunit and a beta 1 subunit of the HLA protein, or fragments thereof, present in dimer form. In some embodiments, the placeholder peptide is a CLIP peptide. In some embodiments, the placeholder peptide is a CMV peptide. In some embodiments, the method further comprises measuring the IC50 of displacement of the placeholder peptide by the target peptide. In some embodiments, the IC50 of displacement of the placeholder peptide by the target peptide is less than 500 nM. In some embodiments, the at least one protein from the one or more proteins encoded by the HLA class II allele of a cell of the subject is an HLA class II tetramer or multimer. In some embodiments, the target peptide is further identified by mass spectrometry. In some embodiments, the at least one protein encoded by the HLA class II allele of a cell of the subject is a recombinant protein. In some embodiments, the at least one protein encoded by the HLA class II allele of a cell of the subject is expressed in a eukaryotic cell.

In one aspect, provided herein is assay method for verifying the specificity of a candidate peptide for binding an HLA class II protein, the method comprising: expressing in a eukaryotic cell, a polynucleic acid construct comprising a nucleic acid sequence encoding an HLA class II protein comprising an alpha chain and beta chain or portions thereof, capable of binding a peptide comprising an MHC- II-binding epitope, and wherein the expressed HLA class II protein or portions thereof remains associated with a placeholder peptide; isolating the HLA class II protein or portions thereof expressed in the eukaryotic cell; performing a peptide exchange assay by (a) adding increasing amount of the candidate peptide to determine whether the candidate peptide displaces the placeholder peptide associated with the HLA class II protein or portions thereof; and (b) calculating the IC50 of the displacement reaction to determine the affinity of the candidate peptide to the HLA class II protein or portions thereof relative to the placeholder peptide, thereby verifying the specificity of the candidate peptide for binding an HLA class II protein.

In some embodiments, the identity of the peptide is known. In some embodiments, the identity of the peptide is not known. In some embodiments, the identity of the peptide is determined by mass spectrometry.

In some embodiments, the peptide exchange assay comprises detection of peptide fluorescent probes or tags. In some embodiments, the placeholder peptide is a CLIP peptide.

In some embodiments, the polynucleic acid construct comprises an expression vector, further comprising one or more of: a promoter, a linker, one or more protease cleavage sites, a secretion signal, dimerization factors, ribosomal skipping sequence, one or more tags for purification and or detection.

In one aspect, provided herein is a method for assaying immunogenicity of a MHC class II binding peptide, the method comprising: selecting a protein encoded by an HLA class II allele predicted by a machine-learning HLA-peptide presentation prediction model to bind to the peptide; wherein the prediction model has a positive predictive value of at least 0.1 at a recall rate of at least 0.1%, from 0.1%-50% or at the most 50% and wherein the protein has a probability greater than a threshold presentation prediction probability value for presenting the identified peptide sequence; contacting the peptide with the selected protein encoded by the HLA class II allele such that the peptide competes with a placeholder peptide associated with the selected protein encoded by the HLA class II allele, and displaces the placeholder peptide, thereby forming a complex comprising the HLA class II protein and the identified peptide; contacting the HLA class II protein and the identified peptide complex with a CD4+ T cell, assaying for one or more of activation parameters of the CD4+ T cell, selected from induction of a cytokine, induction of a chemokine and expression of a cell surface marker.

In some embodiments, the HLA class II allele is a tetramer or multimer. In some embodiments, the cytokine is IL-2. In some embodiments, the cytokine is IFN-gamma.

In one aspect, provided herein is a method for inducing a CD4+ T cells activation in a subject for cancer immunotherapy, the method comprising: identifying a peptide sequence associated with cancer and comprising a cancer mutation, wherein identifying comprises comparing DNA, RNA or protein sequences from the cancer cells of the subject to DNA, RNA or protein sequences from the normal cells of the subject; selecting a protein encoded by an HLA class II allele that is normally expressed by a cell of the subject, and predicted by a machine-learning HLA-peptide presentation prediction model to bind to the peptide; wherein the prediction model has a positive predictive value of at least 0.1 at a recall rate of at least 0.1%, from 0.1%-50% or at the most 50% and wherein the protein has a probability greater than a threshold presentation prediction probability value for presenting the identified peptide sequence; contacting the identified peptide with the selected protein encoded by the HLA class II allele to verify whether the identified peptide competes with a placeholder peptide associated with the selected protein encoded by the HLA class II allele to displace the placeholder peptide with an IC50 value of less than 500 nM; purifying the identified peptide; and administer an effective amount of the identified peptide to the subject.

In one aspect, provided herein is a method of manufacturing HLA class II tetramers or multimers, the method comprising: expressing in a eukaryotic cell, a vector comprising a nucleic acid sequence encoding an alpha chain and a beta chain of HLA protein, a linker, one or more protease cleavage sites, a secretion signal, a biotinylation motif and at least one tag for identification or for purification, such that each HLA protein alpha 1 and beta 1 heterodimers is secreted in dimerized state, wherein the heterodimer is associated with a placeholder peptide, purifying the secreted heterodimer from cell medium, validating the peptide binding activity using peptide exchange assay, adding streptavidin thereby conjugating heterodimers into tetramers, purifying the tetramers and having an yield of greater than 1 mg/L.

In some embodiments, the vector comprises a CMV promoter. In some embodiments, the vector comprises a sequence encoding a placeholder peptide linked via a cleavable site to the beta1 chain. In some embodiments, peptide exchange assay involves prior cleavage of the placeholder peptide from the beta chain. In some embodiments, the cleavable site is a thrombin cleavage site. In some embodiments, peptide exchange assay is a FRET assay. In some embodiments, the purification is by any one of: column chromatography, batch chromatography, ion exchange chromatography, size exclusion chromatography, affinity chromatography or LC-MS.

In one aspect, provided herein is a composition comprising HLA class II tetramers comprising either HLA-DR, or HLA-DP, or HLA-DQ heterodimers, each heterodimer comprising an alpha and a beta chain, purified and present at a concentration of greater than 0.25 mg/L. In some embodiments, the HLA class II tetramer comprises heterodimer pairs selected from a group consisting of: protein may be selected from the group consisting of an HLA-DR, and HLA-DP or an HLA-DQ protein. In some embodiments, the HLA protein is selected from the group consisting of: HLA-DPB1*01:01/HLA-DPA1*01:03, HLA-DPB1*02:01/HLA-DPA1*01:03, HLA-DPB1*03:01/HLA-DPA1*01:03, HLA-DPB1*04:01/HLA-DPA1*01:03, HLA-DPB1*04:02/HLA-DPA1*01:03, HLA-DPB1*06:01/HLA-DPA1*01:03, HLA-DQB1*02:01/HLA-DQA1*05:01, HLA-DQB1*02:02/HLA-DQA1*02:01, HLA-DQB1*06:02/HLA-DQA1*01:02, HLA-DQB1*06:04/HLA-DQA1*01:02, HLA-DRB1*01:01, HLA-DRB1*01:02, HLA-DRB1*03:01, HLA-DRB1*03:02, HLA-DRB1*04:01, HLA-DRB1*04:02, HLA-DRB1*04:03, HLA-DRB1*04:04, HLA-DRB1*04:05, HLA-DRB1*04:07, HLA-DRB1*07:01, HLA-DRB1*08:01, HLA-DRB1*08:02, HLA-DRB1*08:03, HLA-DRB1*08:04, HLA-DRB1*09:01, HLA-DRB1*10:01, HLA-DRB1*11:01, HLA-DRB1*11:02, HLA-DRB1*11:04, HLA-DRB1*12:01, HLA-DRB1*12:02, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16:01, HLA-DRB3*01:01, HLA-DRB3*02:02, HLA-DRB3*03:01, HLA-DRB4*01:01, HLA-DRB5*01:01).

In some embodiments, the heterodimer pairs are expressed in a eukaryotic cell. In some embodiments, the heterodimer pair is encoded by a vector. In some embodiments, the vector comprises: a nucleic acid sequence encoding an alpha chain and a beta chain of HLA protein, a secretion signal, a biotinylation motif and at least one tag for identification or for purification, such that each HLA protein alpha 1 and beta1 heterodimers is secreted in dimerized state, wherein the secreted heterodimer is associated with a placeholder peptide. In some embodiments, the vector comprises: a nucleic acid sequence encoding an alpha chain and a beta chain of HLA protein, a secretion signal, a biotinylation motif and at least one tag for identification or for purification, such that each HLA protein alpha 1 and beta1 heterodimers is secreted in dimerized state, wherein the secreted heterodimer is associated with a placeholder peptide.

In some embodiments, HLA class II heterodimers secreted from eukaryotic cells into cell culture medium, and is purified by any one of: column or batch chromatography, ion exchange chromatography, size exclusion chromatography, affinity chromatography or LC-MS.

In one aspect, provided herein is a method of screening a drug comprising a polypeptide sequence for immunogenicity in a subject, the method comprising: inputting amino acid information of peptide sequences of the polypeptide sequence, using a computer processor, into a machine-learning HLA-peptide presentation prediction model to generate a set of presentation predictions for the peptide sequences, each presentation prediction representing a probability that one or more proteins encoded by an HLA class I or II allele of a cell of the subject will present an epitope sequence of a given peptide sequence; wherein the machine-learning HLA-peptide presentation prediction model comprises: a plurality of predictor variables identified at least based on training data wherein the training data comprises: sequence information of sequences of peptides presented by an HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables; (b) determining or predicting that each of the peptide sequences of the polypeptide sequence would not be immunogenic to the subject based on the set of presentation predictions; and (c) administering to the subject a composition comprising the drug.

In one aspect, provided herein is a method of screening a drug comprising a polypeptide sequence for immunogenicity in a subject, the method comprising: (a) inputting amino acid information of peptide sequences of the polypeptide sequence, using a computer processor, into a machine-learning HLA-peptide presentation prediction model to generate a set of presentation predictions for the peptide sequences, each presentation prediction representing a probability that one or more proteins encoded by an HLA class I or II allele of a cell of the subject will present an epitope sequence of a given peptide sequence; wherein the machine-learning HLA-peptide presentation prediction model comprises: a plurality of predictor variables identified at least based on training data; wherein the training data comprises: sequence information of sequences of peptides presented by an HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables; (b) determining or predicting that at least one of the peptide sequences of the polypeptide sequence would be immunogenic to the subject based on the set of presentation predictions.

In one embodiment, the method further comprises deciding not to administer the drug to the subject.

In one embodiment, the drug comprises and antibody or binding fragment thereof.

In one embodiment, the peptide sequences of the polypeptide sequences comprise each contiguous peptide sequence of the polypeptide sequence that has a length of 8, 9, 10, 11 or 12 amino acids, and wherein the protein encoded by an HLA class I or II allele of a cell of the subject is a protein encoded by an HLA class I allele of a cell of the subject.

In one embodiment, the peptide sequences of the polypeptide sequences comprise each contiguous peptide sequence of the polypeptide sequence that has a length of 15, 16, 17, 18, 19, 20, 21, 22, 23, 24, or 25 amino acids, and wherein the protein encoded by an HLA class I or II allele of a cell of the subject is a protein encoded by a class II MHC allele of a cell of the subject.

In one aspect, provided herein is a method of treating a subject with an autoimmune disease or condition comprising: (a) identifying or predicting an epitope of an expressed protein presented by an HLA class I or II of a cell of the subject, wherein a complex comprising the identified or predicted epitope and the HLA class I or II is targeted by a CD8 or CD4 T cell of the subject; (b) identifying a T cell receptor (TCR) that binds to the complex; (c) expressing the TCR in a regulatory T cell from the subject or an allogeneic regulatory T cell; and (d) administering the regulatory T cell expressing the TCR to the subject.

In one embodiment, the autoimmune disease or condition is diabetes.

In one embodiment, the cell is an islet cell.

In one aspect, provided herein is a method of treating a subject with an autoimmune disease or condition comprising administering to the subject a regulatory T cell expressing a T cell receptor (TCR) that binds to a complex comprising (i) an epitope of an expressed protein identified or predicted to be presented by an HLA class I or II of a cell of the subject and (ii) the HLA class I or II, wherein the complex is targeted by a CD8 or CD4 T cell of the subject.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

MAPTAC™ can be used for high-throughput peptide binding assays where peptides bound to HLA class II are measured after isolation with MAPTAC™ constructs at different time points and under different conditions, such as heating at 37° C., to obtain the sequences of populations of peptides with different stabilities using LC-MS/MS.

In one aspect, provided herein is a method for treating a cancer in a subject the method comprising: identifying peptide sequences, wherein the peptide sequences are associated with cancer, wherein identifying comprises comparing DNA, RNA or protein sequences from the cancer cells of the subject to DNA, RNA or protein sequences from the normal cells of the subject; inputting amino acid information of the peptide sequences identified, using a computer processor, into a machine-learning HLA-peptide presentation prediction model to generate a set of presentation predictions for the peptide sequences identified, each presentation prediction representing a probability that one or more proteins encoded by an HLA class II allele of a cell of the subject will present a given sequence of a peptide sequence identified; wherein the machine-learning HLA-peptide presentation prediction model comprises: a plurality of predictor variables identified at least based on training data wherein the training data comprises: sequence information of sequences of peptides presented by an HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables; and selecting a subset of the peptide sequences identified based on the set of presentation predictions for preparing the personalized cancer therapy; and administering to the subject a composition comprising one or more of the peptides, wherein the prediction model has a positive predictive value of at least 0.1 at a recall rate of at least 0.1%, from 0.1%-50% or at most 50%.

In some embodiments, the machine-learning HLA-peptide presentation prediction model comprises sequence information of sequences of peptides presented by an HLA protein expressed in cells and identified by mass spectrometry after performing reverse phase offline fractionation.

In some embodiments, the prediction model exhibits a 1.1× to 100× fold improvement compared to NetMHCIIpan. In some embodiments, the prediction model exhibits a 1.1, 2, 3, 4, 5, 6, 7, 7.4, 8, 9, 10, 11, 12, 13, 14, 15, 16, 17, 18, 18, 20, 21, 22, 23, 24, 25, 26, 27, 28, 29, 30, 31, 32, 33, 34, 35, 36, 37, 38, 39, 40, 41, 42, 43, 44, 45, 50, 55, 60, 61, 62, 63, 64, 65, 66, 67, 68, 69, 70, 71, 72, 73, 74, 75, 76, 77, 78, 79, 80, 81, 8, 83, 84, 85, 86, 87, 88, 89, 90, 91, 92, 93, 94, 95, 96, 97, 98, 99, 100-fold or more improvement compared to NetMHCIIpan.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG." herein), of which:

FIG. 3 shows that examples of MS-derived motifs match known patterns and show consistency across transfected cell lines.

FIG. 4 is a bar plot showing the performance of the binding predictor (neonmhc2) and NetMHCIIpan applied to a validation dataset consisting of observed mass spec peptides and decoy peptides which are generated at a ratio of 1:19 (hits:decoys) by randomly shuffling the hit peptides. For the NEON binding predictor neonmhc2, a separate model is built for each MHC II allele shown. The height of the bars shows the positive predictive value (PPV), defined as the fraction of predicted binders in the validation set which were indeed hit peptides. The alleles are sorted by the model's performance when predicting for that allele.

FIG. 5 shows the performance of the HLA class II binding predictor when trained/validated on sets of peptides with different scored peak intensity (SPI) cutoffs. For each allele-specific model that is trained, shown is the model's performance in 3 settings: trained and evaluated on datasets using observed MS hit peptides of larger than or equal to 70 SPI, trained on peptides with larger than or equal to 50 SPI and validated on peptides with larger than or equal to 70 SPI, and trained and validated on peptides with larger than or equal to 50 SPI.

FIGS. 7B, 7C and 7D show that, generally, for the 35 HLA-DR alleles collected, when the training set size increases, the value of PPV increases.

Evaluated peptides include only those posted to IEDB the year after NetMHCIIpan was released.

Figure 16:
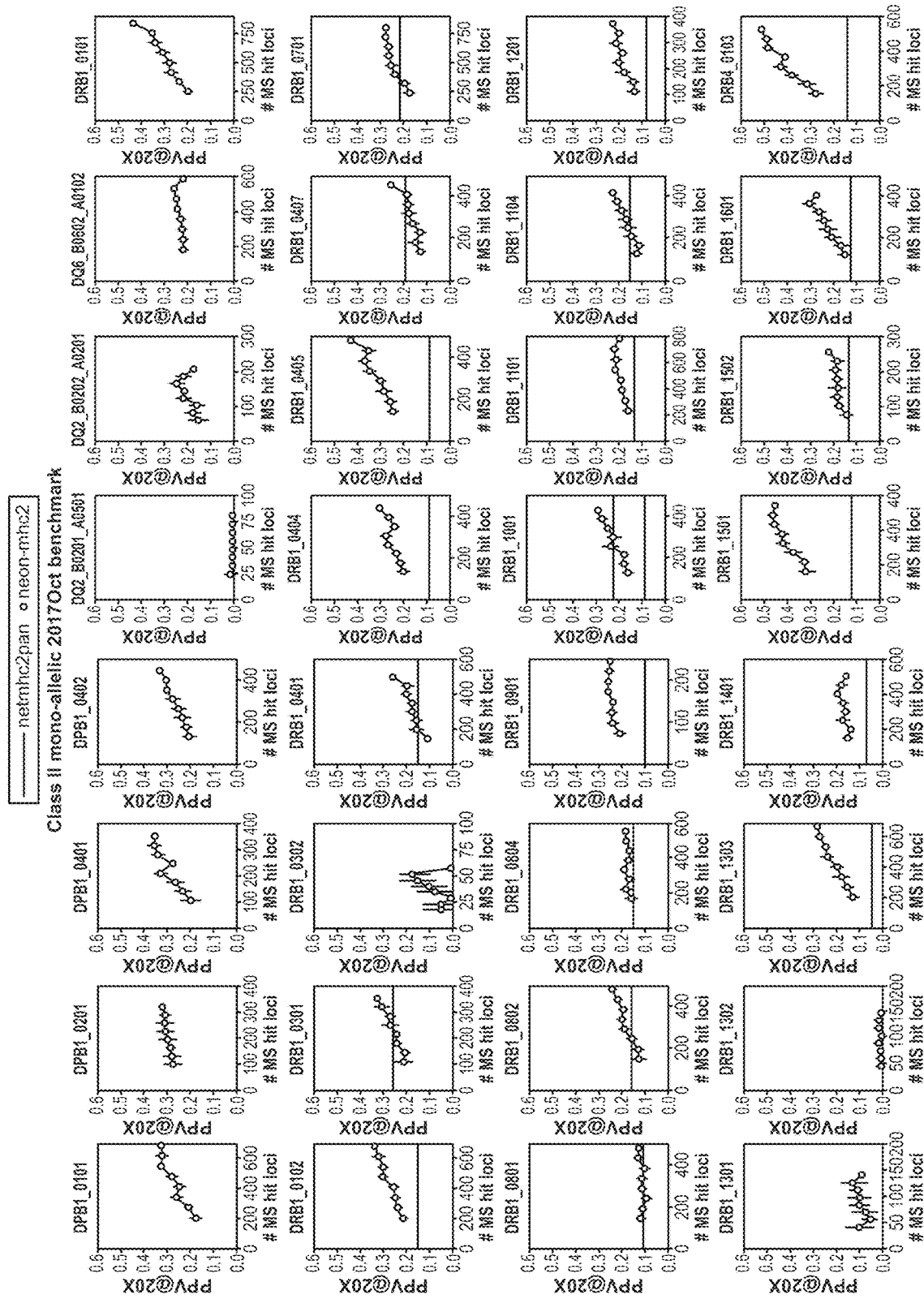

FIG. 16 is an exemplary depiction of the performance of neonmhc2 as a function of training data set size.

FIG. 17A depicts exemplary cluster assignments for MAPTAC™ peptides (20 per allele) spiked into pan-DR and pan-class II MHC MS datasets. Datasets were deconvolved using GibbsCluster. Each box represents one MAPTAC™ peptide. The color shading of the box indicates which cluster it was assigned to, and gray bars indicate which allele the peptide actually came from. The total number of clusters in the Gibbs cluster solution (right side) was selected using a mutual information (MI) metric. The MI score also determines how the samples are sorted; samples with high-MI solutions appear at the top.

Figure 17B:
Figure 17B:
Figure 17B:
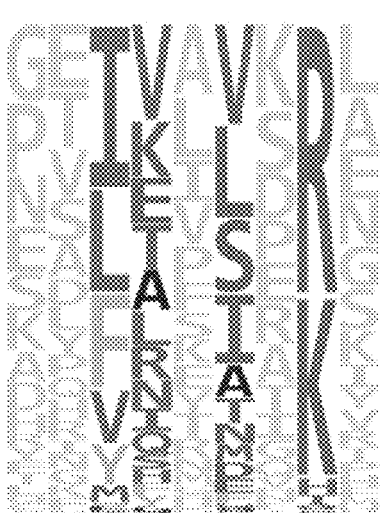
Figure 17B:

FIG. 17B depicts exemplary core-binding sequence logos for multi-allelic MS data deconvolved by GibbsCluster. Each set of peptides corresponds to the cluster that aligned best with the MAPTAC™ spike-ins.

Figure 17C:
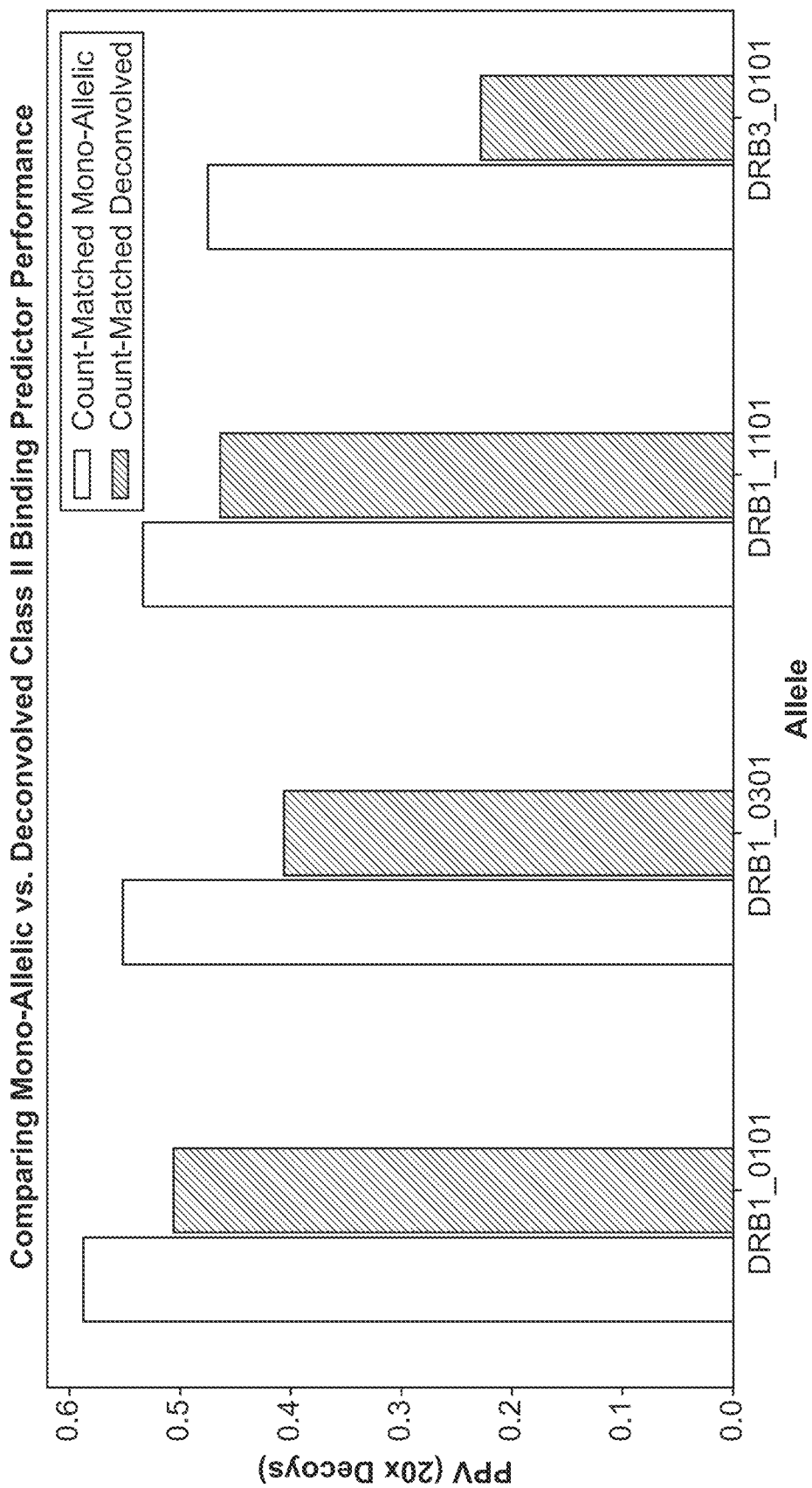

FIG. 17C depicts representative performance of models using either MAPTAC™ data or deconvolved multi-allelic data to predict hold-out MAPTAC™ peptides. For each allele, the larger of the two data sources (usually MAPTAC™) was down-sampled so that the predictors would be based on an equal number of training examples. NetMHCIIpan performance is shown as an additional comparison.

Figure 17D:
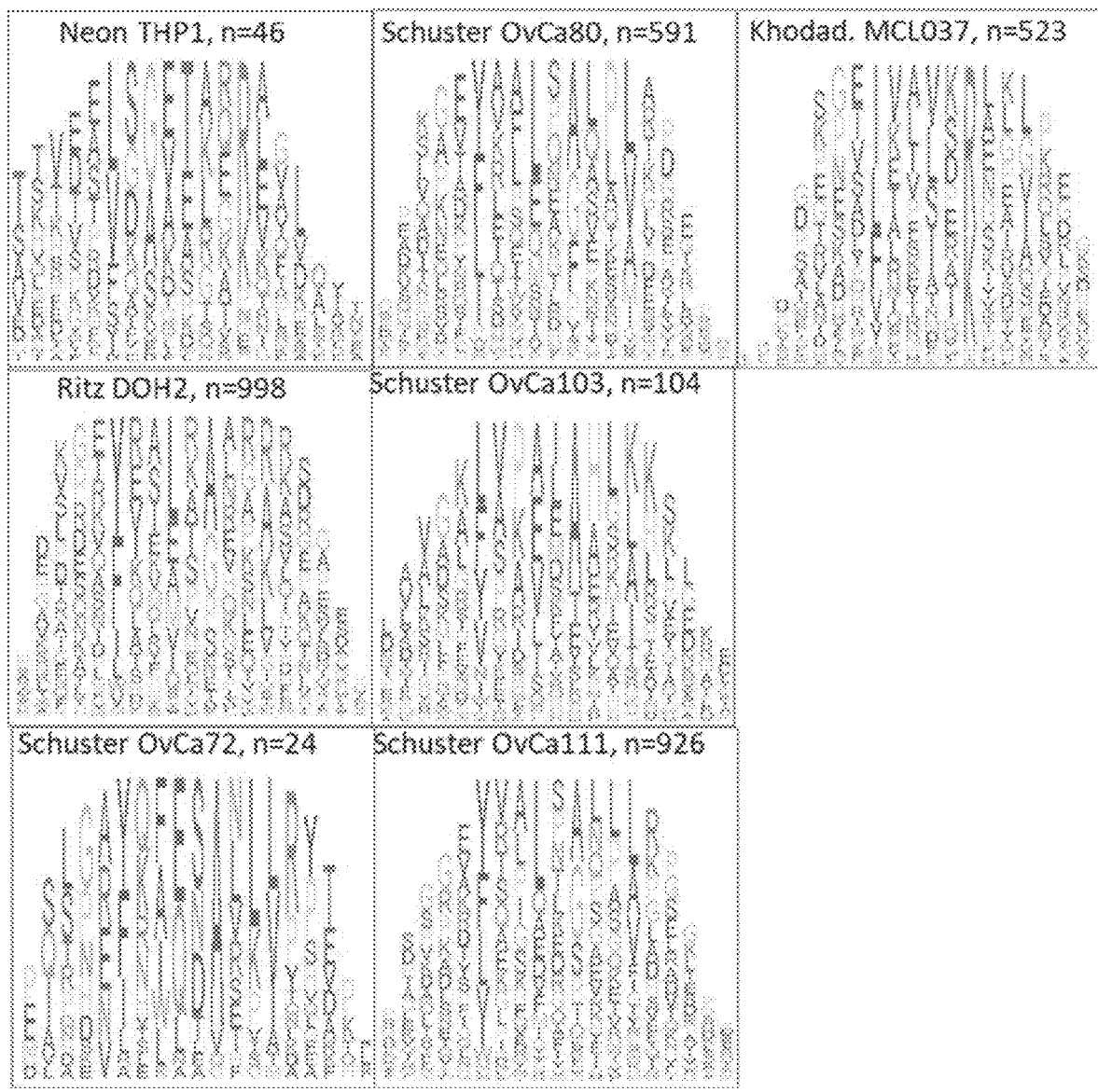

FIG. 17D depicts exemplary core binding sequence logos derived from multi-allelic MS data from the indicated sources.

Figure 18A:
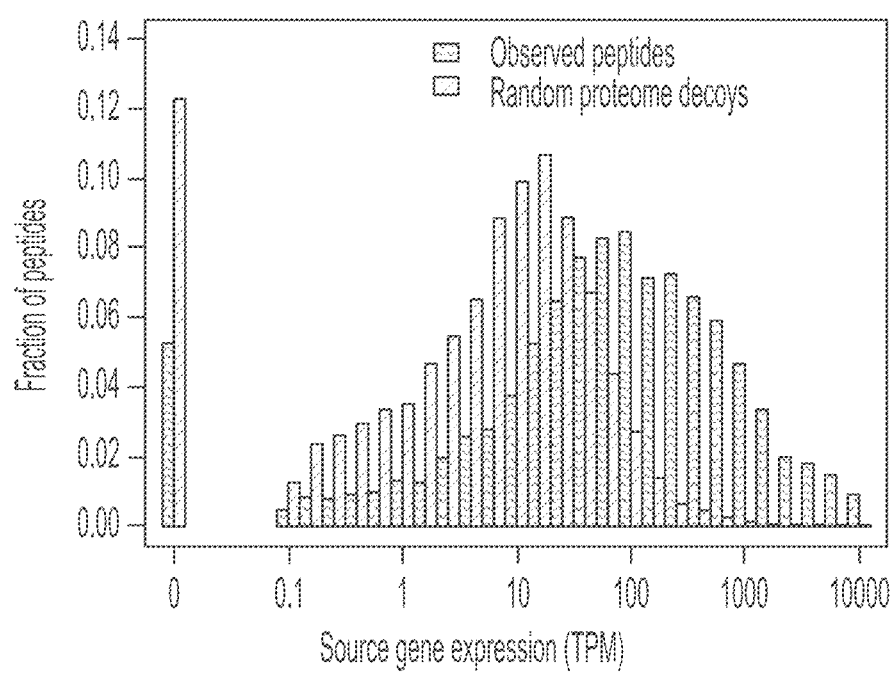

FIG. 18A depicts an exemplary graph of fraction of peptides vs source gene expression (transcripts per million (TPM)) for MS-observed peptides and random proteome decoys (data replotted from Schuster et al. 2017).

Figure 18B:
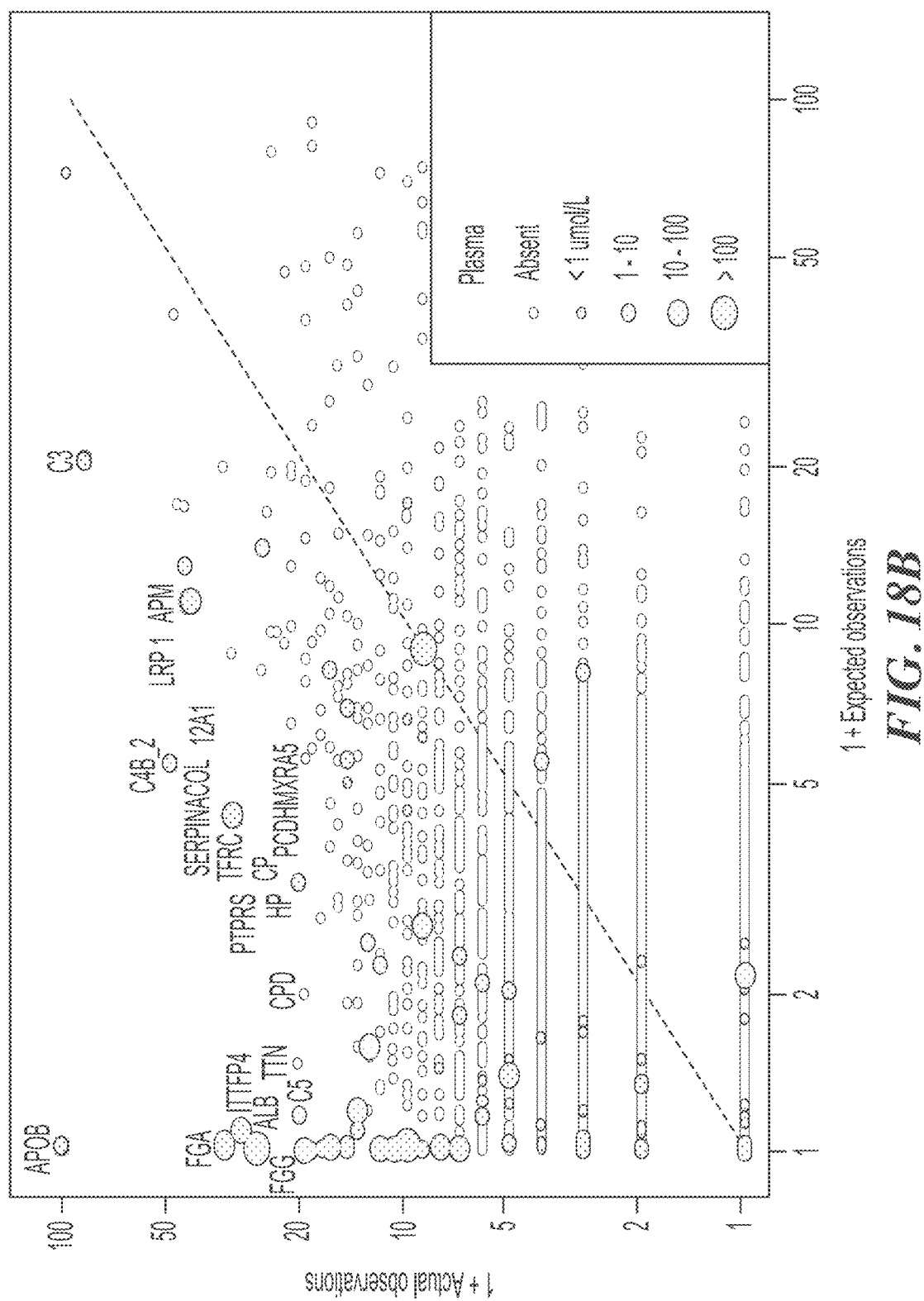

FIG. 18B depicts exemplary observed vs. expected number of Class II peptides per gene as determined by a joint analysis of colorectal cancer, melanoma, and ovarian cancer datasets (Loffler et al., 2018, and Schuster et al., 2017). The expected count is derived by multiplying gene length by expression level. Expected and observed counts were summed across relevant samples. Genes with known presence in plasma are marked according to their concentration (Inset).

Figure 18C:
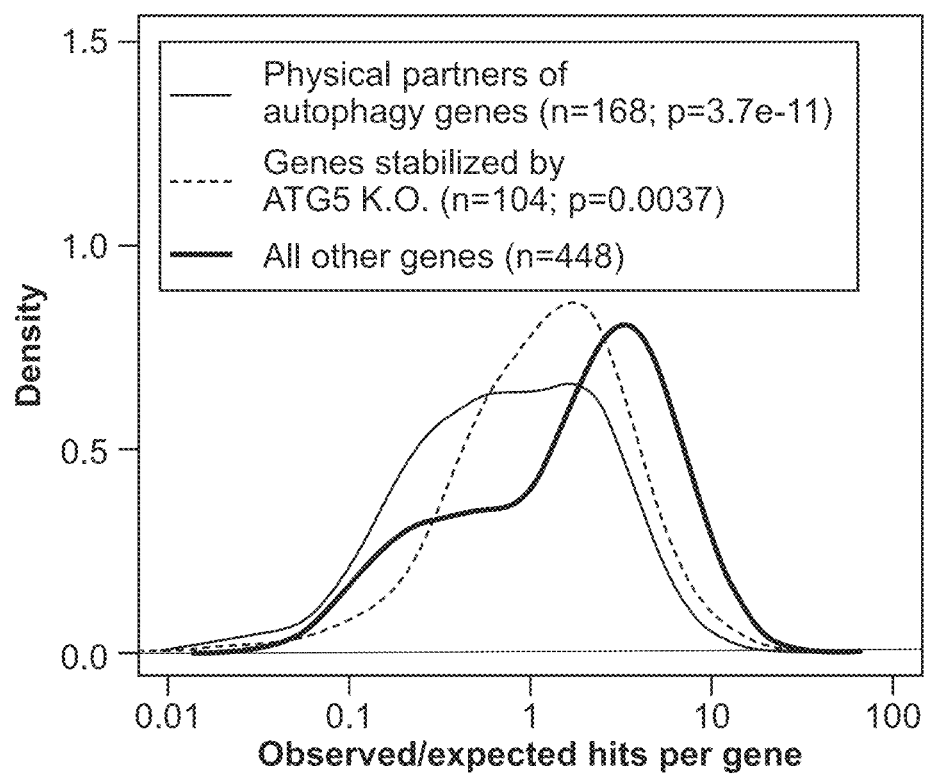

FIG. 18C depicts exemplary distribution of enrichment scores (ratio of observed to expected observations, as in FIG. 18B) for genes associated with autophagy.

Figure 18D:
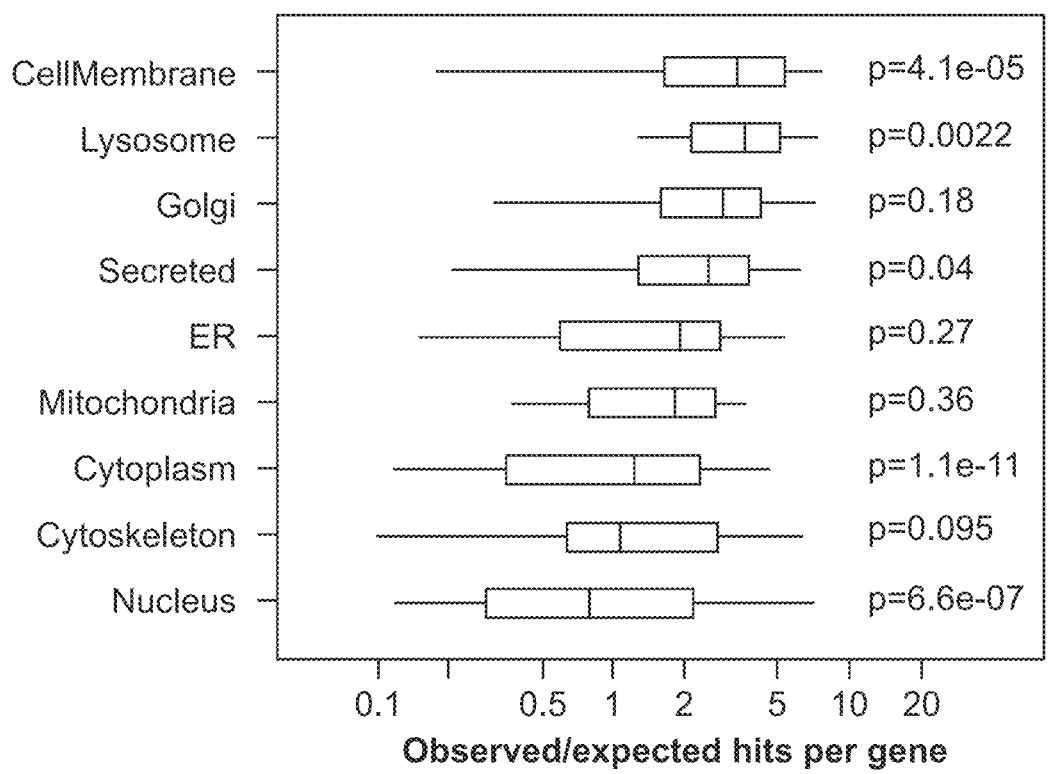

FIG. 18D depicts exemplary distribution of enrichment scores according to the localization of each source gene. Source gene localization was determined using Uniprot (uniprot_sprot.dat).

Figure 18E:
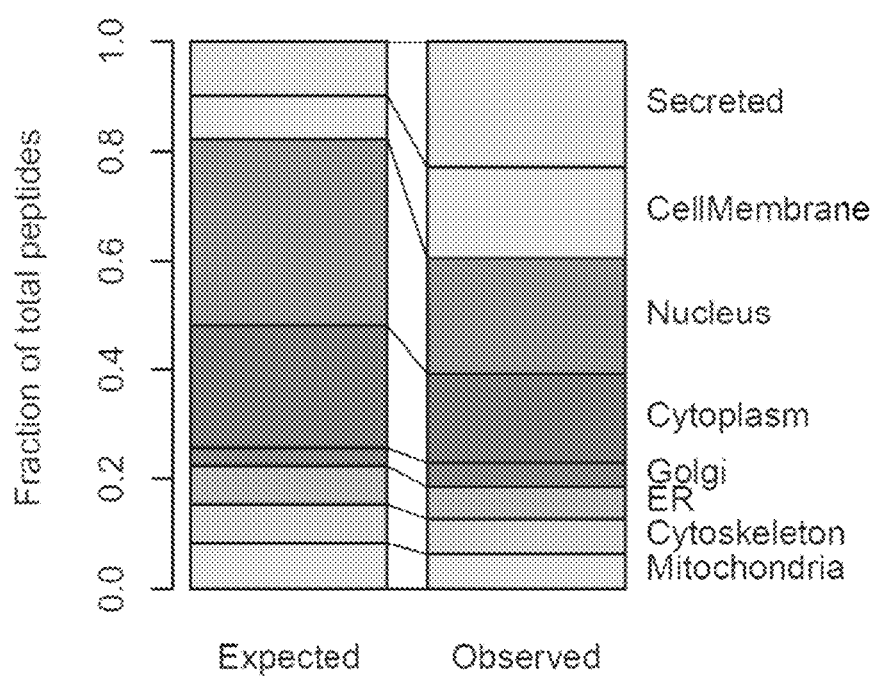

FIG. 18E depicts exemplary data representing comparison of the expected versus observed frequency of fraction of total number of peptides having MHC-II binding affinity, segregated based on their cellular localization properties.

Figure 18F:
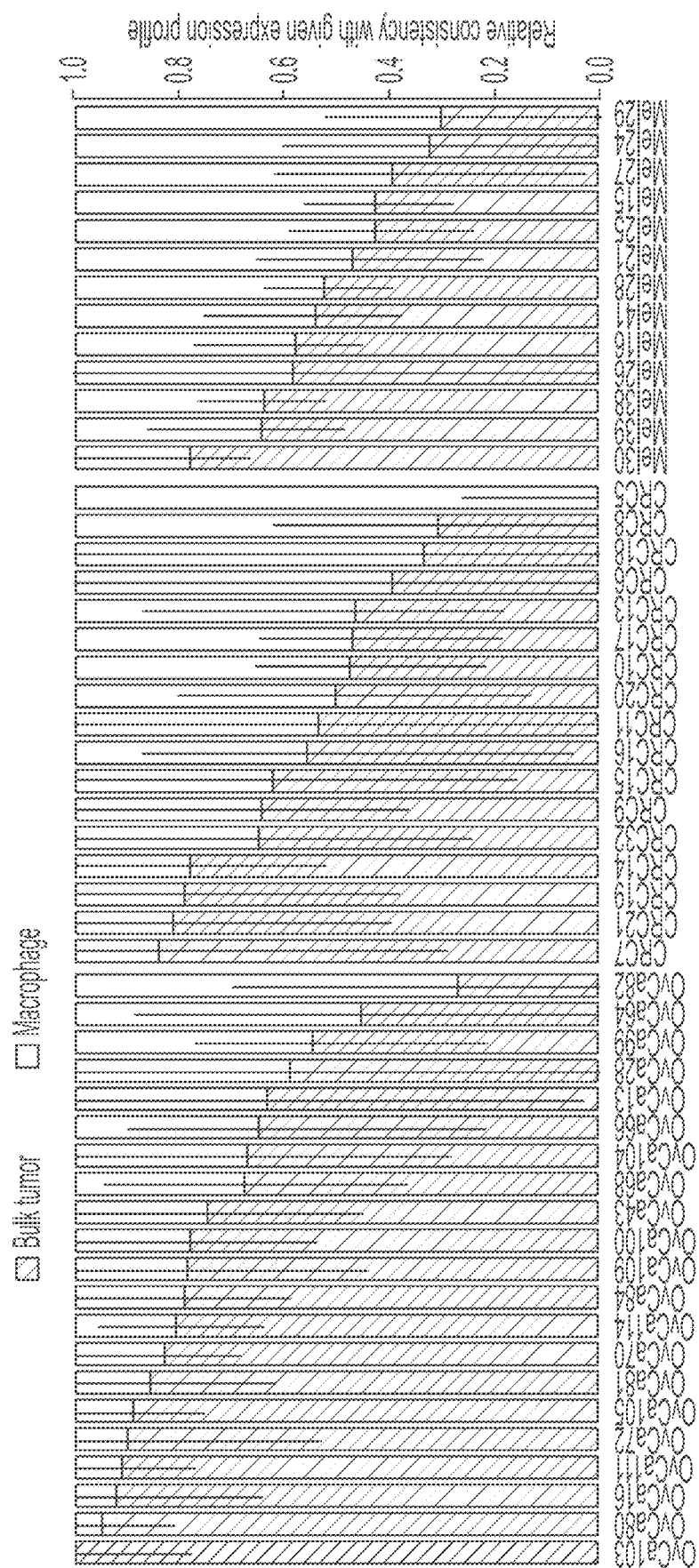

FIG. 18F depicts exemplary representative data of relative concordance of peptides in observations with respect to two different gene expression profiles. For each sample, gene-level peptide counts were modeled as a linear combination of a bulk tumor gene expression and professional APC (macrophage) gene expression profile. The ratio of the coefficients determines the relative concordance of each expression profile with the peptide repertoire. Error bars correspond to a 95% confidence interval computed by bootstrap resampling.

Figure 19A:
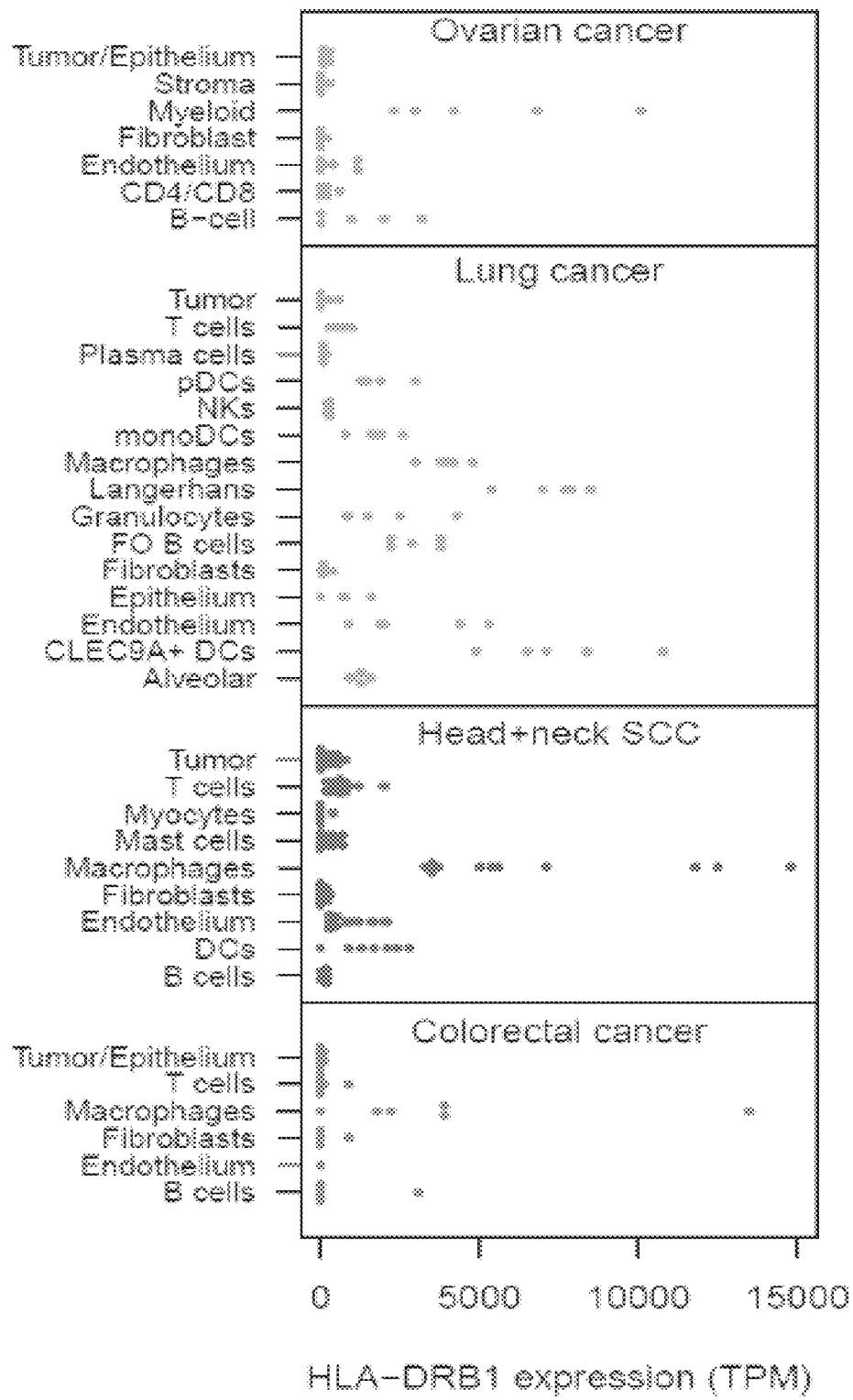

FIG. 19A depicts exemplary representative data of expression levels of HLA-DRB1 in the five example studies. Each dot represents expression in an individual cell type in an individual patient, averaged over cells.

Figure 19B:
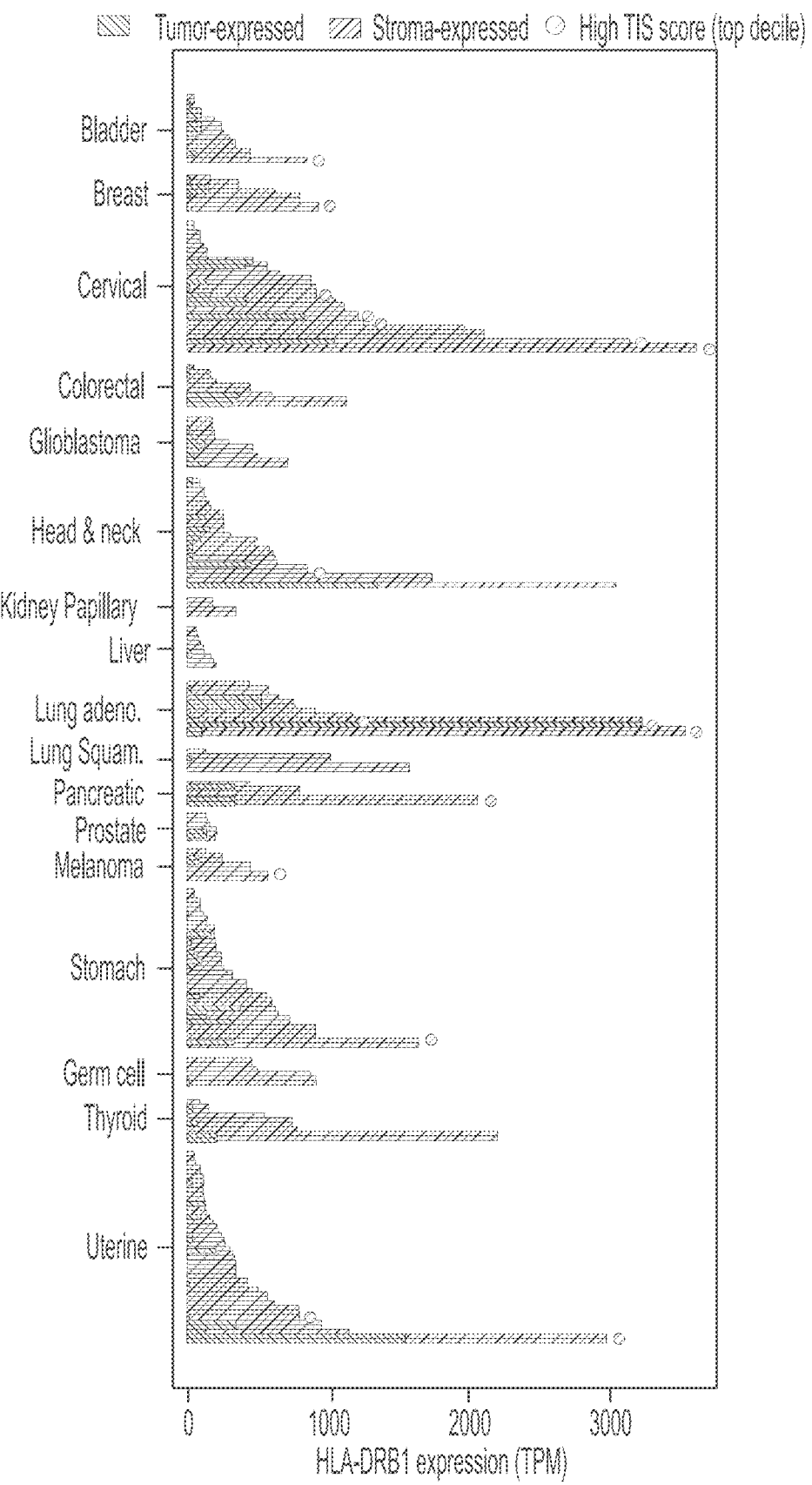

FIG. 19B depicts exemplary representative data of tumor and stromal derived HLA-DRB1 expression as inputted from RNA-Seq of TCGA patients. Horizontal bars correspond to individual patients and are grouped by tumor type. Patients were included if they had a mutation in HLA class II pathway gene (CIITA, CD74 or CTSSS) as determined by DNA-based mutation calls. For each patient, the fraction of HLA-DRB1 expression attributable to the tumor estimated as min(1,2f), where f is the fraction of RNA-Seq reads in CIITA, CD74, or CTSS exhibiting a mutation.

Figure 19C:
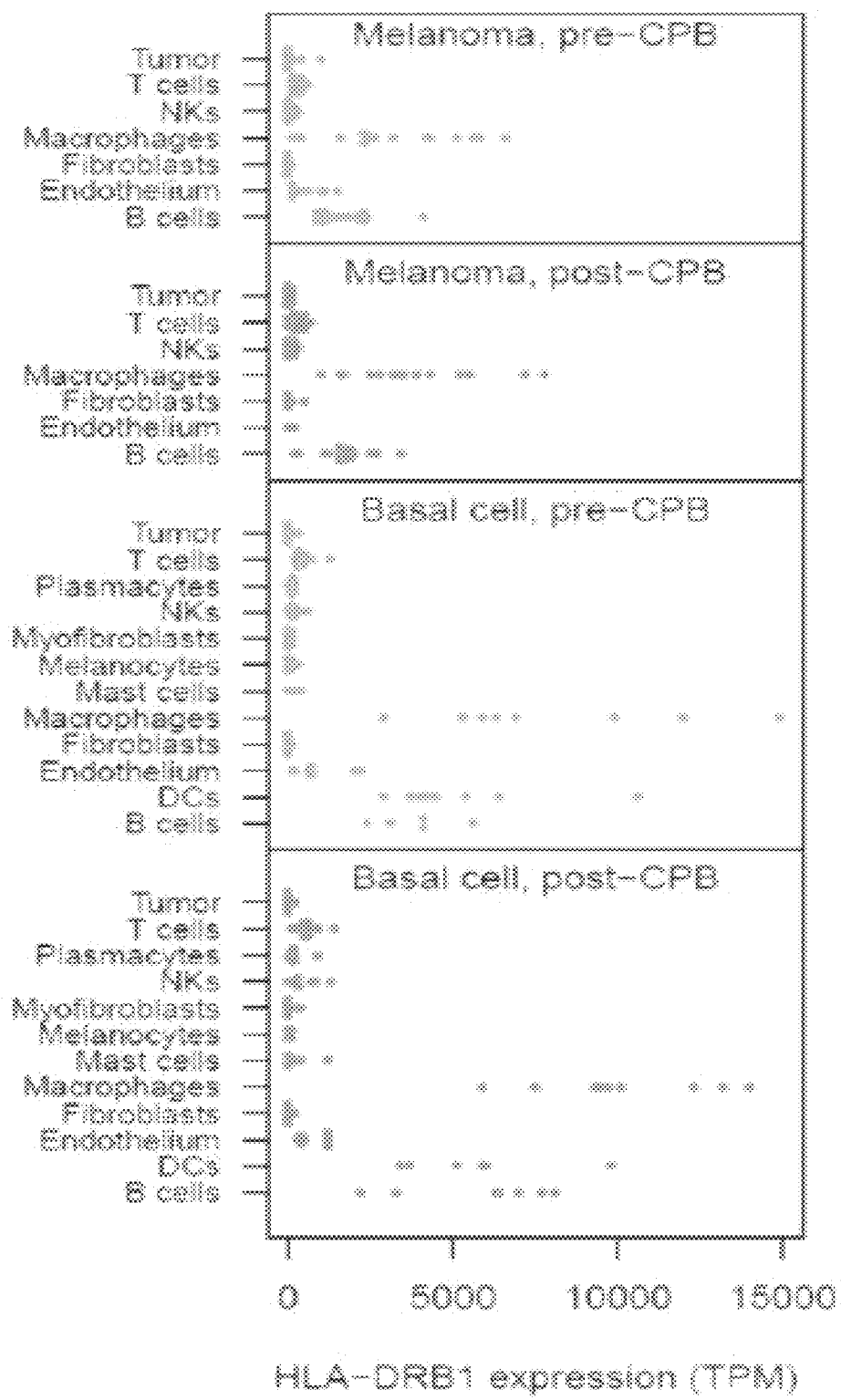

FIG. 19C depicts exemplary representative data of additional single-cell RNA-Seq studies that include biopsies pre- and post-checkpoint blockade immunotherapy.

Figure 20:
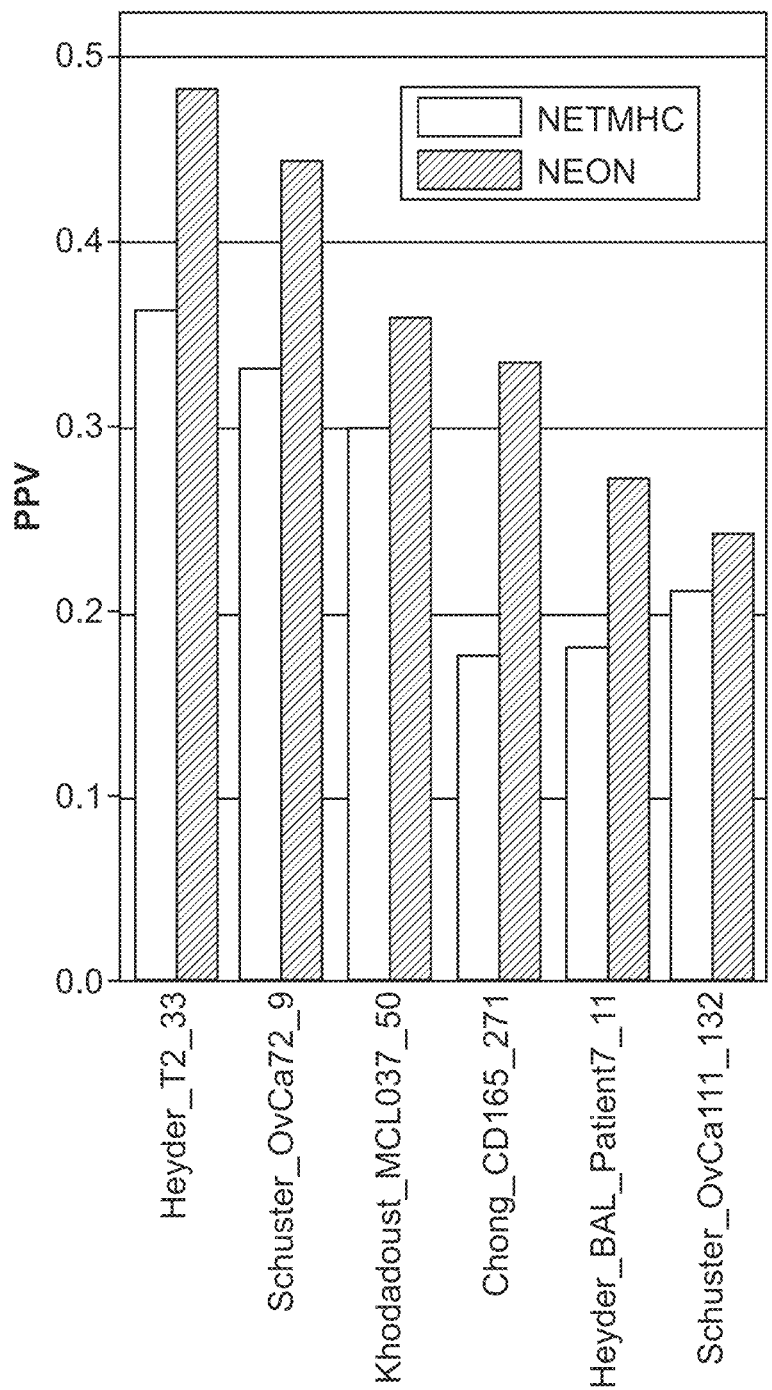

FIG. 20 depicts exemplary representative experimental data assessing prediction overall performance on natural donor tissues.

Figure 21A:
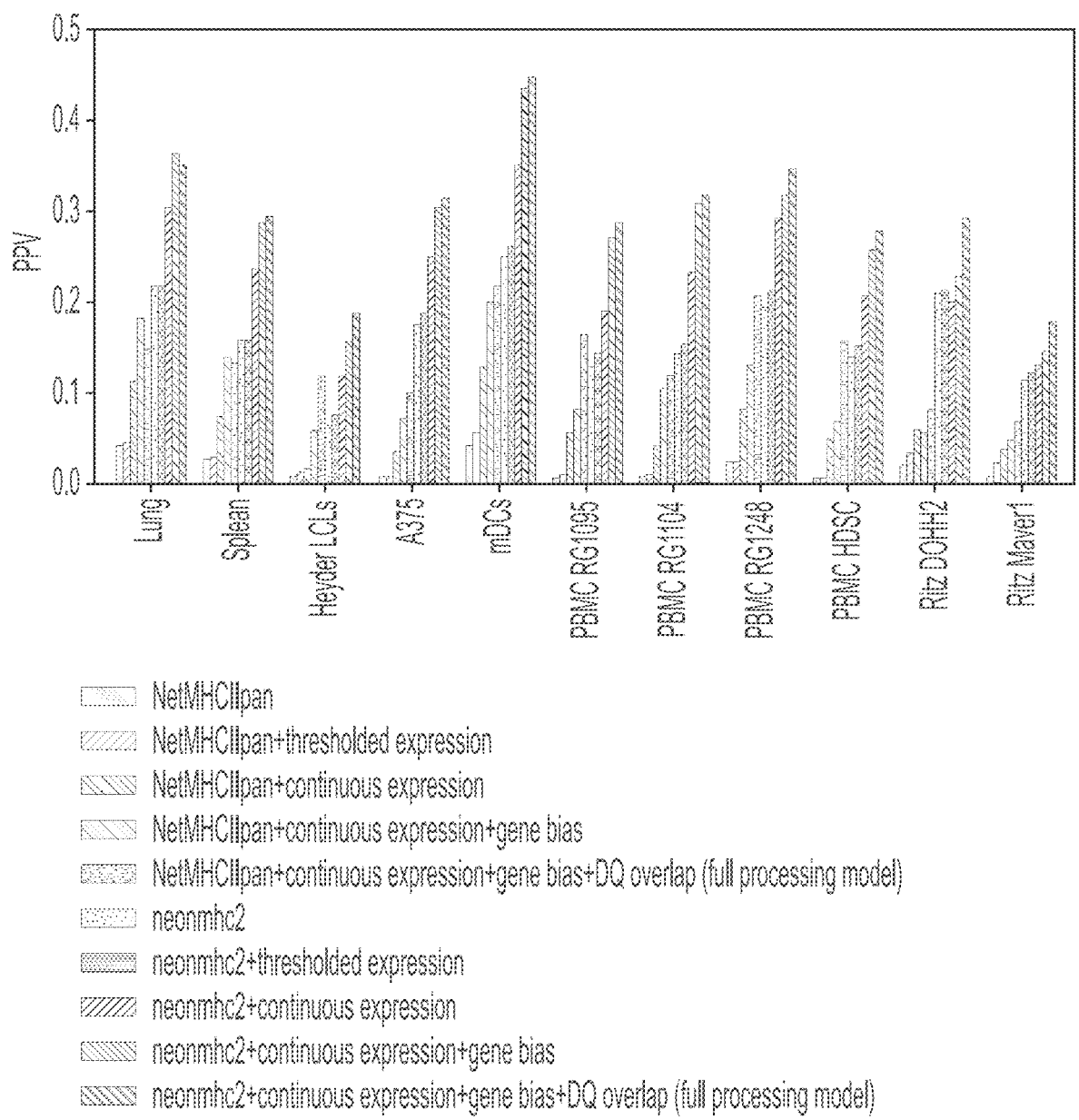

FIG. 21A depicts exemplary representative data, showing that the integrated presentation model predicts cellular HLA class II ligandomes. It represents. PPV at a 1:499 hit-to-decoy ratio for pan-DR datasets (also analyzed in FIG. 30B and FIG. 32E). Predictors use binding prediction (NetMHCIIpan or neonmhc2) and optionally employ gene expression, gene bias (per FIG. 32A), and overlap with previously observed HLA-DQ peptides. For each candidate peptide, the binding score was calculated as the maximum across the HLA-DR alleles in the sample genotype.

Figure 21B:
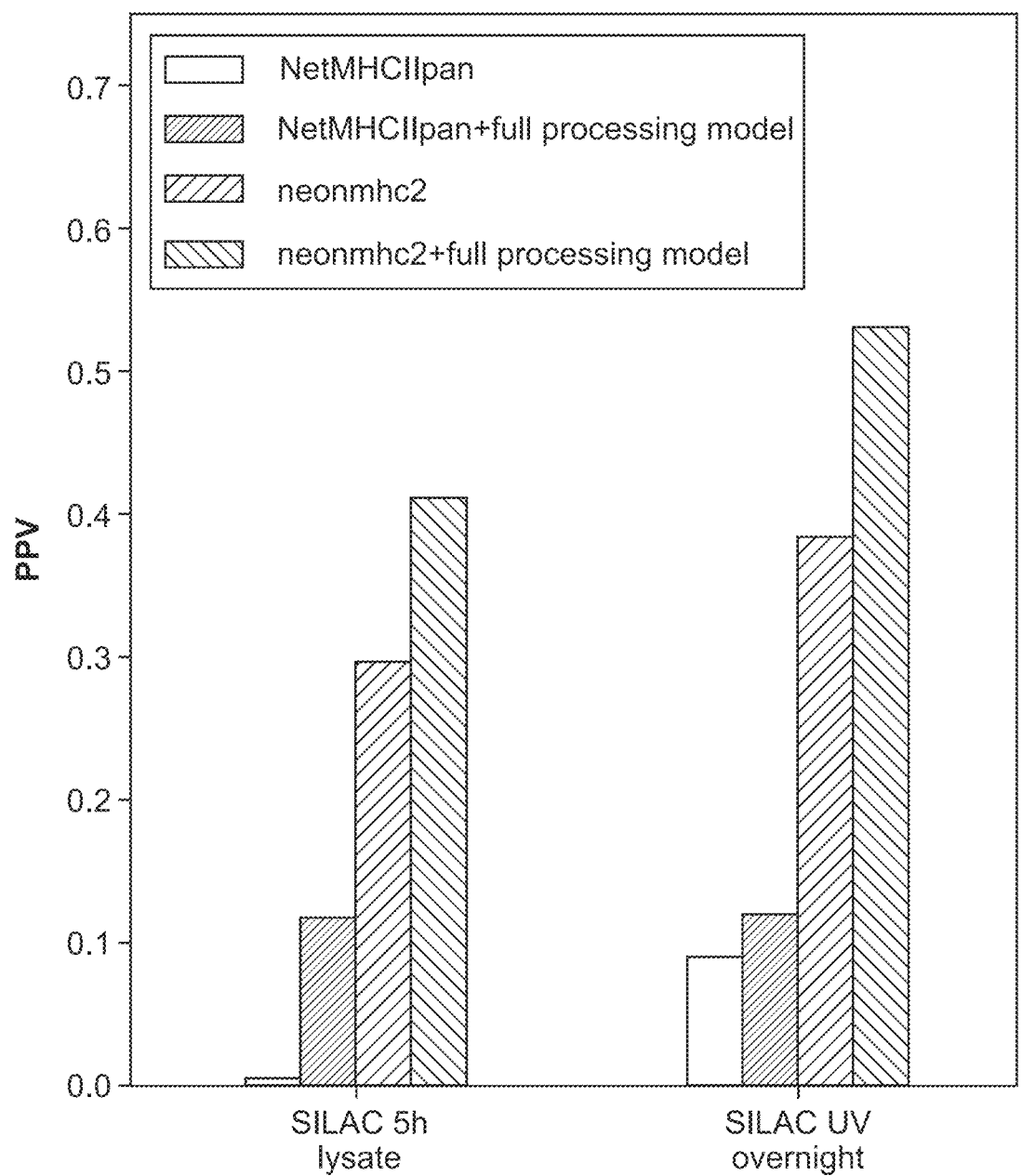

FIG. 21B depicts exemplary representative data, showing prediction performance for tumor-derived peptides as identified using SILAC, presented by dendritic cells (analyzed from cell lysates) using the same hit:decoy ratio and performance metrics as in FIG. 21A, with and without use of processing features.

Figure 21C:
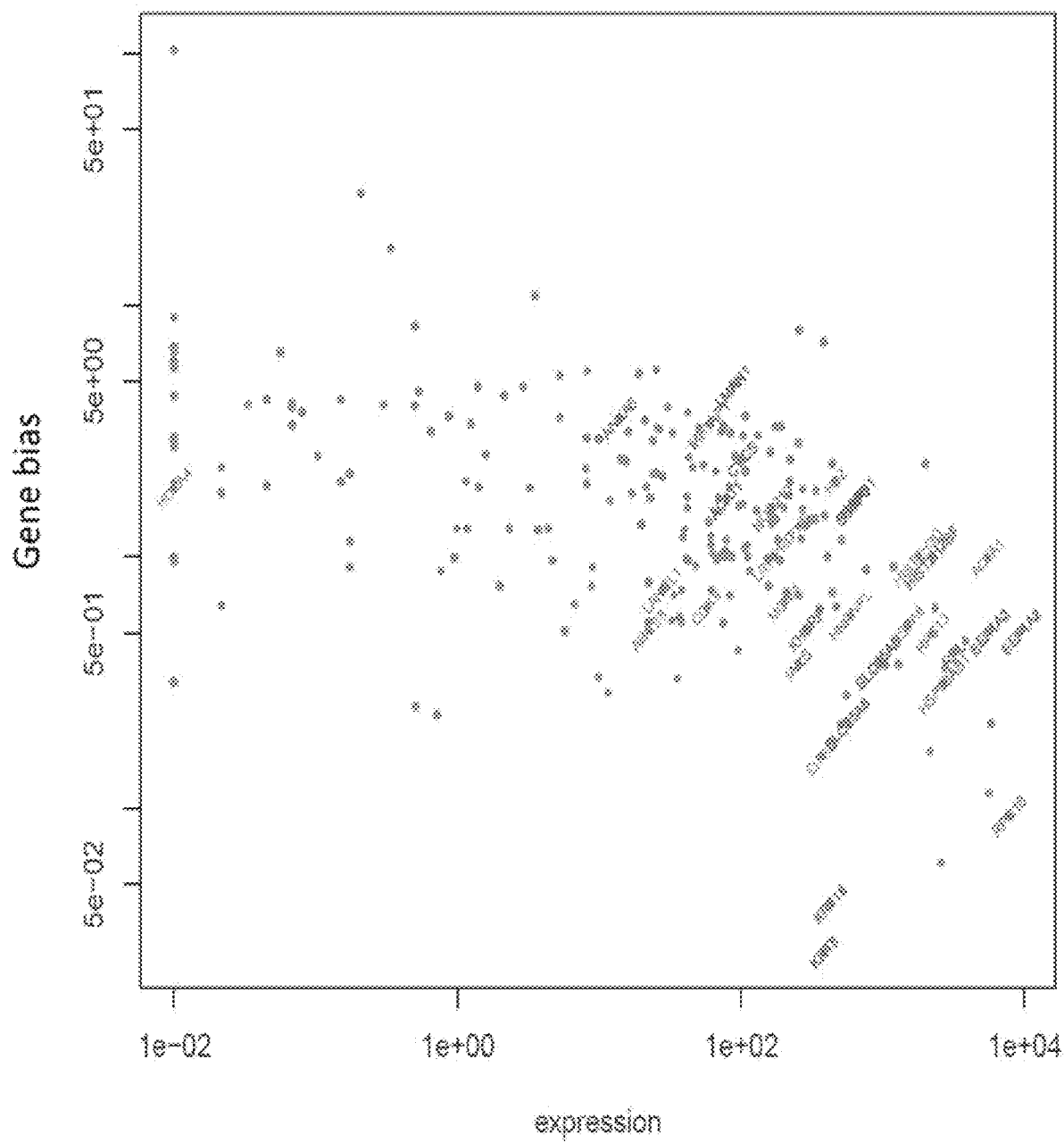

FIG. 21C depicts exemplary expression and gene bias scores for heavy-labeled peptides observed in an UV treatment experiment (plotted according to K562 expression) as compared to light-labeled peptides (plotted according to DC expression).

Figure 21D:

FIG. 21D depicts an exemplary diagram representing overlap of heavy-labeled peptide source genes according to the lysate and UV-treatment experiments. Gene names are shaded by functional class.

Figure 22A:
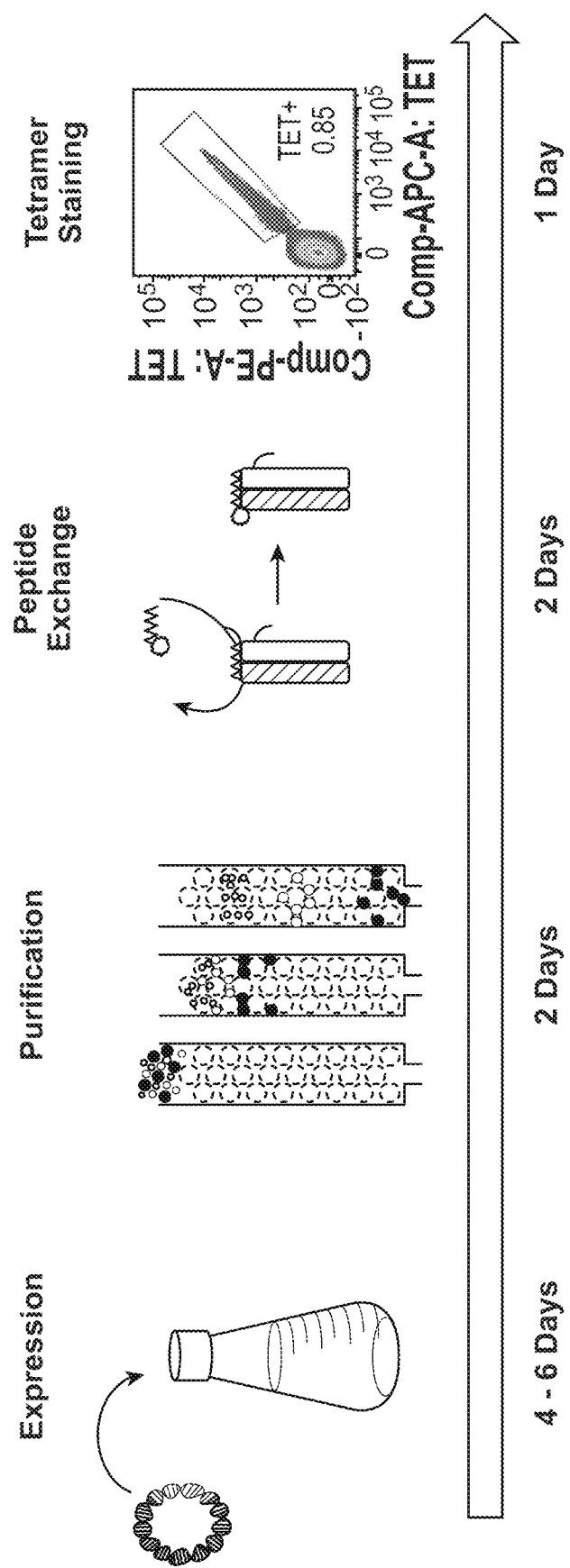

FIG. 22A depicts an exemplary flow diagram representing an assay protocol disclosed herein, to validate HLA class II-driven CD4+ T cells and T cell responses.

Figure 22B:
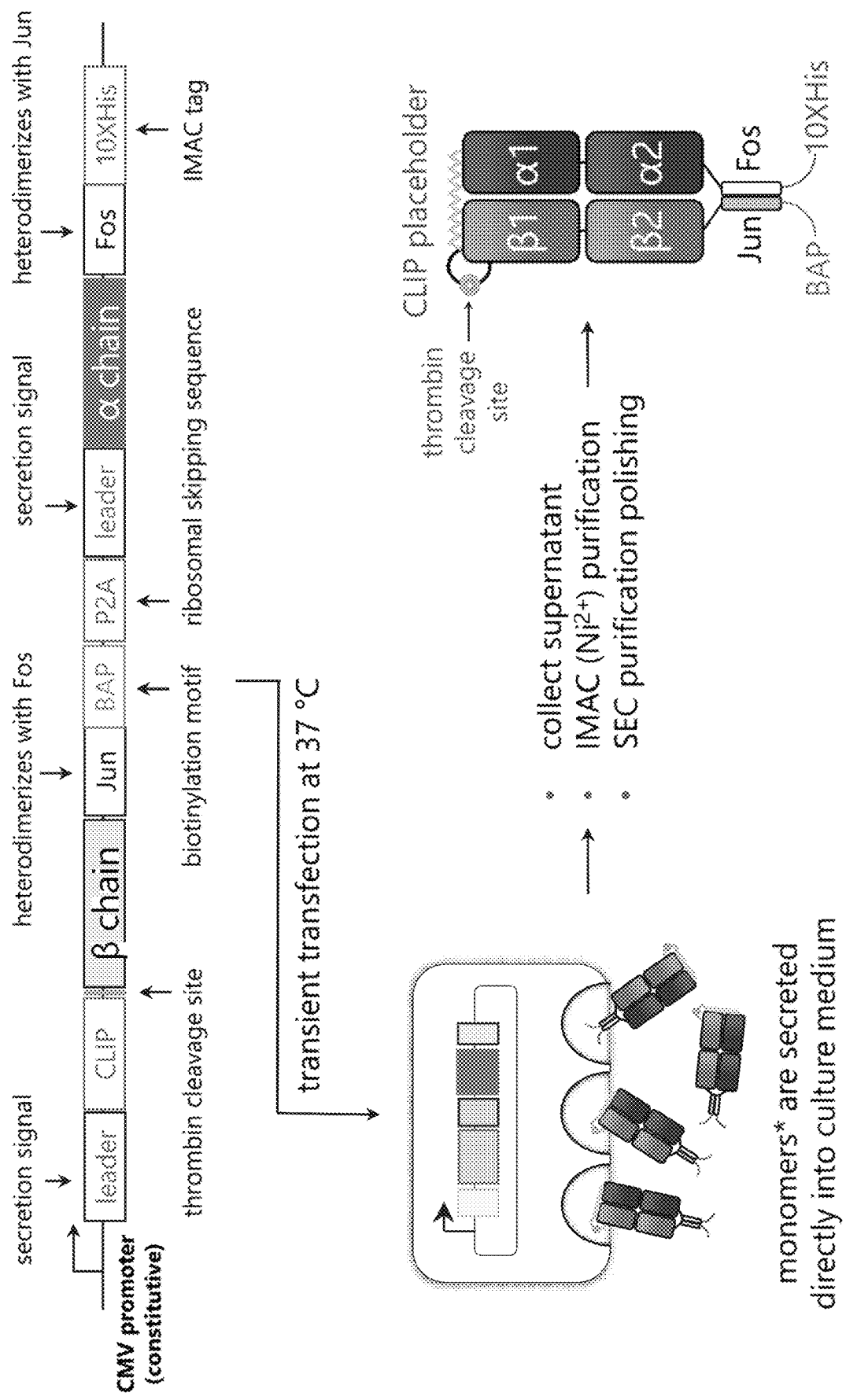

FIG. 22B depicts an exemplary HLA protein dimer construct design for peptide exchange assay (upper panel) and a graphical representation of an exemplary assay workflow (lower panel). Figure discloses "10×His" as SEQ ID NO: 20.

Figure 23:
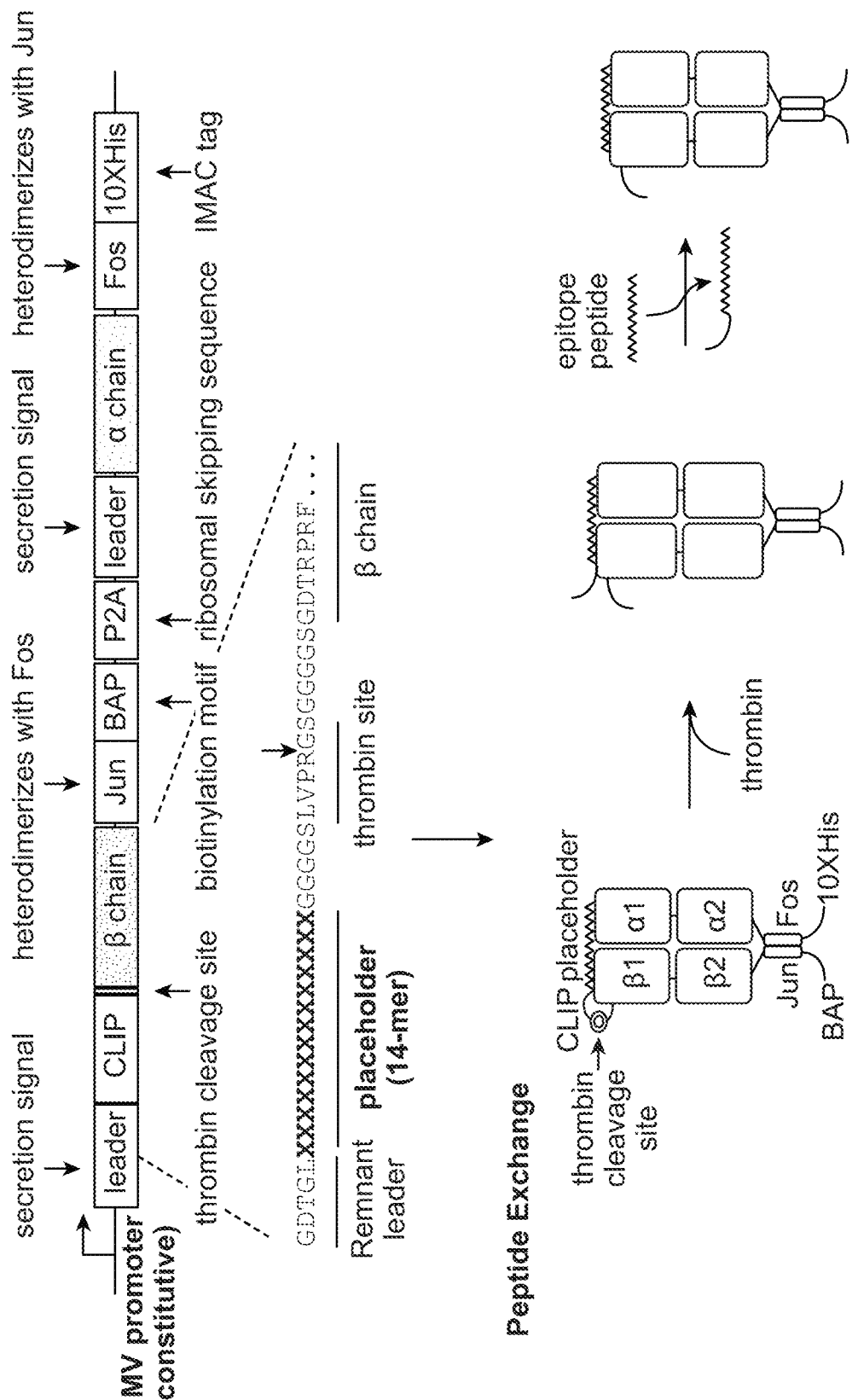

FIG. 23 depicts an exemplary graphical illustration of an exemplary vector design for MHC-II expression for screening new binding peptides, and a representation of the expressed protein product. Figure discloses SEQ ID NO: 39 and discloses "10×His" as SEQ ID NO: 20.

Figure 24:
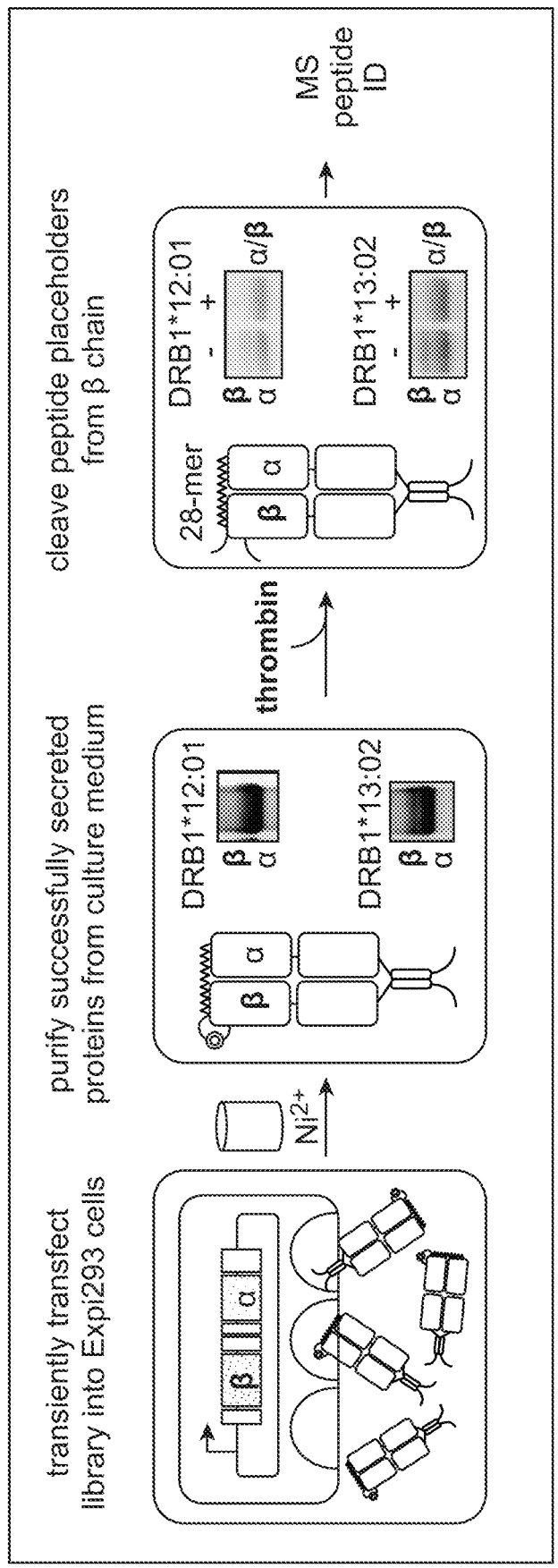

FIG. 24 depicts an exemplary flow diagram of transfection, purification and cleavage of placeholder peptide from beta chain.

FIG. 25A depicts an exemplary graphical illustration showing vector encoding CLIP peptides that are associated with increased secretion of expressed MHC-II peptides. Figure discloses SEQ ID NO: 21.

FIG. 25B depicts an exemplary graphical representation with the shorter and longer forms of the nucleic acids encoding CLIP0 and CLIP1 respectively. Figure discloses SEQ ID NOS 1 and 21, respectively, in order of appearance.

FIG. 25C depicts an exemplary representative result of a Coomassie gel analysis of the alpha and beta chains with or without the longer clip.

Figure 26A:
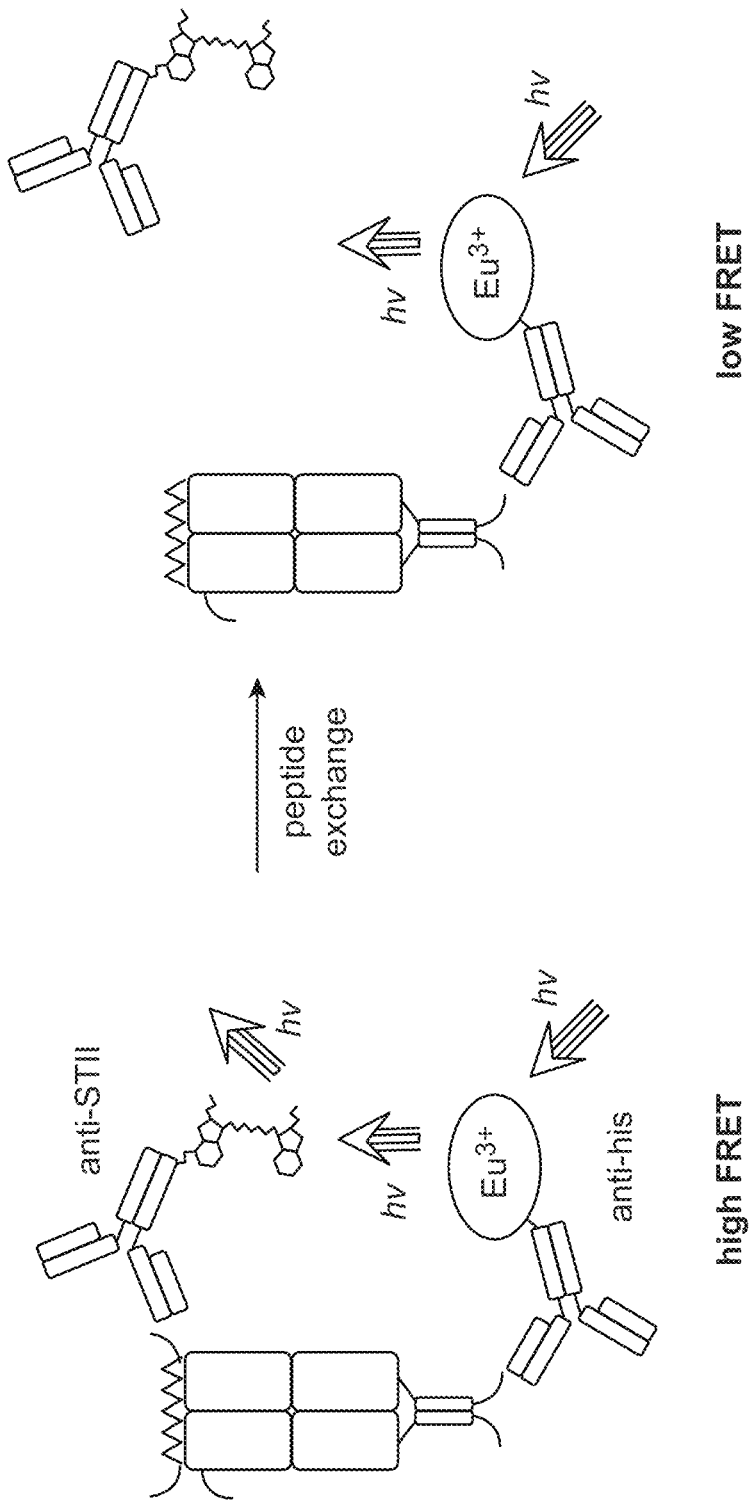

FIG. 26A depicts an exemplary graphical illustration of the TR-FRET assay.

Figure 26B:
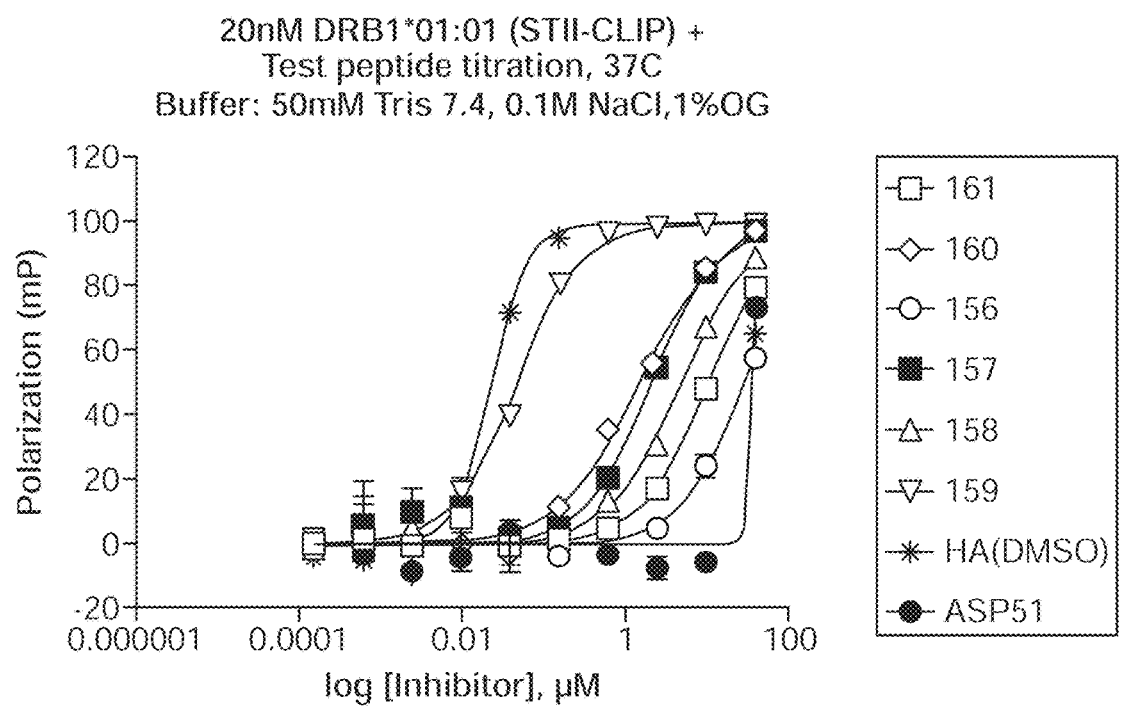

FIG. 26B depicts exemplary representative polarization data from an HLA class II peptide binding assay using Fluorescence Resonance Energy Transfer (FRET) assay using specific peptides.

Figure 26C:
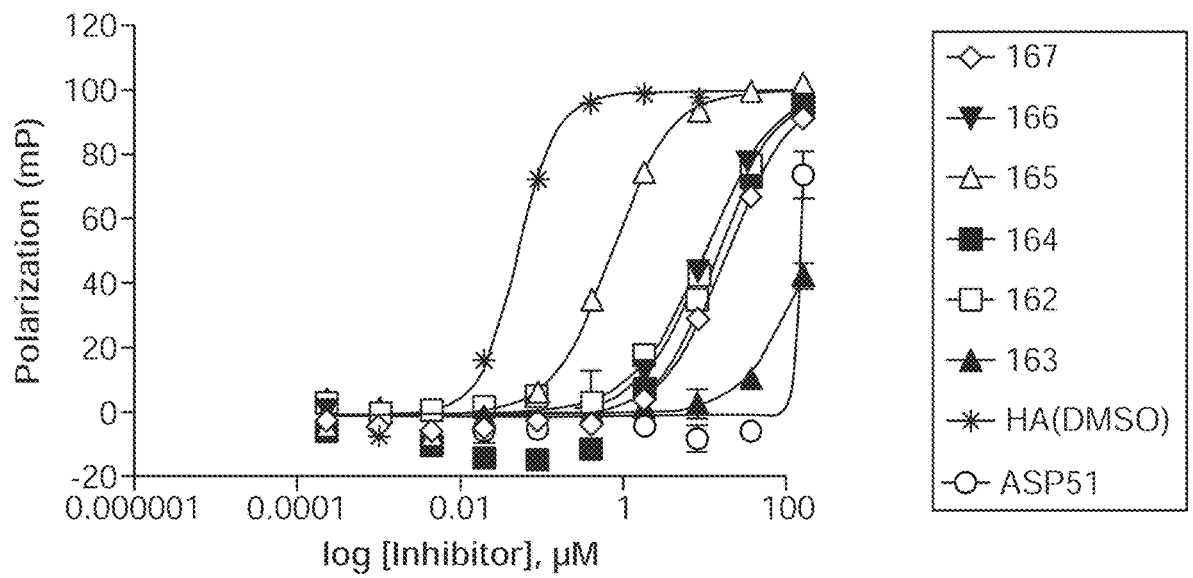

FIG. 26C depicts exemplary representative polarization data from an HLA class II peptide binding assay using Fluorescence Resonance Energy Transfer (FRET) assay using specific peptides.

Figure 26D:
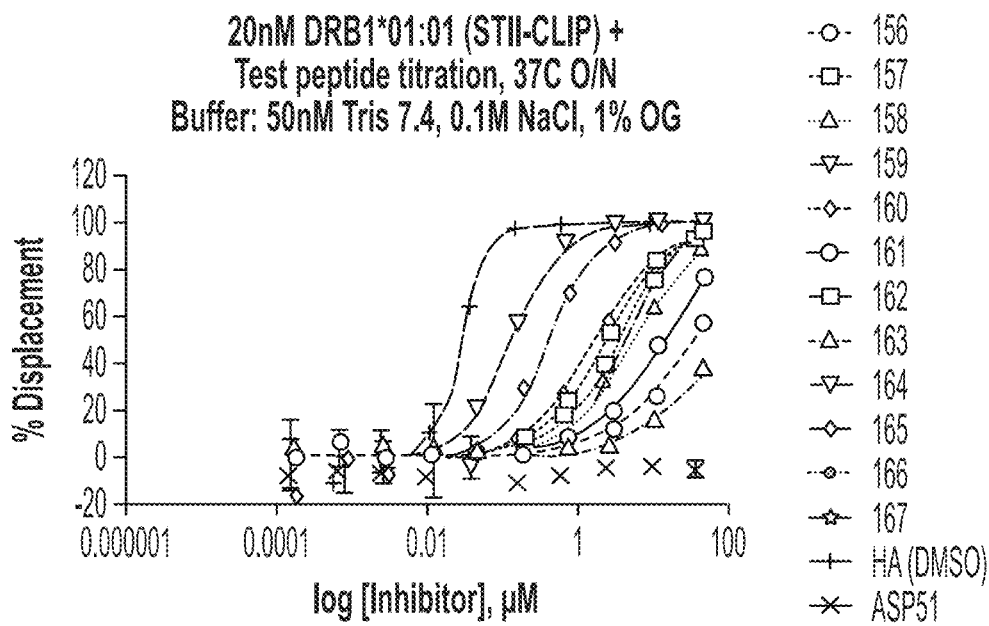

FIG. 26D depicts an exemplary percent displacement of MHC-construct bound peptide that was calculated from increase in fluorescence.

Figure 26E:
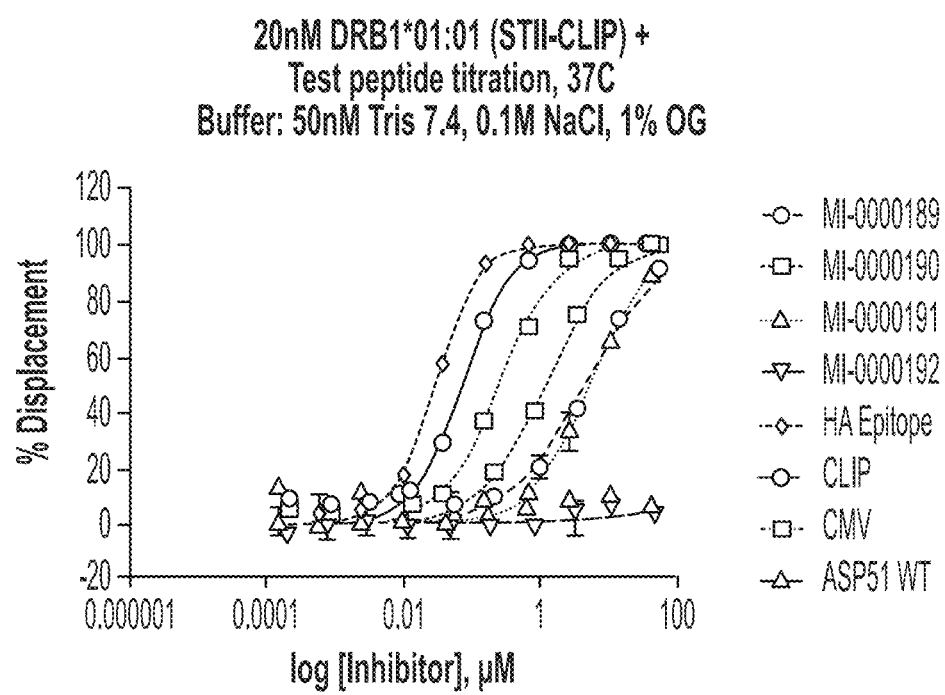

FIG. 26E depicts an exemplary percent displacement of MHC-construct bound peptide that was calculated from increase in fluorescence.

Figure 26F:
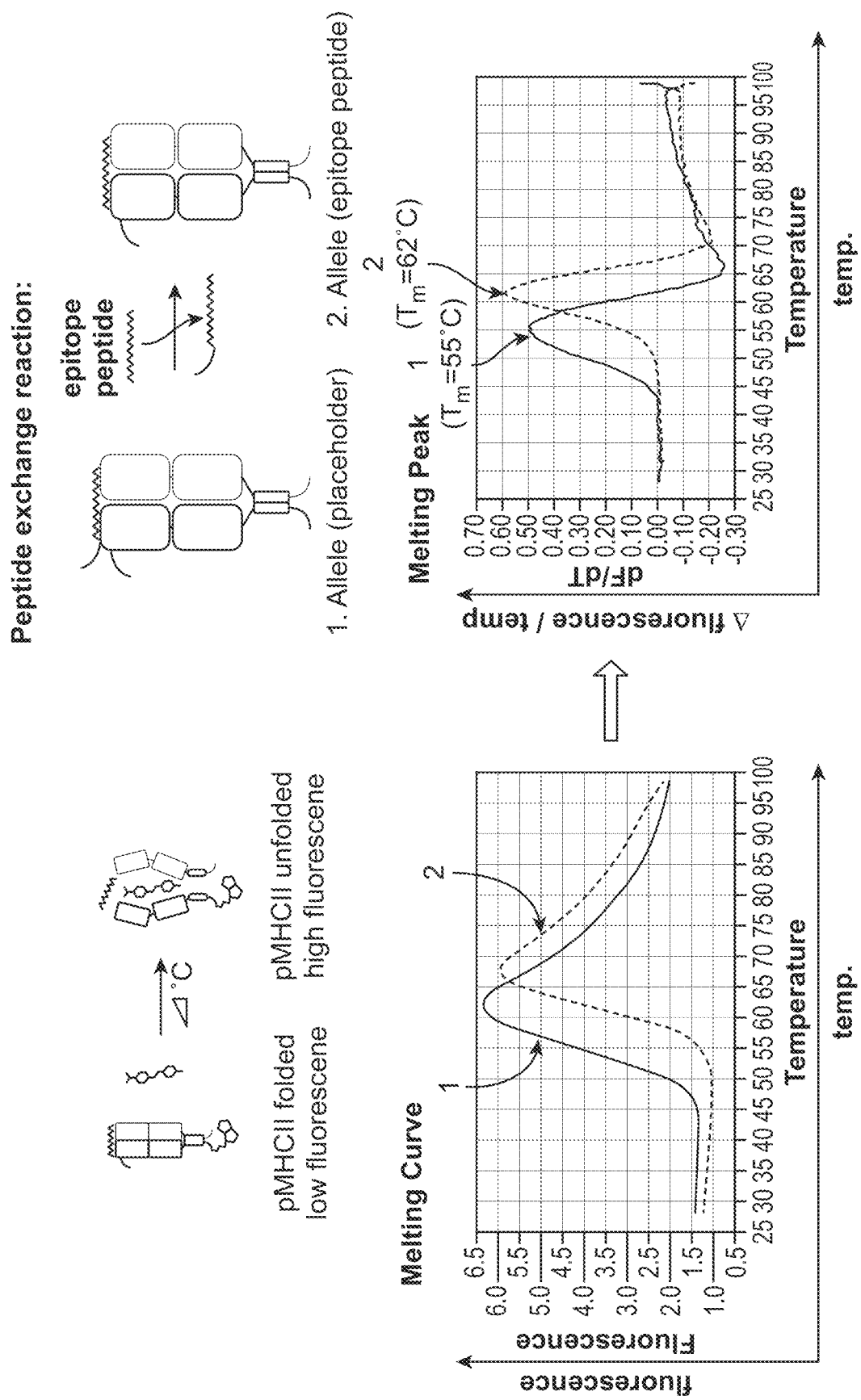

FIG. 26F depicts an exemplary peptide exchange using assay using differential scanning fluorometry (DSF). A graphical representation is depicted showing an exemplary mechanism of detecting peptide dissociation from MHC class II with heat which also dissociates the MHC class II heterodimer, resulting in binding of the fluorophore and high fluorescence. An exemplary schematic of placeholder peptide dislodgement by epitope peptide is also depicted. Exemplary melting curves plotted over temperature are also depicted.

Figure 26G:
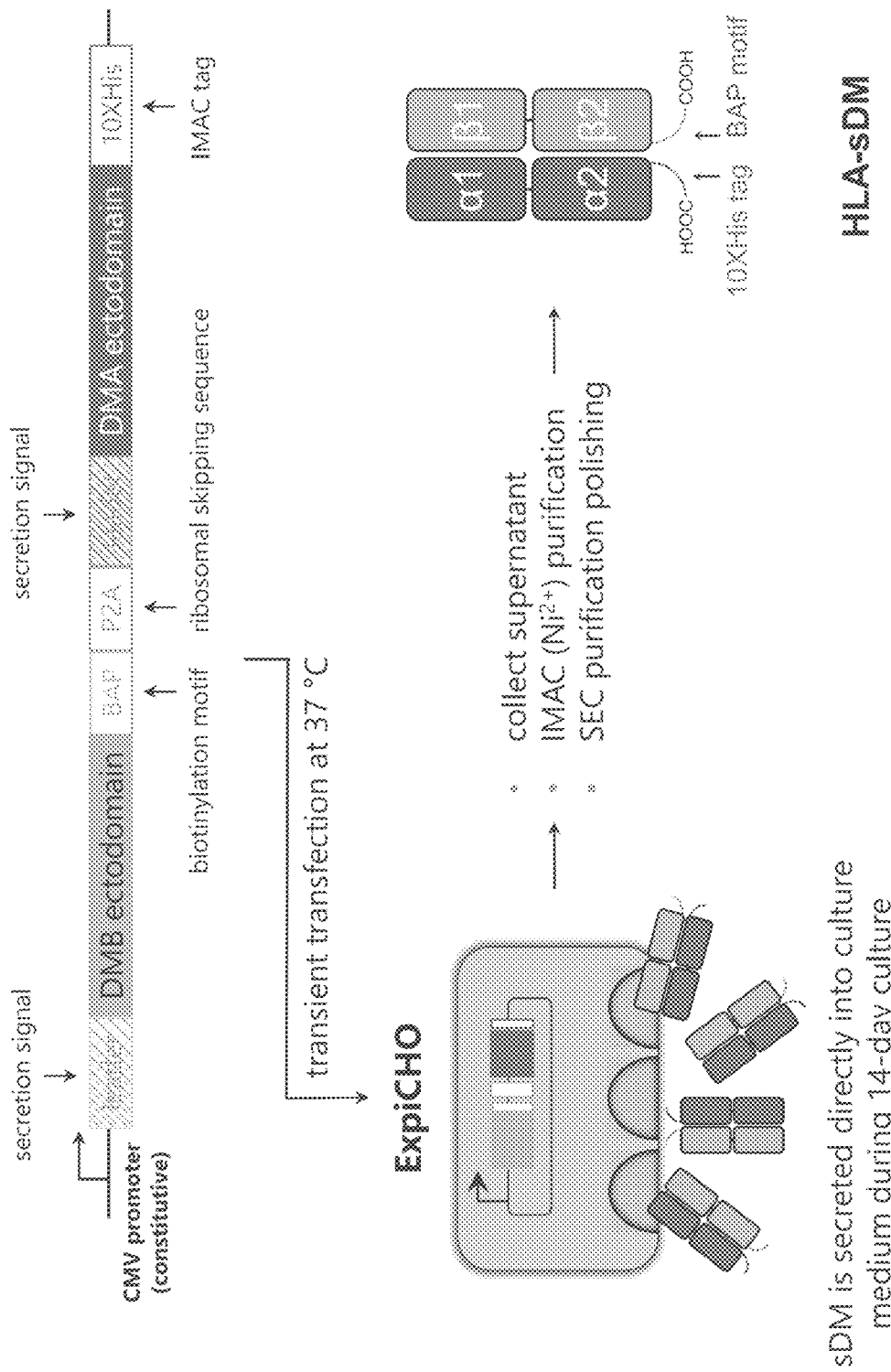

FIG. 26G depicts an exemplary soluble HLA-DM construct and its use for the performance of MHC Class II peptide exchange. The construct depicted contains a CMV promoter, a coding sequence for HLA-DM beta chain and a coding sequence for a HLA-DM alpha chain downstream of a secretion sequence (leader) and a BAP sequence at the 3'end of the beta chain coding sequence; a His tag at the 3'end of the alpha chain coding sequence. The two chains are be separated by an intervening ribosomal skipping sequence. The construct was expressed in Expi-CHO cells and the protein secreted into the medium culture medium was purified. Figure discloses "10×His" as SEQ ID NO: 20.

Figure 26H:
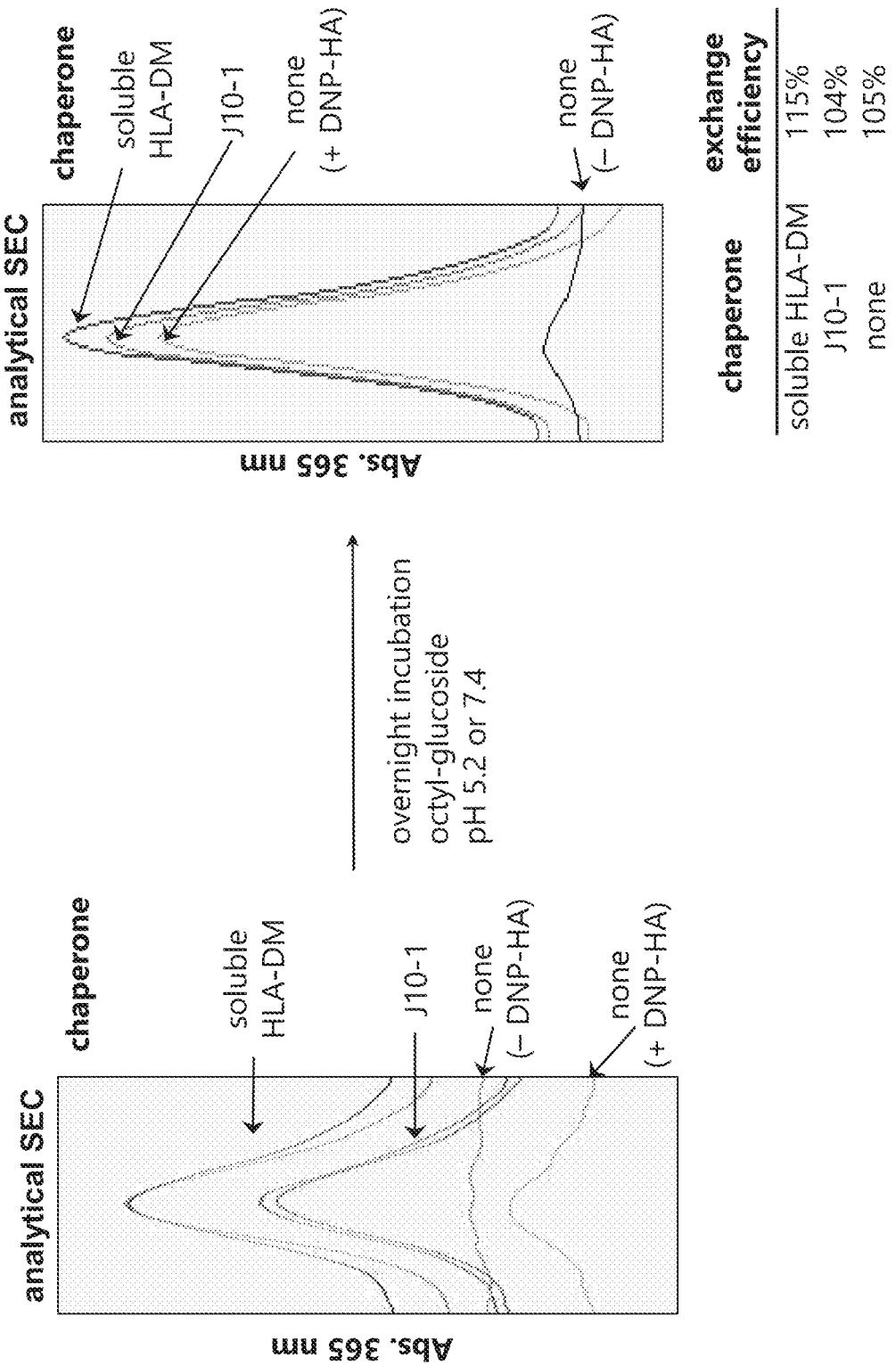

FIG. 26H shows exemplary size exclusion chromatography data using HLA-sDM to perform peptide exchange.

Figure 27A:
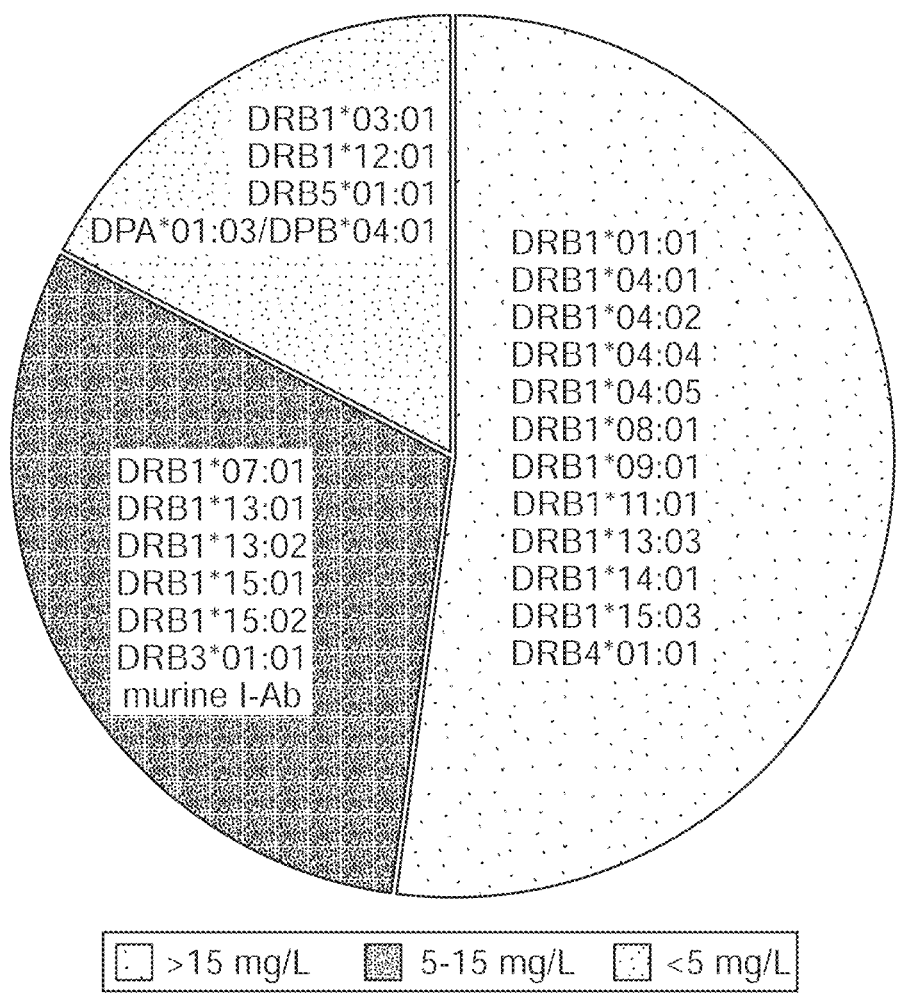

FIG. 27A depicts an exemplary graphical illustration of an exemplary DRB tetramer repertoire build.

Figure 27B:
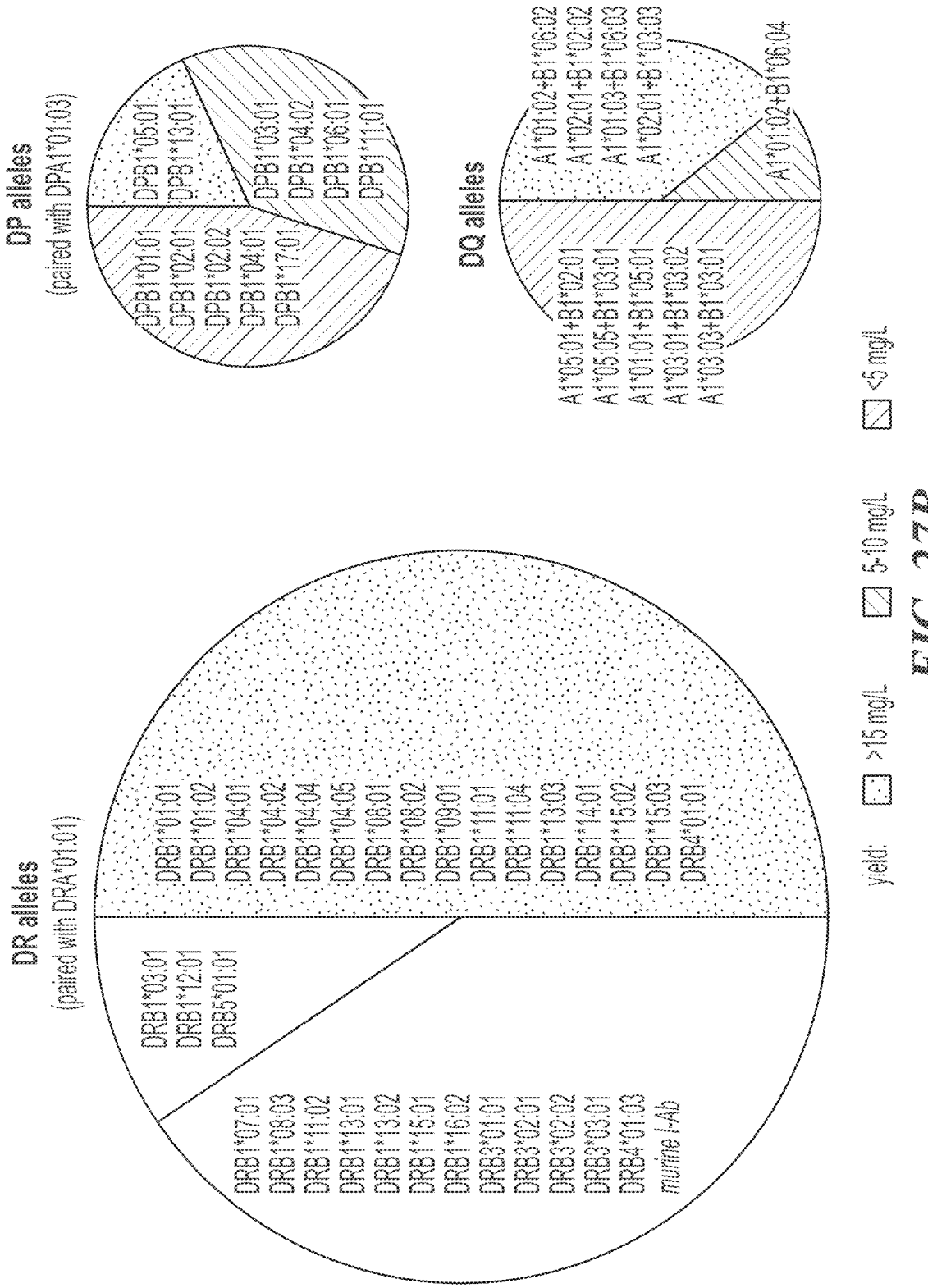

FIG. 27B depicts an exemplary graphical illustration of an exemplary class II tetramer repertoire build.

Figure 27C:
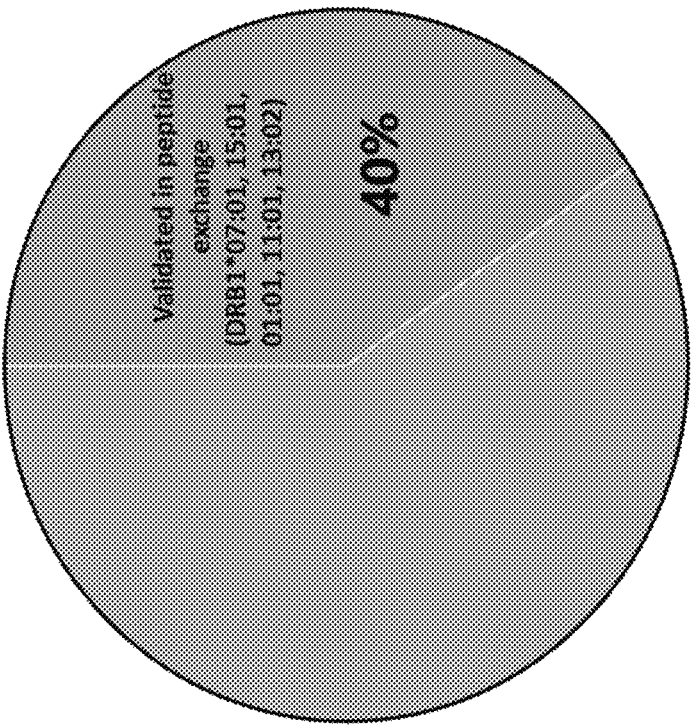

FIG. 27C depicts an exemplary graphical illustration of a summary of DRB tetramer repertoire coverage for the DRB1 allele for peptide exchange.

Figure 27D:
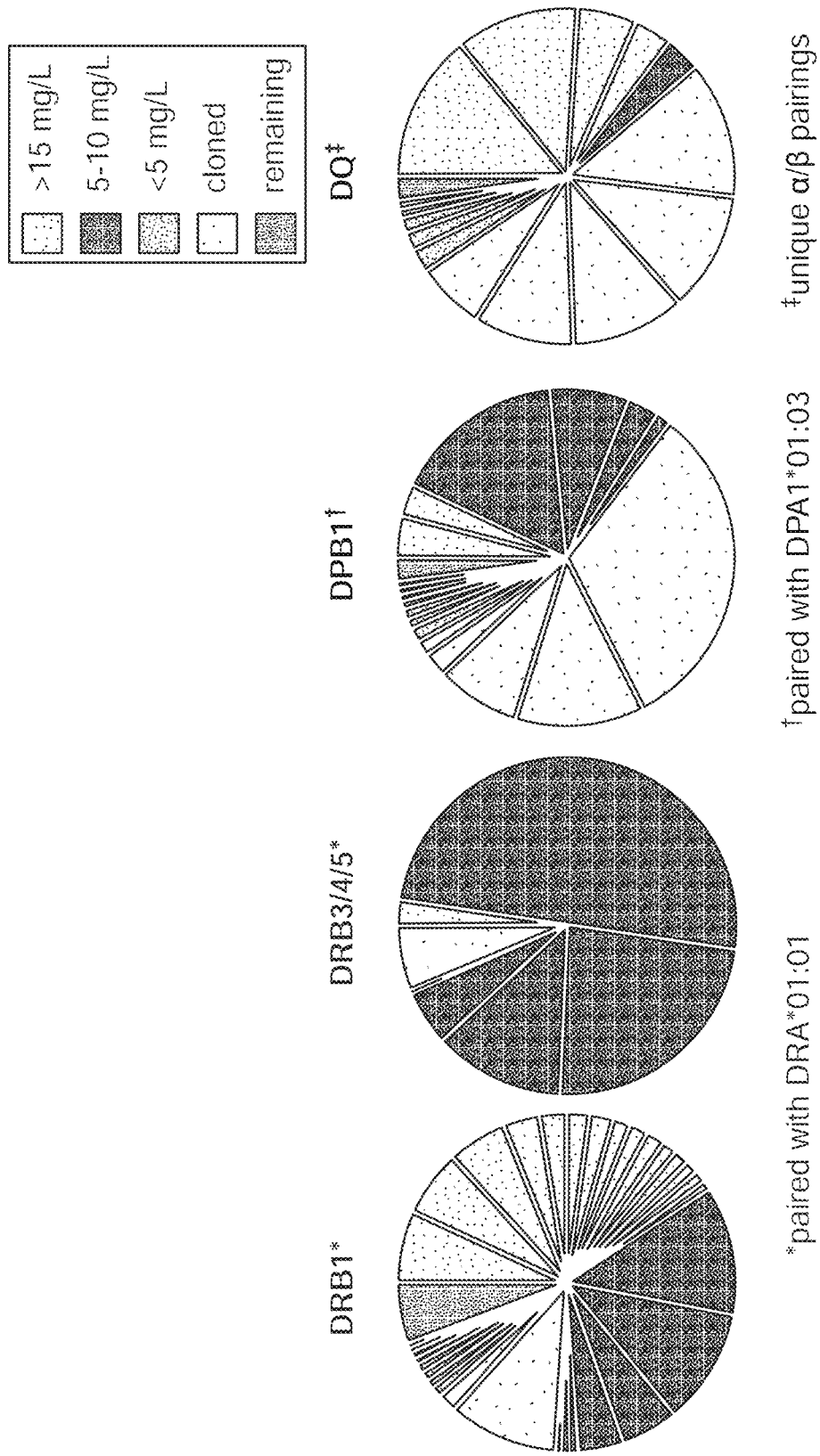

FIG. 27D depicts exemplary coverage of human MHC class II allele production.

Figure 27E:
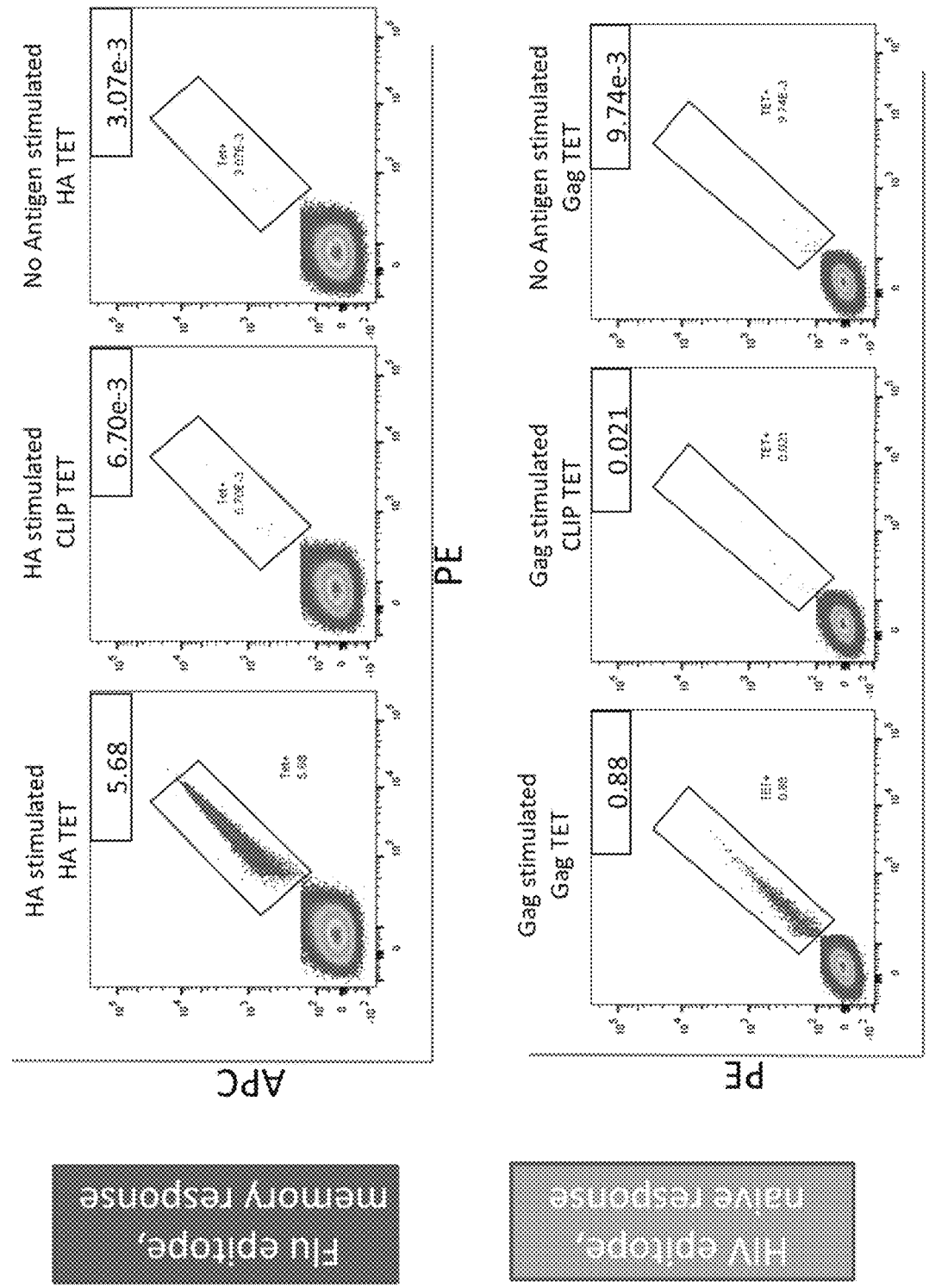

FIG. 27E shows an exemplary result from tetramer staining of samples induced with Flu epitopes (memory response) or HIV epitopes (naive response).

Figure 28A:
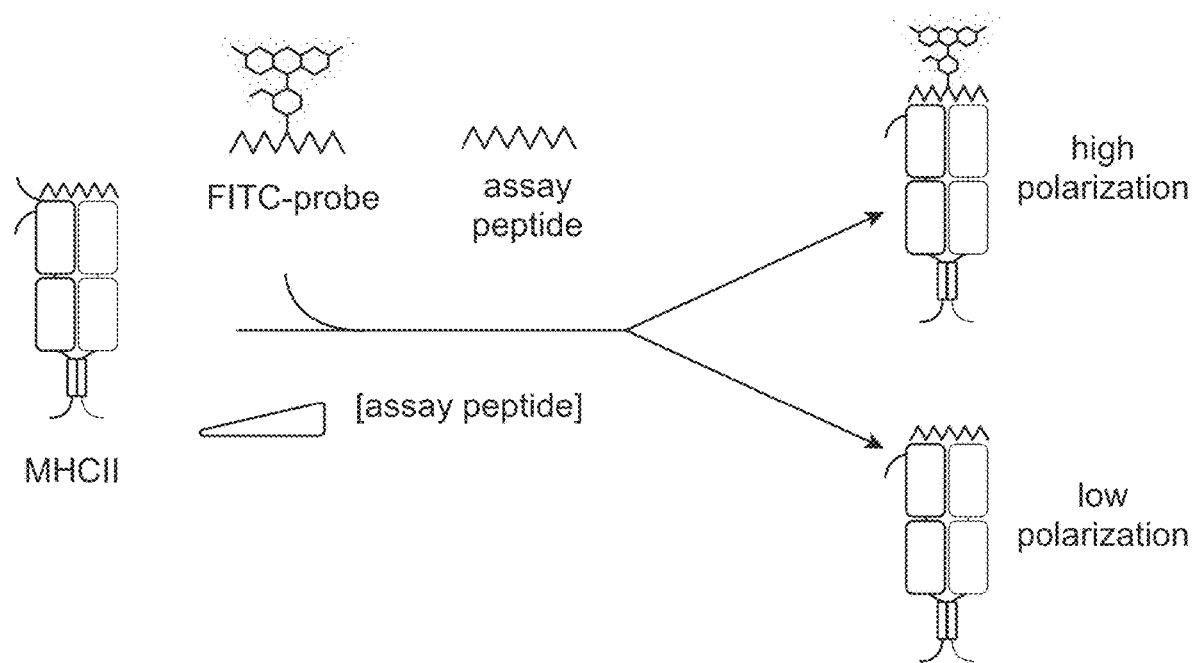

FIG. 28A depicts an exemplary graphical representation of a method of evaluation of peptides for HLA class II restriction by fluorescence polarization assay that enables a screening method to rapidly identify allele restriction for epitope peptides. The assay principle depicted in FIG. 28A allows for affinity measurements, and an unambiguous measurement of peptide exchange.

Figure 28B:
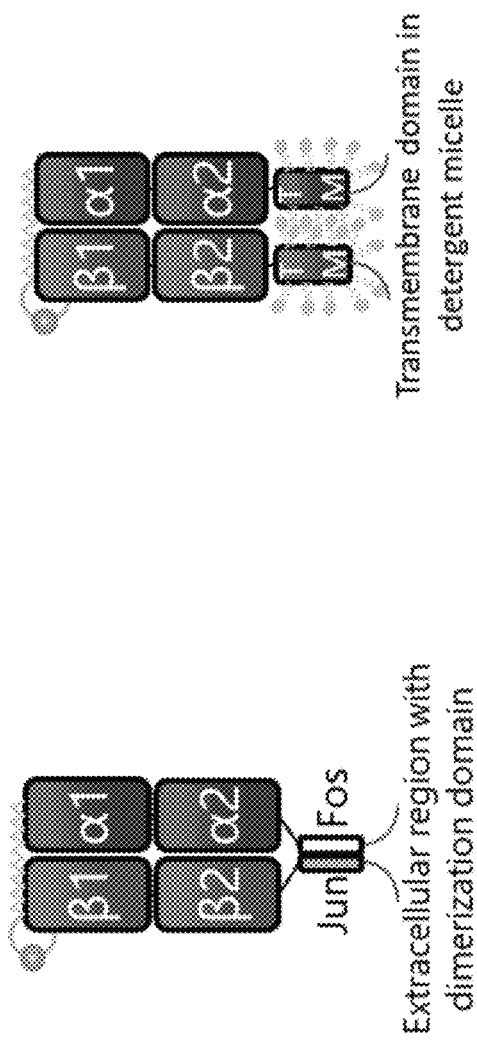

FIG. 28B depicts an exemplary summary of the multiple assay conditions explored (upper panel) in the fluorescence polarization assay with DRB1*01:01. Also depicted is an illustration of a soluble MHC class II allele and a full-length MHC class II allele with the transmembrane domain in a detergent micelle (lower panel), both of which were constructed with placeholder peptide with the cleavable linker for use in the assay.

Figure 28C:
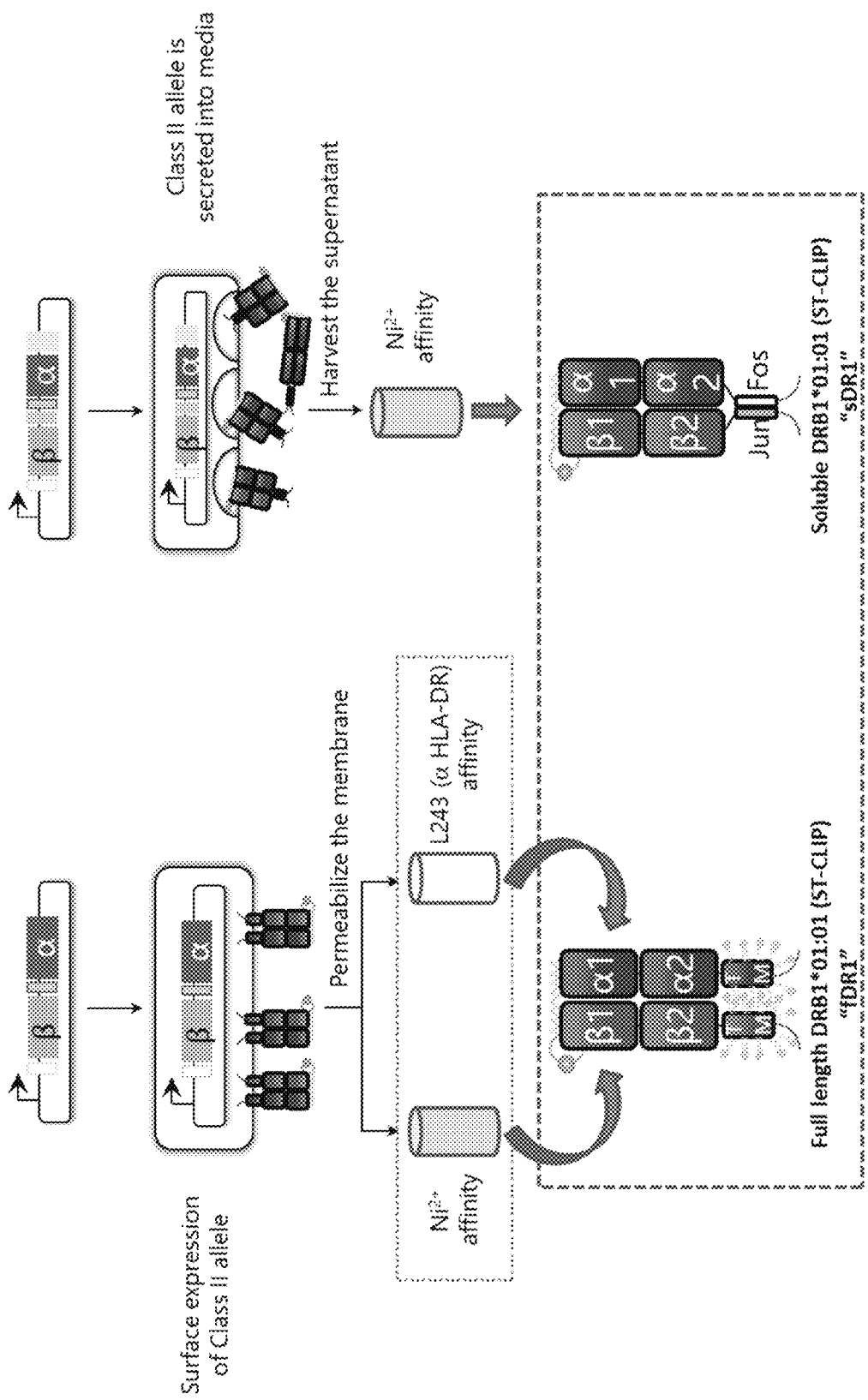

FIG. 28C depicts an exemplary graphical representation of the assays for investigating the full length and the soluble allele previously shown in FIG. 28B lower panel. In short, both the full length and the soluble alleles are expressed in cells. The membrane bound full length allele form is harvested by permeabilizing the membrane, while the secreted form is harvested from the cell supernatant. The harvested Class II HLA allele proteins are purified by passing through nickel ($Ni^{2+}$) columns.

Figure 28D:
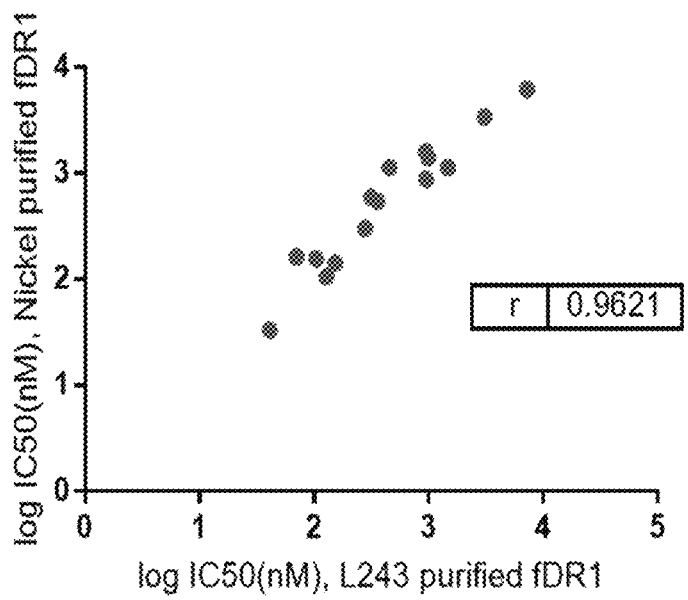

FIG. 28D depicts exemplary data showing that purification method does not affect peptide potency. Shown on the left are average IC50 values from experiments using L243 purified full length HLA-DR1 and $Ni^{2+}$ purified full-length HLA-DR1.

Figure 28E:
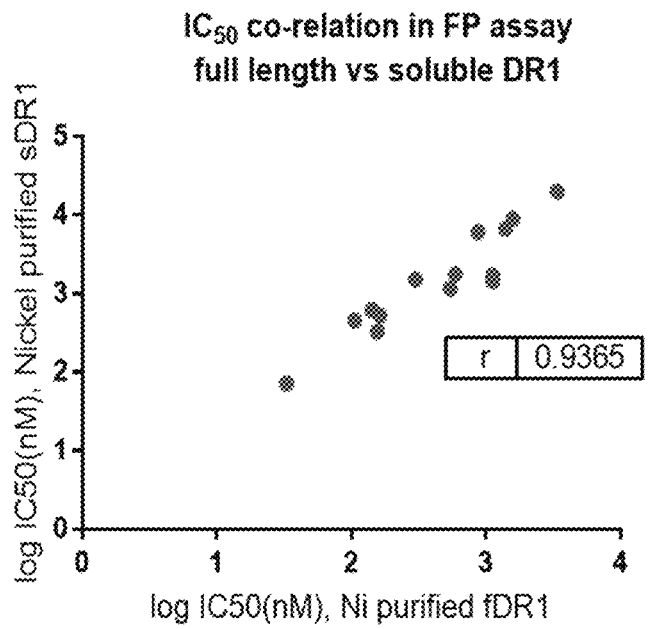

FIG. 28E depicts exemplary data showing choice of the soluble form (sDR1) or the full-length form (fDR1) does not affect the peptide potency. Shown on the left are average IC50 values from experiments using sDR1 form or fDR1. FP, fluorescence polarization.

Figure 28F:
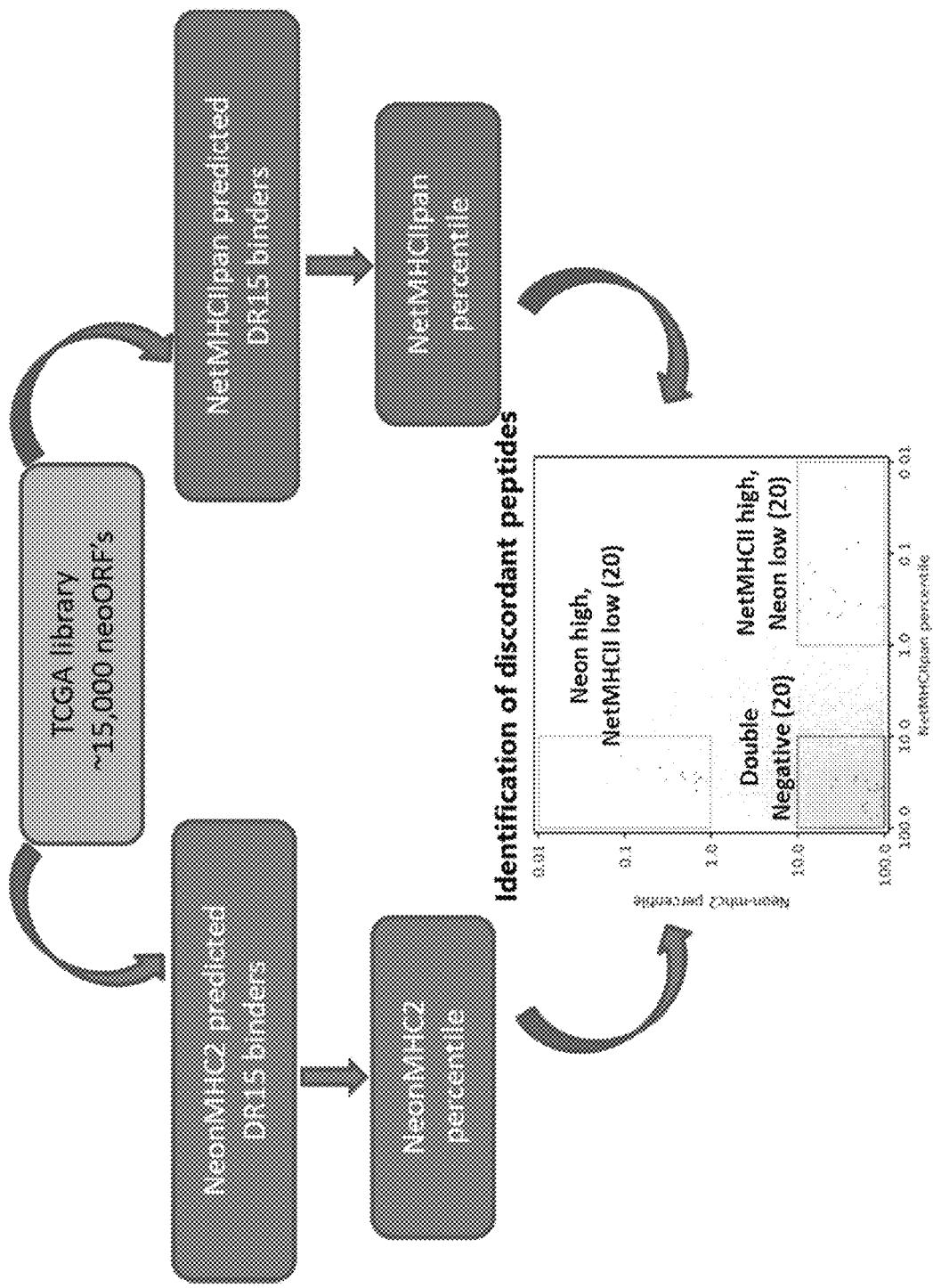

FIG. 28F depicts an exemplary graphical view of an exemplary evaluation of neonmhc2 and NetMHCIIpan predicted peptides in binding assay and identification of discordant peptides.

Figure 28G:
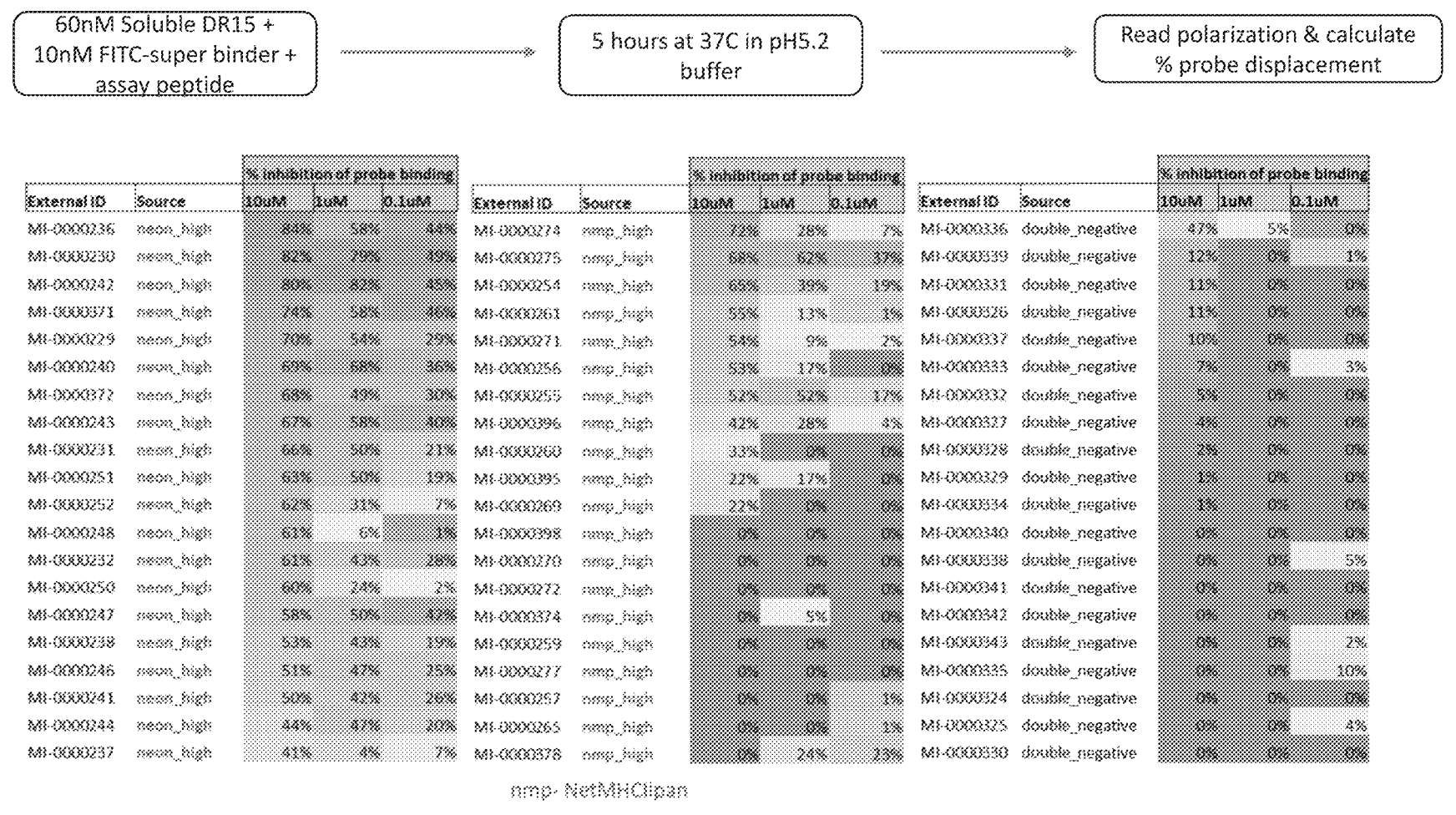

FIG. 28G depicts exemplary fluorescence polarization binding screen data for evaluation of neonmhc2 predicted peptides; shown as heat map as also the percent inhibition of probe binding indicated for each concentration of the peptide used.

Figure 28H:
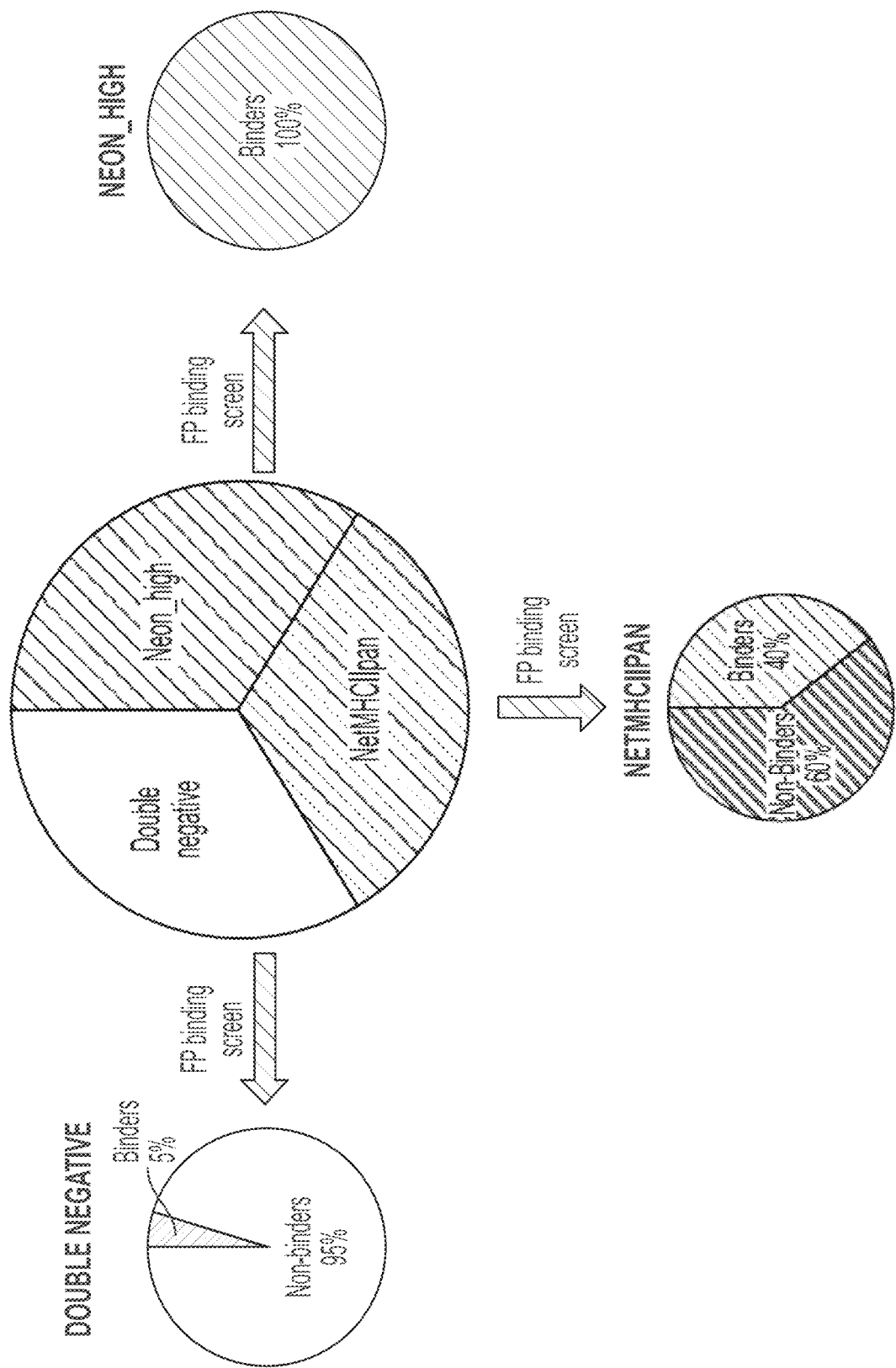

FIG. 28H depicts a summary of an evaluation of neonmhc2 predicted peptides in an exemplary binding assay.

Figure 29:
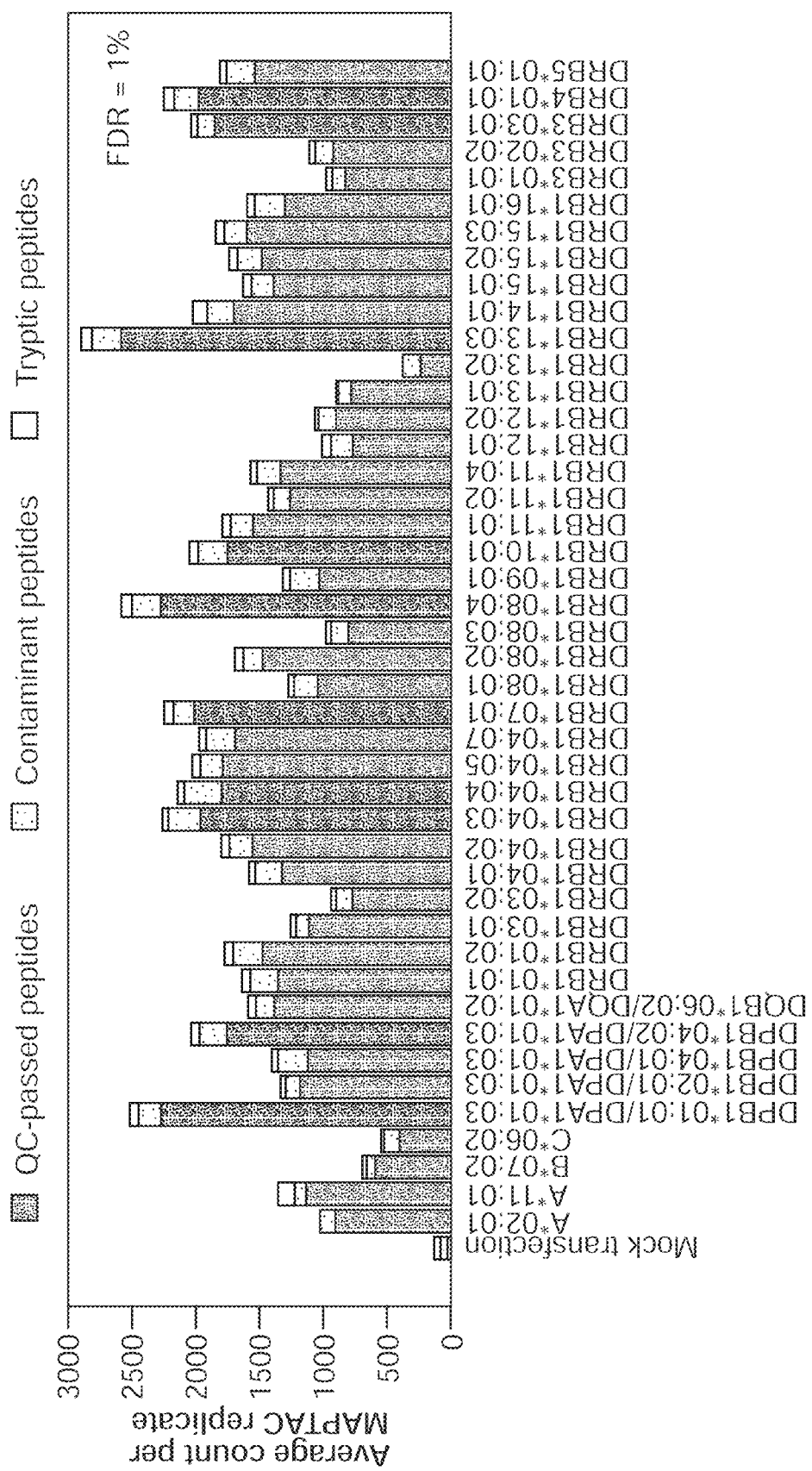

FIG. 29 depicts an exemplary average count of peptides from an average MAPTAC™ experimental replicate (50 million cells), per each HLA allele.

Figure 30A:
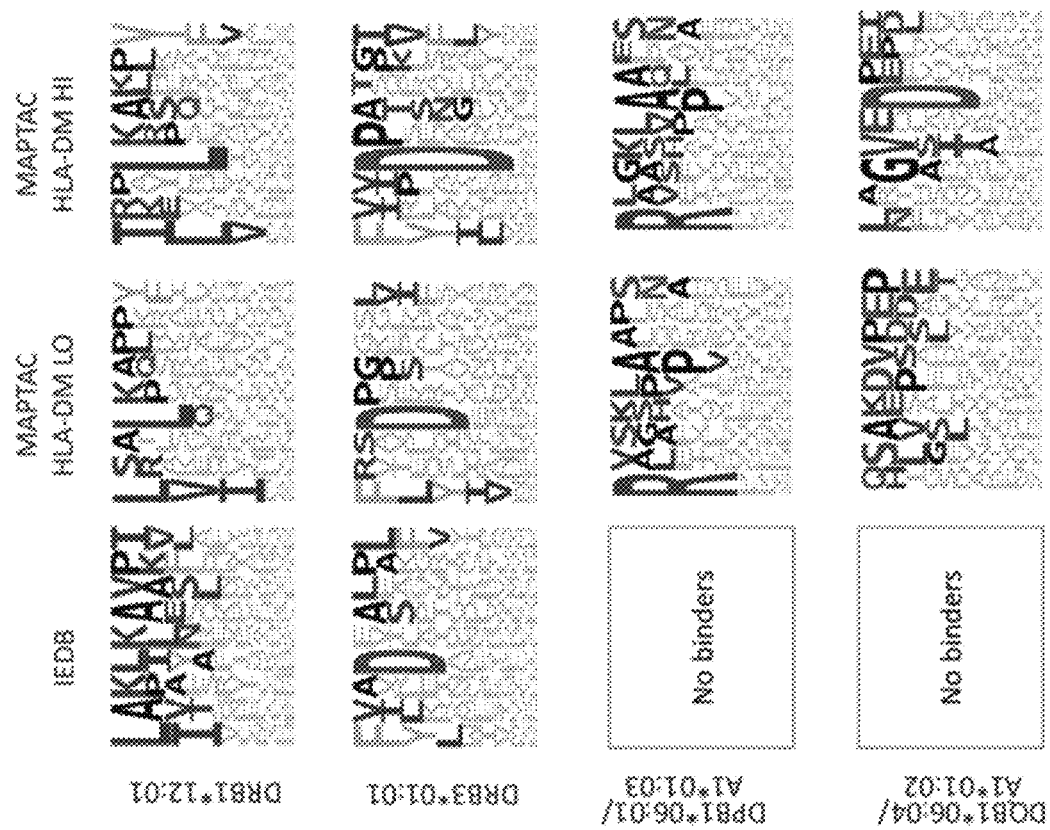
Figure 30B:
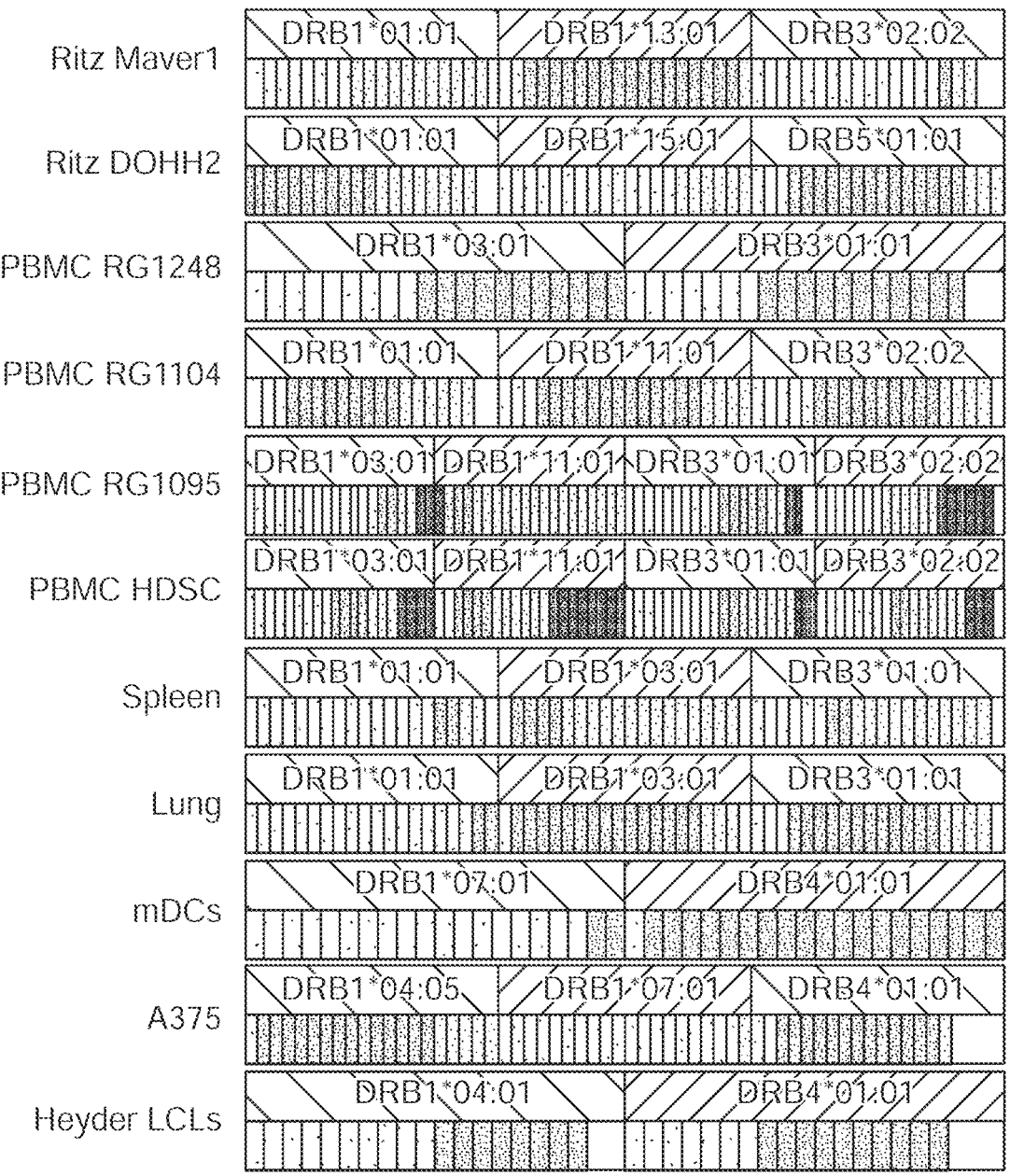
Figure 30C:
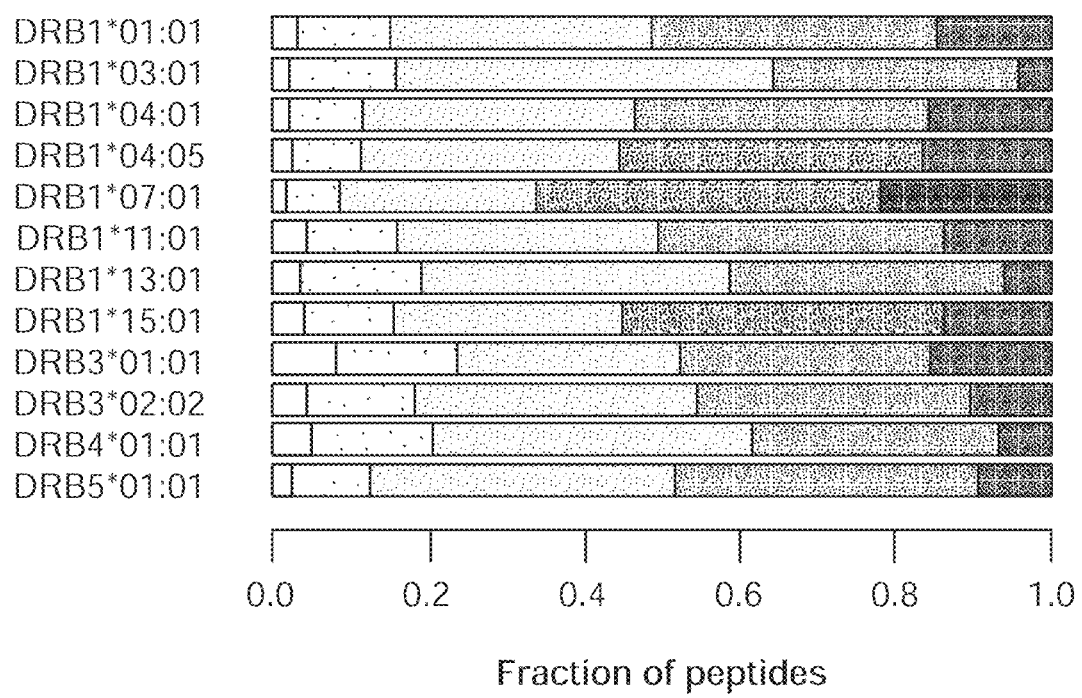

FIGS. 30A-30C depict an exemplary binding core analysis for HLA class II MAPTAC™ alleles+/−HLA-DM and multi-allelic deconvolution fidelity. FIG. 30A depicts exemplary sequence logos for one representative HLA-DR, -DQ, and -DP allele according to MAPTAC™ with and without HLA-DM co-transfection (expi293 cell line) and IEDB wherein the height of each amino acid is proportional to its frequency. Amino acids with frequency greater than 10% are shown in darker shading according to chemical properties; all others are shown in lighter shading. Peptides were aligned according to the GibbsCluster tool (Supplemental Methods), and logos represent all peptides, including those that did not closely match the overall motif (e.g. no peptides are sequestered in a "trash" cluster). FIG. 30B depicts an exemplary description of cluster assignments for MAPTAC™ peptides (20 per allele) spiked into pan-DR MS datasets. Datasets were deconvolved using GibbsCluster. Each colored box represents one MAPTAC™ peptide. The shading of the box indicates which cluster it was assigned to, and gray bars indicate which allele the peptide came from. FIG. 30C depicts an exemplary graph showing that the share of peptides exhibiting 0, 1, 2, 3, or 4 expected residues in anchor positions, for alleles shown in FIG. 30B. Anchor positions were defined as the four positions with lowest entropy, and the "expected" residues were defined as those with ≥10% frequency in those positions.

Figure 31A:
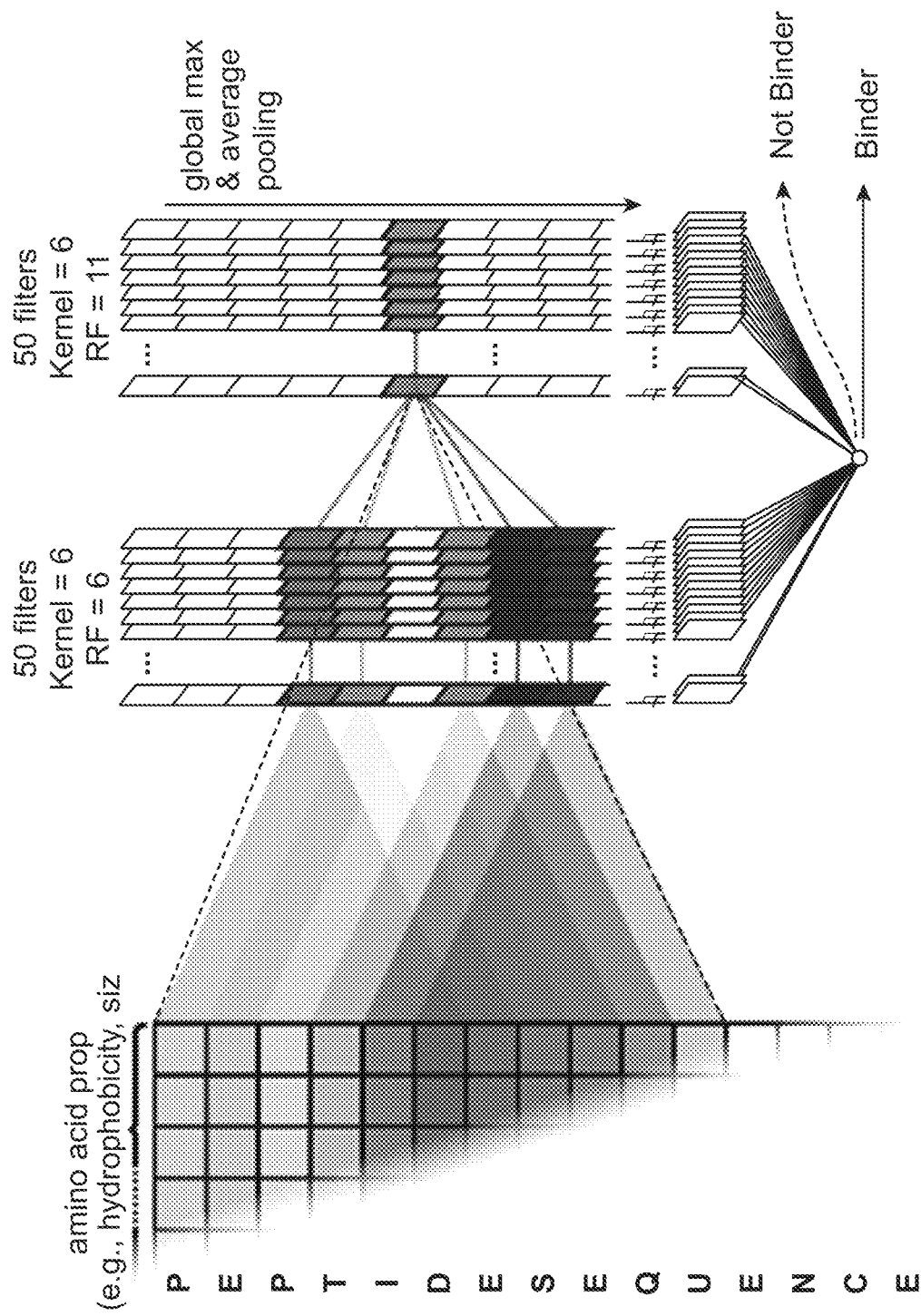
Figure 31B:
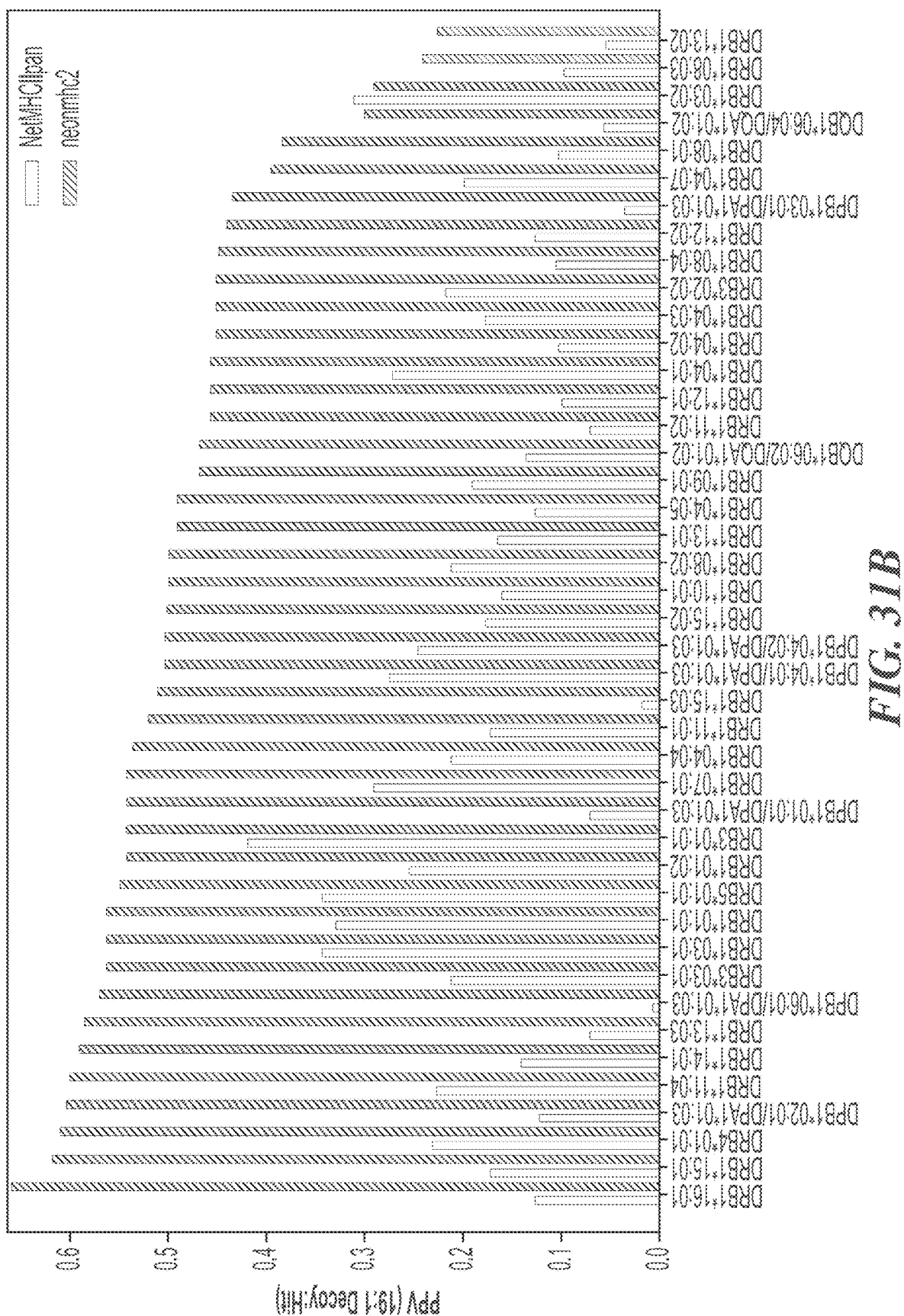
Figure 31C:
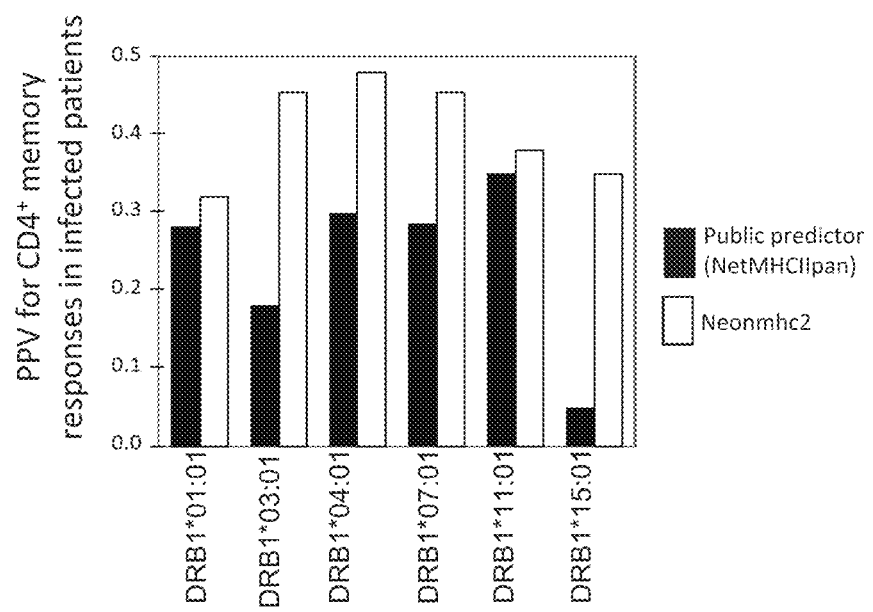
Figure 31F:
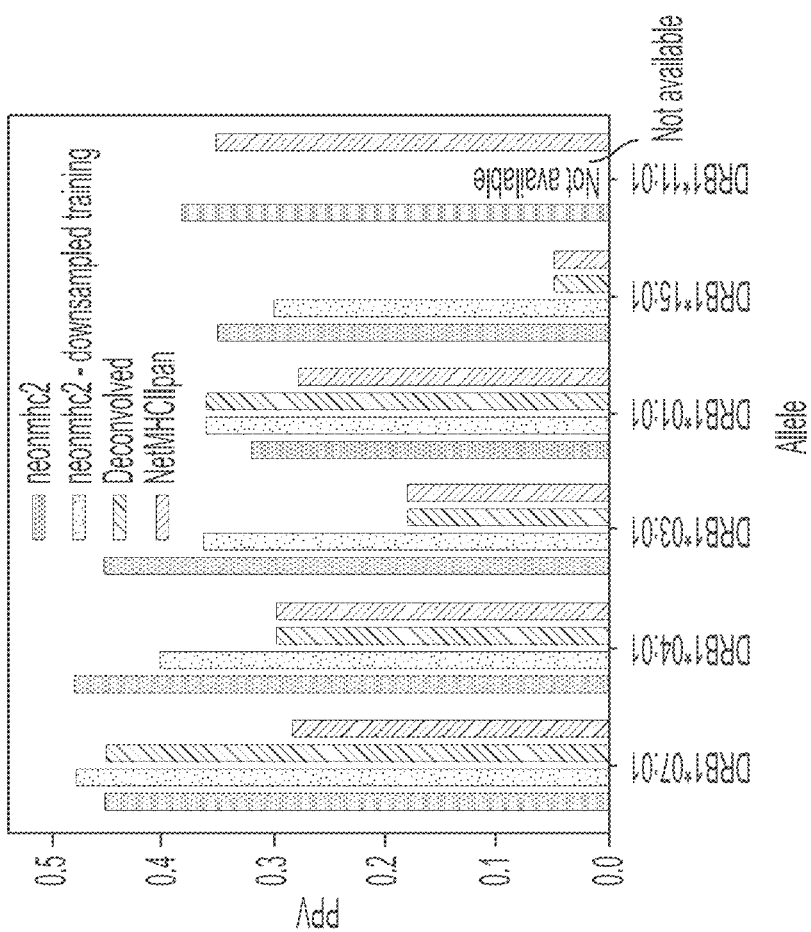
Figure 31E:
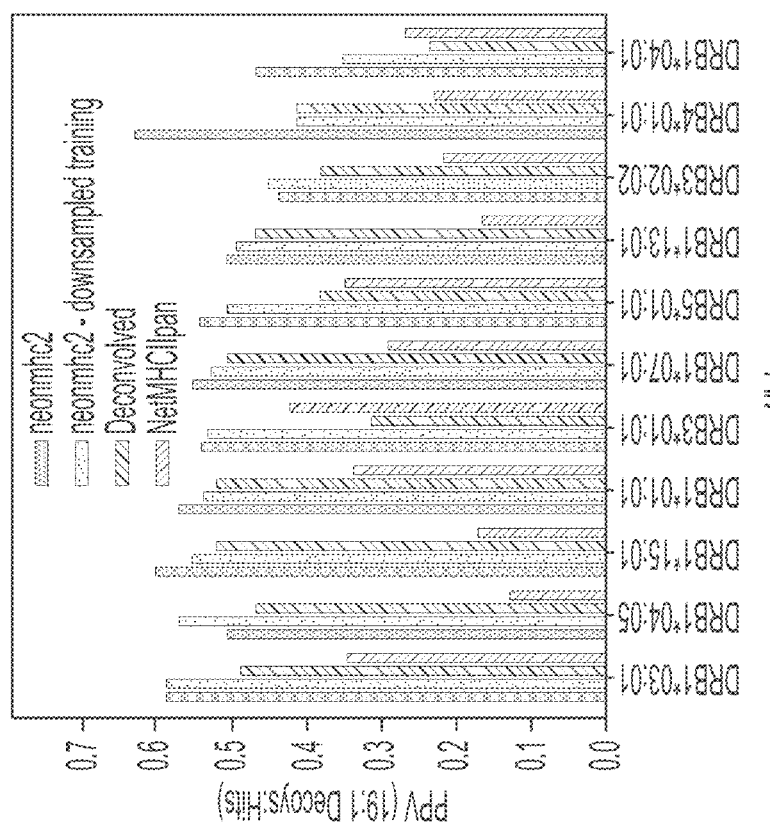

FIGS. 31A-31F depict an exemplary architecture and benchmarking of the neonmhc2 binding prediction algorithm. FIG. 31A depicts an exemplary architecture of a convolutional neural network (CNN) trained to distinguish mono-allelic HLA class II peptides from scrambled length-matched decoys. The schematic indicates the usage of an amino acid feature embedding layer, 2 convolutional layers of width 6, the presence of skip-to-end connections, and a combination of average- and max-pooling operations as input to a final logistic output node. FIG. 31B depicts an exemplary positive predictive value (PPV) for NetMHCIIpan and neonmhc2 as evaluated on a partition of MAP-TAC™ data that was not used for training or hyper-parameter optimization. For each allele, n MS-observed peptides were scored in conjunction with 19n length-matched decoys sampled from the same set of source genes, and each predictor's n top-ranked peptides (e.g. the top 5%) were called as positives. According to this evaluation protocol, PPV is identical to recall because the number of false positives and false negatives is necessarily equal. FIG. 31C depicts an exemplary PPV for NetMHCIIpan and neonmhc2 on the TGEM data set. For each allele, the n top-ranked peptides were called positives, where n is the number of confirmed immunogenic epitopes in the evaluated set. FIG. 31D depicts exemplary ex vivo T cell induction results for neoantigen peptides. Peptides were selected based on high neonmhc2 scores and weak NetMHCIIpan scores for HLA-DRB1*11:01. Figure discloses SEQ ID NOS 87-89, 91, 90, 2, 92-94, 3, and 95-96, respectively, in order of appearance. FIG. 31E depicts comparison of models trained on monoallelic MAPTAC data versus deconvolved multiallelic data as evaluated on held-out monoallelic data. Values are as shown for neonmhc2 where the training dataset is down-sampled to match the size of the deconvolution training set. FIG. 31F shows PPV on the TGEM dataset for NetMHCIIpan-v3.1, the deconvolution-trained predictor, and neonmhc2 (with and without down-sampling). For each allele, the n top-ranked peptides were called positives, where n is the number of confirmed immunogenic epitopes in the evaluated set.

FIGS. 32A-32E depict exemplary gene representation and protein processing in HLA class II tumor peptidomes. FIG. 32A depicts exemplary results of observed vs. expected number of HLA class II peptides per gene as determined by a joint analysis of colorectal cancer, melanoma, and ovarian cancer datasets. The expected count is derived by multiplying gene length by expression level. Expected and observed counts were summed across relevant samples. Genes with known presence in plasma are marked according to their concentration. FIG. 32B depicts exemplary results of expected vs. observed frequency of peptides per cellular localization. FIG. 32C depicts exemplary results of distribution of enrichment scores (ratio of observed to expected observations, as in part FIG. 32B) for genes regulated by the proteasome. Gene sets include those with known ubiquitination sites and those that increase in abundance upon application of a proteasome inhibitor. FIG. 32D depicts a diagram presenting three exemplary working models for how HLA class II peptides are processed, according to which i) cathepsins and other enzyme break cleave proteins into peptide fragments that are subsequently bound by HLA, ii) proteins or unfolded polypeptides bind HLA and are subsequently cleaved to peptide length iii) proteins are partially digested before binding and further trimmed after binding. Each model corresponds to a different prediction approach. FIG. 32E depicts absolute increase in PPV observed for logistic regression models that included processing-related variables and neonmhc2 binding predictions as compared to models that only used binding predictions. Evaluation was conducted on eleven samples that were profiled by HLA-DR antibody (the same samples analyzed in FIG. 30B); each point corresponds to one sample. Asterisks mark significant improvements (*: $p<0.01$, : $p<0.001$, *: $p<0.0001$) according to two-tailed paired t-tests. The same analysis is shown in FIG. 40B but instead using NetMHCIIpan as the base predictor. Methods for decoy selection and PPV calculation are identical to those used in FIG. 31B.

Figure 33A:
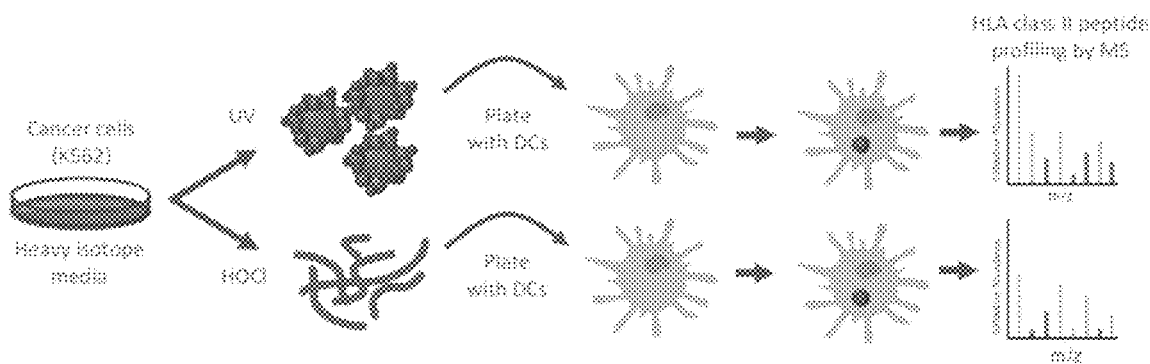
Figure 33B:
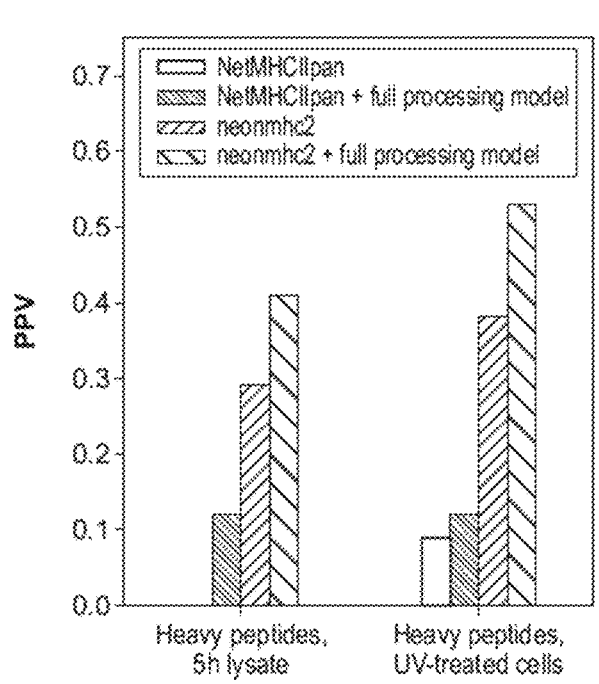
Figure 33C:
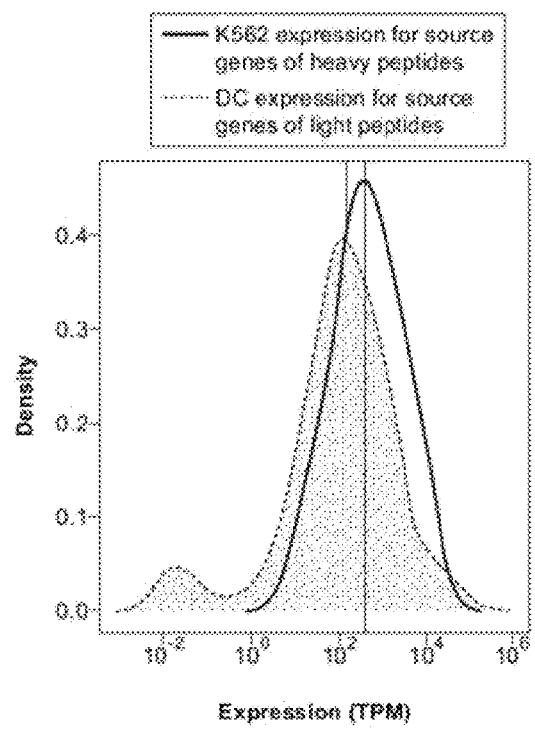
Figures 33D, 33E:
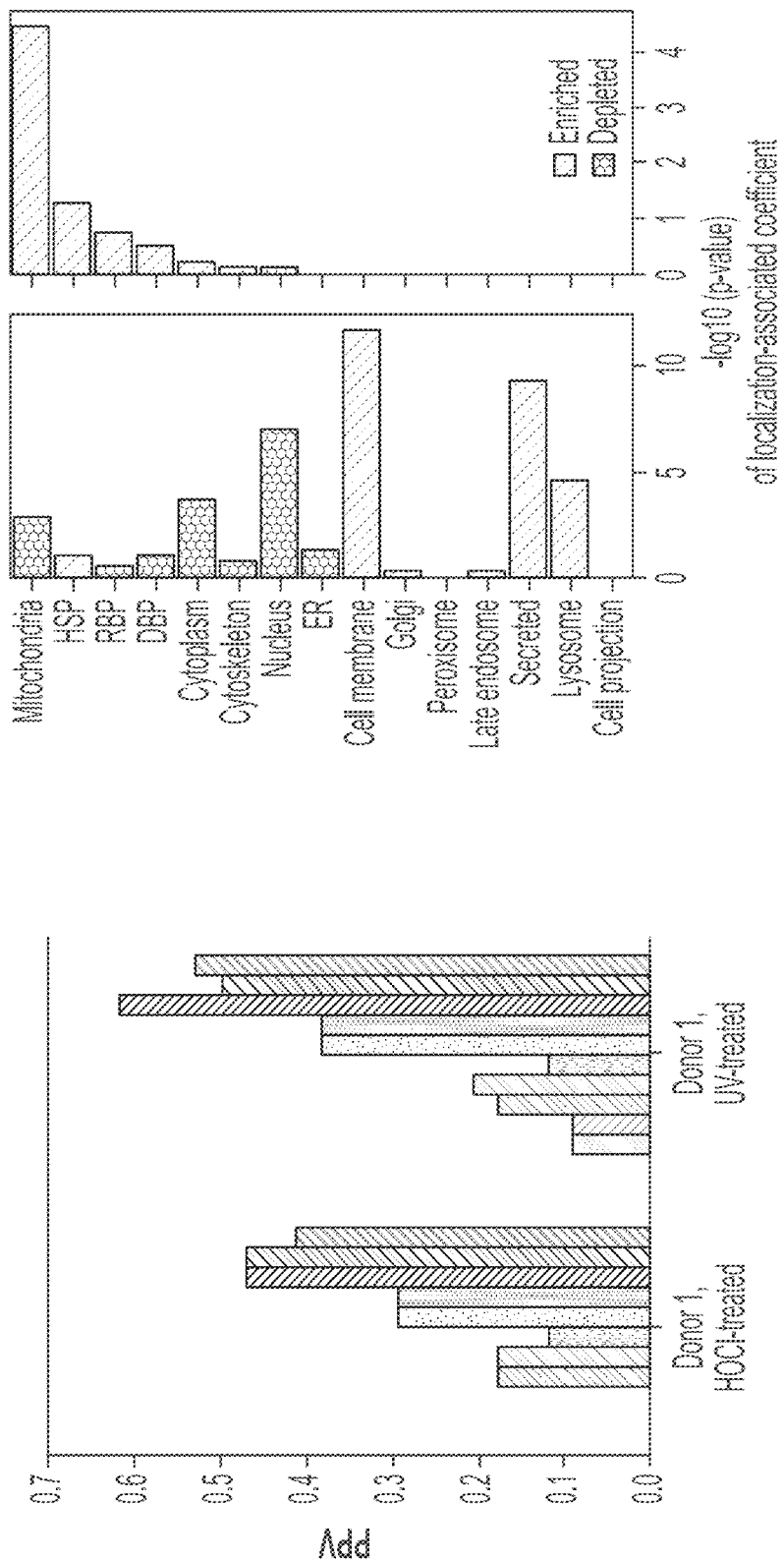
Figure 33G:
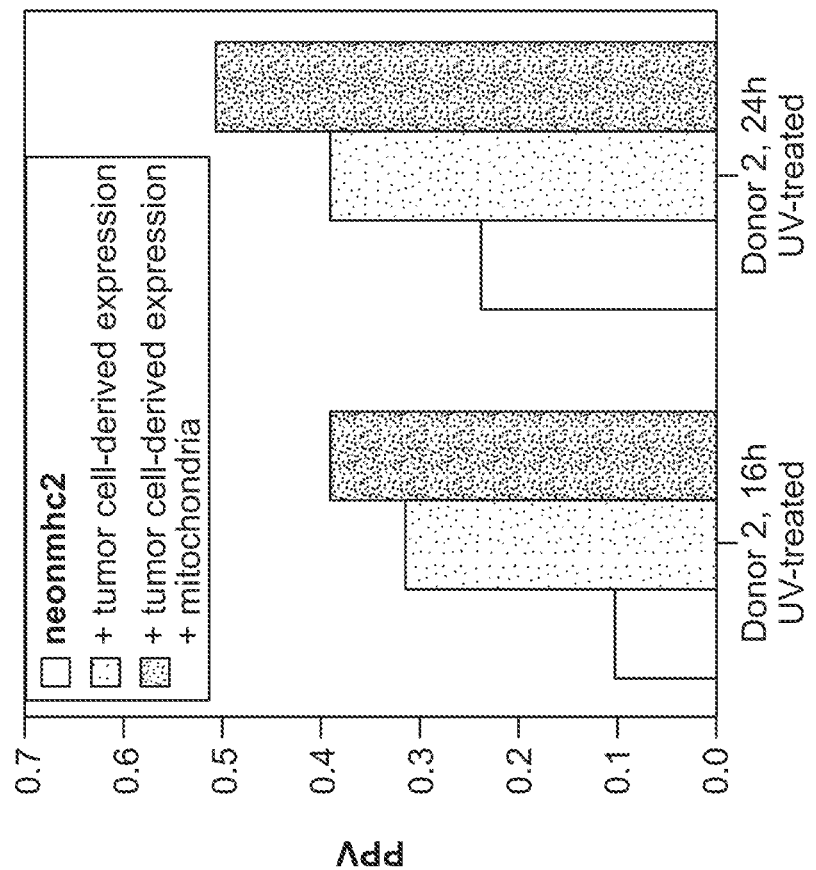
Figure 33F:
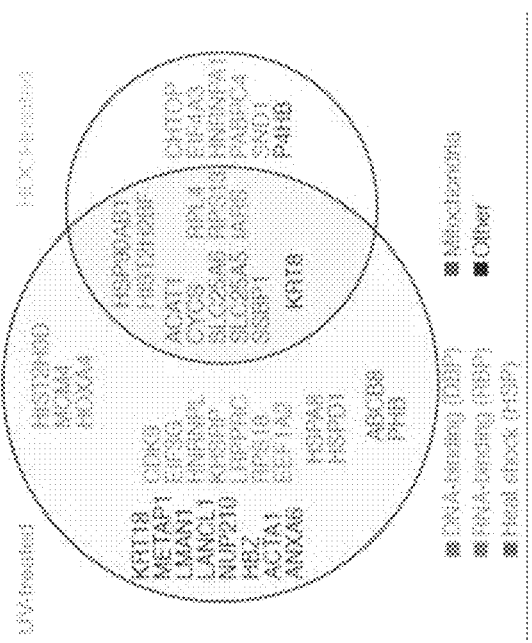

FIGS. 33A-33G depict exemplary results of identification and prediction tumor antigens presented by dendritic cells. FIG. 33A depicts an exemplary graphical representation of experimental workflow for identifying DC-presented HLA-II ligands that originate from cancer cells (K562). Cancer cells were grown in SILAC media to full incorporation, either lysed or irradiated, and then plated with monocyte-derived dendritic cells. Presented peptides were isolated by pan-DR antibody and sequenced by LC-MS/MS. FIG. 33B depicts exemplary data representing prediction performance for tumor-derived peptides presented by dendritic cells using the same hit-to-decoy ratio and performance metrics as in FIG. 21A. Performance is shown for NetMHCIIpan- and neonmhc2-based models with and without use of processing features. FIG. 33C depicts exemplary gene expression distribution for source genes of heavy-labeled peptides observed in the UV-treatment experiment (plotted according to K562 expression) as compared to the source genes of light-labeled peptides (plotted according to DC expression). FIG. 33D shows an exemplary graph of PPV at a 1:499 hit-to-decoy ratio for predicting presented tumor antigens using NetMHCIIpan- and neonmhc2-based models with and without processing features. Data points from left to right represent samples: Donor 1 HOC1 treated cells: NetMHCIIpan continuous expression; NetMHCIIpan continuous expression+gene bias; NetMHCIIpan continuous expression+gene bias+DQ overlap, full processing mode; Donor 1, UV-treated: neonmhc2; neonmhc2+threshold expression; neonmhc2+continuous expression; neonmhc2+continuous expression+gene bias; neonmhc2+continuous expression+gene bias+DQ overlap. FIG. 33E depicts significance of various gene localizations and functional classes in predicting heavy (K562-derived and light (DC-derived) peptides respectively. P-values are calculated according to logistic regression that controls for neonmhc2 binding score and source gene expression. Bar shading indicate sign associated with coefficient in the regression. FIG. 33F depicts an exemplary graphical representation of results showing overlap of tumor cell-derived peptide source genes (shaded by functional class) in the UV- and HOC1-treated experiments. FIG. 33G depicts exemplary data showing PPV for predicting presented tumor antigens in a second donor using logistic models fit on heavy-labeled peptides observed in the first donor. Models were fit using neonmhc2 binding alone; binding and expression; or binding, expression, and a binary variable indicating if a peptide was from a mitochondria gene.

Figure 34A:
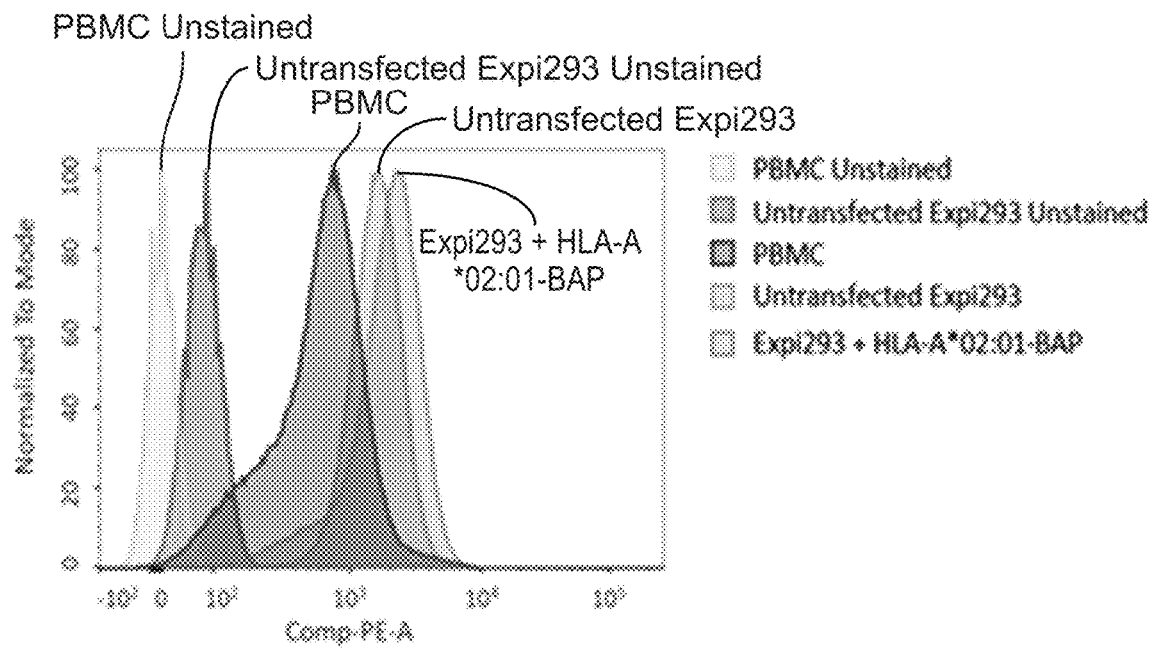
Figure 34B:
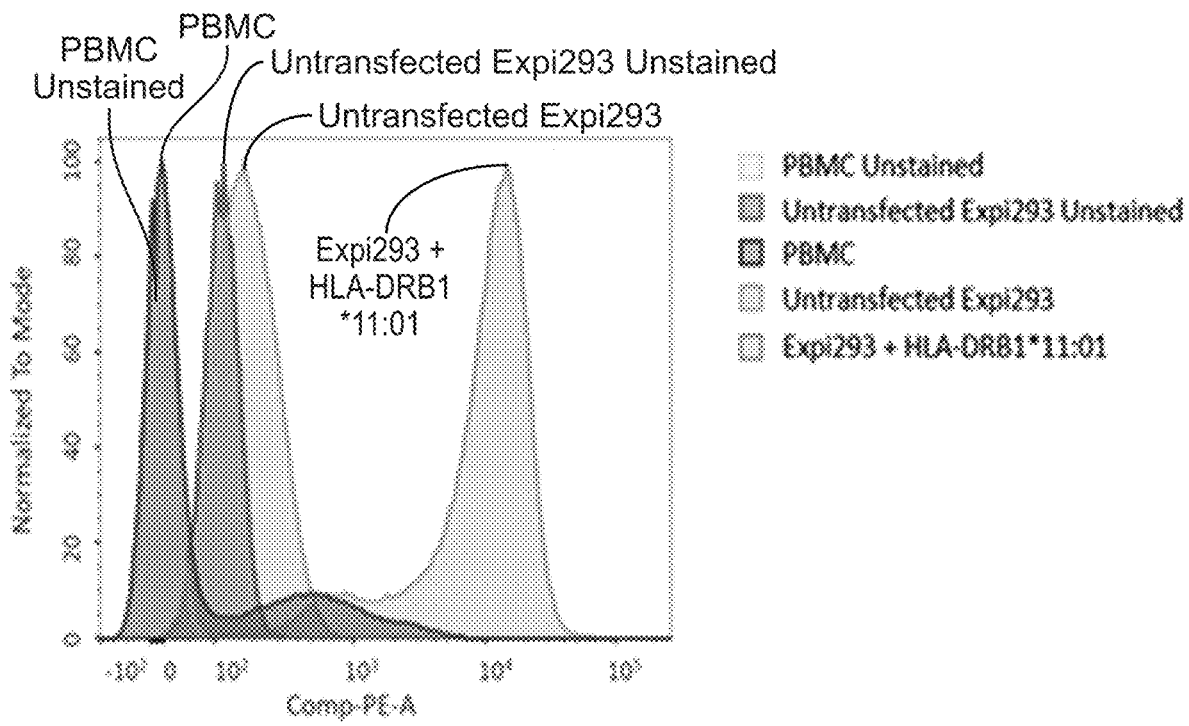

FIGS. 34A-34B depict exemplary characterization of MAPTAC™ data related to FIG. 29. FIG. 34A depicts an exemplary HLA cell surface analysis by FACS of Expi293 cell lines transfected with MAPTAC™ constructs coding for affinity-tagged HLA-A*02:01-BAP FIG. 34B depicts an exemplary HLA cell surface analysis by FACS of Expi293 cell lines transfected with MAPTAC™ constructs coding for affinity-tagged HLA-DRB1*11:01-BAP (bottom). HLA cell surface expression of transfected Expi293 cells were compared with stained untransfected Expi293, unstained untransfected Expi293, stained PBMCs, and unstained PBMCs. All HLA class I stains utilized W6/32 (pan-HLA class I), while HLA class II stains utilized REA332 (pan-HLA class II).

FIG. 35 depicts an exemplary comparison of MAPTAC™ and IEDB logos, related to FIG. 30A. Measured and NetMHCIIpan-predicted affinities for MS-observed peptides that did not exhibit good NetMHCIIpan scores but were well supported by MS (scored peak intensity >70 and nested set size ≥1).

Figure 36A:
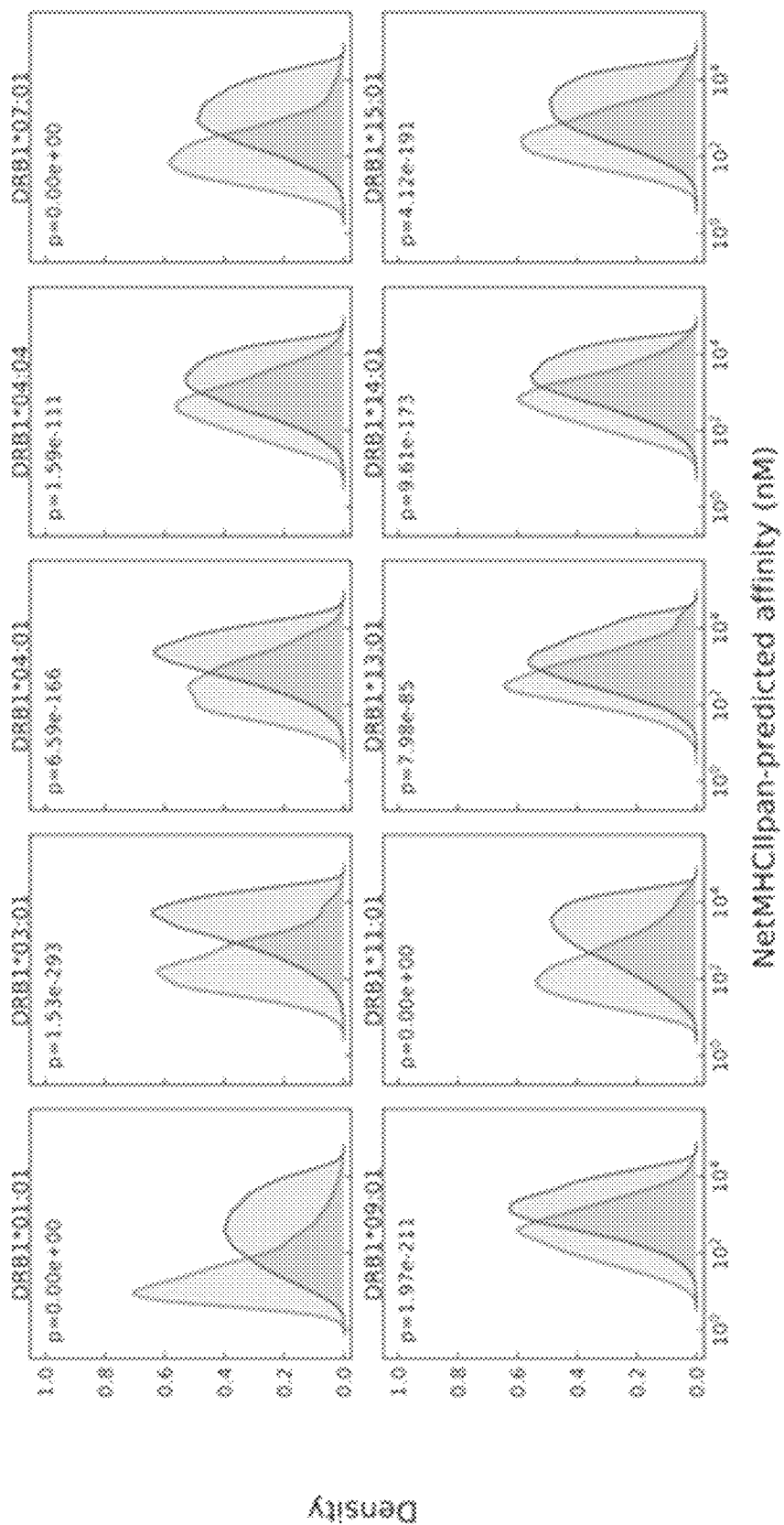
Figure 36C:
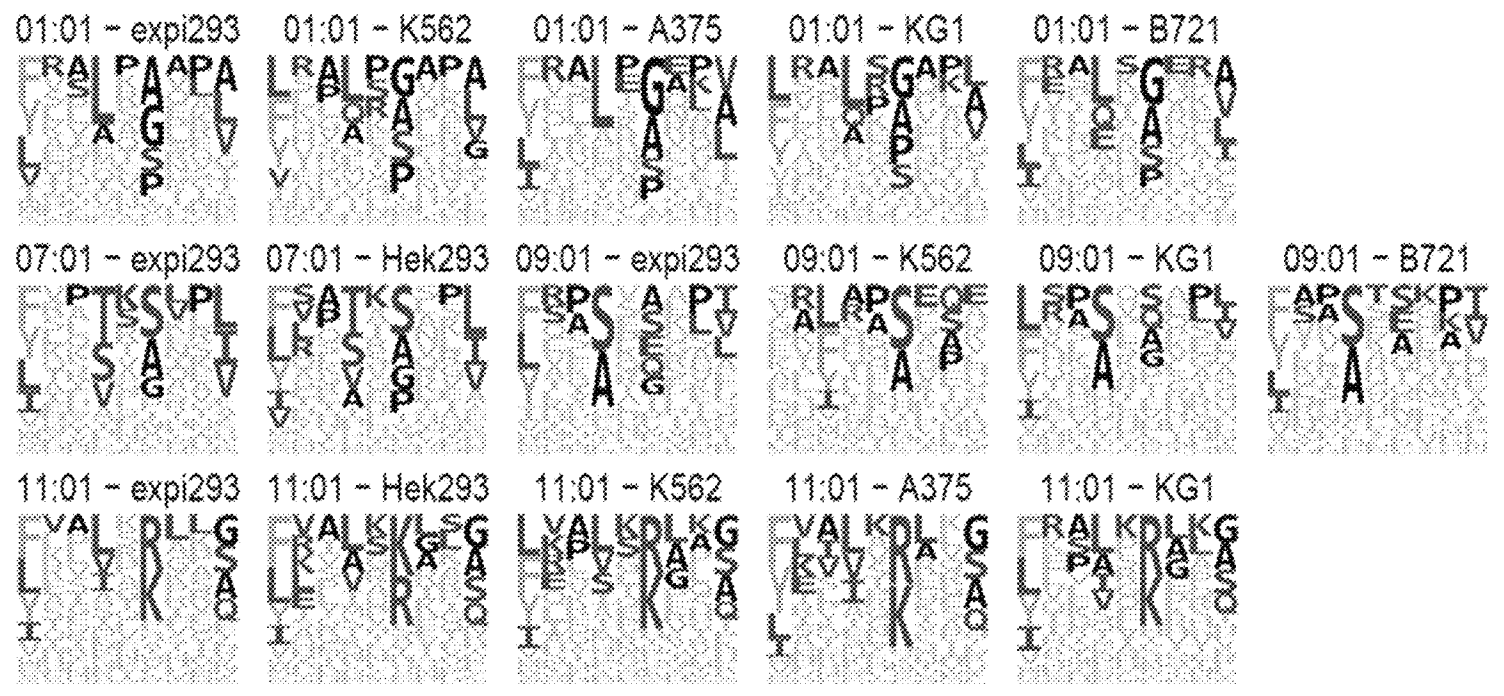

FIGS. 36A-36C depict an exemplary analysis of HLA-DR1 MAPTAC™ data fidelity, related to FIGS. 30A-30C. FIG. 36A depicts exemplary NetMHCIIpan3.1 scores for HLA-DR1 MAPTAC™ peptides (lengths 12-23) as compared to 50,000 length-matched decoy peptides randomly sampled from the proteome(blue), for common alleles. FIG. 36B depicts exemplary measured and NetMHCIIpan-predicted affinities for exemplary MS-observed peptides that did not exhibit good NetMHCIIpan scores but were well-supported by MS (scored peak intensity>70 and nested set size ≥1). Figure discloses SEQ ID NOS 40-86, top to bottom, left to right, respectively, in order of appearance. FIG. 36C depicts exemplary HLA class II sequence logos for HLA-DRB1 alleles as determined by MAPTAC™ in different cell types.

Figure 37A:
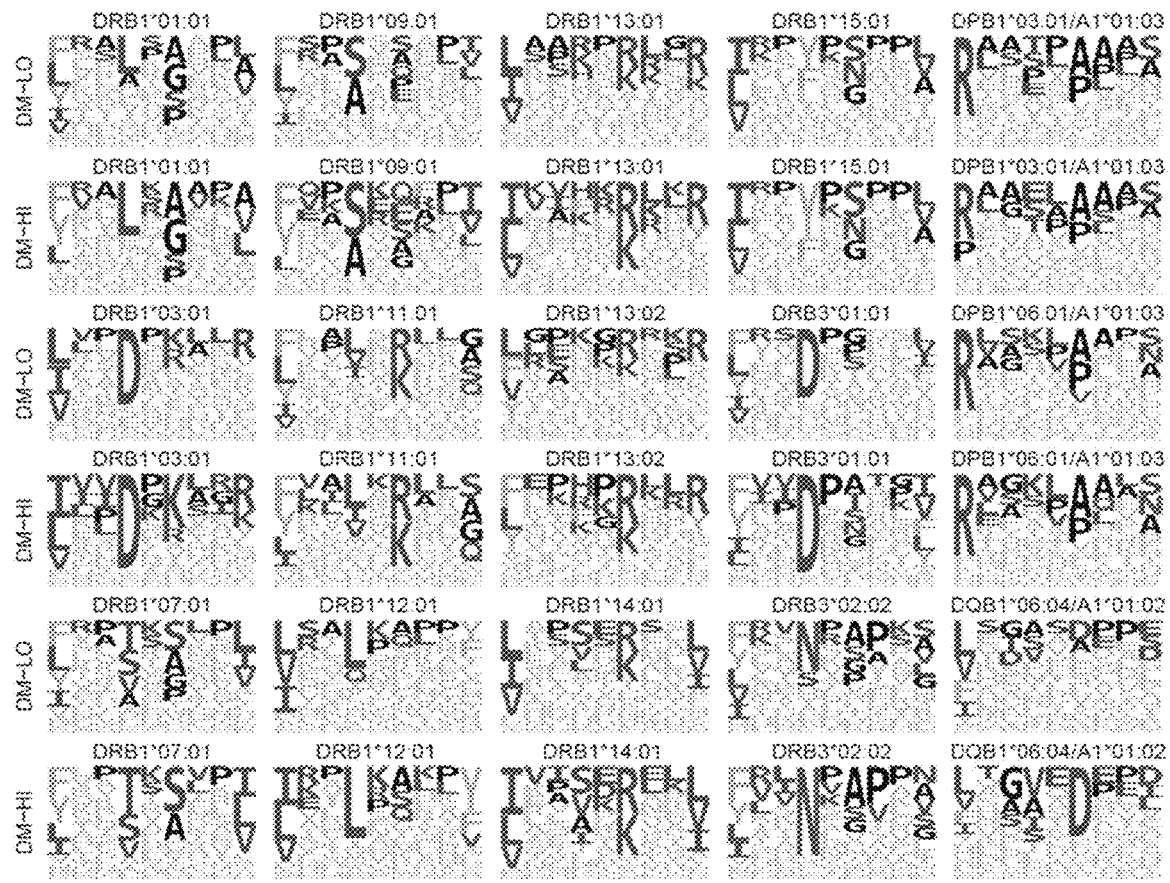
Figure 37B:
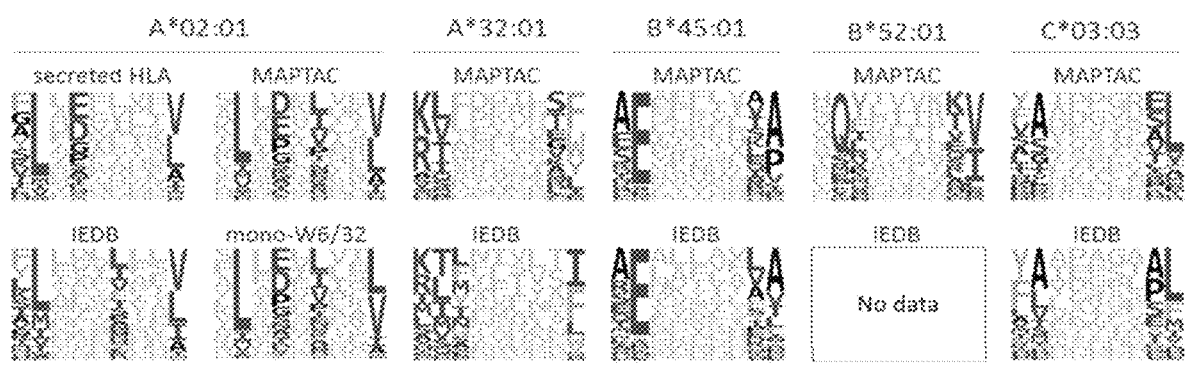
Figure 37C:
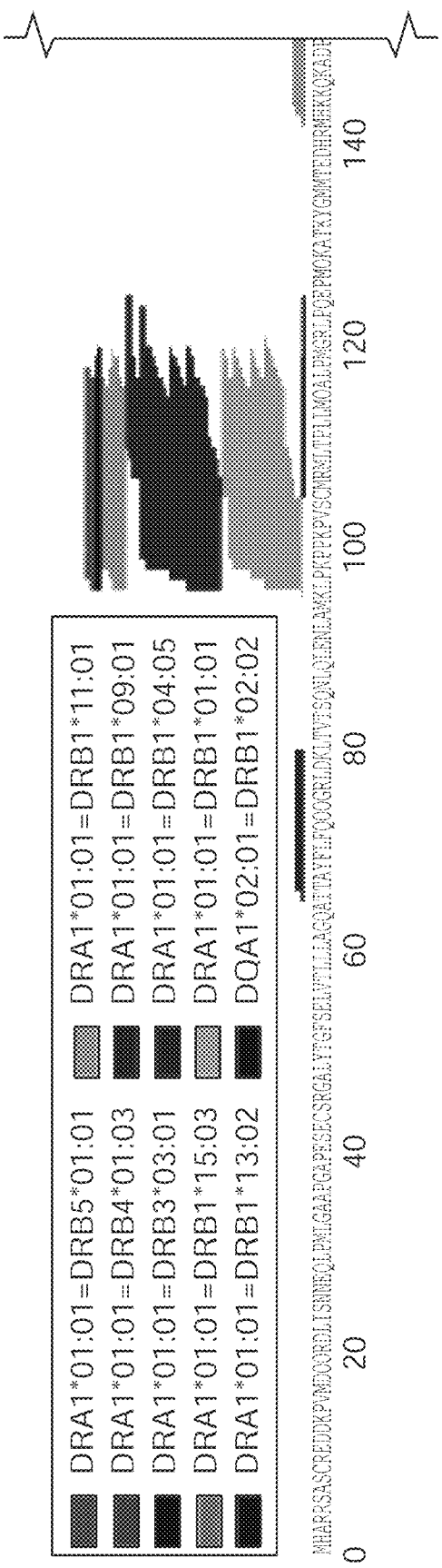
Figure 37D:
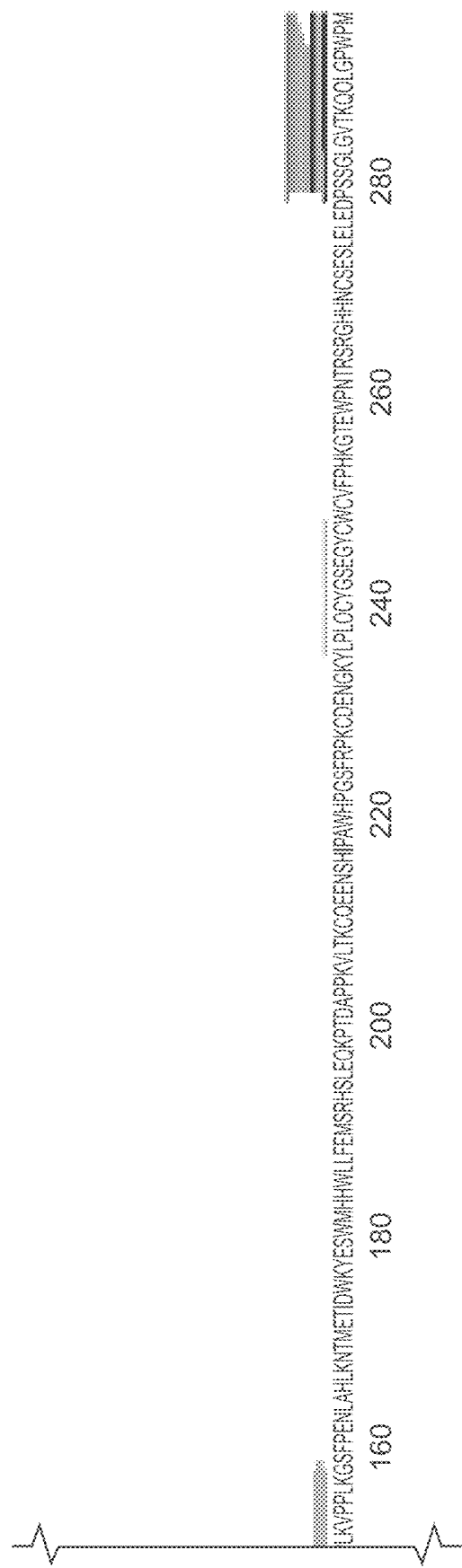

FIGS. 37A-37C and 37D (continuation of FIG. 37C) depict an additional exemplary analysis of MAPTAC™ motifs, related to FIGS. 30A-30C. FIG. 37A depicts MAPTAC™-derived sequence logos for experiments with and without HLA-DM co-transfection (expi293 cell line). FIG. 37B depicts sequence logos for several HLA class I alleles according to MAPTAC™ and IEDB. Note that A*32:01 does not show a high frequency Q at P2 and C*03:03 does not show a high frequency Y at P9, differing with previous studies that used multi-allelic deconvolution; the logo for B*52:01 is previously unpublished. FIGS. 37C and 37D (continuation of FIG. 37C) depicts an exemplary alignment of MAPTAC™-observed peptides to the gene sequence of CD74.

Figure 38X:
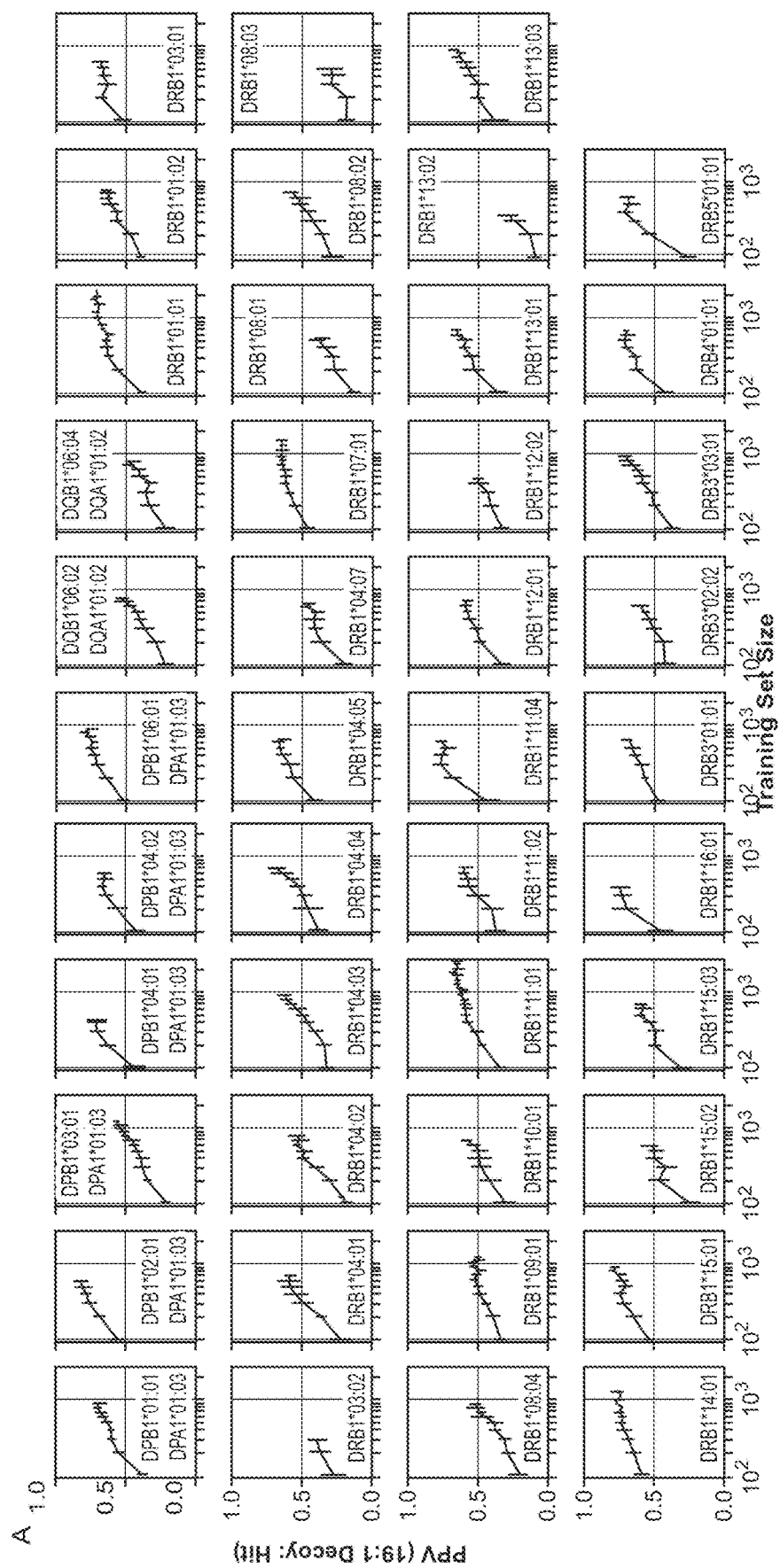
Figure 38Y:
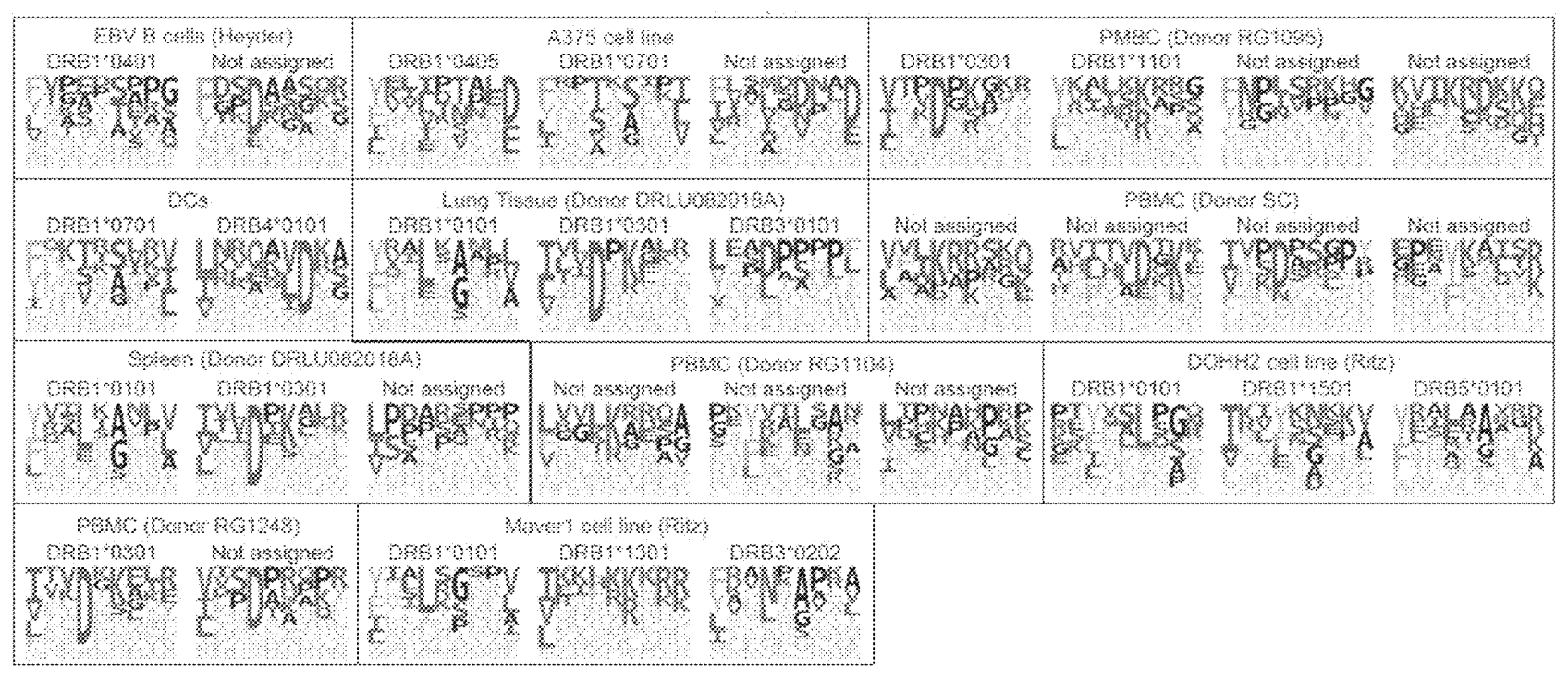
Figure 38B:
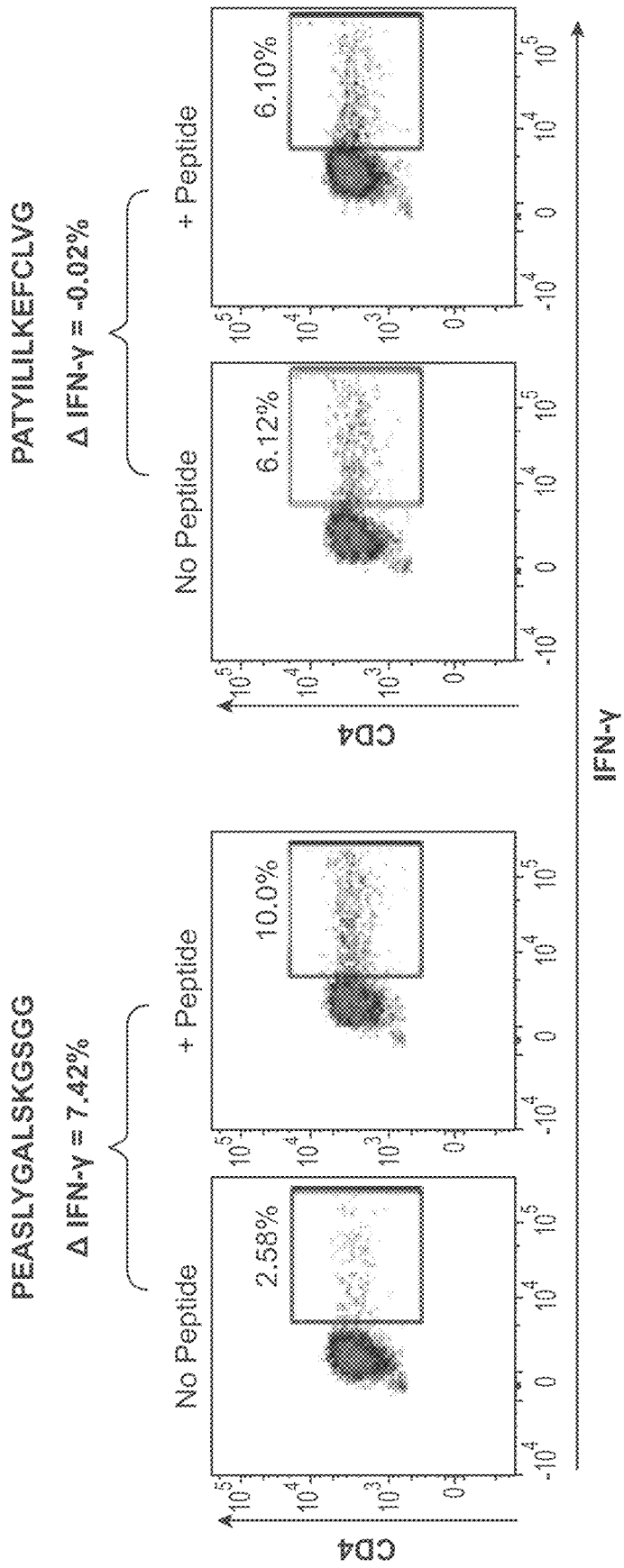
Figure 38D:
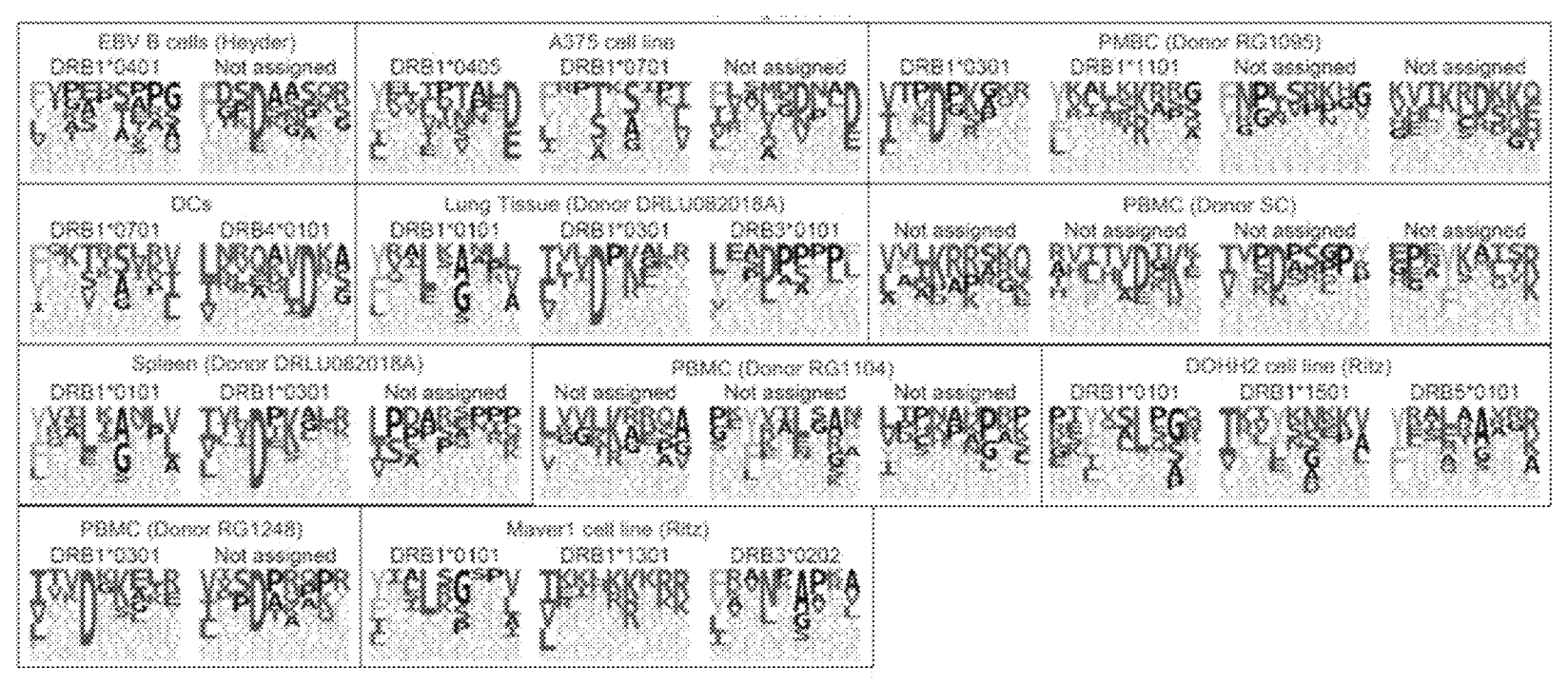

FIGS. 38X, 38Y, 38B-38D depict exemplary neonmhc2 performance statistics and T cell flow staining, related to FIGS. 31A-31D. FIG. 38X depicts an exemplary performance of neonmhc2 as a function of training data set size. PPV was evaluated in the same manner and using the same evaluation peptides as in FIG. 31B; however, the training data was randomly down-sampled to mimic smaller training data sets. FIG. 38Y depicts exemplary sequence logos for peptide clusters derived from multi-allelic HLA-DR ligandome using GibbsCluster (default settings; "trash cluster allowed). FIG. 38B depicts exemplary representative flow cytometry plots of IFN-γ expression by CD4+ cells from induction samples recalled with neoantigen peptides predicted with neonmhc2. Delta values were calculated by subtracting the percent of CD4+ cells expressing IFN-γ when recalled with neoantigen (+Peptide) from the percent of CD4+ expressing IFN-γ when recalled in the presence of no neoantigen (No Peptide). The left two flow plots are representative of a neoantigen that induced a CD4+ T cell T cell response (PEASLYGALSKGSGG (SEQ ID NO: 2)) and a neoantigen that did not induce a T cell response (PATYILILKEFCLVG (SEQ ID NO: 3)). FIG. 38C depicts exemplary delta values from wells recalled with single neonmch2 neoantigen peptides. Peptides were considered an induction hit if they had a positive response (delta response above 3%, highlighted). Figure discloses SEQ ID NOS 87-91, 2, 92-94, 3, and 95-96, respectively, in order of appearance. FIG. 38D shows exemplary sequence logos for peptide clusters derived for multi-allelic HLA-DR ligandomes using GibbsCluster (default settings; "trash" cluster allowed).

Figure 39A:
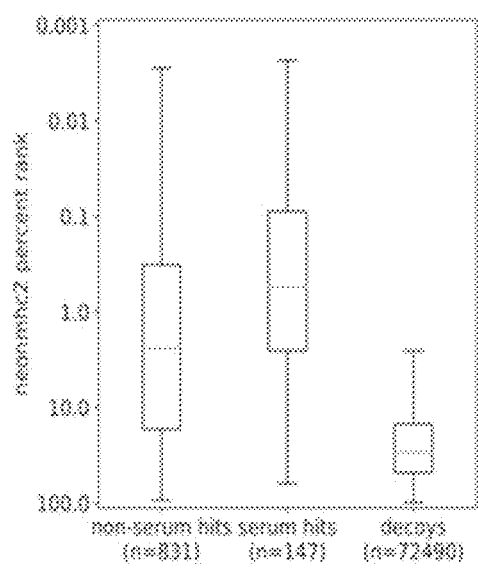
Figure 39B:
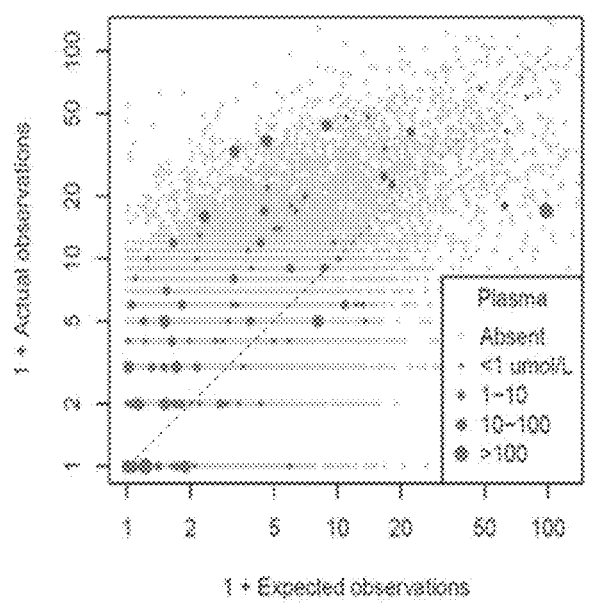
Figure 39C:
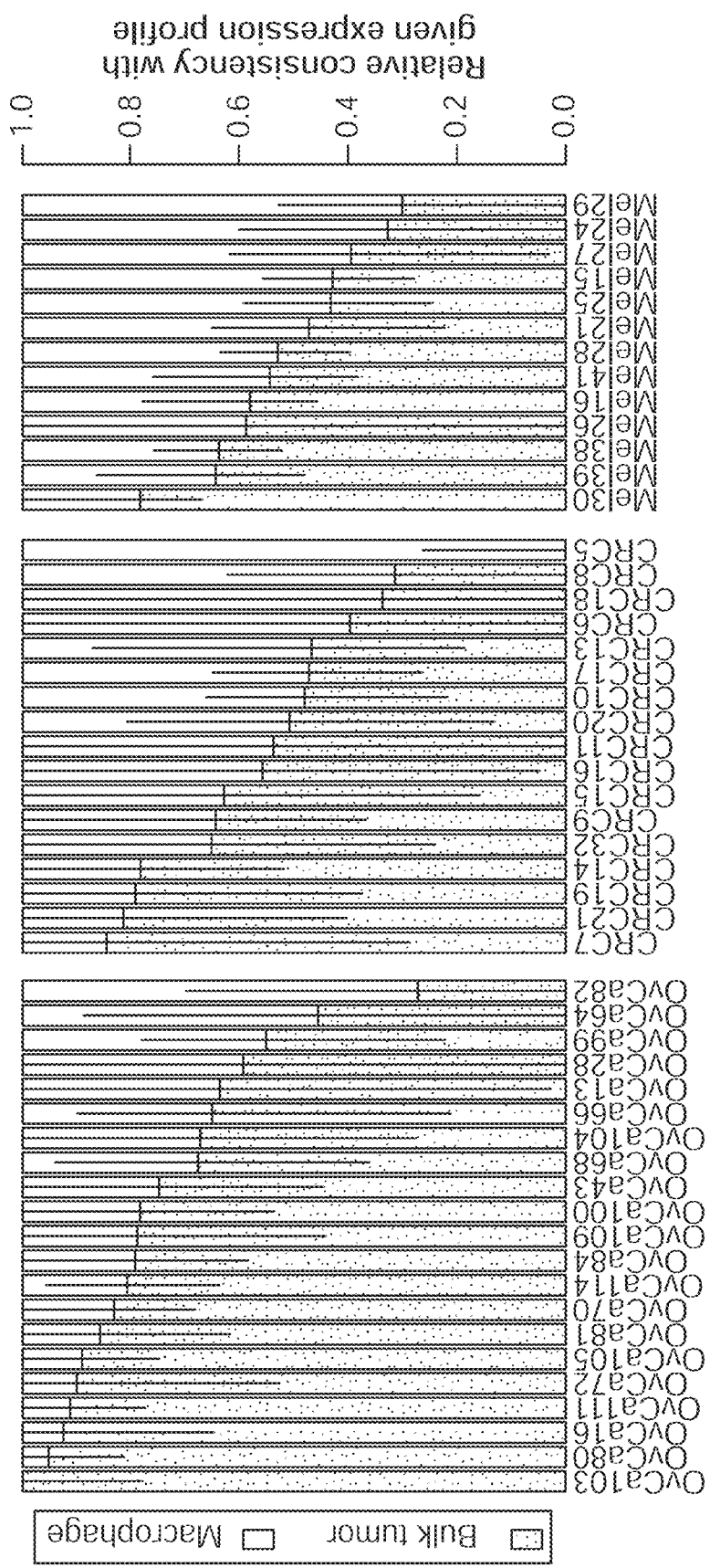

FIGS. 39A-39C depict an additional exemplary cell-of-origin analysis for HLA class II, related to FIGS. 32A-32E. FIG. 39A depicts exemplary percent-rank neonmhc2 scores for HLA class II peptides observed in 4 PBMC samples profiled by pan-DR antibody (RG1248, RG1104, RG1095, and HDSC from FIG. 30B), according to whether the peptide source gene is present in human plasma. For each peptide, the best (lowest) percent rank was used across the alleles present in the donor. Scores for random length-matched proteome decoys are shown for comparison. Box plots mark the 5th, 25th, 50th, 75th, and 95th percentiles. FIG. 39B depicts exemplary counts of observed vs. expected peptides per gene for HLA class I, using the same methodology as in FIG. 32A. Data correspond to the same tumor types (colorectal, ovarian, and melanoma). Genes present in human plasma are highlighted and sized according to their concentration. FIG. 39C depicts an exemplary relative concordance of peptide observations with respect to two different gene expression profiles. For each sample, gene-level peptide counts were modeled as a linear combination of a bulk tumor gene expression and professional APC gene expression profile. The ratio of the coefficients determines the relative concordance of each expression profile with the peptide repertoire. Error bars correspond to a 95% confidence interval computed by bootstrap resampling.

FIGS. 40A-40B depict an additional exemplary analysis of processing motifs related to FIGS. 32A-32E. FIG. 40A depicts exemplary amino acid frequencies near N-terminal and C-terminal peptide cut sites relative to average proteome frequencies (applies for upstream positions U3-U1 and downstream positions D1-D3) or relative to average peptide frequencies (applies for internal positions N1-C1) as observed in donor PBMC, monocyte-derived dendritic cells, colorectal cancer, melanoma, ovarian cancer, and the expi293 cell line (used for most MAPTAC™ data generation). FIG. 40B depicts the same analysis as FIG. 32E but using NetMHCIIpan as the base predictor. Absolute increase in PPV observed for logistic regression models that included processing-related variables in addition to NetMHCIIpan predictions (as compared to NetMHCIIpan-only models) for eight samples profiled by HLA-DR antibody (the same samples analyzed in FIG. 31B). Asterisks mark significant improvements (*: $p<0.01$, : $p<0.001$, *: $p<0.0001$) according to two-tailed paired t-tests.

Figure 41:
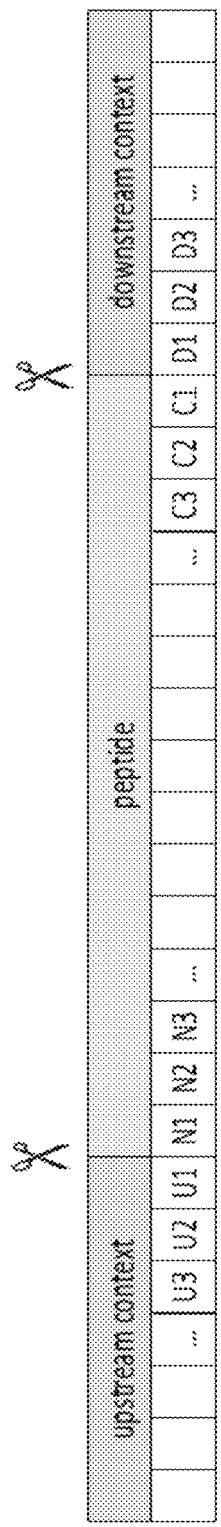

FIG. 41 depicts an exemplary naming system used to refer to positions upstream of peptides, within peptides, and downstream of peptides.

Figure 42A:
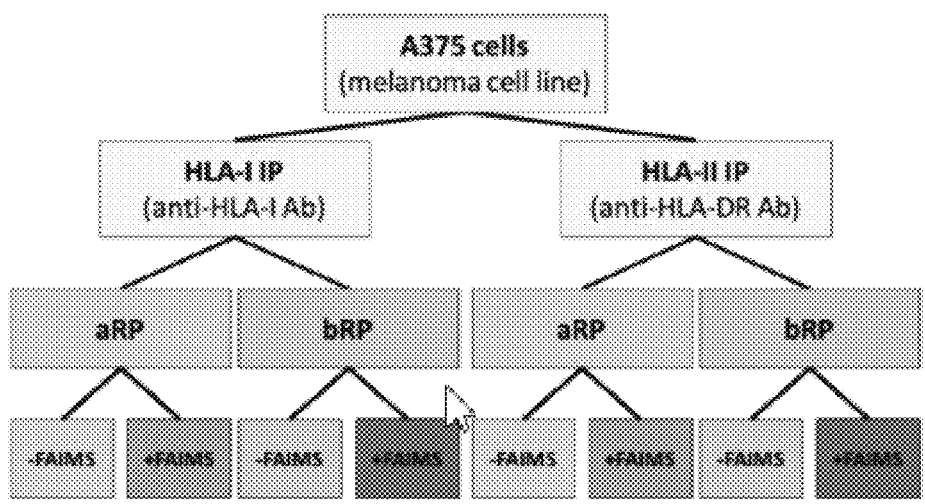

FIG. 42A depicts a diagram representing an exemplary workflow for analysis of endogenously processed and HLA-1 and HLA class II presented peptides by nLC-MS/MS.

Figure 42B:
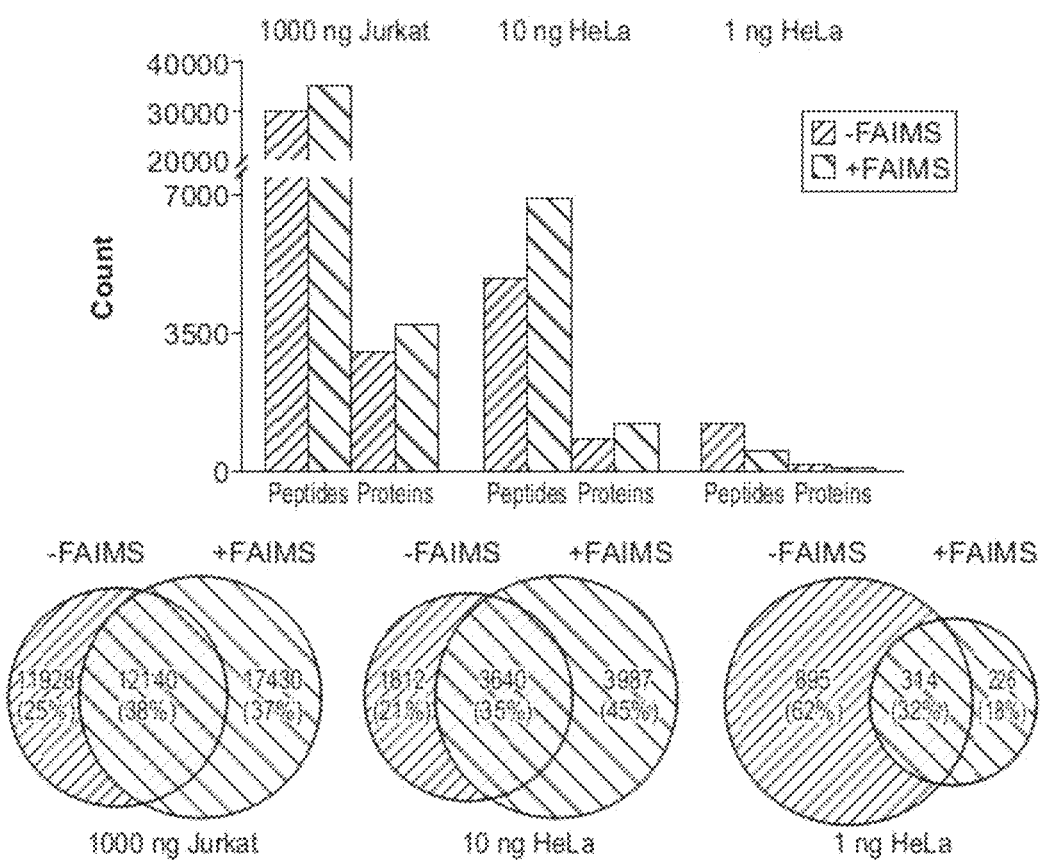

FIG. 42B depicts a graph showing exemplary experimental results from nLC-MS/MS analysis of tryptic peptides with or without FAIMS. Representative overlap in the detections of HLA-1 and HLA class II peptides by nLC-MS/MS analysis with or without FAIMS at the analysis scale as indicated are also depicted.

Figure 43A:
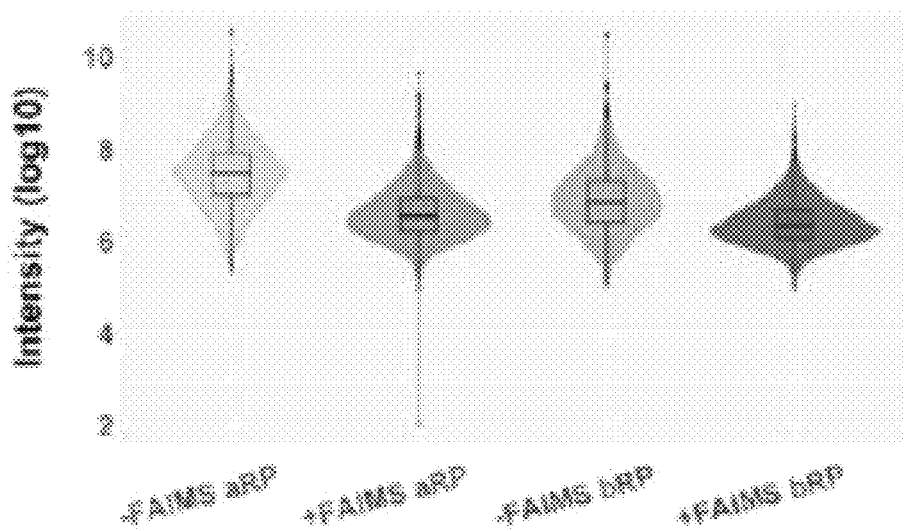

FIG. 43A depicts exemplary HLA class I acidic and basic reverse phase fractionated peptide detections with or without FAIMS.

Figure 43B:
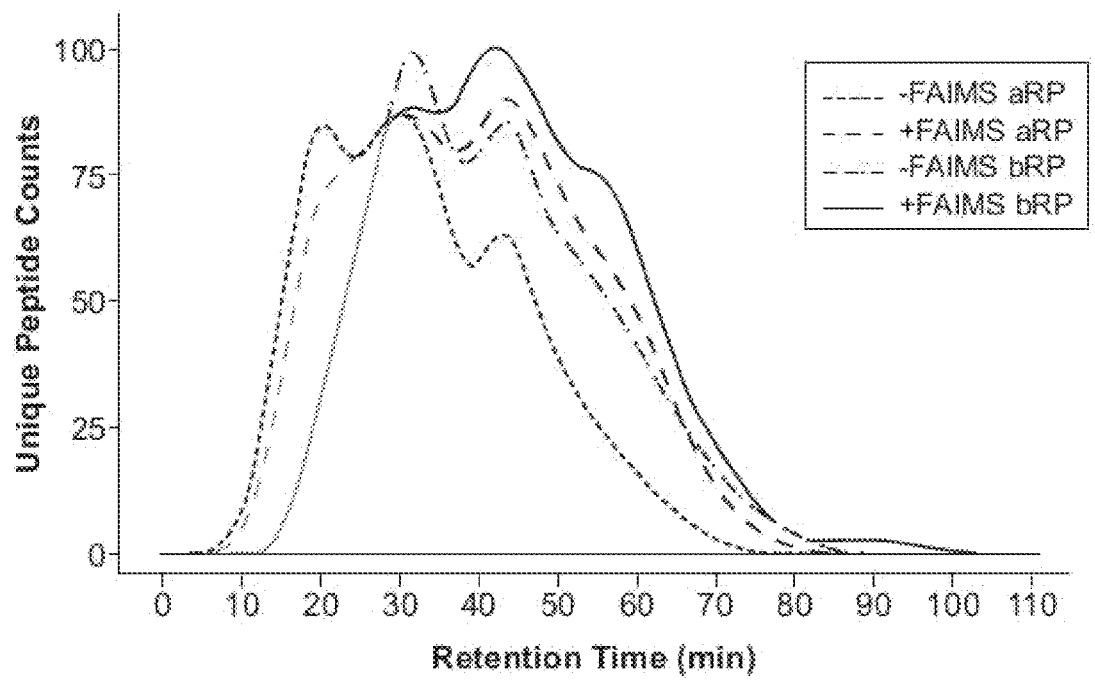

FIG. 43B depicts exemplary experimental results showing detection of HLA class I bound unique peptides plotted over retention time.

Figure 44A:
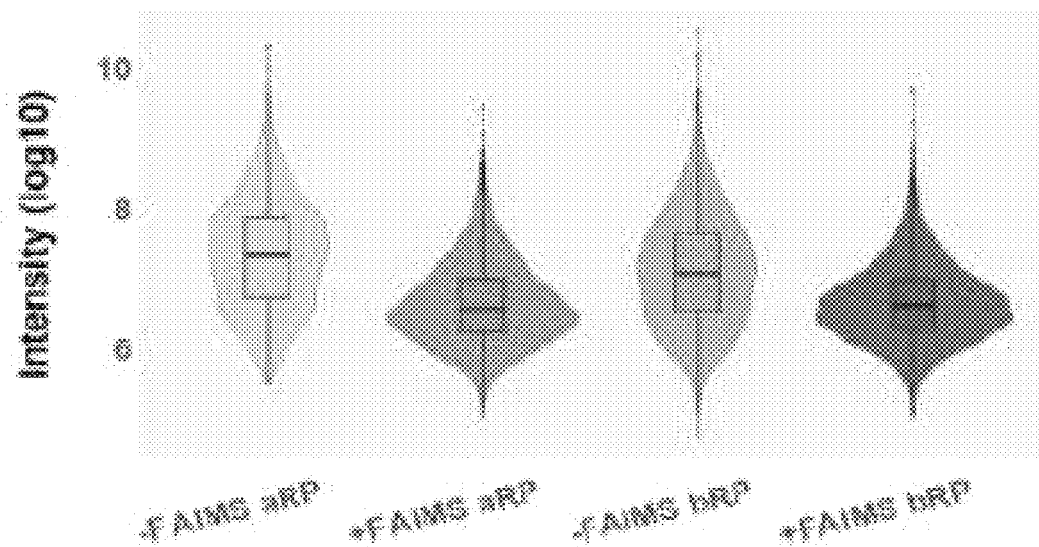

FIG. 44A depicts exemplary HLA class II acidic and basic reverse phase fractionated peptide detections with or without FAIMS.

Figure 44B:
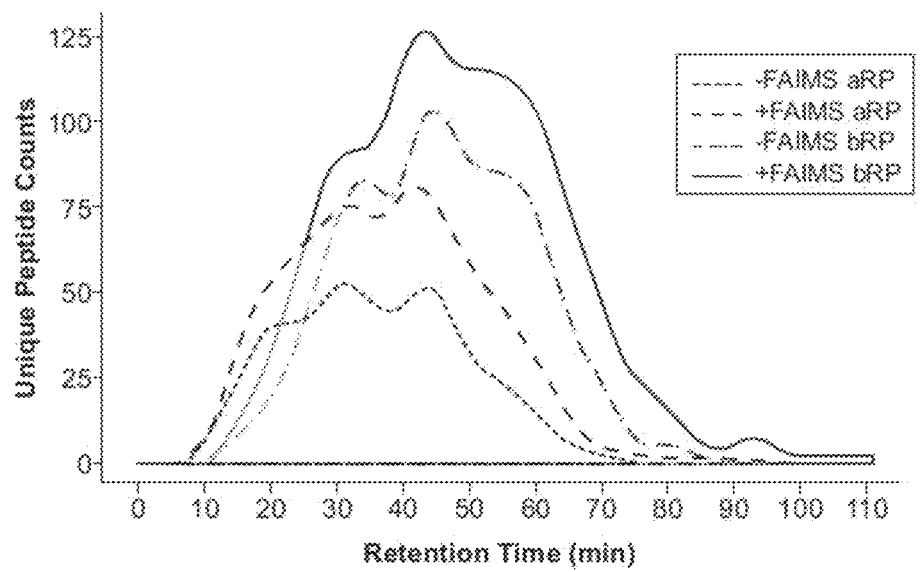

FIG. 44B depicts exemplary experimental results showing detection of HLA class II bound unique peptides plotted over retention time.

Figure 45A:
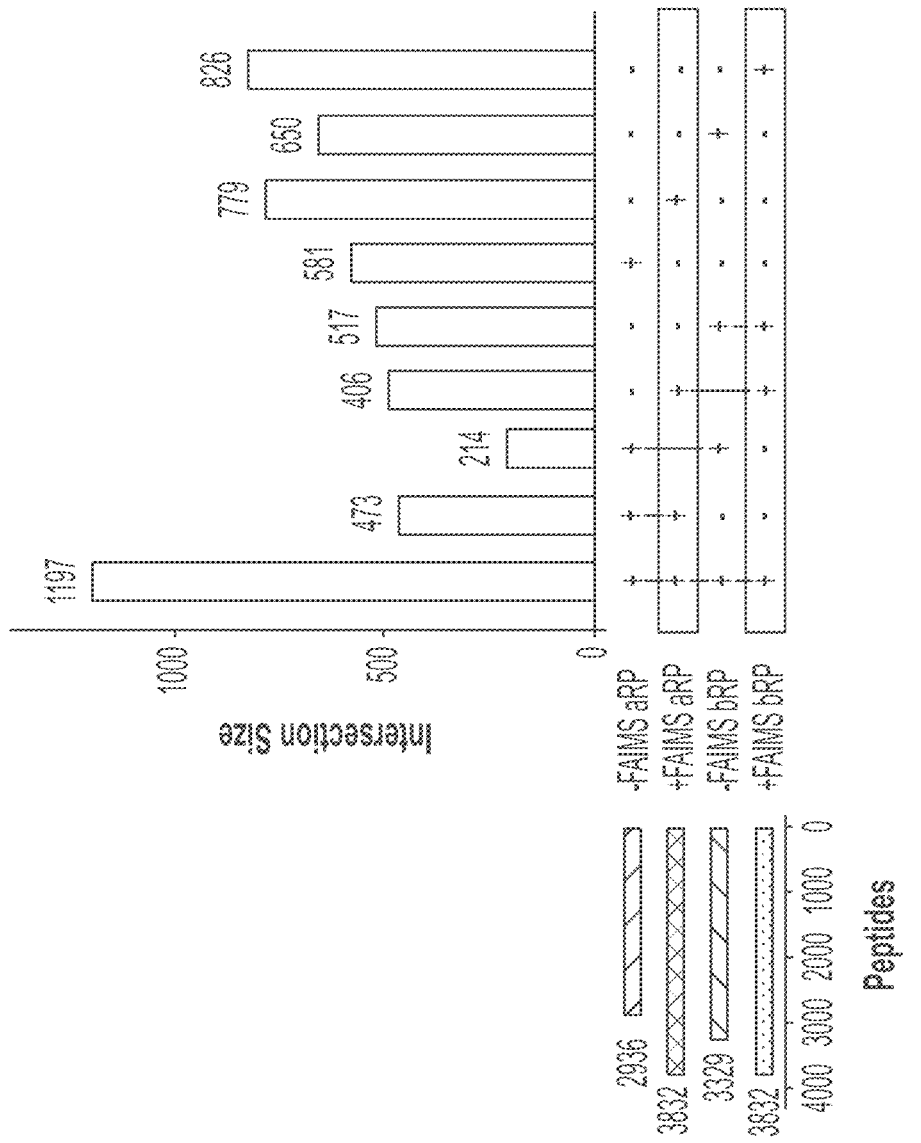
Figure 45B:
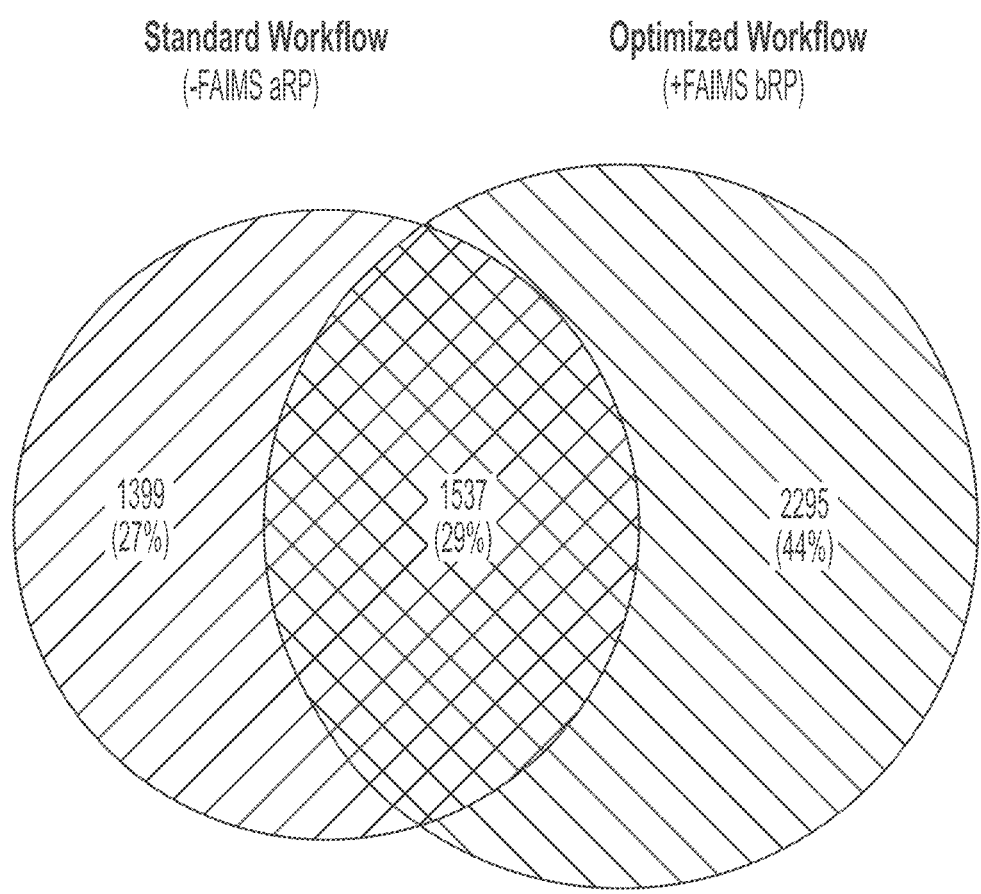

FIGS. 45A and 45B depict an exemplary graph of intersection size of HLA class I binding peptides detected using the methods indicated (left) and a Venn diagram of an exemplary standard workflow and an optimized workflow for LC-MS/MS detection of HLA class I binding peptides (right).

Figure 46A:
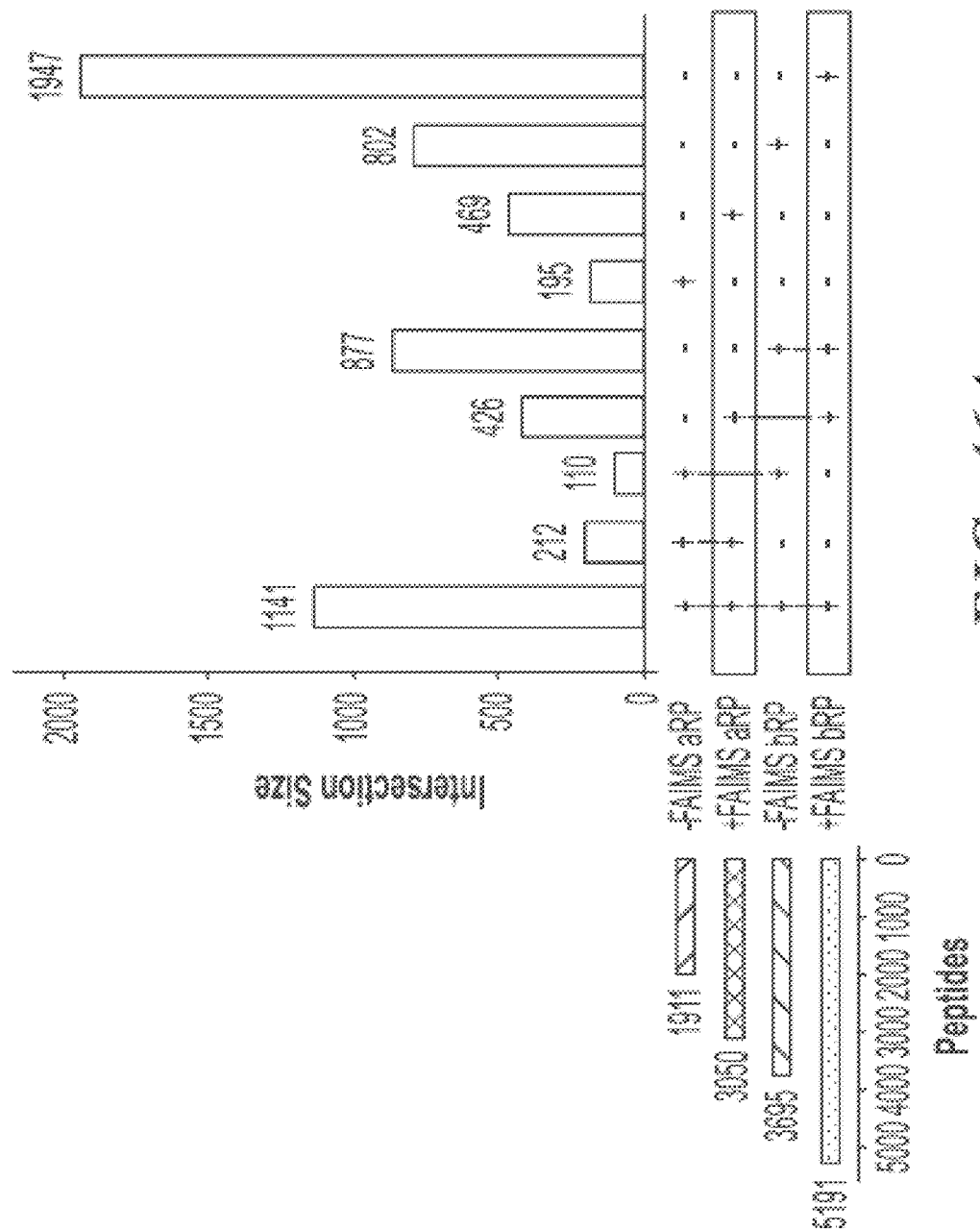
Figure 46B:
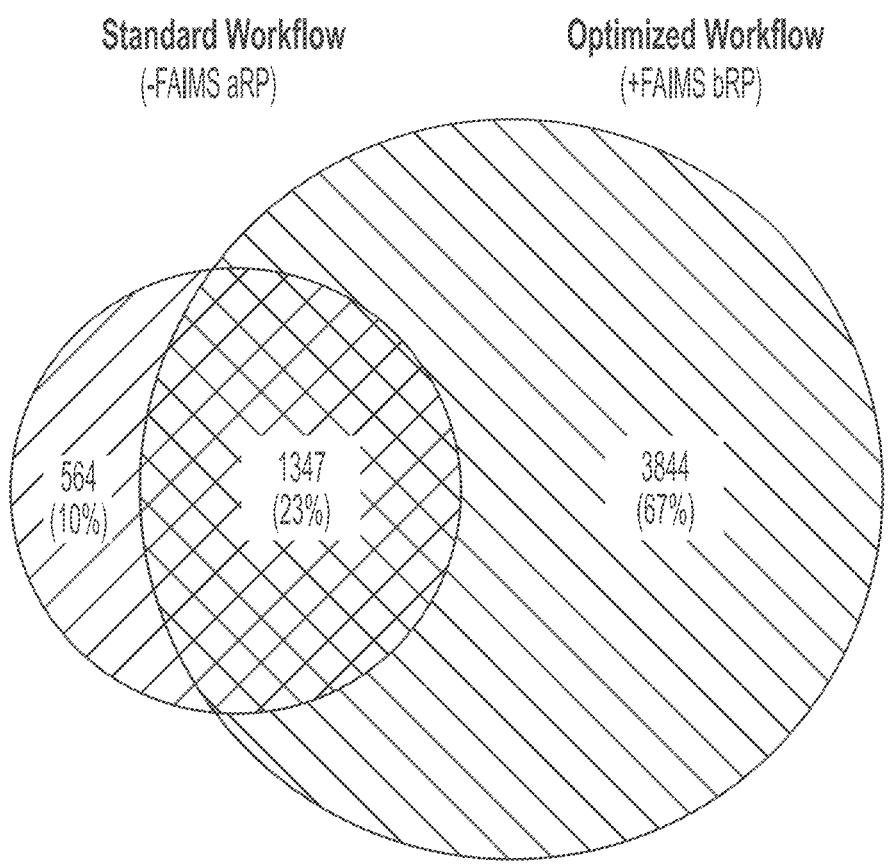

FIGS. 46A and 46B depict an exemplary graph of intersection size of HLA class II binding peptides detected using the methods indicated (left) and a Venn diagram of an exemplary standard workflow and an optimized workflow for LC-MS/MS detection of HLA class II binding peptides (right).

DETAILED DESCRIPTION

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the present disclosure can be described in the context of a single embodiment, the features can also be provided separately or in any suitable combination. Conversely, although the present disclosure can be described herein in the context of separate embodiments for clarity, the disclosure can also be implemented in a single embodiment.

The present disclosure is based on the important finding that the presentation of antigens, specifically cancer antigens by specific HLA class II alpha and beta chain pairs can be predicted with high degree of confidence using a new computer-based machine-learning HLA-peptide presentation prediction model which allows use of HLA class II specific peptides for improved immunotherapy.

In one aspect, the present disclosure provides method for predicting peptides that can accurately pair with, or bind to, a specific HLA class II alpha and beta chain heterodimer, such that the high fidelity binding of the peptide to HLA class II protein (comprising the alpha and beta chain heterodimer) ensures presentation of the specific peptide to the T lymphocytes, thereby eliciting a specific immune response and avoid any cross-reactivity or immune promiscuity. Several recent studies have shown that CD4+ T cells can also recognize HLA class II presented ligands and contribute to tumor control. Cancer vaccines and other immunotherapies would ideally take advantage of directing CD4+ T cell responses, but current efforts have forgone HLA class II antigen prediction entirely because the accuracy of current prediction tools is inadequate.

In one aspect, the present disclosure provides method for predicting peptides that can accurately bind to a specific HLA class II protein, such that a more sustained and robust immune response can be activated with the peptide, when the peptide is administered therapeutically to a subject expressing the specific cognate HLA class II protein, by means of the ability of HLA class II protein's activation of CD4+ T cells and stimulate immunological memory. In some embodiments, the method provided herein exhibits an improvement in a specific HLA class II protein prediction over currently available predictor. In some embodiments, the method provided herein exhibits at least about a 1.1-fold improvement in a specific HLA class II protein prediction over currently available predictor. In some embodiments, the method provided herein exhibits at least about a 2-fold improvement in a specific HLA class II protein prediction over currently available predictor. In some embodiments, the method provided herein exhibits at least about a 3-fold improvement in a specific HLA class II protein prediction over currently available predictor. In some embodiments, the method provided herein exhibits at least about a 4-fold improvement in a specific HLA class II protein prediction over currently available predictor. In some embodiments, the method provided herein exhibits at least about a 5-fold improvement in a specific HLA class II protein prediction over currently available predictor. In some embodiments, the method provided herein exhibits at least about a 6-fold improvement in a specific HLA class II protein prediction over currently available predictor. In some embodiments, the method provided herein exhibits at least about a 7-fold improvement in a specific HLA class II protein prediction over currently available predictor. In some embodiments, the method provided herein exhibits at least about a 8-fold improvement in a specific HLA class II protein prediction over currently available predictor. In some embodiments, the method provided herein exhibits at least about a 9-fold improvement in a specific HLA class II protein prediction over currently available predictor. In some embodiments, the method provided herein exhibits at least about a 10-fold improvement in a specific HLA class II protein prediction over currently available predictor. In some embodiments, the method provided herein exhibits at least about a 15-fold improvement in a specific HLA class II protein prediction over currently available predictor. In some embodiments, the method provided herein exhibits at least about a 20-fold improvement in a specific HLA class II protein prediction over currently available predictor. In some embodiments, the method provided herein exhibits at least about a 30-fold improvement in a specific HLA class II protein prediction over currently available predictor. In some embodiments, the method provided herein exhibits at least about a 40-fold improvement in a specific HLA class II protein prediction over currently available predictor. In some embodiments, the method provided herein exhibits at least about a 50-fold improvement in a specific HLA class II protein prediction over currently available predictor. In some embodiments, the method provided herein exhibits at least about a 60-fold improvement in a specific HLA class II protein prediction over currently available predictor.

In one aspect, presented herein are methods of immunotherapy tailored or personalized for a specific subject. Every subject or patient expresses a specific array of HLA class I and HLA class II proteins. HLA typing is a well-known technique that allows determination of the specific repertoire of HLA proteins expressed by the subject. Once the HLA heterodimers expressed by a specific subject is known, having an improved, sophisticated and reliable method as described herein for predicting peptides that can bind to a specific HLA class II alpha and beta chain heterodimer, with high fidelity can ensure that a specific immune response can be generated tailored specifically for the subject.

In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The terms "one or more" or "at least one," such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

Reference in the specification to "some embodiments," "an embodiment," "one embodiment" or "other embodiments" means that a feature, structure, or characteristic described in connection with the embodiments is included in at least some embodiments, but not necessarily all embodiments, of the present disclosure.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the disclosure can be used to achieve methods of the disclosure.

The term "about" or "approximately" as used herein when referring to a measurable value such as a parameter, an amount, a temporal duration, and the like, is meant to encompass variations of +/−20% or less, +/−10% or less, +1-5% or less, or +/−1% or less of and from the specified value, insofar such variations are appropriate to perform in the present disclosure. It is to be understood that the value to which the modifier "about" or "approximately" refers is itself also specifically disclosed.

The term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

A "receptor" is to be understood as meaning a biological molecule or a molecule grouping capable of binding a ligand. A receptor can serve to transmit information in a cell, a cell formation or an organism. The receptor comprises at least one receptor unit and can contain two or more receptor units, where each receptor unit can consist of a protein molecule, e.g., a glycoprotein molecule. The receptor has a structure that complements the structure of a ligand and can complex the ligand as a binding partner. Signaling information can be transmitted by conformational changes of the receptor following binding with the ligand on the surface of a cell. According to the present disclosure, a receptor can refer to proteins of MHC classes I and II capable of forming a receptor/ligand complex with a ligand, e.g., a peptide or peptide fragment of suitable length. The class I and class II MHC peptides that are encoded by HLA class I and class II alleles are often referred to here as HLA class I and HLA class II peptides respectively, or HLA class I and HLA class II peptides, or HLA class I class II proteins, or HLA class I and HLA class II proteins, or HLA class I and class II molecules, or such common variants thereof, as is well understood within the context of the discussion by one of ordinary skill in the art.

A "ligand" is a molecule which is capable of forming a complex with a receptor. According to the present disclosure, a ligand is to be understood as meaning, for example, a peptide or peptide fragment which has a suitable length and suitable binding motifs in its amino acid sequence, so that the peptide or peptide fragment is capable of binding to and forming a complex with proteins of MHC class I or MHC class II (i.e., HLA class I and HLA class II proteins).

An "antigen" is a molecule capable of stimulating an immune response, and can be produced by cancer cells or infectious agents or an autoimmune disease. Antigens recognized by T cells, whether helper T lymphocytes (T helper (TH) cells) or cytotoxic T lymphocytes (CTLs), are not recognized as intact proteins, but rather as small peptides in association with HLA class I or class II proteins on the surface of cells. During the course of a naturally occurring immune response, antigens that are recognized in association with HLA class II molecules on antigen presenting cells (APCs) are acquired from outside the cell, internalized, and processed into small peptides that associate with the HLA class II molecules. APCs can also cross-present peptide antigens by processing exogenous antigens and presenting the processed antigens on HLA class I molecules. Antigens that give rise to peptides that are recognized in association with HLA class I MHC molecules are generally peptides that are produced within the cells, and these antigens are processed and associated with class I MHC molecules. It is now understood that the peptides that associate with given HLA class I or class II molecules are characterized as having a common binding motif, and the binding motifs for a large number of different HLA class I and II molecules have been determined. Synthetic peptides that correspond to the amino acid sequence of a given antigen and that contain a binding motif for a given HLA class I or II molecule can also be synthesized. These peptides can then be added to appropriate APCs, and the APCs can be used to stimulate a T helper cell or CTL response either in vitro or in vivo. The binding motifs, methods for synthesizing the peptides, and methods for stimulating a T helper cell or CTL response are all known and readily available to one of ordinary skill in the art.

The term "peptide" is used interchangeably with "mutant peptide" and "neoantigenic peptide" in the present specification. Similarly, the term "polypeptide" is used interchangeably with "mutant polypeptide" and "neoantigenic polypeptide" in the present specification. By "neoantigen" or "neoepitope" is meant a class of tumor antigens or tumor epitopes which arises from tumor-specific mutations in expressed protein. The present disclosure further includes peptides that comprise tumor specific mutations, peptides that comprise known tumor specific mutations, and mutant polypeptides or fragments thereof identified by the method of the present disclosure. These peptides and polypeptides are referred to herein as "neoantigenic peptides" or "neoantigenic polypeptides." The polypeptides or peptides can be a variety of lengths, either in their neutral (uncharged) forms or in forms which are salts, and either free of modifications such as glycosylation, side chain oxidation, phosphorylation, or any post-translational modification or containing these modifications, subject to the condition that the modification not destroy the biological activity of the polypeptides as herein described. In some embodiments, the neoantigenic peptides of the present disclosure can include: for HLA class I, 22 residues or less in length, e.g., from about 8 to about 22 residues, from about 8 to about 15 residues, or 9 or 10 residues; for HLA Class II, 40 residues or less in length, e.g., from about 8 to about 40 residues in length, from about 8 to about 24 residues in length, from about 12 to about 19 residues, or from about 14 to about 18 residues. In some embodiments, a neoantigenic peptide or neoantigenic polypeptide comprises a neoepitope.

The term "epitope" includes any protein determinant capable of specific binding to an antibody, antibody peptide, and/or antibody-like molecule (including but not limited to a T cell receptor) as defined herein. Epitopic determinants typically consist of chemically active surface groups of molecules such as amino acids or sugar side chains and generally have specific three-dimensional structural characteristics as well as specific charge characteristics.

A "T cell epitope" is a peptide sequence which can be bound by the MHC molecules of class I or II in the form of a peptide-presenting MHC molecule or MHC complex and then, in this form, be recognized and bound by cytotoxic T-lymphocytes or T-helper cells, respectively.

The term "antibody" as used herein includes IgG (including IgG1, IgG2, IgG3, and IgG4), IgA (including IgA1 and IgA2), IgD, IgE, IgM, and IgY, and is meant to include whole antibodies, including single-chain whole antibodies, and antigen-binding (Fab) fragments thereof. Antigen-binding antibody fragments include, but are not limited to, Fab, Fab' and F(ab')2, Fd (consisting of VH and CH1), single-chain variable fragment (scFv), single-chain antibodies, disulfide-linked variable fragment (dsFv) and fragments comprising either a VL or VH domain. The antibodies can be from any animal origin. Antigen-binding antibody fragments, including single-chain antibodies, can comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies can be monoclonal, polyclonal, chimeric, humanized, and human monoclonal and polyclonal antibodies which, e.g., specifically bind an HLA-associated polypeptide or an HLA-HLA binding peptide (HLA-peptide) complex. A person of skill in the art will recognize that a variety of immunoaffinity techniques are suitable to enrich soluble proteins, such as soluble HLA-peptide complexes or membrane bound HLA-associated polypeptides, e.g., which have been proteolytically cleaved from the membrane. These include techniques in which (1) one or more antibodies capable of specifically binding to the soluble protein are immobilized to a fixed or mobile substrate (e.g., plastic wells or resin, latex or paramagnetic beads), and (2) a solution containing the soluble protein from a biological sample is passed over the antibody coated substrate, allowing the soluble protein to bind to the antibodies. The substrate with the antibody and bound soluble protein is separated from the solution, and optionally the antibody and soluble protein are disassociated, for example by varying the pH and/or the ionic strength and/or ionic composition of the solution bathing the antibodies. Alternatively, immunoprecipitation techniques in which the antibody and soluble protein are combined and allowed to form macromolecular aggregates can be used. The macromolecular aggregates can be separated from the solution by size exclusion techniques or by centrifugation.

The term "immunopurification (IP)" (or immunoaffinity purification or immunoprecipitation) is a process well known in the art and is widely used for the isolation of a desired antigen from a sample. In general, the process involves contacting a sample containing a desired antigen with an affinity matrix comprising an antibody to the antigen covalently attached to a solid phase. The antigen in the sample becomes bound to the affinity matrix through an immunochemical bond. The affinity matrix is then washed to remove any unbound species. The antigen is removed from the affinity matrix by altering the chemical composition of a solution in contact with the affinity matrix. The immunopurification can be conducted on a column containing the affinity matrix, in which case the solution is an eluent. Alternatively, the immunopurification can be in a batch process, in which case the affinity matrix is maintained as a suspension in the solution. An important step in the process is the removal of antigen from the matrix. This is commonly achieved by increasing the ionic strength of the solution in contact with the affinity matrix, for example, by the addition of an inorganic salt. An alteration of pH can also be effective to dissociate the immunochemical bond between antigen and the affinity matrix.

An "agent" is any small molecule chemical compound, antibody, nucleic acid molecule, or polypeptide, or fragments thereof.

An "alteration" or "change" is an increase or decrease. An alteration can be by as little as 1%, 2%, 3%, 4%, 5%, 10%, 20%, 30%, or by 40%, 50%, 60%, or even by as much as 70%, 75%, 80%, 90%, or 100%.

A "biologic sample" is any tissue, cell, fluid, or other material derived from an organism. As used herein, the term "sample" includes a biologic sample such as any tissue, cell, fluid, or other material derived from an organism. "Specifically binds" refers to a compound (e.g., peptide) that recognizes and binds a molecule (e.g., polypeptide), but does not substantially recognize and bind other molecules in a sample, for example, a biological sample.

"Capture reagent" refers to a reagent that specifically binds a molecule (e.g., a nucleic acid molecule or polypeptide) to select or isolate the molecule (e.g., a nucleic acid molecule or polypeptide).

As used herein, the terms "determining", "assessing", "assaying", "measuring", "detecting" and their grammatical equivalents refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

A "fragment" is a portion of a protein or nucleic acid that is substantially identical to a reference protein or nucleic acid. In some embodiments, the portion retains at least 50%, 75%, or 80%, or 90%, 95%, or even 99% of the biological activity of the reference protein or nucleic acid described herein.

The terms "isolated," "purified", "biologically pure" and their grammatical equivalents refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of the present disclosure is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications can give rise to different isolated proteins, which can be separately purified.

An "isolated" polypeptide (e.g., a peptide from an HLA-peptide complex) or polypeptide complex (e.g., an HLA-peptide complex) is a polypeptide or polypeptide complex of the present disclosure that has been separated from components that naturally accompany it. Typically, the polypeptide or polypeptide complex is isolated when it is at least 60%, by weight, free from the proteins and naturally-occurring organic molecules with which it is naturally associated. The preparation can be at least 75%, at least 90%, or at least 99%, by weight, a polypeptide or polypeptide complex of the present disclosure. An isolated polypeptide or polypeptide complex of the present disclosure can be obtained, for example, by extraction from a natural source, by expression of a recombinant nucleic acid encoding such a polypeptide or one or more components of a polypeptide complex, or by chemically synthesizing the polypeptide or one or more components of the polypeptide complex. Purity can be measured by any appropriate method, for example, column chromatography, polyacrylamide gel electrophoresis, or by HPLC analysis. In some cases, an HLA allele-encoded MHC Class II protein (i.e., an MHC class II peptide) is interchangeably referred to within this document as an HLA class II protein (or HLA class II peptide).

The term "vectors" refers to a nucleic acid molecule capable of transporting or mediating expression of a heterologous nucleic acid. A plasmid is a species of the genus encompassed by the term "vector." A vector typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the cell. A vector can be a DNA or RNA vector. Other forms of expression vectors known by those skilled in the art which serve the equivalent functions can also be used, for example, self-replicating extrachromosomal vectors or vectors capable of integrating into a host genome. Exemplary vectors are those capable of autonomous replication and/or expression of nucleic acids to which they are linked.

The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins or RNA sequences. However, in some embodiments, the constituent amino acids of a spacer can be selected to influence some property of the molecule such as the folding, net charge, or hydrophobicity of the molecule. Suitable linkers for use in an embodiment of the present disclosure are well known to those of skill in the art and include, but are not limited to, straight or branched-chain carbon linkers, heterocyclic carbon linkers, or peptide linkers. The linker is used to separate two antigenic peptides by a distance sufficient to ensure that, in some embodiments, each antigenic peptide properly folds. Exemplary peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also can be used in the linker sequence. Still other amino acid sequences that can be used as linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180.

The term "neoplasia" refers to any disease that is caused by or results in inappropriately high levels of cell division, inappropriately low levels of apoptosis, or both. Glioblastoma is one non-limiting example of a neoplasia or cancer. The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. Cancers include, but are not limited to, B cell cancer (e.g., multiple myeloma, Waldenstrom's macroglobulinemia), the heavy chain diseases (such as, for example, alpha chain disease, gamma chain disease, and mu chain disease), benign monoclonal gammopathy, and immunocytic amyloidosis, melanomas, breast cancer, lung cancer, bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present disclosure include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers can be characterized in various other ways including, but not limited to, serous, endometrioid, mucinous, clear cell, brenner, or undifferentiated. In some embodiments, the present disclosure is used in the treatment, diagnosis, and/or prognosis of lymphoma or its subtypes, including, but not limited to, mantle cell lymphoma. Lymphoproliferative disorders are also considered to be proliferative diseases.

The term "vaccine" is to be understood as meaning a composition for generating immunity for the prophylaxis and/or treatment of diseases (e.g., neoplasia/tumor/infectious agents/autoimmune diseases). Accordingly, vaccines are medicaments which comprise antigens and are intended to be used in humans or animals for generating specific defense and protective substance by vaccination. A "vaccine composition" can include a pharmaceutically acceptable excipient, carrier or diluent. Aspects of the present disclosure relate to use of the technology in preparing an antigen-based vaccine. In these embodiments, vaccine is meant to refer one or more disease-specific antigenic peptides (or corresponding nucleic acids encoding them). In some embodiments, the antigen-based vaccine contains at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, or more antigenic peptides. In some embodiments, the antigen-based vaccine contains from 2 to 100, 2 to 75, 2 to 50, 2 to 25, 2 to 20, 2 to 19, 2 to 18, 2 to 17, 2 to 16, 2 to 15, 2 to 14, 2 to 13, 2 to 12, 2 to 10, 2 to 9, 2 to 8, 2 to 7, 2 to 6, 2 to 5, 2 to 4, 3 to 100, 3 to 75, 3 to 50, 3 to 25, 3 to 20, 3 to 19, 3 to 18, 3 to 17, 3 to 16, 3 to 15, 3 to 14, 3 to 13, 3 to 12, 3 to 10, 3 to 9, 3 to 8, 3 to 7, 3 to 6, 3 to 5, 4 to 100, 4 to 75, 4 to 50, 4 to 25, 4 to 20, 4 to 19, 4 to 18, 4 to 17, 4 to 16, 4 to 15, 4 to 14, 4 to 13, 4 to 12, 4 to 10, 4 to 9, 4 to 8, 4 to 7, 4 to 6, 5 to 100, 5 to 75, 5 to 50, 5 to 25, 5 to 20, 5 to 19, 5 to 18, 5 to 17, 5 to 16, 5 to 15, 5 to 14, 5 to 13, 5 to 12, 5 to 10, 5 to 9, 5 to 8, or 5 to 7 antigenic peptides. In some embodiments, the antigen-based vaccine contains 2, 3, 4, 5, 6, 7, 8, 9, 10, 11, 12, 13, 14, 15, 16, 17, 18, 19, or 20 antigenic peptides. In some cases, the antigenic peptides are neoantigenic peptides. In some cases, the antigenic peptides comprise one or more neoepitopes.

The term "pharmaceutically acceptable" refers to approved or approvable by a regulatory agency of the Federal or a state government or listed in the U.S. Pharmacopeia or other generally recognized pharmacopeia for use in animals, including humans. A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent. A "pharmaceutically acceptable salt" of pooled disease specific antigens as recited herein can be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluene sulfonic, methane sulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled disease specific antigens provided herein, including those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

Nucleic acid molecules useful in the methods of the disclosure include any nucleic acid molecule that encodes a polypeptide of the disclosure or a fragment thereof. Such nucleic acid molecules need not be 100% identical with an endogenous nucleic acid sequence, but will typically exhibit substantial identity. Polynucleotides having substantial identity to an endogenous sequence are typically capable of hybridizing with at least one strand of a double-stranded nucleic acid molecule. "Hybridize" refers to when nucleic acid molecules pair to form a double-stranded molecule between complementary polynucleotide sequences, or portions thereof, under various conditions of stringency. (See, e.g., Wahl, G. M. and S. L. Berger (1987) Methods Enzymol. 152:399; Kimmel, A. R. (1987) Methods Enzymol. 152: 507). For example, stringent salt concentration can ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions can ordinarily include temperatures of at least about 30° C., at least about 37° C., or at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In an exemplary embodiment, hybridization can occur at 30° C. in 750 mM NaCl, 75 mM trisodium citrate, and 1% SDS. In another exemplary embodiment, hybridization can occur at 37° C. in 500 mM NaCl, 50 mM trisodium citrate, 1% SDS, 35% formamide, and 100 μg/ml denatured salmon sperm DNA (ssDNA). In another exemplary embodiment, hybridization can occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, or less than about 15 mM NaCl and 1.5 mM trisodium citrate. Stringent temperature conditions for the wash steps can include a temperature of at least about 25° C., of at least about 42° C., or at least about 68° C. In exemplary embodiments, wash steps can occur at 25° C. in 30 mM NaCl, 3 mM trisodium citrate, and 0.1% SDS. In other exemplary embodiments, wash steps can occur at 42° C. in 15 mM NaCl, 1.5 mM trisodium citrate, and 0.1% SDS. In another exemplary embodiment, wash steps can occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Substantially identical" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence can be at least 60%, 80% or 85%, 90%, 95%, 96%, 97%, 98%, or even 99% or more identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program can be used, with a probability score between e-3 and e-m° indicating a closely related sequence. A "reference" is a standard of comparison.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The terms "treat," "treated," "treating," "treatment," and the like are meant to refer to reducing, preventing, or ameliorating a disorder and/or symptoms associated therewith (e.g., a neoplasia or tumor or infectious agent or an autoimmune disease). "Treating" can refer to administration of the therapy to a subject after the onset, or suspected onset, of a disease (e.g., cancer or infection by an infectious agent or an autoimmune disease). "Treating" includes the concepts of "alleviating", which refers to lessening the frequency of occurrence or recurrence, or the severity, of any symptoms or other ill effects related to the disease and/or the side effects associated with therapy. The term "treating" also encompasses the concept of "managing" which refers to reducing the severity of a disease or disorder in a patient, e.g., extending the life or prolonging the survivability of a patient with the disease, or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "prevent", "preventing", "prevention" and their grammatical equivalents as used herein, means avoiding or delaying the onset of symptoms associated with a disease or condition in a subject that has not developed such symptoms at the time the administering of an agent or compound commences.

The term "therapeutic effect" refers to some extent of relief of one or more of the symptoms of a disorder (e.g., a neoplasia, tumor, or infection by an infectious agent or an autoimmune disease) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian can start doses of the compounds of the present disclosure employed in a pharmaceutical composition at levels lower than that required in order to achieve the desired therapeutic effect and gradually increase the dosage until the desired effect is achieved. Disease, condition, and disorder are used interchangeably herein.

Those of ordinary skill in the art will recognize that the terms "peptide tag," "affinity tag," "epitope tag," or "affinity acceptor tag" are used interchangeably herein. As used herein, the term "affinity acceptor tag" refers to an amino acid sequence that permits the tagged protein to be readily detected or purified, for example, by affinity purification. An affinity acceptor tag is generally (but need not be) placed at or near the N- or C-terminus of an HLA allele. Various peptide tags are well known in the art. Non-limiting examples include poly-histidine tag (e.g., 4 to 15 consecutive His residues (SEQ ID NO: 4), such as 8 consecutive His residues (SEQ ID NO: 5)); poly-histidine-glycine tag; HA tag (e.g., Field et al., Mol. Cell. Biol., 8:2159, 1988); c-myc tag (e.g., Evans et al., Mol. Cell. Biol., 5:3610, 1985); Herpes simplex virus glycoprotein D (gD) tag (e.g., Paborsky et al., Protein Engineering, 3:547, 1990); FLAG tag (e.g., Hopp et al., BioTechnology, 6:1204, 1988; U.S. Pat. Nos. 4,703,004 and 4,851,341); KT3 epitope tag (e.g., Martine et al., Science, 255:192, 1992); tubulin epitope tag (e.g., Skinner, Biol. Chem., 266:15173, 1991); T7 gene 10 protein peptide tag (e.g., Lutz-Freyemuth et al., Proc. Natl. Acad. Sci. USA, 87:6393, 1990); streptavidin tag (StrepTag™ or StrepTagII™; see, e.g., Schmidt et al., J. Mol. Biol., 255(5):753-766, 1996 or U.S. Pat. No. 5,506, 121; also commercially available from Sigma-Genosys); or a VSV-G epitope tag derived from the Vesicular Stomatis viral glycoprotein; or a V5 tag derived from a small epitope (Pk) found on the P and V proteins of the paramyxovirus of simian virus 5 (SV5). In some embodiments, the affinity acceptor tag is an "epitope tag," which is a type of peptide tag that adds a recognizable epitope (antibody binding site) to the HLA-protein to provide binding of corresponding antibody, thereby allowing identification or affinity purification of the tagged protein. Non-limiting example of an epitope tag is protein A or protein G, which binds to IgG. In some embodiments, the matrix of IgG Sepharose 6 Fast Flow chromatography resin is covalently coupled to human IgG. This resin allows high flow rates, for rapid and convenient purification of a protein tagged with protein A. Numerous other tag moieties are known to, and can be envisioned by, the ordinarily skilled artisan, and are contemplated herein. Any peptide tag can be used as long as it is capable of being expressed as an element of an affinity acceptor tagged HLA-peptide complex.

As used herein, the term "affinity molecule" refers to a molecule or a ligand that binds with chemical specificity to an affinity acceptor peptide. Chemical specificity is the ability of a protein's binding site to bind specific ligands. The fewer ligands a protein can bind, the greater its specificity. Specificity describes the strength of binding between a given protein and ligand. This relationship can be described by a dissociation constant (KD), which characterizes the balance between bound and unbound states for the protein-ligand system.

The term "affinity acceptor tagged HLA-peptide complex" refers to a complex comprising an HLA class I or class II-associated peptide or a portion thereof specifically bound to a single allelic recombinant HLA class I or class II peptide comprising an affinity acceptor peptide.

The terms "specific binding" or "specifically binding" when used in reference to the interaction of an affinity molecule and an affinity acceptor tag or an epitope and an HLA peptide mean that the interaction is dependent upon the presence of a particular structure (e.g., the antigenic determinant or epitope) on the protein; in other words, the affinity molecule is recognizing and binding to a specific affinity acceptor peptide structure rather than to proteins in general.

As used herein, the term "affinity" refers to a measure of the strength of binding between two members of a binding pair, for example, an "affinity acceptor tag" and an "affinity molecule" and an HLA-binding peptide and an HLA class I or II molecule. KD is the dissociation constant and has units of molarity. The affinity constant is the inverse of the dissociation constant. An affinity constant is sometimes used as a generic term to describe this chemical entity. It is a direct measure of the energy of binding. Affinity can be determined experimentally, for example by surface plasmon resonance (SPR) using commercially available Biacore SPR units. Affinity can also be expressed as the inhibitory concentration 50 (IC50), that concentration at which 50% of the peptide is displaced. Likewise, ln IC50 refers to the natural log of the IC50. $K_{off}$ refers to the off-rate constant, for example, for dissociation of an affinity molecule from the affinity acceptor tagged HLA-peptide complex.

In some embodiments, an affinity acceptor tagged HLA-peptide complex comprises biotin acceptor peptide (BAP) and is immunopurified from complex cellular mixtures using streptavidin/NeutrAvidin beads. The biotin-avidin/streptavidin binding is the strongest non-covalent interaction known in nature. This property is exploited as a biological tool for a wide range of applications, such as immunopurification of a protein to which biotin is covalently attached. In an exemplary embodiment, the nucleic acid sequence encoding the HLA allele implements biotin acceptor peptide (BAP) as an affinity acceptor tag for immunopurification. BAP can be specifically biotinylated in vivo or in vitro at a single lysine residue within the tag (e.g., U.S. Pat. Nos. 5,723,584; 5,874,239; and 5,932,433; and U.K Pat. No. GB2370039). BAP is typically 15 amino acids long and contains a single lysine as a biotin acceptor residue. In some embodiments, BAP is placed at or near the N- or C-terminus of a single allele HLA peptide. In some embodiments, BAP is placed in between a heavy chain domain and β2 microglobulin domain of an HLA class I peptide. In some embodiments, BAP is placed in between β-chain domain and α-chain domain of an HLA class II peptide. In some embodiments, BAP is placed in loop regions between α1, α2, and α3 domains of the heavy chain of HLA class I, or between α1 and α2 and β1 and β2 domains of the α-chain and β-chain, respectively of HLA class II. Exemplary constructs designed for HLA class I and II expression implementing BAP for biotinylation and immunopurification are described in FIG. 2.

As used herein, the term "biotin" refers to the compound biotin itself and analogues, derivatives and variants thereof. Thus, the term "biotin" includes biotin (cis-hexahydro-2-oxo-1H-thieno [3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-E-aminocaproic acid-N-hydroxysuccinimide ester, sulfosuccinimideiminobiotin, biotinbromoacetylhydrazide, p-diazobenzoyl biocytin, 3-(N-maleimidopropionyObiocytin, desthiobiotin, and the like. The term "biotin" also comprises biotin variants that can specifically bind to one or more of a Rhizavidin, avidin, streptavidin, tamavidin moiety, or other avidin-like peptides.

As used herein, a "PPV determination method" can refer to a presentation PPV determination method. For example, a "PPV determination method" can refer to a method comprising (a) processing amino acid information of a plurality of test peptide sequences using an HLA peptide presentation prediction model, such as a machine learning HLA peptide presentation prediction model, to generate a plurality of test presentation predictions, each test presentation prediction indicative of a likelihood that one or more proteins encoded by a class II HLA allele of a cell, such as a class II HLA allele of a cell of a subject, can present a given test peptide sequence of the plurality of test peptide sequences, wherein the plurality of test peptide sequences comprises at least 500 test peptide sequences comprising (i) at least one hit peptide sequence identified by mass spectrometry to be presented by an HLA protein expressed in cells and (ii) at least 499 decoy peptide sequences contained within a protein encoded by a genome of an organism, such as an organism that is the same species as the subject, wherein the plurality of test peptide sequences comprises a ratio of less than one of the number of hit peptide sequences to the number of decoy peptide sequences, such as a ratio of 1:499 of the at least one hit peptide sequences to the at least 499 decoy peptide sequences; (b) identifying or calling a top percentage of the plurality of test peptide sequences, such as a top 0.2% of the plurality of test peptide sequences, as being presented by the class II HLA allele of a cell; and (c) calculating a PPV of the HLA peptide presentation prediction model, wherein the PPV is the fraction of the test peptide sequences of the plurality that were identified or called as being presented by the class II HLA allele of a cell that are peptides observed by mass spectrometry as being presented by the class II HLA allele of a cell. In some embodiments, a decoy peptide is of the same length, i.e., comprises the same number of amino acids as a hit peptide. In some embodiments, a decoy peptide may comprise one more or one less amino acid as compared to the hit peptide. In some embodiments the decoy peptide is a peptide that is an endogenous peptide. In some embodiments a decoy peptide is a synthetic peptide. In some embodiments the decoy peptide is an endogenous peptide that has been identified by mass spectrometry to bind to a first MHC class I or class II protein, wherein the first MHC class I or class II protein is distinct from a second MHC class I or class II protein that binds to a hit peptide. In some embodiments, the decoy peptide may be a scrambled peptide, e.g., the decoy peptide may comprise an amino acid sequence in which the amino acid positions are rearranged relative to that of the hit peptide within the length of the peptide. In some embodiments, the PPV determination method can be a presentation PPV determination method. In some embodiments, the ratio of the number of hit peptide sequences to the number of decoy peptide sequences is about 1:10, 1:20, 1:50, 1:100, 1:250, 1:500, 1:1000, 1:1500, 1:2000, 1:2500, 1:5000, 1:7500, 1:10000, 1:25000, 1:50000 or 1:100000. In some embodiments, the at least one hit peptide sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 hit peptide sequences. In some embodiments, the at least 499 decoy peptide sequences comprises at least 500 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 decoy peptide sequences. In some embodiments, the at least 500 test peptide sequences comprises at least 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 test peptide sequences. In some embodiments, identifying or calling a top percentage of the plurality of test peptide sequences as being presented by the class II HLA allele of a cell comprises identifying or calling a top 0.20%, 0.30%, 0.40%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90%, 5.00%, 5.10%, 5.20%, 5.30%, 5.40%, 5.50%, 5.60%, 5.70%, 5.80%, 5.90%, 6.00%, 6.10%, 6.20%, 6.30%, 6.40%, 6.50%, 6.60%, 6.70%, 6.80%, 6.90%, 7.00%, 7.10%, 7.20%, 7.30%, 7.40%, 7.50%, 7.60%, 7.70%, 7.80%, 7.90%, 8.00%, 8.10%, 8.20%, 8.30%, 8.40%, 8.50%, 8.60%, 8.70%, 8.80%, 8.90%, 9.00%, 9.10%, 9.20%, 9.30%, 9.40%, 9.50%, 9.60%, 9.70%, 9.80%, 9.90%, 10%, 11%, 12%, 13%, 14%, 15%, 16%, 17%, 18%, 19% or 20% as being presented by the class II HLA allele of a cell. In some embodiments, the cell is a mono-allelic cell.

As used herein, a "PPV determination method" can refer to a binding PPV determination method. For example, a "PPV determination method" can refer to a method comprising (a) processing amino acid information of a plurality of test peptide sequences using an HLA peptide binding prediction model, such as a machine learning HLA peptide binding prediction model, to generate a plurality of test binding predictions, each test binding prediction indicative of a likelihood that the one or more proteins encoded by a class II HLA allele of a cell, such as a class II HLA allele of a cell of a subject, binds to a given test peptide sequence of the plurality of test peptide sequences, wherein the plurality of test peptide sequences comprises at least 20 test peptide sequences comprising (i) at least one hit peptide sequence identified by mass spectrometry to be presented by an HLA protein expressed in cells and (ii) at least 19 decoy peptide sequences contained within a protein comprising at least one peptide sequence identified by mass spectrometry to be presented by an HLA protein expressed in cells, wherein the plurality of test peptide sequences comprises a ratio of less than one of the number of hit peptide sequences to the number of decoy peptide sequences, such as a ratio of 1:19 of the at least one hit peptide sequences to the at least 19 decoy peptide sequences; (b) identifying or calling a top percentage of the plurality of test peptide sequences, such as a top 5% of the plurality of test peptide sequences, as binding to the HLA protein; and (c) calculating a PPV of the HLA peptide binding prediction model, wherein the PPV is the fraction of the test peptide sequences of the plurality that were identified or called as binding to the class II HLA allele of a cell that are peptides observed by mass spectrometry as being presented by the class II HLA allele of a cell. In some embodiments, the ratio of the number of hit peptide sequences to the number of decoy peptide sequences is about 1:2, 1:3, 1:4, 1:5, 1:10, 1:20, 1:25, 1:30, 1:40, 1:50, 1:75, 1:100, 1:200, 1:250, 1:500 or 1:1000. In some embodiments, the at least one hit peptide sequence comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 hit peptide sequences. In some embodiments, the at least 19 decoy peptide sequences comprises at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 decoy peptide sequences. In some embodiments, the at least 20 test peptide sequences comprises at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 52500, 55000, 57500, 60000, 62500, 65000, 67500, 70000, 72500, 75000, 77500, 80000, 82500, 85000, 87500, 90000, 92500, 95000, 97500, 100000, 125000, 150000, 175000, 200000, 225000, 250000, 275000, 300000, 325000, 350000, 375000, 400000, 425000, 450000, 475000, 500000, 600000, 700000, 800000, 900000 or 1000000 test peptide sequences. In some embodiments, identifying or calling a top percentage of the plurality of test peptide sequences as being presented by the class II HLA allele of a cell comprises identifying or calling a top 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% as being presented by the class II HLA allele of a cell. In some embodiments, the cell is a mono-allelic cell.

Human Leukocyte Antigen (HLA) System

The immune system can be classified into two functional subsystems: the innate and the adaptive immune system. The innate immune system is the first line of defense against infections, and most potential pathogens are rapidly neutralized by this system before they can cause, for example, a noticeable infection. The adaptive immune system reacts to molecular structures, referred to as antigens, of the intruding organism. Unlike the innate immune system, the adaptive immune system is highly specific to a pathogen. Adaptive immunity can also provide long-lasting protection; for example, someone who recovers from measles is now protected against measles for their lifetime. There are two types of adaptive immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in T cells, of the body. Cytotoxic T cells recognize these antigens and kill the cells that harbor the antigens.

The term "major histocompatibility complex (MHC)", "MHC molecules", or "MHC proteins" refers to proteins capable of binding peptides resulting from the proteolytic cleavage of protein antigens and representing potential T cell epitopes, transporting them to the cell surface and presenting the peptides to specific cells, e.g., in cytotoxic T-lymphocytes or T-helper cells. The human MHC is also called the HLA complex. Thus, the term "human leukocyte antigen (HLA) system", "HLA molecules" or "HLA proteins" refers to a gene complex encoding the MHC proteins in humans. The term MHC is referred as the "H-2" complex in murine species. Those of ordinary skill in the art will recognize that the terms "major histocompatibility complex (MHC)", "MHC molecules", "MHC proteins" and "human leukocyte antigen (HLA) system", "HLA molecules", "HLA proteins" are used interchangeably herein.

HLA proteins are classified into two types, referred to as HLA class I and HLA class II. The structures of the proteins of the two HLA classes are very similar; however, they have very different functions. HLA class I proteins are present on the surface of almost all cells of the body, including most tumor cells. HLA class I proteins are loaded with antigens that usually originate from endogenous proteins or from pathogens present inside cells and are then presented to naïve or cytotoxic T-lymphocytes (CTLs). HLA class II proteins are present on antigen presenting cells (APCs), including but not limited to dendritic cells, B cells, and macrophages. They mainly present peptides, which are processed from external antigen sources, e.g. outside of the cells, to helper T cells. Most of the peptides bound by the HLA class I proteins originate from cytoplasmic proteins produced in the healthy host cells of an organism itself, and do not normally stimulate an immune reaction.

Figures 1A, 1B:
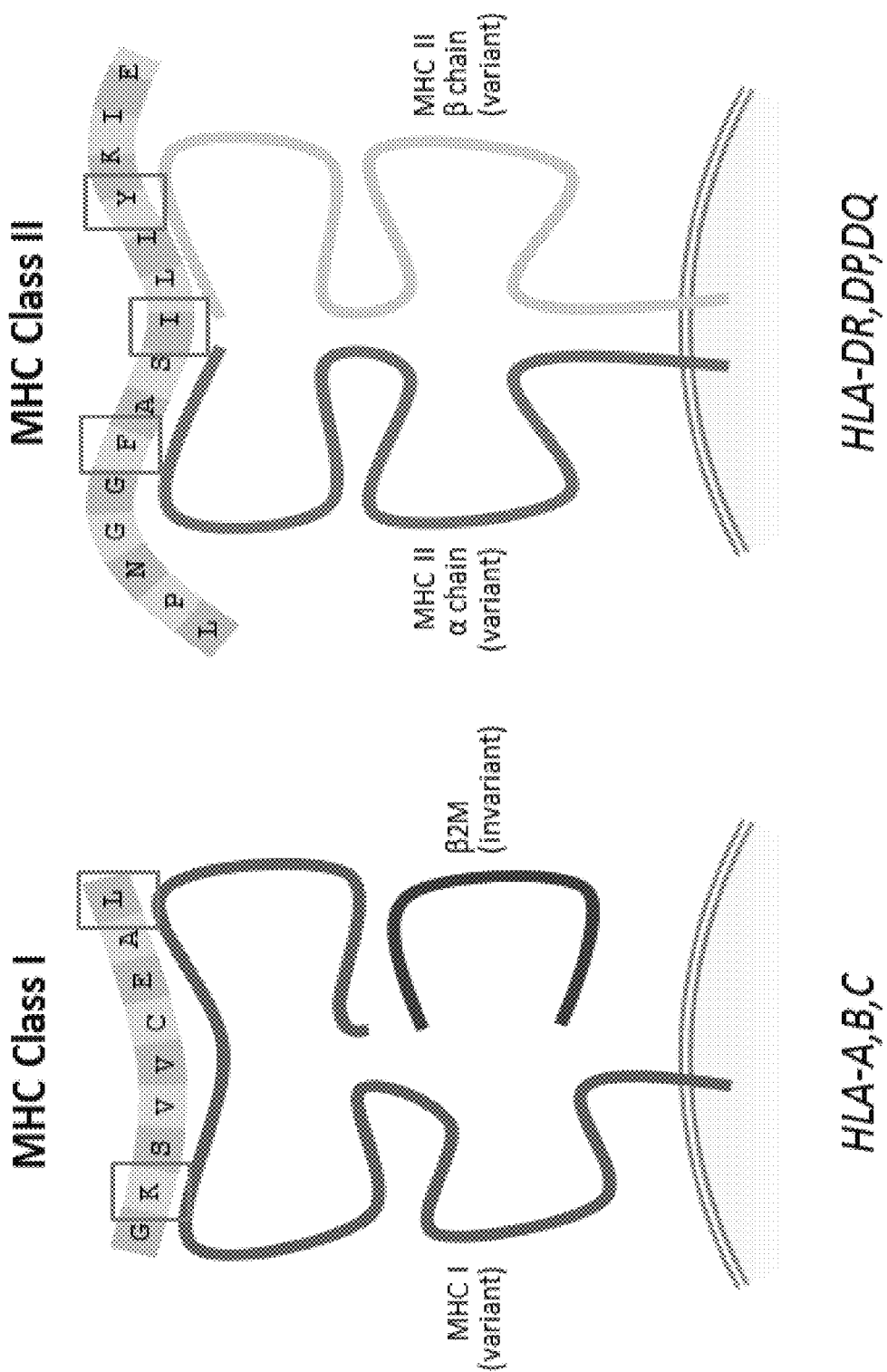
FIG. 1A diagram representing a peptide docked onto MHC Class I protein. Figure discloses SEQ ID NO: 36.
FIG. 1B depicts an exemplary diagram representing a peptide docked onto MHC Class II protein. Figure discloses SEQ ID NO: 37.

HLA class I molecules (FIG. 1) consist of two non-covalently linked polypeptide chains, an HLA-encoded a chain (heavy chain, 44 to 47 kD) and a non-HLA encoded subunit called (32 microglobulin (or, (β2m), (12 kD). The α chain has three extracellular domains, a 1, α2 and α3 and a transmembrane region, of which the α1 and α2 regions are capable of binding a peptide of about 7 to 13 amino acids (e.g., about 8 to 11 amino acids, or 9 or 10 amino acids). An HLA class 1 molecule binds to a peptide that has the suitable binding motifs, and presents it to cytotoxic T-lymphocytes. HLA class 1 heavy chains can be the protein product of an HLA-A allele, also termed as an HLA-A monomer, or the protein product of HLA-B allele (likewise, an HLA-B monomer) or the protein product of HLA-C allele (an HLA-C monomer), each of which complexes with a β-2-microglobulin. The α1 rests upon the non-HLA protein β2m; β2m is encoded by beta-2-microglobulin gene located on human chromosome 15. The α3 domain is connected to the transmembrane region, anchoring the HLA class I molecule to the cell membrane. The peptide being presented is held by the floor of the peptide-binding groove, in the central region of the α1/α2 heterodimer (a molecule composed of two non-identical subunits). HLA class I-A, HLA class I-B or HLA class I-C are highly polymorphic. Each of a HLA class 1-A gene (termed HLA-A gene), a HLA class 1-B gene (termed HLA-B gene) and a HLA class 1-C gene (termed HLA-C gene) contains 8 exons, exon 1 encodes the leader peptide, exons 2 and 3 encode the α1 and α2 domains, exon 5 encodes the transmembrane region and exons 6 and 7 encode the cytoplasmic tail. Polymorphisms of exon 2 and exon 3 are responsible for the peptide binding specificity of each class 1 molecule. HLA class I-B gene (HLA-B) has many possible variations, expression patterns and presented antigens. This group is subdivided into a group encoded within HLA loci, e.g., HLA-E, HLA-F, HLA-G, as well as those not, e.g., stress ligands such as ULBPs, Rae1 and H60. The antigen/ligand for many of these molecules remains unknown, but they can interact with each of CD8+ T cells, NKT cells, and NK cells.

In some embodiments, the present disclosure utilizes a non-classical HLA class I-E allele. HLA-E molecules are recognized by natural killer (NK) cells and CD8+ T cells. HLA-E is expressed in almost all tissues including lung, liver, skin and placental cells. HLA-E expression is also detected in solid tumors (e.g., osteosarcoma and melanoma). HLA-E molecule binds to TCR expressed on CD8+ T cells, resulting in T cell activation. HLA-E is also known to bind CD94/NKG2 receptor expressed on NK cells and CD8+ T cells. CD94 can pair with several different isoforms of NKG2 to form receptors with potential to either inhibit (NKG2A, NKG2B) or promote (NKG2C) cellular activation. HLA-E can bind to a peptide derived from amino acid residues 3-11 of the leader sequences of most HLA-A, -B, —C, and -G molecules, but cannot bind to its own leader peptide. HLA-E has also been shown to present peptides derived from endogenous proteins similar to HLA-A, -B, and -C alleles. Under physiological conditions, the engagement of CD94/NKG2A with HLA-E, loaded with peptides from the HLA class I leader sequences, usually induces inhibitory signals. Cytomegalovirus (CMV) utilizes the mechanism for escape from NK cell immune surveillance via expression of the UL40 glycoprotein, mimicking the HLA-A leader. However, it is also reported that CD8+ T cells can recognize HLA-E loaded with the UL40 peptide derived from CMV Toledo strain and play a role in defense against CMV. A number of studies revealed several important functions of HLA-E in infectious disease and cancer.

The peptide antigens attach themselves to the molecules of HLA class I by competitive affinity binding within the endoplasmic reticulum before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

MHC molecules are highly polymorphic, that is, there are many MHC variants. Each variant is encoded by a variation of the gene encoding the protein, and each such variant gene is called an allele. For human beings, MHC is known as Human Leukocyte Antigens (HLA), which involves three types of HLA class II molecules: DP, DQ and DR. HLA class II peptides (FIG. 1) have two chains, α and β, each having two domains—α1 and α2 and β1 and β2—each chain having a transmembrane domain, α2 and β2, respectively, anchoring the HLA class II molecule to the cell membrane. The peptide-binding groove is formed from the heterodimer of α1 and β1. The most widely studied HLA-DR molecules have DRA and DRB, corresponding to α and β domains, respectively. The DRB is diverse, DRA is almost identical. Thus, the binding specificity of a DRB allele indicates that of the corresponding HLA-DR. Each MHC protein has its own binding specificity, meaning that a set of peptides binding to an MHC molecule can be different from those to another MHC molecule. Classic molecules present peptides to CD4+ lymphocytes. Nonclassic molecules, accessories, with intracellular functions, are not exposed on cell membranes but in internal membranes in lysosomes, normally loading the antigenic peptides onto classic HLA class II molecules.

In HLA class II system, phagocytes such as macrophages and immature dendritic cells take up entities by phagocytosis into phagosomes—though B cells exhibit the more general endocytosis into endosomes—which fuse with lysosomes whose acidic enzymes cleave the uptaken protein into many different peptides. Autophagy is another source of HLA class II peptides. Via physicochemical dynamics in molecular interaction with the HLA class II variants borne by the host, encoded in the host's genome, a particular peptide exhibits immunodominance and loads onto HLA class II molecules. These are trafficked to and externalized on the cell surface. The most studied subclasses of HLA class II genes are: HLA-DPA1, HLA-DPB1, HLA-DQA1, HLA-DQB1, HLA-DRA, and HLA-DRB1.

Presentation of peptides by HLA class II molecules to CD4+ helper T cells is required for immune responses to foreign antigens (Roche and Furuta, 2015). Once activated, CD4+ T cells promote B cell differentiation and antibody production, as well as CD8+ T cell (CTL) responses. CD4+ T cells also secrete cytokines and chemokines that activate and induce differentiation of other immune cells. HLA class II molecules are heterodimers of α- and β-chains that interact to form a peptide-binding groove that is more open than HLA class I peptide-binding grooves (Unanue et al., 2016). Peptides bound to HLA class II molecules are believed to have a 9-amino acid binding core with flanking residues on either N- or C-terminal side that overhang from the groove (Jardetzky et al., 1996; Stern et al., 1994). These peptides are usually 12-16 amino acids in length and often contain 3-4 anchor residues at positions P1, P4, P6/7 and P9 of the binding register (Rossjohn et al., 2015).

HLA alleles are expressed in codominant fashion, meaning that the alleles (variants) inherited from both parents are expressed equally. For example, each person carries 2 alleles of each of the 3 class I genes, (HLA-A, HLA-B and HLA-C) and so can express six different types of HLA class II. In the HLA class II locus, each person inherits a pair of HLA-DP genes (DPA1 and DPB1, which encode α and β chains), HLA-DQ (DQA1 and DQB1, for α and β chains), one gene HLA-DRα (DRA1), and one or more genes HLA-DRβ (DRB1 and DRB3, -4 or -5). HLA-DRB1, for example, has more than nearly 400 known alleles. That means that one heterozygous individual can inherit six or eight functioning HLA class II alleles: three or more from each parent. Thus, the HLA genes are highly polymorphic; many different alleles exist in the different individuals inside a population. Genes encoding HLA proteins have many possible variations, allowing each person's immune system to react to a wide range of foreign invaders. Some HLA genes have hundreds of identified versions (alleles), each of which is given a particular number. In some embodiments, the HLA class I alleles are HLA-A*02:01, HLA-B*14:02, HLA-A*23:01, HLA-E*01:01 (non-classical). In some embodiments, HLA class II alleles are HLA-DRB*01:01, HLA-DRB*01:02, HLA-DRB*11:01, HLA-DRB*15:01, and HLA-DRB*07:01.

Subject specific HLA alleles or HLA genotype of a subject can be determined by any method known in the art. In exemplary embodiments, HLA genotypes are determined by any method described in International Patent Application number PCT/US2014/068746, published Jun. 11, 2015 as WO2015085147, which is incorporated herein by reference in its entirety. Briefly, the methods include determining polymorphic gene types that can comprise generating an alignment of reads extracted from a sequencing data set to a gene reference set comprising allele variants of the polymorphic gene, determining a first posterior probability or a posterior probability derived score for each allele variant in the alignment, identifying the allele variant with a maximum first posterior probability or posterior probability derived score as a first allele variant, identifying one or more overlapping reads that aligned with the first allele variant and one or more other allele variants, determining a second posterior probability or posterior probability derived score for the one or more other allele variants using a weighting factor, identifying a second allele variant by selecting the allele variant with a maximum second posterior probability or posterior probability derived score, the first and second allele variant defining the gene type for the polymorphic gene, and providing an output of the first and second allele variant.

In some embodiments the MHC class II peptide: antigenic peptide binding and presenting prediction methods described herein have the capacity to predict binders from a large repertoire MHC class II peptides encoded by individual HLA alleles. In some embodiments, the MAPTAC technology is trained with a large database of mass spectrometry validated HLA-matched peptides. In some embodiments, the large database of mass spectrometry validated HLA-matched peptides comprise greater than $1.2 \times 10^{\wedge}6$ such HLA-matched peptides. In some embodiments, the large database of mass spectrometry validated HLA-matched peptides cover greater than 150 HLA alleles including both MHC Class I and Class II allelic subtypes. In some embodiments, the database covers at least 95% of US population for HLA-I and HLA-II (DR subtype).

As described herein, there is a large body of evidence in both animals and humans that mutated epitopes are effective in inducing an immune response and that cases of spontaneous tumor regression or long term survival correlate with CD8+ T cell responses to mutated epitopes and that "immunoediting" can be tracked to alterations in expression of dominant mutated antigens in mice and man.

Sequencing technology has revealed that each tumor contains multiple, patient-specific mutations that alter the protein coding content of a gene. Such mutations create altered proteins, ranging from single amino acid changes (caused by missense mutations) to additions of long regions of novel amino acid sequences due to frame shifts, read-through of termination codons or translation of intron regions (novel open reading frame mutations; neoORFs). These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient. In essence, short peptides (8-24 amino acids long) containing a cancer associated mutation are candidates for cancer immunotherapy.

In some embodiments the algorithm driving the prediction method can be further utilized for mutation calling on a peptide. In some embodiments, the prediction method may be used for determining driver mutation status, and/or RNA expression status, and/or cleavage prediction within the peptide.

The term "T cell" includes CD4+ T cells and CD8+ T cells. The term T cell also includes both T helper 1 type T cells and T helper 2 type T cells. T cells as used herein are generally classified by function and cell surface antigens (cluster differentiation antigens, or CDs), which also facilitate T cell receptor binding to antigen, into two major classes: helper T (TH) cells and cytotoxic T-lymphocytes (CTLs).

Mature helper T (TH) cells express the surface protein CD4 and are referred as CD4+ T cells. Following T cell development, matured, naïve T cells leave the thymus and begin to spread throughout the body, including the lymph nodes. Naïve T cells are those T cells that have never been exposed to the antigen that they are programmed to respond to. Like all T cells, they express the T cell receptor-CD3 complex. The T cell receptor (TCR) consists of both constant and variable regions. The variable region determines what antigen the T cell can respond to. CD4+ T cells have TCRs with an affinity for MHC class II, proteins and CD4 are involved in determining MHC affinity during maturation in the thymus. MHC class II proteins are generally only found on the surface of specialized antigen-presenting cells (APCs). Specialized antigen presenting cells (APCs) are primarily dendritic cells, macrophages and B cells, although dendritic cells are the only cell group that expresses MHC Class II constitutively (at all times). Some APCs also bind native (or unprocessed) antigens to their surface, such as follicular dendritic cells, but unprocessed antigens do not interact with T cells and are not involved in their activation. The peptide antigens that bind to HLA class I proteins are typically shorter than peptide antigens that bind to HLA class II proteins.

Cytotoxic T-lymphocytes (CTLs), also known as cytotoxic T cells, cytolytic T cells, CD8+ T cells, or killer T cells, refer to lymphocytes which induce apoptosis in targeted cells. CTLs form antigen-specific conjugates with target cells via interaction of TCRs with processed antigen (Ag) on target cell surfaces, resulting in apoptosis of the targeted cell. Apoptotic bodies are eliminated by macrophages. The term "CTL response" is used to refer to the primary immune response mediated by CTL cells. Cytotoxic T-lymphocytes have both T cell receptors (TCR) and CD8 molecules on their surface. T cell receptors are capable of recognizing and binding peptides complexed with the molecules of HLA class I. Each cytotoxic T-lymphocyte expresses a unique T cell receptor which is capable of binding specific MHC/peptide complexes. Most cytotoxic T cells express T cell receptors (TCRs) that can recognize a specific antigen. In order for the TCR to bind to the HLA class I molecule, the former must be accompanied by a glycoprotein called CD8, which binds to the constant portion of the HLA class I molecule. Therefore, these T cells are called CD8+ T cells. The affinity between CD8 and the MHC molecule keeps the T cell and the target cell bound closely together during antigen-specific activation. CD8+ T cells are recognized as T cells once they become activated and are generally classified as having a pre-defined cytotoxic role within the immune system. However, CD8+ T cells also have the ability to make some cytokines.

"T cell receptors (TCR)" are cell surface receptors that participate in the activation of T cells in response to the presentation of antigen. The TCR is generally made from two chains, alpha and beta, which assemble to form a heterodimer and associates with the CD3-transducing subunits to form the T cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable regions of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

The term "HLA peptidome" refers to a pool of peptides which specifically interacts with a particular HLA class and can encompass thousands of different sequences. HLA peptidomes include a diversity of peptides, derived from both normal and abnormal proteins expressed in the cells. Thus, the HLA peptidomes can be studied to identify cancer specific peptides, for development of tumor immunotherapeutics and as a source of information about protein synthesis and degradation schemes within the cancer cells. In some embodiments, HLA peptidome is a pool of soluble HLA peptides (sHLA). In some embodiments, HLA peptidome is a pool of membrane associated HLA (mHLA).

"Antigen presenting cell" or "APC" includes professional antigen presenting cells (e.g., B lymphocytes, macrophages, monocytes, dendritic cells, Langerhans cells), as well as other antigen presenting cells (e.g., keratinocytes, endothelial cells, astrocytes, fibroblasts, oligodendrocytes, thymic epithelial cells, thyroid epithelial cells, glial cells (brain), pancreatic beta cells, and vascular endothelial cells). An "antigen presenting cell" or "APC" is a cell that expresses the Major Histocompatibility complex (MHC) molecules and can display foreign antigen complexed with MHC on its surface.

Mono-Allelic HLA Cell Lines

Figure 2:
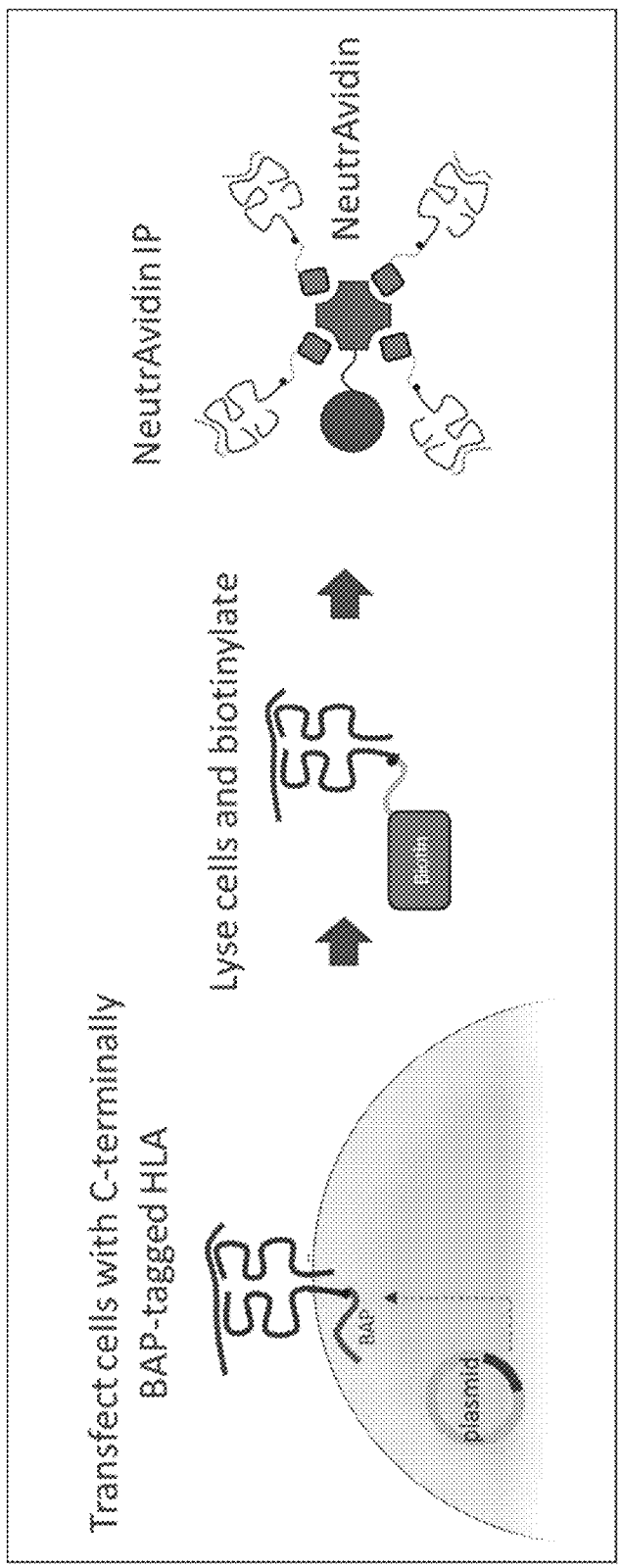
FIG. 2 depicts an exemplary experimental approach for generating mono-allelic HLA class II binding peptide data. HLA class II peptides are introduced into any cell, including a cell not expressing HLA class II so that specific HLA class II allele(s) are expressed in the cell. Populations of genetically engineered HLA expressing cells are harvested, lysed, and their HLA-peptide complexes are tagged (e.g., biotinylated) and immunopurified (e.g., using the biotin-streptavidin interaction). HLA-associated peptides specific to a single HLA can be eluted from their tagged (e.g., biotinylated) complexes and evaluated (e.g., sequenced using high resolution LC-MS/MS).

A mono-allelic cell line expressing either a single HLA class I allele, a single pair of HLA class II alleles, or a single HLA class I allele and a single pair of HLA class II alleles can be generated by transducing or transfecting a suitable cell population with a polynucleic acid, e.g., a vector, coding a single HLA allele (FIG. 2). Suitable cell populations include, e.g., HLA class I deficient cells lines in which a single HLA class I allele is exogenously expressed, HLA class II deficient cell lines in which a single exogenous pair of HLA class II alleles are expressed, or class I and class II deficient cell lines in which a single HLA class I and/or single pair of class II alleles are exogenously expressed. As an exemplary embodiment, the HLA class I deficient B cell line is B721.221. However, it is clear to a skilled person that other cell populations can be generated which are HLA class I and/or HLA class II deficient. An exemplary method for deleting/inactivating endogenous HLA class I or HLA class II genes includes CRISPR-Cas9 mediated genome editing in, for example, THP-1 cells. In some embodiments, the populations of cells are professional antigen presenting cells, such as macrophages, B cells, and dendritic cells. The cells can be B cells or dendritic cells. In some embodiments, the cells are tumor cells or cells from a tumor cell line. In some embodiments, the cells are isolated from a patient. In some embodiments, the cells contain an infectious agent or a portion thereof. In some embodiments, the population of cells comprises at least 107 cells. In some embodiments, the population of cells are further modified, such as by increasing or decreasing the expression and/or activity of at least one gene. In some embodiments, the gene encodes a member of the immunoproteasome. The immunoproteasome is known to be involved in the processing of HLA class I binding peptides and includes the LMP2 (β1i), MECL-1 (β2i), and LMP7 (β5i) subunits. The immunoproteasome can also be induced by interferon-gamma. Accordingly, in some embodiments, the population of cells can be contacted with one or more cytokines, growth factors, or other proteins. The cells can be stimulated with inflammatory cytokines such as interferon-gamma, IL-10, IL-6, and/or TNF-α. The population of cells can also be subjected to various environmental conditions, such as stress (heat stress, oxygen deprivation, glucose starvation, DNA damaging agents, etc.). In some embodiments, the cells are contacted with one or more of a chemotherapy drug, radiation, targeted therapies, or immunotherapy. The methods disclosed herein can therefore be used to study the effect of various genes or conditions on HLA peptide processing and presentation. In some embodiments, the conditions used are selected so as to match the condition of the patient for which the population of HLA-peptides is to be identified.

A single HLA-allele of the present disclosure can be encoded and expressed using a viral based system (e.g., an adenovirus system, an adeno associated virus (AAV) vector, a poxvirus, or a lentivirus). Plasmids that can be used for adeno associated virus, adenovirus, and lentivirus delivery have been described previously (see e.g., U.S. Pat. Nos. 6,955,808 and 6,943,019, and U.S. Patent application No. 20080254008, hereby incorporated by reference). Among vectors that can be used in the practice of the present disclosure, integration in the host genome of a cell is possible with retrovirus gene transfer methods, often resulting in long term expression of the inserted transgene. In an exemplary embodiment, the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors can be used in the practice of the present disclosure). Moreover, lentiviral vectors are able to transduce or infect non-dividing cells and typically produce high viral titers.

Selection of a retroviral gene transfer system can depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that can be used in the practice of the present disclosure include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700). Also, useful in the practice of the present disclosure is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience DOI: 10.1002/jgm.845). The vectors can have cytomegalovirus (CMV) promoter driving expression of the target gene. Accordingly, the present disclosure contemplates amongst vector(s) useful in the practice of the present disclosure: viral vectors, including retroviral vectors and lentiviral vectors.

Any HLA allele can be expressed in the cell population. In an exemplary embodiment, the HLA allele is an HLA class I allele. In some embodiments, the HLA class I allele is an HLA-A allele or an HLA-B allele. In some embodiments, the HLA allele is an HLA class II allele. Sequences of HLA class I and class II alleles can be found in the IPD-IMGT/HLA Database. Exemplary HLA alleles include, but are not limited to, HLA-A*02:01, HLA-B*14:02, HLA-A*23:01, HLA-E*01:01, HLA-DRB*01:01, HLA-DRB*01:02, HLA-DRB*11:01, HLA-DRB*15:01, and HLA-DRB*07:01.

In some embodiments, the HLA allele is selected so as to correspond to a genotype of interest. In some embodiments, the HLA allele is a mutated HLA allele, which can be non-naturally occurring allele or a naturally occurring allele in an afflicted patient. The methods disclosed herein have the further advantage of identifying HLA binding peptides for HLA alleles associated with various disorders as well as alleles which are present at low frequency. Accordingly, in some embodiments, the method provided herein can identify the HLA allele even if it is present at a frequency of less than 1% within a population, such as within the Caucasian population.

In some embodiments, the nucleic acid sequence encoding the HLA allele further comprises an affinity acceptor tag which can be used to immunopurify the HLA-protein. Suitable tags are well-known in the art. In some embodiments, an affinity acceptor tag is poly-histidine tag, poly-histidine-glycine tag, poly-arginine tag, poly-aspartate tag, poly-cysteine tag, poly-phenylalanine, c-myc tag, Herpes simplex virus glycoprotein D (gD) tag, FLAG tag, KT3 epitope tag, tubulin epitope tag, T7 gene 10 protein peptide tag, streptavidin tag, streptavidin binding peptide (SPB) tag, Strep-tag, Strep-tag II, albumin-binding protein (ABP) tag, alkaline phosphatase (AP) tag, bluetongue virus tag (B-tag), calmodulin binding peptide (CBP) tag, chloramphenicol acetyl transferase (CAT) tag, choline-binding domain (CBD) tag, chitin binding domain (CBD) tag, cellulose binding domain (CBP) tag, dihydrofolate reductase (DHFR) tag, galactose-binding protein (GBP) tag, maltose binding protein (MBP), glutathione-S-transferase (GST), Glu-Glu (EE) tag, human influenza hemagglutinin (HA) tag, horseradish peroxidase (HRP) tag, NE-tag, HSV tag, ketosteroid isomerase (KSI) tag, KT3 tag, LacZ tag, luciferase tag, NusA tag, PDZ domain tag, AviTag, Calmodulin-tag, E-tag, S-tag, SBP-tag, Softag 1, Softag 3, TC tag, VSV-tag, Xpress tag, Isopeptag, SpyTag, SnoopTag, Profinity eXact tag, Protein C tag, S1-tag, S-tag, biotin-carboxy carrier protein (BCCP) tag, green fluorescent protein (GFP) tag, small ubiquitin-like modifier (SUMO) tag, tandem affinity purification (TAP) tag, HaloTag, Nus-tag, Thioredoxin-tag, Fc-tag, CYD tag, HPC tag, TrpE tag, ubiquitin tag, a VSV-G epitope tag derived from the Vescular Stomatis viral glycoprotein, or a V5 tag derived from a small epitope (Pk) found on the P and V proteins of the paramyxovirus of simian virus 5 (SV5). In some embodiments, the affinity acceptor tag is an "epitope tag," which is a type of peptide tag that adds a recognizable epitope (antibody binding site) to the HLA-protein to provide binding of corresponding antibody, thereby allowing identification or affinity purification of the tagged protein. Non-limiting example of an epitope tag is protein A or protein G, which binds to IgG. In some embodiments, affinity acceptor tags include the biotin acceptor peptide (BAP) or Human influenza hemagglutinin (HA) peptide sequence. Numerous other tag moieties are known to, and can be envisioned by, the ordinarily skilled artisan, and are contemplated herein. Any peptide tag can be used as long as it is capable of being expressed as an element of an affinity acceptor tagged HLA-peptide complex.

Figure 3:
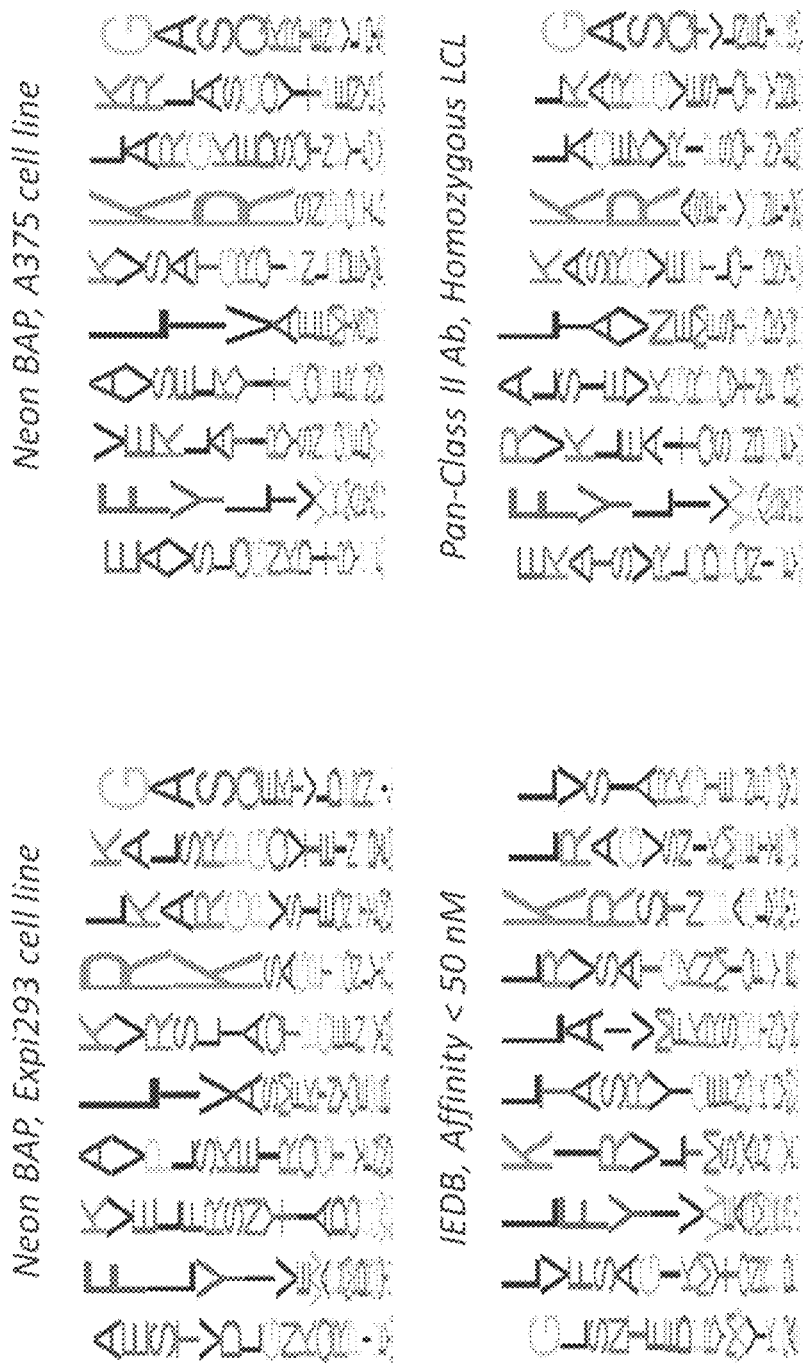
FIG. 3 depicts an exemplary sequence logo representation of HLA class II-DRB1*11:01-associated peptides across Neon BAP, Expi293 cell line; Neon BAP, A375 cell line; IEDB, Affinity <50 nM; and Pan-HLA Class II Ab, Homozygous LCL.

The methods provided herein comprise isolating HLA-peptide complexes from the cells transfected or transduced with affinity pulldown of HLA constructs (FIG. 3). In some embodiments, the complexes can be isolated using standard immunoprecipitation techniques known in the art with commercially available antibodies. The cells can be first lysed. HLA class I-peptide complexes can be isolated using HLA class I specific antibodies such as the W6/32 antibody, while HLA class II-peptide complexes can be isolated using HLA class II specific antibodies such as the M5/114.15.2 monoclonal antibody. In some embodiments, the single (or pair of) HLA alleles are expressed as a fusion protein with a peptide tag and the HLA-peptide complexes are isolated using binding molecules that recognize the peptide tags.

The methods further comprise isolating peptides from said HLA-peptide complexes and sequencing the peptides. The peptides are isolated from the complex by any method known to one of skill in the art, such as acid elution. While any sequencing method can be used, methods employing mass spectrometry, such as liquid chromatography—mass spectrometry (LC-MS or LC-MS/MS, or alternatively HPLC-MS or HPLC-MS/MS) are utilized in some embodiments. These sequencing methods are well-known to a skilled person and are reviewed in Medzihradszky K F and Chalkley R J. Mass Spectrom Rev. 2015 January-February; 34(1):43-63.

In some embodiments, the population of cells expresses one or more endogenous HLA alleles. In some embodiments, the population of cells is an engineered population of cells lacking one or more endogenous HLA class I alleles. In some embodiments, the population of cells is an engineered population of cells lacking endogenous HLA class I alleles. In some embodiments, the population of cells is an engineered population of cells lacking one or more endogenous HLA class II alleles. In some embodiments, the population of cells is an engineered population of cells lacking endogenous HLA class II alleles or an engineered population of cells lacking endogenous HLA class I alleles and endogenous HLA class II alleles. In some embodiments, the population of cells comprises cells that have been enriched or sorted, such as by fluorescence activated cell sorting (FACS). In some embodiments, fluorescence activated cell sorting (FACS) is used to sort the population of cells. In some embodiments, the population of cells is previously FACS sorted for cell surface expression of either HLA class I or class II or both HLA class I and class II. For example, FACS can be used to sort the population of cells for cell surface expression of an HLA class I allele, an HLA class II allele, or a combination thereof Methods for Preparing a Personalized Cancer Vaccine Once a mutation specific for a cancer is identified, such that the mutation exists in the DNA in cancer cells but not in the normal cells of the same human subject, and the mutation leads to a change in one or more amino acids in the protein encoded by the DNA, the mutation can be a target for the host immune response. A natural immune response can be directed against the mutated protein leading to the destruction of cancer cells expressing the protein. Because of the natural tolerance response and immunocompromised environment in the cancerous tissue, immunotherapy is a clinical path that attempts augmenting such immune response to override the body's tolerance and immunosuppressive effects. A protein or a peptide comprising the mutation as described above is therefore a suitable candidate for immunotherapy.

A mutated protein is ingested by professional phagocytes acting as antigen presenting cells (APCs), chopped and displayed as antigens on the cell surface for T cell activation in an antigen presentation complex comprising a Major Histocompatibility Complex (MHC) protein. Human MHC proteins are called Human Leukocytic antigens, HLAs. The MHC protein can be a MHC-class I or a class II protein, and while several functional distinctions are attributed to the presentation of peptides by either class I or class II MHC proteins (HLA class I and HLA class II proteins), one salient distinction lies in the fact that HLA class I-peptide complexes present antigens to cytotoxic CD8+ T cells, whereas the HLA class II peptide complexes are also capable of activating CD4+ T cell leading to prolonged immune response. CD8+ T cells are indispensable in the task of cell-by-cell elimination of a diseased cell, such as an infected cell or a tumor cell. CD4+ T cells have a more sustained effects upon activation, the most important of those being generation of immunological memory. CD4 subsets are differentially recruited according to the type of immunologic threat, and multiple subsets with overlapping or disparate functions may be co-recruited. This helps in balancing the immunological response with respect to the pathogenic threat. In these respects, HLA class II peptide mediated antigen presentation effects a sustained and tailored immune response. On the other hand, HLA class II binding to peptides may be promiscuous and therefore non-specific peptide binding and presentation to the immune system leads to aberrant immune response, such as autoimmunity.

In one aspect, the present disclosure provides method for predicting peptides that can accurately pair with, or bind to, a specific HLA class II alpha and beta chain heterodimer, such that the high fidelity binding of the peptide to HLA class II protein (comprising the alpha and beta chain heterodimer) ensures presentation of the specific peptide to the T lymphocytes, thereby eliciting a specific immune response and avoid any cross-reactivity or immune promiscuity.

In one aspect, the present disclosure provides method for predicting peptides that can accurately bind to a specific HLA class II protein, such that a more sustained and robust immune response can be activated with the peptide, when the peptide is administered therapeutically to a subject expressing the specific cognate HLA class II protein, by dint of the ability of HLA class II protein's activation of CD4+ T cells and stimulate immunological memory. In some embodiments, the given peptide that is predicted to bind to a HLA class II protein with high specificity is a peptide comprising a mutation, wherein the mutation is prevalent in a cancer or a tumor cell of a subject; whereas the same HLA class II protein predicted to bind the mutated peptide either (a) does not bind, or (b) binds with distinctly lower affinity to the corresponding non-mutated wild type peptide compared to the affinity for binding to the mutated peptide of the subject. The preferential binding of the HLA to the mutated peptide is advantageous in the development of an immunotherapeutic, since the cells expressing the wild type peptide will be spared from the immune attack by the T cells reactive to the HLA-presented peptide. In some embodiments, predicted peptides that bind specifically to the HLA class II proteins are peptides that have post-translation modifications. Exemplary post-translational modifications include but are not limited to: phosphorylation, ubiquitylation, dephosphorylation, glycosylation, methylation, or, acetylation. In some embodiments, the predicted peptides are subjected to post-translational modifications prior for use in immunotherapy.

In some embodiments, the immunotherapy methods and strategies disclosed herein could also be applicable in suppressing unwanted immune activation, such as, in an autoimmune reaction. Specifically, peptides identified as potential binders for specific HLA subtypes could be tailored to bind to the specific HLA molecule and induces tolerance rather than cause immunogenic response.

In one aspect, presented herein are methods of immunotherapy tailored or personalized for a specific subject. Every subject or patient expresses a specific array of HLA class I and HLA class II proteins. HLA typing is a well-known technique that allows determination of the specific repertoire of HLA proteins expressed by the subject. Once the HLA heterodimers expressed by a specific subject is known, having an improved, sophisticated and reliable method as described herein for predicting peptides that can bind to a specific HLA class II alpha and beta chain heterodimer, with high fidelity can ensure that a specific immune response can be generated tailored specifically for the subject.

The genes coding for HLA heterodimers are highly polymorphic, with more 4,000 HLA class II allele variants identified across the human population. From maternal and paternal HLA haplotypes, an individual can inherit different alleles for each of the HLA class II loci, and each HLA class II heterodimer is made of an $\alpha$- and $\beta$-chain. Because of the large number of α- and β-chain pairing combinations, especially for HLA-DP and HLA-DQ alleles, the population of possible HLA heterodimers is highly complex. HLA class II heterodimers are translated in the endoplasmic reticulum (ER) and assembled into a stable complex with the invariant chain (Ii) derived from the protein CD74. The Ii stabilizes the class II complex by allowing proper protein folding and enables the export of HLA class II heterodimers into endosomal/lysosomal compartments. Inside these HLA class II loading compartments, the Ii is proteolytically cleaved by cathepsins into a placeholder peptide called CLIP. CLIP is then exchanged for higher-affinity peptides in a low pH environment by the chaperone HLA-DM, a non-classical HLA class II heterodimer. High affinity peptide-loaded HLA class II complexes are then to the trans-Golgi and finally to the cell surface for display for CD4+ T cells.

Each HLA heterodimer is estimated to bind thousands of peptides with allele-specific binding preferences. In fact, each HLA allele is estimated to bind and present 1,000-10,000 unique peptides to T cells. Given such diversity in HLA binding, accurate prediction of whether a peptide is likely to bind to a specific HLA allele is highly challenging. Less is known about allele-specific peptide-binding characteristics of HLA class II molecules because of the heterogeneity of α- and β-chain pairing, complexity of data limiting the ability to confidently assign core binding epitopes, and the lack of immunoprecipation grade, allele-specific antibodies required for high-resolution biochemical analyses. Furthermore, analyzing peptide epitopes derived from a given HLA allele raises ambiguity when multiple HLA alleles are presented on a cell surface.

Predictions for candidate neoantigens are predominantly made for HLA class I epitopes (given the availability of experimental data for class I prediction algorithms compared to class II), yet CD4+ T cell responses are often observed in both pre-clinical and clinical personalized neoantigen vaccination studies. These observations demonstrate that HLA class II epitope processing and presentation may also play a critical role in cancer treatment. Although HLA class II prediction algorithms exist, they are inaccurate because the open-ended peptide-binding groove on HLA class II heterodimers allows for longer peptides (generally 15-40 amino acids) to bind, which increases the heterogeneity and complexity of epitope presentation. Further work to better understand the characteristics of HLA class II peptide-binding cores and the cellular processes involved in class II epitope processing and presentation is therefore required. The proteomics field is currently limited by the complexity of HLA class II heterodimer formation and the availability of immunoprecipation grade antibodies for HLA class II-peptide complex isolation. To overcome these challenges, a monoallelic HLA profiling workflow was developed that relies on LC-MS/MS for the characterization of allele-specific HLA class II-ligandomes to class II epitope prediction methods. The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, exemplary materials and methods are described herein. Accordingly, the terminology used herein is for the purpose of describing particular embodiments only, and is not intended to be limiting.

Disclosed herein are methods to preparing a personalized cancer vaccine. The method for preparing a personalized cancer vaccine may comprise identifying peptide sequences with a mutation expressed in cancer cells of a subject; inputting amino acid position information of the peptide sequences identified, using a computer processor, into a machine-learning HLA-peptide presentation prediction model to generate a set of presentation predictions for the peptide sequences identified, each presentation prediction representing a probability that one or more proteins encoded by a class II MHC allele of a cancer cell of the subject will present a given sequence of a peptide sequence identified; and selecting a subset of the peptide sequences identified based on the set of presentation predictions for preparing the personalized cancer vaccine.

In some embodiments, one or more results obtained from a method described herein may provide a quantitative value or values indicative of one or more of the following: a likelihood of diagnostic accuracy, a likelihood of a presence of a condition in a subject, a likelihood of a subject developing a condition, a likelihood of success of a particular treatment, or any combination thereof. In some embodiments, a method as described herein may predict a risk or likelihood of developing a condition. In some embodiments, a method as described herein may be an early diagnostic indicator of developing a condition. In some embodiments, a method as described herein may confirm a diagnosis or a presence of a condition. In some embodiments, a method as described herein may monitor the progression of a condition. In some embodiments, a method as described herein may monitor the efficacy of a treatment for a condition in a subject.

Method for Identification of MHC-II Peptides

In one aspect, presented herein is a method of identifying one or more peptides that are presented by MHC-II proteins for immune activation. In some embodiments, the one r more peptides comprise an epitope. In some embodiments, the method involves computational prediction of the likelihood that specific epitopes are presented by an MHC-II protein. In some embodiments, the method involves computational prediction of the specificity of an epitope for MHC-II presentation. In some embodiments, the computational prediction methods involve an assessment of peptide-MHC interactions. In some embodiments, the computational prediction methods involve an prediction of the allelic specificity of a peptide for antigen presentation.

In some embodiments, the computational prediction methods involve integration of bioinformatics information, for example, nucleotide sequences, structural motifs of biomolecules, protein-protein interaction features and functional potency such as immunogenicity. In some embodiments, the computational prediction methods involve machine learning. Many immunoinformatics methods for prediction of peptide-MHC interactions have been developed for both MHC class I and II, based on machine learning approaches such as simple pattern motif, support vector machine (SVM), hidden Markov model (HMM), neural network (NN) models, quantitative structure-activity relationship (QSAR) analysis, structure-based methods, and biophysical methods. These methods can be divided into two categories, namely, intra-allele (allele-specific) and trans-allele (pan-specific) methods. Intra-allelic methods are trained for a specific MHC molecule on a limited set of experimental peptide-binding data and applied for prediction of peptides binding to that molecule. Because of the extreme polymorphism of MHC molecules, the existence of thousands of allele variants, combined with the lack of sufficient experimental binding data, it is impossible to build a prediction model for each allele. Thus, trans-allele and general purpose methods such as NetMHCIIpan (Karosiene E et al., NetMHCIIpan-3.0, a common pan-specific MHC class II prediction method including all three human MHC class II isotypes, HLA-DR, HLA-DP and HLADQ. Immunogenetics (2013) 65(10):711-24), and TEPITOPEpan (Zhang L, et al., TEPITOPEpan: extending TEPITOPE for peptide binding prediction covering over 700 HLA-DR molecules. PLoS One (2012) 7(2):e30483) have been developed using peptide-binding data expanding over many alleles or across species. Similar methods for MHC-I are also available such as NetMHCpan and KISS.

In some embodiments, the peptide sequences may not be expressed in normal cells of the subject. In some embodiments, each and every cell of the subject may not be cancer cells. The cancer cells may be produced through different cancers, including, but not limited to, thyroid cancer, adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer, or Waldenstrom's macroglobulinemia.

The identifying may comprise comparing DNA, RNA or protein sequences from the cancer cells of the subject to DNA, RNA or protein sequences from the normal cells of the subject. The DNA, RNA or protein sequences from the cancer cells of the subject may be different from the DNA, RNA or protein sequences from the normal cells of the subject. The identifying may identify nucleic acid variants with high sensitivity.

The machine-learning HLA-peptide presentation prediction model may comprise a plurality of predictor variables identified at least based on training data. The training data may comprises sequence information of sequences of peptides presented by an HLA protein expressed in cells and identified by mass spectrometry; training peptide sequence information comprising amino acid position information, wherein the training peptide sequence information is associated with the HLA protein expressed in cells; and a function representing a relation between the amino acid position information received as input and the presentation likelihood generated as output based on the amino acid position information and the predictor variables.

In some embodiments, the training data may further comprise structured data, time-series data, unstructured data, and relational data. Unstructured data may comprise audio data, image data, video, mechanical data, electrical data, chemical data, and any combination thereof, for use in accurately simulating or training robotics or simulations. Time-series data may comprise data from one or more of a smart meter, a smart appliance, a smart device, a monitoring system, a telemetry device, or a sensor. Relational data comprises data from a customer system, an enterprise system, an operational system, a website, web accessible application program interface (API), or any combination thereof. This may be done by a user through any method of inputting files or other data formats into software or systems.

In some embodiments, the training data may be stored in a database. A database can be stored in computer readable format. A computer processor may be configured to access the data stored in the computer readable memory. In some embodiments, the computer system may be used to analyze the data to obtain a result. The result may be stored remotely or internally on storage medium, and communicated to personnel such as medication professionals. In some embodiments, the computer system may be operatively coupled with components for transmitting the result. Components for transmitting can include wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples or wireless communication components can include a Wi-Fi receiver, a component for accessing a mobile data standard such as a 3G or 4G LTE data signal, or a Bluetooth receiver. In some embodiments, all these data in the storage medium is collected and archived to build a data warehouse.

In some embodiments, the database comprises an external database. The external database may be a medical database, for example, but not limited to, Adverse Drug Effects Database, AHFS Supplemental File, Allergen Picklist File, Average WAC Pricing File, Brand Probability File, Canadian Drug File v2, Comprehensive Price History, Controlled Substances File, Drug Allergy Cross-Reference File, Drug Application File, Drug Dosing & Administration Database, Drug Image Database v2.0/Drug Imprint Database v2.0, Drug Inactive Date File, Drug Indications Database, Drug Lab Conflict Database, Drug Therapy Monitoring System (DTMS) v2.2/DTMS Consumer Monographs, Duplicate Therapy Database, Federal Government Pricing File, Healthcare Common Procedure Coding System Codes (HCPCS) Database, ICD-10 Mapping Files, Immunization Cross-Reference File, Integrated A to Z Drug Facts Module, Integrated Patient Education, Master Parameters Database, Medi-Span Electronic Drug File (MED-File) v2, Medicaid Rebate File, Medicare Plans File, Medical Condition Picklist File, Medical Conditions Master Database, Medication Order Management Database (MOMD), Parameters to Monitor Database, Patient Safety Programs File, Payment Allowance Limit-Part B (PAL-B) v2.0, Precautions Database, RxNorm Cross-Reference File, Standard Drug Identifiers Database, Substitution Groups File, Supplemental Names File, Uniform System of Classification Cross-Reference File, or Warning Label Database.

In some embodiments, the training data may also be obtained through other data sources. The data sources may include sensors or smart devices, such as appliances, smart meters, wearables, monitoring systems, data stores, customer systems, billing systems, financial systems, crowd source data, weather data, social networks, or any other sensor, enterprise system or data store. Example of smart meters or sensors may include meters or sensors located at a customer site, or meters or sensors located between customers and a generation or source location. By incorporating data from a broad array of sources, the system may be capable of performing complex and detailed analyses. In some embodiments, the data sources may include sensors or databases for other medical platforms without limitation.

HLA-typing is conventionally carried out by either serological methods using antibodies or by PCR-based methods such as Sequence Specific Oligonucleotide Probe Hybridization (SSOP), or Sequence Based Typing (SBT). While the first is hampered by the potentially high degree of cross reactivity and limited resolution capabilities, the second suffers from difficulties associated with the efficiency of the PCR due to very limited possibilities for positioning primers because of polymorphic positions.

In some embodiments, the sequence information is identified by either sequencing methods or methods employing mass spectrometry, such as liquid chromatography—mass spectrometry (LC-MS or LC-MS/MS, or alternatively HPLC-MS or HPLC-MS/MS). These sequencing methods may be well-known to a skilled person and are reviewed in Medzihradszky K F and Chalkley R J. Mass Spectrom Rev. 2015 January-February; 34(1):43-63. In some embodiments, the mass spectrometry is mono-allelic mass spectrometry. In some embodiments, the mass spectrometry may be MS analysis, MS/MS analysis, LC-MS/MS analysis, or a combination thereof. In some embodiments, MS analysis may be used to determine a mass of an intact peptide. For example, the determining can comprise determining a mass of an intact peptide (e.g., MS analysis). In some embodiments, MS/MS analysis may be used to determine a mass of peptide fragments. For example, the determining can comprise determining a mass of peptide fragments, which can be used to determine an amino acid sequence of a peptide or portion thereof (e.g., MS/MS analysis). In some embodiments, the mass of peptide fragments may be used to determine a sequence of amino acids within the peptide. In some embodiments, LC-MS/MS analysis may be used to separate complex peptide mixtures. For example, the determining can comprise separating complex peptide mixtures, such as by liquid chromatography, and determining a mass of an intact peptide, a mass of peptide fragments, or a combination thereof (e.g., LC-MS/MS analysis). This data can be used, e.g., for peptide sequencing.

In some embodiments, the training peptide sequence information comprises amino acid position information of training peptides. In some embodiments, the training peptide sequence information comprises at most about 90%, 80%, 70%, 60%, 50%, 40%, 30%, 20%, 10% or less sequence information of sequences of peptides presented by an HLA protein expressed in cells and identified by mass spectrometry. In some embodiments, the training peptide sequence information may comprise at least about 10%, 20%, 30%, 40%, 50%, 60%, 70%, 80%, 90% or more sequence information of sequences of peptides presented by an HLA protein expressed in cells and identified by mass spectrometry.

Any information and data may be paired with a subject who is the source of the information and data. The subject or medical professional can retrieve the information and data from a storage or a server through a subject identity. A subject identity may comprise patient's photo, name, address, social security number, birthday, telephone number, zip code, or any combination thereof. A subject identity may be encrypted and encoded in a visual graphical code. A visual graphical code may be a one-time barcode that can be uniquely associated with a subject identity. A barcode may be a UPC barcode, EAN barcode, Code 39 barcode, Code 128 barcode, ITF barcode, CodaBar barcode, GS1 DataBar barcode, MSI Plessey barcode, QR barcode, Datamatrix code, PDF417 code, or an Aztec barcode. A visual graphical code may be configured to be displayed on a display screen. A barcode may comprise QR that can be optically captured and read by a machine. A barcode may define an element such as a version, format, position, alignment, or timing of the barcode to enable reading and decoding of the barcode. A barcode can encode various types of information in any type of suitable format, such as binary or alphanumeric information. A QR code can have various symbol sizes as long as the QR code can be scanned from a reasonable distance by an imaging device. A QR code can be of any image file format (e.g. EPS or SVG vector graphs, PNG, TIF, GIF, or JPEG raster graphics format).

In some embodiments, the function representing a relation between the amino acid position information received as input and the presentation likelihood generated as output based on the amino acid position information and the predictor variables comprises a linear or non-linear function. The function may be, for example, a rectified linear unit (ReLU) activation function, a Leaky ReLu activation function, or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

In some embodiments, the linear function is obtained through linear regression. In some embodiments, the linear regression is a method to predict a target variable by fitting the best linear relationship between the dependent and independent variable. The best fit may mean that the sum of all the distances between the shape and the actual observations at each point is the least. Linear regression may comprise simple linear regression or multiple linear regression. The simple linear regression may use a single independent variable to predict a dependent variable. The multiple linear regressions may use more than one independent variables to predict a dependent variable by fitting a best linear relationship. The non-linear function may be obtained through non-linear regression. The nonlinear regression may be a form of regression analysis in which observational data are modeled by a function which is a nonlinear combination of the model parameters and depends on one or more independent variables. The nonlinear regression may comprise a step function, piecewise function, spline, and generalized additive model.

In some embodiments, the presentation likelihood is presented by one-dimensional values (e.g., probabilities). In some embodiments, the probability is configured to measure the likelihood that an event may occur. In some embodiments, the probability ranges from about 0 and 1, 0.1 to 0.9, 0.2 to 0.8, 0.3 to 0.7, or 0.4 to 0.6. The higher the probability of an event, the more likely the event may occur. In some embodiments, the event comprises any type of situation, including, by way of non-limiting examples, whether the HLA-peptide will present some peptide with certain amino acid position information, and whether a person will be sick based on amino acid position information. In some embodiments, the likelihood may be presented by multi-dimensional values. The multi-dimensional values may be presented by multi-dimensional space, heatmap, or spreadsheet.

In one embodiment, selecting a subset of the peptide sequences identified based on the set of presentation predictions is configured to prepare the personalized cancer vaccine. In some embodiments, the subset comprises at most about 90%, 80%, 70%, 60%, 50%, 40%, 30%, 20%, 10% or less of the peptide sequences identified based on the set of presentation predictions. In other cases, the subset may comprise at least about 10%, 20%, 30%, 40%, 50%, 60%, 70%, 80%, 90% or more of the peptide sequences identified based on the set of presentation predictions. A cancer vaccine may be a vaccine that either treats existing cancer or prevents development of a cancer. Vaccines may be prepared from samples taken from the patient, and may be specific to that patient.

In some embodiments, a Poxvirus is used in the disease (e.g., cancer) vaccine or immunogenic composition. These include orthopoxvirus, avipox, vaccinia, MVA, NYVAC, canarypox, ALVAC, fowlpox, TROVAC, etc. Advantages of the vectors may include simple construction, ability to accommodate large amounts of foreign DNA and high expression levels. Information concerning poxviruses that can be used in the practice of the disclosure, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC.1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants can be found in scientific and patent literature.

In some embodiments, a vaccinia virus is used in the disease vaccine or immunogenic composition to express an antigen. The recombinant vaccinia virus may be able to replicate within the cytoplasm of the infected host cell and the polypeptide of interest may therefore induce an immune response.

In some embodiments, ALVAC is used as a vector in a disease vaccine or immunogenic composition. ALVAC may be a canarypox virus that can be modified to express foreign transgenes and has been used as a method for vaccination against both prokaryotic and eukaryotic antigens.

In some embodiments, a Modified Vaccinia Ankara (MVA) virus is used as a viral vector for an antigen vaccine or immunogenic composition. MVA may be a member of the Orthopoxvirus family and has been generated by about 570 serial passages on chicken embryo fibroblasts of the Ankara strain of Vaccinia virus (CVA). As a consequence of these passages, the resulting MVA virus may comprise 31 kilobases fewer genomic information compared to CVA, and is highly host-cell restricted. MVA may be characterized by its extreme attenuation, namely, by a diminished virulence or infectious ability, but still holds an excellent immunogenicity. When tested in a variety of animal models, MVA may be proven to be avirulent, even in immuno-suppressed individuals. Moreover, MVA-BN®-HER2 may be a candidate immunotherapy designed for the treatment of HER-2-positive breast cancer and is currently in clinical trials.

In some embodiments, a positive predictive value (PPV) is used as part of the prediction model. A PPV, also known as a precision measurement, is the probability that an individual diagnosed with a disease or condition through, for example, a test or model, actually has the disease or condition. It can be calculated by dividing the number of true positive results by the total number of results that returned positive (results that include false positives). PPV=True Positives/(True positives+False positives). For example, if in a set of 100 patients, the model identified a positive result in 50 patients, of which 25 were true positives, the PPV would be 25/50=0.5. A PPV closer to 1 represents a more accurate diagnosis method, such as a test or model. A PPV may be used to determine the accuracy of the prediction model. A PPV may be used to adjust the prediction model to accommodate for false positive results that may be generated by the model.

A recall rate may be used as part of the prediction model. A recall rate may be considered as the percentage of true positive results out of the total number of positives in the sample set. Recall=True Positives/(True positives+False Negatives). For example, if in a set of 100 patients, the model identified a positive result in 50 patients, of which 25 were true positives, and there were a total of 75 positives in the set of patients, the recall rate would be {25/(25+25)}× 100=50%. A recall rate may be used to determine the accuracy of the prediction model. A recall rate may be used to adjust the prediction model to accommodate for false positive results or false negative results that may be generated by the model.

In some embodiments, the prediction model has a positive predictive value of at least 0.05, 0.1, 0.2, 0.25, 0.3, 0.4, 0.5, 0.6, 0.7, 0.8, 0.9 or greater at a recall rate of from 0.1%-10%. In some embodiments, the prediction model may have a positive predictive value of at most 0.9, 0.8, 0.7, 0.6, 0.5, 0.4, 0.3, 0.2, 0.1 or less at a recall rate of from 0.1%40%. The prediction model may have a positive predictive value of at least 0.05, 0.1, 0.2, 0.3, 0.4, 0.5, 0.6, 0.7, 0.8, 0.9 or greater at a recall rate less than 0.1%. In some embodiments, the prediction model may have a positive predictive value of at most 0.9, 0.8, 0.7, 0.6, 0.5, 0.4, 0.3, 0.2, 0.1 or less at a recall rate less than 0.1%. The prediction model may have a positive predictive value of at least 0.05, 0.1, 0.2, 0.3, 0.4, 0.5, 0.6, 0.7, 0.8, 0.9 or greater at a recall rate more than 10%. In some embodiments, the prediction model may have a positive predictive value of at most 0.9, 0.8, 0.7, 0.6, 0.5, 0.4, 0.3, 0.2, 0.1 or less at a recall rate more than 10%.

In some embodiments, the prediction model has a positive predictive value of at least 0.05, 0.1, 0.2, 0.25, 0.3, 0.4, 0.5, 0.6, 0.7, 0.8, 0.9 or greater at a recall rate of 0.1% to 10%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of 0.1% to 0.5%, 0.1% to 1%, 0.1% to 2%, 0.1% to 3%, 0.1% to 4%, 0.1% to 5%, 0.1% to 6%, 0.1% to 7%, 0.1% to 8%, 0.1% to 9%, 0.1% to 10%, 0.5% to 1%, 0.5% to 2%, 0.5% to 3%, 0.5% to 4%, 0.5% to 5%, 0.5% to 6%, 0.5% to 7%, 0.5% to 8%, 0.5% to 9%, 0.5% to 10%, 1% to 2%, 1% to 3%, 1% to 4%, 1% to 5%, 1% to 6%, 1% to 7%, 1% to 8%, 1% to 9%, 1% to 10%, 2% to 3%, 2% to 4%, 2% to 5%, 2% to 6%, 2% to 7%, 2% to 8%, 2% to 9%, 2% to 10%, 3% to 4%, 3% to 5%, 3% to 6%, 3% to 7%, 3% to 8%, 3% to 9%, 3% to 10%, 4% to 5%, 4% to 6%, 4% to 7%, 4% to 8%, 4% to 9%, 4% to 10%, 5% to 6%, 5% to 7%, 5% to 8%, 5% to 9%, 5% to 10%, 6% to 7%, 6% to 8%, 6% to 9%, 6% to 10%, 7% to 8%, 7% to 9%, 7% to 10%, 8% to 9%, 8% to 10%, or 9% to 10%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of 0.1%, 0.5%, 1%, 2%, 3%, 4%, 5%, 6%, 7%, 8%, 9%, or 10%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of at least 0.1%, 0.5%, 1%, 2%, 3%, 4%, 5%, 6%, 7%, 8%, or 9%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of at most 0.5%, 1%, 2%, 3%, 4%, 5%, 6%, 7%, 8%, 9%, or 10%.

In some embodiments, the prediction model has a positive predictive value of at least 0.05, 0.1, 0.2, 0.25, 0.3, 0.4, 0.5, 0.6, 0.7, 0.8, 0.9 or greater at a recall rate of 10% to 20%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of 10% to 11%, 10% to 12%, 10% to 13%, 10% to 14%, 10% to 15%, 10% to 16%, 10% to 17%, 10% to 18%, 10% to 19%, 10% to 20%, 11% to 12%, 11% to 13%, 11% to 14%, 11% to 15%, 11% to 16%, 11% to 17%, 11% to 18%, 11% to 19%, 11% to 20%, 12% to 13%, 12% to 14%, 12% to 15%, 12% to 16%, 12% to 17%, 12% to 18%, 12% to 19%, 12% to 20%, 13% to 14%, 13% to 15%, 13% to 16%, 13% to 17%, 13% to 18%, 13% to 19%, 13% to 20%, 14% to 15%, 14% to 16%, 14% to 17%, 14% to 18%, 14% to 19%, 14% to 20%, 15% to 16%, 15% to 17%, 15% to 18%, 15% to 19%, 15% to 20%, 16% to 17%, 16% to 18%, 16% to 19%, 16% to 20%, 17% to 18%, 17% to 19%, 17% to 20%, 18% to 19%, 18% to 20%, or 19% to 20%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of 10%, 11%, 12%, 13%, 14%, 15%, 16%, 17%, 18%, 19%, or 20%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of at least 10%, 11%, 12%, 13%, 14%, 15%, 16%, 17%, 18%, or 19%. In some embodiments, the prediction model has a positive predictive value of at least 0.05, 0.1, 0.2, 0.25, 0.3, 0.4, 0.5, 0.6, 0.7, 0.8, 0.9 or greater at a recall rate of at most 11%, 12%, 13%, 14%, 15%, 16%, 17%, 18%, 19%, or 20%.

In some embodiments, the prediction model has a positive predictive value of at least 0.05, 0.1, 0.2, 0.25, 0.3, 0.4, 0.5, 0.6, 0.7, 0.8, 0.9 or greater at a recall rate of at least 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20%. For example, prediction model may have a positive predictive value of at least 0.1 at a recall rate of at least 10%. For example, prediction model may have a positive predictive value of at least 0.2 at a recall rate of at least 10%. For example, prediction model may have a positive predictive value of at least 0.3 at a recall rate of at least 10%. For example, prediction model may have a positive predictive value of at least 0.4 at a recall rate of at least 10%. For example, prediction model may have a positive predictive value of at least 0.5 at a recall rate of at least 10%. For example, prediction model may have a positive predictive value of at least 0.6 at a recall rate of at least 10%. For example, prediction model may have a positive predictive value of at least 0.7 at a recall rate of at least 10%. For example, prediction model may have a positive predictive value of at least 0.8 at a recall rate of at least 10%. For example, prediction model may have a positive predictive value of at least 0.9 at a recall rate of at least 10%. For example, prediction model may have a positive predictive value of at least 0.1 at a recall rate of at least 5%. For example, prediction model may have a positive predictive value of at least 0.2 at a recall rate of at least 5%. For example, prediction model may have a positive predictive value of at least 0.3 at a recall rate of at least 5%. For example, prediction model may have a positive predictive value of at least 0.4 at a recall rate of at least 5%. For example, prediction model may have a positive predictive value of at least 0.5 at a recall rate of at least 5%. For example, prediction model may have a positive predictive value of at least 0.6 at a recall rate of at least 5%. For example, prediction model may have a positive predictive value of at least 0.7 at a recall rate of at least 5%. For example, prediction model may have a positive predictive value of at least 0.8 at a recall rate of at least 5%. For example, prediction model may have a positive predictive value of at least 0.9 at a recall rate of at least 5%. For example, prediction model may have a positive predictive value of at least 0.1 at a recall rate of at least 20%. For example, prediction model may have a positive predictive value of at least 0.2 at a recall rate of at least 20%. For example, prediction model may have a positive predictive value of at least 0.3 at a recall rate of at least 20%. For example, prediction model may have a positive predictive value of at least 0.4 at a recall rate of at least 20%. For example, prediction model may have a positive predictive value of at least 0.5 at a recall rate of at least 20%. For example, prediction model may have a positive predictive value of at least 0.6 at a recall rate of at least 20%. For example, prediction model may have a positive predictive value of at least 0.7 at a recall rate of at least 20%. For example, prediction model may have a positive predictive value of at least 0.8 at a recall rate of at least 20%. For example, prediction model may have a positive predictive value of at least 0.9 at a recall rate of at least 20%.

In some embodiments, the prediction model has a positive predictive value of at least 0.05, 0.1, 0.2, 0.25, 0.3, 0.4, 0.5, 0.6, 0.7, 0.8, 0.9 or greater at a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20%. For example, prediction model may have a positive predictive value of at least 0.1 at a recall rate of about 10%. For example, prediction model may have a positive predictive value of at least 0.2 at a recall rate of about 10%. For example, prediction model may have a positive predictive value of at least 0.3 at a recall rate of about 10%. For example, prediction model may have a positive predictive value of at least 0.4 at a recall rate of about 10%. For example, prediction model may have a positive predictive value of at least 0.5 at a recall rate of about 10%. For example, prediction model may have a positive predictive value of at least 0.6 at a recall rate of about 10%. For example, prediction model may have a positive predictive value of at least 0.7 at a recall rate of about 10%. For example, prediction model may have a positive predictive value of at least 0.8 at a recall rate of about 10%. For example, prediction model may have a positive predictive value of at least 0.9 at a recall rate of about 10%. For example, prediction model may have a positive predictive value of at least 0.1 at a recall rate of about 5%. For example, prediction model may have a positive predictive value of at least 0.2 at a recall rate of about 5%. For example, prediction model may have a positive predictive value of at least 0.3 at a recall rate of about 5%. For example, prediction model may have a positive predictive value of at least 0.4 at a recall rate of about 5%. For example, prediction model may have a positive predictive value of at least 0.5 at a recall rate of about 5%. For example, prediction model may have a positive predictive value of at least 0.6 at a recall rate of about 5%. For example, prediction model may have a positive predictive value of at least 0.7 at a recall rate of about 5%. For example, prediction model may have a positive predictive value of at least 0.8 at a recall rate of about 5%. For example, prediction model may have a positive predictive value of at least 0.9 at a recall rate of about 5%. For example, prediction model may have a positive predictive value of at least 0.1 at a recall rate of about 20%. For example, prediction model may have a positive predictive value of at least 0.2 at a recall rate of about 20%. For example, prediction model may have a positive predictive value of at least 0.3 at a recall rate of about 20%. For example, prediction model may have a positive predictive value of at least 0.4 at a recall rate of about 20%. For example, prediction model may have a positive predictive value of at least 0.5 at a recall rate of about 20%. For example, prediction model may have a positive predictive value of at least 0.6 at a recall rate of about 20%. For example, prediction model may have a positive predictive value of at least 0.7 at a recall rate of about 20%. For example, prediction model may have a positive predictive value of at least 0.8 at a recall rate of about 20%. For example, prediction model may have a positive predictive value of at least 0.9 at a recall rate of about 20%.

In some embodiments, the prediction model has a positive predictive value of at least 0.05, 0.1, 0.2, 0.25, 0.3, 0.4, 0.5, 0.6, 0.7, 0.8, 0.9 or greater at a recall rate of less than 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20%. For example, prediction model may have a positive predictive value of at least 0.1 at a recall rate of at most 10%. For example, prediction model may have a positive predictive value of at least 0.2 at a recall rate of at most 10%. For example, prediction model may have a positive predictive value of at least 0.3 at a recall rate of at most 10%. For example, prediction model may have a positive predictive value of at least 0.4 at a recall rate of at most 10%. For example, prediction model may have a positive predictive value of at least 0.5 at a recall rate of at most 10%. For example, prediction model may have a positive predictive value of at least 0.6 at a recall rate of at most 10%. For example, prediction model may have a positive predictive value of at least 0.7 at a recall rate of at most 10%. For example, prediction model may have a positive predictive value of at least 0.8 at a recall rate of at most 10%. For example, prediction model may have a positive predictive value of at least 0.9 at a recall rate of at most 10%. For example, prediction model may have a positive predictive value of at least 0.1 at a recall rate of at most 5%. For example, prediction model may have a positive predictive value of at least 0.2 at a recall rate of at most 5%. For example, prediction model may have a positive predictive value of at least 0.3 at a recall rate of at most 5%. For example, prediction model may have a positive predictive value of at least 0.4 at a recall rate of at most 5%. For example, prediction model may have a positive predictive value of at least 0.5 at a recall rate of at most 5%. For example, prediction model may have a positive predictive value of at least 0.6 at a recall rate of at most 5%. For example, prediction model may have a positive predictive value of at least 0.7 at a recall rate of at most 5%. For example, prediction model may have a positive predictive value of at least 0.8 at a recall rate of at most 5%. For example, prediction model may have a positive predictive value of at least 0.9 at a recall rate of at most 5%. For example, prediction model may have a positive predictive value of at least 0.1 at a recall rate of at most 20%. For example, prediction model may have a positive predictive value of at least 0.2 at a recall rate of at most 20%. For example, prediction model may have a positive predictive value of at least 0.3 at a recall rate of at most 20%. For example, prediction model may have a positive predictive value of at least 0.4 at a recall rate of at most 20%. For example, prediction model may have a positive predictive value of at least 0.5 at a recall rate of at most 20%. For example, prediction model may have a positive predictive value of at least 0.6 at a recall rate of at most 20%. For example, prediction model may have a positive predictive value of at least 0.7 at a recall rate of at most 20%. For example, prediction model may have a positive predictive value of at least 0.8 at a recall rate of at most 20%. For example, prediction model may have a positive predictive value of at least 0.9 at a recall rate of at most 20%.

In some embodiments, at a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model has a positive predictive value of 0.05% to 0.6%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of 0.05% to 0.1%, 0.05% to 0.15%, 0.05% to 0.2%, 0.05% to 0.25%, 0.05% to 0.3%, 0.05% to 0.35%, 0.05% to 0.4%, 0.05% to 0.45%, 0.05% to 0.5%, 0.05% to 0.55%, 0.05% to 0.6%, 0.1% to 0.15%, 0.1% to 0.2%, 0.1% to 0.25%, 0.1% to 0.3%, 0.1% to 0.35%, 0.1% to 0.4%, 0.1% to 0.45%, 0.1% to 0.5%, 0.1% to 0.55%, 0.1% to 0.6%, 0.15% to 0.2%, 0.15% to 0.25%, 0.15% to 0.3%, 0.15% to 0.35%, 0.15% to 0.4%, 0.15% to 0.45%, 0.15% to 0.5%, 0.15% to 0.55%, 0.15% to 0.6%, 0.2% to 0.25%, 0.2% to 0.3%, 0.2% to 0.35%, 0.2% to 0.4%, 0.2% to 0.45%, 0.2% to 0.5%, 0.2% to 0.55%, 0.2% to 0.6%, 0.25% to 0.3%, 0.25% to 0.35%, 0.25% to 0.4%, 0.25% to 0.45%, 0.25% to 0.5%, 0.25% to 0.55%, 0.25% to 0.6%, 0.3% to 0.35%, 0.3% to 0.4%, 0.3% to 0.45%, 0.3% to 0.5%, 0.3% to 0.55%, 0.3% to 0.6%, 0.35% to 0.4%, 0.35% to 0.45%, 0.35% to 0.5%, 0.35% to 0.55%, 0.35% to 0.6%, 0.4% to 0.45%, 0.4% to 0.5%, 0.4% to 0.55%, 0.4% to 0.6%, 0.45% to 0.5%, 0.45% to 0.55%, 0.45% to 0.6%, 0.5% to 0.55%, 0.5% to 0.6%, or 0.55% to 0.6%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of 0.05%, 0.1%, 0.15%, 0.2%, 0.25%, 0.3%, 0.35%, 0.4%, 0.45%, 0.5%, 0.55%, or 0.6%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of at least 0.05%, 0.1%, 0.15%, 0.2%, 0.25%, 0.3%, 0.35%, 0.4%, 0.45%, 0.5%, or 0.55%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of at most 0.1%, 0.15%, 0.2%, 0.25%, 0.3%, 0.35%, 0.4%, 0.45%, 0.5%, 0.55%, or 0.6%.

At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of 0.45% to 0.98%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of 0.45% to 0.5%, 0.45% to 0.55%, 0.45% to 0.6%, 0.45% to 0.65%, 0.45% to 0.7%, 0.45% to 0.75%, 0.45% to 0.8%, 0.45% to 0.85%, 0.45% to 0.9%, 0.45% to 0.96%, 0.45% to 0.98%, 0.5% to 0.55%, 0.5% to 0.6%, 0.5% to 0.65%, 0.5% to 0.7%, 0.5% to 0.75%, 0.5% to 0.8%, 0.5% to 0.85%, 0.5% to 0.9%, 0.5% to 0.96%, 0.5% to 0.98%, 0.55% to 0.6%, 0.55% to 0.65%, 0.55% to 0.7%, 0.55% to 0.75%, 0.55% to 0.8%, 0.55% to 0.85%, 0.55% to 0.9%, 0.55% to 0.96%, 0.55% to 0.98%, 0.6% to 0.65%, 0.6% to 0.7%, 0.6% to 0.75%, 0.6% to 0.8%, 0.6% to 0.85%, 0.6% to 0.9%, 0.6% to 0.96%, 0.6% to 0.98%, 0.65% to 0.7%, 0.65% to 0.75%, 0.65% to 0.8%, 0.65% to 0.85%, 0.65% to 0.9%, 0.65% to 0.96%, 0.65% to 0.98%, 0.7% to 0.75%, 0.7% to 0.8%, 0.7% to 0.85%, 0.7% to 0.9%, 0.7% to 0.96%, 0.7% to 0.98%, 0.75% to 0.8%, 0.75% to 0.85%, 0.75% to 0.9%, 0.75% to 0.96%, 0.75% to 0.98%, 0.8% to 0.85%, 0.8% to 0.9%, 0.8% to 0.96%, 0.8% to 0.98%, 0.85% to 0.9%, 0.85% to 0.96%, 0.85% to 0.98%, 0.9% to 0.96%, 0.9% to 0.98%, or 0.96% to 0.98%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of 0.45%, 0.5%, 0.55%, 0.6%, 0.65%, 0.7%, 0.75%, 0.8%, 0.85%, 0.9%, 0.96%, or 0.98%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of at least 0.45%, 0.5%, 0.55%, 0.6%, 0.65%, 0.7%, 0.75%, 0.8%, 0.85%, 0.9%, or 0.96%. At a recall rate of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, or 20% the prediction model may have a positive predictive value of at most 0.5%, 0.55%, 0.6%, 0.65%, 0.7%, 0.75%, 0.8%, 0.85%, 0.9%, 0.96%, or 0.98%.

Methods of Training a Machine-Learning HLA-Peptide Presentation Prediction Model In an aspect, a method of training a machine-learning HLA-peptide presentation prediction model may comprise inputting amino acid position information sequences of HLA-peptides isolated from one or more HLA-peptide complexes from a cell expressing an HLA class II allele into the HLA-peptide presentation prediction model using a computer processor; training the machine-learning HLA-peptide presentation prediction model may comprise adjusting weighted values on nodes of a neural network to best match the provided training data.

The training data may comprise sequence information of sequences of peptides presented by an HLA protein expressed in cells and identified by mass spectrometry; training peptide sequence information comprising amino acid position information of training peptides, wherein the training peptide sequence information is associated with the HLA protein expressed in cells; and a function representing a relation between the amino acid position information received as input and a presentation likelihood generated as output based on the amino acid position information and the predictor variables. The training data, training peptide sequence information, function, and presentation likelihood are disclosed elsewhere herein.

The trained algorithm may comprise one or more neural networks. A neural network may be a type of computing system based upon a graph of several connected neurons (or nodes) in a series of layers. A neural network may comprise an input layer, to which data is presented; one or more internal, and/or "hidden," layers; and an output layer, from which results are presented. A neural network may learn the relationships between an input data set and a target data set by adjusting a series of connection weights. A neuron may be connected to neurons in other layers via connections that have weights, which are parameters that control the strength of a connection. The number of neurons in each layer may be related to the complexity of a problem to be solved. The minimum number of neurons required in a layer may be determined by the problem complexity, and the maximum number may be limited by the ability of a neural network to generalize. Input neurons may receive data being presented and then transmit that data to a node in the first hidden layer through connection weights, which are modified during training. The result node may sum up the products of all pairs of inputs and their associated weights. The weighted sum may be offset with a bias to adjust the value of the result node. The output of a node or neuron may be gated using a threshold or activation function. An activation function may be a linear or non-linear function. An activation function may be, for example, a rectified linear unit (ReLU) activation function, a Leaky ReLu activation function, or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

A hidden layer in the neural network may process data and transmit its result to the next layer through a second set of weighted connections. Each subsequent layer may "pool" results from previous layers into more complex relationships. Neural networks may be trained with a known sample set of training data (data collected from one or more sensors) by allowing them to modify themselves during (and after) training so as to provide a desired output from a given set of inputs, such as an output value. A trained algorithm may comprise convolutional neural networks, recurrent neural networks, dilated convolutional neural networks, fully connected neural networks, deep generative models, and Boltzmann machines.

Weighing factors, bias values, and threshold values, or other computational parameters of a neural network, may be "taught" or "learned" in a training phase using one or more sets of training data. For example, parameters may be trained using input data from a training data set and a gradient descent or backward propagation method so that output value(s) from a neural network are consistent with examples included in a training data set.

The number of nodes used in an input layer of a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of node used in an input layer may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller. In some instance, the total number of layers used in a neural network (including input and output layers) may be at least about 3, 4, 5, 10, 15, 20, or greater. In other instances, the total number of layers may be at most about 20, 15, 10, 5, 4, 3 or less.

In some instances, the total number of learnable or trainable parameters, e.g., weighting factors, biases, or threshold values, used in a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of learnable parameters may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller.

A neural network may comprise a convolutional neural network. A convolutional neural network may comprise one or more convolutional layers, dilated layers or fully connected layers. The number of convolutional layers may be between 1-10 and dilated layers between 0-10. The total number of convolutional layers (including input and output layers) may be at least about 1, 2, 3, 4, 5, 10, 15, 20, or greater, and the total number of dilated layers may be at least about 1, 2, 3, 4, 5, 10, 15, 20, or greater. The total number of convolutional layers may be at most about 20, 15, 10, 5, 4, 3 or less, and the total number of dilated layers may be at most about 20, 15, 10, 5, 4, 3 or less. In some embodiments, the number of convolutional layers is between 1-10 and fully connected layers between 0-10. The total number of convolutional layers (including input and output layers) may be at least about 1, 2, 3, 4, 5, 10, 15, 20, or greater, and the total number of fully connected layers may be at least about 1, 2, 3, 4, 5, 10, 15, 20, or greater. The total number of convolutional layers may be at most about 20, 15, 10, 5, 4, 3 or less, and the total number of fully connected layers may be at most about 20, 15, 10, 5, 4, 3 or less.

A convolutional neural network (CNN) may be a deep and feed-forward artificial neural network. A CNN may be applicable to analyzing visual imagery. A CNN may comprise an input, an output layer, and multiple hidden layers. Hidden layers of a CNN may comprise convolutional layers, pooling layers, fully connected layers and normalization layers. Layers may be organized in 3 dimensions: width, height and depth.

Convolutional layers may apply a convolution operation to an input and pass results of a convolution operation to a next layer. For processing images, a convolution operation may reduce the number of free parameters, allowing a network to be deeper with fewer parameters. In a convolutional layer, neurons may receive input from only a restricted subarea of a previous layer. Convolutional layer's parameters may comprise a set of learnable filters (or kernels). Learnable filters may have a small receptive field and extend through the full depth of an input volume. During a forward pass, each filter may be convolved across the width and height of an input volume, compute a dot product between entries of a filter and an input, and produce a 2-dimensional activation map of that filter. As a result, a network may learn filters that activate when it detects some specific type of feature at some spatial position in an input.

Pooling layers may comprise global pooling layers. Global pooling layers may combine outputs of neuron clusters at one layer into a single neuron in the next layer. For example, max pooling layers may use the maximum value from each of a cluster of neurons at a prior layer; and average pooling layers may use an average value from each of a cluster of neurons at the prior layer. Fully connected layers may connect every neuron in one layer to every neuron in another layer. In a fully-connected layer, each neuron may receive input from every element of a previous layer. A normalization layer may be a batch normalization layer. A batch normalization layer may improve performance and stability of neural networks. A batch normalization layer may provide any layer in a neural network with inputs that are zero mean/unit variance. Advantages of using batch normalization layer may include faster trained networks, higher learning rates, easier to initialize weights, more activation functions viable, and simpler process of creating deep networks.

A neural network may comprise a recurrent neural network. A recurrent neural network may be configured to receive sequential data as an input, such as consecutive data inputs, and a recurrent neural network software module may update an internal state at every time step. A recurrent neural network can use internal state (memory) to process sequences of inputs. A recurrent neural network may be applicable to tasks such as handwriting recognition or speech recognition, next word prediction, music composition, image captioning, time series anomaly detection, machine translation, scene labeling, and stock market prediction. A recurrent neural network may comprise fully recurrent neural network, independently recurrent neural network, Elman networks, Jordan networks, Echo state, neural history compressor, long short-term memory, gated recurrent unit, multiple timescales model, neural Turing machines, differentiable neural computer, neural network pushdown automata, or any combination thereof.

A trained algorithm may comprise a supervised or unsupervised learning method such as, for example, SVM, random forests, clustering algorithm (or software module), gradient boosting, logistic regression, and/or decision trees. Supervised learning algorithms may be algorithms that rely on the use of a set of labeled, paired training data examples to infer the relationship between an input data and output data. Unsupervised learning algorithms may be algorithms used to draw inferences from training data sets to output data. Unsupervised learning algorithms may comprise cluster analysis, which may be used for exploratory data analysis to find hidden patterns or groupings in process data. One example of an unsupervised learning method may comprise principal component analysis. Principal component analysis may comprise reducing the dimensionality of one or more variables. The dimensionality of a given variables may be at least 1, 5, 10, 50, 100, 200, 300, 400, 500, 600, 700, 800, 900, 1000, 1100, 1200 1300, 1400, 1500, 1600, 1700, 1800, or greater. The dimensionality of a given variables may be at most 1800, 1600, 1500, 1400, 1300, 1200, 1100, 1000, 900, 800, 700, 600, 500, 400, 300, 200, 100, 50, 10 or less.

A training algorithm may be obtained through statistical techniques. In some embodiments, statistical techniques may comprise linear regression, classification, resampling methods, subset selection, shrinkage, dimension reduction, nonlinear models, tree-based methods, support vector machines, unsupervised learning, or any combination thereof.

A linear regression may be a method to predict a target variable by fitting the best linear relationship between a dependent and independent variable. The best fit may mean that the sum of all distances between a shape and actual observations at each point is the least. Linear regression may comprise simple linear regression and multiple linear regression. A simple linear regression may use a single independent variable to predict a dependent variable. A multiple linear regression may use more than one independent variable to predict a dependent variable by fitting a best linear relationship.

A classification may be a data mining technique that assigns categories to a collection of data in order to achieve accurate predictions and analysis. Classification techniques may comprise logistic regression and discriminant analysis. Logistic regression may be used when a dependent variable is dichotomous (binary). Logistic regression may be used to discover and describe a relationship between one dependent binary variable and one or more nominal, ordinal, interval or ratio-level independent variables. A resampling may be a method comprising drawing repeated samples from original data samples. A resampling may not involve a utilization of a generic distribution tables in order to compute approximate probability values. A resampling may generate a unique sampling distribution on a basis of an actual data. In some embodiments, a resampling may use experimental methods, rather than analytical methods, to generate a unique sampling distribution. Resampling techniques may comprise bootstrapping and cross-validation. Bootstrapping may be performed by sampling with replacement from original data, and take "not chosen" data points as test cases. Cross validation may be performed by split training data into a plurality of parts.

A subset selection may identify a subset of predictors related to a response. A subset selection may comprise best-subset selection, forward stepwise selection, backward stepwise selection, hybrid method, or any combination thereof. In some embodiments, shrinkage fits a model involving all predictors, but estimated coefficients are shrunken towards zero relative to the least squares estimates. This shrinkage may reduce variance. A shrinkage may comprise ridge regression and a lasso. A dimension reduction may reduce a problem of estimating n+1 coefficients to a simpler problem of m+1 coefficients, where m<n. It may be attained by computing n different linear combinations, or projections, of variables. Then these n projections are used as predictors to fit a linear regression model by least squares. Dimension reduction may comprise principal component regression and partial least squares. A principal component regression may be used to derive a low-dimensional set of features from a large set of variables. A principal component used in a principal component regression may capture the most variance in data using linear combinations of data in subsequently orthogonal directions. The partial least squares may be a supervised alternative to principal component regression because partial least squares may make use of a response variable in order to identify new features.

A nonlinear regression may be a form of regression analysis in which observational data are modeled by a function which is a nonlinear combination of model parameters and depends on one or more independent variables. A nonlinear regression may comprise a step function, piecewise function, spline, generalized additive model, or any combination thereof.

Tree-based methods may be used for both regression and classification problems. Regression and classification problems may involve stratifying or segmenting the predictor space into a number of simple regions. Tree-based methods may comprise bagging, boosting, random forest, or any combination thereof. Bagging may decrease a variance of prediction by generating additional data for training from the original dataset using combinations with repetitions to produce multistep of the same carnality/size as original data. Boosting may calculate an output using several different models and then average a result using a weighted average approach. A random forest algorithm may draw random bootstrap samples of a training set. Support vector machines may be classification techniques. Support vector machines may comprise finding a hyperplane that best separates two classes of points with the maximum margin. Support vector machines may constrain an optimization problem such that a margin is maximized subject to a constraint that it perfectly classifies data.

Unsupervised methods may be methods to draw inferences from datasets comprising input data without labeled responses. Unsupervised methods may comprise clustering, principal component analysis, k-Mean clustering, hierarchical clustering, or any combination thereof.

The mass spectrometry may be mono-allelic mass spectrometry. In some embodiments, the mass spectrometry may be MS analysis, MS/MS analysis, LC-MS/MS analysis, or a combination thereof. In some embodiments, MS analysis may be used to determine a mass of an intact peptide. For example, the determining can comprise determining a mass of an intact peptide (e.g., MS analysis). In some embodiments, MS/MS analysis may be used to determine a mass of peptide fragments. For example, the determining can comprise determining a mass of peptide fragments, which can be used to determine an amino acid sequence of a peptide or portion thereof (e.g., MS/MS analysis). In some embodiments, the mass of peptide fragments may be used to determine a sequence of amino acids within the peptide. In some embodiments, LC-MS/MS analysis may be used to separate complex peptide mixtures. For example, the determining can comprise separating complex peptide mixtures, such as by liquid chromatography, and determining a mass of an intact peptide, a mass of peptide fragments, or a combination thereof (e.g., LC-MS/MS analysis). This data can be used, e.g., for peptide sequencing.

The peptides may be presented by an HLA protein expressed in cells through autophagy. Autophagy may allow the orderly degradation and recycling of cellular components. The autophagy may comprise macroautophagy, microautophagy and Chaperone mediated autophagy. The peptides may be presented by an HLA protein expressed in cells through phagocytosis. The phagocytosis may be a major mechanism used to remove pathogens and cell debris. For example, when a macrophage ingests a pathogenic microorganism, the pathogen becomes trapped in a phagosome which then fuses with a lysosome to form a phagolysosome. In HLA class II, phagocytes such as macrophages and immature dendritic cells may take up entities by phagocytosis into phagosomes—though B cells exhibit the more general endocytosis into endosomes—which fuse with lysosomes whose acidic enzymes cleave the uptaken protein into many different peptides.

The quality of the training data may be increased by using a plurality of quality metrics. The plurality of quality metrics may comprise common contaminant peptide removal, high scored peak intensity, high score, and high mass accuracy. The scored peak intensity may be used prior to performing scoring. The MS/MS Search first screens the MS/MS spectrum against candidate sequences using a simple filter. This filter may be minimum scored peak intensity. Using the scored peak intensity may enhance search speed by allowing candidate sequences to be rapidly and summarily rejected once a sufficient number of spectral peaks are examined and found not to meet the threshold established by this filter. The scored peak intensity may be at least 50%. The scored peak intensity may be at least 70%. The scored peak intensity may be at least 10%, 20%, 30%, 40%, 50%, 60%, 70%, 80%, 90% or greater. In some cases, the scored peak intensity may be at most 90%, 80%, 70%, 60%, 50%, 40%, 30%, 20%, 10% or less. The score may be at least 7. The score may be at least 1, 2, 3, 4, 5, 6, 7, 8, 9, 10, 15, 20 or greater. In some cases, the score may be at most about 20, 15, 10, 9, 8, 7, 6, 5, 4, 3, 2, 1 or less. The mass accuracy may be at most 5 ppm. The mass accuracy may be at most 10 ppm, 9 ppm, 8 ppm, 7 ppm, 6 ppm, 5 ppm, 4 ppm, 3 ppm, 2 ppm, 1 ppm or less. The mass accuracy may be at least 1 ppm, 2 ppm, 3 ppm, 4 ppm, 5 ppm, 6 ppm, 7 ppm, 8 ppm, 9 ppm, 10 ppm or greater.

In some embodiments, a mass accuracy is at most 2 ppm. In some embodiments, a backbone cleavage score is at least 5. In some embodiments, a backbone cleavage score is at least 8.

The peptides presented by an HLA protein expressed in cells may be peptides presented by a single immunoprecipitated HLA protein expressed in cells. Immunoprecipitation (IP) may be the technique of precipitating a protein antigen out of solution using an antibody that specifically binds to that particular protein. This process can be used to isolate and concentrate a particular protein from a sample containing many thousands of different proteins. Immunoprecipitation may require that the antibody be coupled to a solid substrate at some point in the procedure.

The peptides presented by an HLA protein expressed in cells may be peptides presented by a single exogenous HLA protein expressed in cells. The single exogenous HLA protein may be created by introducing one or more exogenous peptides to the population of cells. In some embodiments, the introducing comprises contacting the population of cells with the one or more exogenous peptides or expressing the one or more exogenous peptides in the population of cells. In some embodiments, the introducing comprises contacting the population of cells with one or more nucleic acids encoding the one or more exogenous peptides. In some embodiments, the one or more nucleic acids encoding the one or more peptides is DNA. In some embodiments, the one or more nucleic acids encoding the one or more peptides is RNA, optionally wherein the RNA is mRNA. In some embodiments, the enriching does not comprise use of a tetramer (or multimer) reagent.

The peptides presented by an HLA protein expressed in cells may be peptides presented by a single recombinant HLA protein expressed in cells. The recombinant HLA protein may be encoded by a recombinant HLA class I or HLA class II allele. The HLA class I may be selected from the group consisting of HLA-A, HLA-B, HLA-C. The HLA class I may be a non-classical class-I-b group. The HLA class I may be selected from the group consisting of HLA-E, HLA-F, and HLA-G. The HLA class I may be a non-classical class-I-b group selected from the group consisting of HLA-E, HLA-F, and HLA-G. In some embodiments, the HLA class II comprises an HLA class II α-chain, an HLA class II β-chain, or a combination thereof.

The plurality of predictor variables may comprise a peptide-HLA affinity predictor variable. The plurality of predictor variables may comprise a source protein expression level predictor variable. The source protein expression level may be the expression level of the source protein of the peptide within a cell. In some embodiments, the expression level may be determined by measuring the amount of source protein or the amount of RNA encoding the source protein. The plurality of predictor variables may comprise peptide sequence, amino acid physical properties, peptide physical properties, expression level of the source protein of a peptide within a cell, protein stability, protein translation rate, ubiquitination sites, protein degradation rate, translational efficiencies from ribosomal profiling, protein cleavability, protein localization, motifs of host protein that facilitate TAP transport, host protein is subject to autophagy, motifs that favor ribosomal stalling (e.g., polyproline or polylysine stretches), protein features that favor NMD (e.g., long 3' UTR, stop codon >50nt upstream of last exon:exon junction and peptide cleavability).

The plurality of predictor variables may comprise a peptide cleavability predictor variable. The peptide cleavability may be associated with a cleavable linker or a cleavage sequence. In some embodiments, the cleavable linker is a ribosomal skipping site or an internal ribosomal entry site (IRES) element. In some embodiments, the ribosomal skipping site or IRES is cleaved when expressed in the cells. In some embodiments, the ribosomal skipping site is selected from the group consisting of F2A, T2A, P2A, and E2A. In some embodiments, the IRES element is selected from common cellular or viral IRES sequences. A cleavage sequence, such as F2A, or an internal ribosome entry site (IRES) can be placed between the α-chain and β2-microglobulin (HLA class I) or between the α-chain and β-chain (HLA class II). In some embodiments, a single HLA class I allele is HLA-A*02:01, HLA-A*23:01 and HLA-B*14:02, or HLA-E*01:01, and HLA class II allele is HLA-DRB*01:01, HLA-DRB*01:02 and HLA-DRB*11:01, HLA-DRB*15:01, or HLA-DRB*07:01. In some embodiments, the cleavage sequence is a T2A, P2A, E2A, or F2A sequence. For example, the cleavage sequence can be E G R G S L T C G D V E N P G P (SEQ ID NO:6)(T2A), A T N F S L K Q A G D V E N P G P (SEQ ID NO:7)(P2A), Q C T N Y A L K L A G D V E S N P G P (SEQ ID NO:8)(E2A), or V K Q T L N F D L K L A G D V E S N P G P (SEQ ID NO:9)(F2A).

In some embodiments, the cleavage sequence may be a thrombin cleavage site CLIP.

The peptides presented by the HLA protein may comprise peptides that are identified by searching a no-enzyme specificity without modification peptide database. The peptide database may be a no-enzyme specificity peptide database, such as a without modification database or a with modification (e.g., phosphorylation or cysteinylation) database. In some embodiments, the peptide database is a polypeptide database. In some embodiments, the polypeptide database may be a protein database. In some embodiments, the method further comprises searching the peptide database using a reversed-database search strategy. In some embodiments, the method further comprises searching a protein database using a reversed-database search strategy. In some embodiments, a de novo search is performed, e.g., to discover new peptides that are not included in a normal peptide or protein database. The peptide database may be generated by providing a first and a second population of cells each comprising one or more cells comprising an affinity acceptor tagged HLA, wherein the sequence affinity acceptor tagged HLA comprises a different recombinant polypeptide encoded by a different HLA allele operatively linked to an affinity acceptor peptide; enriching for affinity acceptor tagged HLA-peptide complexes; characterizing a peptide or a portion thereof bound to an affinity acceptor tagged HLA-peptide complex from the enriching; and generating an HLA-allele specific peptide database.

The peptides presented by the HLA protein may comprise peptides identified by comparing a MS/MS spectra of the HLA-peptides with MS/MS spectra of one or more HLA-peptides in a peptide database.

There may be mutation on either peptides or nucleic acid that encodes peptides. The mutation may be selected from the group consisting of a point mutation, a splice site mutation, a frameshift mutation, a read-through mutation, and a gene fusion mutation. The point mutation may be a genetic mutation where a single nucleotide base is changed, inserted or deleted from a sequence of DNA or RNA. The splice site mutation may be a genetic mutation that inserts, deletes or changes a number of nucleotides in the specific site at which splicing takes place during the processing of precursor messenger RNA into mature messenger RNA. The frameshift mutation may be a genetic mutation caused by indels (insertions or deletions) of a number of nucleotides in a DNA sequence that is not divisible by three. The mutation may also comprise insertions, deletions, substitution mutations, gene duplications, chromosomal translocations, and chromosomal inversions.

In some embodiments, the HLA class II protein comprises an HLA-DR protein.

In some embodiments, the HLA class II protein comprises an HLA-DP protein.

In some embodiments, the HLA class II protein comprises an HLA-DQ protein.

In some embodiments, the HLA class II protein may be selected from the group consisting an HLA-DR, and HLA-DP or an HLA-DQ protein. In some embodiments, the HLA protein is an HLA class II protein selected from the group consisting of: HLA-DPB1*01:01/HLA-DPA1*01:03, HLA-DPB1*02:01/HLA-DPA1*01:03, HLA-DPB1*03:01/HLA-DPA1*01:03, HLA-DPB1*04:01/HLA-DPA1*01:03, HLA-DPB1*04:02/HLA-DPA1*01:03, HLA-DPB1*06:01/HLA-DPA1*01:03, HLA-DQB1*02:01/HLA-DQA1*05:01, HLA-DQB1*02:02/HLA-DQA1*02:01, HLA-DQB1*06:02/HLA-DQA1*01:02, HLA-DQB1*06:04/HLA-DQA1*01:02, HLA-DRB1*01:01, HLA-DRB1*01:02, HLA-DRB1*03:01, HLA-DRB1*03:02, HLA-DRB1*04:01, HLA-DRB1*04:02, HLA-DRB1*04:03, HLA-DRB1*04:04, HLA-DRB1*04:05, HLA-DRB1*04:07, HLA-DRB1*07:01, HLA-DRB1*08:01, HLA-DRB1*08:02, HLA-DRB1*08:03, HLA-DRB1*08:04, HLA-DRB1*09:01, HLA-DRB1*10:01, HLA-DRB1*11:01, HLA-DRB1*11:02, HLA-DRB1*11:04, HLA-DRB1*12:01, HLA-DRB1*12:02, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16:01, HLA-DRB3*01:01, HLA-DRB3*02:02, HLA-DRB3*03:01, HLA-DRB4*01:01, HLA-DRB5*01:01). The peptides presented by the HLA protein may have a length of from 15-40 amino acids. The peptides presented by the HLA protein may have a length of at least 1, 2, 3, 4, 5, 6, 7, 8, 9, 10, 11, 12, 13, 14, 15, 16, 17, 18, 19, 20, 21, 22, 23, 24, 25, 26, 27, or greater amino acids. In some embodiments, the peptides presented by the HLA protein may have a length of at most 30, 29, 28, 27, 26, 25, 24, 23, 22, 21, 20, 19, 18, 17, 16, 15, 14, 13, 12, 11, or less amino acids.

The peptides presented by the HLA protein may comprise peptides identified by (a) isolating one or more HLA complexes from a cell line expressing a single HLA class II allele; (b) isolating one or more HLA-peptides from the one or more isolated HLA complexes; (c) obtaining MS/MS spectra for the one or more isolated HLA-peptides; and (d) obtaining a peptide sequence that corresponds to the MS/MS spectra of the one or more isolated HLA-peptides from a peptide database; wherein one or more sequences obtained from steps (a, b, c) and (d) identifies the sequence of the one or more isolated HLA-peptides.

The isolating may comprise isolating HLA-peptide complexes from the cells transfected or transduced with affinity tagged HLA constructs. In some embodiments, the complexes can be isolated using standard immunoprecipitation techniques known in the art with commercially available antibodies. The cells can be first lysed. HLA class II-peptide complexes can be isolated using HLA class II specific antibodies such as the M5/114.15.2 monoclonal antibody. In some embodiments, the single (or pair of) HLA alleles are expressed as a fusion protein with a peptide tag and the HLA-peptide complexes are isolated using binding molecules that recognize the peptide tags.

The isolating may comprise isolating peptides from the HLA-peptide complexes and sequencing the peptides. The peptides are isolated from the complex by any method known to one of skill in the art, such as acid elution. While any sequencing method can be used, methods employing mass spectrometry, such as liquid chromatography—mass spectrometry (LC-MS or LC-MS/MS, or alternatively HPLC-MS or HPLC-MS/MS) are utilized in some embodiments. These sequencing methods may be well-known to a skilled person and are reviewed in Medzihradszky K F and Chalkley R J. Mass Spectrom Rev. 2015 January-February; 34(1):43-63.

Additional candidate components and molecules suitable for isolation or purification may comprise binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes. Purification methods such as cation exchange chromatography can be used to separate conjugates by charge difference, which effectively separates conjugates into their various molecular weights. The content of the fractions obtained by cation exchange chromatography can be identified by molecular weight using conventional methods, for example, mass spectroscopy, SDS-PAGE, or other known methods for separating molecular entities by molecular weight.

In some embodiments, the method further comprises isolating peptides from the affinity acceptor tagged HLA-peptide complexes before the characterizing. In some embodiments, an HLA-peptide complex is isolated using an anti-HLA antibody. In some cases, an HLA-peptide complex with or without an affinity tag is isolated using an anti-HLA antibody. In some cases, a soluble HLA (sHLA) with or without an affinity tag is isolated from media of a cell culture. In some cases, a soluble HLA (sHLA) with or without an affinity tag is isolated using an anti-HLA antibody. For example, an HLA, such as a soluble HLA (sHLA) with or without an affinity tag, can be isolated using a bead or column containing an anti-HLA antibody. In some embodiments, the peptides are isolated using anti-HLA antibodies. In some cases, a soluble HLA (sHLA) with or without an affinity tag is isolated using an anti-HLA antibody. In some cases, a soluble HLA (sHLA) with or without an affinity tag is isolated using a column containing an anti-HLA antibody. In some embodiments, the method further comprises removing one or more amino acids from a terminus of a peptide bound to an affinity acceptor tagged HLA-peptide complex.

The personalized cancer vaccine may further comprise an adjuvant. For example, poly-ICLC, an agonist of TLR3 and the RNA helicase-domains of MDA5 and RIG3, has shown several desirable properties for a vaccine adjuvant. These properties may include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways may be seen in subjects vaccinated with poly-ICLC and in volunteers who had received the highly effective, replication-competent yellow fever vaccine. Furthermore, >90% of ovarian carcinoma patients immunized with poly-ICLC in combination with a NYESO-1 peptide vaccine (in addition to Montanide) showed induction of CD4+ and CD8+ T cell, as well as antibody responses to the peptide in a recent phase 1 study.

The personalized cancer vaccine may further comprise an immune checkpoint inhibitor. The immune checkpoint inhibitor may comprise a type of drug that blocks certain proteins made by some types of immune system cells, such as T cells, and some cancer cells. These proteins help keep immune responses in check and can keep T cells from killing cancer cells. When these proteins are blocked, the "brakes" on the immune system are released and T cells are able to kill cancer cells better. Examples of checkpoint proteins found on T cells or cancer cells include PD-1/PD-L1 and CTLA-4/B7-1/B7-2. Some immune checkpoint inhibitors are used to treat cancer.

The training data may further comprise structured data, time-series data, unstructured data, and relational data.

Unstructured data may comprise audio data, image data, video, mechanical data, electrical data, chemical data, and any combination thereof, for use in accurately simulating or training robotics or simulations. Time-series data may comprise data from one or more of a smart meter, a smart appliance, a smart device, a monitoring system, a telemetry device, or a sensor. Relational data comprises data from a customer system, an enterprise system, an operational system, a website, web accessible application program interface (API), or any combination thereof. This may be done by a user through any method of inputting files or other data formats into software or systems.

The training data may be uploaded to a cloud-based database. The cloud-based database may be accessible from local and/or remote computer systems on which the machine learning-based sensor signal processing algorithms are running. The cloud-based database and associated software may be used for archiving electronic data, sharing electronic data, and analyzing electronic data. The data or datasets generated locally may be uploaded to a cloud-based database, from which it may be accessed and used to train other machine learning-based detection systems at the same site or a different site. Sensor device and system test results generated locally may be uploaded to a cloud-based database and used to update the training data set in real time for continuous improvement of sensor device and detection system test performance.

The training may be performed using convolutional neural networks. The convolutional neural network (CNN) is described elsewhere herein. The convolutional neural networks may comprise at least two convolutional layers. The number of convolutional layers may be between 1-10 and the dilated layers between 0-10. The total number of convolutional layers (including input and output layers) may be at least about 1, 2, 3, 4, 5, 10, 15, 20, or greater, and the total number of dilated layers may be at least about 1, 2, 3, 4, 5, 10, 15, 20, or greater. The total number of convolutional layers may be at most about 20, 15, 10, 5, 4, 3 or less, and the total number of dilated layers may be at most about 20, 15, 10, 5, 4, 3 or less. In some embodiments, the number of convolutional layers is between 1-10 and the fully connected layers between 0-10. The total number of convolutional layers (including input and output layers) may be at least about 1, 2, 3, 4, 5, 10, 15, 20, or greater, and the total number of fully connected layers may be at least about 1, 2, 3, 4, 5, 10, 15, 20, or greater. The total number of convolutional layers may be at most about 20, 15, 10, 5, 4, 3 or less, and the total number of fully connected layers may be at most about 20, 15, 10, 5, 4, 3 or less.

The convolutional neural networks may comprise at least one batch normalization step. The batch normalization layer may improve the performance and stability of neural networks. The batch normalization layer may provide any layer in a neural network with inputs that are zero mean/unit variance. The total number of batch normalization layers may be at least about 3, 4, 5, 10, 15, 20 or more. The total number of batch normalization layers may be at most about 20, 15, 10, 5, 4, 3 or less The convolutional neural networks may comprise at least one spatial dropout step. The total number of spatial dropout steps may be at least about 3, 4, 5, 10, 15, 20 or more, and the total number of spatial dropout steps may be at most about 20, 15, 10, 5, 4, 3 or less.

The convolutional neural networks may comprise at least one global max pooling step. The global pooling layers may combine the outputs of neuron clusters at one layer into a single neuron in the next layer. For example, max pooling layers may use the maximum value from each of a cluster of neurons at the prior layer; and average pooling layers may use the average value from each of a cluster of neurons at the prior layer. The convolutional neural networks may comprise at least about 1, 2, 3, 4, 5, 10, 15, 20, or greater global max pooling steps. The convolutional neural networks may comprise at most about 20, 15, 10, 5, 4, 3 or less global max pooling steps.

The convolutional neural networks may comprise at least one dense layer. The convolutional neural networks may comprise at least about 1, 2, 3, 4, 5, 10, 15, 20, or greater dense layers. The convolutional neural networks may comprise at most about 20, 15, 10, 5, 4, 3 or less dense layers.

Therapeutic Methods

Personalized immunotherapy using tumor-specific peptides has been described. Tumor neoantigens, which arise as a result of genetic change (e.g., inversions, translocations, deletions, missense mutations, splice site mutations, etc.) within malignant cells, represent the most tumor-specific class of antigens. Neoantigens have rarely been used in cancer vaccine or immunogenic compositions due to technical difficulties in identifying them, selecting optimized antigens, and producing neoantigens for use in a vaccine or immunogenic composition. Efficiently choosing which particular peptides to utilize as an immunogen requires the ability to predict which tumor-specific peptides would efficiently bind to the HLA alleles present in a patient and would be effectively presented to the patient's immune system for inducing anti-tumor immunity. One of the critical barriers to developing curative and tumor-specific immunotherapy is the identification and selection of highly specific and restricted tumor antigens to avoid autoimmunity. This is particularly important in case of candidate tumor specific peptides for immunotherapy that are presented by MHC class II antigens, because there is a certain level of promiscuity in MHC class II-peptide binding and presentation to the immune system. At the same time, MHC class II presented peptides are required for activation of not only cytotoxic cells but also CD4+ve memory T cells. MHC class II mediated immunogenic response is therefore needed for a robust, offer long term immunogenicity for greater effectiveness in tumor protection. These problems can be addressed by: having a reliable peptide-MHC predicting algorithm and having a reliable system for assaying and validating the peptide-MHC interaction and immunogenicity. Therefore, in some embodiments, a highly efficient and immunogenic cancer vaccine may be produced by identifying candidate mutations in neoplasias/tumors which are present at the DNA level in tumor but not in matched germline samples from a high proportion of subjects having cancer; analyzing the identified mutations with one or more peptide-MHC binding prediction algorithms to identify which MHC (human leukocytic antigen or HLA in case of humans) bind to a high proportion of patient HLA alleles; and synthesizing the plurality of neoantigenic peptides selected from the sets of all neoantigen peptides and predicted binding peptides for use in a cancer vaccine or immunogenic composition suitable for treating a high proportion of subjects having cancer.

For example, translating peptide sequencing information into a therapeutic vaccine can include prediction of mutated peptides that can bind to HLA peptides of a high proportion of individuals. Efficiently choosing which particular mutations to utilize as immunogen requires the ability to predict which mutated peptides would efficiently bind to a high proportion of patient's HLA alleles. Recently, neural network based learning approaches with validated binding and non-binding peptides have advanced the accuracy of prediction algorithms for the major HLA-A and -B alleles. However, although using advanced neural network-based algorithms has helped to encode HLA-peptide binding rules, several factors limit the power to predict peptides presented on HLA alleles.

For example, translating peptide sequencing information into a therapeutic vaccine can include formulating the drug as a multi-epitope vaccine of long peptides. Targeting as many mutated epitopes as practically possible takes advantage of the enormous capacity of the immune system, prevents the opportunity for immunological escape by down-modulation of an immune targeted gene product, and compensates for the known inaccuracy of epitope prediction approaches. Synthetic peptides provide a useful means to prepare multiple immunogens efficiently and to rapidly translate identification of mutant epitopes to an effective vaccine. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens).

For example, translating peptide sequencing information into a therapeutic vaccine can include a combination with a strong vaccine adjuvant. Effective vaccines can require a strong adjuvant to initiate an immune response. For example, poly-ICLC, an agonist of TLR3 and the RNA helicase-domains of MDA5 and RIG3, has shown several desirable properties for a vaccine adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NYESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile.

In some embodiments, immunogenic peptides can be identified from cells from a subject with a disease or condition. In some embodiments, immunogenic peptides can be specific to a subject with a disease or condition. In some embodiments, immunogenic peptides can bind to an HLA that is matched to an HLA haplotype of a subject with a disease or condition.

In some embodiments, a library of peptides can be expressed in the cells. In some embodiments, the cells comprise the peptides to be identified or characterized. In some embodiments, the peptides to be identified or characterized are endogenous peptides. In some embodiments, the peptides are exogenous peptides. For example, the peptides to be identified or characterized can be expressed from a plurality of sequences encoding a library of peptides.

Prior to disclosure of the instant specification, the majority of LC-MS/MS studies of the HLA peptidome have used cells expressing multiple HLA peptides, which requires peptides to be assigned to 1 of up to 6 HLA class I alleles using pre-existing bioinformatic predictors or "deconvolution" (Bassani-Sternberg and Gfeller, 2016). Thus, peptides that do not closely match known motifs could not confidently be reported as binders to a given HLA allele.

Provided herein are methods of prediction of peptides, such as mutated peptides, that can bind to HLA peptides of individuals. In some embodiments, the application provides methods of identifying from a given set of antigen comprising peptides the most suitable peptides for preparing an immunogenic composition for a subject, said method comprising selecting from a given set of peptides the plurality of peptides capable of binding an HLA protein of the subject, wherein said ability to bind an HLA protein is determined by analyzing the sequence of peptides with a machine which has been trained with peptide sequence databases corresponding to the specific HLA-binding peptides for each of the HLA-alleles of said subject. Provided herein are methods of identifying from a given set of antigen comprising peptides the most suitable peptides for preparing an immunogenic composition for a subject, said method comprising selecting from a given set of peptides the plurality of peptides determined as capable of binding an HLA protein of the subject, ability to bind an HLA protein is determined by analyzing the sequence of peptides with a machine which has been trained with a peptide sequence database obtained by carrying out the methods described herein above. Thus, in some embodiments, the present disclosure provides methods of identifying a plurality of subject-specific peptides for preparing a subject-specific immunogenic composition, wherein the subject has a tumor and the subject-specific peptides are specific to the subject and the subject's tumor, said method comprising: sequencing a sample of the subject's tumor and a non-tumor sample of the subject; determining based on the nucleic acid sequencing: non-silent mutations present in the genome of cancer cells of the subject but not in normal tissue from the subject, and the HLA genotype of the subject; and selecting from the identified non-silent mutations the plurality of subject-specific peptides, each having a different tumor epitope that is specific to the tumor of the subject and each being identified as capable of binding an HLA protein of the subject, as determined by analyzing the sequence of peptides derived from the non-silent mutations in the methods for predicting HLA binding described herein.

In some embodiments, disclosed herein, is a method of characterizing HLA-peptide complexes specific to an individual.

In some embodiments, a method of characterizing HLA-peptide complexes specific to an individual is used to develop an immunotherapeutic in an individual in need thereof, such as a subject with a condition or disease.

Provided herein is a method of providing an anti-tumor immunity in a mammal comprising administering to the mammal a polynucleic acid comprising a sequence encoding a peptide identified according to a method described. Provided herein is a method of providing an anti-tumor immunity in a mammal comprising administering to the mammal an effective amount of a peptide with a sequence of a peptide identified according to a method described herein. Provided herein is a method of providing an anti-tumor immunity in a mammal comprising administering to the mammal a cell comprising a peptide comprising the sequence of a peptide identified according to a method described herein. Provided herein is a method of providing an anti-tumor immunity in a mammal comprising administering to the mammal a cell comprising a polynucleic acid comprising a sequence encoding a peptide comprising the sequence of peptide identified according to a method described herein. In some embodiments, the cell presents the peptide as an HLA-peptide complex.

Provided herein is a method of treating a disease or disorder in a subject, the method comprising administering to the subject a polynucleic acid comprising a sequence encoding a peptide identified according to a method described herein. Provided herein is a method of treating a disease or disorder in a subject, the method comprising administering to the subject an effective amount of a peptide comprising the sequence of a peptide identified according to a method described herein. Provided herein is a method of treating a disease or disorder in a subject, the method comprising administering to the subject a cell comprising a peptide comprising the sequence of a peptide identified according to a method described herein. Provided herein is a method of treating a disease or disorder in a subject, the method comprising administering to the subject a cell comprising a polynucleic acid comprising a sequence encoding a peptide comprising the sequence of a peptide identified according to a method described herein. In some embodiments, the disease or disorder is cancer. In some embodiments, the method further comprises administering an immune checkpoint inhibitor to the subject.

Disclosed herein, in some embodiments, are methods of developing an immunotherapeutic for an individual in need thereof by characterizing HLA-peptide complexes comprising: a) providing a population of cells derived from the individual in need thereof wherein one or more cells of the population of cells comprise a polynucleic acid comprising a sequence encoding an affinity acceptor tagged HLA class I or HLA class II allele, wherein the sequence encoding an affinity acceptor tagged HLA comprises: i) a sequence encoding a recombinant HLA class I or HLA class II allele operatively linked to ii) a sequence encoding an affinity acceptor peptide; b) expressing the affinity acceptor tagged HLA in at least one cell of the one or more cells of the population of cells, thereby forming affinity acceptor tagged HLA-peptide complexes in the at least one cell; c) enriching for the affinity acceptor tagged HLA-peptide complexes, characterizing HLA-peptide complexes specific to the individual in need thereof; and d) developing the immunotherapeutic based on an HLA-peptide complex specific to the individual in need thereof; wherein the individual has a disease or condition.

In some embodiments, the immunotherapeutic is a nucleic acid or a peptide therapeutic.

In some embodiments, the method comprises introducing one or more peptides to the population of cells. In some embodiments, the method comprises contacting the population of cells with the one or more peptides or expressing the one or more peptides in the population of cells. In some embodiments, the method comprises contacting the population of cells with one or more nucleic acids encoding the one or more peptides.

In some embodiments, the method comprises developing an immunotherapeutic based on peptides identified in connection with the patient-specific HLAs. In some embodiments, the population of cells is derived from the individual in need thereof.

In some embodiments, the method comprises expressing a library of peptides in the population of cells. In some embodiments, the method comprises expressing a library of affinity acceptor tagged HLA-peptide complexes. In some embodiments, the library comprises a library of peptides associated with the disease or condition. In some embodiments, the disease or condition is cancer or an infection with an infectious agent or an autoimmune disease. In some embodiments, the method comprises introducing the infectious agent or portions thereof into one or more cells of the population of cells. In some embodiments, the method comprises characterizing one or more peptides from the HLA-peptide complexes specific to the individual in need thereof, optionally wherein the peptides are from one or more target proteins of the infectious agent or the autoimmune disease. In some embodiments, the method comprises characterizing one or more regions of the peptides from the one or more target proteins of the infectious agent or autoimmune disease. In some embodiments, the method comprises identifying peptides from the HLA-peptide complexes derived from an infectious agent or an autoimmune disease.

In some embodiments, the infectious agent is a pathogen. In some embodiments, the pathogen is a virus, bacteria, or a parasite.

In some embodiments, the virus is selected from the group consisting of: BK virus (BKV), Dengue viruses (DENV-1, DENV-2, DENV-3, DENV-4, DENV-5), cytomegalovirus (CMV), Hepatitis B virus (HBV), Hepatitis C virus (HCV), Epstein-Barr virus (EBV), an adenovirus, human immunodeficiency virus (HIV), human T cell lymphotrophic virus (HTLV-1), an influenza virus, RSV, HPV, rabies, mumps rubella virus, poliovirus, yellow fever, hepatitis A, hepatitis B, Rotavirus, varicella virus, human papillomavirus (HPV), smallpox, zoster, and combinations thereof.

In some embodiments, the bacteria is selected from the group consisting of: *Klebsiella* spp., *Tropheryma whipplei*, *Mycobacterium leprae*, *Mycobacterium lepromatosis*, and *Mycobacterium tuberculosis*. In some embodiments, the bacteria is selected from the group consisting of: typhoid, pneumococcal, meningococcal, *Haemophilus* B, anthrax, tetanus toxoid, meningococcal group B, bcg, cholera, and combinations thereof.

In some embodiments, the parasite is a helminth or a protozoan. In some embodiments, the parasite is selected from the group consisting of: *Leishmania* spp. (e.g. *L. major, L. infantum, L. braziliensis, L. donovani, L. chagasi, L. mexicana*), *Plasmodium* spp. (e.g. *P. falciparum, P. vivax, P. ovale, P. malariae*), *Trypanosoma cruzi, Ascaris lumbricoides, Trichuris trichiura, Necator americanus*, and *Schistosoma* spp. (*S. mansoni, S. haematobium, S. japonicum*).

In some embodiments, the immunotherapeutic is an engineered receptor. In some embodiments, the engineered receptor is a chimeric antigen receptor (CAR), a T cell receptor (TCR), or a B cell receptor (BCR), an adoptive T cell therapy (ACT), or a derivative thereof. In other aspects, the engineered receptor is a chimeric antigen receptor (CAR). In some aspects, the CAR is a first generation CAR. In other aspects, the CAR is a second generation CAR. In still other aspects, the CAR is a third generation CAR.

In some aspects, the CAR comprises an extracellular portion, a transmembrane portion, and an intracellular portion. In some aspects, the intracellular portion comprises at least one T cell co-stimulatory domain. In some aspects, the T cell co-stimulatory domain is selected from the group consisting of CD27, CD28, TNFRS9 (4-1BB), TNFRSF4 (OX40), TNFRSF8 (CD30), CD40LG (CD40L), ICOS, ITGB2 (LFA-1), CD2, CD7, KLRC2 (NKG2C), TNFRS18 (GITR), TNFRSF14 (HVEM), or any combination thereof.

In some aspects, the engineered receptor binds a target. In some aspects, the binding is specific to a peptide identified from the method of characterizing HLA-peptide complexes specific to an individual suffering from a disease or condition.

In some aspects, the immunotherapeutic is a cell as described in detail herein. In some aspects, the immunotherapeutic is a cell comprising a receptor that specifically binds a peptide identified from the method characterizing HLA-peptide complexes specific to an individual suffering from a disease or condition. In some aspects, the immunotherapeutic is a cell used in combination with the peptides/nucleic acids of this invention. In some embodiments, the cell is a patient cell. In some embodiments, the cell is a T cell. In some embodiments, the cell is tumor infiltrating lymphocyte.

In some aspects, a subject with a condition or disease is treated based on a T cell receptor repertoire of the subject. In some embodiments, an antigen vaccine is selected based on a T cell receptor repertoire of the subject. In some embodiments, a subject is treated with T cells expressing TCRs specific to an antigen or peptide identified using the methods described herein. In some embodiments, a subject is treated with an antigen or peptide identified using the methods described herein specific to TCRs, e.g., subject specific TCRs. In some embodiments, a subject is treated with an antigen or peptide identified using the methods described herein specific to T cells expressing TCRs, e.g., subject specific TCRs. In some embodiments, a subject is treated with an antigen or peptide identified using the methods described herein specific to subject specific TCRs.

In some embodiments, an immunogenic antigen composition or vaccine is selected based on TCRs identified in a subject. In one embodiment, identifying a T cell repertoire and testing it in functional assays is used to determine an immunogenic composition or vaccine to be administered to a subject with a condition or disease. In some embodiments, the immunogenic composition is an antigen vaccine. In some embodiments, the antigen vaccine comprises subject specific antigen peptides. In some embodiments, antigen peptides to be included in an antigen vaccine are selected based on a quantification of subject specific TCRs that bind to the antigens. In some embodiments, antigen peptides are selected based on a binding affinity of the peptide to a TCR. In some embodiments, the selecting is based on a combination of both the quantity and the binding affinity. For example, a TCR that binds strongly to an antigen in a functional assay but is not highly represented in a TCR repertoire can be a good candidate for an antigen vaccine because T cells expressing the TCR would be advantageously amplified.

In some embodiments, antigens are selected for administering to a subject based on binding to TCRs. In some embodiments, T cells, such as T cells from a subject with a disease or condition, can be expanded. Expanded T cells that express TCRs specific to an immunogenic antigen peptide identified using the method described herein can be administered back to a subject. In some embodiments, suitable cells, e.g., PBMCs, are transduced or transfected with polynucleotides for expression of TCRs specific to an immunogenic antigen peptide identified using the method described herein and administered to a subject. T cells expressing TCRs specific to an immunogenic antigen peptide identified using the method described herein can be expanded and administered back to a subject. In some embodiments, T cells that express TCRs specific to an immunogenic antigen peptide identified using the method described herein that result in cytolytic activity when incubated with autologous diseased tissue can be expanded and administered to a subject. In some embodiments, T cells used in functional assays result in binding to an immunogenic antigen peptide identified using the method described herein can be expanded and administered to a subject. In some embodiments, TCRs that have been determined to bind to subject specific immunogenic antigen peptides identified using the method described herein can be expressed in T cells and administered to a subject.

The methods described herein can involve adoptive transfer of immune system cells, such as T cells, specific for selected antigens, such as tumor or pathogen associated antigens. Various strategies can be employed to genetically modify T cells by altering the specificity of the T cell receptor (TCR), for example by introducing new TCR α- and β-chains with specificity to an immunogenic antigen peptide identified using the method described herein (see, e.g., U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

Chimeric antigen receptors (CARs) can be used to generate immunoresponsive cells, such as T cells, specific for selected targets, such a immunogenic antigen peptides identified using the method described herein, with a wide variety of receptor chimera constructs (see, e.g., U.S. Pat. Nos. 5,843,728; 5,851,828; 5,912, 170; 6,004,811; 6,284,240; 6,392,013; 6,410,014; 6,753,162; 8,211,422; and, PCT Publication WO9215322).

Alternative CAR constructs can be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3 or FcRy or scFv-FcRy (see, e.g., U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain, e.g., scFv-CD28/OX40/4-1BB-CD3 (see, e.g., U.S. Pat. Nos. 8,911,993; 8,916,381; 8,975,071; 9,101,584; 9,102,760; 9,102,761). Third-generation CARs include a combination of costimulatory endodomains, such a CD3C-chain, CD97, GDI 1a-CD18, CD2, ICOS, CD27, CD154, CDS, OX40, 4-1BB, or CD28 signaling domains, e.g., scFv-CD28-4-1BB-CD3C or scFv-CD28-OX40-CD3Q (see, e.g., U.S. Pat. Nos. 8,906,682; 8,399,645; 5,686,281; PCT Publication No. WO2014134165; PCT Publication No. WO2012079000). In some embodiments, costimulation can be coordinated by expressing CARs in antigen-specific T cells, chosen so as to be activated and expanded following, for example, interaction with antigen on professional antigen-presenting cells, with costimulation. Additional engineered receptors can be provided on the immunoresponsive cells, e.g., to improve targeting of a T cell attack and/or minimize side effects.

Alternative techniques can be used to transform target immunoresponsive cells, such as protoplast fusion, lipofection, transfection or electroporation. A wide variety of vectors can be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), can be used to introduce CARs, for example using 2nd generation antigen-specific CARs signaling through CD3 and either CD28 or CD137. Viral vectors can, for example, include vectors based on HIV, SV40, EBV, HSV or BPV.

Cells that are targeted for transformation can, for example, include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells can be differentiated. T cells expressing a desired CAR can, for example, be selected through co-culture with γ-irradiated activating and propagating cells (APC), which co-express the cancer antigen and co-stimulatory molecules. The engineered CAR T cells can be expanded, for example, by co-culture on APC in presence of soluble factors, such as IL-2 and IL-21. This expansion can, for example, be carried out so as to provide memory CAR T cells (which, for example, can be assayed by non-enzymatic digital array and/or multi-panel flow cytometry). In this way, CAR T cells that have specific cytotoxic activity against antigen-bearing tumors can be provided (optionally in conjunction with production of desired chemokines such as interferon-γ). CAR T cells of this kind can, for example, be used in animal models, for example to threaten tumor xenografts.

Approaches such as the foregoing can be adapted to provide methods of treating and/or increasing survival of a subject having a disease, such as a neoplasia or pathogenic infection, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction). Dosing in CAR T cell therapies can, for example, involve administration of from 106 to 109 cells/kg, with or without a course of lymphodepletion, for example with cyclophosphamide.

To guard against possible adverse reactions, engineered immunoresponsive cells can be equipped with a transgenic safety switch in the form of a transgene that renders the cells vulnerable to exposure to a specific signal. For example, the herpes simplex viral thymidine kinase (TK) gene can be used in this way, for example by introduction into allogeneic T lymphocytes used as donor lymphocyte infusions following stem cell transplantation. In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see, e.g., U.S. Patent Publication No. 20130071414; PCT Patent Publication WO2011146862; PCT Patent Publication WO201401 1987; PCT Patent Publication WO2013040371). In a further refinement of adoptive therapies, genome editing can be used to tailor immunoresponsive cells to alternative implementations, for example providing edited CAR T cells.

Cell therapy methods can also involve the ex vivo activation and expansion of T cells. In some embodiments, T cells can be activated before administering them to a subject in need thereof. Examples of these type of treatments include the use tumor infiltrating lymphocyte (TIL) cells (see U.S. Pat. No. 5,126,132), cytotoxic T cells (see U.S. Pat. Nos. 6,255,073; and 5,846,827), expanded tumor draining lymph node cells (see U.S. Pat. No. 6,251,385), and various other lymphocyte preparations (see U.S. Pat. Nos. 6,194,207; 5,443,983; 6,040,177; and 5,766,920).

An ex vivo activated T cell population can be in a state that maximally orchestrates an immune response to cancer, infectious diseases, or other disease states, e.g., an autoimmune disease state. For activation, at least two signals can be delivered to the T cells. The first signal is normally delivered through the T cell receptor (TCR) on the T cell surface. The TCR first signal is normally triggered upon interaction of the TCR with peptide antigens expressed in conjunction with an MHC complex on the surface of an antigen-presenting cell (APC). The second signal is normally delivered through co-stimulatory receptors on the surface of T cells. Co-stimulatory receptors are generally triggered by corresponding ligands or cytokines expressed on the surface of APCs.

It is contemplated that the T cells specific to immunogenic antigen peptides identified using the method described herein can be obtained and used in methods of treating or preventing disease. In this regard, the disclosure provides a method of treating or preventing a disease or condition in a subject, comprising administering to the subject a cell population comprising cells specific to immunogenic antigen peptides identified using the method described herein in an amount effective to treat or prevent the disease in the subject. In some embodiments, a method of treating or preventing a disease in a subject, comprises administering a cell population enriched for disease-reactive T cells to a subject in an amount effective to treat or prevent cancer in the mammal. The cells can be cells that are allogeneic or autologous to the subject.

The disclosure further provides a method of inducing a disease specific immune response in a subject, vaccinating against a disease, treating and/or alleviating a symptom of a disease in a subject by administering the subject an antigenic peptide or vaccine.

The peptide or composition of the disclosure can be administered in an amount sufficient to induce a CTL response. An antigenic peptide or vaccine composition can be administered alone or in combination with other therapeutic agents. Exemplary therapeutic agents include, but are not limited to, a chemotherapeutic or biotherapeutic agent, radiation, or immunotherapy. Any suitable therapeutic treatment for a particular disease can be administered. Examples of chemotherapeutic and biotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol®), pilocarpine, prochloroperazine, rituximab, tamoxifen, taxol, topotecan hydrochloride, trastuzumab, vinblastine, vincristine and vinorelbine tartrate. In addition, the subject can be further administered an anti-immunosuppressive or immunostimulatory agent. For example, the subject can be further administered an anti-CTLA antibody or anti-PD-1 or anti-PD-L1.

The amount of each peptide to be included in a vaccine composition and the dosing regimen can be determined by one skilled in the art. For example, a peptide or its variant can be prepared for intravenous (i.v.) injection, sub-cutaneous (s.c.) injection, intradermal (i.d.) injection, intraperitoneal (i.p.) injection, intramuscular (i.m.) injection. Exemplary methods of peptide injection include s.c, i.d., i.p., i.m., and i.v. Exemplary methods of DNA injection include i.d., i.m., s.c, i.p. and i.v. Other methods of administration of the vaccine composition are known to those skilled in the art.

A pharmaceutical composition can be compiled such that the selection, number and/or amount of peptides present in the composition is/are disease and/or patient-specific. For example, the exact selection of peptides can be guided by expression patterns of the parent proteins in a given tissue to avoid side effects. The selection can be dependent on the specific type of disease, the status of the disease, earlier treatment regimens, the immune status of the patient, and the HLA-haplotype of the patient. Furthermore, the vaccine according to the present disclosure can contain individualized components, according to personal needs of the particular patient. Examples include varying the amounts of peptides according to the expression of the related antigen in the particular patient, unwanted side-effects due to personal allergies or other treatments, and adjustments for secondary treatments following a first round or scheme of treatment.

Computer Control Systems

Figure 10:
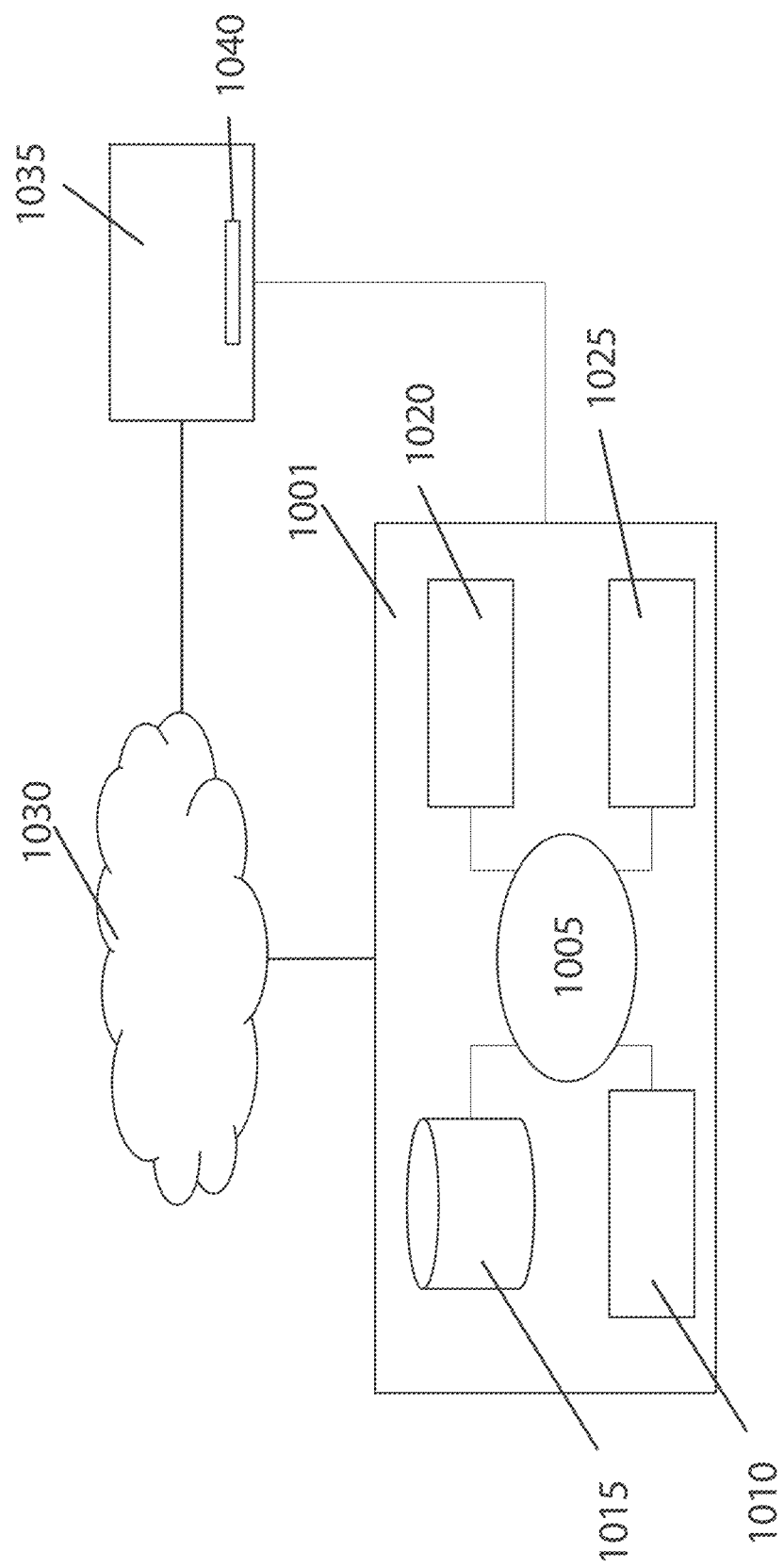
FIG. 10 depicts an exemplary computer control system that is programmed or otherwise configured to implement methods provided herein.

The present disclosure provides computer control systems that are programmed to implement methods of the disclosure. FIG. 10 shows a computer system (1001) that is programmed or otherwise configured to train a machine-learning HLA-peptide presentation prediction model. The computer system (1001) can regulate various aspects of the present disclosure, such as, for example, inputting amino acid position information, transferring imputed information into datasets, and generating a trained algorithm with the datasets. The computer system (1001) can be an user electronic device or a remote computer system. The electronic device can be a mobile electronic device.

The computer system (1001) includes a central processing unit (CPU, also "processor" and "computer processor" herein) (1005), which can be a single core or multi core processor, either through sequential processing or parallel processing. The computer system (1001) also includes a memory unit or device (1010) (e.g., random-access memory, read-only memory, flash memory), a storage unit (1015) (e.g., hard disk), a communication interface (1020) (e.g., network adapter) for communicating with one or more other systems, and peripheral devices (1025), either external or internal or both, such as a printer, monitor, USB drive and/or CD-ROM drive. The memory (1010), storage unit (1015), interface (1020) and peripheral devices (1025) are in communication with the CPU (1005) through a communication bus (solid lines), such as a motherboard. The storage unit (1015) can be a data storage unit (or data repository) for storing data. The computer system (1001) can be operatively coupled to a computer network ("network") (1030) with the aid of the communication interface (1020). The network (1030) can be the Internet, an internet and/or extranet, or an intranet and/or extranet that is in communication with the Internet. The network (1030) in some cases is a telecommunication and/or data network. The network (1030) can include one or more computer servers, which can enable a peer-to-peer network that supports distributed computing. The network (1030), in some cases with the aid of the computer system (1001), can implement a client-server structure, which may enable devices coupled to the computer system (1001) to behave as a client or a server.

The CPU (1005) can execute a sequence of machine-readable instructions, which can be embodied in a program or software. The instructions may be stored in memory (1010). The instructions can be directed to the CPU (1005), which can subsequently program or otherwise configure the CPU (1005) to implement methods of the present disclosure. Examples of operations performed by the CPU (1005) can include fetch, decode, execute, and writeback.

The CPU (1005) can be part of a circuit, such as an integrated circuit. One or more other components of the system (1001) can be included in the circuit. In some cases, the circuit is an application specific integrated circuit (ASIC).

The storage unit (1015) can store files, such as drivers, libraries and saved programs. The storage unit (1015) can store user data, e.g., user preferences and user programs. The computer system (1001) in some cases can include one or more additional data storage units that are external to the computer system (1001), such as located on a remote server that is in communication with the computer system (1001) through an intranet or the Internet.

The computer system (1001) can communicate with one or more remote computer systems through the network (1030). For instance, the computer system (1001) can communicate with a remote computer system or user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system (1001) via the network (1030).

Methods as described herein can be implemented by way of machine (e.g., computer processor) executable code stored on an electronic storage location of the computer system (1001), such as, for example, in memory (1010) or a data storage unit (1015). The machine executable or machine readable code can be provided in the form of software. During use, the code can be executed by the processor (1005). In some cases, the code can be retrieved from the storage unit (1015) and stored in memory (1010) for ready access by the processor (1005). In some situations, the storage unit (1015) can be precluded, and machine-executable instructions are stored in memory (1010).

The code can be pre-compiled and configured for use with a machine having a processer adapted to execute the code, or it can be compiled during runtime. The code can be supplied in a programming language that can be selected to enable the code to execute in a pre-compiled or as-compiled fashion.

Aspects of the systems and methods provided herein, such as the computer system (1001), can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on a storage unit, such as a hard disk, or in memory (e.g., read-only memory, random-access memory, flash memory). "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system (1001) can include or be in communication with an electronic display (1035) that comprises a user interface (UI) (1040) for providing, for example, probability that one or more proteins encoded by a class II MHC allele of a cancer cell of the subject will present a given sequence of a peptide sequence identified. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit (1005). The algorithm can, for example, input amino acid position information, transfer imputed information into datasets, and generate a trained algorithm with the datasets.

EXAMPLES

The examples provided below are for illustrative purposes only and do not limit the scope of the claims provided herein.

Example 1. HLA Class II Binding Predictor Performance

Figure 4:
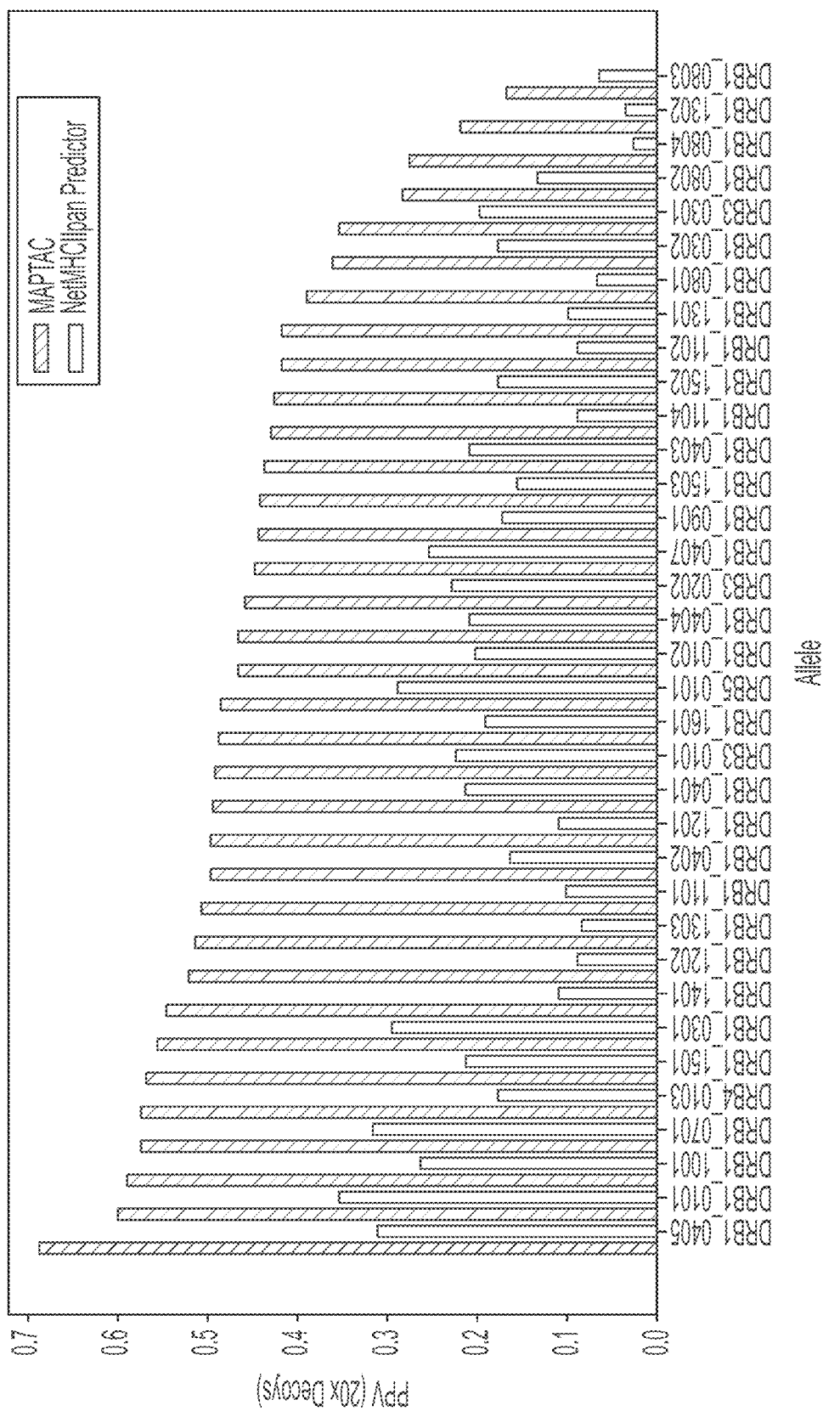
FIG. 4 is an exemplary depiction of the HLA class II binding predictor performance.

In this example, a validation dataset comprising observed mass spec peptides and decoy peptides which are generated at a ratio of 1:19 (hits:decoys) by randomly shuffling the hit peptides were used to analyze the performance of the binding predictor neonmhc2 (NEON) and NetMHCIIpan (FIG. 4). For the NEON binding predictor, a separate model was built for each MHC II allele shown. The height of the bars showed the positive predictive value (PPV). The alleles are sorted by the model's performance when predicting for that allele. The NEON binding predictor showed higher PPV across all the alleles when compared with NetMHCIIpan.

Figure 5:
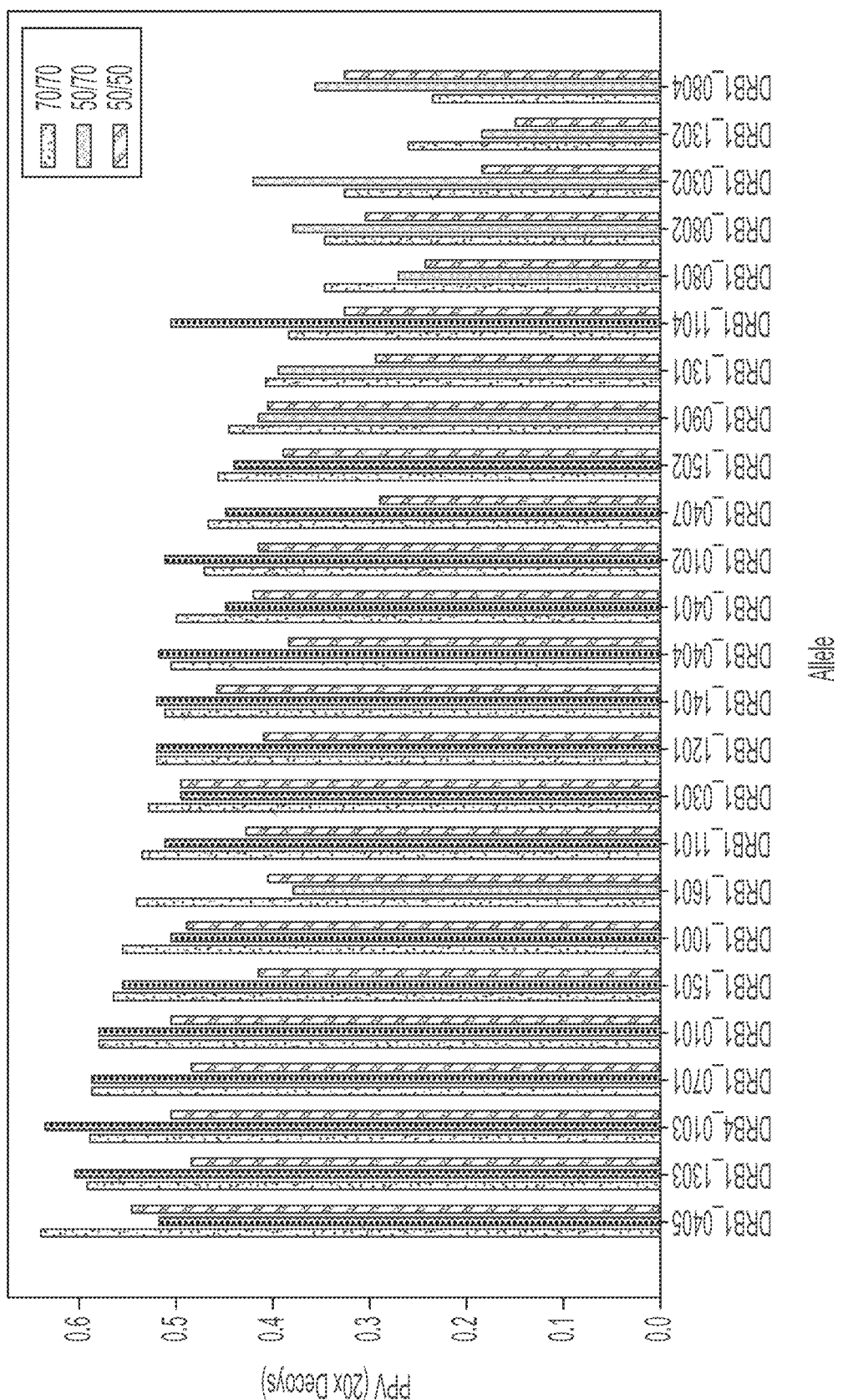
FIG. 5 depicts an exemplary effect of scored peak intensity (SPI) thresholds on binding predictor validation.

In this example, the effect of SPI thresholds on binding predictor validation was also tested (FIG. 5). The performance of the HLA class II binding predictor was shown when trained/validated on sets of peptides with different scored peak intensity (SPI) cutoffs. The different SPI cutoffs conditions were used: trained and evaluated on datasets using observed MS hit peptides of larger than or equal to 70 SPI, trained on peptides with larger than or equal to 50 SPI and validated on peptides with larger than or equal to 70 SPI, and trained and validated on peptides with larger than or equal to 50 SPI.

Figure 6:
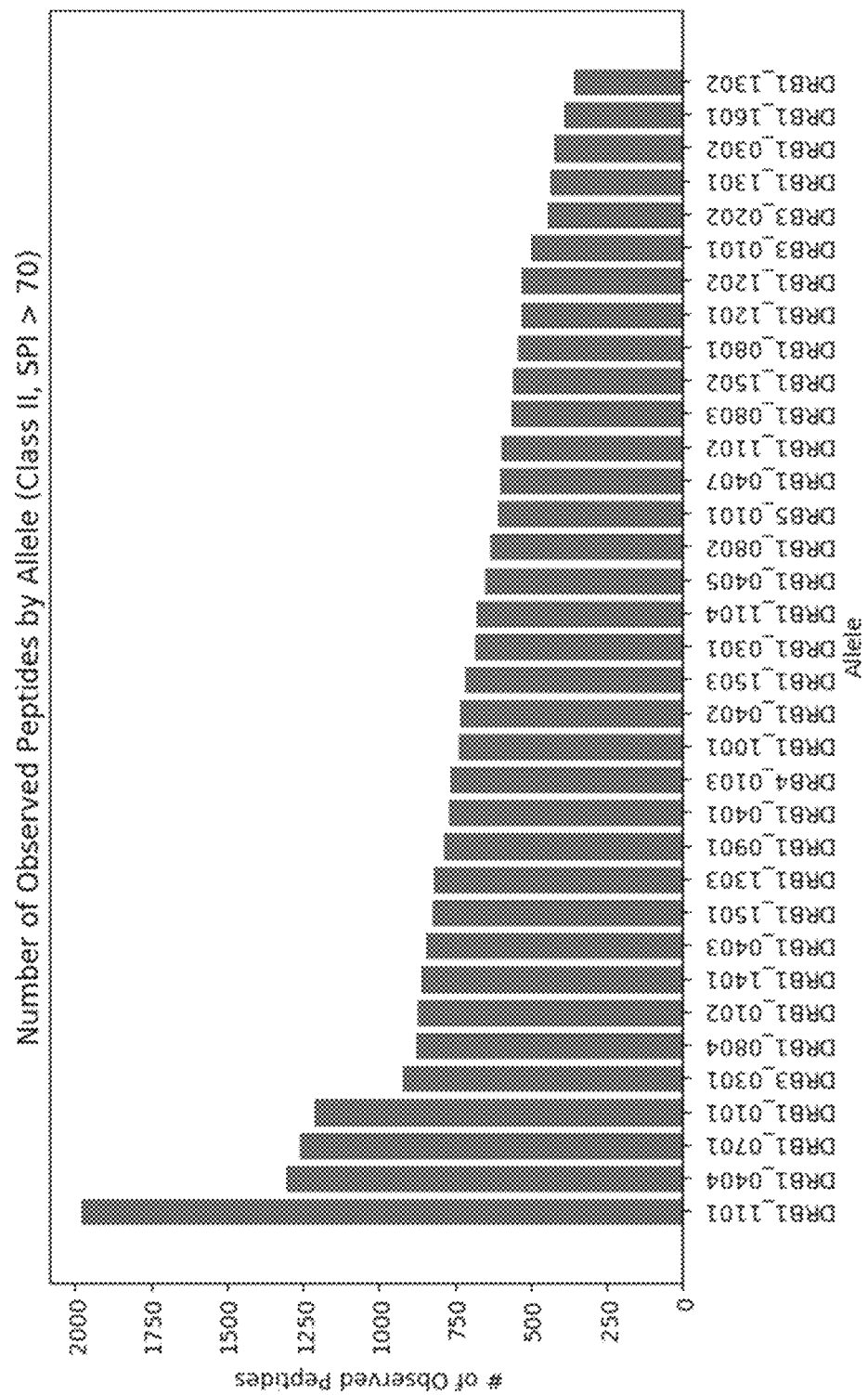
FIG. 6 depicts an exemplary bar plot showing representative data from number of observed peptides by allele profiling by LC-MS/MS with larger than or equal to 70 scored peak intensity (SPI) cutoffs. Each bar represents the total number of observed peptides of an allele. There are collected data for 35 HLA-DR alleles. The collected data for 35 HLA-DR alleles have >95% population coverage for HLA-DR (USA allele frequencies).

In this example, data for 35 HLA-DR alleles, which had >95% population coverage for HLA-DR (USA allele frequencies), were collected to show the number of observed peptides by allele profiling by LC-MS/MS with larger than or equal to 70 scored peak intensity (SPI) cutoffs (FIG. 6).

Figure 7A:
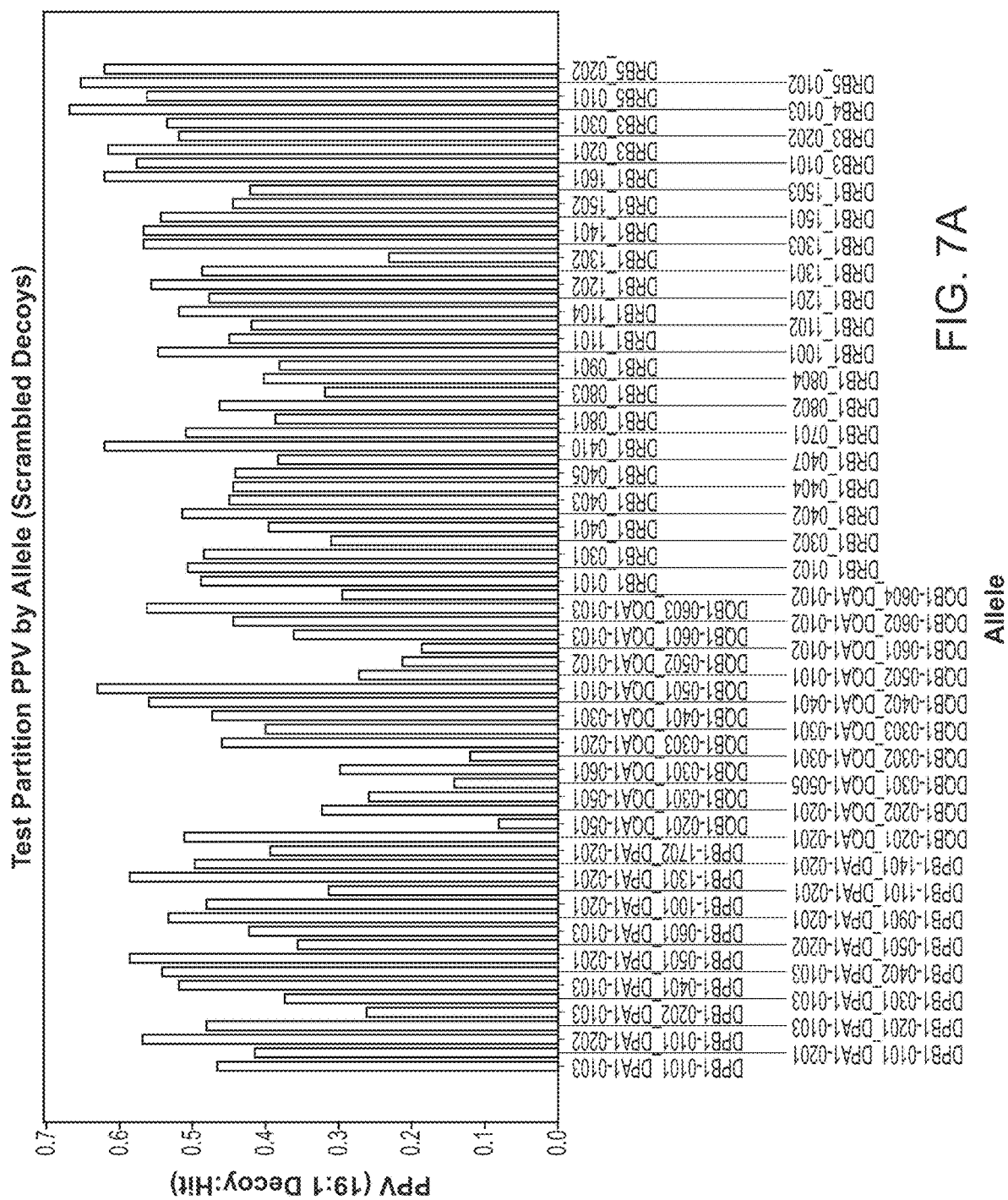
FIG. 7A shows the PPV of the model when applied to test partition of data for the indicated HLA class II alleles. The decoy peptides used were scrambled sequences of the positive (hit) peptide sequences at a hit to decoy ratio of 1:19. PPV was determined by identifying the top-scoring 5% of peptides in the test partition and determining the fraction of them that were positive for binding to the protein encoded by the respective HLA class II allele.

In one exemplary set up, a model PPV analysis was applied to test partition data for each class II allele that were generated thus far for Neonmhc2 program. The test partition data was composed of positive example (e.g. a hit sample peptide) that are MS-observed class II binders and negative examples (e.g. a decoy sample peptide) that are scrambled versions of the positive examples. The hit: decoy ratio was kept 1:19, for example, for each positive sample, 19 negative samples were included (i.e., 5% positive sample) and test partition was performed for validation. PPV scores were generated by selecting the best-scoring 5% of the peptides, in the test partition and interrogating what fraction of those are positive. Results are indicated in FIG. 7A.

Figure 7B:
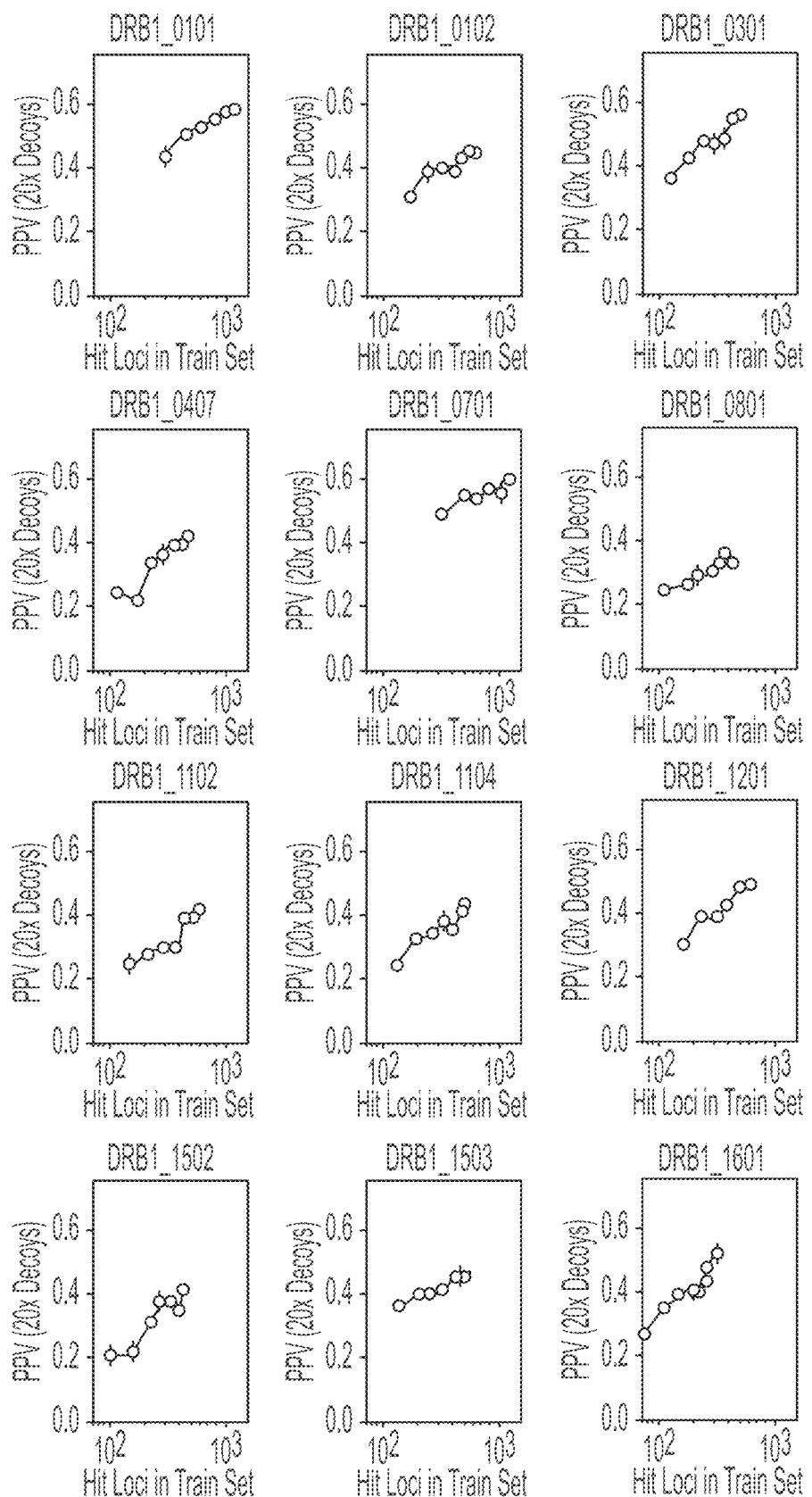
FIGS. 7B-7D depict exemplary prediction performance as a function of training set size (curves obtained by artificially down-sampling the training set).
Figure 7C:
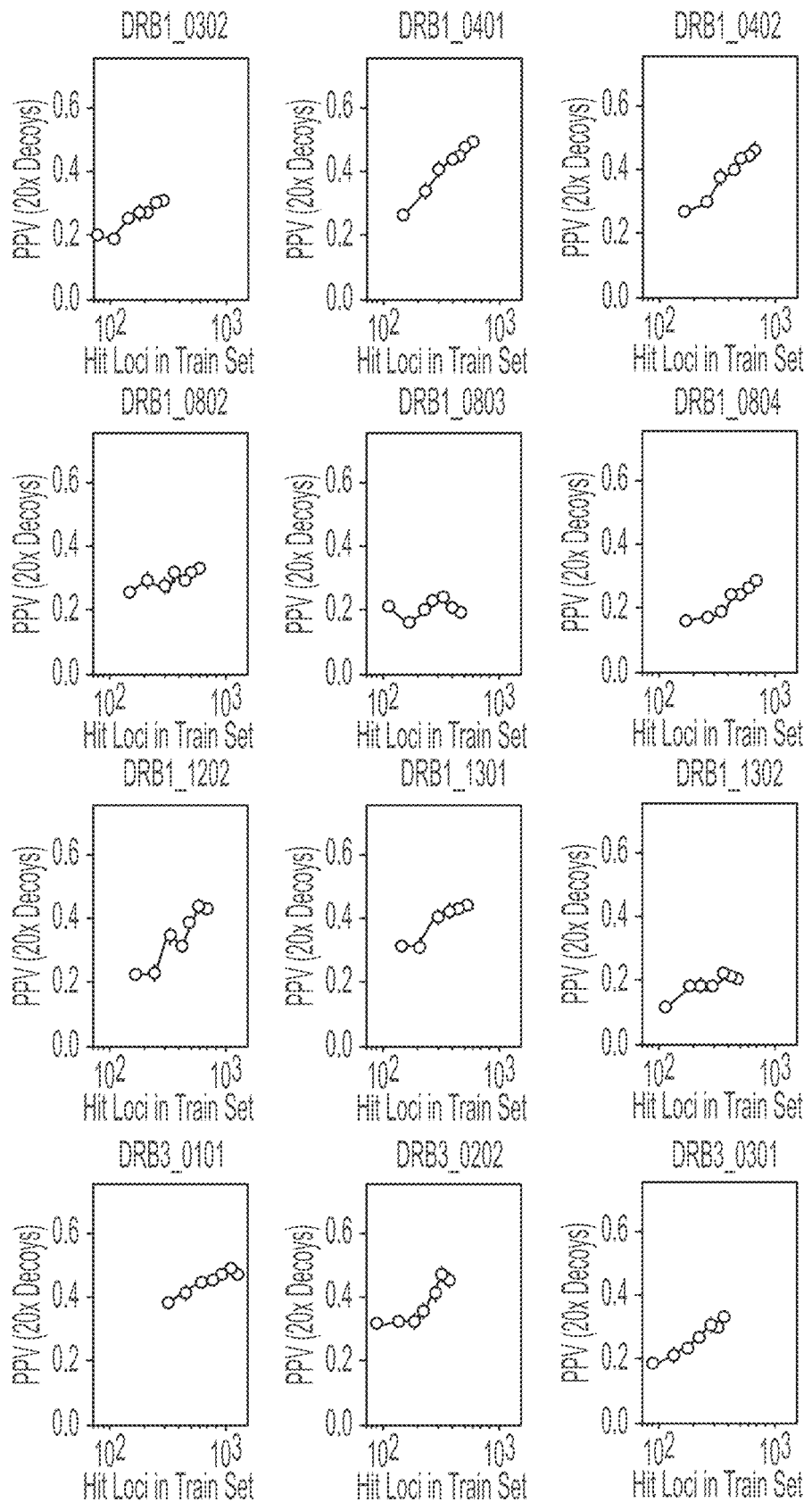
Figure 7D:
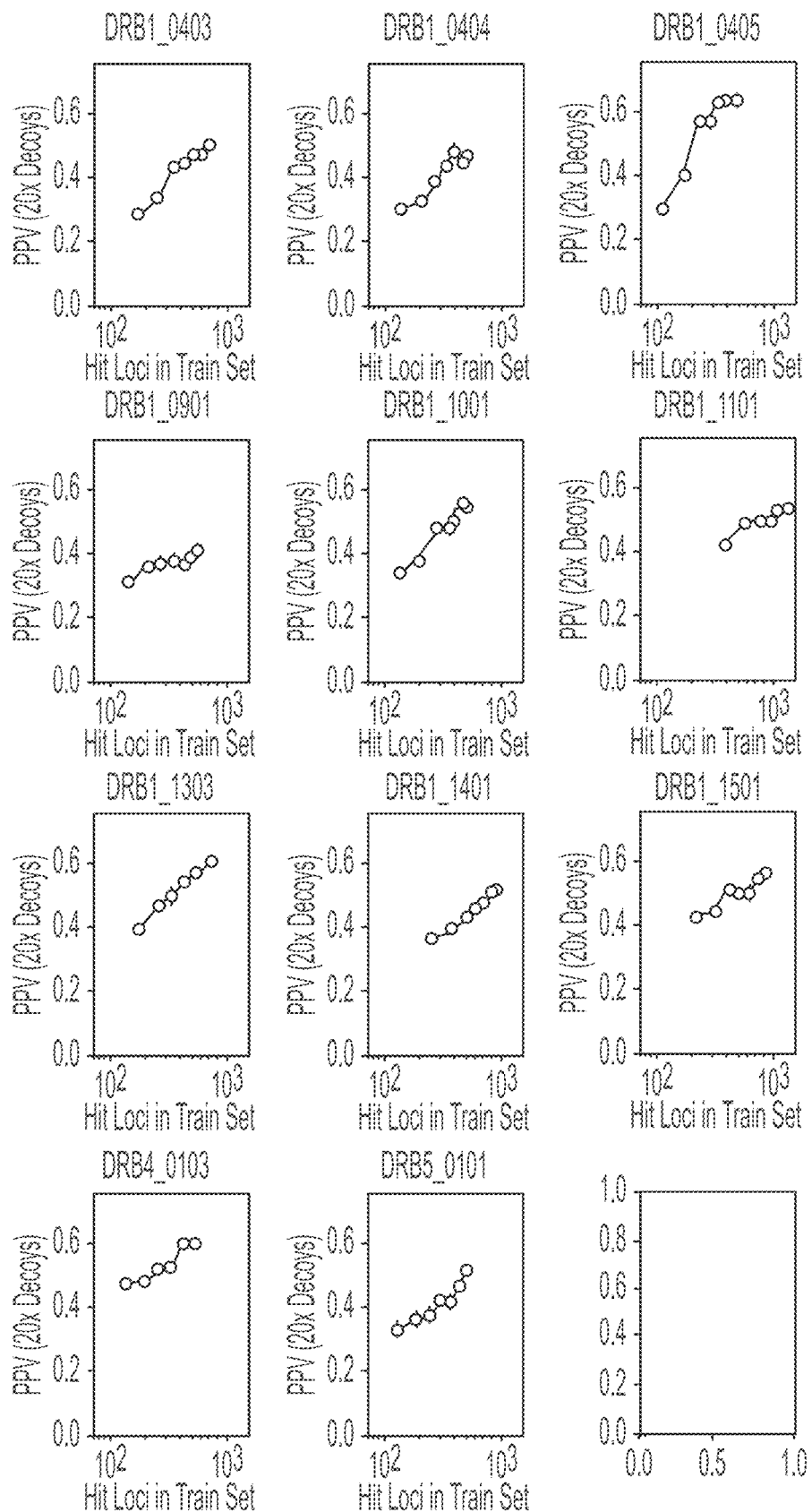

It was observed that for the HLA-DR alleles collected, when the training set size increased, the value of PPV increased (FIGS. 7B-7D).

Figure 8:
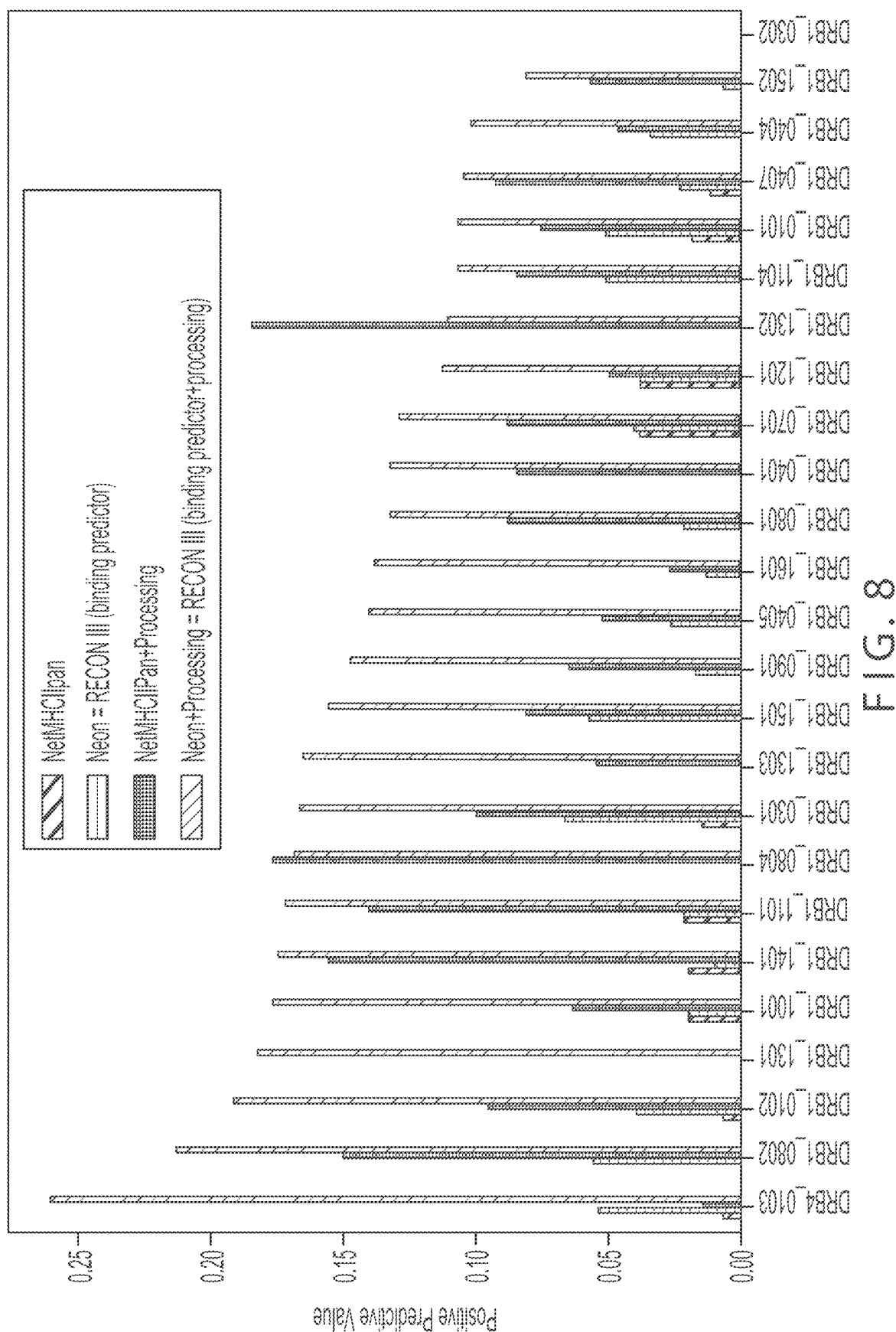
FIG. 8 depicts an exemplary graph, demonstrating that processing-related variables can improve prediction further. Distinguish MS-observed peptides random sequences selected from protein-coding exome may be distinguished. On the training data partition, a logistic regression may be fit to predict HLA class II presentation using binding strength (NetMHCIIpan or Neon's predictor) and processing features (RNA-Seq expression and a derived gene-level bias term). On a separate evaluation partition, exonic positions overlapping MS-observed MHC II peptides ("hits") may be scored alongside random exonic positions not observed in MS (1:499 ratio). The top 0.2% (1/500) may be called as positives, and positive predictive value may be assessed this threshold.

In this example, the processing-related variables improved prediction further (FIG. 8). On the training data partition, a logistic regression was fit to predict HLA class II presentation using binding strength (NetMHCIIpan or Neon's predictor) and processing features (RNA-Seq expression and a derived gene-level bias term). On a separate evaluation partition, exonic positions overlapping MS-observed MHC II peptides ("hits") was scored alongside random exonic positions not observed in MS (1:499 ratio). In general, Neon with processing-related variables showed higher PPV than NetMHCIIpan, Neon's predictor, and NetMHCIIpan with processing-related variables.

Example 2. A Neural Network Architecture

Figure 9:
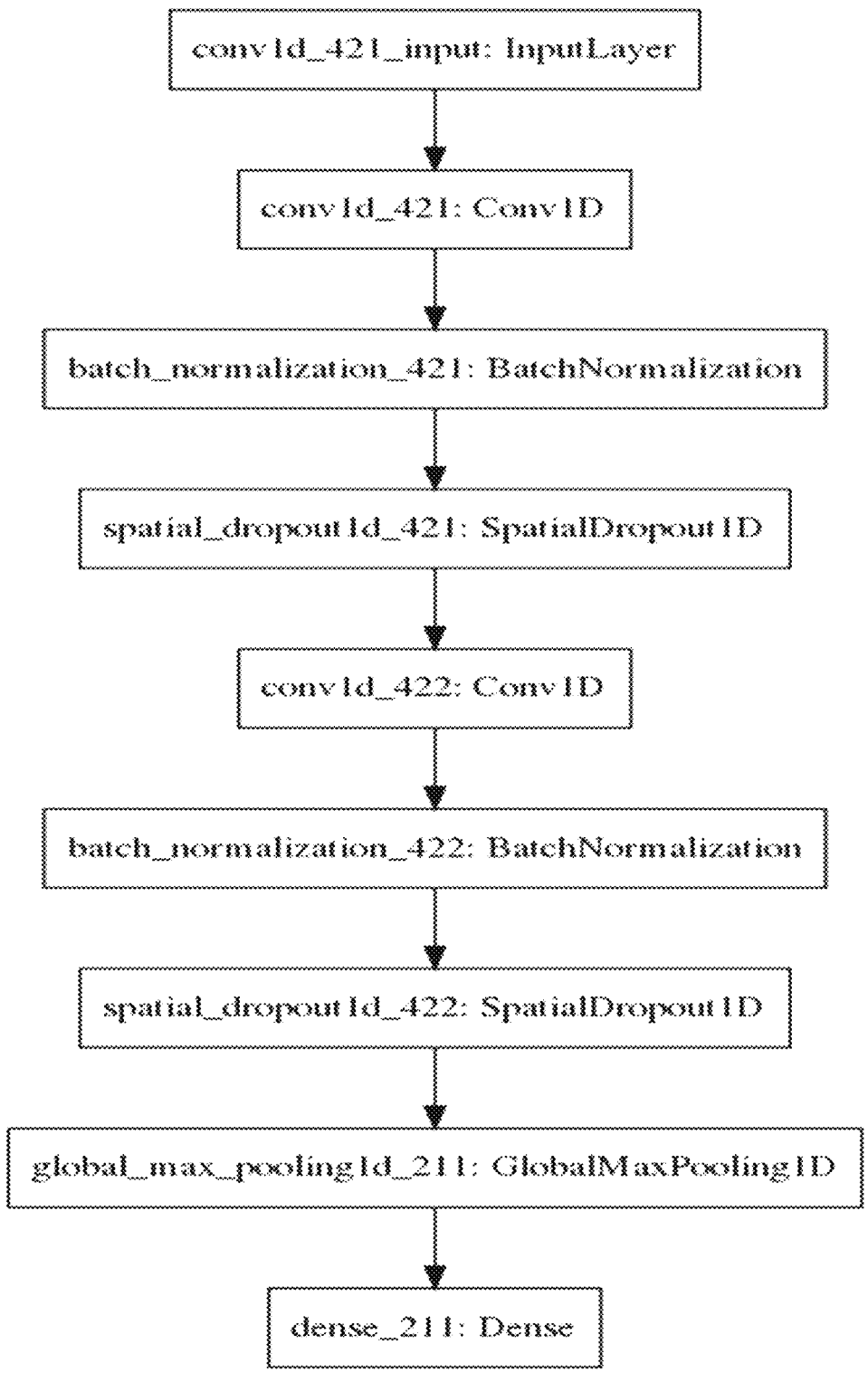
FIG. 9 depicts an exemplary neural network architecture. Input peptides are represented as 20mers, with shorter peptides being filled in with "missing" characters. Each peptide has a 31-dimensional embedding, so the input into the neural network is a 20×31 matrix. Before being processed by the neural network, feature normalization on the 20×31 matrix is performed based on feature value means and standard deviations in the training set. The first convolutional layer has a kernel of 9 amino acids and 50 filters (also called channels) with a Rectified Linear Unit (ReLU) activation function. This is followed by batch normalization then spatial dropout with a dropout rate of 20%. This is followed by another convolutional layer with a kernel of 3 amino acids and 20 filters with a ReLU activation function and then again followed by batch normalization and spatial dropout with a dropout rate of 20%. Global max pooling is then applied, taking the maximally-activated neuron in each of the 20 filters; then these 20 values are passed into a fully connected (dense) layer with a single neuron using a Sigmoid activation function. The output of this layer is treated as the binding/non-binding prediction. L2 regularization is applied to the weights of the first convolutional layer, second convolutional layer, and dense layer with weights of 0.05, 0.1, and 0.01, respectively. Additional models used have varied the number of convolutional layers and the kernel size of each layer.

In this example, a neural network was used to obtain the training algorithm (FIG. 9). Input peptides were represented as 20mers, with shorter peptides being filled in with "missing" characters. Each peptide had a 31-dimensional embedding, so the input into the neural network was a 20×31 matrix. Before being processed by the neural network, feature normalization on the 20×31 matrix was performed based on feature value means and standard deviations in the training set. The first convolutional layer had a kernel of 9 amino acids and 50 filters (also called channels) with a ReLU activation function. This was followed by batch normalization and then spatial dropout with a dropout rate of 20%. This was followed by another convolutional layer with a kernel of 3 and with 20 filters and a ReLU activation function and then again followed by batch normalization and spatial dropout with a dropout rate of 20%. Global max pooling was then applied, taking the maximally-activated neuron in each of the 20 filters and then these 20 values were passed into a fully connected (dense) layer with a single neuron using a Sigmoid activation function. This output was treated as the binding/non-binding prediction. L2 regularization was applied to the weights of the first convolutional layer, second convolutional layer, and dense layer with weights of 0.05, 0.1, and 0.01, respectively.

Example 3. A Scalable Protocol for Mono-Allelic MHC Class II Ligand Profiling

Currently knowledge of MHC Class II binding motifs can be based on two in vitro binding assays, one that calculates an EC50 using cellular MHC and another that calculates an IC50 using purified MHC. The leading HLA class II prediction algorithm NetMHCIIpan is trained exclusively on these data.

Limited number of human HLA class II alleles are currently supported by more than 200 examples of confirmed binding peptides (affinity <100 nM) (FIG. 12E), which are nearly all 15mers. These experiments cover only the most common Caucasian HLA-DR alleles with limited coverage of alleles specific to non-Caucasian populations (e.g., HLA-DRB1*15:02) and almost no coverage for common HLA-DP and HLA-DQ alleles. Current HLA class II prediction performance, even on the common Caucasian alleles, significantly lags the accuracy of MHC class I; ROC curves are only modestly better than random.

With these limitations in mind, a novel biotechnology was developed herein that was termed Mono-Allelic Capture by Tagged Allele capture (MAPTAC™) that enables efficient isolation of HLA class II binding peptides binding an MHC protein encoded by a single allele for MS-based identification (FIGS. 11A and 11B); this approach works for HLA class I as well. As applied to HLA class II, the alpha and beta chains of a chosen allele are encoded on a genetic construct, with a biotin-acceptor peptide (BAP) sequence placed at the C-terminus of the beta chain. These cells are then lysed and incubated with BirA enzyme to biotinylate the C-terminus of the beta chain of the capture allele. NeutrAvidin pulldown purifies a population of MHC-bound peptides, which are further isolated by size exclusion and sequenced with best-in-class LC-MS/MS protocols.

In some embodiments, the LC-MS/MS analysis is evaluated using high field asymmetric waveform ion mobility spectrometry (FAIMS). In some embodiments, peptides are subjected to both acidic reverse-phase (aRP) and basic reverse-phase (bRP) offline fractionation prior to analysis by nLC-MS/MS.

Figure 12A:
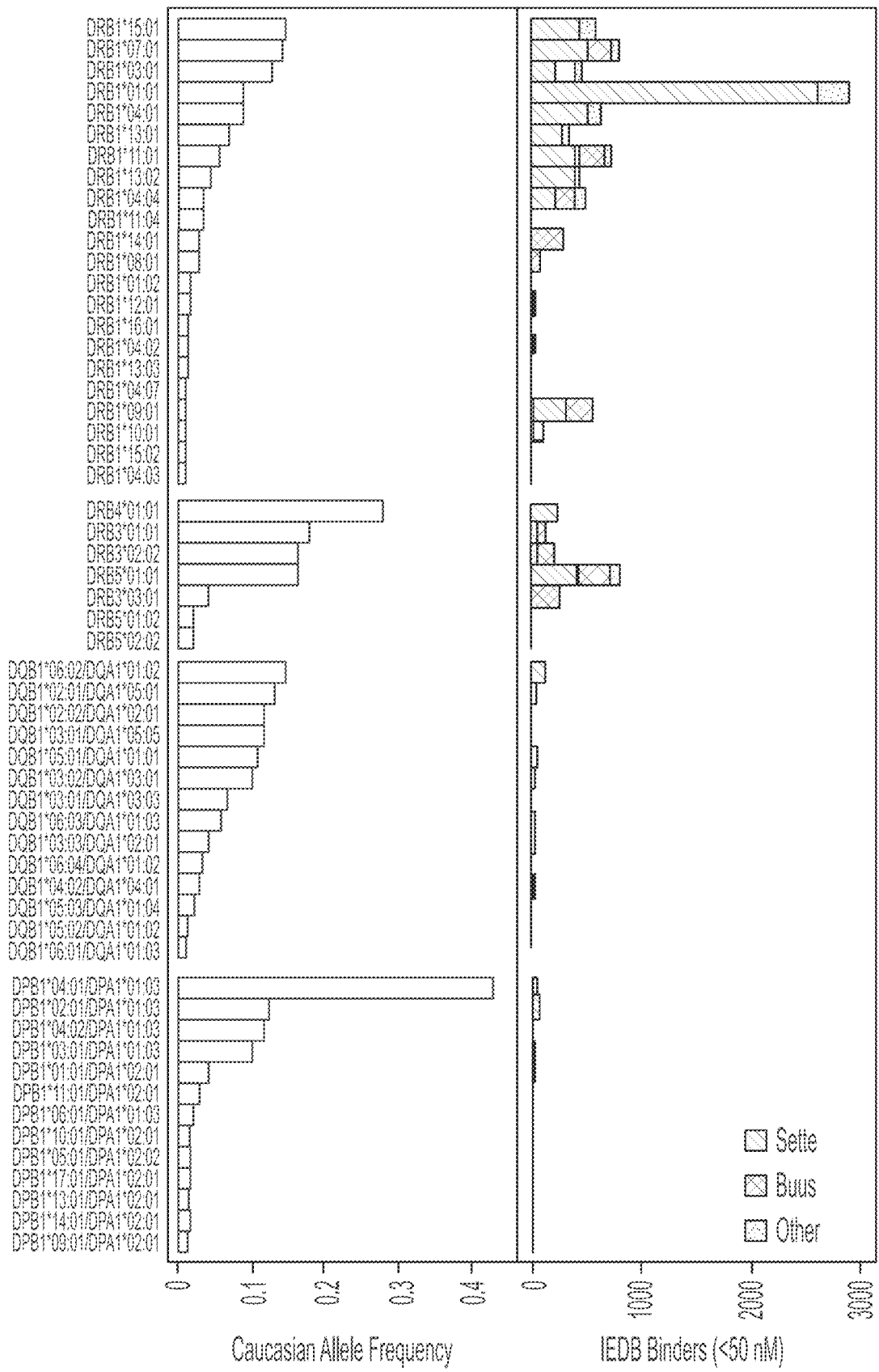
FIG. 12A depicts Caucasian frequencies for HLA-DR, -DP, and -DQ alleles present in >1% of individuals and counts of peptides from the indicated sources measured as strong binders (<50 nM).
Figure 12B:
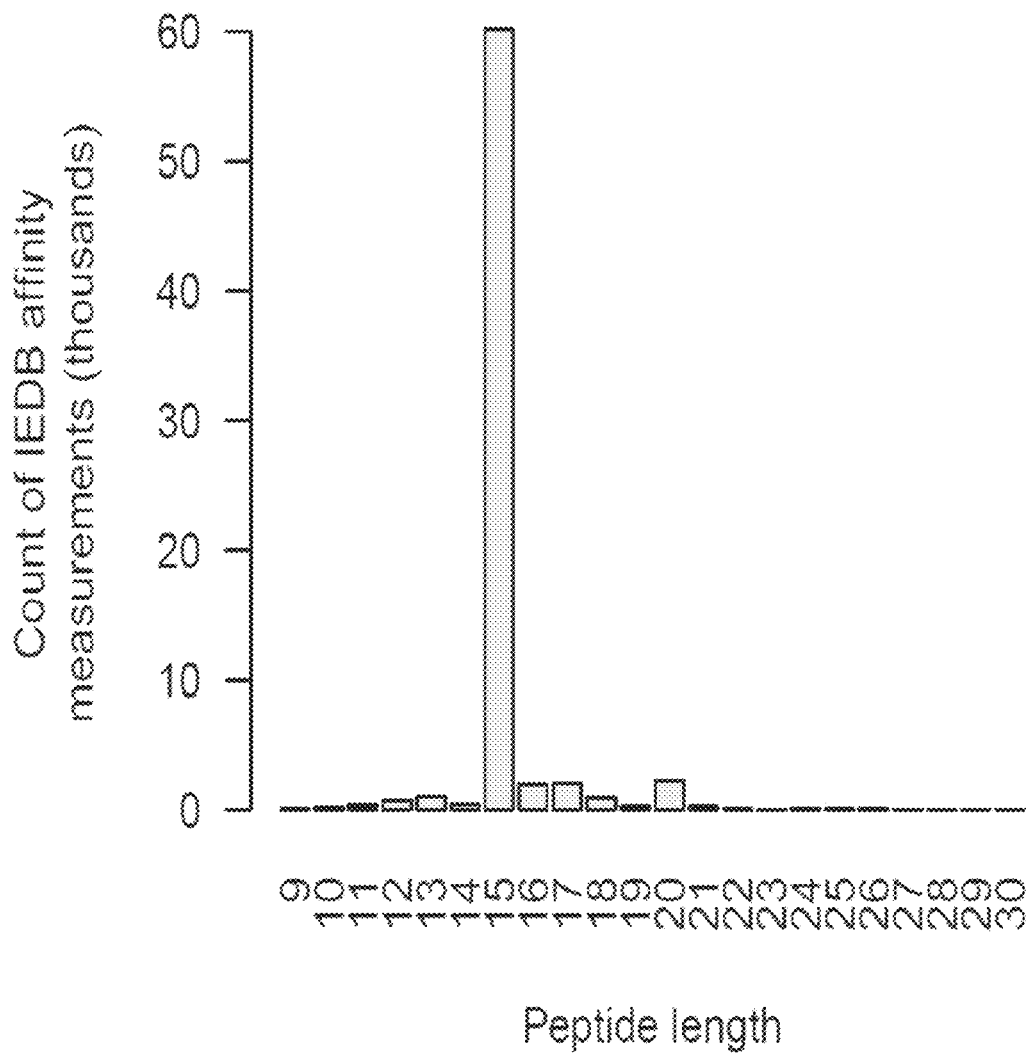
FIG. 12B depicts exemplary length distributions of IEDB peptides with associated HLA class II affinity measurements.
Figure 12C:
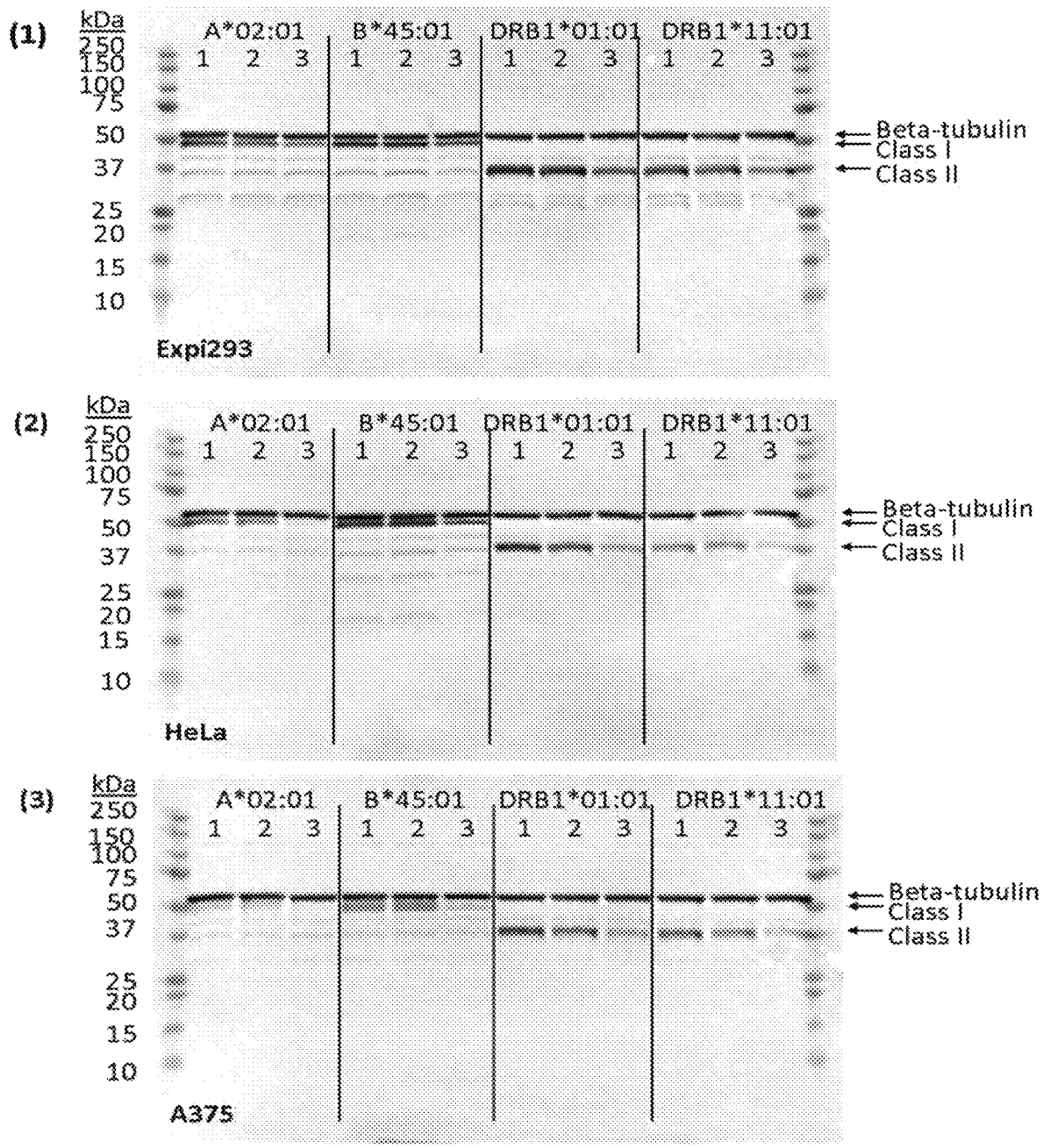
FIG. 12C depicts exemplary Western blots of (1) Expi293, (2) HeLa, and (3) A375 cell lines individually transfected with two HLA class I and two HLA class II alleles: HLA-A*02:01, HLA-B*45:01, HLA-DRB1*01:01, and HLA-DRB1*11:01. Membranes were blotted with anti-biotin ligase epitope tag to visualize biotin acceptor peptide (BAP) and anti-beta-tubulin as a loading control. Lanes correspond to the following fractions collected during the MAPTAC™ protocol: lane 1 input, lane 2 biotinylated input, and lane 3 input after pull-down.

A two-day transfection was sufficient to achieve robust expression of the construct (FIG. 12B) with appropriate cell surface localization in three distinct cell lines (expi293, A375, and B721) for four different alleles (FIG. 12C).

Because HLA-DRA is functionally invariant, this approach achieves single-allele resolution even if the capture beta chain pairs with endogenous alpha chain. This means that the approach can be used to profile HLA-DR alleles regardless of pre-existing HLA genotype and expression level in the given cell line.

For HLA-DP and HLA-DQ, the alpha and beta chains are both variable and both contribute to peptide binding, so single-allele resolution is expected only if the native alpha chain is not expressed or if the native allele is homozygous and matches the capture allele. Alternatively, one can use a beta chain-only capture to establish a background of peptides corresponding to the native alpha chain.

Profiled alleles included five HLA-DR alleles (DRB1*03:01, DRB1*09:01, DRB1*11:01, DRB3*01:01, and DRB3*02:02) as well as one HLA-DP allele (DPB1*01:01/DPA1*01:03), one HLA-DQ allele (DQB1*06:02/DQA1*01:02), and two Class I alleles (Table 1). In all cases, 2-3 replicates were sufficient to observe at least 1500 unique peptides (FIG. 11B). Among the alleles profiled, only a small percentage of hits corresponded to known contaminants or perfect tryptics; on the other hand, mock transfections returned relatively few peptides, which were mostly identifiable as known contaminants or perfect tryptics (FIG. 11B). Table 1 shows a summary of the samples used in the exemplary experiments.

TABLE 1

| Donor | DR1 | DR3/4/5 |
| --- | --- | --- |
| D001000763 | DRB1*03:01, DRB1*11:01 | DRB3*01:01, DRB3*02:02 |
| HD84 | DRB1*01:01 | Not present |
| RG1248 | DRB1*03:01 | DRB3*01:01 |
| RG1095 | DRB1*03:01, DRB1*11:01 | DRB3*01:01, DRB3*02:02 |
| RG1104 | DRB1*01:01, DRB1*11:01 | DRE3*02:02 |
| 2010113472 | DRB1*01:01, DRB1*11:01 | DRE3*02:02 |
| 2010113438 | DRB1*03:01, DRB1*11:01 | DRB3*01:01, DRB3*02:02 |

Since the ends of MHC II binding peptides do not need to fit within the MHC binding groove, multiple distinct peptide species can bind equally well if they share the same core binding sequence. When the peptides were pooled with overlapping sequence into "nested sets", 500-700 unique nested sets per HLA class II allele were observed; these were typically derived from 500-600 unique genes. Length distributions for HLA class I and HLA class II binding peptides match those observed in previous MS studies that used antibody-based pulldowns (FIG. 11C).

Among the putative MHC-binding peptides, most amino acids were represented at levels consistent with their source proteome frequencies. Exceptions included cysteine, methionine, and tryptophan, which were depleted, consistent with previous MS-based studies of MHC II peptides. Depletions of cysteine, methionine, and tryptophan were not observed in allele-matched high-affinity peptides (<50 nM) from IEDB; however, the IEDB peptides did show enrichments in leucine and methionine and depletions of proline, aspartic acid, and glutamic acid with respect to the proteome.

Example 4. MAPTAC™ Protocol Uncovers Known and Novel MHC II Binding Motifs

Figure 13:
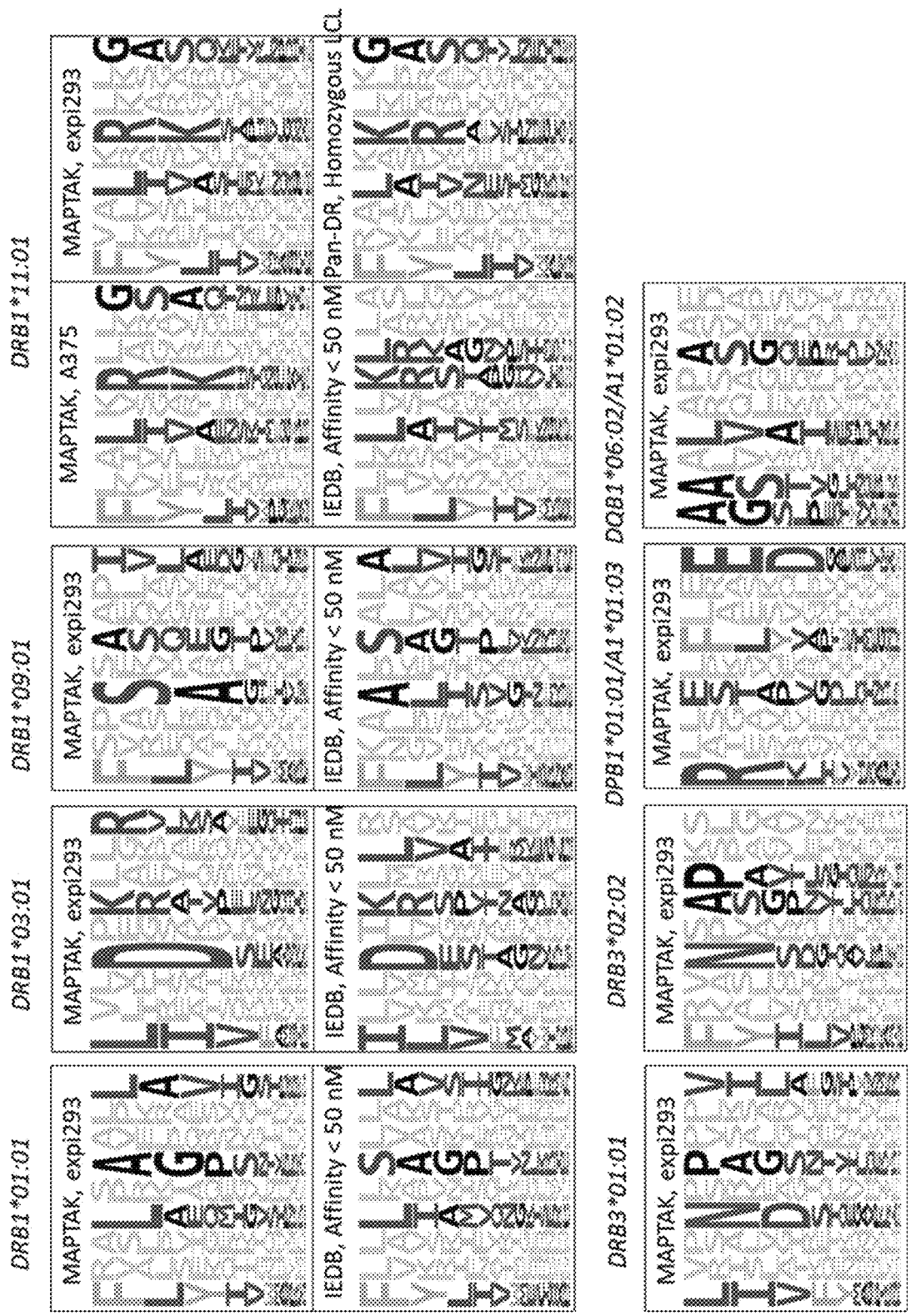
FIG. 13 depicts an exemplary representation of core binding sequence logos for MHC II alleles per MAPTAC™ and IEDB. Sequence logos are graphical representations wherein the height of each amino acid is proportional to its frequency of occurrence in a peptide that binds to the MHC protein encoded by the allele. Positions with lowest entropy are represented by shading, where the shadings correspond to amino acid properties. Peptides are derived from the indicated data sets and are aligned according to a CNN-based predictor (Methods). Logos represent all peptides including those that did not closely match the overall motif (e.g., no peptides are sequestered in a "trash" cluster).
Figure 14A:
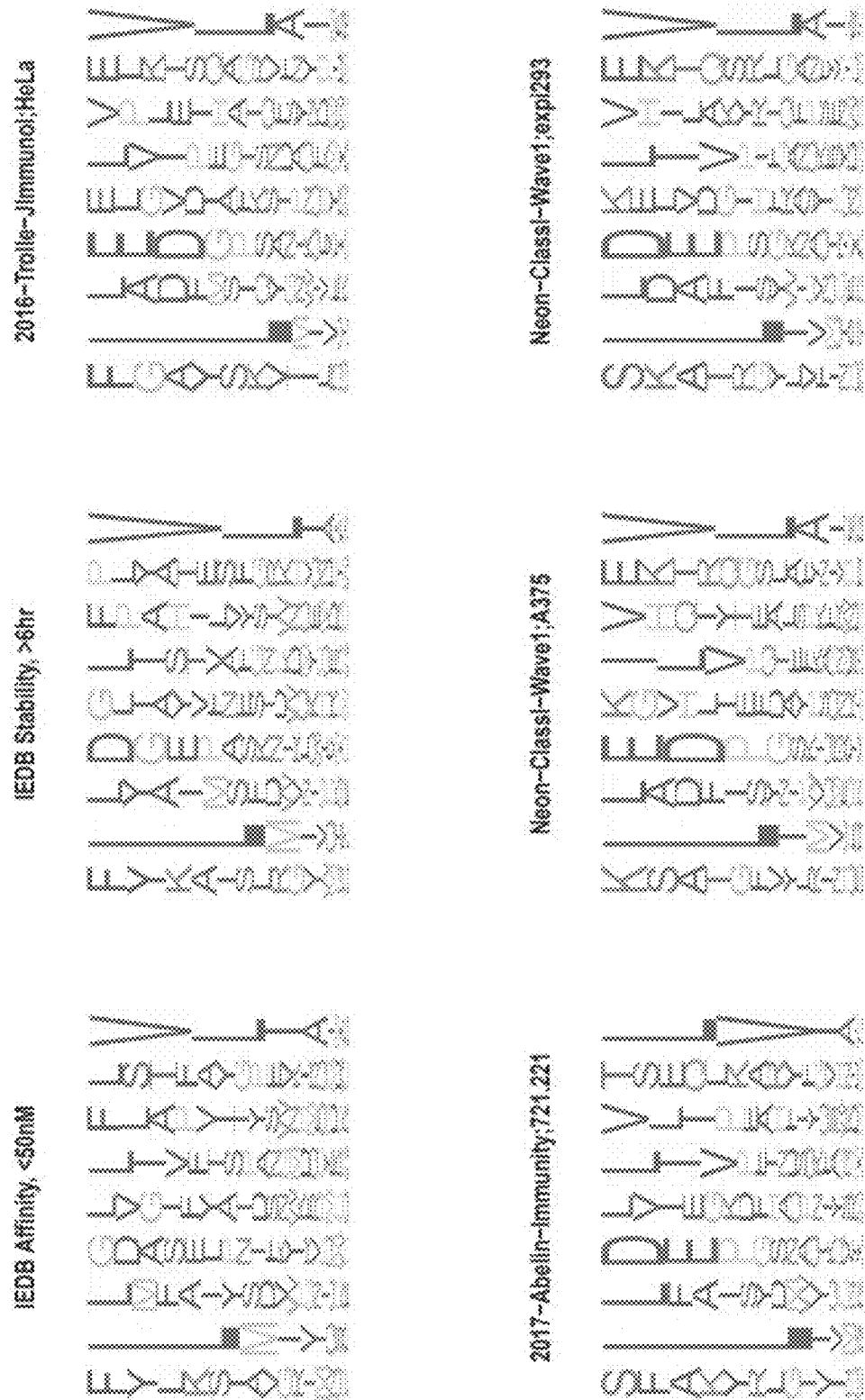
FIG. 14A depicts exemplary sequence logos for HLA-A*02:01 binding peptides (ligands) analyzed using different HLA-ligand profiling technologies including binding assays, stability assays, soluble HLA (sHLA) mass spectrometry, mono-allelic mass spectrometry, and MAPTAC™ in two different cell lines (A375 & expi293).

Since the MHC-binding subsequence of Class II peptides are not at a fixed position with respect to the N- or C-terminus, accurate Class II motif discovery must dynamically consider different binding register possibilities for each binder peptide. The Gibb's Cluster tool addresses this challenge through an expectation maximization (EM) algorithm. The use of a novel motif discovery approach using convolutional neural networks (CNNs) was explored. CNNs have been successful in the field of computer vision, which similarly seeks to achieve translationally invariant pattern recognition. CNNs were trained to distinguish MHC binding peptides from scrambled versions of themselves and then aligned the positive examples according to the subsequences that had achieved maximum node activation in the penultimate network layer. As applied to the mono-allelic MS data, this approach yielded motifs consistent with Gibbs clustering and showed anchors at relative positions 1, 4, 6, and 9 (FIG. 13). These motifs were highly consistent with CNN-derived motifs observed for high affinity binders from IEDB (affinity <50 nM; FIG. 13). For DRB1*11:01, was further validated that the motif was stable across cell lines and consistent with a DRB1*11:01 homozygous cell line previously profiled with a pan-DR antibody. Similarly, motifs derived for MHC Class I alleles were consistent with those from affinity-based methods and previous MS-based studies (FIG. 14A).

Figure 14B:
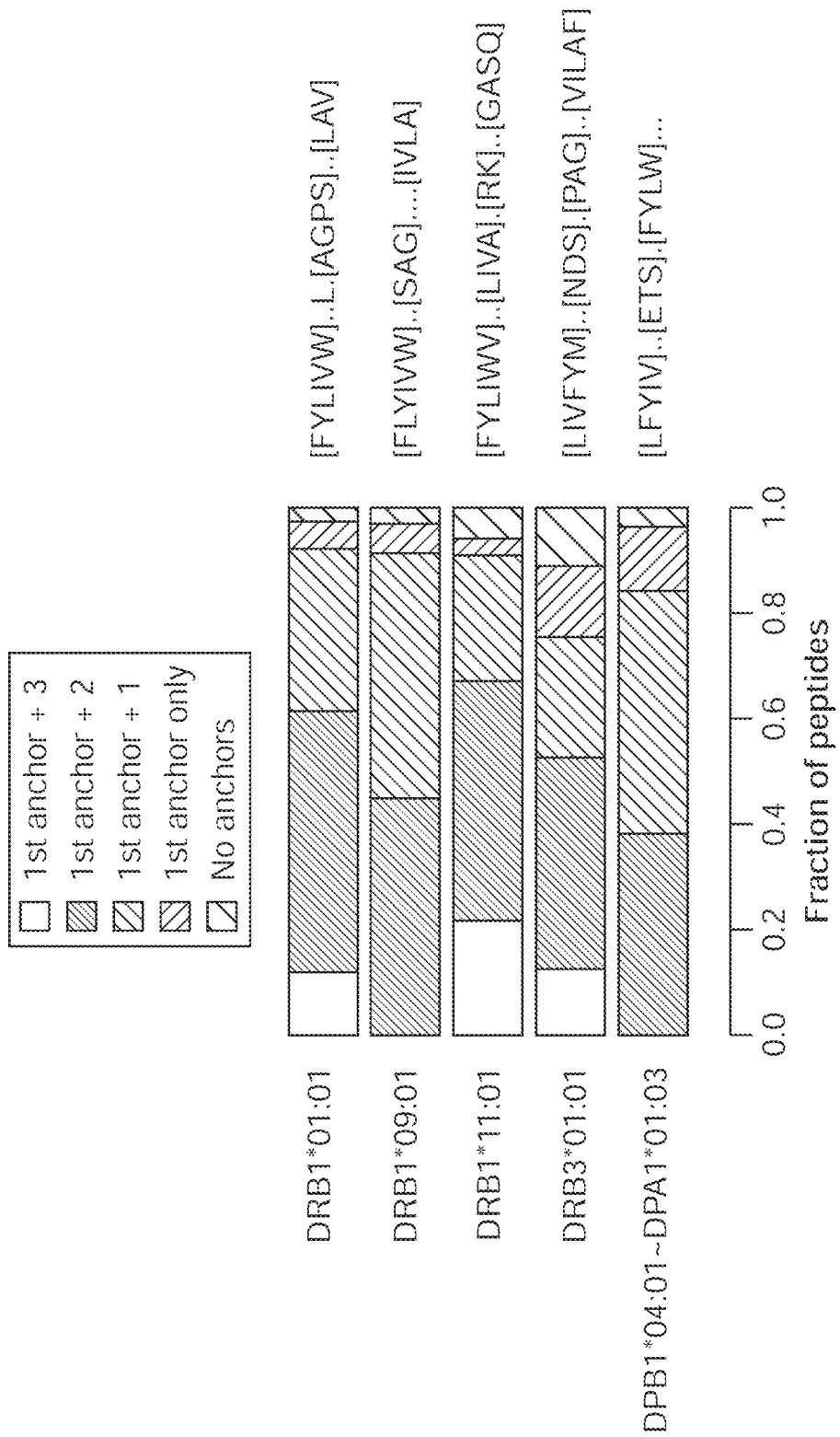
FIG. 14B depicts an exemplary fraction of MAPTAC™ peptides exhibiting 0, 1, 2, 3, and 4 of the heuristically defined anchors.
Figure 14C:
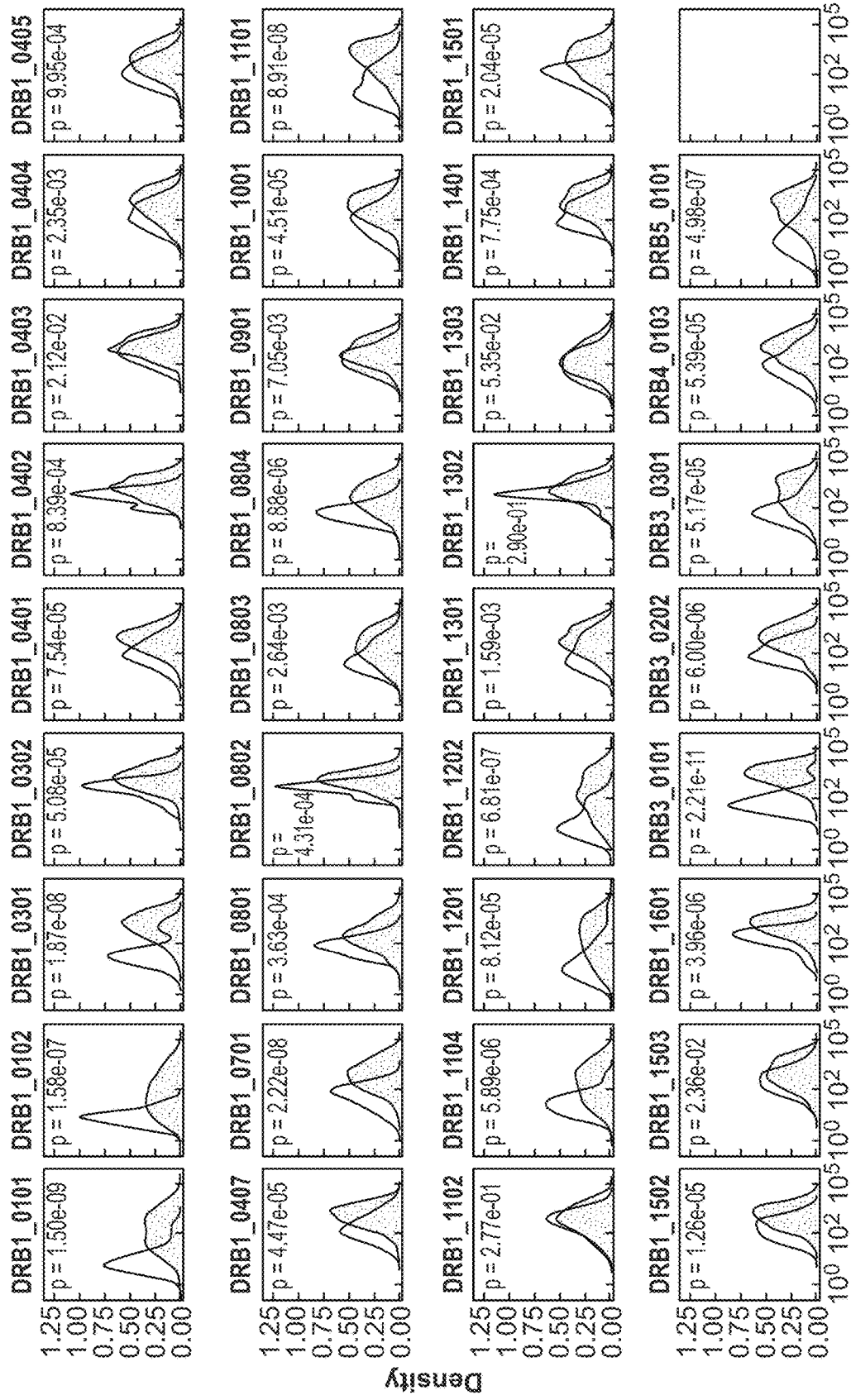
FIG. 14C depicts an exemplary distribution of NetMHCIIpan-predicted binding affinities for MAPTAC™-observed peptides (20 peptides per allele, each with SPI>70 and a nested set of size >=2) and length-matched decoys sampled from the proteome.

Although all the MHC class II alleles showed discernable motifs, the entropy at anchor positions was notably higher than that observed for MHC class I alleles. Accordingly, preferred amino acids at each anchor position for each MHC class II allele were defined and it was observed that only 10-20% of peptides exhibit ideal residues in all four anchor positions and as many as 60% exhibit two or fewer expected anchors (FIG. 14B and FIG. 30C). 13-17mers were scored for binding potential using NetMHCIIpan, and while the MS-observed peptides were enriched for predicted binding potential in all cases, there was significant overlap with scores of length-matched random peptides (FIG. 14C, and FIG. 36A).

Example 5. Algorithms Trained on Mono-Allelic MHC II MS Data Predict Immunogenicity Next, whether data from the mono-allelic MS platform could generate improved MHC class II binding predictors were considered. Building on the CNN approach, a multilayer network with filter sizes, skip connections, and a total receptive field were created (FIG. 31A). To train and assess this deep learning model, termed neonmhc2, the proteome were partitioned into three partitions representing 75%, 12.5%, and 12.5% of genes. The first partition was used to train CNNs via stochastic gradient descent, and the second was used for architecture and hyper-parameter optimization. The third partition was used to evaluate performance only once at the end of analysis. To ensure the integrity of the evaluation, care was taken to place all genes in paralogous gene groups in the same partition.

Since MS exhibits some degree of residue bias, particularly against cysteine (FIG. 12D), this problem was mitigated by using negative training examples (termed decoys) generated by randomly permuting the sequences of positive examples. Since this approach carries the risk of learning sequence properties of natural proteins, which could artificially inflate prediction performance, model evaluation employed a distinct decoy generation strategy wherein decoys were sampled randomly from non-observed subsequences of peptide source genes. Calculating positive predictive value (PPV) at a 1:19 hit-to-decoy ratio showed that neonmhc2 has improved PPV relative to NetMHCIIpan in predicting MS peptides in the evaluation partition (FIG. 4 and FIG. 31B). Experiments artificially down-sampling the size of neonmhc2's training dataset suggest that its performance is data-limited and would improve with deeper coverage data (FIG. 16).

The ability of neonmhc2 was explored to predict binding affinity, the data type on which NetMHCIIpan is trained. To deprive NetMHCpan the benefit of training and evaluating on the same peptide measurements, the evaluation was run using a slightly older version of NetMHCIIpan scoring peptides deposited to IEDB. Using a Kendall Tau statistic to assess prediction accuracy, NetMHCIIpan score similarly or slightly better than the MS-based predictor in all cases (FIG. 15B). Interestingly, performance depended on the type of affinity assay performed. While the neonmhc2 modestly lagged NetMHCIIpan when predicting affinity measurements from Sette and colleagues, it more substantially lagged NetMHCIIpan when predicting measurements from Buus and colleagues. Considering these results collectively, there appeared to be intrinsic differences between these platforms, but it was not immediately clear which approach was more correct.

To achieve improved clarity, the ability to predict natural CD4 T cell responses was assessed. Data from IEDB was generally unsuitable for this purpose since the allele restriction of responses is almost always either undefined or imputed. Therefore, a large dataset of tetramer-guided epitope mapping (TGEM) data was assembled. These studies all used comprehensive overlapping peptide screening rather than prediction prioritization, removing observation bias in favor of NetMHCIIpan. Meanwhile, the allele restriction is unambiguous. For all alleles for which there was sufficient data for assessment, the neonmhc2 substantially out-performed NetMHCpan, which performed only slightly better than random. Thus, MAPTAC™ platform may be the best-in-class for training models that identify immunogenic MHC class II epitopes.

Example 6. Algorithms Trained on Multi-Allelic MS Data are Inferior

Given that there are numerous multiallelic class II databases in the public domain based on standard pan-DR and pan-II antibody purification, whether a suitable predictor could have been trained using multi-allelic data only was tested. Several groups have shown success in deconvolving MHC class I allele motifs from multi-allelic Class I data, though these efforts have not yet translated into a publicly available predictor. Deconvolution of Class II motifs is additionally complicated by the need to simultaneously resolve both the binding register and cluster membership of each peptide. While the Gibbs Cluster tool has been used to explore the possibility of Class II deconvolution, the fidelity of this approach has not been extensively validated.

To assess the accuracy of Class II deconvolution, publicly available pan-DR datasets with known genotype were selected. For each dataset, twenty peptides of our monoallelic data were spiked in for each allele in the donor's genotype (1-2 DR1 alleles plus 0-2 DR3/4/5 alleles, depending on haplotype and zygosity). Gibbs Clustering tool was run on each dataset and whether the spike-in peptides were appropriately co-clustered were observed according to their known allele of origin. In early versions of this analysis, either the cluster number to the allele number was fixed or the Gibbs cluster was allowed to automatically determine the most optimal number of clusters; however, neither approach appeared to deconvolve the peptides accurately). To give the algorithm an assist, the most optimal cluster count was selected by calculating the adjusted mutual information between the true source alleles of the spike-in peptides and their assigned clusters. Nonetheless, in all but several cases, peptides were distributed across diverse clusters without respect to their source allele (FIG. 17A). These results suggest that current deconvolution protocols may not be reliably accurate for MHC Class II.

One caveat to this analysis is that some peptides may be capable of binding more than one allele. In line with that, the next question is whether binding motifs derived from multi-allelic data may nonetheless reasonably match those observed from mono-allelic data. To assess this, clusters with the best correspondence to the capture peptides of each single allele were selected and motifs based on these populations were built. (see, for example, FIG. 17B). While many motifs clearly demonstrated some of the known anchors, other positions were discordant with the mono-allelic motif or discordant between source data sets. Additionally, there were clear cases in which spurious anchors had emerged. Finally, we assessed whether the deconvolved data could be used to train CNNs that could predict peptides in the evaluation partition of our mono-allelic dataset. Models trained on deconvoluted multi-allelic data fell short of MAPTAC™-trained models in all cases (FIG. 17C).

Example 7. Source Protein Features Influence Presentation Likelihood

For MHC Class I, the proteasome plays an important role in determining the repertoire of presented epitopes; therefore, how protein-to-peptide processing shapes the Class II repertoire that was characterized.

First, the exact positions of the N- and C-termini of MHC Class II peptides observed in several tissue-based peptide profiling data sets were focused on. Comparing position-based amino acid frequencies with respect to decoy peptides, significant enrichments and depletions was observed. This pattern is consistent with recent observations. Interestingly, the overall pattern does not match the known cleavage preference of Cathepsin S ([RPI][FMLW][KQTR][ALS]), the best characterized Class II processing enzyme.

To determine the predictive potential of this motif, NN-based predictors for the N- and C-termini were built and a logistic regression that used the two cleavage variables along with predicted binding potential (per MS-trained CNN) was fit to distinguish true MS peptides from length-matched decoy peptides sampled from the same source genes.

This predictor provided a modest improvement in peptide prediction over a model that considered binding potential alone; however, since the immunogenicity of MHC class II binding epitopes (interchangeably termed, Class II epitopes) may not depend on the exact position of peptide cleavage, the question is whether the model would still add value if the exact site of cleavage was unknown. Therefore, the prediction scheme was run a second time, withholding the exact cleavage positions of hits and decoys, instead scoring composite cleavability scores across protein positions in the vicinity (+1-15 AA) of the imputed binding core. Interestingly, there was no improvement in performance over the binding-only predictor. These results are consistent with previous work, which showed that the addition of Class II cleavage prediction could improve prediction of MS-observed ligands, but not T cell recognition, which is presumably agnostic to the exact peptide termini.

A model was suggested in which a significant fraction of MHC II peptides are "chewed back" from their N- and C-termini after MHC binding. Under this model, the penultimate proline signature arises because proline blocks the procession of exopeptidases. In this scenario, the motif derived from direct analysis MHC ligand termini is potentially misleading because it reflects downstream editing rather than the initial step of peptide fragment generation. Therefore, other sequence features were determined in the vicinity of Class II peptides that might be able to explain their generation. First, the canonical Cathepsin S signature was searched for, but there was no enrichment in Cathepsin S sites near MS-observed Class II peptides vs. length-matched decoy peptides sampled from the peptide source genes. Because this processing signature may reflect a complex ensemble of enzymes, a de novo CNN was trained based on the upstream and downstream protein context (+−25 AAs) around observed peptides and decoys.

A third model in which peptide availability is determined by the folded or semi-unfolded state of the protein rather than its primary sequence was considered. Homology-based ACCPRO was used to predict secondary structure and regions of solvent accessibility, and an ensemble of predictors was used to identify intrinsically disordered domains.

If processing-preferred regions are inherently difficult to predict, it might be possible to simply build a catalog of all protein regions covered by at least one peptide in a large collection of previously published multi-allelic Class II MS data and use overlap as a prediction feature. Admittedly, the overlap feature is contaminated with binding information since the alleles represented in the previously published data may have the same or similar binding motifs. Nonetheless, even this feature only modestly improved the prediction of presented peptides suggesting that MHC Class II peptides may not be subject to strong processing hotspots.

The next question was which genes contribute the most to the Class II binding peptides repertoire. Gene-level features, such as expression level, are already known to provide a large boost when predicting MHC Class I ligands. Leveraging previously published MS datasets profiling the Class II binding repertoires of human tissues, it was observed that MS-observed peptides are more highly expressed than random decoy peptides (sampled from the proteome) by an order of magnitude (FIG. 18A). Nonetheless, it was noticed that about 5% of Class II peptides map to a gene that is ostensibly not expressed according to representative RNA-Seq data. Based on this pattern, the degree to which each gene was over- or under-represented in the Class II peptide repertoire was sought to be quantified by proposing a baseline expectation that the number of observations for each gene should be proportional to the product of its length and expression level (FIG. 18B). Among the over-represented genes, there was a clear enrichment for proteins expressed in human tissue serum, which produced many Class II-binding peptides but were ostensibly not expressed in the native tissue. This is consistent with the known role of MHC Class II in presenting antigens sampled from the extracellular environment.

Since autophagy is another well-established Class II processing pathway, the ratio of observed to expected peptides for each gene (excluding any gene with fewer than five observed peptides and fewer than five expected peptides) was determined and determined if there was enrichment with respect to the physical partners of known autophagy genes or genes stabilized by Atg5 knockout in mice (FIG. 18C). Neither gene set appeared to be enriched in the Class II data; in fact, physical partners of autophagy genes seemed to be modestly under-represented.

Looking across all cellular localizations (FIG. 18D and FIG. 18E), few compartments were definitively over- or under-represented. The two most enriched compartments were the cell membrane and the lysosome, each generating approximately twice the expected number of Class II peptides. It is not clear whether the enrichment of membrane proteins relates to membrane recycling into autophagosomes or Golgi routing of membrane proteins directly into the autophagy pathway. The apparent contradiction between the enrichment of lysosomal proteins and the previously observed depletion of autophagy genes indicated that these trends are highly sensitive to the specific subset of autophagy-related genes being considered. FIG. 18F shows relative concordance of peptide observations with respect to two different gene expression profiles, bulk tumor and professional antigen presenting cells.

Example 8. Accurate MHC II Prediction Requires Understanding the Endocytic Pathway In addition to understanding the source pathway of Class II genes, it may be critical to understand which cell types are responsible for most Class II presentation. In the case of cancer, non-professional APCs, including fibroblasts and the tumor itself, are thought to present Class II within inflamed tumor microenvironments (TMEs). To gain further insight, HLA-DRB1 expression was analyzed in three recently published single-cell RNA-Seq datasets that profiled lung cancer, head and neck cancer, and melanoma. Averaging across cells to the patient-cell type level, it was clear that canonical APCs (macrophages, dendritic cells, and B cells) present much greater levels of Class II than the tumor and other stromal cell types, and this trend is consistent across multiple patients and tumor types.

To probe whether immunotherapy disrupted this trend, additional single-cell RNA-Seq from checkpoint blockade-responsive tumor types were analyzed, and HLA-DRB1 expression was assessed before and after treatment. A melanoma cohort, which included one confirmed responder, showed uniformly low HLA-DRB1 expression by tumor cells in both the pre-therapy and post-therapy biopsies (FIG. 19C). A basal cell carcinoma cohort which showed a 55% clinical response rate to anti-PD-1 therapy, likewise exhibited low tumor cell-derived HLA-DRB1 expression regardless of time point (FIG. 19C).

These results suggested that most intra-tumoral HLA class II presentation is driven primarily by professional APCs and "hot" TME conditions do not guarantee divergence from the general pattern.

Because tumor cells can outnumber APCs in the tumor microenvironment, their lower levels of MHC class II expression may nonetheless be immunologically relevant. To assess how much of overall Class II expression comes from tumor cells vs. stroma, TCGA patients with mutations in Class II-specific genes (focusing on CITTA, CD74, and CTSS) were identified and the fraction of RNA-Seq reads exhibited the somatic (tumor-specific) variant was determined. This information was used to impute what fraction of HLA-DRB1 expression derived from tumor vs. stroma (FIG. 19B). Based on mutations identified in 153 patients representing 17 distinct tumor types, a dominant pattern was observed in which most Class II expression appears to arise from non-tumor cells. Focusing on just the patients with highest levels of T cell infiltration (top 10%, as identified using a previously published 18-gene signature (Ayers et al., 2017), low tumor HLA-DR expression still appears to be the norm, with only 3 of 16 patients expressing >1000 TPM (tumor progression and metastasis).

To probe whether immunotherapy disrupted this trend, additional single-cell RNA-Seq from checkpoint blockade-responsive tumor types were analyzed, and HLA-DRB1 expression was assessed before and after treatment. A melanoma cohort, which included one confirmed responder, showed uniformly low HLA-DRB1 expression by tumor cells in both the pre-therapy and post-therapy biopsies (FIG. 19C). A basal cell carcinoma cohort which showed a 55% clinical response rate to anti-PD-1 therapy, likewise exhibited low tumor cell-derived HLA-DRB1 expression regardless of time point (FIG. 19C).

These results suggested that most intra-tumoral HLA class II presentation is driven primarily by professional APCs and "hot" TME conditions do not guarantee divergence from the general pattern.

Example 9. New Prediction Concepts Enable More Accurate Identification of Immunogenic Neoantigens In order to explore the utility of neonmhc2 and associated processing rules, the performance in several prediction scenarios was considered. First, the ability to predict MS-identified peptides was assessed on PMBC from seven healthy donors profiled with a pan-DR antibody. This analysis can control for any systematic biases inherent to the MAPTAC™ system or our production cell lines. Using a 1:499 ratio of hits to decoys and sampling decoys at random from the protein-coding exome, the positive predictive value of neonmhc2 and NetMHCIIpan base models as well as models that incorporated additional processing features were assessed (expression, gene-level bias per FIG. 18B, and overlap with a previous MHC II peptide). These models confirmed substantial improvements in both binding and processing prediction (FIG. 20).

FIG. 21A shows a comparison of the NetMHCIIpan and neonmhc2 with further processing parameter or features as indicated. Prediction performance for eight MS samples profiled by HLA-DR antibody (the same samples analyzed in Example 6, FIG. 17A). Predictors minimally employ HLA-binding prediction (either NetMHCIIpan or neonmhc2) and optionally employ additional processing related variables: gene expression, gene bias (e.g., per FIG. 18B, FIG. 18C, FIG. 19B), and overlap with a previously observed HLA-DQ peptide. In this example, decoys were sampled from the proteome at random (including genes that never produced an MS-observed peptide) to achieve a 1:499 ratio of hits to decoys, which nearly saturates available decoy sequences. Positive predictive value was calculated in a manner analogous to FIG. 4, e.g., the top 0.2% of peptides were called as positives and PPV is the fraction of positives that are true MS-observed peptides. For each candidate peptide in each sample, the binding score was calculated as the maximum across the HLA-DR alleles present in the sample genotype. Although there is a fair correlation in the trends of peptides found by the two methods, the model described herein shows a more robust outcome. FIG. 21B (see also, FIG. 33B) represents prediction performance for tumor-derived peptides presented by dendritic cells (Lysate) using the same hit: decoy ratio and performance metrics as in FIG. 21A. Performance is shown for NetMHCIIpan and models described herein with and without use of processing features. FIG. 21C shows the expression level and gene bias score for each heavy-labeled peptide. FIG. 21D is a diagram representing overlap of heavy-labeled peptide source genes according to the lysate and UV-treatment experiments.

Example 10. Expression of Class-II HLA Peptides in Cell Lines and Isolating MHC-II-Bound Peptides Construct Design, Cell Culture and HLA-Peptide Immunoprecipitation In this exemplary study, mono-allelic cell lines were generated by transfecting a single affinity-tagged HLA construct into cell lines (A375, HEK293T, Expi293, HeLa) and affinity-tagged HLA-peptide complexes were immunoprecipitated. In FIGS. 12A and 12E, MHC Class II allele frequencies are allele frequencies obtained from allelefrequencies.net/ unless otherwise noted. Allele frequencies for the U.S. population were imputed by assuming an admixture of 62.3% European, 13.3% African, 6.8% Asian, and 17.6% Hispanic.

With regards to FIG. 12A and FIG. 12E, the mhc_ligand_full.csv dataset was downloaded from IEDB data on Sep. 21, 2018. Valid affinity measurements were required to have a "Method/Technique" equal to "cellular MHC/competitive/fluorescence", "cellular MHC/competitive/radioactivity", "cellular MHC/direct/fluorescence", "purified MHC/competitive/fluorescence", "purified MHC/competitive/radioactivity", or "purified MHC/direct/fluorescence" and an "Assay Group" equal to "dissociation constant KD", "dissociation constant KD (~EC50)", "dissociation constant KD (IC50)", "half maximal effective concentration (EC50)", or "half maximal inhibitory concentration (IC50)". A measurement was attributed to the Soren Buus group (University of Copenhagen, Denmark) if the string "Buus" appeared in the "Authors" field. Otherwise, if the authors field included the strings "Sette" or "Sidney", a measurement was attributed to the Alessandro Sette group (La Jolla Institute for Immunology, U.S.A). All other measurements were labeled as "Other". For the purposes of enumerating strong binders, only peptides with a measured affinity stronger than 50 nM were counted (FIG. 12A). FIG. 12E includes additional data from tools.iedb.org/main/datasets/, and strong binders with affinity <100 nM are enumerated.

DNA Construct Design

The gene sequences for HLA class I and HLA class II alleles were identified by the IPD-IMGT/HLA webpage (ebi.ac.uk/ipd/imgt/hla) and used to design recombinant expression constructs. For HLA class I, the α-chain was fused with a C-terminal GSGGSGGSAGG linker (SEQ ID NO: 10), followed by the biotin-acceptor-peptide (BAP) tag sequence GLNDIFEAQKIEWHE (SEQ ID NO: 11), a stop codon, and a variable DNA barcode, and cloned into the pSF Lenti vector (Oxford Genetics, Oxford, UK) via the NcoI and XbaI restriction sites. The HLA class II constructs were similarly cloned into pSF Lenti via the NcoI and XbaI restriction sites and consisted of the β-chain sequence fused on the C-terminus to the linker-BAP sequence from the class I construct (SGGSGGSAGGGLNDIFEAQKIEWHE (SEQ ID NO: 12)), followed by another short GSG linker an a F2A ribosomal skipping sequence (VKQTLNFDLLKLAGDVESNPGP (SEQ ID NO: 13)), the sequence of the α-chain, an HA tag (GSYPYDVPDYA (SEQ ID NO: 14)), a stop codon, and a variable DNA barcode. The identity of all DNA sequences was verified by Sanger sequencing.

Cell Culture and Transient Transfections

Expi293 cells (Thermo Scientific) were grown in Expi293 medium (Thermo Scientific) with 8% $CO_2$ at 37° C. with shaking at 125 rpm. Expi293 cells were maintained at cell densities between $0.5\times10^6$/mL and $6\times10^6$/mL with regular biweekly passaging. 30 mL of the Expi293 cell suspension was used for transient transfections at a cell density of approximately $3\times10^6$/mL and >90% viability. Briefly, 30 ug DNA (1 μg/mL DNA per mL cell suspension) was diluted into 1.5 mL Opti-MEM medium (Thermo Scientific) in one tube while 80 μL ExpiFectamine™ 293 transfection reagent (Thermo Scientific) was diluted into a second tube containing 1.5 mL Opti-MEM. These two tubes were incubated at room temperature for five minutes, combined, mixed gently, and incubated at room temperature for 30 minutes. The DNA and ExpiFectamine mixture was added to Expi293 cells and incubated at 37° C., 8% $CO_2$, 80% relative humidity. After 48 h, transfected cells were harvested in four technical replicates at $50\times10^6$ cells per tube, centrifuged, washed once with 1× Gibco DPBS (Thermo Scientific), and flash frozen in liquid nitrogen for mass spectrometric analysis. An aliquot of $1\times10^6$ cells was collected from each transfection batch and analyzed via anti-BAP (Rockland Immunochemicals Inc., Limerick, Pa.) or anti-HA (Bio-Rad, Hercules, Calif.) western blot to verify affinity-tagged HLA protein expression.

A375 cells (ATCC) were grown in DMEM with 10% FBS and maintained at cultures at no greater than 80% confluence with regular passaging. For mass spectrometry experiments A375 cells were cultured in a 500 $cm^2$ plate at a seeding density of $18.5\times10^6$ cells/mL in 100 mL, as calculated from a 70% confluent cell number. After 24 hours, cells were transfected with TransIT-X2 (Mirus Bio, Madison, Wis.) by following the TransIT system protocol adjusted for the total culture volume. After 48 h, cell medium was aspirated, and cells were washed with 1× Gibco DPBS (Thermo Scientific). For harvest, A375 cells were incubated for 10 minutes at 37° C. with 30 mL non-enzymatic cell dissociation solution (Sigma-Aldrich), centrifuged, washed with 1×DPBS, and aliquoted at $50\times10^6$ cells per sample. 293T and HeLa cells were purchased from ATCC and were cultured at 37° C. at 5% $CO_2$ in DMEM, 10% FBS, 2 mM L-glutamine or DMEM+10% FBS, respectively. Both cell lines were transfected with the HLA constructs using the TransIT LT1 reagent (Mirus Bio, Madison, Wis.) following the manufactures instructions and processed 48 h after transfection as described for the A375 cells. From all samples, an aliquot of $1\times10^6$ cells was collected from each transfection and analyzed via anti-BAP (Rockland Immunochemicals Inc., Limerick, Pa.) or anti-HA (Bio-Rad, Hercules, Calif.) western blot to verify affinity-tagged HLA protein expression.

BirA Protein Expression and Purification

The pET19 vector encoding *E. coli* BirA fused to a C-terminal hexa-histidine tag (SEQ ID NO: 15) was used. Chemical competent *E. coli* BL21 (DE3) cells (New England Biolabs) were transformed with the BirA expression plasmid, grown at 37° C. in LB broth plus 100 μg/ml ampicillin to an $OD_{600}$ of 0.6-0.8 and cooled to 30° C. before expression was induced by adding 0.4 mM isopropyl-β-D-thiogalactopyranoside. *E. coli* cell growth continued at 30° C. for 4 h. *E. coli* cells were harvested by centrifugation at 8000×g for 30 minutes at 4° C. and stored at −80° C. until use. Frozen cell pellets expressing recombinant BirA were resuspended in IMAC buffer (50 mM $NaH_2PO_4$ pH 8.0, 300 mM NaCl) with 5 mM Imidazole, incubated with 1 mg/ml lysozyme for 20 minutes on ice and the lysed by sonication. Cellular debris and insoluble materials were removed by centrifugation at 16,000×g for 30 minutes at 4° C. The cleared supernatant was subsequently loaded on a HisTrap HP 5 mL column using the AKTA pure chromatography system (GE Healthcare), washed with IMAC buffer plus 25 mM and 50 mM imidazole before elution with 500 mM imidazole. Fractions containing BirA were pooled and dialyzed against 20 mM Tris-HCl pH 8.0 with 25 mM NaCl and were loaded on a HiTrap Q HP 5 mL column (GE Healthcare) and eluted by applying a linear gradient from 25 to 600 mM NaCl. Fractions containing highly pure BirA were pooled, buffer exchanged in storage buffer (20 mM Tris-HCl pH 8.0 100 mM NaCl, 5% glycerol) and concentrated to around 5-10 mg/mL, aliquoted, and flash frozen in liquid nitrogen for storage at −80° C. BirA protein concentration was determined by UV spectroscopy at OD using a calculated 280 run extinction coefficient of $\varepsilon=47,440$ $M^{-1}$ $cm^{-1}$.

Western Blotting Protocol

Samples were added to XT Sample Buffer and XT Reducing Agent (Bio-Rad, Hercules, Calif.), heated at 95° C. for five minutes, then a volume corresponding to 100,000 cells was loaded into 10% Criterion XT Bis-Tris gels (Bio-Rad) and electrophoresed at 200 V for 35 minutes using a PowerPac Basic Power Supply (Bio-Rad, Hercules, Calif.) with XT MES Running Buffer (Bio-Rad, Hercules, Calif.). The gels were rinsed briefly with water, then proteins were transferred to PVDF membranes within Invitrogen iBlot Transfer Stacks (Thermo Fisher Scientific) using setting P3 on an Invitrogen iBlot2 Gel Transfer Device (Thermo Scientific). The Precision Plus Protein All Blue Standard (Bio-Rad, Hercules, Calif.) was used to monitor molecular weights. Next, membranes were washed 3×five minutes with Pierce TBS Tween 20 (TBST) buffer (25 mM Tris, 0.15 mM NaCl, 0.05% (v/v) Tween 20, pH 7.5), blocked for 1 h at room temperature in TBST-M (TBST containing 5% (w/v) nonfat instant dry milk), then incubated overnight at 4° C. in TBST-B (TBST containing 5% (w/v) Bovine Serum Albumin (Sigma Aldrich)] and a 1:5,000 dilution of both rabbit anti-beta tubulin antibody (catalog #ab6046, Abcam) and rabbit anti-biotin ligase epitope tag antibody (catalog #100-401-B21, Rockland Immunochemicals). Next, the membranes were washed 3×five minutes with TBST, incubated for 1 h at room temperature in TBST-M containing a 1:10,000 dilution of goat anti-rabbit IgG (H+L-horseradish peroxidase-conjugated antibody (catalog #170-6515, Bio-Rad, Hercules, Calif.), then washed at room temperature 3× five minutes with TBST. Finally, membranes were bathed with Pierce ECL Western Blotting Substrate (Thermo Fisher Scientific, Rockford, Ill.), developed using a ChemiDoc XRS+ Imager (Bio-Rad), and visualized using Image Lab software (Bio-Rad).

Affinity-Tagged HLA-Peptide Complex Isolation

Affinity-tagged HLA-peptide complex isolations were performed from cells expressing BAP-tagged HLA alleles and negative control cell lines that expressed only endogenous HLA-peptide complexes without BAP tags. The NeutrAvidin beaded agarose resin was washed three times with 1 mL cold PBS before use in HLA-peptide affinity purification. Frozen pellets containing 50×10$^6$ cells expressing BAP-tagged HLA peptides were thawed on ice for 20 minutes and gently lysed by hand pipetting in 1.2 mL cold lysis buffer [20 mM Tris-Cl pH 8, 100 mM NaCl, 6 mM MgCl2, 1.5% (v/v) Triton X-100, 60 mM octyl glucoside, 0.2 mM of 2-Iodoacetamide, 1 mM EDTA pH 8, 1 mM PMSF, 1× complete EDTA-free protease inhibitor cocktail (Roche, Basel, Switzerland)]. Lysates were incubated end/over/end at 4° C. for 15 minutes with ≥250 units Benzonase nuclease (Sigma-Aldrich) to degrade DNA/RNA and centrifuged at 15,000×g at 4° C. for 20 minutes to remove cellular debris and insoluble materials. Cleared supernatants were transferred to new tubes and BAP-tagged HLA peptides were biotinylated by incubating end/over/end at room temperature for 10 minutes in a 1.5 mL tube with 0.56 µM biotin, 1 mM ATP, and 3 µM BirA. The supernatants were incubated end/over/end at 4° C. for 30 minutes with a volume corresponding to 200 µL of Pierce high-capacity NeutrAvidin beaded agarose resin (Thermo Scientific) slurry to affinity-enrich biotinylated-HLA-peptide complexes. Finally, the HLA-bound resin was washed four times with 1 mL of cold wash buffer (20 mM Tris-Cl pH 8, 100 mM NaCl, 60 mM octyl glucoside, 0.2 mM of 2-Iodoacetamide, 1 mM EDTA pH 8), then washed four times with 1 mL of cold 10 mM Tris-Cl pH 8. Between washes, the HLA-bound resin was gently mixed by hand then pelleted by centrifugation at 1,500×g at 4° C. for one minute. The washed HLA-bound resin was stored at −80° C. or immediately subjected to HLA-peptide elution and desalting.

Antibody-Based HLA-Peptide Complex Isolation

HLA class II DR-peptide complexes were isolated from healthy donor peripheral blood mononuclear cells (PBMCs). A volume corresponding to 75 µL of GammaBind Plus Sepharose resin was washed three times with 1 mL cold PBS, incubated end/over/end with 10 µg of the antibody at 4° C. overnight, then washed with three times with 1 mL cold PBS before use in HLA-peptide immunoprecipitation. Frozen PBMC pellets containing 50×10$^6$ cells were thawed on ice for 20 minutes and gently lysed by pipetting in 1.2 mL cold lysis buffer [20 mM Tris-Cl pH 8, 100 mM NaCl, 6 mM MgCl2, 1.5% (v/v) Triton X-100, 60 mM octyl glucoside, 0.2 mM of 2-Iodoacetamide, 1 mM EDTA pH 8, 1 mM PMSF, 1× complete EDTA-free protease inhibitor cocktail (Roche, Basel, Switzerland)]. Lysates were incubated end/over/end at 4° C. for 15 minutes with >250 units Benzonase nuclease (Sigma-Aldrich) to degrade DNA/RNA and centrifuged at 15,000×g at 4° C. for 20 minutes to remove cellular debris and insoluble materials. The supernatants were then incubated end/over/end at 4° C. for 3 hours with an anti-HLA DR antibody (TAL 1B5, product #sc-53319; Santa Cruz Biotechnology, Dallas, Tex.) bound to GammaBind Plus Sepharose resin (GE Life Sciences) to immunoprecipitate HLA DR-peptide complexes. Finally, the HLA-bound resin was washed four times with 1 mL of cold wash buffer (20 mM Tris-Cl pH 8, 100 mM NaCl, 60 mM octyl glucoside, 0.2 mM of 2-Iodoacetamide, 1 mM EDTA pH 8), then washed four times with 1 mL of cold 10 mM Tris-Cl pH 8. Between washes, the HLA-bound resin was gently mixed then pelleted by centrifugation at 1,500×g at 4° C. for 1 minute. The washed HLA-bound resin was stored at −80° C. or immediately subjected to HLA-peptide elution and desalting.

HLA-Peptide Elution and Desalting

HLA-peptides were eluted from affinity-tagged and endogenous HLA complexes and simultaneously desalted using a Sep-Pak (Waters, Milford, Mass.) solid-phase extraction system. In brief, Sep-Pak Vac 1 cc (50 mg) 37-55 µm particle size tC18 cartridges were attached to a 24-position extraction manifold (Restek,), activated two times with 200 µL MeOH followed by 100 µL of 50% (v/v) ACN/1% (v/v) FA, then washed four times with 500 µL 1% (v/v) FA. To dissociate HLA-peptides from affinity-tagged HLA peptides and facilitate peptide binding to the tC18 solid-phase, 400 µL of 3% (v/v) ACN/5% (v/v) FA was added to the tubes containing HLA-bound beaded agarose resin. The slurry was mixed by pipetting, then transferred to the Sep-Pak cartridges. The tubes and pipette tips were rinsed with 1% (v/v) FA (2×200 µL) and the rinsate was transferred to the cartridges. 100 fmol of Pierce Peptide Retention Time Calibration (PRTC) mixture (Thermo Scientific) was added to the cartridges as a loading control. The beaded agarose resin was incubated two times for five minutes with 200 µL of 10% (v/v) AcOH to further dissociate HLA-peptides from the affinity-tagged HLA peptides, then washed four times with 500 µL 1% (v/v) FA. HLA-peptides were eluted off the tC18 into new 1.5 mL micro tubes (Sarstedt,) by step fractionating with 250 µL of 15% (v/v) ACN/1% (v/v) FA followed by 2×250 µL of 30% (v/v) ACN/1% (v/v) FA. The solutions used for activation, sample loading, washing, and elution flowed via gravity, but vacuum (≤−2.5 PSI) was used to remove the remaining eluate from the cartridges. Eluates containing HLA-peptides were frozen, dried via vacuum centrifugation, and stored at −80° C. before being subjected to a second desalting workflow.

Secondary desalting of the HLA-peptide samples was performed with in-house built StageTips packed using two 16-gauge punches of Empore C18 solid phase extraction disks (3M, St. Paul, Minn.) as previously described. StageTips were activated two times with 100 μL of MeOH followed by 50 μL of 50% (v/v) ACN/0.1% (v/v) FA, then washed three times with 100 μL of 1% (v/v) FA. The dried HLA-peptides were solubilized by adding 200 μL of 3% (v/v) ACN/5% (v/v) then and loaded onto StageTips. The tubes and pipette tips were rinsed with 1% (v/v) FA (2×100 μL) and the rinse volume was transferred to the StageTips, then the StageTips were washed five times with 100 μL 1% (v/v) FA. Peptides were eluted using a step gradient of 20 μL 15% (v/v) ACN/0.1% (v/v) FA followed by two 20 μL cuts of 30% (v/v) ACN/0.1% (v/v) FA. Sample loading, washes, and elution were performed on a tabletop centrifuge with a maximum speed of 1,500-3,000×g. Eluates were frozen, dried via vacuum centrifugation, and stored at −80° C.

HLA-Peptide Sequencing by Tandem Mass Spectrometry

All nanoLC-ESI-MS/MS analyses employed the same LC separation conditions described below. Samples were chromatographically separated using a Proxeon Easy NanoLC 1200 (Thermo Scientific, San Jose, Calif.) fitted with a PicoFrit (New Objective, Inc., Woburn, Mass.) 75 μm inner diameter capillary with a 10-μm emitter was packed at 1000 psi of pressure with He to ~30-40 cm with 1.9 μm particle size/200 Å pore size of C18 Reprosil beads and heated at 60° C. during separation. The column was equilibrated with 10× bed volume of buffer A (0.1% (v/v) FA and 3% (v/v) ACN), samples were loaded in 4 μL 3% (v/v) ACN/5% (v/v) FA, and peptides were eluted with a linear gradient from 7-30% of Buffer B (0.1% (v/v) FA and 80% (v/v) ACN) over 82 minutes, 30-90% Buffer B over six minutes, then held at 90% Buffer B for 15 minutes to wash the column. A subset of samples was eluted with a linear gradient from 6-40% of Buffer B over 84 minutes 40-60% Buffer B over nine minutes, then held at 90% Buffer B for five minutes and 50% Buffer B for nine minutes to wash the column. Linear gradients for sample elution were run at a rate of 200 nL/min and yielded ~13 sec median peak widths.

During data-dependent acquisition, eluted peptides were introduced into an Orbitrap Fusion Lumos mass spectrometer (Thermo Scientific) equipped with a Nanospray Flex Ion source (Thermo Scientific) at 2.2-2.5 kV. A full-scan MS was acquired at a resolution of 60,000 from 300 to 1,700 m/z (AGC target 4e5, 50 ms max IT). Each full scan was followed by a 2 sec cycle time, or top 10, of data-dependent MS2 scans at resolution 15,000, using an isolation width of 1.0 m/z, a collision energy of 34 (HLA class I data) and 38 (HLA class II data), an ACG Target of 5e4, and a max fill time of 250 ms max ion time. An isolation width of 1.0 m/z was used because HLA class II peptides tend to be longer (median 16 amino acids with a subset of peptides >40 amino acids), so the monoisotopic peak is not always the tallest peak in the isotope cluster and the mass spectrometer acquisition software places the tallest isotopic peak in the center of the isolation window in the absence of a specified offset. The 1.0 m/z isolation window will therefore allow for the co-isolation of the monoisotopic peak even when it is not the tallest peak in the isotopic cluster as the charge states of class II peptides are often +2 or higher. Dynamic exclusion was enabled with a repeat count of 1 and an exclusion duration of 5 sec to enable ~3 PSMs per precursor selected. Isotopes were excluded while dependent scans on a single charge state per precursor was disabled because HLA-peptide identification relies on PSM quality, so multiple PSMs of different charge states further increases our confidence of peptide identifications. Charge state screening for HLA class II data collection was enabled along with monoisotopic precursor selection (MIPS) using Peptide Mode to prevent triggering of MS/MS on precursor ions with charge state 1 (only for alleles with basic anchor residues), >7, or unassigned. For HLA class I data collection, precursor ions with charge state 1 (mass range 800-1700 m/z) and 2-4 were selected, while charge states >4 and unassigned were excluded.

Detection of peptides using High field asymmetric waveform ion mobility spectrometry (FAIMS) was assessed using the following protocol. Endogenously processed and presented HLA class I and HLA class II peptides from A375 cells were subjected to both acidic reverse phase (aRP) and basic reverse phase (bRP) offline fractionation prior to analysis by nLC-MS/MS using orbitrap fusion lumos tribid mass spectrometer equipped without or with FAIMS interface. FIG. 42A demonstrates the workflow. FIG. 42B, shows benchmarking of FAIMS with low amounts of tryptic samples Jurkat cell, HeLa cells. Both HLA class I binding and HLA class II binding peptides were analyzed using FAIMS (FIG. 43A and FIG. 43B; and FIG. 44A and FIG. 44B respectively). In each case, a slight improvement in peptide detection, especially with bRP fractionated peptides. FIGS. 45A and 45B and FIGS. 46 A and 46B show the intersection size.

Interpretation of LC-MS/MS Data

This section is related to, for example, FIG. 29. Mass spectra were interpreted using the Spectrum Mill software package v6.0 pre-Release (Agilent Technologies, Santa Clara, Calif.). MS/MS spectra were excluded from searching if they did not have a precursor MH+ in the range of 600-2000 (Class I)/600-4000 (Class II), had a precursor charge >5 (Class I)/>7 (Class II), or had a minimum of <5 detected peaks. Merging of similar spectra with the same precursor m/z acquired in the same chromatographic peak was disabled. MS/MS spectra were searched against a database that contained all UCSC Genome Browser genes with hg19 annotation of the genome and its protein coding transcripts (63,691 entries; 10,917,867 unique 9mer peptides) combined with 264 common contaminants. Prior to the database search, all MS/MS had to pass the spectral quality filter with a sequence tag length >2, e.g., minimum of 3 masses separated by the in-chain mass of an amino acid. A minimum backbone cleavage score (BCS) of 5 was set, and ESI QExactive HLAv2 scoring scheme was used. All spectra from native HLA-peptide samples, not reduced and alkylated, were searched using a no-enzyme specificity, fixed modification of cysteine as cysteinylation, with the following variable modifications: oxidized methionine (m), pyroglutamic acid (N-term q), carbamidomethylation (c). Reduced and alkylated HLA-peptide samples were searched using a no-enzyme specificity, fixed modification of cysteine as carbamidomethylation, with the following variable modifications: oxidized methionine (m), pyroglutamic acid (N-term q), cysteinylation (c). A precursor mass tolerance of ±10 ppm, product mass tolerance of ±10 ppm, and a minimum matched peak intensity of 30% was used for both native and reduced and alkylated HLA-peptide datasets. Peptide spectrum matches (PSMs) for individual spectra were automatically designated as confidently assigned using the Spectrum Mill autovalidation module to apply target-decoy based FDR estimation at the PSM rank to set scoring threshold criteria. An auto thresholds strategy using a minimum sequence length of 7, automatic variable range precursor mass filtering, and score and delta Rank1-Rank2 score thresholds optimized across all LC-MS/MS runs for an HLA allele yielding a PSM FDR estimate of <1.0% for each precursor charge state.

Identified peptides that passed the PSM FDR estimate of <1.0% were further filtered for contaminants by removing all peptides assigned to the 264 common contaminants proteins in the reference database and by removing peptides identified in the negative control MAPTAC' affinity pull-downs. Additionally, all peptide identifications that mapped to an in silico tryptic digest of the reference database were removed, as these peptides cannot be ruled out as tryptic contaminants from sample carry-over on the uPLC column.

Monoallelic Assignment of HLA-DR, -DQ, DP Heterodimers Using MAPTAC™ Protocol

Mono-allelic HLA assignment to LC-MS/MS identified peptides followed two approaches. Because allelic variation in HLA-DRA1 is limited and not considered to influence peptide binding, all data from DR experiments (profiling DRB1, 3, 4 and 5) were considered as mono-allelic meaning peptides were most likely bound to HLA class II heterodimers comprising capture beta chains paired with the capture alpha chains. However, the possibility remains that some peptides may have bound to HLA II heterodimers comprising knock-in the beta chains paired with a distinct endogenously expressed alpha chains.

Conversely, for HLA-DP and HLA-DQ loci, the alpha chains exhibit important allelic variants such that the presence of both knock-in and endogenous alpha chain alleles creates the potential for multiple heterodimers. For example, knock-in alpha and beta chains coding for distinct HLA-DP and HLA-DQ heterodimers can each pair with endogenously expressed alpha and beta chains making up to four unique heterodimers for each HLA-DP and HLA-DQ MAPTAC™ construct. Therefore, binding specificities among the purified MAPTAC™ peptide population are not mono-allelic. To mitigate this endogenous pairing problem, a construct that lacked the alpha chain was used that (sans-alpha knock-ins) enabled us to identify the population of peptides that likely bind to HLA heterodimers comprising endogenously alpha chains and MAPTAC™ beta chains. These peptides were computationally subtracted from the corresponding alpha+beta chain MAPTAC™ experiments to approximate a population of peptides specific to the mono-allelic MAPTAC™ alpha+beta combination.

Each peptide was assigned to one or more protein-coding transcripts within the UCSC hg19 gene annotation. Since many peptide identifications overlap others and thus constitute mostly redundant information, the peptides were grouped into "nested sets", each meant to correspond to ~1 unique binding event, as shown in FIG. 11C. For instance, the peptides GKAPILIATDVASRGLDV (SEQ ID NO: 16), GKAPILIATDVASRGLD (SEQ ID NO: 17), and KAPILIATDVASRGLDV (SEQ ID NO: 18) all contain the conserved sequence KAPILIATDVASRGLD (SEQ ID NO: 19), and probably all bind MHC in the same register. In order to nest peptides of a given data set, a graph was built in which each node corresponded to a unique peptide, and an edge was created between any pair of peptides sharing at least one 9mer and mappable to at least one common transcript. The clusters command in the R package igraph was used to identify clusters of connected nodes, and each cluster was defined as a nested set. This procedure guarantees that any two peptides that meet the edge criteria (≥1 common 9mer and ≥1 common transcript) are placed within the same nested set.

Analysis of Previously Published MS Data

The following section relates to at least FIGS. 12A-12F, FIG. 35, FIG. 36A-36B, FIG. 38D, FIGS. 39A-39C, FIGS. 40A-40B. Published LC-MS/MS datasets that provided .raw files were reprocessed using the Spectrum Mill software package v6.0 pre-Release (Agilent Technologies, Santa Clara, Calif.). Datasets that were collected on Thermo Orbitrap instruments (e.g. Velos, QExactive, Fusion, Lumos) that utilized HCD fragmentation and MS and MS/MS data collection in the orbitrap (high resolution) were analyzed using the parameters described in the above section "Interpretation of LC-MS/MS Data". For MS and MS/MS high resolution datasets that utilized CID fragmentation, the same parameters as above were used with an ESI Orbitrap scoring scheme. For datasets with MS data collection in the orbitrap and MS/MS data collection in the ion trap, the following same parameters above were also used with the following deviations. For HCD data, the ESI QExactive HLAv2 scoring scheme was used, while the ESI Orbitrap scoring scheme was used for CID data. A precursor mass tolerance of ±10 ppm, product mass tolerance of ±0.5 Da was used. For both high- and low-resolution MS/MS datasets, peptide spectrum matches (PSMs) for individual spectra were automatically designated as confidently assigned using the Spectrum Mill autovalidation module to apply target-decoy based FDR estimation at the PSM rank to set scoring threshold criteria. An auto thresholds strategy using a minimum sequence length of 7, automatic variable range precursor mass filtering, and score and delta Rank1-Rank2 score thresholds optimized across all LC-MS/MS runs for an HLA allele yielding a PSM FDR estimate of <1.0% for each precursor charge state.

Figure 11A:
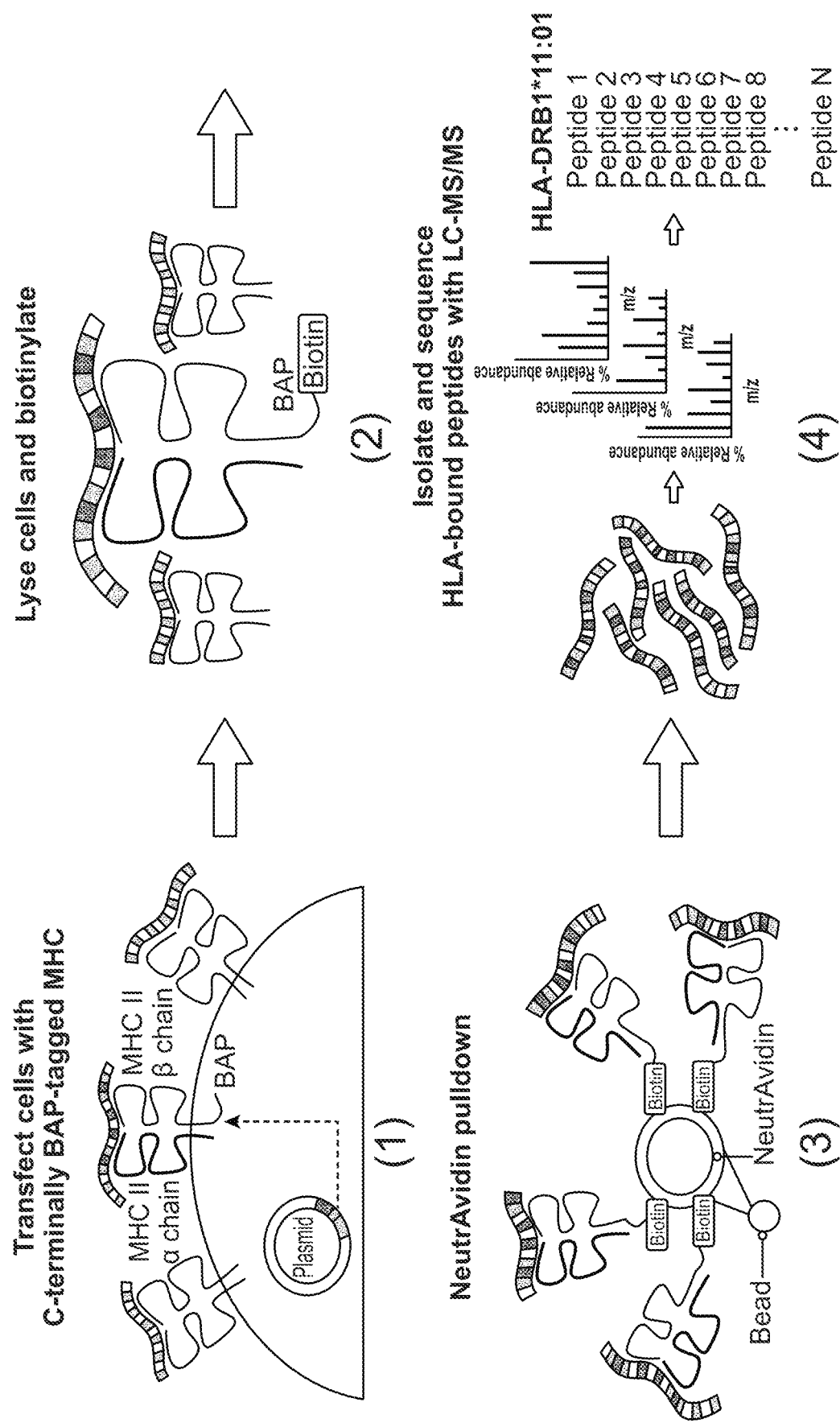
FIG. 11A depicts an exemplary overview of the MAPTAC™ experimental workflow. Figure discloses SEQ ID NO: 38.
Figure 11B:
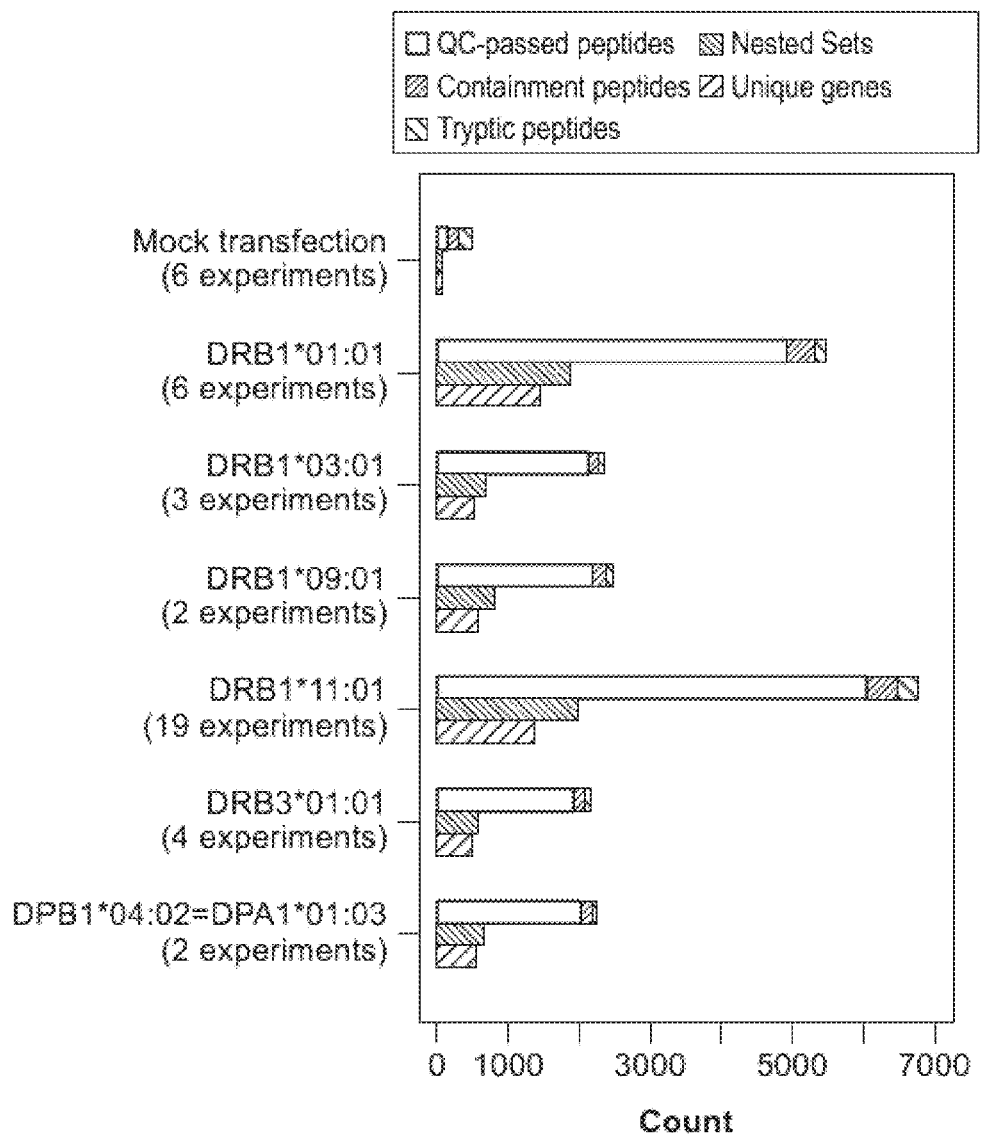
FIG. 11B depicts exemplary per-allele peptide counts, merged across replicates.
Figure 11C:
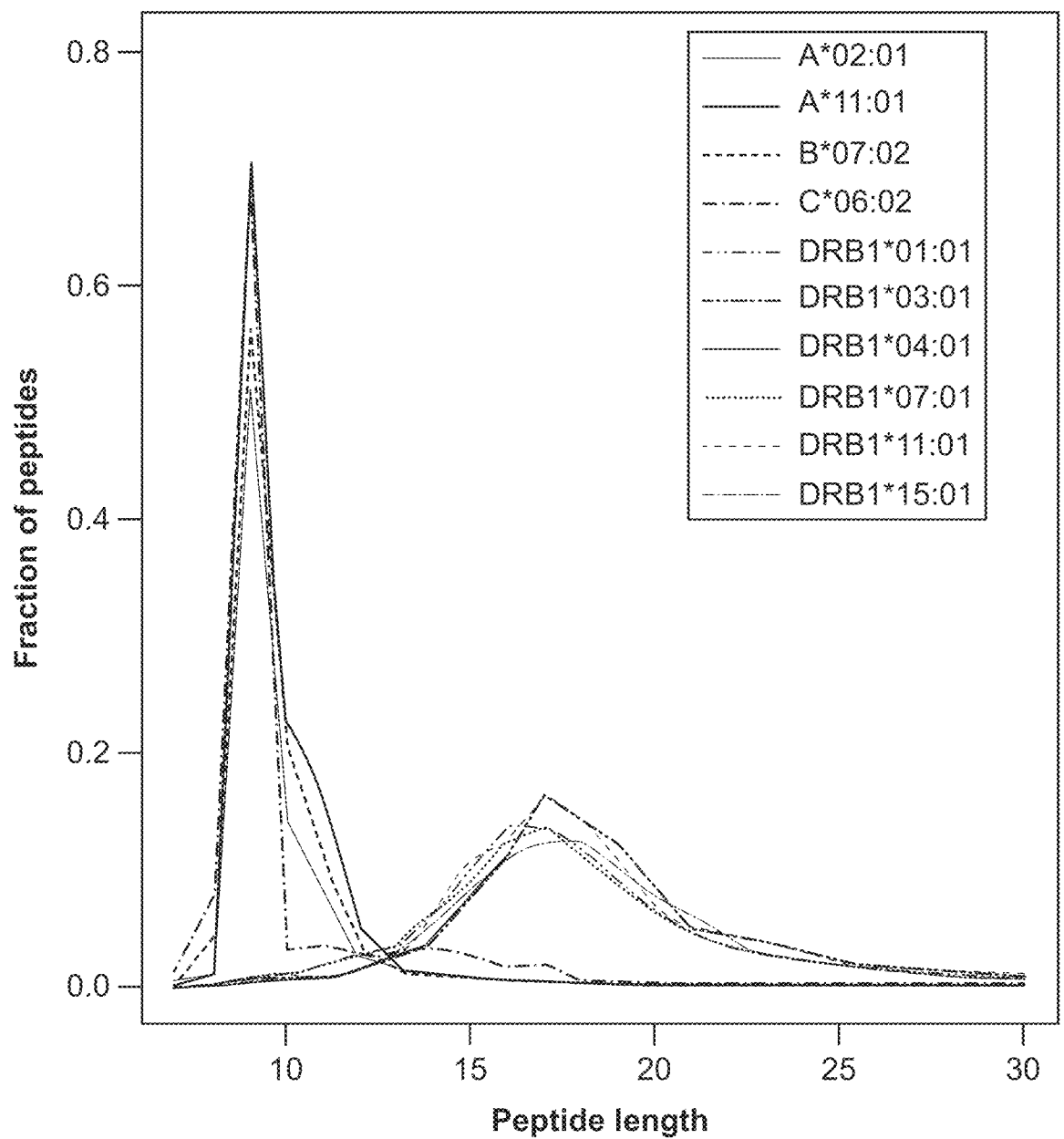
FIG. 11C depicts exemplary peptide length distributions for HLA class I and HLA class II alleles profiled by MAPTAC™.
Figure 11D:
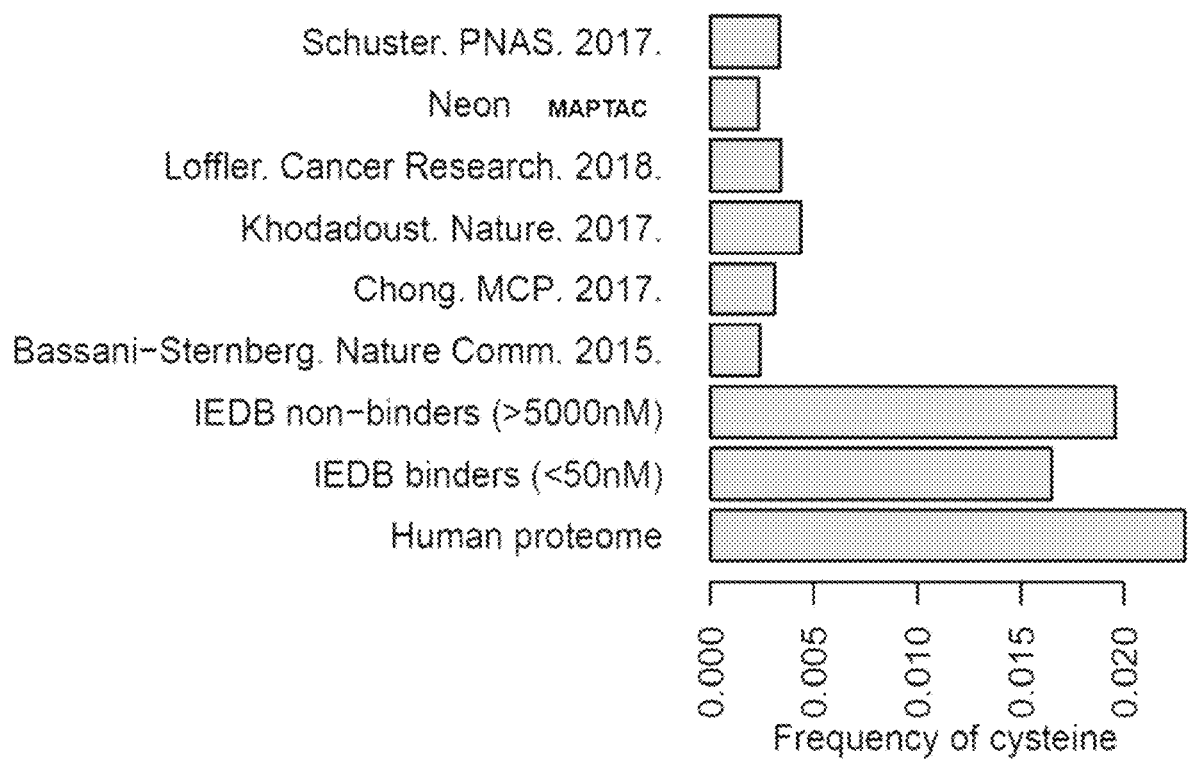
FIG. 11D depicts exemplary per-residue cysteine frequencies observed for MAPTAC™ and IEDB (alleles DRB1*01:01, DRB1*03:01, DRB1*09:01, and DRB1*11:01), the human proteome, and multi-allelic MS data from previous publications.

Amino acid frequencies in the human proteome were calculated based on sequences for all protein-coding genes in the UCSC hg19 annotation (selecting one transcript at random for genes represented by multiple transcript isoforms), as shown in FIG. 11D. IEDB frequencies were determined by identifying the unique set of peptides with at least one affinity observation ≤50 nM (excluding some peptides with hexavalent polyhistidine at their C-terminus). MAPTAC™ frequencies were first considered in the context of the standard forward-phase protocol across five DRB1 alleles alleles (DRB1*01:01, DRB1*03:01, DRB1*09:01, and DRB1*11:01), using only one peptide (the longest) per nested set. In addition, MAPTAC™ frequencies were separately calculated for the basic reverse-phase protocol across several alleles. MS data from external datasets were analyzed without respect to potential allele of origin and likewise using the longest peptide per nested set.

Building Class I (HLA Class I Binding Peptide) Sequence Logos

For each Class I allele (as depicted in FIG. 14A), a length-9 sequence logo was created by profiling amino acid frequencies in the first five positions (mapping to logo positions 1-5) and last four positions (mapping to logo positions 6-9) of corresponding peptides. In this manner, peptides contributed to the sequence logo regardless of their length. As in the Class II logos, letter heights are proportional to the frequency of each amino acid in each position, and darker shading is used for low-entropy positions.

Predicted Affinities of MS-Observed Peptides

This section is at least related to FIG. 14C. For each class II allele, all unique peptides length 14 through 17 were identified and scored for binding potential using NetMHCII-pan. For comparison, random length-matched peptides were sampled from the human proteome. Density distributions (as depicted in FIG. 14C) were determined based on log-transformed values. Some alleles were excluded from the analysis since NetMHCIIpan does not support their prediction.

Measured Affinities for MS-Observed Peptides

Peptides were selected for affinity measurement if they had poor predicted NetMHCIIpan binding affinity (>100 nM for DRB1*01:01 or >500 nM for DRB1*09:01 and DRB1*11:01) or if they exhibited ≤2 of the heuristically defined anchors to be testing in a previously published biochemical MHC-peptide affinity assay.

Establishment of Training, Tuning, and Testing Proteome Partitions

Figure 15A:
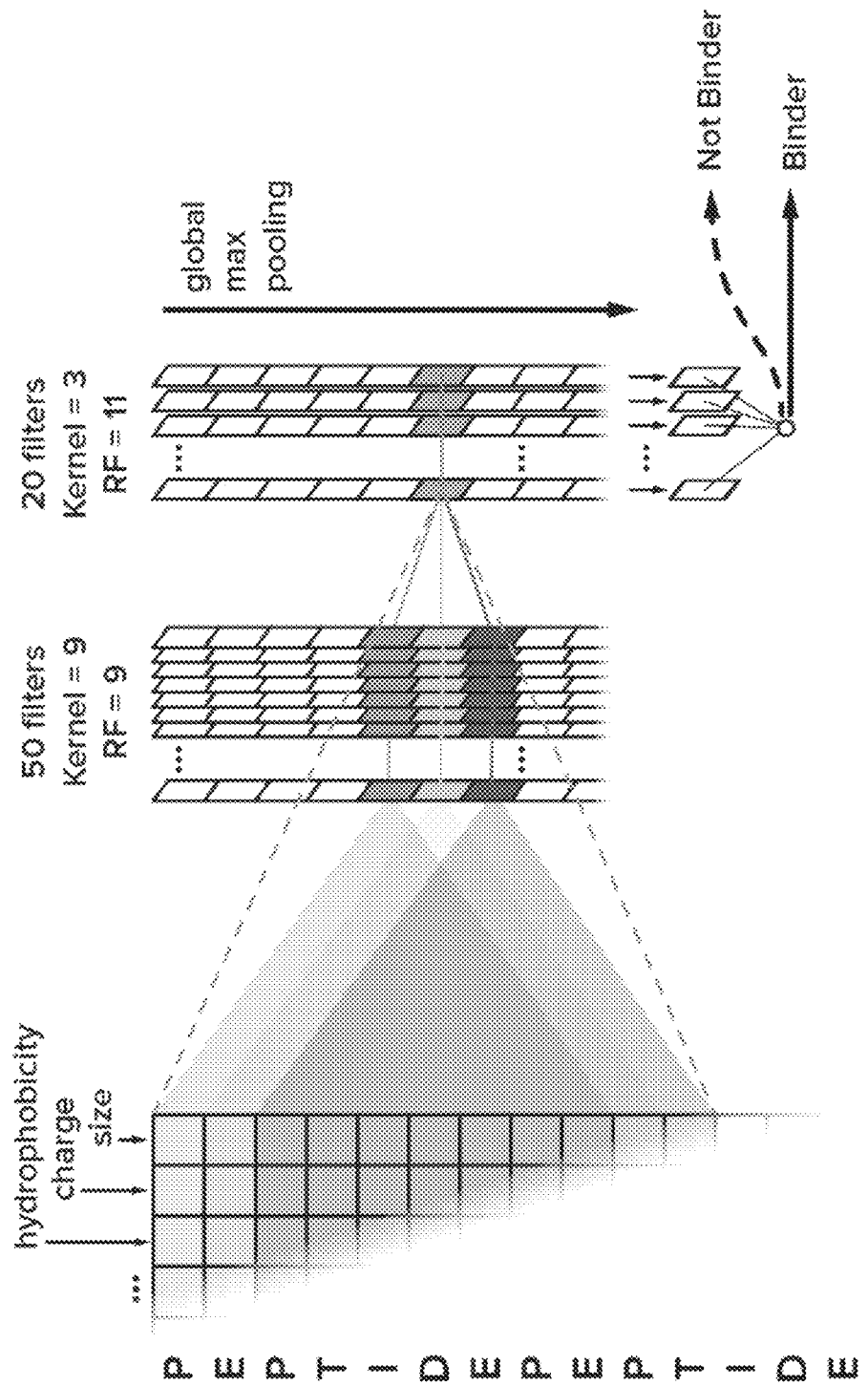
FIG. 15A depicts an exemplary architecture of a convolutional neural network (CNN) trained to distinguish mono-allelic MHC peptides from scrambled length-matched decoys. The schematic indicates the usage of an amino acid feature embedding, 2 convolutional layers with different filter sizes, and the usage of global max pooling as input to a final logistic output node.
Figure 15B:
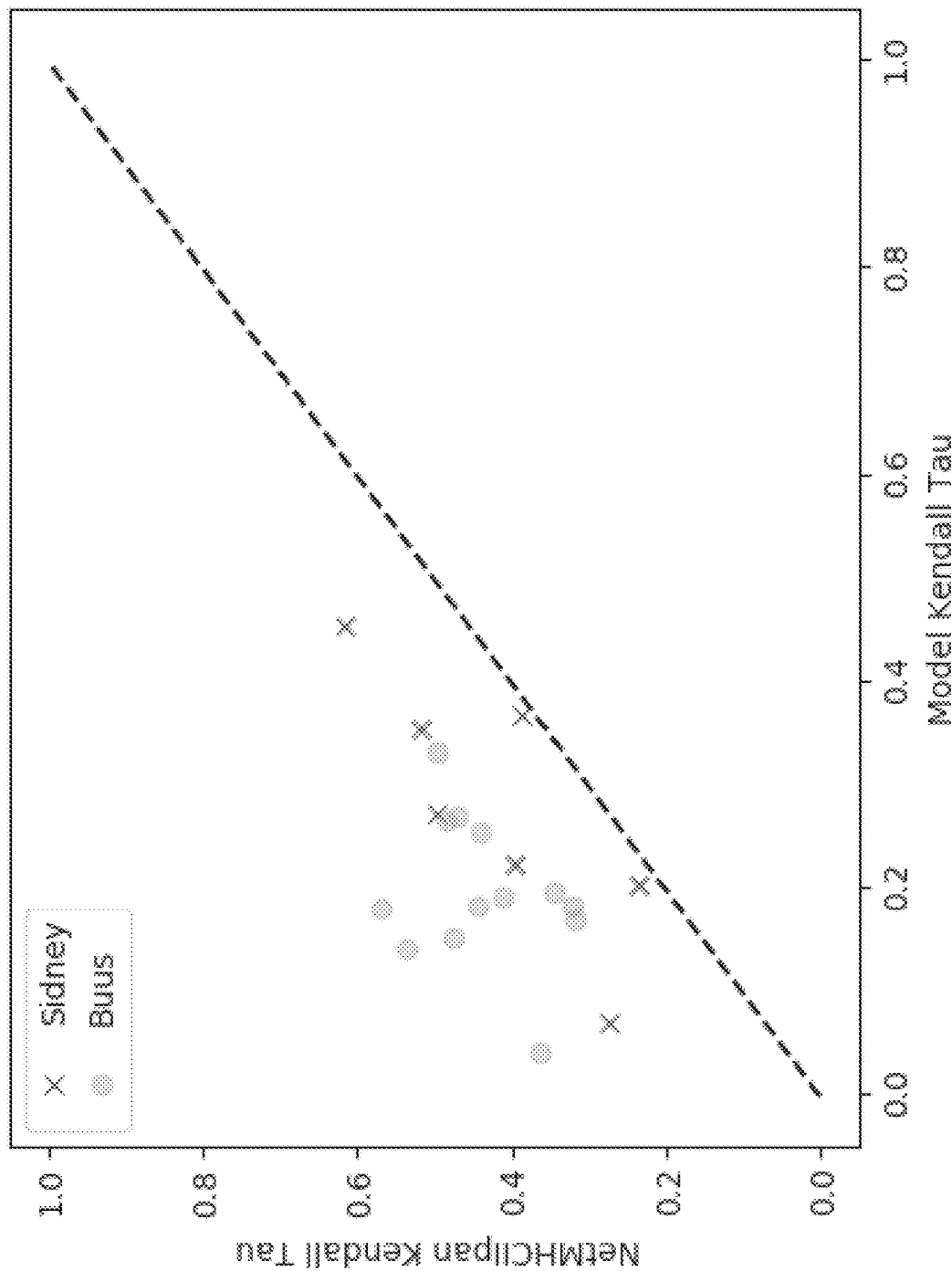
FIG. 15B is an exemplary result that shows Kendall Tau statistics for the correlation of measured IEDB affinities with binding predictions either from neonmhc2 or NetMHCIIpan.

This section is related to at least FIG. 15A (see also, FIG. 31A). A graph was created in which each node represents a protein-coding transcript and edges are present between all pairs of transcripts sharing at least 5 unique 9mers of amino sequence content (UCSC hg19 gene annotation). The clusters command in the R package igraph (cran.r-project.org/web/packages/igraph/citation.html) was used to identify clusters of connected nodes, and each cluster was defined as a "transcript group". In this manner, if two transcripts shared an edge (≥5 shared 9mers), they were guaranteed to be placed in the same transcript group. Transcript groups were randomly sampled, placing 75% in the train partition, 12.5% in the tune partition, and 12.5% in the test partition. In all analyses, MS-observed peptides (and non-observed decoy peptides) were placed in partitions (train, tune, or test) according to the partition of their source transcripts. In very rare instances in which the source transcripts mapped to multiple different partitions, the assignment preference order was train (most preferred), tune, and then test (least preferred). The same partitioning of the proteome was used in all partition-based analyses. The graph-based approach of partitioning the proteome was used to minimize the likelihood that similar peptide sequences would appear during training and evaluation, which could artificially inflate prediction performance.

Architecture and Training of a CNN-Based Class II Binding Predictor

In relation to at least FIG. 15A, while amino acids may be represented by a "one-hot" encoding, others have opted to encode amino acids using the PMBEC matrix and the BLOSUM matrix, in which similar amino acids have similar feature profiles. For the purposes of our peptide featurization, a unique matrix based amino acid proximities was generated in solved protein structures. The concept of this approach is that the typical neighbors of an amino acid should reflect its chemical properties. For each amino acid in each of 100,000 DSSP protein structures (cdn.rcsb.org/etl/kabschSander/ss.txt.gz,), the residue that was closest in 3D space but at least 10 amino acids away in primary sequence was determined. Using this data, the number of times the nearest neighbor of alanine was alanine was determined, the number of times the nearest neighbor of alanine was a cysteine, etc., to create a 20×20 matrix of proximity counts. Each element of the matrix was divided by the product of its corresponding column and row sums, and the entire matrix was log-transformed. Finally, the mean value of the entire matrix was subtracted from each element. Three additional physical features—hydrophobicity, charge, and size—were added as additional columns such that each amino acid was represented by 23 input features.

Benchmarking Prediction Performance on MAPTAC™-Observed Peptides, Related to FIGS. 21A-B For the purpose of assessing prediction performance for a given allele, it was necessary to define a set of peptides that could have been observed (because they are present in the proteome) but were not observed in the MS data. These negative examples were termed "natural decoys" (in contrast to the "scrambled decoys" described above). As guiding principles, it was decided:

1. The length distribution of natural decoys should match the length distribution of MS-observed hits.
2. Natural decoys should not contain sequence redundant with other natural decoys.
3. Natural decoys should not overlap hits.
4. Natural decoys should come from genes that produced at least one hit.

The following pseudocode represents the process an evaluation satisfying these principles was created:

---

Initialize two empty lists of hits, $H_{minimal}$ and $H_{exhaustive}$
For each nested set S of MS-observed peptides:
    If none of the peptides in S can be mapped to a transcript in the train or tune partition:
        Add the shortest peptide in S to $H_{minimal}$
        Add all peptides in S to $H_{exhaustive}$
Initialize an empty list of decoy peptides, D
For each protein-coding transcript (longest first, shortest last) in the test partition:
    If no peptides in $H_{exhaustive}$ map to the transcript:
        Skip to the next transcript
    Cover the transcript's protein sequence with a set of overlapping peptides P, where the peptide lengths are randomly sampled from the length distribution of $H_{minimal}$. The overlap is 8 amino acids. (The last peptide
in P will typically dangle over the end of the protein.)
        While the last peptide in P still dangles:
        Subtract 1 amino acid from the length of the longest peptide in P
        For each peptide in P:
            If it does not share a 9mer with a peptide in $H_{exhaustive}$ and it does contain a 9mer not observed in any peptide in D:
                Add the peptide to D
            Otherwise:
                Reject the peptide
$H_{minimal}$ and D constitute the evaluation data set

---

To evaluate performance on this set, all n hit peptides were evaluated by the predictor (neonmhc2 or NetMHCIIpan) and scored along with a set of 19n decoys (randomly sampled without replacement from the complete set of decoys). The top 5% of peptides in the combined set were labeled as positive calls, and the positive predictive value (PPV) was calculated as the fraction of positive calls that were hits. Note that since the number of positives is constrained to be equal to the number of hits, recall is equal to PPV in this evaluation scenario. The application of a consistent 1:19 ratio across alleles helps stabilize the performance values, which are otherwise highly influenced by the number of hits observed for each allele. This was deemed appropriate since it was assumed the number of hits relates more to experimental conditions and replicate count than intrinsic properties of the allele. The 1:19 ratio is not far from what was to be used if down-sampling was not implemented.

Benchmarking Prediction Performance on IEDB Affinity Measurements

As related to FIG. 15B, since NetMHCIIpan is trained on IEDB affinity data, its out-of-sample performance was evaluated using a slightly outdated version and IEDB measurements. The correspondence of predicted and measured affinities was determined by Kendall's tau coefficient. The same statistic was used to assess the performance of neonmhc2 on the same set of measurements. Evaluations were conducted separately by allele and by publishing group (Sette or Buus).

Benchmarking Prediction Performance of Natural CD4+ T Cell Responses

Since the vast majority of CD4+ T cell responses documented in IEDB have an unknown or computationally imputed Class II allele restriction, the subset of records was focused on that were confirmed experimentally by Class II tetramer. Nearly all such records were deposited by the William Kwok Laboratory (Benaroya Research Institute, Seattle, Wash.), which uses the blood of immune-reactive individuals to perform tetramer-guided epitope mapping (TGEM) of diverse pathogens and allergens. Since negative peptides were posted for some studies but not others, the source publications were reviewed to reconstruct the complete set of positive and negative peptide reactivities. All 20-mer peptides were scored by neonmhc2 and by NetMHCIIpan. To calculate positive predictive value (PPV) across alleles in a comparable way across alleles, the negative examples for each allele were randomly down-sampled until there was 1:19 ratio of positives to negatives. PPV was calculated as the fraction of experimentally confirmed positives among the top-scored 5% of peptides. Performance was also evaluated by receiver-operator curves.

Assessing the Performance of MHC II Peptide Deconvolution

To assess the ability the GibbsCluster (v2.0) tool to cluster multi-allelic MHC Class II peptide data by allele of origin, peptides from a diverse set of published DR-specific experiments on subjects of known DR genotype (Table 2) were first curated. In some cases, the original publication provided HLA-DRB1 typing but omitted typing for HLA-DRB3/4/5. To address these cases, it was assumed the DR1:DR3/4/5 linkages provided by IMGT, and if that was insufficient to resolve four-digit typing, the linkages observed in the population "USASanFranciscoCaucasian" (allelefrequencies.net, population ID 3098: Table 2 were used.

TABLE 2

| DRB1 | DRB3/4/5 | Haplotype Freq. (%) |
| --- | --- | --- |
| DRB1*03:01 | DRB3*01:01 | 23.2 |
| DRB1*04:01 | DRB4*01:01 | 9 |
| DRB1*04:02 | DRB4*01:01 | 2.2 |
| DRB1*04:04 | DRB4*01:01 | 3.2 |
| DRB1*07:01 | DRB4*01:01 | 13.2 |
| DRB1*09:01 | DRB4*01:01 | 2.8 |
| DRB1*11:01 | DRB3*02:02 | 7.2 |
| DRB1*11:04 | DRB3*02:02 | 2.8 |
| DRB1*13:01 | DRB3*02:02 | 2.6 |

TABLE 2-continued

| DRB1 | DRB3/4/5 | Haplotype Freq. (%) |
| --- | --- | --- |
| DRB1*13:02 | DRB3*03:01 | 2.6 |
| DRB1*14:01 | DRB3*02:02 | 2.2 |
| DRB1*15:01 | DRB5*01:01 | 28.6 |

Note that DRB4*01:01 has been shown to be identical to DRB4*01:03 (ebi.ac.uk/cgi-bin/ipd/imgt/hla/get_allele.cgi?DRB4*0101)

For each DRB1/3/4/5 allele present in each (imputed) genotype, twenty peptides from our mono-allelic MAP-TAC™ data were spiked in. These augmented datasets were then submitted to GibbsCluster-v2.0.

Characterizing Observed Cleavage Sites of MHC II Peptides

Disclosed herein is a large dataset of naturally processed and presented peptides MHC II peptides by merging peptide identifications across several studies that used immunopurification to profile human tissues (Table 2). Since many peptides share the same N-terminus (e.g. GKAPILI-ATDVASRGLDV (SEQ ID NO: 16) and GKAPILI-ATDVASRGLD (SEQ ID NO: 17)) or the same C-terminus (e.g. GKAPILIATDVASRGLD (SEQ ID NO: 17) and KAP-ILIATDVASRGLD (SEQ ID NO: 19)), two sets of non-redundant cut sites were curated, one for N-termini and one for C-termini. Then, an equivalent number of unique non-observed N-terminal and C-terminal cut sites were sampled at random from the set of genes that had produced at least one MHC II peptide. These four data sets were referred to as N-terminal hits, C-terminal hits, N-terminal decoys, and C-terminal decoys. In addition, a naming system was used to refer to positions upstream of peptides, within peptides, and downstream of peptides which is shown in FIG. 41.

The frequency of each amino acid was determined for positions U10 through N3 for N-terminal hits, and these frequencies were compared to those observed for N-terminal decoys. To determine whether hits and decoys showed a significant difference in the rate of a given amino acid at a given position, a 2×2 table (e.g. count of hits for which U1 is lysine, count of decoys for which U1 is lysine; count of hits for which U1 is not lysine, and count of decoys for which U1 is not lysine) was created and scored by a Chi-square test. An analogous approach was use for analyzing amino acid frequencies in positions C3 through D10 of C-terminal hits and decoys.

A second analysis considered statistical linkages between residues immediately preceding and following cleavage events. First, the count of U1:N1 pairs (A:A, A:C, A:D, Y:V, Y:W, Y:Y) was compared for N-terminal hits vs. N-terminal decoys, and significance of enrichment/depletion for each pair was determined by a Chi-square test of a 2×2 contingency table (e.g. count of hits with P:K, count of decoys with P:K; count of hits without P:K, count of decoys without P:K). An analogous approach was used for analyzing C1:D1 pair frequencies of C-terminal hits and decoys.

Benchmarking the Performance of Various Class II Cleavage Predictors

Peripheral blood from healthy donors was profiled for DR-binding peptides. These samples were used to benchmark the ability of cleavage-related variables/predictors to enhance the identification of presented Class II epitopes.

To build integrated predictors that predict peptide presentation using both binding potential and cleavage potential, a dataset was first constructed using the same approach described for FIG. 4 but using the "tune" partition rather than the "test" partition. In short, this meant using a 1:20 ratio of hits to decoys, where decoys are length-matched to hits and are randomly sampled from the set of genes that generated at least one hit. Binding potential was calculated using neonmhc2, and because these samples were multi-allelic, the binding score for each peptide candidate peptide was taken to be the average of the 1-4 DR alleles indicated by each donor's genotype. This fitting process determined the relative weights that would be placed on the binding and cleavage variables in forward prediction.

To determine the performance of forward prediction, evaluation hits and decoys (1:19 ratio) were obtained from the "test" partition using the same protocol just described. PPV was calculated in the same manner as for FIG. 4. Several different cleavage predictors were assessed as shown in Table 3.

TABLE 3

PSM with known cleavage site
PSM with unknown cleavage site
To score a candidate peptide, the 9mer core was first imputed. Next, the maximum PSM score was calculated across three regions: the 10 amino acids upstream of the core (regardless of the location of the true N-terminal cleavage site), the core sequence, and the 10 amino acids after core. A logistic regression was trained on the tune partition (see above) using the neonmhc2 binding score as well as the three region-specific PSM scores.
Novel neural network, unknown cleavage site
Cathepsin motifs, unknown cleavage site
Structural features
Within the SCRATCH suite (Cheng J, Randall A Z, Sweredoski M J & Baldi P (2005) SCRATCH: a protein structure and structural feature prediction server. Nucleic Acids Res. 33: W72-6 Available at: dx.doi.org/10.1093/nar/gki396), the tool ACCpro20 was used to predict relative solvent accessibility (RSA), and the tool SSpro8 was used to predict features of secondary structure (H: alpha-helix G: 310-helix I: pi-helix E: extended strand B: beta-bridge T: turn S: bend C: other). Per-residue scores of sequence disorder (d2p2.pro/download) were likewise determined over the entirety of the proteome, scoring on a 0-5 scale according to the number of prediction engines labeling the position as disordered (servers used: anchor, espritz-d, espritz-n, espritz-x, iupred-l, and iupred-s). Finally, topological domains (transmembrane, signal, extracellular, lumenal, and disulfide) were determined at the residue level using Uniprot (uniprot_sprot.dat). For each candidate peptide, average RSA and average disorder score were calculated over a 21mer window centered on the predicted 9mer core. Over the same 21-residue window, percent composition was calculated for secondary structure features and topological features. Four logistic regression models were trained on the "tune" partition using the following input features:
1. Neonmhc2 binding score and solvent Accessibility (RSA)
2. Neonmhc2 binding score and disorder score
3. Neonmhc2 binding score and eight SSpro8-derived features representing secondary structure
4. Neonmhc2 binding score and five Uniprot features representing topology
Overlap with a previously observed peptide
MS-based peptide identifications were pooled across many multi-allelic Class II experiments from the public domain. A new feature was created representing whether a new candidate peptide overlapped with one of these previously observed peptides. Specifically, the feature was set to 1 if it shared at least one 9mer with any peptide in the large set of previously observed MHC II ligands; otherwise the feature was set to 0. A logistic regression was trained on the "tune" partition using the neonmhc2 binding score and the overlap feature.

Relationship Between MHC Class II Presentation and Expression

Peptides were pooled across previously published MS experiments that profiled the HLA-DR ligandomes of human ovarian tissues. For each sample with available RNA-Seq data, the raw fastqs were downloaded from SRA and aligned to the UCSC hg19 transcriptome using bowtie2. Transcript level gene quantification was performed using transcripts per million (TPM) as calculated by RSEM. The expression estimates were further processed by summing to the gene level, dropping non-coding genes, and renormalizing such that the total TPM summed to 1000000 (renormalizing across protein-coding genes accounts for library-to-library variation in ncRNA abundance).

For each gene in each tissue sample, its expression level in the sample and whether it produced at least one peptide in the sample was considered. Across all MS experiments, these observations were binned according to expression level and peptide generating status (see FIG. 18A).

Identification of Over- and Under-Represented Genes

To identify genes over- and under-represented in MHC II ligandomes, data was compiled from five previous studies that profiled ovarian tissue, colorectal tissue, and cutaneous melanomas, lung cancers and head and neck cancers. For each gene, our baseline assumption was that it should yield peptides in proportion to its length multiplied by its expression level. To determine the length of each gene, the unique 9mers across all transcript isoforms were enumerated. Gene-level expression was obtained by summing across transcript isoforms. The observed number of peptides mapping to each gene was determined at the nested set level (e.g. peptides GKAPILIATDVASRGLDV (SEQ ID NO: 16), GKAPILI-ATDVASRGLD (SEQ ID NO: 17), and KAPILIATDVAS-RGLDV (SEQ ID NO: 18) counted as a single observation).

Many samples from the ovarian study had corresponding RNA-Seq data, but some did not. In those cases, expression was estimated averaging across the samples with available RNA-Seq data. For the colorectal and melanoma studies, there was no corresponding RNA-Seq for any samples, so averages were calculated across surrogate samples using data from GTEx and TCGA. In all cases, raw fastqs were obtained and aligned and quantified them according to the same protocols as described above for the ovarian study's RNA-Seq.

Two matrices were created representing expected and observed counts, referred to as E and O, respectively, wherein rows correspond to genes and columns correspond to samples. The matrix E was first populated by multiplying each gene's length by its expression in each sample; then the columns of E were rescaled to make the column sums of E match the column sums of O. Finally, analysis was made at the gene level by comparing the row sums of E to the row sums of O. Genes were highlighted according to their presence and concentration in human plasma.

Analysis of Genes Related to Autophagy

Two autophagy-related gene sets were defined. The first set comprised proteins experimentally identified as physical interaction partners of known autophagy-related genes. For each canonical autophagy-related gene (genenames.org/cgi-bin/genefamilies/set/1022) used as bait in an IP-MS experiment deposited in the Autophagy Interaction Network data base (accessed from besra.hms.harvard.edu/ipmsmsdbs/cgi-bin/downloads.cgi), the top 100 protein identifications according to the "WD" confidence score (besra.hms.harvard.edu/ipmsmsdbs/cgi-bin/tutorial.cgi) were identified. Pooling across 22 experiments, a set of 1004 unique genes were obtained confidently associated with at least one canonical autophagy-related gene. (FIG. 18C)

A second set of autophagy-related genes were identified using a study that measured pan-proteome protein abundance in baby mouse kidney epithelial (iBMK) cells pre- and post-ATG5 knockout using SILAC (sciencedirect.com/science/article/pii/S1097276514006121). Genes with at-statistic >5 were classified as being stabilized by ATG5 knockout (pre-starvation conditions; variable "Intercept t" in supplemental data file mmc2.xls). To map each mouse Uniprot ID to an hg19 UCSC ID, the human UCSC protein sequence was determined with which the mouse Uniprot sequence shared the most 9mers. (FIG. 18C)

Based on FIG. 18B, the ratio R of observed to expected peptides per gene was calculated, adding a pseudocount of one to both the numerator and the denominator, e.g. R=(O+1)/(E+1). Log(R) was taken to represent the relative enrichment (Log(R)>0) or depletion (Log(R)<0) of each gene felt that there was insufficient information to quantify relative enrichment/depletion for these genes. Among the genes with valid Log(R) calculations, Log(R) distributions were plotted for those in the IP-MS dataset, those in the SILAC dataset, and those in neither dataset (FIG. 18C).

Analysis of Source Gene Localization, Related to FIG. 18D

Using the same log(R) score as described above, distributions according to the localization of each source gene was plotted (FIG. 18D). Source gene localization was determined using Uniprot (uniprot_sprot.dat).

Analysis of Class II Expression Data in Single-Cell RNA-Seq Data, Related to FIG. 19A Single-cell RNA-Seq data were obtained from three previously published data sets that profiled human tumor samples.

The first study included data from cutaneous melanomas. The file "GSE72056_melanoma_single_cell_revised_v2.txt" was downloaded from Gene Expression Omnibus (ncbi.nlm.nih.gov/geo/; accession: GSE72056). Cells with tumor status flag "2" were treated as tumor cells, and cells labeled with tumor status flag "1" and immune cell type flag equal to "1" through "6" were treated as T cells, B cells, Macrophages, Endothelium, Fibroblasts, and NKs, respectively. All other cells were dropped. Data were natively presented in units of log 2(TPM/10+1) and were thus mathematically converted to a TPM scale. Once on the TPM scale, the data for each cell was renormalized to sum to 1,000,000 over the set of protein-coding UCSC gene symbols (protein-coding genes not appearing in the expression matrix were implicitly treated as having zero expression). Finally, single-cell observations corresponding to the same cell type and same source biopsy where averaged to produce expression estimates at the patient-cell type level.

The second study included data from head and neck tumors. The file "GSE103322_HNSCC_all_data.txt" was downloaded from the Gene Expression Omnibus (ncbi.nlm.nih.gov/geo/; accession: GSE103322). The data in this table are in units of log 2(TPM/10+1); therefore, the values were mathematically converted to TPM units. As with the melanoma study, the data for each cell was renormalized to sum to 1,000,000 over the set of protein-coding UCSC gene symbols, and single-cell observations corresponding to the same cell type and same source biopsy where averaged. Data corresponding to the lymph node biopsies were excluded.

The third study included data from untreated non-small cell lung. The files "RawDataLung.table.rds" and "metadata.xlsx" were downloaded from ArrayExpress (ebi.ac.uk/arrayexpress/; accessions: E-MTAB-6149 and E-MTAB-6653). The data (already in TPM) units, were re-scaled to sum to 1,000,000 over the set of protein-coding genes as previously described. Finally, single-cell observations corresponding to the same cell type and same source biopsy where averaged to produce expression estimates at the patient-cell type level. Similar studies in colorectal and ovarian cancers were performed. Results are indicated in FIG. 19A.

For simplicity, cell types were merged to a coarser granularity than natively reported in Table 4.

TABLE 4

| Coarse designation | Constituent cell types |
|---|---|
| Alveolar | "Alveolar", excluding "cuboidal alveolar type 2 (AT2) cells" |
| FO B cells | "follicular B cells" |
| Plasma cells | "plasma B cells" |
| CLEC9A+ DCs | "cross-presenting dendritic cells" |
| monoDCs | "monocyte-derived dendritic cells" |
| pDCs | "plasmacytoid dendritic cells" |
| Langerhans | "Langerhans cells" |
| Macrophages | "macrophages" |
| Granulocytes | "granulocytes" |
| Endothelium | "normal endothelial cell", "tumor endothelial cell", and "lower quality endothelial cell", excluding "lymphatic EC" |
| Epithelium | "epithelial cell" and "lower quality epithelial cell" |
| Fibroblasts | "COL12A1-expressing fibroblasts", "COL4A2-expressin fibroblasts", "GABARAP-expressing fibroblasts", "lower quality fibroblasts", "normal lungfibroblasts", "PLA2G2A-expressing fibroblasts", and "TFPI2-expressing fibroblasts" |
| T cells | "regulatory T cells", "CD4+ T cells" and "CD8+ T cells" |
| NKs | "natural killer cells" |
| Tumor | "cancer cells" |
| Excluded from analysis | "erythroblasts" and "MALT B cells" |

Expression levels of HLA-DRB1 in the five studies are plotted in FIG. 19A.

Characterization of Tumor-Derived Vs. Stroma-Derived Class II Expression

To determine the relative amount of MHC class II binding peptide expression attributable to tumor vs. stroma, mutations were identified in Class II pathways genes in TCGA patients (called based on DNA), and for each patient bearing a Class II mutation, the relative expression of the mutated and non-mutated copies were quantified of the gene the corresponding RNA-Seq. Further, it was assumed:

1. Mutated reads arise from the tumor
2. Non-mutated reads arise for the stroma or the wildtype allele in the tumor
3. The tumor retains a wildtype copy with expression approximately equal to the mutated copy Based on this, it was determined that for an observed mutant allele fraction off the fraction of Class II expression attributable to tumor was approximately 2f and not greater than 100%. Three genes—CIITA, CD74, and CTSS—were selected as core Class II pathway genes and assessed for mutations (not excluding synonymous and UTR mutations) in TCGA (data downloaded from TumorPortal (tumorportal.org/): BRCA, CRC, HNSC, DLBCL, MM, LUAD; TCGA bulk download (tcga-data.nci.nih.gov): CESC, LIHC, PAAD, PRAD, KIRP, TGCT, UCS; Synapse (synapse.org/M Synapse:syn1729383): GBM, KIRC, LAML, UCEC, LUSC, OV, SKCM; or the original TCGA publication (cancergenome.nih.gov/publications): BLCA, KICH, STAD, and THCA). These genes were selected based on their known roles in Class II expression and their tight correlation with HLA-DRB1 across a cohort of 8500 GTEx samples. Other genes with equivalent correlation with HLA-DRB1 (HLA-DRA1, HLA-DPA1, HLA-DQA1, HLA-DQB1, and HLA-DPB1) were excluded because their polymorphic nature makes them prone to false positive mutation calls. Naturally, only a small fraction of patients had a mutation in CIITA, CD74, or CTSS, and for some tumor types, there were no patients available to analyze.

Sequences of original whole exome sequencing (WES) in Binary Sequence Alignment/Map (BAM) format were visually assessed (IGV tool) to confirm that the mutation was present in the tumor sample and not present in the normal sample. Mutant vs. wildtype read counts were obtained from corresponding RNA-Seq using pysam. Overall HLA-DRB1 expression was determined based on expression data downloaded from the Genomic Data Commons (gdc.cancer.gov), which was renormalized to sum to 1,000,000 over the set of protein-coding genes. The fraction of HLA-DRB1 expression attributable to the tumor (FIG. 19B) was estimated as min(1,2f), where f is the fraction of RNA-Seq reads in CIITA, CD74, or CTSS exhibiting a mutation.

Assessing Prediction Overall Performance on Natural Donor Tissues

Peripheral blood from seven healthy donors was profiled with a DR-specific antibody as described in the section "Antibody-based HLA-peptide complex isolation" above. Based on these results, two datasets were defined: one for fitting multivariate logistic regressions and another for evaluating the prediction performance of the regressions.

The first dataset was built by using the hit and decoy selection algorithm previously described in relation to FIG. 4. In short, this means representing each nested set with one hit peptide (the shortest peptide in the nested set) and tiling length-matched decoys over genes such that they overlap minimally with hits and minimally with each other. However, two important details differ from algorithm outlined for FIG. 4. First, the hits and decoys are selected from genes in the "tune" partition (rather than the "test" partition), and second, decoys were allowed to map to genes that showed zero hits. Logistic regression models with MHC binding scores (from NetMHCIIpan or neonmhc2) as well as other input features (expression, gene bias, etc.) were trained on this dataset.

The second data set (used for evaluation), was built in an identical manner, except it used the hits and decoys drawn from the "test" partition. In addition to binding scores, the following variables were used in a subset of the regressions, as shown in Table 5.

TABLE 5

| | |
|---|---|
| NetMHCIIpan Affinity | Derived from NetMHCIIpan. For each candidate peptide, the strongest score was taken across all DR alleles in the donor's genotype. |
| MS-based binding score | Derived from neonmhc2. For each candidate peptide, the strongest score was taken across all DR alleles in the donor's genotype. |
| Expression | Gene expression estimates were obtained by analyzing data from bowtie2, RSEM, and renormalization over protein-coding genes only, values averaged over N samples |
| Hotspot | Indicator variable (0/1) for whether the candidate peptide shares at least one 9mer with any of the previously published multi-allelic datasets |
| Gene bias | (1 + observed)/(1 + expected) per the analysis |
| Cross presentation | Indicator variable (0/1) for whether the candidate peptide comes from a gene observed to be cross-presented on MHC class II by DCs. |

For the purpose of performance evaluation, all n hit peptides were evaluated by the given logistic regression and scored along with a set of 499n decoys (randomly sampled without replacement from the complete set of decoys). The top 0.2% of peptides in the combined set were labeled as positive calls, and the positive predictive value (PPV) was calculated as the fraction of positive calls that were hits. Note that since the number of positives is constrained to be equal to the number of hits, recall is exactly equal to PPV in this evaluation scenario. The application of a consistent 1:499 ratio across alleles helps stabilize the performance values, which are otherwise highly influenced by the number of hits observed for each donor. This was deemed appropriate since it was assumed the number of hits relates more to experimental conditions than intrinsic properties of the donor's cells. The 1:499 ratio is not far from what would be used if down-sampling was not implemented.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Example 11: High-Throughput Identification and Validation of HLA Class II Allele Binding Epitopes In this example, a representative reliable, high-throughput method using time resolved fluorescence energy transfer (TR-FRET) for identification and validation of novel MHC-II allele-binding peptides is described. The assay has several parts, (1) transfecting cells with a vector construct suitable for expressing and secreting MHC-II α and β chains having a fluorescence tag for the FRET assay, (2) purifying the secreted MHC-II construct protein products, (3) performing a peptide exchange assay (FIG. 22A). FIG. 22B and FIG. 23 further exemplify the design and the procedure. The assay as described herein promotes fast and efficient detection and validation protocol, as it may not require stable cell lines, and encompasses simple isolation strategies. In addition, the tetramer or multimer can be used to detect antigen-specific CD4 cells, for example, after neonmhc2 predicted epitopes are administered in vivo, and the immune response generated thereafter is used to verify CD4+ T cell response.

CLIP-TR-FRET Assay for Identifying High Affinity MHC Class-II Binding Peptides

Presented herein are exemplary vectors for expression of HLA class II α and β chains driven by a CMV promoter in a single construct, the protein product of which yields a properly folded α and β chain pairs. In a properly folded α and β chain form, the α1 subunit and the β1 subunit are in dimer form, the α1 subunit and the β1 subunits forming the open accepting end, capable of accepting a peptide, resembling physiological configurations. For the purpose of this assay, these vector expressed HLA protein products with the properly folded α and β chain form are called HLA monomers. The expression construct comprises a linker, one or more peptide cleavage sites, secretion signal, dimerization factors, for example c-Fos and Jun, linked with a biotinylation motif (BAP) and a 10×-His-Tag (SEQ ID NO: 20). A placeholder peptide is used to stabilize the monomers and help in secretion. A placeholder peptide can be a CMV peptide. A placeholder peptide can be a CLIP peptide. A placeholder peptide can be a peptide identified via MS based ligandome for the alleles. A placeholder peptide can be bound covalently to the HLA peptides at the open α1-β1 peptide accepting end.

An exemplary construct used herein encodes a CLIP placeholder peptide with a thrombin cleavage moiety placed between the CLIP and the β chain, as shown in FIG. 23 (upper panel). Upon transfection and culture of the transfected cells, such that they reach optimal growth, the cell culture supernatant (medium) comprising the secreted proteins (monomers) were collected and passed through nickel ($Ni^{2+}$) columns for purification (FIG. 24). Expression levels and purification was examined by Coomassie staining. The 28-mer CLIP peptide remains associated with the β chain, which is cleaved by treatment with thrombin (FIG. 24) and thereafter may be dislodged by competing with test (e.g., candidate) HLA-Class-II binding peptide. A test peptide that successfully dislodges the CLIP peptide is accountably a cognate peptide for binding to the MHC-II heterodimer of the construct, based on ability to displace the CLIP peptide as measured by its IC50. A de novo test peptide could be used for a competitive displacement reaction as described above can then be identified by mass spectrometry (MS).

A large collection of HLA-DR heterodimer constructs were made with CLIP placeholder peptides which were successfully secreted and peptide exchange assays were performed.

It was observed that the peptide placeholder CLIP, derived from CD74, has significant effect on the secretion of HLA class II monomers. The edited canonical CLIP peptide having the CD74 sequence PVSKMRMATPLLMQA (SEQ ID NO: 1) (designated as CLIP0 in FIG. 25A-25C) was generally used as placeholder sequence. However, it was seen that some HLA-DR peptides, for example, DRB1*12:01 and DRB1*13:02 had low yield with the canonical peptide (Table 6). It was observed that certain HLA DRB allelic dimers have a binding sequence longer sequence covering the whole or parts of the amino acids in the sequence: LPKPPKPVSKMRMATPLLMQALPM (SEQ ID NO: 21) (CLIP1) (FIG. 25A). Indeed, using CLIP1 sequence instead of CLIP0 sequence in case of DRB1*12:01 and DRB1*13:02 improved the secretion yield of the HLA dimers (FIG. 25B-25C).

TABLE 6

| DRB1* | Peptide placeholder | SEQ ID NO: | Yield (mg/L) |
|---|---|---|---|
| 01:01 | PVSKMRMATPLLMQA (CLIP) | 1 | 20 |
| | LPLKMLNIPSINVH (CMV) | 22 | 100 |
| | PKYVKQNTLKLAT (HA) | 23 | 85 |
| 12:01 | PVSKMRMATPLLMQA (CLIP) | 1 | <3 |
| 13:02 | PVSKMRMATPLLMQA (CLIP) | 1 | <3 |

De Novo Screen of Peptides by Successful Peptide Exchange Assay Using STII-TR-FRET Peptides can be screened de novo using the assay involving expressing HLA-monomer proteins described above in cell lines, such as Expi293 cells, collected and purified from the supernatant, and subjected to peptide exchange assay. HLA class II binding peptides predicted by the prediction algorithms were tested using peptide exchange assay. Peptides exchange assay can be performed using a method involving fluorescence polarization. For example, any fluorophore can be used to label either the placeholder peptide, or to label the test peptide, or to label both using two different fluorophores. Change is florescence either by loss of the bound placeholder peptide that was previously labeled with a fluorophore, or by fluorescence emission of a released fluorophore that was otherwise quenched by biochemical reactions in its HLA bound form, can be recorded for quantitative assessment of the displacement reaction. Alternatively, replacement of a non-fluorescent placeholder peptide with a labeled fluorescent peptide could be recorded to quantitatively determine the displacement reaction. In an exemplary assay, FITC-labeled placeholder CLIP peptide was used to displace an existing covalently bound peptide such as a CMV peptide. The FITC-labeled peptide when bound with HLA induces high polarization. When the FITC-placeholder peptide is titrated with a test peptide, the test peptide displaces the FITC-CLIP, which leads to lowering of fluorescence.

A peptide exchange assay can also be performed using time resolved FRET (TR-FRET) technology instead of fluorescence polarization as described herein. In an exemplary TR-FRET assay described herein, cells were transfected with an HLA monomer construct having a placeholder peptide that comprises a Streptag II (STII) moiety. The STII moiety was detected by an Alexa-647-tagged antibody for STII. At the same time, the His-tag attached to the Jun terminal of the monomer construct described earlier in this example, which is present close to the α2-β2 end of the HLA peptides, was detected by an Europium III (Eu) compound coupled anti-His antibody (FIG. 26A). The Eu complex acts as an energy donor, whereas the Alexa647 acts as the acceptor in the FRET reaction when the placeholder peptide remains bound to the HLA monomer. When a test peptide displaced the STII-CLIP placeholder, Alexa-647-αSTII peptide is freed but it can no longer be detected by fluorescence. The TR-FRET assay was found to be more reliable than the fluorescence polarization. Additionally, the assay had much reduced background signal. (Fluorescence readout data are shown in FIGS. 26B-26E). The assay provides high throughput identification platform for HLA-peptide pairs. As shown in Table 7 below, the test peptide (or candidate peptides) P-156 to P-191 exhibited a wide range of displacement capabilities, and binding affinity as determined by the calculated IC50 with each run. Lower IC50 demonstrates higher displacement capability, and higher binding affinity.

TABLE 7

| Peptide | IC50 (nm) Run 1 | IC50 (nm) Run 2 | Avg IC50 (nM) | Std. Dev (nM) | Comments |
|---|---|---|---|---|---|
| P-156 | 36294 | 38246 | 37270 | 976 | |
| P-157 | 2550 | 2243 | 2397 | 154 | |
| P-158 | 5786 | 5815 | 5800 | 15 | |
| P-159 | 58 | 94 | 76 | 18 | |
| P-160 | 1668 | 2020 | 1844 | 176 | |
| P-161 | 13541 | 14401 | 13971 | 430 | |
| P-162 | 3298 | 3636 | 3467 | 169 | |
| P-163 | >40,000 | >40,000 | >40,000 | N/A | <50% displacement at 40 µM |
| P-164 | 4553 | 4353 | 4453 | 100 | |
| P-165 | 357 | 422 | 389 | 32 | |

TABLE 7-continued

| Peptide | IC50 (nm) Run 1 | IC50 (nm) Run 2 | Avg IC50 (nM) | Std. Dev (nM) | Comments |
|---|---|---|---|---|---|
| P-166 | 3448 | 3104 | 3276 | 172 | |
| P-167 | 6612 | 5906 | 6259 | 353 | |
| P-189 | 4597 | — | — | — | |
| P-190 | 1137 | — | — | — | |
| P-191 | 5167 | — | — | — | |
| P-192 | >40,000 | | | | No displacement up to 40 μM |
| HA | 23 | 23 | 23 | 0 | |
| ASP51 | >40,000 | >40,000 | N/A | N/A | No displacement up to 40 μM. |

Peptide Exchange Validation Using Differential Scanning Fluorometry (DSF)

In this method a high throughput assay for screening peptides that can bind to a particular HLA allele and also, the intensity of the peptide binding to the HLA dimer is determined (FIG. 26F). In this assay a fluorescent probe is used, which binds to the hydrophobic residues of a protein and therefore can bind to the MHC alleles, only when the alleles dissociate from each other by application of heat. When an MHC class II dimer binds a cognate peptide, the dimers are held together in its dimeric form. When heat is applied to an MHC dimer-peptide in bound form, the weak binding peptides dissociate faster from the MHC class II protein dimer, allowing the fluorophore to bind to the dissociated MHC alpha and beta chains and producing high fluorescence. Fluorescence is recorded as a function of temperature. Representative melting curves are shown in FIG. 26F. Melting curves can be compared to determine the strong binders (fluorescence detected at higher temperature) from weak binders (fluorescence detected at lower temperature).

Use of soluble HLA-DM (HLA-sDM) as a catalyst for MHC class H peptide exchange: HLA-DM is a natural chaperone and peptide exchange catalyst for HLA-DR, -DP, and -DQ molecules. It is an integral membrane protein and occurs as a heterodimer of alpha and beta polypeptide chains (DMA and DMB). Peptide exchange as described in this section is performed using a soluble form of HLA-DM (e.g., HLA-sDM protein) as chaperon for the HLA-DR, -DP, and -DQ exchanges. HLA-sDM protein is produced via a transient transfection in Expi-CHO cells as shown in FIG. 26G. Briefly, a recombinant HLA-sDM construct is designed, as shown graphically in FIG. 26G upper half. The recombinant HLA-sDM construct comprises a CMV constitutive promoter, upstream of a leader sequence and operably linked with the promoter. The leader sequence helps in the secretion of the product (secretion signal). At the 3'-end of the leader sequence a coding sequence for HLA-DM beta chain ectodomain (and lacks a transmembrane domain) is introduced. A sequence encoding a biotinylation motif (BAP) is ligated 3' of the beta chain-encoding sequence. A sequence encoding the HLA-DM alpha chain ectodomain (and lacks a transmembrane domain) is placed with a secretion sequence (leader) at its 5' end, separated from the BAP sequence by an intervening ribosomal skipping sequence. The HLA-DM alpha chain sequence is ligated at the 3' end with a 10×HIS-tag (SEQ ID NO: 20). Once formed the heterodimeric HLA-sDM is secreted outside the cell. When this construct is expressed in Expi-CHO cells the HLA-sDM protein is secreted into the medium culture medium.

Expi-CHO cells were transfected with a plasmid vector expressing the HLA-sDM construct, and cultured over a period of about 14 days. The protein was secreted into the culture medium over the period of culture. The HLA-sDM protein was purified from the culture in a process very similar to purifying MHC-II proteins. MHC-II peptide exchange can be performed efficiently with acid and HLA-sDM, or without acid, and with octyl glucoside. Size exclusion chromatography was performed to assess peptide exchange, results were as shown in FIG. 26H. All peptide exchange assays were performed using of HLA-sDM or octyl-glucoside as the catalyst.

HLA-Class II Tetramer (or Multimer) Repertoire

A large repertoire of HLA class II tetramers were generated for the purpose of testing epitope: HLA binding and dissociation kinetics in a biochemical assay. These class II tetramers thus generated are used for assaying peptide binding and presentation. For example, the tetramers were used in peptide exchange assay. As shown in FIG. 27A, 12 tetramers were generated and stored at a concentration of greater than 15 mg/ml; six tetramers and four at <5 mg/ml. HLA tetramers are used for flow cytometry to identify neo-antigen reactive CD4+ T cells. Influenza virus epitope (HA) and HIV epitopes were tested for T cell recognition when presented by HLA tetramers (FIG. 27E).

FIGS. 27B-27D depict various subsets of HLA class II tetramers that were generated and purified. As shown in FIG. 27B, a large repertoire of DRB1 heterodimer tetramers were constructed and purified at greater than 15 mg/L concentration. FIGS. 27C and 27D summarize the coverage of human MHC class II allele constructs produced and validated for fluorescent based peptide binding assays. Table 8A, Table 8B and Table 8C provide lists of the allelic tetramers manufactured, with corresponding secretion yield concentrations of the purified product.

TABLE 8A

| HLA heterodimer | Secretion Yield |
|---|---|
| DRB1*01:01 | >15 mg/L |
| DRB1*04:01 | >15 mg/L |
| DRB1*04:02 | >15 mg/L |
| DRB1*04:04 | >15 mg/L |
| DRB1*04:05 | >15 mg/L |
| DRB1*08:01 | >15 mg/L |
| DRB1*09:01 | >15 mg/L |
| DRB1*11:01 | >15 mg/L |
| DRB1*13:03 | >15 mg/L |
| DRB1*14:01 | >15 mg/L |
| DRB1*15:03 | >15 mg/L |
| DRB1*01:02 | >15 mg/L |
| DRB1*11:04 | >15 mg/L |
| DRB1*15:02 | >15 mg/L |
| DRB4*01:01 | >15 mg/L |
| DRB1*07:01 | 5-15 mg/L |
| DRB1*13:01 | 5-15 mg/L |
| DRB1*13:02 | 5-15 mg/L |
| DRB1*15:01 | 5-15 mg/L |
| DRB1*15:02 | 5-15 mg/L |
| DRB3*01:01 | 5-15 mg/L |
| DRB1*08:03 | 5-15 mg/L |
| DRB1*11:02 | 5-15 mg/L |
| DRB1*16:02 | 5-15 mg/L |
| DRB3*02:01 | 5-15 mg/L |
| DRB3*02:02 | 5-15 mg/L |
| DRB3*03:01 | 5-15 mg/L |
| murine I-Ab | 5-15 mg/L |
| DRB1*03:01 | <5 mg/L |
| DRB1*12:01 | <5 mg/L |
| DRB5*01:01 | <5 mg/L |
| DPA*01:03/DPB*04:01 | <5 mg/L |

TABLE 8B

| HLA heterodimer | Secretion Yield |
|---|---|
| DPB1*05:01 | >15 mg/L |
| DPB1*13:01 | >15 mg/L |
| DPB1*03:01 | 5-15 mg/L |
| DPB1*04:02 | 5-15 mg/L |
| DPB1*06:01 | 5-15 mg/L |
| DPB1*11:01 | 5-15 mg/L |
| DPB1*01:01 | <5 mg/L |
| DPB1*02:01 | <5 mg/L |
| DPB1*02:02 | <5 mg/L |
| DPB1*04:01 | <5 mg/L |
| DPB1*17:01 | <5 mg/L |

TABLE 8C

| HLA heterodimer | Secretion Yield |
|---|---|
| A1*02:02 + B1*06:02 | >15 mg/L |
| A1*02:01 + B1*02:02 | >15 mg/L |
| A1*01:03 + B1*06:03 | >15 mg/L |
| A1*02:01 + B1*03:03 | >15 mg/L |
| A1*01:02 + B1*06:04 | 5-15 mg/L |
| A1*05:01 + B1*02:01 | <5 mg/L |
| A1*05:05 + B1*03:01 | <5 mg/L |
| A1*01:01 + B1*05:01 | <5 mg/L |
| A1*03:01 + B1*03:02 | <5 mg/L |
| A1*03:03 + B1*03:01 | <5 mg/L |

The MHC-II tetramer product pipeline further includes DRB3, 4, and 5 alleles, and DP and DQ alleles.

Peptide Exchange Validation Using Fluorescence Polarization (FP)

Fluorescence polarization microscopy was used in an assay to distinguish peptide bound to MHC class II proteins versus free peptides. A fluorescence-tagged placeholder peptide when bound to an MHC class II dimer, results in high polarized light by fluorescence polarization (FP) microscopy, compared to its released form, when a non-fluorophore tagged competing epitope peptide remains bound to the MHC class II dimer by displacing the placeholder peptide. FIG. 28A exhibits the principle via a graphical representation. In brief, the assay is performed in the following generalized method, and variations are either indicated in the respective descriptions or are easily understood by one of skill in the art.

Reagents as described in Table 9 (below) are assembled in a reaction tube (e.g., 1.5 ml Eppendorf tube), mixed well and incubated at 37° C. for 2 hours. 25 ml of 10×PBS is added to the mixture at the end of incubation time to neutralize the peptide exchange reaction.

TABLE 9

| Ingredients | Stock Concentrations | Final Concentration |
|---|---|---|
| Thrombin digested MHC class II allele | Variable | 5 µM |
| Exchange Peptide/peptide of interest | 10 mM | 50 µM |
| Sodium Acetate, pH 5.2 | 1M | 100 mM |
| Sodium Chloride | 5M | 50 mM |
| Soluble DM | variable | 5 µM |
| MiliQ water | | Up to 100 µl |

The exchanged peptide is detected, for example, by staining; or stored at −80° C. by snap freezing in liquid nitrogen for evaluation later.

FIGS. 28B and 28C provide an overview of the assay development for HLA DRB1*01:01, using FP, and the various conditions used. In some examples, the effect of pH on the assay was determined. In short, both the full length and the soluble alleles are expressed in cells. The membrane bound full length allele form is harvested by permeabilizing the membrane, while the secreted form is harvested from the cell supernatant. The harvested HLA class II proteins are purified by passing through nickel ($Ni^{2+}$) columns. In some examples, effect of detergent (1% Octyl glucoside vs 1.6% NP40 was evaluated in membrane permeabilization for harvesting full length MHCII alleles. In some examples, effect of temperature, or the probe used, or the purification methods or the target format were individually evaluated (FIG. 28B).

Effect of purification method using either conformation specific antibody L243 or His-tag purification were evaluated. The results are shown in FIG. 28D. Each data point is depicted in the table on the left and is represented as a single dot in the graph on the right. The dots in the graph align roughly along a 45-degree angle to either axes, and with a r value of 0.9621, which indicate that the IC50 values from both the purification methods are in agreement with each other. It also shows that the rank order of peptide potencies does not change between the purification methods.

Effect of the choice of the HLA class II proteins in soluble form (sDR1) versus the full-length form (fDR1) was evaluated and FIG. 28E shows that choice of target format does not affect the peptide potency. Shown on the left are average IC50 values from experiments using sDR1 form or fDR1. These data are plotted to obtain the graph on the right hand side. The data points, each depicted by a single dot, align roughly along a 45 degree angle to either axes, and with a r value of 0.9365, which indicate that the IC50 values from both the forms used correlate well with each other. It also shows that the rank order of peptide potencies does not change between the purification methods.

FIG. 28F shows a graphical view of an exemplary evaluation method of neonmhc2 and NetMHCIIpan predicted peptides in binding assay and identification of discordant peptides. Fluorescence polarization assay was used to evaluate the Neonmhc2 and NetMHCIIpan predicted peptides in actual peptide binding assays. For the assay, 60 nM of thrombin digested soluble HLA-DRB1*15:01 was incubated with an FITC-tagged super binder probe peptide (PVVHFFK(FITC)NIVTPRTPPY (SEQ ID NO: 24)) (10 nM per assay) and the assay peptide for 5 hours at 37° C. in an assay buffer (pH 5.2). Fluorescence polarization was examined from which, % probe displacement was calculated. As shown in FIG. 28G, inhibition of the super binder fluorescent peptide was proportional to the concentration of the predicted peptide indicating good specificity of the assay. Striking differences are seen between the performances of the Neonmhc2 and the NetMHCIIpan predicted peptides. With Neonmhc2 predicted peptides more peptides were positively bound, and with higher degree of inhibition; whereas the NetMHCIIpan predicted peptides were overall poor performers in comparison to the Neonmhc2 peptides. FIG. 28H summarizes the evaluation of Neonmhc2 predicted peptides in binding assay. As depicted by the pie charts, of the double negative peptides (peptides that were not predicted by any of the NetMHCIIpan or Neonmhc2) only 5% turned out to be binders and 95% non-binders. Of the NetMHCII predicted peptides, 40% were binders by fluorescence polarization detection of probe displacement assay, and of the Neonmhc2 predicted peptides to be binders, 100% were found to be true binders by the probe displacement assay.

FITC-labelled probes were prepared by reviewing previously published peptides shown by Sette et al., to bind specific alleles. These peptide sequences were then analyzed using predicted class II binding core to identify the minimal 9-mer core of the peptide and the anchor residues. This information was then considered when selecting a residue position for lysine substitution and FITC labelling. For example, in the table below (Table 10) the sequences as described in Sette et al. (Sidney J, Southwood S, Moore C, et al. Measurement of MHC/peptide interactions by gel filtration or monoclonal antibody capture. *Curr Protoc Immunol.* 2013; Chapter 18: Unit-18.3. doi:10.1002/0471142735.im1803s100) (hereinafter "Sette's Sequences")) are listed. The predicted class II binding core for each peptide were underlined in the context of a specific allele. The bold font denotes anchor positions that were identified as a result of epitope improvement. In some cases, the same peptide sequence can be used for different alleles.

TABLE 10

| Shorthand ID | Allele | Sette's Sequences | SEQ ID NO: | Probe Sequences Selected | SEQ ID NO: |
|---|---|---|---|---|---|
| SB-DR7/11 | DRB1*07:01 | YATFFIKANSKFIGITE | 25 | YATFF*I*KANSKFIGITE | 25 |
| SB-DR7/11 | DRB1*11:01 | YATFFIKANSKFIGITE | 25 | YATFF*I*KANSKFIGITE | 25 |
| SB-DR9 | DRB1*09:01 | TLSVTFIGAAPLILSY | 26 | TLSVTFIGAAPKILSY | 29 |
| SB-DR4/15 | DRB1*15:01 | PVVHFFKNIVTPRTPPY | 27 | PVVHFFKNIVTPRTPPY | 27 |
| SB-DR4/15 | DRB1*04:01 | PVVHFFKNIVTPRTPPY | 27 | PVVHFFKNIVTPRTPPY | 27 |
| SB-DR3 | DRB1*03:01 | YARIRRDGCLLRLVD | 28 | YARI*K*RDGCLLRLVD | 30 |

Based on positioning as described above, an internal lysine for FITC conjugation was chosen by focusing on positions within the binding core (underlined); italicized were these positions as appropriate positions for FITC conjugation. For sequences that did not have an internal lysine for FITC conjugation, a manual approach was undertaken where a comparison to an allele's binding motif to the peptide sequence was performed, and a position for internal lysine substitution was selected for the DRB1*09:01 and DRB1*03:01 peptides (see above table). More specifically, a leucine residue for DRB1*09:01, and an arginine residue for DRB1*03:01 were substituted with lysines to allow for FITC conjugation. This substitution strategy was based on the MAPTAC-derived motifs, where manual identification of positions with no strong amino acid preference (also in the middle of the neonmhc2 predicted 9-mer core) because the conjugated fluorophore may be more likely to emit polarized light when bound (i.e., more restricted motion of the fluorophore).

Example 12: HLA Class II Binding and Processing Rules for Identifying Therapeutically Targetable Cancer Antigens Increasing evidence indicates CD4+ T cells can recognize cancer-specific antigens and control tumor growth. However, it remains difficult to predict the antigens that will be presented by human leukocyte antigen class II molecules (HLA class II)—hindering efforts to optimally target them therapeutically. Obstacles include inaccurate peptide-binding prediction and unsolved complexities of the HLA class II pathway. In this Example, an improved technology for discovering HLA class II binding motifs is described. Further, described herein is a comprehensive analysis of tumor-ligandomes conducted to learn processing rules relevant in the tumor microenvironment (TME).

40 HLA class II alleles were profiled and it was shown that binding motifs are highly sensitive to HLA-DM, a peptide loading chaperone. The intratumoral HLA class II presentation was revealed to be dominated by professional antigen presenting cells (APCs), rather than cancer cells. Integrating these observations, algorithms were developed as described herein, that accurately predict APC ligandomes, including peptides from phagocytosed cancer cells. These tools and biological insights can enhance HLA class II directed cancer therapies.

A promising new class of therapies seeks to treat cancer by inducing T cell responses against cancer antigens and somatically mutated sequences called neoantigens. At present, these efforts have focused primarily on eliciting CD8+ T cell responses toward HLA class I (HLA class I) presented ligands. However, several recent studies have shown that CD4+ T cells can also recognize HLA class II presented ligands and contribute to tumor control. Cancer vaccines and other immunotherapies would ideally take advantage of directing CD4+ T cell responses, but current efforts have forgone HLA class II antigen prediction entirely because the accuracy of current prediction tools is inadequate.

A key factor preventing the accurate identification of HLA class II cancer antigens is the availability of comprehensive, high-quality data required to learn the rules of peptide binding. Data are needed for the three highly polymorphic canonical HLA class II loci, HLA-DR, -DP, and -DQ, wherein each allelic variant exhibits distinct peptide binding preferences. A widely used method to define peptide-binding motifs is a biochemical assay that measures the affinity of a single peptide in the absence of physiological chaperones, such as HLA-DM. Measured affinity data coverage is limited to common Caucasian HLA-DR alleles, and even for these alleles, prediction accuracy significantly lags that of HLA class I. In principle, mass spectrometry (MS)-based ligandomics should enable improved prediction by offering scalability and endogenous peptide-loading conditions. Nonetheless, natural ligandomes are multi-allelic, concealing the peptide-to-allele mapping information required to obtain accurate training data. There has been progress solving this problem for HLA class I, which uses both deconvolution and mono-allelic HLA class II cell lines mono-allelic HLA class II ligandome datasets have been generated using low-throughput transgenic mouse models HLA class II deficient cell lines, or cell lines that have homozygous HLA-DR allele.

Another challenge is the ambiguity around which tumor antigens are most likely to enter the HLA class II presentation pathway. Recent MS-based studies have surveyed the HLA class II ligandomes of tumor samples but have not addressed if professional APCs or the cancer cells are presenting the therapeutically relevant HLA class II antigens. Furthermore, it is not currently known whether HLA class II processing of tumor antigens is primarily dependent on phagocytosis or autophagy. Depending on which pathway dominates in the relevant cell type, there could be drastic differences in terms of which proteins are preferred as sources for HLA class II peptide ligands. Compounding the problem, there is no systematic approach for determining which regions within proteins are most likely to produce HLA class II ligands, even though prevailing theories hold that protein sequence features should influence HLA class II processing potential.

To investigate the processing and presentation rules of therapeutically targetable HLA class II antigens, a two-pronged approach of i) improving peptide-binding prediction and ii) determining how HLA class II ligands are processed and presented in the TME was followed. In order to learn allele-specific peptide binding rules, a scalable mono-allelic HLA ligandome profiling workflow called MAPTAC™ (Mono-Allelic Purification with Tagged Allele Constructs) was developed, that utilizes MS to sequence endogenously presented HLA class II ligands. MAPTAC™ allowed to clearly resolve peptide binding motifs for 40 HLA class II alleles and train binding prediction algorithms that could accurately identify immunogenic viral epitopes and neoantigens. To improve HLA class II processing prediction, tumor samples were analyzed, establishing professional APCs as the primary source of intratumoral HLA class II expression and defining the set of genes and gene regions preferentially processed by these cells. It was then demonstrated that algorithms that integrate binding and processing features can predict natural APC ligandomes and, more importantly, the subset of HLA class II ligands derived from endocytosed cancer cells. These advances in understanding the processing and presentation rules of therapeutically relevant HLA class II antigens will enable therapies that aim to harness CD4+ T cell responses.

Experimental Procedures

MAPTAC™ Construct Design and Cell Culture

For HLA class I, the α-chain was fused with a C-terminal GSG linker, followed by the biotin-acceptor-peptide (BAP) sequence, a stop codon, and a variable DNA barcode, and cloned into the pSF Lenti vector (Oxford Genetics). The HLA class II constructs were similarly cloned into pSF Lenti and consisted of the β-chain sequence with the same linker-BAP sequence fused on the C-terminus, followed by another short GSG linker, an F2A ribosomal skipping sequence, the sequence of the α-chain with a C-terminal HA tag, a stop codon, and a variable DNA barcode. MAPTAC™ constructs were transfected or transduced into Expi293, HEK293T, A375, HeLa, KG-1, K562 and B721.221 cells.

HLA-Peptide Isolation Protocols

Flash frozen cell pellets containing $50 \times 10^6$ cells expressing BAP-tagged HLA were thawed on ice for 20 minutes and gently lysed by hand pipetting in 1.2 mL cold lysis buffer. After clearing DNA, RNA, and cellular debris, supernatants were transferred to new 1.5 mL tubes and BAP-tagged HLA were biotinylated by incubation at room temperature for 10 minutes with 0.56 µM biotin, 1 mM ATP, and 3 µM BirA. The biotinylated lysates were incubated with 200 µL of NeutrAvidin resin at 4° C. for 30 minutes to affinity-enrich biotinylated HLA-peptide complexes. After washes, the HLA-bound resin was pelleted by centrifugation at 1,500×g at 4° C. for one minute and stored at −80° C. or immediately subjected to HLA-peptide elution and desalting using Sep-Pak solid-phase extraction. For profiling the endogenous HLA class II ligandomes of healthy donor materials, HLA-peptide complexes were isolated using in-house generated anti-HLA-DR antibody L243 or with the commercially available TAL 1B5 antibody.

HLA-Peptide Sequencing by Tandem Mass Spectrometry

All nanoLC-ESI-MS/MS analyses employed the same LC separation conditions, instrument parameters, and data analytics. Briefly, samples were chromatographically separated using a Proxeon Easy NanoLC 1200 fitted with a PicoFrit column packed in-house with C18 Reprosil beads and heated at 60° C. During data-dependent acquisition, eluted peptides were introduced into an Orbitrap Fusion Lumos mass spectrometer equipped with a Nanospray Flex Ion source. Mass spectra were interpreted using the Spectrum Mill software package v6.0 pre-Release. Identified peptides that passed the PSM FDR estimate of <1% were filtered for contaminants by removing all peptides assigned to the 264 common contaminants proteins in the reference database and by removing peptides identified negative control MAPTAC™ affinity pulldowns. Additionally, all peptide that mapped to an in silico tryptic digest of the reference database were removed to account for tryptic sample carry-over. Raw mass spectrometry datasets will be deposited in MassIVE upon acceptance (massive.ucsd.edu).

Machine Learning Approaches for Binding Motifs and Binding Prediction

For each allele, an ensemble of convolution neural networks was trained to distinguish MAPTAC™ peptides from scrambled decoys. Each network comprised two ReLU-activated convolutional layers, each with 50 6-wide filters. The maximum and average activation per filter per layer were routed into a final dense layer with sigmoid activation. Regularization was achieved through L2-norm, 20% spatial dropout after each convolutional layer, and early stopping, and tuned per allele according to a hold-out partition of non-redundant peptides (~12.5%). In performance benchmarking, NetMHCIIpan-v3.1 predictions were calculated as the maximum-scoring 15mer within each query peptide, an approach which performed uniformly better than the native NetMHCIIpan-v3.1 predictions.

CD4+ T Cell Induction Assay

PBMCs were co-cultured with peptide pulsed mDCs at a 1:10 ratio for a total of 3 stimulations. Induced T cells were then labelled with a unique two-color barcode as described previously and cultured overnight at a 1:10 ratio with peptide pulsed and matured autologous mDCs. Cells were subsequently assessed for production of IFN-γ in response to peptide by flow cytometry. Induction samples that positively responded to peptide were samples that induced IFN-γ production at 3% higher than the no peptide control.

APC Endocytosis of SILAC-Labeled Tumor Cells

K562 cells (ATCC, Manassas, Va.) were grown for 5 doublings in RPMI media for SILAC (ThermoFisher) containing the heavy isotopically amino acids, L-Lysine 2HCl $^{13}C_6$ $^{15}N_2$ (Life Technologies) and L-leucine $^{13}C_6$ (Life Technologies). Monocytic derived dendritic cells (mDCs) were co-cultured at a 1:3 ratio either overnight with UV-treated K562 cells or for 5 h with lysate generated following HOC1 treatment. Cells were harvested, pelleted, and flash frozen in liquid nitrogen for proteomic analysis.

Results

MAPTAC™: A Scalable Platform for Mono-Allelic HLA Class II Ligand Profiling

Current knowledge of HLA class II binding motifs is based primarily on data generated using two biochemical binding assays. In one such former approach, an assay peptide and a radio-labeled competitor peptide are co-incubated with cellularly-derived HLA extracts to determine an IC50. In another approach, a conformationally specific antibody measures the proportion of HLA bound to the assay peptide in order to determine an EC50. Data from these assays are compiled in the Immune Epitope Database (IEDB) and used to train HLA class II prediction algorithms such as NetMHCIIpan. The five most common Caucasian HLA-DRB1 alleles are well-supported in IEDB (3326-8967 peptides each), though only about 29% of these are strong binders (affinity<100 nM), and 85% of IEDB peptides overall are exact 15mers (FIG. 12B, FIG. 12E). HLA-DP and HLA-DQ alleles and non-Caucasian HLA-DR alleles (e.g. HLA-DRB1*15:02) are supported by considerably less data.

To create a high-quality dataset with the allelic breadth to support a diverse patient population, the MAPTAC™ was developed, a technology that enables efficient isolation of HLA class II peptides binding a single allele for MS-based identification (FIG. 11A). The alpha and beta chains of a chosen HLA class II heterodimer are encoded by a genetic construct with a biotin-acceptor peptide (BAP) sequence placed at the C-terminus of the beta chain. Since HLA-DRA is functionally invariant, MAPTAC™ yields mono-allelic HLA-DR results regardless of potential pairing between exogenous beta chain and endogenous alpha chain. For HLA-DP and HLA-DQ, which exhibit a limited set of functional alpha chain variants, the cell line is chosen to have matching or non-expressed alpha chain alleles. Importantly, this approach also works for HLA class I, with the BAP tag appended to the HLA class I heavy chain.

A 48-hour transfection achieved robust expression of the MAPTAC™ construct (FIG. 12C) with normal levels of cell surface presentation (FIGS. 34A and 34B). This was demonstrated in 7 distinct cell lines (expi293, A375, KG-1, K562, HeLa, HEK293, and B72.221) and for 40 HLA class II alleles, providing data for all three canonical HLA class II loci: HLA-DR, -DP, and -DQ. The average number of unique peptide identifications per replicate (~50 million cells) that passed quality control filters ranged from 236 to 2580 across alleles (FIG. 29), with a median of 1319 peptides. Several process variations were employed to increase data depth, including HLA-DM over-expression, and peptide reduction and alkylation. Only a small percentage of MS hits corresponded to known contaminants, tryptic peptides, and mock transfections (empty plasmid) (FIG. 11B and FIG. 29). Length distributions for MAPTAC™ HLA class I and HLA class II peptides match those observed in previous MS studies utilizing antibody-based pulldowns (FIG. 11C).

Figure 12D:
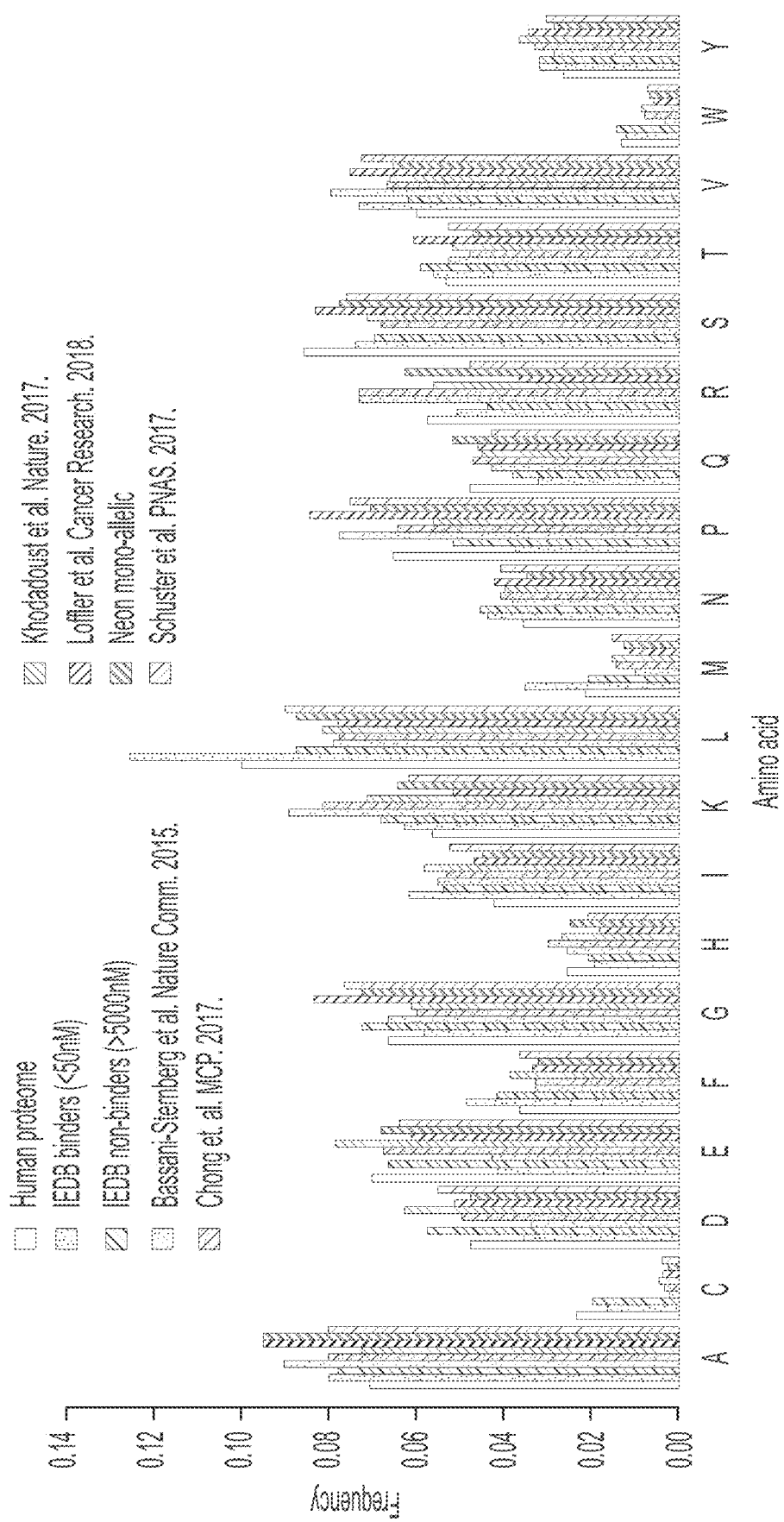
FIG. 12D depicts exemplary per-residue amino acid frequencies observed for MAPTAC™ and IEDB (alleles DRB1*01:01, DRB1*03:01, DRB1*09:01, and DRB1*11:01), the human proteome, and multi-allelic MS data from previous publications.
Figure 12E:
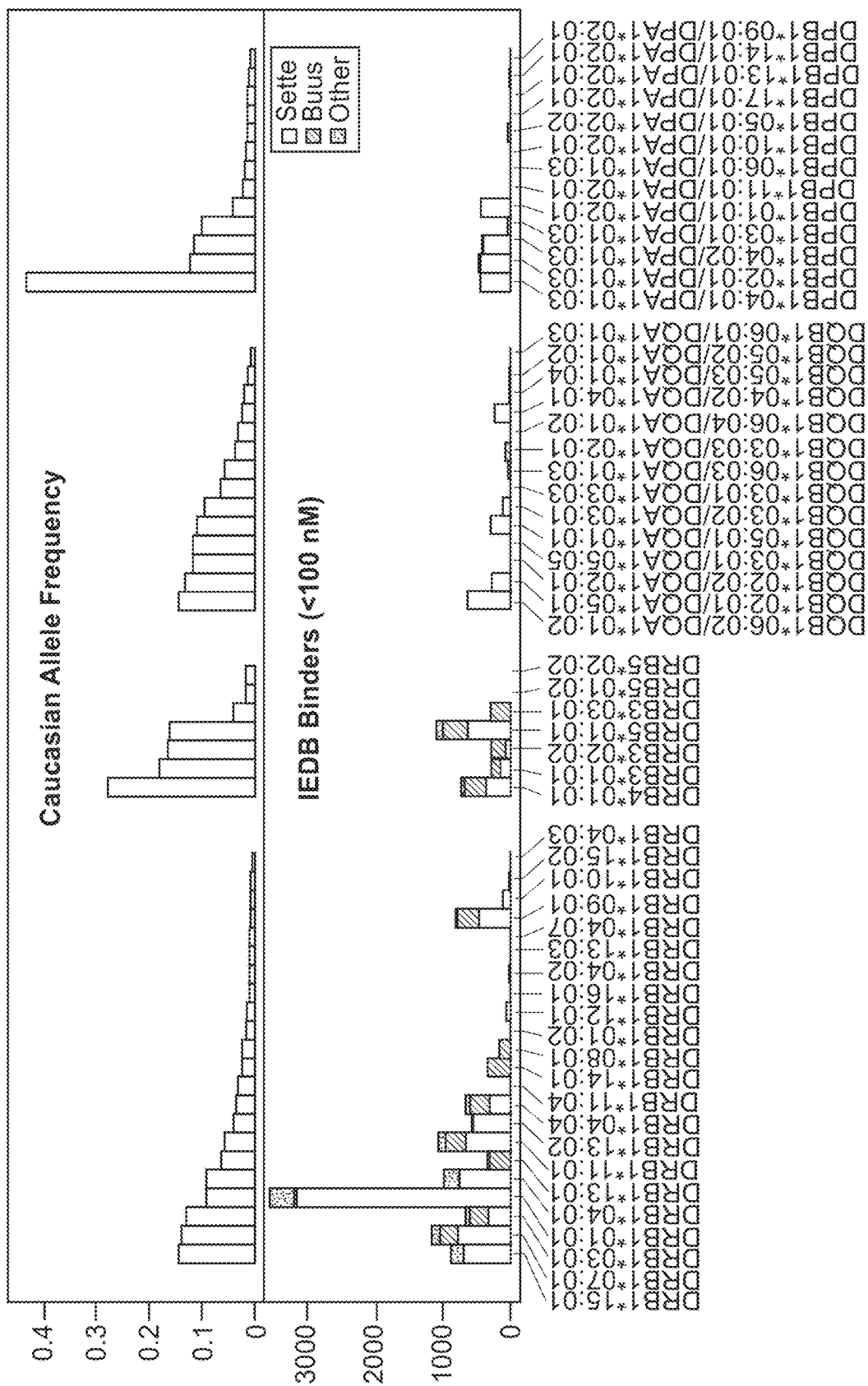
FIG. 12E depicts Caucasian frequencies for HLA-DR, -DP, and -DQ alleles present in >1% of individuals and counts of peptides from the indicated sources measured as strong binders (<50 nM). This figure includes additional data relative to FIG. 12A. The additional data were taken from: tools.iedb.org/main/datasets/.
Figure 12F:
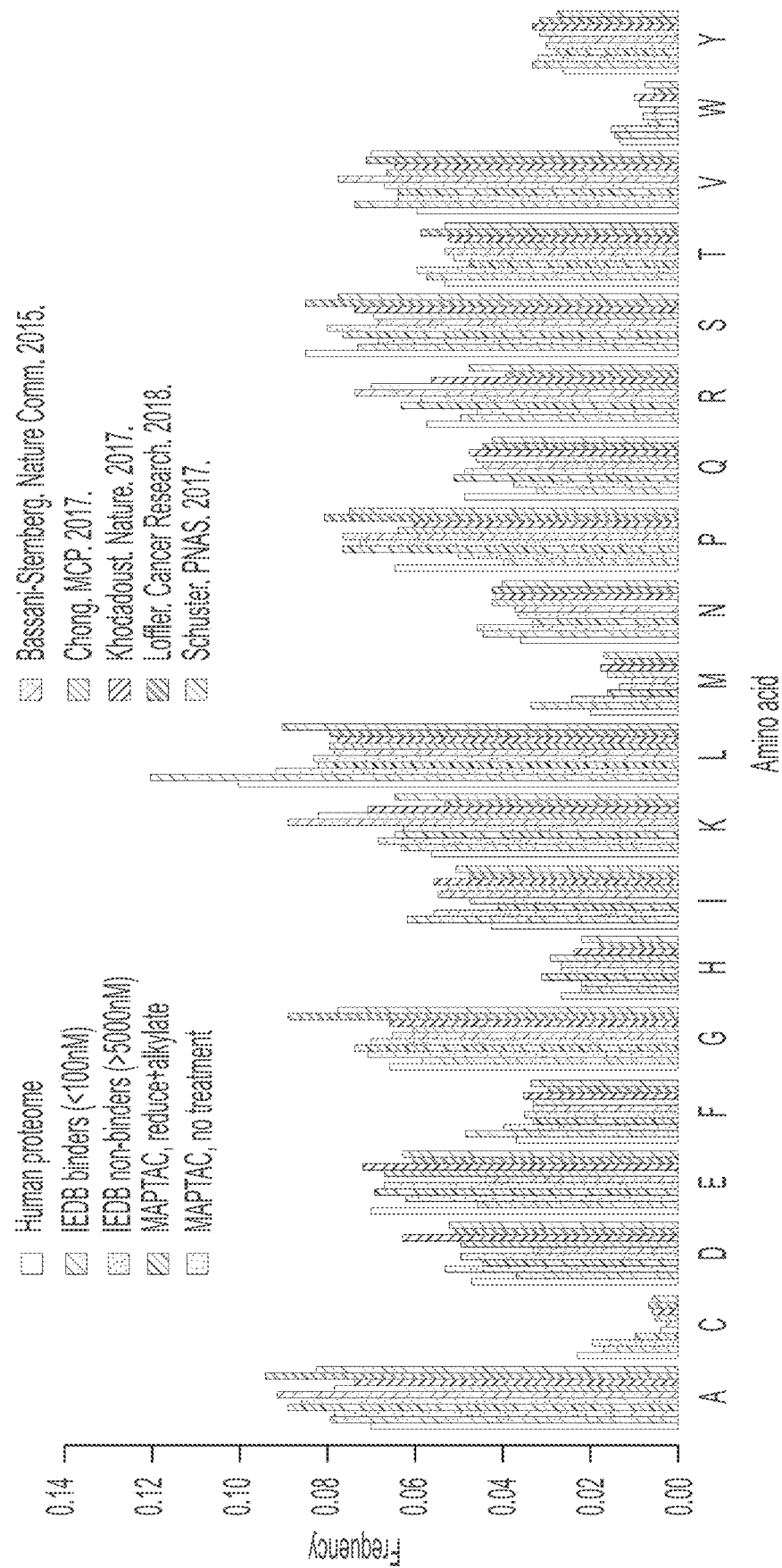
FIG. 12F depicts exemplary per-residue amino acid frequencies observed for MAPTAC™ (reduced and alkylated), MAPTAC™ (no treatment) and IEDB (alleles DRB1*01:01, DRB1*03:01, DRB1*09:01, and DRB1*11:01), the human proteome, and multi-allelic MS data from previous publications

Among the MAPTAC™ HLA class II peptides, most amino acids were represented at levels consistent with source proteome frequencies (FIG. 12D and FIG. 12F). Exceptions included C, M, and W, which were depleted by 85%, 34%, and 42%, respectively, consistent with previous MS-based studies of HLA class II peptides. Reduction and alkylation of HLA class II peptides nearly tripled the frequency of C, though it was still under-represented with respect to the proteome (FIG. 12F). Depletions of C, M, and W were not observed in allele-matched high-affinity peptides (<100 nM) from IEDB. Conversely, IEDB binders exhibited depletions of D (−39%) and E (−37%) as well as an enrichment in M (+65%) when compared to IEDB non-binders (>5000 nM). Thus, MAPTAC™ exhibits defined biases that are in line with those observed with other technologies.

MAPTAC™ Resolves HLA Class II Peptide Binding Motifs

MAPTAC™ was used to resolve allele-specific HLA class II binding motifs. 40 HLA class II alleles were profiled, 15 of which were previously uncharacterized (<30 peptides with <100 nM affinity in IEDB) including alleles common in non-Caucasian populations (DRB1*12:02, DRB1*15:03, and DRB1*04:07). Since HLA class II peptides can be longer than the number of residues in the binding groove, it is not immediately evident which portion of each peptide is HLA-interacting (the "core") vs. overhanging; however, resolving the binding core is critical to characterizing binding motifs. To identify the binding core, peptides to a consensus binding core were aligned using the tool GibbsCluster-2.0, which uses an expectation maximization algorithm to iteratively nominate a binding register for each peptide and re-learn the binding motif across peptides. With few exceptions, binding core motifs for common HLA-DR alleles showed strong agreement with IEDB-based motifs (FIG. 35). MAPTAC™-observed peptides did not always show strong NetMHCIIpan scores for common alleles (FIG. 36A); yet, observed binders that were poorly predicted by NetMHCIIpan were shown to have very strong measured affinities (FIG. 36B) indicating that these observations are unlikely to be false positives. Notably, MAPTAC™ motifs were always stable across multiple cell lines (FIG. 36C).

Typically, MAPTAC™ and IEDB agreed on the highest frequency amino acids at anchor positions (~4 most highly conserved positions), but MAPTAC™ motifs generally showed lower entropy (manifested by taller letter heights in sequence logos). Interestingly, when cells were co-transfected with MAPTAC™ constructs and HLA-DM, the entropy at anchor positions decreased even further for most alleles (FIG. 30A and FIG. 37A). This was consistently observed across 12 HLA-DR alleles, showing HLA-DM's pervasive effect as a repertoire "editor" and suggesting that models based on affinity assays that lack HLA-DM and other loading chaperones may learn binding rules that don't apply in vivo. The effect of HLA-DM was also evident with respect to the presence of CLIP peptides. Without HLA-DM co-transfection, CD74-derived peptides were observed in 10 HLA-DR alleles and matched known CLIP variants (FIGS. 37C and 37D); meanwhile, CLIP peptides were not observed in any of our HLA-DM co-transfection experiments.

The effect of HLA-DM was not evident for the HLA-DP alleles analyzed (FIG. 30A and FIG. 37A), which may relate to the presence of an unusual positively charged P1 anchor not previously reported. HLA-DM is thought to act primarily on N-terminal side of bound peptides, as such, the unusual P1 anchor was not a marker for HLA-DM insensitivity as HLA-DP motifs with hydrophobic P1 anchors were also unaltered by the presence of HLA-DM (FIG. 37A). On the other hand, HLA-DQB1*06:04/A1*01:02 was profoundly affected by HLA-DM (FIG. 30A). Without HLA-DM co-transfection, this allele's binding motif was not discernable, indicating that chaperone-free loading onto some HLA-DQ alleles yields a large proportion of non-physiological binders.

Given the availability of published multi-allelic HLA class II datasets, whether our allele-specific peptides could have been effectively identified was investigated, using in silico deconvolution methods. Several groups have shown success in deconvolving HLA class I allele motifs from multi-allelic HLA class I data; however, deconvolution of HLA class II motifs is complicated by the need to simultaneously resolve both the binding core and allele assignment of each peptide. To assess the accuracy of HLA class II deconvolution, the HLA-DR ligandomes were analyzed from eight samples profiled by pan-DR antibody (PBMCs and published cell lines. For each dataset, twenty peptides were spiked in of mono-allelic data matching each allele in the sample's genotype (1-2 DR1 alleles plus 0-2 DR3/4/5 alleles, depending on haplotype and zygosity. GibbsCluster tool (which can also be used for deconvolution; was used to partition peptides into groups and observed whether the spike-in peptides were appropriately co-clustered according to their known origin allele. In all cases, peptides were distributed across diverse clusters, showing only modest association with the correct source alleles (FIG. 30B) and indicating that HLA class II training data based on deconvolution is likely to bear significant errors.

To understand the poor performance of the deconvolution, the mono-allelic MAPTAC™ data was reviewed to determine the frequency of "obvious" anchors that could serve as guideposts for GibbsCluster. Accordingly, obvious amino acids (those with frequency >10%) at each anchor position (the four positions with lowest entropy) for each HLA class II allele were defined. Only 10-20% of peptides exhibit ideal residues in all four anchor positions and as many as 50% exhibit two or fewer obvious anchors (FIG. 30C). Given the low frequency of peptides that exhibit most of the expected anchors, it is not surprising that a large fraction of peptides would be hard to classify on a purely computational basis. Thus, MAPTAC™ addresses a major source of ambiguity that is non-trivial to resolve with in silico methods.

The motifs for HLA class I alleles could also be defined using MAPTAC™. This included alleles whose binding profiles were previously undefined (e.g. B*52:01, common in Japan). For previously characterized alleles, it was seen that there was good correspondence in the motifs derived from affinity-based methods and previous mono-allelic MS studies. Nonetheless, it was noted that some discrepancies exist with respect to multi-allelic MS-based studies that employed deconvolution methods to define motifs (FIG. 37B).

Algorithms Trained on MAPTAC™ Data Predict Immunogenicity

Whether MAPTAC™ data could generate HLA class II binding predictors with improved accuracy was considered. Since the HLA-binding subsequence of HLA class II peptides are not at a fixed position with respect to the N- or C-terminus, the learning algorithm must dynamically consider different binding core possibilities for each peptide. To address this constraint, convolutional neural networks (CNNs) were employed, which have been successful in the field of computer vision because of their proficiency in translationally invariant pattern recognition. For each allele, an ensemble of CNNs were trained (FIG. 31A), calling the overall predictor "neonmhc2."

To account for the fact that MS exhibits some degree of amino acid residue bias, particularly against C, negative training examples (termed decoys) were generated by randomly permuting the sequences of observed binders (termed hits). As this approach carries the risk of learning sequence properties of natural proteins, decoys were sampled randomly from non-observed subsequences of peptide source genes of HLA class II ligands. To calculate positive predictive value (PPV) for each allele, n MS-observed peptides were scored in conjunction with 19n length-matched decoys sampled from the same set of source genes, and each predictor's n top-ranked peptides (i.e. the top 5%) were called as positives. PPV in this case is identical to recall because the number of false positives and the number of false negatives is equal. Calculating positive predictive value (PPV) at a 1:19 hit-to-decoy ratio showed that neonmhc2 improved PPV relative to NetMHCIIpan in predicting MAPTAC™-observed peptides (FIG. 31B; Table 11).

TABLE 11

| MHC Class II allele | PPV for NetMHCIIpan | PPV for neonmhc2 |
|---|---|---|
| DRB1*16:01 | 0.13 | 0.66 |
| DRB1*15:01 | 0.17 | 0.61 |
| DRB4*01:01 | 0.23 | 0.62 |
| DPB1*02:01/DPA1*01:03 | 0.12 | 0.52 |
| DRB1*11:04 | 0.22 | 0.60 |
| DRB1*14:01 | 0.14 | 0.59 |
| DRB1*13:03 | 0.08 | 0.58 |
| DPB1*06:01/DPA1*01:03 | 0.01 | 0.48 |
| DRB3*03:01 | 0.21 | 0.57 |
| DRB1*03:01 | 0.35 | 0.55 |
| DRB1*01:01 | 0.34 | 0.56 |
| DRB5*01:01 | 0.35 | 0.54 |
| DRB1*01:02 | 0.27 | 0.54 |
| DRB3*01:01 | 0.43 | 0.54 |
| DPB1*01:01/DPA1*01:03 | 0.08 | 0.53 |
| DRB1*07:01 | 0.29 | 0.54 |
| DRB1*04:04 | 0.22 | 0.55 |
| DRB1*11:01 | 0.17 | 0.52 |
| DRB1*15:03 | 0.02 | 0.50 |
| DPB1*04:01/DPA1*01:03 | 0.27 | 0.52 |
| DPB1*04:02/DPA1*01:03 | 0.25 | 0.53 |
| DRB1*15:02 | 0.17 | 0.50 |
| DRB1*10:01 | 0.15 | 0.48 |
| DRB1*08:02 | 0.21 | 0.50 |
| DRB1*13:01 | 0.16 | 0.49 |
| DRB1*04:05 | 0.13 | 0.50 |
| DRB1*09:01 | 0.19 | 0.47 |
| DQB1*06:02/DQA1*01:02 | 0.14 | 0.49 |
| DRB1*11:02 | 0.07 | 0.46 |
| DRB1*12:01 | 0.1 | 0.46 |
| DRB1*04:01 | 0.27 | 0.45 |
| DRB1*04:02 | 0.1 | 0.46 |
| DRB1*04:03 | 0.18 | 0.45 |
| DRB3*02:02 | 0.22 | 0.45 |
| DRB1*08:04 | 0.1 | 0.44 |
| DRB1*12:02 | 0.12 | 0.44 |
| DPB1*03:01/DPA1*01:03 | 0.03 | 0.48 |
| DRB1*04:07 | 0.21 | 0.40 |
| DRB1*08:01 | 0.11 | 0.37 |
| DQB1*06:04/DQA1*01:02 | 0.06 | 0.37 |
| DRB1*03:02 | 0.31 | 0.29 |
| DRB1*08:03 | 0.1 | 0.24 |
| DRB1*13:02 | 0.06 | 0.22 |

Saturation experiments, in which the training dataset size is down-sampled to varying degrees, suggests that neonmhc2's performance is data-limited and would likely improve with more data (FIG. 38X).

Analysis of the observation of low fidelity of HLA class II deconvolution in FIG. 30B suggest that comparable prediction performance could not have been achieved without mono-allelic data. To test this, a recently published computational workflow that uses deconvolution to train allele-specific binding predictors on multi-allele MS data (Barra et al., 2018) was followed. Inspecting GibbsCluster logos for eleven multi-allelic samples (the same samples in FIG. 30B), it was observed that many clusters (13/32) did not bear any resemblance to an allele known to be in the sample (FIG. 38Y). Using pre-existing knowledge of what the motifs should look like, only the legitimate clusters (marked in FIG. 38Y) were selected and predictors with the same CNN architecture was built. These models were then evaluated alongside neonmhc2 on bona fide mono-allelic data (a hold-out partition of MAPTAC™ data not used for training) The models trained on deconvolved multi-allelic data usually exceeded NetMHCIIpan but were inferior to MAPTAC™-trained neonmhc2 (FIG. 31E). The superiority of the monoallelic data was maintained even when the MAPTAC™ dataset was down sampled such that the size of the respective training data sets was identical.

In order to ensure that the apparent prediction improvements would hold when evaluated on non-MS data, a large dataset of allele-specific CD4+ memory T cell responses were curated which were detected by tetramer-guided epitope mapping (TGEM). Notably, these tetramer data rely on chaperone-free peptide exchange, so they may be subject to the same biases as conventional affinity assays (Archila and Kwok, 2017). Nonetheless, neonmhc2 out-performed NetMHCIIpan for all alleles with sufficient data for assessment (at least 20 positive examples) (FIG. 31C). The performance (measured by PPV) of NetMHCIIpan was variable, dropping as low as 5% for DRB1*15:01 (in contrast, neonmhc2's performance never fell below 30% PPV), and approached that of neonmhc2 on only two alleles, including the well-studied HLA-DRB1*01:01. On the other hand, neonmhc2 showed convincing improvement on all other evaluated alleles, including the two most common Caucasian HLA-DR alleles (DRB1*07:01 and DRB1*15:01). These results indicate that prediction improvements of neonmhc2 over NetMHCIIpan can be validated in a non-MS-based benchmark and likely extend across most alleles.

To assess the therapeutic relevance of neonmhc2, it was determined whether neonmhc2 could identify neoantigens capable of eliciting CD4+ T cell responses in an ex vivo induction assay (see Methods). Focusing on DRB1*11:01, which is a common allele with many affinity assay-confirmed binders in IEDB (only surpassed by DRB1*01:01 and DRB1*07:01; FIG. 12E), a set of The Cancer Genome Atlas (TCGA)-observed neoantigen sequences was scored and a subset was selected that were preferred by neonmhc2 (top 1% of predictions) but were not selected by NetMHCIIpan (bottom 90% of predictions). This set was further refined by removing peptides that may bind other HLA-DR alleles present in the induction materials. Most neonmhc2-selected peptides (8/12) yielded CD4+ T cell responses as measured by IFNγ expression in response to recall with the peptide (FIG. 31D, FIG. 38B and FIG. 38C). These results demonstrate that MAPTAC™-trained predictor can identify immunogenic HLA class II neoantigen sequences not identified by NetMHCIIpan.

Professional APCs are the Dominant HLA Class II Presenters in the Tumor Microenvironment Having developed a technology that enabled both characterization and prediction of HLA class II allele-specific peptide binding preferences, it was sought to complement the binding prediction improvements with further insights into antigen processing, which are critical for prioritizing the protein sequences most likely to produce HLA class II cancer antigens. To address these questions in the context of the TME, non-MAPTAC™ datasets were analyzed including single cell RNA-Seq and published MS-based studies that surveyed HLA class II ligandomes in tumors. Which cell types in the microenvironment are most likely to present therapeutically targetable cancer antigens was considered. Currently, there is no consensus as to whether cancer antigens are presented by professional APCs that have endocytosed tumor proteins or by the tumor cells themselves. To that end, HLA-DRB1 expression was analyzed in five published single-cell RNA-Seq datasets that profiled lung cancer, head and neck cancer, colorectal cancer, ovarian cancer, and melanoma, and found that canonical APCs (macrophages, dendritic cells, and B cells) express much greater levels of HLA class II than the tumor cells and other stromal cell types in the TME. This observation is consistent across multiple patients and tumor types (FIG. 19A). Because tumor cells can outnumber APCs in the TME, their lower levels of HLA class II expression may nonetheless be immunologically relevant. To assess how much of the overall HLA class II expression comes from tumor cells vs. stroma, TCGA patients with mutations in HLA class II-specific genes (focusing on CITTA, CD74, and CTSS) were identified and determined what fraction of RNA-Seq reads exhibited the somatic variant in order to impute what fraction of HLA-DRB1 expression derived from tumor vs. stroma (FIG. 19B, see Methods). Based on mutations identified in 153 patients representing 17 distinct tumor types, most HLA class II expression appeared to arise from non-tumor cells. In fact, 45% percent of patients showed zero tumor-derived HLA class II expression. Focusing on the patients with highest levels of T cell infiltration (top 10%, as identified using a previously published 18-gene signature (Ayers et al., 2017), low tumor HLA-DR expression still appeared to be the norm, with only 3 of 16 patients expressing >1000 TPM. To probe whether immunotherapy disrupted this trend, we analyzed additional single-cell RNA-Seq from checkpoint blockade-responsive tumor types and assessed HLA-DRB1 expression before and after treatment. A melanoma cohort, which included one confirmed responder, showed uniformly low HLA-DRB1 expression by tumor cells in both the pre-therapy and post-therapy biopsies (FIG. 19C). A basal cell carcinoma cohort which showed a 55% clinical response rate to anti-PD1 therapy, likewise exhibited low tumor cell-derived HLA-DRB1 expression regardless of time point (FIG. 19C). These results suggest that most intra-tumoral HLA class II presentation is driven primarily by professional APCs and "hot" TME conditions do not guarantee divergence from this general pattern.

Specific Genes have Privileged Access to the HLA Class II Presentation Pathway

In order to determine source genes of epitopes that are preferentially presented by tumor-resident APCs and whether they arise from autophagy or endocytosis three published HLA class II ligandome studies were analyzed, that were performed using tumor tissues.

First, the degree that each gene was represented in tumor HLA class II ligandomes was quantified assuming that the number of observations for each gene should be proportional to the product of its length and expression level (FIG. 18B). A clear enrichment for proteins expressed in human plasma was observed, especially albumin, fibrinogen, complement factors, apolipoprotein, and transferrin, despite not being expressed in the native tissue. Concerned that these identifications represent non-specific binding in HLA ligandomes, neonmhc2 binding scores were assessed for plasma-derived peptides in four PBMC HLA-DR ligandomes (FIG. 39A); the peptides displayed strong binding scores, suggesting that they were HLA binding. Plasma-derived proteins were not significantly enriched in tumor HLA class I ligandome data (FIG. 39B). The enrichment of plasma genes in HLA class II ligandomes is consistent APCs "sipping" extracellular proteins from tissue serum via micropinocytosis. Additional enrichments for genes involved in leukocyte cellular adhesion was also observed, such as ITGAM (11×-enriched), LCP1 (8×), ITGAV (6×), and ICAM1 (6×) suggesting that APCs are actively recycling their own membranes. MUC16, which was recently reported as enriched in ovarian cancer HLA class I ligandomes, was not over-represented.

Cellular localization was also considered to further interrogate gene bias in the HLA class II antigen presentation pathway. When genes were grouped by localization, secreted and membrane genes were represented twice as often as expected based on gene expression, underscoring an important role for macropinocytosis in shaping HLA class II ligandomes. Nonetheless, more than half of HLA class II peptides arise from compartments inconsistent with macropinocytosis, such as the nucleus and cytoplasm. It was reasoned that if many of these genes are presented via autophagy, then there should be a corresponding deficit of genes known to be cleared by the proteasome. Indeed, proteins known to contain ubiquitin sites generated peptides less often that would have been expected based on their length and expression (FIG. 32C). Depletion was also observed for proteins whose levels are known to increase upon proteasome inhibition. These are patterns that would be expected for autophagy but not necessarily for phagocytosis, suggesting that APC peptide ligandomes partially represent their own intracellular proteomes.

To address the origin of HLA class II antigens presented by APCs in the TME, it was considered whether it might be possible to directly deconvolve the origin of source genes by determining whether nuclear and cytosolic peptide identifications were more consistent with an APC-specific or a bulk tumor gene expression profile (FIG. 39C). Though there was significant uncertainty in the estimates (assessed by regression-based model and bootstrap resampling; Supplemental Methods), HLA class II ligandomes were best explained by a mixture of both tumor and APC gene expression profiles. Taken together with the observed depletion of proteasome-cleared proteins, this result suggests that intratumoral APCs present a mixture of exogenous and endogenous proteins.

Some Gene Regions are Preferentially Processed but Lack Evident Cleavage Motifs

There are multiple theories about which sequences are preferred for antigen processing (FIG. 32D). According to one model, enzymes cleave source proteins before they bind HLA class II, as is the case with HLA class I (Sercarz and Maverakis, 2003). A second model poses that the peptide binding occurs first and bound peptides are subsequently trimmed by exopeptidase enzymes until they are sterically hindered by HLA class II. In a third model, peptide cleavage events occur both before and after HLA-binding. Because there are competing models for how HLA class II peptides are generated, three different frameworks for prediction were generated (FIG. 32D). The first assumes that endopeptidases dominate ("cleave first"); a second model assumes that HLA class II engages full-length proteins that are subsequently trimmed inward by exopeptidases ("bind first"); and a third model poses that enzymatic digestion occurs both before and after HLA binding ("hybrid"). Each model required a different algorithmic approach. Specifically, an algorithm motivated by the cleave-first perspective should focus on the amino acids motifs at the edges of MS-observed ligands); however, an algorithm motivated by bind-first perspective would do better to ignore these motifs and focus on local protein structural properties that dictate HLA binding accessibility. A hybrid model-inspired algorithm should look upstream and downstream of observed HLA class II peptides for candidate precursor cut sites.

Of the three approaches considered, only the cleave-first algorithm yielded a measurable improvement over baseline models (FIG. 32E and FIG. 40B). However, it appears that this approach learns hallmarks of exopeptidase trimming present in the positive example peptides (e.g., a penultimate proline signature (Barra et al., 2018)) as it failed to add value if the exact cut sites of query peptides were masked (STAR Methods).

Pivoting to a purely empirical approach, protein regions observed in published HLA-DQ ligandomes (Bergseng et al., 2015) were catalogued and used overlap to predict HLA-DR ligands. The overlap variable yielded a modest improvement in prediction performance (3.1% increase in PPV on average over neonmhc2 alone) (FIG. 32E). Assuming that HLA-DQ and HLA-DR alleles share the same HLA-II processing environment but do not share binding motifs, this result indicates certain gene regions are indeed favored for processing but are not tied to cleavage motifs or conformational properties in obvious ways.

Groups have reported positive results using the observed termini of MS-observed peptides to train processing algorithms, an approach that assumes the "cleave-first" model. However, in reviewing amino acid enrichments adjacent to peptide termini in multiple distinct cell lines and tissue types (FIG. 40A), patterns were observed that seemed more consistent with post-binding trimming. These included the lack of correspondence with the known motif of the HLA class II processing enzyme, cathepsin S, and the enrichment of poorly-cleavable P at penultimate peptide positions, a motif that could arise if P blocks the procession of trimming enzymes. To test whether the "cleave-first" assumption is correct, neural network models were trained on peptide termini and evaluated them in two different ways: i) scoring cleavability on the exact N- and C-termini of each peptide or ii) scoring the best site in a range ±15AA of each peptide's predicted binding core (Supplemental Methods). It was hypothesized that both approaches should add predictive value if the cleave-first model is correct, but only the first approach did (FIG. 32E and FIG. 40B). Thus, the neural network can discern HLA class II from decoys based on telltale features in ligands (e.g. penultimate P) but it is irrelevant when the cut sites are not known a priori—as is always the case when predicting immunogenic peptides from a primary protein sequence. This subtle distinction has the potential to cause confusion in the field.

With the "bind first" theory, MS-observed and decoy peptides were scored for solvent accessibility, as well as for intrinsically disordered domains. Solvent accessible or disordered domains could be enriched in HLA class II ligands if protein structure dictates availability for HLA binding. However, these features also proved non-predictive (FIG. 32E). A hybrid model was then considered in which enzymes partially digest the protein before peptide binding, after which additional trimming occurs. In this model, precursor cleavage sites exist further upstream and downstream of the observed termini of MS ligands. Accordingly, a CNN was trained based on the extended protein context (±30 AAs) to detect distal signals corresponding to precursor cuts. This model did not show predictive value either (FIG. 32E). Finally, as processing-preferred regions proved difficult to predict based on primary sequence, protein regions observed in published HLA-DQ ligandomes were catalogued and used overlap to predict HLA-DR ligands. The overlap variable yielded a modest improvement in prediction performance (3.1% increase in PPV on average over neonmhc2 alone) (FIG. 32E). Assuming that HLA-DQ and HLA-DR alleles share the same HLA class II processing environment but do not share peptide binding motifs, this result indicates certain gene regions are indeed favored for processing but do not show obvious cleavage motifs or special conformational properties.

Integrating Presentation Rules Greatly Enhances HLA-DR Ligandome Prediction

To quantify how binding rules synergize with processing-related features, a multi-variate models was created for predicting HLA-DR ligandomes of HLA class II-presenting cell lines, dendritic cells, and healthy donor peripheral blood mononuclear cells (PBMCs). Although the presented peptides are not mutated, the prediction scenario mimics that of neoantigen prediction, in which randomly sampled genomic loci must be evaluated in terms of their ability to produce HLA class II peptides. Using a 1:499 ratio of hits to decoys and sampling decoys at random from the protein-coding exome, the performance of neonmhc2- and NetMHCIIpan-based models was assessed as well as models that incorporated additional processing features including RNA-Seq-derived expression, gene-level bias (per FIG. 32A, see related FIG. 39B), and overlap with a previously observed HLA-DQ peptides. To make the model consistent with how mutated tumor epitope targets are prioritized for the treatment of cancer, the gene-level bias feature was modified to neutralize preference for plasma genes that are not relevant sources of neoantigens.

These integrative algorithms confirmed substantial improvements in both binding and processing prediction (FIG. 21A). Specifically, the full model showed a 7.4× to 61× fold-change improvement over a model using NetMHCIIpan binding predictions alone, depending on the dataset being evaluated. Expression and gene bias both provided substantial independent contributions to prediction accuracy. The DQ overlap feature made smaller contribution but consistently provided a positive improvement. Importantly, affinity-based models were only half as accurate as MAPTAC™-based models even when provided the full benefit of processing-related prediction variables.

Benchmarking Prediction Accuracy Using Tumor-Derived HLA Class II Peptides Presented by Professional APCs Having assessed our accuracy in predicting HLA class II ligandomes, attention was shifted to testing whether tumor-derived ligands endocytosed by professional APCs could be predicted. Our observation that most HLA class II expression in the TME is from professional APC's indicates that this processing route is likely the most relevant pathway for tumor antigen presentation. Unfortunately, conventional MS-based ligandomes of tumor tissues do not identify which peptides originate from endocytosed tumor proteins. Therefore, an experiment was devised in which were profiled the HLA-DR ligandomes of dendritic cells (DCs) that had been "fed" SILAC-labeled tumor cells (FIG. 33A).

To label tumor-derived proteins, an HLA class II-deficient cancer cell line (K562) was grown in media containing isotopically-labeled L and K achieving greater than 95% labeling efficiency. DCs were fed either lysed tumor cells (to mimic macropinocytosis of tumor debris) or UV treated whole tumor cells (to mimic phagocytosis of whole cells). HLA-DR binding peptides were profiled using MS to identify peptides bearing heavy- or light-labeled amino acids. The experiment yielded 29 heavy-labeled peptides and the whole-cell experiment yielded 56 heavy-labeled peptides for the lysate and UV experiments, respectively (Table 10). Peptides bearing more than one L or K showed complete labeling in all but two cases indicating that the heavy-labeled peptides originated from tumor cells and not from newly translated DC proteins, which would show discordant labeling. Both untreated DCs and DCs that were harvested after incubating 10 minutes with lysate yielded no heavy-labeled peptides.

Using the integrated prediction algorithm disclosed here, the ability to predict tumor-derived peptides was assessed. Consistent with our previous result in predicting natural HLA class II ligandomes, neonmhc2-based models achieved much greater prediction accuracy than NetMHCIIpan-based models (FIG. 33D).

Unlike gene expression, the gene bias and DQ-overlap features did not improve prediction of the endocytosed antigens suggesting that the patterns that were learned from bulk tissue ligandomes were not as relevant for this class of epitopes. Analyzing the source genes of heavy-labeled peptides, the RNA-binding proteins (RBPs) DNA-binding proteins (DBPs) heat shock proteins (HSPs) and mitochondrial proteins (FIG. 21D) were noticed as opposed to the predominance of secreted and membrane proteins seen in the ligandome experiments (FIG. 32A). It was not clear whether this represented distinct processing preferences. Indeed, the source proteins were typically highly expressed in K562 (median expression 430 TPM compared to 130 TPM for unlabeled peptides), suggesting the detection limit might drive the observed gene preferences.

To gain clarity, logistic regression models were built to test whether gene localization and functional categories could improve peptide prediction beyond models that already account for gene expression. RBPs, DBPs and HSPs were no longer significant when the binding and expression were accounted for, but mitochondrial proteins remained significant (p=2.6e-4: FIG. 33E). Notably, the pattern of enrichment was completely distinct from what was observed in the light labeled peptides.

To determine whether mitochondrial enrichment could improve prediction, data were collected from new donor with the aim for deeper coverage by increasing the cellular input, focusing on the UV-treatment protocol only, and adding a 24-hour incubation timepoint in addition to the overnight timepoint. This experiment yielded 77 and 59 heavy labeled peptides for the overnight and 24-hour timepoints, respectively, and jointly identified 78 unique source genes. Using a logistic regression model that accounts for mitochondrial preference (trained on the original SILAC data), we were able to improve PPV by a net increase of 8-12% over models that include binding and expression only (FIG. 33G). These improvements were significant (p=1.1e-9 and p=1.5e=-8, for 16 h and 24 h, respectively). These preferences could not have been learned from bulk ligandomes and can be used to enable more accurate epitope prediction.

The presence of HLA class II presentation in the TME has been associated with positive outcomes in patients treated with cancer immunotherapies. Unfortunately, the inaccuracy of HLA class II ligand prediction and the ambiguities around how tumor antigens are presented in the TME have slowed the development of therapies that target HLA class II antigens. Therefore, a mono-allelic-profiling technology called MAPTAC™ was developed as described herein, and comprehensively analyzed tumor ligandomes to define HLA class II ligand processing rules. MAPTAC™ enabled rapid profiling of 40 HLA class II alleles, including 35 HLA-DRB1 alleles that cover 95% of U.S. patients. Furthermore, neonmhc2, our binding prediction algorithm trained on MAPTAC™ data, outperformed NetMHCIIpan in predicting memory CD4+ T cell responses, even for the alleles with the most pre-existing affinity measurements available for NetMHCIIpan training. It was observed that neonmhc2 was superior in performance to NetMHCIIpan in identifying memory $CD4^+$ T cell responses in the TGEM validation dataset. Furthermore, the algorithms disclosed herein also excelled at predicting ex vivo induced $CD4^+$ T cell responses against neoantigens, successfully identifying immunogenic neoepitopes which would not have been prioritized by NetMHCIIpan. Meanwhile, analysis of single-cell RNA-Seq tumor data revealed that the most relevant tumor antigens are likely dominantly expressed by infiltrating APCs phagocytosing tumor cells. Thus, which genes and gene regions are preferentially presented in the TME was investigated and multivariate models were created that accurately predicted HLA-DR ligandomes and tumor-derived ligands presented by phagocytic APCs. These models greatly exceed the positive predictive value of NetMHCIIpan.

An advantage of directly profiling endogenously processed and presented HLA class II ligands using MAPTAC™ in contrast to conventional peptide binding assays is that peptide loading chaperones such as HLA-DM are present. HLA-DM is known to play a role in editing the HLA class II peptide repertoire of APCs, which motivated us to study the effects of its differential expression on HLA class II ligandomes. When HLA-DM was over-expressed in HLA-DR MAPTAC™ experiments, the binding motifs were more clearly resolved than in the experiments without HLA-DM over-expression. Surprisingly, HLA-DM had a profound effect on HLA-DQB1*06:04/A1*01:02, demonstrating that learning accurate peptide binding rules for some HLA-DQ alleles may require the presence of this peptide loading chaperone. Conversely, two HLA-DP alleles showed no effect (Yin et al., 2015), suggesting a relationship between HLA-DM sensitivity and P1 anchor preferences that were unusual for these two HLA-DP alleles. Beyond HLA-DM, the MAPTAC™ platform provides a way to rapidly learn how other key chaperones and proteins involved in the HLA class II pathway, such as CD74 or HLA-DO, may impact the peptide binding repertoires of HLA class II alleles.

With respect to tumor biology, our most consequential observation was that APCs are responsible for dominant HLA class II expression in the TME for the tumor types evaluated. This suggests that the presentation of therapeutically relevant tumor antigens likely depends on the phagocytosis of apoptotic tumor cells or macropinocytosis of secreted tumor proteins. Although there are reports of direct CD4 T cell killing, the data provided suggests that CD4 T cells more typically play a supportive role in the TME, primarily recognizing tumor antigens presented on infiltrating leukocytes. Thus, the anti-tumor effects of CD4 T cells are probably mostly mediated by the secretion of chemokines and cytokines that regulate the trafficking and activation of other immune cells, including those with direct cytolytic function. While this is more mechanistically complicated, one benefit is that the tumor has less control over whether HLA class II antigens get presented, suggesting that immune escape via loss-of-function mutations, a common mechanism by which tumors avoid HLA class I presentation, may not be as frequent with HLA class II. Future studies that carefully define which APC populations are responsible for presenting endocytosed tumor antigens and whether there are ways to enhance recruitment of these phagocytic cells to the TME will be beneficial for the field. Additionally, it would be useful to understand how different modes of tumor cell death, such as hypoxia, chemotherapy, and radiation, result in various levels of tumor antigen capture by these APCs, which may lead to optimal therapeutic combinations with HLA class II targeting therapies.

Finally, a comprehensive analysis of HLA class II ligandomes led to the observation that certain genes appear to be presented more often than their transcript expression levels would predict. Learning gene level biases from tumor cells facilitated improved prediction of APC HLA class II ligandomes; however, it is possible that some of these signals are less relevant for neoantigen prediction. For example, enrichments were detected that appear to relate to autophagy and membrane recycling in APCs rather than the uptake of exogenous antigens. Interestingly, when ""tumor cells were "fed" to dendritic cells in vitro, the source gene identifications instead showed enrichment for RNA-binding proteins. It is tempting to speculate that RNA-binding proteins are preferentially presented since such a mechanism would promote the presentation of pathogen epitopes and potentially explain reactivities against RNA-binding proteins observed in systemic lupus erythematosus and other autoimmune conditions. In any case, it is important to note that the utility of our SILAC-based HLA ligandomics workflow is not limited to tumor antigens, as it can also be applied to study antigens involved in infectious disease and autoimmunity.

In summary, the rules of HLA class II processing and presentation are significantly more complex than for HLA class I. For this reason, the antigens that drive CD4+ T cell responses often remain undefined. Our advances in defining HLA class II binding and processing rules will enable the identification of targetable cancer antigens and other disease-related epitopes that can be translated to more effective therapies.

Example 13: Supplemental Information

Summary of Experiments and Data Sources with Associated Meta Data

Exhaustive list of data sets, including MAPTAC™ data, non-MAPTAC™ manuscript data, and previously published data. Relevant associated features, such as sample genotype, are provided where appropriate. B) Unique peptide identifications merged across experimental MAPTAC™ replicates, PBMC donors, cell lines, and SILAC-feeding experiments. Contaminants and perfect tryptic peptides are removed. See for example, at least FIGS. 12E-12F, 34A-34B, among others.

Spike-in Peptides for Deconvolution Analysis

An exemplary list of 20 example peptides used per allele in the spike-in analysis. Peptides were selected by requiring a minimum SPI of 70, length between 12 and 20 amino acids, and by not allowing a 9mer overlap with any binders observed for other MAPTAC™-profiled DR alleles. Additionally, no two spike-in peptides for a given allele share a 9mer. See for example, at least FIGS. 35, 36A-36C, among others.

Collated TGEM Data Set for Selected Alleles Supplemental Experimental Procedures HLA class II tetramer results for DRB1*01:01, DRB1*03:01, DRB1*04:01, DRB1*07:01, DRB1*11:01, and DRB1*15:01 for diverse pathogen and allergen peptides and their corresponding NetMHCIIpan and neonmhc2 predictions. Data were curated from papers published by Kwok and colleagues. See FIG. 38X, 38Y, 38B-38C, among others.

Supplemental Methods

HLA Class II Allele Frequencies and Affinity Data Statistics, Related to FIGS. 12A and 12E

Allele frequencies were obtained from resource, bioinformatics.bethematchclinical.org/hla-resources/haplotype-frequencies/high-resolution-hla-alleles-and-haplotypes-in-the-us-population. The mhc_ligand_full.csv dataset was downloaded from IEDB data (iedb.org/database_export_v3.php) on Sep. 21, 2018. Valid affinity measurements were required to have a "Method/Technique" equal to "cellular MHC/competitive/fluorescence", "cellular MHC/competitive/radioactivity", "cellular MHC/direct/fluorescence", "purified MHC/competitive/fluorescence", "purified MHC/competitive/radioactivity", or "purified MHC/direct/fluorescence" and an "Assay Group" equal to "dissociation constant KD", "dissociation constant KD (~EC50)", "dissociation constant KD (~IC50)", "half maximal effective concentration (EC50)", or "half maximal inhibitory concentration (IC50)". A measurement was attributed to the Soren Buus group (University of Copenhagen, Denmark) if the string "Buus" appeared in the "Authors" field. Otherwise, if the authors field included the strings "Sette" or "Sidney", a measurement was attributed to the Alessandro Sette group (La Jolla Institute for Immunology, U.S.A). All other measurements were labeled as "Other". For the purposes of enumerating strong binders, only peptides with a measured affinity stronger than 100 nM were counted MAPTAC™ Protocol Overview, Related to FIG. 2: DNA Construct Design The gene sequences for HLA class I and HLA class II alleles were identified by the IPD-IMGT/HLA webpage (ebi.ac.uk/ipd/imgt/hla) and used to design recombinant expression constructs. For HLA class I, the α-chain was fused with a C-terminal GSGGSGGSAGG linker (SEQ ID NO: 10), followed by the biotin-acceptor-peptide (BAP) tag sequence GLNDIFEAQKIEWHE (SEQ ID NO: 11), a stop codon, and a variable DNA barcode, and cloned into the pSF Lenti vector (Oxford Genetics, Oxford, UK) via the NcoI and XbaI restriction sites. The HLA class II constructs (DR, DP and DQ) were similarly cloned into pSF Lenti via the NcoI and XbaI restriction sites and consisted of the β-chain sequence fused on the C-terminus to the linker-BAP sequence from the HLA class I construct (SGGSGGSAGG-GLNDIFEAQKIEWHE (SEQ ID NO: 12)), followed by another short GSG linker an a F2A ribosomal skipping sequence (VKQTLNFDLLKLAGDVESNPGP (SEQ ID NO: 13)), the sequence of the α-chain, an HA tag (GSY-PYDVPDYA (SEQ ID NO: 14)), a stop codon, and a variable DNA barcode. For all DR alleles the beta-chain was paired with DRA*01:01. The HLA-DM construct was cloned similarly to the HLA class II constructs except that it lacked the BAP-sequence and the HA-tag. HLA-DM was added to a subset of the HLA class II experiments. The identity of all DNA sequences was verified by Sanger sequencing.

Cell Culture and Transient Transfections

Expi293 cells (Thermo Scientific) were grown in Expi293 medium (Thermo Scientific) with 8% $CO_2$ at 37° C. on an orbital shaker at 125 rpm. Expi293 cells were maintained at cell densities between $0.5 \times 10^6$/mL and $6 \times 10^6$/mL with regular biweekly passaging. 30 mL of the Expi293 cell suspension was used for transient transfections at a cell density of approximately $3 \times 10^6$/mL and >90% viability. Briefly, 30 ug DNA (1 μg DNA per mL cell suspension) was diluted into 1.5 mL Opti-MEM medium (Thermo Scientific) in one tube while 80 μL ExpiFectamine™ 293 transfection reagent (Thermo Scientific) was diluted into a second tube containing 1.5 mL Opti-MEM. These two tubes were incubated at room temperature for five minutes, combined, mixed gently, and incubated at room temperature for 30 minutes. The DNA and ExpiFectamine mixture were added to Expi293 cells and incubated at 37° C., 8% $CO_2$, 80% relative humidity. After 48 h, transfected cells were harvested in four technical replicates at $50 \times 10^6$ cells per tube, centrifuged, washed once with 1× Gibco DPBS (Thermo Scientific), and flash frozen in liquid nitrogen for mass spectrometric analysis. An aliquot of $1 \times 10^6$ cells was collected from each transfection batch and analyzed via anti-BAP (Rockland Immunochemicals Inc., Limerick, Pa.) or anti-HA (Bio-Rad, Hercules, Calif.) using western blot analysis to verify affinity-tagged HLA protein expression. Expi293's endogenous HLA class II genotype was determined to be DRB1*15:01, DRB1*01:01, DPB1*04:02, DPA1*01:03, DQB1*06:02, DQA1*01:02 (Laboratory Corporation of America, Burlington, N.C.). In some experiments, the HLA class II alleles were co-transfected with HLA-DM, in which case the DNA concentration used for both plasmids was dropped to 0.5 μg DNA per mL cell suspension.

A375 cells (ATCC) were grown in DMEM with 10% FBS and maintained at cultures at no greater than 80% confluence with regular passaging. For mass spectrometry experiments A375 cells were cultured in a 500 $cm^2$ plate at a seeding density of $18.5 \times 10^6$ cells/mL in 100 mL, as calculated from a 70% confluent cell number. After 24 hours, cells were transfected with TransIT-X2 (Mirus Bio) by following the TransIT system protocol adjusted for the total culture volume. After 48 h, cell medium was aspirated, and cells were washed with 1× Gibco DPBS (Thermo Scientific). For harvest, A375 cells were incubated for 10 minutes at 37° C. with 30 mL non-enzymatic cell dissociation solution (Sigma-Aldrich), centrifuged, washed with 1×DPBS, and aliquoted at $50 \times 10^6$ cells per sample. 293T and HeLa cells were purchased from ATCC and were cultured at 37° C. at 5% CO2 in DMEM, 10% FBS, 2 mM L-glutamine or DMEM+10% FBS, respectively. Both cell lines were transfected with the HLA constructs using the TransIT LT1 reagent (Mirus Bio) following the manufactures instructions and processed 48 h after transfection as described for the A375 cells. From all samples, an aliquot of $1 \times 10^6$ cells was collected from each transfection and analyzed via anti-BAP (Rockland Immunochemicals Inc., Limerick, Pa.) or anti-HA (Bio-Rad, Hercules, Calif.) western blot to verify affinity-tagged HLA protein expression. B721.221 cells were obtained from Fred Hutchison Cancer Center (Seattle, Wash.) and were cultured in RPMI-1640 plus glutamax (Thermo Fisher Scientific) with 10% heat inactivated fetal bovine serum plus 1% penicillin/streptomycin (both Thermo Fisher Scientific). Cells were cultured twice weekly and discarded after 25 passages. K562 cells and KG-1 cells (ATCC, Manassas, Va.) were grown in IMDM (Thermo Fisher Scientific) media plus 10% heat inactivated FBS, 1% penicillin/streptomycin, 1% sodium pyruvate, and 1% MEM-NEAA. Cells were cultured twice weekly and discarded after 25 passages.

Lentivirus for transduction of B721.221, KG-1, and K562 cells were produced in HEK293T cells grown to 80% confluency. Six micrograms of the genome vector psFLenti encoding HLA class I or HLA class II (described in previous sections) was mixed with 5.3 ug of the lentivirus packaging vector psPAX2 and 1.8 1 ug of the envelope vector pMD.2. DNA was mixed with Opti-MEM (Thermo Fisher Scientific) and the transfection reagent, Fugene H D (Promega, Madison, Wis.), and the mixture was incubated at room temperature for 15 minutes. The mixture was then added dropwise onto the dish of HEK293T cells and incubated for 72 hours. Supernatant was then harvested, and lentiviral titers were tested using Lenti-X GoStix (Takara Bio Inc., Japan). For transduction, cells were seeded in 12-well flat bottom plates (Corning Inc., Corning, N.Y.) and mixed with lentiviral supernatant with 6 ug/ml polybrene (Sigma-Aldrich). Cells mixed with lentivirus were spun at 32° C. at 800×g for 90 minutes. Cells were resuspended in warm media and incubated in a 37° C. incubator at 5% $CO_2$ for 72 hours. Cells were then selected using 1 ug/ml puromycin for 2 weeks. After selection, at least 50 million cells were harvested, centrifuged, washed once with 1× Gibco DPBS (Thermo Scientific), and flash frozen in liquid nitrogen for mass spectrometric analysis.

BirA Protein Expression and Purification

The pET19 vector encoding *E. coli* BirA fused to a C-terminal hexa-histidine tag (SEQ ID NO: 15) was used. Chemical competent *E. coli* BL21 (DE3) cells (New England Biolabs) were transformed with a BirA expression plasmid (pET19 vector encoding *E. coli* BirA fused to a C-terminal hexa-histidine (SEQ ID NO: 15)), grown at 37° C. in LB broth plus 100 μg/ml ampicillin to an $OD_{600}$ of 0.6-0.8 and cooled to 30° C. before expression was induced by adding 0.4 mM isopropyl-β-D-thiogalactopyranoside. *E. coli* cell growth continued at 30° C. for 4 h. *E. coli* cells were harvested by centrifugation at 8000×g for 30 minutes at 4° C. and stored at −80° C. until use. Frozen cell pellets expressing recombinant BirA were resuspended in IMAC buffer (50 mM $NaH_2PO_4$ pH 8.0, 300 mM NaCl) with 5 mM Imidazole, incubated with 1 mg/ml lysozyme for 20 minutes on ice and the lysed by sonication. Cellular debris and insoluble materials were removed by centrifugation at 16,000×g for 30 minutes at 4° C. The cleared supernatant was subsequently loaded on a HisTrap HP 5 mL column using the AKTA pure chromatography system (GE Healthcare), washed with IMAC buffer plus 25 mM and 50 mM imidazole before elution with 500 mM imidazole. Fractions containing BirA were pooled and dialyzed against 20 mM Tris-HCl pH 8.0 with 25 mM NaCl and were loaded on a HiTrap Q HP 5 mL column (GE Healthcare, Chicago, Ill.) and eluted by applying a linear gradient from 25 to 600 mM NaCl. Fractions containing highly pure BirA were pooled, buffer exchanged in storage buffer (20 mM Tris-HCl pH 8.0 100 mM NaCl, 5% glycerol) and concentrated to around 5-10 mg/mL, aliquoted, and flash frozen in liquid nitrogen for storage at −80° C. BirA protein concentration was determined by UV spectroscopy at $OD_{280\ nm}$ using a calculated extinction coefficient of $\varepsilon=47,440\ M^{-1}\ cm^{-1}$.

Western Blotting Protocol

Samples were added to XT Sample Buffer and XT Reducing Agent (Bio-Rad, Hercules, Calif.), heated at 95° C. for five minutes, then a volume corresponding to 100,000 cells was loaded into 10% Criterion XT Bis-Tris gels (Bio-Rad, Hercules, Calif.) and electrophoresed at 200 V for 35 minutes using a PowerPac Basic Power Supply (Bio-Rad, Hercules, Calif.) with XT MES Running Buffer (Bio-Rad, Hercules, Calif.). The gels were rinsed briefly with water, then proteins were transferred to PVDF membranes within Invitrogen iBlot Transfer Stacks (Thermo Fisher Scientific) using setting P3 on an Invitrogen iBlot2 Gel Transfer Device (Thermo Scientific). The Precision Plus Protein All Blue Standard (Bio-Rad, Hercules, Calif.) was used to monitor molecular weights. Next, membranes were washed 3×five minutes with Pierce TBS Tween 20 buffer [(TBST) 25 mM Tris, 0.15 mM NaCl, 0.05% (v/v) Tween 20, pH 7.5, Thermo Fisher Scientific)], blocked for 1 h at room temperature in TBST-M [TBST containing 5% (w/v) nonfat instant dry milk], then incubated overnight at 4° C. in TBST-B [TBST containing 5% (w/v) Bovine Serum Albumin (Sigma Aldrich)] and a 1:5,000 dilution of both rabbit anti-beta tubulin antibody (catalog #ab6046, Abcam, Cambridge, Mass.) and rabbit anti-biotin ligase epitope tag antibody (catalog #100-401-B21, Rockland Immunochemicals, Limerick, Pa.). Next, the membranes were washed 3×five minutes with TBST, incubated for 1 h at room temperature in TBST-M containing a 1:10,000 dilution of goat anti-rabbit IgG (H+L)-horseradish peroxidase-conjugated antibody (catalog #170-6515, Bio-Rad), then washed at room temperature 3×five minutes with TBST. Finally, membranes were bathed with Pierce ECL Western Blotting Substrate (Thermo Fisher Scientific), developed using a ChemiDoc XRS+ Imager (Bio-Rad), and visualized using Image Lab software (Bio-Rad).

Affinity-Tagged HLA-Peptide Complex Isolation

Affinity-tagged HLA-peptide complex isolations were performed from cells expressing BAP-tagged HLA alleles and negative control cell lines that expressed only endogenous HLA-peptide complexes without BAP tags. The NeutrAvidin beaded agarose resin was washed three times with 1 mL cold PBS before use in HLA-peptide affinity purification. Frozen pellets containing $50\times10^6$ cells expressing BAP-tagged HLA molecules were thawed on ice for 20 minutes and gently lysed by hand pipetting in 1.2 mL cold lysis buffer [20 mM Tris-Cl pH 8, 100 mM NaCl, 6 mM MgCl2, 1.5% (v/v) Triton X-100, 60 mM octyl glucoside, 0.2 mM of 2-Iodoacetamide, 1 mM EDTA pH 8, 1 mM PMSF, 1× complete EDTA-free protease inhibitor cocktail (Roche). Lysates were incubated end/over/end at 4° C. for 15 minutes with ≥250 units benzonase nuclease (Sigma-Aldrich) to degrade DNA/RNA and centrifuged at 15,000×g at 4° C. for 20 minutes to remove cellular debris and insoluble materials. Cleared supernatants were transferred to new tubes and BAP-tagged HLA molecules were biotinylated by incubating end/over/end at room temperature for 10 minutes in a 1.5 mL tube with 0.56 μM biotin, 1 mM ATP, and 3 μM BirA. The supernatants were incubated end/over/end at 4° C. for 30 minutes with a volume corresponding to 200 μL of Pierce high-capacity NeutrAvidin beaded agarose resin (Thermo Scientific) slurry to affinity-enrich biotinylated-HLA-peptide complexes. Finally, the HLA-bound resin was washed four times with 1 mL of cold wash buffer (20 mM Tris-Cl pH 8, 100 mM NaCl, 60 mM octyl glucoside, 0.2 mM of 2-Iodoacetamide, 1 mM EDTA pH 8), then washed four times with 1 mL of cold 10 mM Tris-Cl pH 8. Between washes, the HLA-bound resin was gently mixed by hand then pelleted by centrifugation at 1,500×g at 4° C. for one minute. The washed HLA-bound resin was stored at −80° C. or immediately subjected to HLA-peptide elution and desalting.

Antibody-Based HLA-Peptide Complex Isolation

HLA DR-peptide complexes were isolated from healthy donor peripheral blood mononuclear cells (PBMCs). A volume corresponding to 75 μL of GammaBind Plus Sepharose resin was washed three times with 1 mL cold PBS, incubated end/over/end with 10 μg of the antibody at 4° C. overnight, then washed with three times with 1 mL cold PBS before use in HLA-peptide immunoprecipation. Frozen PBMC pellets containing $50\times10^6$ cells were thawed on ice for 20 minutes and gently lysed by pipetting in 1.2 mL cold lysis buffer [20 mM Tris-Cl pH 8, 100 mM NaCl, 6 mM MgCl2, 1.5% (v/v) Triton X-100, 60 mM octyl glucoside, 0.2 mM of 2-Iodoacetamide, 1 mM EDTA pH 8, 1 mM PMSF, 1× complete EDTA-free protease inhibitor cocktail (Roche). Lysates were incubated end/over/end at 4° C. for 15 minutes with >250 units benzonase nuclease (Sigma-Aldrich) to degrade DNA/RNA and centrifuged at 15,000×g at 4° C. for 20 minutes to remove cellular debris and insoluble materials. The supernatants were then incubated end/over/end at 4° C. for 3 hours with an anti-HLA DR antibody (TAL 1B5, product #sc-53319; Santa Cruz Biotechnology, Dallas, Tex.) bound to GammaBind Plus Sepharose resin (GE Life Sciences) to immunoprecipitate HLA DR-peptide complexes. Finally, the HLA-bound resin was washed with 1 mL of cold wash buffer (20 mM Tris-Cl pH 8, 100 mM NaCl, 60 mM octyl glucoside, 0.2 mM of 2-Iodoacetamide, 1 mM EDTA pH 8), then washed four times with 1 mL of cold 10 mM Tris-Cl pH 8. Between washes, the HLA-bound resin was gently mixed then pelleted by centrifugation at 1,500×g at 4° C. for 1 minute. The washed HLA-bound resin was stored at −80° C. or immediately subjected to HLA-peptide elution and desalting.

HLA-Peptide Elution and Desalting

HLA-peptides were eluted from affinity-tagged and endogenous HLA complexes and simultaneously desalted using a Sep-Pak (Waters) solid-phase extraction system. In brief, Sep-Pak Vac 1 cc (50 mg) 37-55 µm particle size tC18 cartridges were attached to a 24-position extraction manifold (Restek), activated two times with 200 µL MeOH followed by 100 µL of 50% (v/v) ACN/1% (v/v) FA, then washed four times with 500 µL 1% (v/v) FA. To dissociate HLA-peptides from affinity-tagged HLA molecules and facilitate peptide binding to the tC18 solid-phase, 400 µL of 3% (v/v) ACN/5% (v/v) FA was added to the tubes containing HLA-bound beaded agarose resin. The slurry was mixed by pipetting, then transferred to the Sep-Pak cartridges. The tubes and pipette tips were rinsed with 1% (v/v) FA (2×200 µL) and the rinsate was transferred to the cartridges. 100 fmol of Pierce Peptide Retention Time Calibration (PRTC) mixture (Thermo Scientific) was added to the cartridges as a loading control. The beaded agarose resin was incubated two times for five minutes with 200 µL of 10% (v/v) AcOH to further dissociate HLA-peptides from the affinity-tagged HLA molecules, then washed four times with 500 µL 1% (v/v) FA. HLA-peptides were eluted off the tC18 into new 1.5 mL micro tubes (Sarstedt) by step fractionating with 250 µL of 15% (v/v) ACN/1% (v/v) FA followed by 2×250 µL of 30% (v/v) ACN/1% (v/v) FA. The solutions used for activation, sample loading, washing, and elution flowed via gravity, but vacuum (≤−2.5 PSI) was used to remove the remaining eluate from the cartridges. Eluates containing HLA-peptides were frozen, dried via vacuum centrifugation, and stored at −80° C. before being subjected to a second desalting workflow. Secondary desalting of the HLA-peptide samples was performed with in-house built StageTips packed using two 16-gauge punches of Empore C18 solid phase extraction disks (3M, St. Paul, Minn.) as previously described. StageTips were activated two times with 100 µL of MeOH followed by 50 µL of 50% (v/v) ACN/0.1% (v/v) FA, then washed three times with 100 µL of 1% (v/v) FA. The dried HLA-peptides were solubilized by adding 200 µL of 3% (v/v) ACN/5% (v/v) then and loaded onto StageTips. The tubes and pipette tips were rinsed with 1% (v/v) FA (2×100 µL) and the rinse volume was transferred to the StageTips, then the StageTips were washed five times with 100 µL 1% (v/v) FA. Peptides were eluted using a step gradient of 20 µL 15% (v/v) ACN/1% (v/v) FA followed by two 20 µL cuts of 30% (v/v) ACN/1% (v/v) FA. Sample loading, washes, and elution were performed on a tabletop centrifuge with a maximum speed of 1,500-3,000×g. Eluates were frozen, dried via vacuum centrifugation, and stored at −80° C.

HLA-Peptide Sequencing by Tandem Mass Spectrometry

All nanoLC-ESI-MS/MS analyses employed the same LC separation conditions described below. Samples were chromatographically separated using a Proxeon Easy NanoLC 1200 (Thermo Scientific, San Jose, Calif.) fitted with a PicoFrit (New Objective, Inc., Woburn, Mass.) 75 µm inner diameter capillary with a 10-µm emitter was packed at 1000 psi of pressure with He to ~30-40 cm with 1.9 µm particle size/200 Å pore size of C18 Reprosil beads (Dr. Maisch GmbH, Ammerbuch, Germany) and heated at 60° C. during separation. The column was equilibrated with 10× bed volume of buffer A [0.1% (v/v) FA and 3% (v/v) ACN], samples were loaded in 4 µL 3% (v/v) ACN/5% (v/v) FA, and peptides were eluted with a linear gradient from 7-30% of Buffer B [0.1% (v/v) FA and 80% (v/v) ACN] over 82 minutes, 30-90% Buffer B over six minutes, then held at 90% Buffer B for 15 minutes to wash the column. A subset of samples was eluted with a linear gradient from 6-40% of Buffer B over 84 minutes 40-60% Buffer B over nine minutes, then held at 90% Buffer B for five minutes and 50% Buffer B for nine minutes to wash the column. Linear gradients for sample elution were run at a rate of 250 nL/min and yielded ~13 sec median peak widths.

During data-dependent acquisition, eluted peptides were introduced into an Orbitrap Fusion Lumos mass spectrometer (Thermo Scientific, San Jose, Calif.) equipped with a Nanospray Flex Ion source (Thermo Scientific, San Jose, Calif.) at 2.2-2.5 kV. A full-scan MS was acquired at a resolution of 60,000 from 300 to 1,700 m/z (AGC target 4e5, 50 ms max IT). Each full scan was followed by a 2 sec cycle time, or top 10, of data-dependent MS2 scans at resolution 15,000, using an isolation width of 1.0 m/z, a collision energy of 34 (HLA class I data) and 38 (HLA class II data), an ACG Target of 5e4, and a max fill time of 250 ms max ion time. An isolation width of 1.0 m/z was used because HLA class II peptides tend to be longer (median 16 amino acids with a subset of peptides >40 amino acids), so the monoisotopic peak is not always the tallest peak in the isotope cluster and the mass spectrometer acquisition software places the tallest isotopic peak in the center of the isolation window in the absence of a specified offset. The 1.0 m/z isolation window will therefore allow for the co-isolation of the monoisotopic peak even when it is not the tallest peak in the isotopic cluster as the charge states of HLA class II peptides are often +2 or higher. Dynamic exclusion was enabled with a repeat count of 1 and an exclusion duration of 5 sec to enable ~3 PSMs per precursor selected. Isotopes were excluded while dependent scans on a single charge state per precursor was disabled because HLA-peptide identification relies on PSM quality, so multiple PSMs of different charge states further increases our confidence of peptide identifications. Charge state screening for HLA class II data collection was enabled along with monoisotopic precursor selection (MIPS) using Peptide Mode to prevent triggering of MS/MS on precursor ions with charge state 1 (only for alleles with basic anchor residues), >7, or unassigned. For HLA class I data collection, precursor ions with charge state 1 (mass range 800-1700 m/z) and 2-4 were selected, while charge states >4 and unassigned were excluded.

Interpretation of LC-MS/MS Data, Related to FIG. 29

Mass spectra were interpreted using the Spectrum Mill software package v6.0 pre-Release (Agilent Technologies, Santa Clara, Calif.). MS/MS spectra were excluded from searching if they did not have a precursor MH+ in the range of 600-2000 (HLA class 1)/600-4000 (HLA class II), had a precursor charge >5 (HLA class I)/>7 (HLA class II), or had a minimum of <5 detected peaks. Merging of similar spectra with the same precursor m/z acquired in the same chromatographic peak was disabled. MS/MS spectra were searched against a database that contained all UCSC Genome Browser genes with hg19 annotation of the genome and its protein coding transcripts (63,691 entries; 10,917,867 unique 9mer peptides) combined with 264 common contaminants. Prior to the database search, all MS/MS had to pass the spectral quality filter with a sequence tag length >2, e.g., minimum of 3 masses separated by the in-chain mass of an amino acid. A minimum backbone cleavage score (BCS) of 5 was set, and ESI QExactive HLAv2 scoring scheme was used. All spectra from native HLA-peptide samples, not reduced and alkylated, were searched using a no-enzyme specificity, fixed modification of cysteine as cysteinylation, with the following variable modifications: oxidized methionine (m), pyroglutamic acid (N-term q), carbamidomethylation (c). Reduced and alkylated HLA-peptide samples were searched using a no-enzyme specificity, fixed modification of cysteine as carbamidomethylation, with the following variable modifications: oxidized methionine (m), pyroglutamic acid (N-term q), cysteinylation (c). A precursor mass tolerance of ±10 ppm, product mass tolerance of ±10 ppm, and a minimum scored peak intensity of 30% was used for both native and reduced and alkylated HLA-peptide datasets. Peptide spectrum matches (PSMs) for individual spectra were automatically designated as confidently assigned using the Spectrum Mill autovalidation module to apply target-decoy based FDR estimation at the PSM rank to set scoring threshold criteria. An auto thresholds strategy using a minimum sequence length of 7, automatic variable range precursor mass filtering, and score and delta Rank1-Rank2 score thresholds optimized across all LC-MS/MS runs for an HLA allele yielding a PSM FDR estimate of <1% for each precursor charge state.

Identified peptides that passed the PSM FDR estimate of <1.0% were further filtered for contaminants by removing all peptides assigned to the 264 common contaminants proteins in the reference database and by removing peptides identified in the negative control MAPTAC' affinity pull-downs. Additionally, all peptide identifications that mapped to an in silico tryptic digest of the reference database were removed, as these peptides cannot be ruled out as tryptic contaminants from sample carry-over on the uPLC column.

To remove potential false positive PSM identifications from the SILAC DC-feeding experiment, it was applied additional quality filters to PSMs identified using the methods described above. All peptides with FDR<1% were filtered for high quality PSMs using the following thresholds: i) scored peak intensity >60% ii) backbone cleavage score 8 and iii) ppm mass tolerance of ±1 ppm from the median ppm observed across all PSM identifications in the same LC-MS/MS replicate.

Monoallelic Assignment of HLA-DR, -DQ, -DP Heterodimers Using MAPTAC™ Protocol

Since only the beta chain of HLA class II is tagged in the MAPTAC' protocol, the pull-down step isolates peptide-MHC complexes regardless of whether they contain knock-in or endogenous alpha chain. In the case of HLA-DR, the allelic variation in the alpha chain is not considered to influence peptide binding; therefore, the relative degree of pairing with endogenous alpha pairing is irrelevant to data interpretation—the data is effectively mono-allelic. However, for HLA-DP and HLA-DQ loci, the alpha chains exhibit important allelic variants such that the presence of both knock-in and endogenous alpha chain alleles creates the potential for 1-3 distinct specificities (depending on whether the cell line has one or two alpha chain alleles and whether either matches the knock-in allele). In principle, this problem can be mitigated by running the protocol with and without a knock-in alpha chain and identifying the set of peptides specific to the with-alpha experiment. The approach of using a cell line was taken herein that expresses a single alpha allele that matches the knock-in alpha allele.

Analysis of Previously Published MS Data, Related to FIGS. 12A-12F, FIGS. 30A-30C, FIGS. 31A-31D, FIG. 21A, FIG. 39A-39B, and FIG. 40A-B Published LC-MS/MS datasets that provided.raw files were reprocessed using the Spectrum Mill software package v6.0 pre-Release (Agilent Technologies, Santa Clara, Calif.). Datasets that were collected on Thermo Orbitrap instruments (e.g., Velos, QExactive, Fusion, Lumos) that utilized HCD fragmentation and MS and MS/MS data collection in the orbitrap (high resolution) were analyzed using the parameters described in the above section "Interpretation of LC-MS/MS Data". For MS and MS/MS high resolution datasets that utilized CID fragmentation, the same parameters as above were used with an ESI Orbitrap scoring scheme. For datasets with MS data collection in the orbitrap and MS/MS data collection in the ion trap, the following same parameters above were also used with the following deviations. For HCD data, the ESI QExactive HLAv2 scoring scheme was used, while the ESI Orbitrap scoring scheme was used for CID data. A precursor mass tolerance of ±10 ppm, product mass tolerance of ±0.5 Da was used. For both high- and low-resolution MS/MS datasets, peptide spectrum matches (PSMs) for individual spectra were automatically designated as confidently assigned using the Spectrum Mill auto validation module to apply target-decoy based FDR estimation at the PSM rank to set scoring threshold criteria. An auto thresholds strategy using a minimum sequence length of 7, automatic variable range precursor mass filtering, and score and delta Rank1-Rank2 score thresholds optimized across all LC-MS/MS runs for an HLA allele yielding a PSM FDR estimate of <1.0% for each precursor charge state. Analysis of peptide identifications from some previously published data revealed a high rate of 9mers (>10%). Since these could potentially represent contaminating HLA class I ligands, short peptides were dropped (length <12) from all external data sets.

Mapping Peptides to Genes and "Nested Sets", Related to FIGS. 30A-30C, FIGS. 31A-31D, and FIGS. 32A-32E Each peptide was assigned to one or more protein-coding transcripts within the UCSC hg19 gene annotation (genome.ucsc.edu/cgi-bin/hgTables). Since many peptide identifications overlap others and thus constitute mostly redundant information, peptides were grouped into "nested sets", each meant to correspond to ~1 unique binding event. For instance, the peptides GKAPILIATDVASRGLDV (SEQ ID NO: 16), GKAPILIATDVASRGLD (SEQ ID NO: 17), and KAPILIATDVASRGLDV (SEQ ID NO: 18) all contain the conserved sequence KAPILIATDVASRGLD (SEQ ID NO: 19), and probably all bind MHC in the same register. In order to nest peptides of a given data set, a graph was built in which each node corresponded to a unique peptide, and an edge was created between any pair of peptides sharing at least one 9mer and mappable to at least one common transcript. The clusters command in the R package igraph (Team, 2014) (cran.r-project.org/web/packages/igraph/citation.html) was used to identify clusters of connected nodes, and each cluster was defined as a nested set. This procedure guarantees that any two peptides that meet the edge criteria (≥1 common 9mer and ≥1 common transcript) are placed within the same nested set. The nests were used for sequence logo generation (logos were generated using the shortest peptide in each nested set; FIG. 30A-30C, machine learning (importance weights across peptides in a nested set sum to one; FIG. 31A-31D), and the gene bias analysis (each nested set was counted as one observation rather than each individual peptide; FIG. 32A-32E).

Analysis of Amino Acid Frequencies, Related to FIG. 12F

Amino acid frequencies in the human proteome were calculated based on sequences for all protein-coding genes in the UCSC hg19 annotation (selecting one transcript at random for genes represented by multiple transcript isoforms). IEDB frequencies were determined by identifying the unique set of peptides with at least one affinity observation ≤100 nM (excluding peptides with hexavalent polyhistidine at their C-terminus). MAPTAC™ frequencies were first considered in the context of the standard forward-phase protocol across five DRB1 alleles (DRB1*01:01, DRB1*03:01, DRB1*09:01, and DRB1*11:01), using only one peptide (the longest) per nested set. In addition, MAPTAC™ frequencies were separately calculated for the subset of samples processed by the reduction and alkylation protocol. MS data from external datasets were analyzed without respect to potential allele of origin and likewise using the longest peptide per nested set.

Building HLA Class I Sequence Logos, Related to FIG. 37B

For each HLA class I allele, a length-9 sequence logo was created by profiling amino acid frequencies in the first five positions (mapping to logo positions 1-5) and last four positions (mapping to logo positions 6-9) of corresponding peptides. In this manner, peptides contributed to the sequence logo regardless of their length. As in the HLA class II logos, letter heights are proportional to the frequency of each amino acid in each position, and darker shading is used for amino acids with frequency ≥10%.

Assessing the Performance of HLA Class II Peptide Deconvolution, Related to FIG. 30B To assess the ability the GibbsCluster (v2.0) tool to cluster multi-allelic HLA class II peptide data by allele of origin, its performance on eight samples were analyzed, including 4 PBMC samples, 1 melanoma cell line (A375), and 3 previously published lymphoblastoid cell lines. For each DRB1/3/4/5 allele present in each sample genotype, twenty peptides were spiked in from our mono-allelic MAPTAC™ data. The spiked peptides were restricted to 12-20mers with SPI≥70 that did not share a 9mer with any peptides in MAPTAC™ data for other HLA-DR alleles or with any spiked peptides for the allele of interest. These augmented datasets were then submitted to GibbsCluster-v2.0 using default HLA class II settings except that was enforced a hydrophobic preference at position 1, as others have previously for deconvolution. For each sample, the number of clusters in the solution was manually specified and set equal to the number of HLA-DR alleles present in the genotype.

Calculating the Fraction of Peptides with Preferred Anchor Residues, Related to FIG. 30C Anchor positions were defined as the four positions with the lowest entropy, and within those positions, "preferred" amino acids included all those with frequency ≥10%. When calculating the fraction of peptides with preferred amino acids at n positions, only one peptide was used per nested set (the shortest).

Predicted Affinities of MS-Observed Peptides, Related to FIG. 36A

For each HLA class II allele, all unique peptides length 14 through 17 were identified and scored for binding potential using NetMHCIIpan-v3.1. For comparison, 50,000 random length-matched peptides were sampled from the human proteome. Density distributions were determined based on log-transformed values.

Measured Affinities for MS-Observed Peptides, Related to FIG. 36B

Peptides were selected for affinity measurement if they had poor predicted NetMHCIIpan-v3.1 binding affinity (>100 nM for DRB1*01:01 or >500 nM for DRB1*11:01) or if they exhibited ≤2 of the heuristically defined anchors.

Establishment of Cross-Validation Partitions, Related to FIG. 31A

A graph was created in which each node represents a protein-coding transcript and edges are present between all pairs of transcripts sharing at least 5 unique 9mers of amino sequence content (UCSC hg19 gene annotation). The clusters command in the R package igraph(Team, 2014) (cran.r-project.org/web/packages/igraph/citation.html) was used to identify clusters of connected nodes, and each cluster was defined as a "transcript group". In this manner, if two transcripts shared an edge (≥5 shared 9mers), they were guaranteed to be placed in the same transcript group. Transcript groups were randomly sampled, dividing the proteome into eight roughly equally sized partitions. MS-observed peptides (and non-observed decoy peptides) were placed in partitions according to the partition of their source transcripts, and these partitions were used for cross-validation and hyper-parameter tuning. The graph-based approach of partitioning the proteome was used to minimize the likelihood that similar peptide sequences would appear during training and evaluation, which could artificially inflate prediction performance.

Architecture and Training of a CNN-Based HLA Class II Binding Predictor, Neonmhc2, Related to FIG. 31A Negative examples (decoys) were generated for training by randomly shuffling the sequences of hit peptides. It was chosen this method of decoy generation, rather than selecting unobserved regions from the proteome, in order to eliminate MS biases that could result in a general amino acid preference. In this way, our binding predictor is unaware of the relative depletion of cysteine, for example (FIG. 12F). Similarly, this prevents our model from learning MS biases related to global properties of the peptides, such as the overall hydrophobicity. This method is related to results depicted in FIG. 31A.

Models were trained for two application scenarios: validating on internal MAPTAC™ data (FIG. 31B) and on external data (FIG. 31C, FIG. 21A, and FIG. 21B). When training models for the former, it was adopted a simple training procedure where network weight optimization was learned using six partitions of the data (train partitions), hyper-parameter optimization and early stopping was performed using the seventh partition (tune partition), and the final validation was performed on the eighth partition (evaluation partition) after the model design was finalized. In the case of external validation, cross-validation was employed, building an ensemble of models for each partition of data whereby it was held out that partition for hyper-parameter tuning and early stopping and used the remaining seven partitions for network weight optimization. Additionally, when scoring non-MS data (FIG. 31C and FIG. 31D), each 12-20mer substring of the target peptide was scored and the highest score was kept.

When training our models, each hit and decoy was down-weighted in the loss function by the size of its source nested set such that each nested set as a whole carried equal weight. When evaluating the model for hyper-parameter tuning, the shortest peptide from each nested set was used in the relevant partition as the positive examples and scrambled versions of those hits as the decoys. Additionally, an overall weighting factor was applied such that the summed weight of the hits equaled the summed weight of the decoys when training. For the final evaluation of the model, as shown in FIG. 31B, the shortest peptide was again selected from each nested set in the evaluation partition (partition 8) but sampled decoys randomly from non-observed subsequences of peptide source genes ("natural decoys", described in a subsequent section). In this way, any biases learned by the model in order to simply discriminate natural sequences from scrambled ones did not inflate our performance on the evaluation partition.

Models were trained using an Adam optimizer with an initial learning rate of 0.003, beta_1 value of 0.9, beta_2 value of 0.999 and no decay (default Keras parameters, except for the learning rate) and used a binary cross-entropy loss function. The initial model weights were set using He initialization. After every 5 epochs of training, the positive predictive value (PPV, described in subsequent section) on the tune partition was measured and the maximum value was tracked. After each epoch, if the training loss did not decrease, the learning rate was multiplied by ⅓. Similarly, each time the PPV was measured on the tune partition, if it did not increase compared to the running maximum the learning rate by ⅓ was multiplied. An early stopping scheme was implemented where, if the training loss failed to decrease for three consecutive epochs or the tune PPV failed to increase above the running maximum for 3 consecutive checks, then training was stopped. When training the model, a fixed hit-to-decoy ratio of 1:39 was used in the training set, and 1:19 in the tune partition.

Featurization: While amino acids may be represented by a "one-hot" encoding, others have opted to encode amino acids using the PMBEC matrix and the BLOSUM matrix (Henikoff and Henikoff, 1992), in which similar amino acids have similar feature profiles. For the purposes of our peptide featurization, a novel matrix based on amino acid proximities was generated in solved protein structures. The concept of this approach is that the typical neighbors of an amino acid should reflect its chemical properties. For each amino acid in each of ~100,000 DSSP protein structures (cdn.rcsb.org/etl/kabschSander/ss.txt.gz), the residue that was closest in 3D space but at least 10 amino acids away in primary sequence was determined. Using this data, the number of times the nearest neighbor of alanine was alanine was determined, the number of times the nearest neighbor of alanine was a cysteine, etc., to create a 20×20 matrix of proximity counts. Each element of the matrix was divided by the product of its corresponding column and row sums, and the entire matrix was log-transformed. Finally, the mean value of the entire matrix was subtracted from each element.

Each amino acid was also encode with 11 binary features describing properties of the amino acid, such as whether it is: acidic (N, Q), aliphatic (I, L, V), aromatic (H, F, W, Y), basic (H, K, R), charged (D, E, H, K, R), hydrophobic (A, C, F, H, I, K, L, M, T, V, W, Y), hydroxylic (S, T), polar (C, S, N, Q, T, D, E, H, K, R,Y, W), small (V, P, A, G, C, S,T, N, D), very small (A, G,C, S), or contains sulfur (M, C). Two features were used to describe the position of each amino acid, one monotonically increasing across the peptide and one indicating an absolute distance from the center of the peptide, both in units of position (not physical distance). Lastly, a single binary feature was included to indicate whether an amino acid was "missing" from that position, which would happen beyond the edges of shorter peptides. The result is that each amino acid is encoded by 20 amino acid proximity features, 11 amino acid property features, 2 position features, and 1 missing character feature for a total of 34 features. All peptides were encoded as 20mers where the central 20 amino acids were used for longer peptides and the missing character value was added symmetrically to the edges of peptides shorter than 20 amino acids.

When examples are input into the neural network, both for training and evaluating, each of the 34 features are normalized by subtracting their mean and dividing by their standard deviation. The mean and standard deviation are calculated based solely on the training set and without regard to position within the peptide.

For each allele, an ensemble of convolutional neural networks was trained in order to predict binding. A sketch of the model architecture is shown in FIG. 31A, depicting two convolutional layers with a kernel size of 6 and 50 filters each. After each layer, global max and mean pooling was applied and the resulting values were input into a final output neuron with sigmoid activation. It is implied but not shown that ReLU activation, batch normalization (Ioffe and Szegedy, 2015), and 20% spatial dropout were applied immediately after each convolutional layer.

When training an ensemble of models for each allele, the architecture was fixed but the amount of L2 regularization was varied. A base L2 regularization weight of 0.05 was used for the first convolutional layer and 0.1 for the second convolutional layer. To vary the amount of L2 regularization, these values were multiplied by 0.1, 0.5, and 1. For each iteration in the ensemble, one model per regularization level was trained and kept the best based on performance on the tune partition. Benchmarking prediction performance on MAPTAC™-observed peptides, related to FIG. 7A In some exemplary assessments of prediction performance value for a given peptide or protein encoded by an HLA allele, a method comprising "scrambled decoys" can be used. The scrambled decoys are peptides having the same peptide length and amino acids as a peptide that is known to bind to given HLA peptide or protein based on, for example, mass spectroscopy data, but the sequence of the amino acids are scrambled. For every single peptide that was identified by mass spectrometry, 19 such scrambled peptide decoys were employed (hit: decoy is 1:19) as shown in FIG. 7A. The presentation prediction model was tested and PPV was determined by analyzing the best-scoring 5% of peptides in the test partition and interrogating what fraction of these were positive. The PPV thus generated is shown in FIG. 7A and Table 12 below.

TABLE 12

| MHC Class II allele | PPV for neonmhc2 |
| --- | --- |
| DPB1-0101_DPA1-0103 | 0.48 |
| DPB1-0101_DPA1-0201 | 0.41 |
| DPB1-0101_DPA1-0202 | 0.56 |
| DPB1-0201_DPA1-0103 | 0.48 |
| DPB1-0202_DPA1-0103 | 0.27 |
| DPB1-0301_DPA1-0103 | 0.36 |
| DPB1-0401_DPA1-0103 | 0.52 |
| DPB1-0402_DPA1-0103 | 0.54 |
| DPB1-0501_DPA1-0201 | 0.59 |
| DPB1-0501_DPA1-0202 | 0.46 |
| DPB1-0601_DPA1-0103 | 0.43 |
| DPB1-0901_DPA1-0201 | 0.53 |
| DPB1-1001_DPA1-0201 | 0.49 |
| DPB1-1101_DPA1-0201 | 0.31 |
| DPB1-1301_DPA1-0201 | 0.58 |
| DPB1-1401_DPA1-0201 | 0.49 |
| DPB1-1701_DPA1-0201 | 0.39 |
| DQB1-0201_DQA1-0201 | 0.49 |
| DQB1-0201_DQA1-0501 | 0.08 |
| DQB1-0202_DQA1-0201 | 0.3 |
| DQB1-0301_DQA1-0501 | 0.27 |
| DQB1-0301_DQA1-0505 | 0.13 |
| DQB1-0301_DQA1-0601 | 0.28 |
| DQB1-0302_DQA1-0301 | 0.1 |
| DQB1-0303_DQA1-0201 | 0.46 |
| DQB1-0303_DQA1-0301 | 0.39 |
| DQB1-0401_DQA1-0301 | 0.47 |
| DQB1-0402_DQA1-0401 | 0.53 |
| DQB1-0501_DQA1-0101 | 0.62 |
| DQB1-0502_DQA1-0101 | 0.26 |
| DQB1-0502_DQA1-0102 | 0.19 |
| DQB1-0601_DQA1-0102 | 0.17 |
| DQB1-0601_DQA1-0103 | 0.35 |

TABLE 12-continued

| MHC Class II allele | PPV for neonmhc2 |
|---|---|
| DQB1-0602_DQA1-0102 | 0.42 |
| DQB1-0603_DQA1-0103 | 0.56 |
| DQB1-0604_DQA1-0102 | 0.28 |
| DRB1_0101 | 0.48 |
| DRB1_0102 | 0.49 |
| DRB1_0301 | 0.47 |
| DRB1_0302 | 0.29 |
| DRB1_0401 | 0.38 |
| DRB1_0402 | 0.49 |
| DRB1_0403 | 0.43 |
| DRB1_0404 | 0.42 |
| DRB1_0405 | 0.41 |
| DRB1_0407 | 0.36 |
| DRB1_0410 | 0.61 |
| DRB1_0701 | 0.49 |
| DRB1_0801 | 0.36 |
| DRB1_0802 | 0.46 |
| DRB1_0803 | 0.30 |
| DRB1_0804 | 0.36 |
| DRB1_0901 | 0.35 |
| DRB1_1001 | 0.54 |
| DRB1_1101 | 0.43 |
| DRB1_1102 | 0.42 |
| DRB1_1104 | 0.51 |
| DRB1_1201 | 0.47 |
| DRB1_1202 | 0.55 |
| DRB1_1301 | 0.42 |
| DRB1_1302 | 0.23 |
| DRB1_1303 | 0.56 |
| DRB1_1401 | 0.56 |
| DRB1_1501 | 0.53 |
| DRB1_1502 | 0.43 |
| DRB1_1503 | 0.41 |
| DRB1_1601 | 0.61 |
| DRB3_0101 | 0.57 |
| DRB3_0201 | 0.6 |
| DRB3_0202 | 0.48 |
| DRB3_0301 | 0.53 |
| DRB4_0103 | 0.67 |
| DRB5_0101 | 0.54 |
| DRB5_0102 | 0.65 |
| DRB5_0202 | 0.63 |

Benchmarking Prediction Performance on MAPTAC™-Observed Peptides, Related to FIG. 31B For the purpose of assessing prediction performance for a given allele, it was necessary to define a set of peptides that could have been observed (because they are present in the proteome) but were not observed in the MS data. These negative examples were trained "natural decoys" (in contrast to the "scrambled decoys" described above). As guiding principles, it was decided: the length distribution of natural decoys should match the length distribution of MS-observed hits, natural decoys should not contain sequence redundant with other natural decoys, natural decoys should not overlap hits, and/or natural decoys should come from genes that produced at least one hit.

The following pseudocode represents the process implemented to create an evaluation satisfying these principles:
Initialize two empty lists of hits, $H_{minimal}$ and $H_{exhaustive}$
For each nested set S of MS-observed peptides:
If none of the peptides in S can be mapped to a transcript in the train or tune partition:
Add the shortest peptide in S to $H_{minimal}$
Add all peptides in S to $H_{exhaustive}$
Initialize an empty list of decoy peptides, D
For each protein-coding transcript (longest first, shortest last) in the test partition:
If no peptides in $H_{exhaustive}$ map to the transcript:
Skip to the next transcript
Cover the transcript's protein sequence with a set of overlapping peptides P, where the peptide lengths are randomly sampled from the length distribution of $H_{minimal}$. The overlap is 8 amino acids. (The last peptide in P will typically dangle over the end of the protein.)
While the last peptide in P still dangles:
Subtract 1 amino acid from the length of the longest peptide in P
For each peptide in P:
If it does not share a 9mer with a peptide in $H_{exhaustive}$ nor with any 9mer observed in any peptide in D:
Add the peptide to D
Otherwise:
Reject the peptide
$H_{minimal}$ and D constitute the evaluation data set
To evaluate performance on this set, all n hit peptides were evaluated by the predictor (neonmhc2 or NetMHCIIpan) and scored along with a set of 19n decoys (randomly sampled without replacement from the complete set of decoys). The top 5% of peptides in the combined set were labeled as positive calls, and the positive predictive value (PPV) was calculated as the fraction of positive calls that were hits. Note that since the number of positives is constrained to be equal to the number of hits, recall is exactly equal to PPV in this evaluation scenario. The application of a consistent 1:19 ratio across alleles helps stabilize the performance values, which are otherwise influenced by the number of hits observed for each allele. This was deemed appropriate since it was assumed the number of hits relates more to experimental conditions and replicate count than intrinsic properties of the allele.

Calculation of NetMHCIIpan Affinities for Non-15Mers, Related to FIG. 31A-D, FIGS. 40A-B, and 33A-D In early analyses, NetMHCIIpan-v3.1 affinity and percent rank predictions for non-15mers performed poorly on benchmarks. However, the following approach markedly improved performance: If a peptide was longer than 15 amino acids all constituent were scored 15mers and selected the strongest prediction as the overall peptide score; if a peptide was shorter than 15 amino acids, G's were padded on the N-terminus to force the peptide to length 15 and scored the resulting extended peptide.

Performance as a Function of Training Set Size, Related to FIGS. 38X and 38Y

To understand how our model's performance is limited by the size of our datasets, a saturation analysis was performed. This involved retraining ensembles of models while varying the fraction of the training data used in order to understand how this affects performance on a hold-out partition. FIGS. 38X and 38Y shows the evaluation partition (partition 8) PPV as a function of the number of hit peptides used in the training set. Each datapoint shows the mean PPV across a collection of 10 models, with the error bar indicating the standard deviation.

Benchmarking Prediction Performance of Natural CD4+ T Cell Responses, Related to FIG. 31C Since the vast majority of CD4+ T cell responses documented in IEDB (tcell_full_v3.zip at iedb.org/database_export_v3.php) have an unknown or computationally imputed HLA class II allele restriction, the subset of records that were confirmed experimentally by HLA class II tetramer were focused on. Nearly all such records were deposited by the William Kwok Laboratory (Benaroya Research Institute, Seattle, Wash.), which uses the blood of immune-reactive individuals to perform tetramer-guided epitope mapping (TGEM) of diverse pathogens and allergens. Since negative peptides were posted for some studies but not others, the source publications were reviewed to reconstruct the complete set of positive and negative peptide reactivities. In some cases, the source publication explicitly listed the negative peptides. In other cases, the negatives were imputed by following the tiling procedure specified in the publication's methods and confirming that the peptide boundaries were consistent with the known positive examples. In this assay depicted in FIG. 31C, viral epitopes were mapped from viral genes of influenza and rhinovirus, and peptide sequences comprising the epitopes were used to predict HLA class II protein binders to each epitope. In this case, a PPV for CD4+ memory T cell response to the peptides was predicted for respective HLA-DRB1 protein. The PPV was determined by asking, of the positive binders, what fraction of the top-ranking epitopes were true hits. Given that the positive pairing of an HLA class II protein molecule with a peptide, and where the HLA molecule is present in the subject infected by the respective virus, a CD4 response will be generated in the subject. A comparison of the predictive efficiency (PPV, in other words predicting the number of true hits) between Neonmhc2 and a publicly available predictor (NetMHCIIpan) is shown in FIG. 31C per each DRB1 protein tested in this exemplary study. Neonmhc2 outperformed NetMHCIIpan for each of the six alleles tested.

All 20mer peptides were scored by neonmhc2 and by NetMHCIIpan-v3.1. PPV was calculated as the fraction of experimentally confirmed positives among the n top-scored peptides, where there were n experimentally confirmed peptides total (FIG. 31C).

T Cell Induction Protocol and Immunogenicity Readouts, Related to FIG. 31D

To generate monocyte derived dendritic cells (mDCs), CD14+ monocytes were isolated from HLA-DRB1*11:01+ healthy donor peripheral blood monocytes (PBMCs) by magnetic separation using human CD14 microbeads as per manufacturer's protocol (Miltenyi Biotec). Isolated CD14+ cells were differentiated for 5 days in Cellgenix GMP DC media supplemented with 800 U/ml rh GM-CSF and 400 U/ml rh IL-4 (Cellgenix). On day 5, mDCs were harvested and pulsed with 0.4 µM peptide for 1 hour at 37 degrees Celsius followed by maturation using 10 ng/ml TNF-α, 10 ng/ml IL-1β, 10 ng/ml IL-6 (Cellgenix), and 0.5 ug/ml PGE1 (Cayman Pharma). After forty-eight hours, mDCs were co-cultured with autologous PBMCs, at a 1:10 ratio with media containing AIMV/RPMI (ThermoFisher), 10% human serum (Sigma-Aldrich), 1% Pen/Strep (ThermoFisher) and supplemented with 5 ng/ml of IL7 and IL15 (Cellgenix). On day 12, T cells were harvested and restimulated on 0.4 µM peptide pulsed matured DCs for 7 days for two additional stimulations, for a total of 3 stimulations.

Induced T cells were labelled with a unique two-color barcode labelling system as described previously and cultured overnight at a 1:10 ratio with peptide pulsed and matured autologous mDCs derived from CD14+ monocytes as described above. The next morning, cells were assessed for production of IFN-γ in response to peptide by flow cytometry. Cells were treated with Golgi Plug/Golgi Stop (BD Biosciences) for four hours at 37° C. Cells were then stained with surface marker antibodies against CD19, CD16, CD14, CD3, CD4, CD8 (BD Biosciences, San Jose, Calif.), as well as Live/Dead Fixable Dead Cell stain (ThermoFisher); see Table 13 below. Samples were then permeabilized and fixed with BD Cytofix/Cytoperm kit (BD Biosciences) per manufacturer's protocol and stained with intracellular antibodies against IFN-γ (BD Biosciences). Samples were run on a BD Fortessa X-20 flow cytometer and analyzed using FlowJo software (Treestar). Induction samples that positively responded to peptide were samples that induced IFN-gamma production at 3% higher than the no peptide control.

TABLE 13

| Marker | Fluorophore | Vendor | Cat# | Clone |
|---|---|---|---|---|
| Live dead stain | IR dye | ThermoFisher | L34976 | |
| CD19 | BUV395 | BD | 563551 | SJ25C1 |
| CD16 | BUV395 | BD | 563784 | 3G8 |
| CD14 | BUV395 | BD | 563562 | MφP9 |
| CD3 | BUV805 | BD | 565511 | SK7 |
| CD4 | AF700 | BD | 557922 | RPA-T4 |
| CD8 | PerCP-Cy5.5 | BD | 565310 | SK1 |
| IFN-γ | APC | BD | 554702 | B27 |

Analysis of HLA Class II Expression Data in Single-Cell RNA-Seq, Related to FIG. 19A Single-cell RNA-Seq data were obtained from three previously published data sets that profiled human tumor samples. The first study included data from cutaneous melanomas. The file "GSE72056_melanoma_single_cell_revised_v2.txt" was downloaded from Gene Expression Omnibus (ncbi.nlm.nih.gov/geo/; accession: GSE72056). Cells with tumor status flag "2" were treated as tumor cells, and cells labeled with tumor status flag "1" and immune cell type flag equal to "1" through "6" were treated as T cells, B cells, Macrophages, Endothelium, Fibroblasts, and NKs, respectively. All other cells were dropped. Data were natively presented in units of log 2 (TPM/10+1) and were thus mathematically converted to a TPM scale. Once on the TPM scale, the data for each cell was renormalized to sum to 1,000,000 over the set of protein-coding UCSC gene symbols (protein-coding genes not appearing in the expression matrix were implicitly treated as having zero expression). Finally, single-cell observations corresponding to the same cell type and same source biopsy where averaged to produce expression estimates at the patient-cell type level.

The second study included data from head and neck tumors. The file "GSE103322_HNSCC_all_data.txt" was downloaded from the Gene Expression Omnibus (ncbi.nlm.nih.gov/geo/; accession: GSE103322). Per personal correspondence with Itay Tirosh (Aug. 22, 2018), the data in this table were also in units of log 2 (TPM/10+1); therefore, the values were mathematically converted to TPM units. As with the melanoma study, the data for each cell was renormalized to sum to 1,000,000 over the set of protein-coding UCSC gene symbols, and single-cell observations corresponding to the same cell type and same source biopsy where averaged. Data corresponding the lymph node biopsies were excluded.

The third study included data from untreated non-small cell lung. The files "RawDataLung.table.rds" and "metadata.xlsx" were downloaded from ArrayExpress (ebi.ac.uk/arrayexpress/; accessions: E-MTAB-6149 and E-MTAB-6653). The data (already in TPM) units, were re-scaled to sum to 1,000,000 over the set of protein-coding genes as previously described. Finally, single-cell observations corresponding to the same cell type and same source biopsy where averaged to produce expression estimates at the patient-cell type level. For simplicity, cell types were merged to a coarser granularity than natively reported in Table 14 below.

TABLE 14

| Coarse designation | Constituent cell types |
| --- | --- |
| Alveolar | "Alveolar", excluding "cuboidal alveolar type 2 (AT2) cells" |
| FO B cells | "follicular B cells" |
| Plasma cells | "plasma B cells" |
| CLEC9A+ DCs | "cross-presenting dendritic cells" |
| monoDCs | "monocyte-derived dendritic cells" |
| pDCs | "plasmacytoid dendritic cells" |
| Langerhans | "Langerhans cells" |
| Macrophages | "macrophages" |
| Granulocytes | "granulocytes" |
| Endothelium | "normal endothelial cell", "tumor endothelial cell", and "lower quality endothelial cell", excluding "lymphatic EC" |
| Epithelium | "epithelial cell" and "lower quality epithelial cell" |
| Fibroblasts | "COL12A1-expressing fibroblasts", "COL4A2-expressing fibroblasts", "GABARAP-expressing fibroblasts", "lower quality fibroblasts", "normal lung fibroblasts", "PLA2G2A-expressing fibroblasts", and "TFPI2-expressing fibroblasts" |
| T cells | "regulatory T cells", "CD4+ T cells" and "CD8+ T cells" |
| NKs | "natural killer cells" |
| Tumor | "cancer cells" |
| Excluded from analysis | "erythroblasts" and "MALT B cells" |

A fourth study included data from colorectal tumors. The file "GSE81861_CRC_tumor_all_cells_FPKM.csv" was downloaded from the Gene Expression Omnibus (ncbi.nlm.nih.gov/geo/; accession: GSE81861). The data (already in TPM) units, were re-scaled to sum to 1,000,000 over the set of protein-coding genes as previously described. Finally, single-cell observations corresponding to the same cell type and same source biopsy where averaged to produce expression estimates at the patient-cell type level. For this study, cells labeled as "epithelium" are presumed to represent a mixture of tumor cells and normal epithelium.

A fifth study included data from serous ovarian cancer tumors. Single-cell RNA sequencing data of 6 ovarian epithelial cancer of two low-grade serous ovarian cancer patients (LG1,LG2) and 4 high-grade serous ovarian cancer patients (HG1,HG2F,HG3,HG4) were obtained from elsewhere. Quality filtering, clustering and analysis followed the steps outlined by Shih et al., 2018. Briefly, the Seurat analysis tool was used to cluster cells passing quality filtering (minimum of 200 expressed genes, where each gene must be detected in at least 3 different cells; in total, 2258 cells). The effects of cell-cycle and the unique transcript count were regressed out. Cells were clustered following principal component analysis, and clusters were assigned to cell types based on their expression of the gene signatures from the original publication. The TPM for the HLA-DRB1 gene was calculated from the normalized unique transcript count of protein coding genes for each cell type for each patient.

Expression levels of HLA-DRB1 in the four studies are plotted in FIG. 19A.

Characterization of Tumor-Derived Vs. Stroma-Derived HLA Class II Expression, Related to FIG. 19B

To determine the relative amount of HLA class II expression attributable to tumor vs. stroma, mutations called from DNA sequencing in HLA class II pathways genes in TCGA patients were identified, and for each patient bearing an HLA class II mutation, the relative expression of the mutated and non-mutated copies of the gene were quantified in the corresponding RNA-Seq. Further, it was assumed mutated reads arise from the tumor, non-mutated reads arise for the stroma or the wildtype allele in the tumor, and the tumor retains a wildtype copy with expression approximately equal to the mutated copy.

Based on this, it was determined that for an observed mutant allele fraction off the fraction of HLA class II expression attributable to tumor was approximately 2f and not greater than 100%. Three genes—CIITA, CD74, and CTSS—were selected as core HLA class II pathway genes and assessed for mutations (not excluding synonymous and UTR mutations) in TCGA (data downloaded from Tumor-Portal (tumorportal.org/): BRCA, CRC, HNSC, DLBCL, MM, LUAD; TCGA bulk download (tcga-data.nci.nih.gov): CESC, LIHC, PAAD, PRAD, KIRP, TGCT, UCS; Synapse (synapse.org/#! Synapse:syn1729383): GBM, KIRC, LAML, UCEC, LUSC, OV, SKCM; or the original TCGA publication (cancergenome.nih.gov/publications): BLCA, KICH, STAD, and THCA). These genes were selected based on their known roles in HLA class II expression and their tight correlation with HLA-DRB1 across a cohort of 8500 GTEx samples. Other genes with equivalent correlation with HLA-DRB1 (HLA-DRA1, HLA-DPA1, HLA-DQA1, HLA-DQB1, and HLA-DPB1) were excluded because their polymorphic nature makes them prone to false positive mutation calls. Naturally, only a small fraction of patients had a mutation in CIITA, CD74, or CTSS, and for some tumor types, there were no patients available to analyze.

Original whole exome sequencing (WES) BAMS were visually assessed (IGV) to confirm that the mutation was present in the tumor sample and not present in the normal sample. Mutant vs. wildtype read counts were obtained from corresponding RNA-Seq using pysam. Overall HLA-DRB1 expression was determined based on expression data downloaded from the Genomic Data Commons (gdc.cancer.gov/), which was renormalized to sum to 1,000,000 over the set of protein-coding genes. The fraction of HLA-DRB1 expression attributable to the tumor (FIG. 19B) was estimated as min(1,2f), where f is the fraction of RNA-Seq reads in CIITA, CD74, or CTSS exhibiting a mutation.

Identification of Over- and Under-Represented Genes, Related to FIG. 32A and FIG. 39B

Samples were analyzed from previously published MS experiments that profiled the MHC-II ligandomes of ovarian cancer, colorectal cancer, and melanoma. Many samples from the ovarian cancer dataset had available RNA-Seq; data for these samples was downloaded from SRA (NCBI BioProject PRJNA398141) and aligned to the UCSC hg19 transcriptome using STAR aligner. For ovarian samples that did not have available RNA-Seq, expression was estimated averaging across the samples with available RNA-Seq. For the colorectal and melanoma studies, there was no corresponding RNA-Seq for any samples, so averages were calculated across surrogate samples using data from TCGA (The Cancer Genome Atlas Network). Transcript level gene quantification was performed using transcripts per million (TPM) as calculated by RSEM version-1.2.31. The expression estimates were further processed by summing to the gene level, dropping non-coding genes, and renormalizing such that the total TPM summed to 1000000 (renormalizing across protein-coding genes accounts for library-to-library variation in ncRNA abundance).

To identify genes over- and under-represented in HLA class II ligandomes, it was analyzed the same three datasets used in the expression analysis. For each gene, our baseline assumption was that it should yield peptides in proportion to its length multiplied by its expression level. To determine the length of each gene, the unique 9mers across all transcript isoforms were enumerated. Gene-level expression was obtained by summing across transcript isoforms. The observed number of peptides mapping to each gene was determined at the nested set level (e.g. peptides GKAPILIATDVASRGLDV (SEQ ID NO: 16), GKAPILIATDVASRGLD (SEQ ID NO: 17), and KAPILIATDVASRGLDV (SEQ ID NO: 18) counted as a single observation).

Two matrices were created representing expected and observed counts, referred to as E and O, respectively, wherein rows correspond to genes and columns correspond to samples. The values in 0 were determined by counting peptides per sample at the nested set level. The matrix E was first populated by multiplying each gene's length by its expression in each sample; then the columns of E were rescaled to make the column sums of E match the column sums of 0. Finally, analysis was made at the gene level by comparing the row sums of E to the row sums of 0 (FIG. 32A). Genes were highlighted according to their presence and concentration in human plasma. An identical approach was used for identifying over- and under-represented gene in HLA class I data, using melanoma, colorectal cancer, and ovarian cancer data from the same set of studies. For the HLA class I analysis, no nesting was applied, but only unique peptides were counted.

Assessment of Binding Scores in Over-Represented Genes, Related to FIG. 39A

It was observed that many of the over-represented genes were plasma genes. A comprehensive list of serum genes was obtained and the neonmhc2 binding scores were compared for HLA DR-bound peptides derived from plasma genes with HLA-DR-bound peptides derived from non-serum genes, as well as with length-matched, non-binding (e.g. not observed in MS) peptides sampled from genes that were represented in the immunopeptidome. For genotyped, multi-allelic datasets that had HLA class II peptides profiled with a pan-DR antibody (the same samples analyzed in FIG. 30B), peptides with neonmhc2 for each DR allele that the sample expressed were scored. The best score output by neonmhc2 over all expressed alleles was taken as the representative score for each peptide. The data was pooled across all usable datasets, and the distributions of the scores for each category of peptide were visualized with a boxplot.

Analysis of Genes Related to Protein Turnover, Related to FIG. 32C

Two gene sets were identified meant to represent proteins whose turnover is regulated by the proteasome. The first gene set comprised genes with at least one observed ubiquitination site in the cell lines KG1, Jurkat, or MM1S. The second set comprised genes whose levels increased upon application of the proteasome inhibitor Bortezomib (BTZ) of a published paper, applying a p-value filter of 0.01 and selecting the 300 genes with the largest upward fold change.

Comparing Explanatory Power of Bulk Tumor Vs. Antigen Presenting Cell Gene Expression, Related to FIG. 39C Four gene expression profiles were created. The first was meant to represent APCs and estimated by averaging cell type-specific profiles from the above-described single-cell RNA-Seq experiments. The average included "macrophages" (from the head and neck study, the lung study, and the melanoma study), "CLEC9A DCs" (from the lung study), and "monoDCs" (from the lung study). The three other expression profiles correspond to bulk tumor profiles from ovarian cancer, colorectal cancer, and melanoma (Data FIG. 19A). The ovarian profile was an average of the samples published by Schuster et al, and the other profiles are derived from the five TCGA samples with the highest tumor cellularity, per tumor type, as previously inferred using the "Absolute" algorithm. For each tumor type, the number of peptides (at the nested-set level) per gene were counted and modeled each gene's peptide count as a function of gene length, APC-specific gene expression, and tumor-specific gene expression using linear regression. The output variable and all input variables were transformed via $\log(x+1)$. Using the model's parameter estimates, the contribution of tumor was calculated as $\beta_{tumor}/(\beta_{tumor}+\beta_{APC})$, and the contribution of APCs was calculated as $\beta_{APC}/(\beta_{tumor}+\beta_{APC})$. For each sample, bootstrap re-sampling (M=100) at the gene level was used to calculate confidence intervals for the explanatory proportions.

Characterizing Observed Cleavage Sites of HLA Class II Peptides, Related to FIG. 40A Naturally processed and presented HLA class II peptides were analyzed from six datasets: PBMC draws, the DC-like MUTZ3 cell line, colorectal cancer tissue, melanoma, ovarian cancer, and the expi293 cell line. Since many peptides share the same N-terminus (e.g. GKAPILIATDVASRGLDV (SEQ ID NO: 16) and GKAPILIATDVASRGLD (SEQ ID NO: 17)) or the same C-terminus (e.g. GKAPILIATDVASRGLD (SEQ ID NO: 17) and KAPILIATDVASRGLD (SEQ ID NO: 19)), two sets of non-redundant cut sites were curated, one for N-termini and one for C-termini. The naming system shown in FIG. 41 was used to refer to positions upstream of peptides, within peptides, and downstream of peptides. Upstream and downstream frequencies ( . . . U1 and D1 . . . ), were compared against proteome amino acid frequencies and scored significant deviations via Chi-square test. Peptide positions (N1 . . . C1), were compared against frequencies as observed in MS peptides.

Benchmarking the Performance of Various HLA Class II Cleavage Predictors, Related to FIG. 40B Four PBMC samples and published datasets were used to benchmark the ability of cleavage-related variables/predictors to enhance the identification of presented HLA class II epitopes.

To build integrated predictors that predict peptide presentation using both binding potential and cleavage potential, constructed datasets were first using the same approach described for FIG. 31B. This meant using a 1:19 ratio of hits to decoys, where decoys are length-matched to hits and are randomly sampled from the set of genes that generated at least one hit. Different datasets were built in this manner for three different purposes:

1. For the solvent accessibility- and disorder-based cleavage predictors, logistic models were fit using HLA class II ligandome data from human tumor tissues. It was presumed that for a peptide to have been observed in a ligandome experiment, it must have been successfully processed. (For the neural network and CNN-based cleavage predictors, training data was generated using the same datasets in a distinct fashion, as explained in the table below.)

2. To evaluate if a given cleavage predictor boosted performance over binding alone, models were fit using mono-allelic MAPTAC™ data generated with B721 and KG1 cells, the most functionally APC-like cell lines were interrogated. Binding potential was calculated using neonmhc2, and a logistic regression determined the relative weights that would be placed on the binding and cleavage variables in forward prediction.

3. To evaluate the performance of forward prediction, datasets were constructed for the PBMC samples and published datasets in the same manner as before. However, because these samples were multi-allelic, the binding score for each peptide candidate peptide was taken to be the maximum scoring of the 1-4 DR alleles indicated by each donor's genotype. PPV was calculated as described for FIG. 31B.

Several different cleavage predictors were assessed
Cleave First Model, Cut Site Known (Neural Network)

To learn a cleavage signal from the MS-observed cut sites, all unique 6mer amino acid sequences from U3 to N3, and C3 to D3 (using the nomenclature introduced in the section, "Characterizing observed cleavage sites of HLA class II peptides, related to FIG. 40A") in the tumor tissue-derived HLA class II ligandomes from were used as positive examples for training two distinct neural networks, modeling N-terminal cuts and C-terminal cuts, respectively. As before, an equivalent number of unique non-observed N-terminal and C-terminal cut sites (negative examples) were synthetically generated by drawing from the amino acid frequency of the proteome for the context, and from the MS-observed ligandome for the peptide. The amino acid sequences were encoded with a subset of the same features used in neonmhc2, specifically, the amino acid proximities based on protein structures, and amino acid properties (e.g. acidic, aliphatic, etc.). For each of the N-terminal and C-terminal observed cut site models, (4=0.0005, Adam optimizer, binary cross-entropy as loss function) a fully connected neural network was then trained with two hidden layers (20 neurons in one layer, followed by 10 neurons in the next) with ReLu activations, followed by a final sigmoid layer. For regularization, a dropout rate of 20% was used L2 norm of 0.001 (for C-terminal model only), and max norm constraint of 4.

To score a candidate peptide, the N-terminal model was applied to the 6mer sequence U3 to N3 with respect to the peptide, and the C-terminal model was applied to C3 to D3. Both N-terminal and C-terminal models were also applied to 6mer sequences tiling across the candidate peptide to evaluate the cleavage propensity of the sequence within the peptide itself. A logistic regression was trained on the MAPTAC' data using the neonmhc2 binding score as well as four neural network outputs, corresponding to the N-terminus, C-terminus, and maximum scoring cut sites for the N-terminal and C-terminal models within the peptide.

Cleave First Model, Cut Site Unknown (+/−15AAs) (Neural Network)

To determine if the cleavage models learned from observed cut sites would be predictive when the precise termini of peptides was not known, the same neural networks learned above was applied to extended context, 15 amino acids beyond the peptide termini. To score a candidate peptide in this case, the maximum score was calculated across three regions: the 15 amino acids upstream of the peptide (regardless of the location of the true N-terminal cleavage site), which was scored with the N-terminal model, the peptide sequence, which was scored with both the N-terminal and C-terminal models, and the 15 amino acids downstream of the peptide, which was scored with the C-terminal model. A logistic regression was trained on the MAPTAC' data using the neonmhc2 binding score as well as the four region-specific (since the peptide itself contributes two sets of values, from the N-terminal and C-terminal models) scores.

Bind First Model, Solvent Accessibility

Within the SCRATCH suite, the tool ACCpro20 was used to predict relative solvent accessibility. The likelihood of a peptide being processed given the peptide's mean solvent accessibility score was then fit with a logistic regression using the tumor tissue data. Finally, a logistic regression was trained on the mono-allelic data using the neonmhc2 binding score and the output from the tumor tissue-trained predictor.

Bind First Model, Disorder

Per-residue scores of sequence disorder were determined over the entirety of the proteome, scoring on a 0-5 scale according to the number of prediction engines labeling the position as disordered (servers used: anchor, espritz-d, espritz-n, espritz-x, iupred-1, and iupred-s). The average disorder score was calculated over each candidate peptide, with the six disorder predictor outputs summed. As with solvent accessibility, first a logistic model was fit using this overall disorder score with the tumor tissue data. This was followed by training a logistic regression on the mono-allelic data using the neonmhc2 binding score and the output from the tumor tissue-trained predictor.

Hybrid Model, Precursor Cut Scan (+/−30AAs) (CNN)

Training data for hits was generated as described for the 'Cleave first, cut site known' cleavage predictor, with the exception that instead of using the unique 6mer sequences from U3 to N3, and C3 to D3, the 30 amino acids flanking the peptides (U30 to U1, and D1 to D30) were taken from as model input. Furthermore, whether a 30mer sequence came from the N-terminal or C-terminal flank was not distinguished, and instead the data was pooled to train a single model to learn a precursor cut signal that was assumed may occur on either side of an observed peptide. In this setting, instead of using synthetic decoys, flanking sequences from unobserved peptides drawn from the same source genes was used as negative examples. Sequences were encoded as before, using the amino acid proximities based on protein structures, and amino acid properties (e.g. acidic, aliphatic, etc.). The architecture of the CNN consisted of two convolutional layers, the first layer with a kernel size of 2 with 48 filters, followed by a layer with a kernel size of 3 and 40 filters. These layers had ReLu activations. The convolutional layers were followed with a global max pooling layer, after which was a final dense layer with a sigmoid activation. The CNN was trained with a learning rate of 0.001, with Adam optimization and binary cross-entropy as the loss function.

To score a candidate peptide, the CNN was applied to the 30 amino acids upstream and 30 amino acids downstream of the peptide, producing an N-terminal flank score and a C-terminal flank score. A logistic regression was trained on the MAPTAC' data using the neonmhc2 binding score and the two CNN scores.

DQ Overlap

MS-based peptide identifications were pooled across HLA-DQ ligandomes from Bergseng et al., 2015. A new feature was created representing whether a new candidate peptide overlapped with one of these previously observed peptides. Specifically, the feature was set to 1 if it shared at least one 9mer with any peptide in the set of previously observed HLA-DQ ligands; otherwise the feature was set to 0. A logistic regression was trained on the mono-allelic data using the neonmhc2 binding score and the overlap feature.

The integrated binding and cleavage models were also all fit and evaluated using NetMHCIIpan as the binding predictor instead in FIG. 40B.

Assessing Prediction Overall Performance on Natural Donor Tissues, Related to FIG. 21A-21B Peripheral blood from seven healthy donors was profiled with a DR-specific antibody as described in the section "Antibody-based HLA-peptide complex isolation" above. Training and evaluation datasets were constructed using the hit and decoy selection algorithm previously described in relation to FIG. 31B. In short, this means representing each nested set with one hit peptide (the shortest peptide in the nested set) and tiling length-matched decoys over genes such that they overlap minimally with hits and minimally with each other. In this setting, the decoy selection was not constrained to MS-observed genes, and decoys were instead randomly sampled without replacement from the entire proteome. A 1:499 hit to decoy rate was utilized, reflecting a rough estimate of the frequency of HLA-DR-presented peptides in the proteome. Logistic regression models with MHC binding scores (from NetMHCIIpan or neonmhc2) as well as other input features (expression, gene bias, and DQ overlap) were trained on MAPTAC™ data from KG1 and B721 cell lines.

The following variables in Table 15 were used in a subset of the regressions.

TABLE 15

| | |
|---|---|
| NetMHCIIpan percent rank | Derived from NetMHCIIpan-v3.1. For each candidate peptide, the strongest score was taken across all DR alleles in the donor's genotype. |
| neonmhc2 percent rank | Derived from neonmhc2. For each candidate peptide, the strongest score was taken across all DR alleles in the donor's genotype. |
| Expression | Gene expression estimates were obtained by analyzing data from (bowtie2, RSEM, and renormalization over protein-coding genes only), values averaged over N samples. Expression was either thresholded (0/1, indicating if expression was non-zero) or treated as a continuous variable. |
| Gene bias | (1 + observed)/(1 + expected) per the analysis in FIG. 32A |
| DQ overlap | Indicator variable (0/1) for whether the candidate peptide shares at least one 9mer with any of the HLA-DQ datasets. HLA-DQ-binding peptides have distinct binding motifs from HLA-DR-binding peptides, so binding propensity should not be learned with this feature. |

The performance of these models on HLA-DR ligandomes from natural donor tissue (PBMC samples, etc.) were then evaluated. Decoys are sampled from the proteome at random (including genes that never produced an MS-observed peptide) to achieve a 1:499 ratio of hits to decoys, which nearly saturates available decoy sequences. A 1:499 hit to decoys rate was used for evaluation (as well as training) The top 0.2% scored peptides in the evaluated dataset were labeled s positive calls, and the PPV was calculated as the fraction of positive calls that were hits (see, e.g., FIG. 21A and Table 15). Note that since the number of positives is constrained to be equal to the number of hits, recall is exactly equal to PPV in this evaluation scenario. The application of a consistent 1:499 ratio across alleles helps stabilize the performance values, which are otherwise highly influenced by the number of hits observed for each donor. This was deemed appropriate since the number of hits was assumed to relate more to experimental conditions than intrinsic properties of the donor's cells.

TABLE 16

| MS Sample | PPV for NetMHCIIpan | PPV for neonmhc2 |
|---|---|---|
| Lung | 0.05 | >0.3 |
| Spleen | 0.025 | ~0.3 |
| Heyder LCLs | 0.01 | ~0.2 |
| A375 | 0.01 | ~0.3 |
| mDCs | 0.05 | >0.44 |
| PBMC sample #1 | 0.01 | ~0.3 |
| PBMC sample #2 | 0.01 | >0.3 |
| PBMC sample #3 | 0.025 | >0.3 |
| PBMC sample #4 | 0.0025 | ~0.275 |

TABLE 16-continued

| MS Sample | PPV for NetMHCIIpan | PPV for neonmhc2 |
|---|---|---|
| Ritz DOHH2 | 0.01 | 0.3 |
| Ritz Maver1 | 0.015 | ~0.175 |

SILAC-Based Identification of DC-Presented Tumor Peptides, Related to FIG. 33A

To generate monocyte derived dendritic cells (mDCs), CD14+ monocytes were isolated from healthy donor peripheral blood monocytes (PBMCs) by magnetic separation using human CD14 microbeads as per manufacturer's protocol (Miltenyi Biotec). Isolated cells were differentiated for 6 days in CellGenix GMP DC media supplemented with 800 U/ml rh GM-CSF and 400 U/ml rh IL-4 (CellGenix, Germany). K562 cells (ATCC, Manassas, Va.) were isotopically labeled using Stable Isotope Labeling with Amino acids in Cell culture (SILAC). Cells were grown for 5 doublings in the presence of RPMI 1640 media for SILAC (ThermoFisher) containing the heavy isotopically amino acids, L-Lysine 2HCl 13C6 15N2 (Life Technologies, Carlsbad, Calif.) and L-leucine 13C6 (Life Technologies, Carlsbad, Calif.) with 15% heat inactivated, dialyzed fetal bovine serum (ThermoFisher). SILAC labeled K562 cells were lysed using 60 μM hypochlorous acid (HOC1) as described previously or treated with UV for 3 hours at room temperature to induce apoptosis and rested overnight. Seventy-five million mDCs were co-cultured with UV treated SILAC labelled K562 cells at a 1:3 ratio for 14 hours at 37° C. or cultured with a 1:3 ratio of K562 lysed with HOC1 for 10 minutes or 5 hours at 37° C. After co-culture, cells were harvested, pelleted and flash frozen in liquid nitrogen for proteomic analysis.

Prediction and Expression Analysis of DC-Presented Tumor Peptides, Related to FIG. 33B and FIG. 21C To calculate PPV for the prediction of heavy-labeled (tumor-derived) peptides, the same model was used and evaluation approach as used in FIG. 33B. Expression for the K562 cell lines was determined based on data from ENCODE (encodeproject.org/experiments/ENCSR545DKY/; libraries ENCLB075GEK and ENCLB365AUY; (ENCODE Project Consortium, 2012)). Expression for dendritic cells was determined based on GSE116412 (averaging of accessions GSM3231102, GSM3231111, GSM3231121, GSM3231133, GSM3231145.

Example 14. Benchmarking FAIMS with Tryptic Peptides

In this example, a standard HLA-peptidomic workflow for using high field asymmetric waveform ion mobility spectrometry (FAIMS) is described. Endogenously processed and presented HLA class I and HLA class II peptides from A375 cells were characterized. The peptides were subjected to both acidic reverse-phase (aRP) and basic reverse-phase (bRP) offline fractionation prior to analysis by nLC-MS/MS using a Thermo Scientific Orbitrap Fusion Lumos Tribrid mass spectrometer equipped without (−) and with (+) the FAIMS Pro interface. The workflow is indicated in a diagram depicted in FIG. 42A. FIG. 42B shows results indicating the FAIMS improves peptide detection in tryptic samples as low as 10 ng. FAIMS increases HLA-1 and HLA class II peptide detections throughout the LC gradient despite the lower MS1 intensity (FIG. 43A and FIG. 44A, data for HLA-1 and HLA class II peptides, respectively). Strikingly, an increase in unique peptide detection is observed in the acidic and basic reverse phase samples, with FAIMS evaluation (FIG. 43B, and FIG. 44B, data for HLA-1 and HLA class II peptides, respectively). This study indicated that Detections of HLA class I and HLA class II peptides increase throughout the LC gradient with FAIMS despite lower MS1 intensity. Combining offline fractionation and FAIMS increases the analysis depth of HLA peptide repertoires, as shown in FIGS. 45A and 45B and FIGS. 46A and 46B, (HLA-1 and HLA class II peptides, respectively).

Example 15—Differential Scanning Fluorometry (DSF) Peptide Exchange Assay

A peptide exchange assay was performed as follows: The following reagents (Table 17) were combined and mixed at 37° C. for 18 hours.

TABLE 17

| Ingredients | Stock Concentrations | Final Concentration |
|---|---|---|
| Thrombin digested DRB1*15:01 (CLIP0), "DR15" | 85.6 mM | 5 mM |
| Exchange Peptide/peptide of interest[4] | 10 mM | 100 mM |
| Sodium Acetate | 1M | 100 mM |
| Sodium Chloride | 5M | 50 mM |
| Octyl glucoside | 10% | 1% |
| MiliQ water | — | Up to 100 ml |

[4]DMSO or peptides with the following sequences were used: PPIDGYPNHPCFEPE (SEQ ID NO: 31) (M230), PQILPYPAPEEAQEN (SEQ ID NO: 32) (M231), PQLRQWWAQGADPLA (SEQ ID NO: 33) (M247), LLRPGQIVAFDSTAQ (SEQ ID NO: 34) (M248) or ASLRSWPSTWAPWAS (SEQ ID NO: 35) (M371).

The buffer was then exchanged using a PD minitrap G-25 desalting column. Sypro orange dye (Fisher S6651) was diluted to 1000× in 100% DMSO. 50 µL working stock of Sypro orange dye at 100× was prepared in desalting buffer. 2 µL of 100× sypro orange dye and 18 µL of desalted peptide exchanged sample was transferred to wells of a 384 white PCR microplate and mixed. The plate was then covered with a transparent plate sealer and the plate was subjected to the following program in a Roche lightcycler 480: (1) heat to 25° C., hold for 10 seconds; (2) increase the temperature to 99° C., read plate 20 times/1° C. (3) bring the temperature down to 25° C. and hold for 10 seconds. Melting temperatures were then calculated. Exemplary results are shown in Table 18 below.

TABLE 18

| Sample | $DT_m$ (sample $T_m$ − control $T_m$) | Average $T_m$ | Slope | Initial | Low | Peak |
|---|---|---|---|---|---|---|
| DR15 + M230 | 21.4 | 79.7 | 0.5 | 2.8 | 2.0 | 4.8 |
| DR15 + M231 | 15.6 | 73.9 | 0.3 | 2.7 | 1.9 | 5.8 |
| DR15 + M247 | 20.1 | 78.4 | 0.4 | 3.0 | 2.3 | 5.0 |
| DR15 + M248 | 5.6 | 63.9 | 0.4 | 1.8 | 1.4 | 5.1 |
| DR15 + M371 | 19.9 | 78.2 | 0.4 | 2.5 | 1.9 | 4.9 |
| DR15 + DMSO (Control) | NA | 58.3 | 0.8 | 2.1 | 1.7 | 9.2 |

The invention claimed is:

1. A method of treating cancer in a human subject in need thereof, comprising:
   (a) inputting amino acid information of a set of candidate peptide sequences using a computer processor, into a trained machine learning class II HLA-peptide presentation prediction model to generate a plurality of presentation predictions, wherein each candidate peptide sequence of the set of candidate peptide sequences is encoded by a genome, transcriptome, or exome of a subject, or a pathogen or a virus in the subject; wherein the plurality of presentation predictions comprises an HLA presentation prediction for each candidate peptide sequence of the set of candidate peptide sequences, wherein each presentation prediction of the plurality of presentation predictions is indicative of a presentation likelihood that a peptide sequence of the set of candidate peptide sequences is presented by one or more proteins encoded by a class II HLA allele of a cell of the subject, and wherein the trained machine learning class II HLA-peptide presentation prediction model comprises
      (i) a plurality of parameters identified at least based on training data comprising:
         (1) sequences of training peptides,
         (2) an identity of a protein encoded by an HLA class II; allele associated with the training peptide sequences, and
         (3) an observation by mass spectrometry that one or more of the training peptides was presented by the protein encoded by the HLA class II allele in training cells; and
      (ii) a function representing a relation between the amino acid sequence information received as input and the presentation likelihood generated as an output based on the amino acid sequence information and the plurality of parameters;
   (b) selecting, based at least on the plurality of presentation predictions, a subset of peptide sequences of the set of candidate peptide sequences to generate a set of selected peptide sequences, wherein the selected subset of peptide sequences (i) are encoded by a genome, transcriptome, or exome of a subject, or a pathogen or a virus in the subject, and (ii) are predicted to be presented by the protein encoded by the HLA class II allele of a cell of the subject; and
   (c) administering to the human subject a pharmaceutical composition comprising:
      (i) a polypeptide with one or more of the selected subset of peptide sequences, (ii) a polynucleotide encoding the polypeptide of (i), (iii) APCs comprising (i) or (ii), or (iv) T cells comprising a T cell receptor (TCR) specific for proteins encoded by a class II HLA allele of the human subject in complex with peptide sequence selected in (b);
   wherein the trained machine learning HLA-peptide presentation prediction model has a positive predictive value (PPV) of at least 0.2 at a recall rate of 10% according to a presentation PPV determination method.

2. The method of claim 1, wherein each sequence of the sequences of training peptides observed by mass spectrometry to be presented by the protein encoded by the HLA class II in training cells has a length of at least 15 amino acids.

3. The method of claim 1, wherein trained machine learning class II HLA-peptide presentation prediction model has a positive predictive value (PPV) of at least 0.3 according to a presentation PPV determination method.

4. The method of claim 3, wherein:
(i) the training cells comprise training cells expressing a single MHC class II complex or a protein encoded by a single allelic variant of a class II HLA locus selected from the group consisting of DR, DP, and DQ, wherein the single MHC class II complex or a protein encoded by the single allelic variant of a class II HLA locus is expressed by a cell of the subject; or
(ii) the training data comprises training data obtained by deconvolution.

5. The method of claim 3, wherein the training cells express a protein encoded by a class II HLA allele of a cell of the subject, wherein the protein encoded by a class II HLA allele comprises an affinity tag.

6. The method of claim 3, wherein the machine learning HLA-peptide presentation prediction model has a positive predictive value (PPV) of at least 0.2 when amino acid information of a plurality of test peptide sequences are processed to generate a plurality of test presentation predictions, each test presentation prediction indicative of a likelihood that the one or more proteins encoded by a class II HLA allele of a cell of the subject can present a given test peptide sequence of the plurality of test peptide sequences,
wherein the plurality of test peptide sequences comprises at least 500 test peptide sequences comprising:
(i) at least one hit peptide sequence identified by mass spectrometry to be presented by an HLA protein expressed in cells, and
(ii) at least 499 decoy peptide sequences contained within a protein encoded by a genome of an organism, wherein the organism and the subject are the same species,
wherein the plurality of test peptide sequences comprises a ratio of 1:499 of the at least one hit peptide sequence to the at least 499 decoy peptide sequences and a top 0.2% of the plurality of test peptide sequences are predicted to be presented by the HLA protein expressed in cells by the machine learning HLA-peptide presentation prediction model.

7. The method of claim 6, wherein:
(i) the at least one hit peptide sequence comprises at least 10 hit peptide sequences, and
(ii) the at least 499 decoy peptide sequences comprise at least 4990 decoy peptide sequences.

8. The method of claim 7, wherein any nine contiguous amino acid subsequences of any of the at least one hit peptides does not overlap with any nine contiguous amino acid sub-sequences of the at least 4990 decoy peptide sequences.

9. The method of claim 1, wherein each peptide sequence of the set of candidate peptide sequences is associated with a cancer.

10. The method of claim 9, wherein each peptide sequence of the set of candidate peptide sequences
(i) comprises a mutation,
(ii) is expressed in a cancer cell of the subject, and
(iii) is not encoded by a genome of a non-cancer cell of the subject.

11. The method of claim 1, wherein the protein encoded by a class II HLA allele is selected from the group consisting of: HLA-DPB1*01:01/HLA-DPA1*01:03, HLA-DPB1*02:01/HLA-DPA1*01:03, HLA-DPB1*03:01/HLA-DPA1*01:03, HLA-DPB1*04:01/HLA-DPA1*01:03, HLA-DPB1*04:02/HLA-DPA1*01:03, HLA-DPB1*06:01/HLA-DPA1*01:03, HLA-DRB1*01:01, HLA-DRB1*01:02, HLA-DRB1*03:01, HLA-DRB1*03:02, HLA-DRB1*04:01, HLA-DRB1*04:02, HLA-DRB1*04:03, HLA-DRB1*04:04, HLA-DRB1*04:05, HLA-DRB1*04:07, HLA-DRB1*07:01, HLA-DRB1*08:01, HLA-DRB1*08:02, HLA-DRB1*08:03, HLA-DRB1*08:04, HLA-DRB1*09:01, HLA-DRB1*10:01, HLA-DRB1*11:01, HLA-DRB1*11:02, HLA-DRB1*11:04, HLA-DRB1*12:01, HLA-DRB1*12:02, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16:01, HLA-DRB3*01:01, HLA-DRB3*02:02, HLA-DRB3*03:01, HLA-DRB4*01:01, HLA-DRB5*01:01, HLA-DRB1*01:01, HLA-DRB1*01:02, HLA-DRB1*03:01, HLA-DRB1*04:01, HLA-DRB1*04:02, HLA-DRB1*04:04, HLA-DRB1*04:05, HLA-DRB1*07:01, HLA-DRB1*08:01, HLA-DRB1*08:02, HLA-DRB1*08:03, HLA-DRB1*09:01, HLA-DRB1*11:01, HLA-DRB1*11:02, HLA-DRB1*11:04, HLA-DRB1*12:01, HLA-DRB1*13:01, HLA-DRB1*13:02, HLA-DRB1*13:03, HLA-DRB1*14:01, HLA-DRB1*15:01, HLA-DRB1*15:02, HLA-DRB1*15:03, HLA-DRB1*16:02, HLA-DRB3*01:01, HLA-DRB3*02:01, HLA-DRB3*02:02, HLA-DRB3*03:01, HLA-DRB4*01:01, HLA-DRB4*01:03, HLA-DRB5*01:01; HLA-DPB1*01:01, HLA-DPB1*02:01, HLA-DPB1*02:02, HLA-DPB1*03:01, HLA-DPB1*04:01, HLA-DPB1*04:02, HLA-DPB1*05:01, HLA-DPB1*06:01, HLA-DPB1*11:01, HLA-DPB1*13:01, HLA-DPB1*17:01, HLA-DQA1*01:01/HLA-DQB1*05:01, HLA-DQA1*01:02/HLA-DQB1*06:02, HLA-DQA1*01:02/HLA-DQB1*06:04, HLA-DQA1*01:03/HLA-DQB1*06:03, HLA-DQA1*02:01/HLA-DQB1*02:02, HLA-DQA1*02:01/HLA-DQB1*03:03, HLA-DQA1*03:01/HLA-DQB1*03:02, HLA-DQA1*03:03/HLA-DQB1*03:01, HLA-DQA1*05:01/HLA-DQB1*02:01 HLA-DQA1*05:05/HLA-DQB1*03:01, and any combination thereof.

12. The method of claim 1, wherein the method comprises obtaining a plurality of polynucleotide sequences of the subject by genome, transcriptome, or exome sequencing, wherein the plurality of polynucleotide sequences encode the set of candidate peptide sequences.

13. The method of claim 12, wherein the genome, transcriptome or exome sequencing is whole genome sequencing, whole transcriptome sequencing, or whole exome sequencing.

14. The method of claim 1, wherein the set of candidate peptide sequences are ranked based on the plurality of presentation predictions.

15. The method of claim 1, wherein each of the peptide sequences of the set of selected peptide sequences binds to a protein encoded by a class II HLA allele of a cell of the subject with an IC50 of 500 nM or less, or a predicted IC50 of 500 nM or less.

16. The method of claim 1, wherein the pharmaceutical composition comprises one or more polypeptides comprising at least two of the selected peptide sequences or one or more polynucleotides encoding at least two of the selected peptide sequences.

17. The method of claim 16, wherein the pharmaceutical composition further comprises an adjuvant.

18. The method of claim 16, wherein the pharmaceutical composition elicits a CD4+ T cell response and/or a CD8+ T cell response in the subject.

19. The method of claim 1, wherein the trained machine learning class II HLA-peptide presentation prediction model has a positive predictive value (PPV) of at least 0.2 according to a presentation PPV determination method, at a recall rate of 20%.

* * * * *